United States Patent
He et al.

(10) Patent No.: US 12,281,114 B2
(45) Date of Patent: Apr. 22, 2025

(54) NK3 MODULATORS AND USES THEREOF

(71) Applicant: Kallyope, Inc., New York, NY (US)

(72) Inventors: Shuwen He, Fanwood, NJ (US); Scott B. Joseph, New York, NY (US); Christopher Moyes, Westfield, NJ (US); Tesfaye Biftu, Freehold, NJ (US); Santhosh F. Neelamkavil, Edison, NJ (US)

(73) Assignee: KALLYOPE, INC., New York, NY (US)

( * ) Notice: Subject to any disclaimer, the term of this patent is extended or adjusted under 35 U.S.C. 154(b) by 0 days.

(21) Appl. No.: 18/800,581

(22) Filed: Aug. 12, 2024

(65) Prior Publication Data
US 2024/0409541 A1  Dec. 12, 2024

Related U.S. Application Data

(63) Continuation of application No. PCT/US2024/024989, filed on Apr. 17, 2024.

(60) Provisional application No. 63/545,395, filed on Oct. 24, 2023, provisional application No. 63/541,107, filed on Sep. 28, 2023, provisional application No. 63/460,109, filed on Apr. 18, 2023.

(51) Int. Cl.
| | |
|---|---|
| C07D 471/04 | (2006.01) |
| A61K 31/437 | (2006.01) |
| A61K 31/4375 | (2006.01) |
| A61K 31/438 | (2006.01) |
| A61K 31/444 | (2006.01) |
| A61K 31/4545 | (2006.01) |
| A61K 31/496 | (2006.01) |
| A61K 31/4985 | (2006.01) |
| A61K 31/506 | (2006.01) |
| A61K 31/5377 | (2006.01) |
| A61K 45/06 | (2006.01) |
| C07D 519/00 | (2006.01) |

(52) U.S. Cl.
CPC .......... *C07D 471/04* (2013.01); *A61K 31/437* (2013.01); *A61K 31/4375* (2013.01); *A61K 31/438* (2013.01); *A61K 31/444* (2013.01); *A61K 31/4545* (2013.01); *A61K 31/496* (2013.01); *A61K 31/4985* (2013.01); *A61K 31/506* (2013.01); *A61K 31/5377* (2013.01); *A61K 45/06* (2013.01); *C07D 519/00* (2013.01)

(58) Field of Classification Search
CPC .. C07D 471/04; C07D 519/00; A61K 31/437; A61K 31/4375; A61K 31/438; A61K 31/444; A61K 31/4545; A61K 31/496; A61K 31/4985; A61K 31/506; A61K 31/5377; A61K 45/06
See application file for complete search history.

(56) References Cited

U.S. PATENT DOCUMENTS

| | | | |
|---|---|---|---|
| 5,846,514 | A | 12/1998 | Foster et al. |
| 6,334,997 | B1 | 1/2002 | Foster et al. |
| 8,153,649 | B2 * | 4/2012 | Klein .............. A61P 3/10 |
| | | | 546/113 |
| 2007/0099896 | A1 | 5/2007 | Sundermann et al. |
| 2011/0257402 | A1 | 10/2011 | Jablonski et al. |
| 2019/0183976 | A1 | 6/2019 | Seen et al. |
| 2021/0369707 | A1 | 12/2021 | Trower et al. |
| 2021/0401821 | A1 | 12/2021 | Fukui et al. |

FOREIGN PATENT DOCUMENTS

| | | |
|---|---|---|
| AU | 2007312659 B2 | 8/2012 |
| WO | WO-9528931 A1 | 11/1995 |
| WO | WO-2005094801 A1 | 10/2005 |
| WO | WO-2007039123 A2 | 4/2007 |
| WO | WO-2012061169 A1 | 5/2012 |
| WO | WO-2016009439 A1 | 1/2016 |
| WO | WO-2016059191 A1 | 4/2016 |
| WO | WO-2017147102 A1 | 8/2017 |
| WO | WO-2020101017 A1 | 5/2020 |
| WO | WO-2022026900 A2 | 2/2022 |
| WO | WO-2022026901 A2 | 2/2022 |
| WO | WO-2023278843 A2 | 1/2023 |
| WO | WO-2023211779 A1 | 11/2023 |
| WO | WO-2024220539 A1 | 10/2024 |

OTHER PUBLICATIONS

Anderson, Philip. O. Handbook of Clinical Drug Data, Tenth Edition. McGraw Hill (2002).
Berge, Stephen M. et al. Pharmaceutical Salts. Journal of Pharmaceutical Sciences 66(1):1-19 (1977).
Bundgaard, Hans et al. Design of Prodrugs pp. 7-9, 21-24 (1985).
Chaplan, Sandra R. et al. Quantitative Assessment of Tactile Allodynia in The Rat Paw. Journal of Neuroscience Methods 53(1):55-63 (1994).
Cui et al., Tacr3 in the lateral habenula differentially regulates orofacial allodynia and anxiety-like behaviors in a mouse model of trigeminal neuralgia. Acta Neuropathol Commun 8(1):44 (2020).
Depypere, Herman et al. Fezolinetant in the Treatment of Vasomotor Symptoms Associated With Menopause. Expert Opinion on Investigational Drugs 30(7):681-694 (2021).
Ding et al. Development and Synthesis of DNA-Encoded Benzimidazole Library. ACS Comb Sci 20(5):251-255 (2018).
Edvinsson et al. Neurokinins and their receptors in the rat trigeminal system: Differential localization and release with implications for migraine pain. Mol Pain 17:1-11 (2021).

(Continued)

*Primary Examiner* — Matthew P Coughlin
*Assistant Examiner* — Quincy McKoy
(74) *Attorney, Agent, or Firm* — WILSON SONSINI GOODRICH & ROSATI

(57) ABSTRACT

The present disclosure relates to compounds useful as modulators of neurokinin receptor 3 (NK3) for the treatment of conditions or disorders.

20 Claims, No Drawings

(56) References Cited

OTHER PUBLICATIONS

Edvinsson et al. Neuropeptides and the Nodes of Ranvier in Cranial Headaches. Front Physiol 12:820037 (2022).

Evans, E Anthony. Synthesis of Radiolabeled Compounds. Journal of Radioanalytical and Nuclear Chemistry 64(1-2):9-32 (1981).

Higuchi, T. et al. Pro-drugs as Novel Delivery Systems, vol. 14 of the A.C.S. Symposium Series and in Bioreversible Carriers in Drug Design, ed. Edward B. Roche, American Pharmaceutical Association and Pergamon Press (1987).

Kabalka, George W. et al. The Synthesis of Radiolabeled Compounds via Organometallic Intermediates. Tetrahedron 45(21):6601-6621 (1989).

Kaswan, P. et al. Ligand-Free, Copper-Catalyzed Ullmann-Type C-N Coupling: Regioselective Synthesis of Azole-Substituted Imidazo[1,2-a]pyridines. Synlett 24(20):2751-2757 (2013) (Includes Supplemental Information).

PCT/US2023/019406 International Search Report and Written Opinion dated Jun. 21, 2023.

PCT/US2024/024989 International Search Report and Written Opinion dated Jul. 10, 2024.

Schank, J.R. GenBank Accession No. NM_001059. Version No. NM_001059.3. *Homo sapiens* tachykinin receptor 3 (TACR3), mRNA: pp. 1-5. Record created Nov. 22, 2018. Retrieved Aug. 12, 2024. Retrieved from: https://www.ncbi.nlm.nih.gov/nuccore/NM_001059.

Sureda-Gibert, Paula et al. Nitroglycerin as a Model of Migraine: Clinical and Preclinical Review. Neurobiology of pain 12:100105, 1-12 (2022).

Uenoyama, Yoshihisa et al. Role of KNDy Neurons Expressing Kisspeptin, Neurokinin B, and Dynorphin a as a GnRH Pulse Generator Controlling Mammalian Reproduction. Frontiers in endocrinology 12:724632, 1-12 (2021).

Wu, Zining et al. Cell-Based Selection Expands the Utility of DNA-Encoded Small-Molecule Library Technology to Cell Surface Drug Targets: Identification of Novel Antagonists of the NK3 Tachykinin Receptor. ACS Combinatorial Science 17(12):722-731 (2015).

PCT/US2024/050690 International Search Report and Written Opinion dated Nov. 28, 2024.

Co-pending U.S. Appl. No. 18/859,693, inventors Kupferman; Justine et al., filed Oct. 24, 2024.

\* cited by examiner

NK3 MODULATORS AND USES THEREOF

CROSS-REFERENCE

This application is a continuation of International Application No. PCT/US2024/024989 filed Apr. 17, 2024, which claims the benefit of U.S. Provisional Application Ser. No. 63/545,395 filed Oct. 24, 2023, U.S. Provisional Application Ser. No. 63/541,107 filed Sep. 28, 2023, and U.S. Provisional Application Ser. No. 63/460,109 filed Apr. 18, 2023, all of which are hereby incorporated by reference in their entireties.

BACKGROUND OF THE INVENTION

Migraine is a painful and debilitating neurological condition of the trigeminovascular system with high prevalence in the general population, affecting approximately 15% of individuals, making it the second leading cause of disability worldwide. Migraine is characterized by recurrent, pulsating headache attacks of moderate to severe pain intensity with sensitivity to movement, visual, auditory, and other sensory input that can last from 4 to 72 hours.

While there are several classes of oral drugs approved for migraine treatment, many of those currently in use are associated with significant side effects, leading to frequent discontinuation and class switching along with poor outcomes. Antibody therapies and small molecules targeting CGRP receptors have fewer reported side effects, but less than a third of migraineurs are responsive to these treatments. Thus, there is significant need for novel therapies to treat migraine and other disorders of the trigeminovascular system such as cluster and medication overuse headache and trigeminal neuralgia.

Described herein are a novel class of neurokinin receptor 3 (NK3) antagonists that can be useful in the treatment of migraine and other disorders of the trigeminovascular system.

BRIEF SUMMARY OF THE INVENTION

Described herein, in certain embodiments, are neurokinin receptor 3 (NK3) (also known as tachykinin receptor 3) modulators useful for the treatment of diseases or disorders. In some embodiments, the NK3 modulators are NK3 antagonists. In some embodiments, the diseases or disorders are a neurokinin receptor 3 (NK3)-dependent diseases or disorders. In some embodiments, the diseases or disorders are selected from the group consisting of: migraine, medication overuse headache, cluster headache, general headache, trigeminal neuralgia, and orofacial pain.

In one aspect, described herein are compounds of Formula (I):

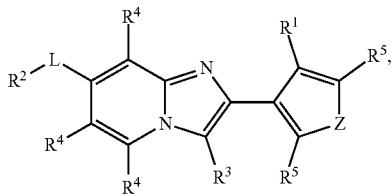

Formula (I)

or a pharmaceutically acceptable salt or solvate thereof, wherein:

Z is a bivalent group selected from —S—, —N=C($R^5$)—, —C($R^5$)=N—, or —C($R^5$)=C($R^5$)—;

$R^1$ is pyrazole, wherein said pyrazole is optionally substituted with 1-3 groups independently selected from $R^6$;

$R^2$ is $C_1$-$C_{10}$ alkyl, $C_1$-$C_{10}$ heteroalkyl, —C(=O)O$R^7$, —C(=O)N($R^8$)($R^7$), —N($R^8$)($R^7$), —C(=N$R^9$)N($R^8$)($R^7$), —N($R^7$)C(=N$R^9$)N($R^8$)($R^7$), $C_6$-$C_{10}$ aryl, 5- to 10-membered heteroaryl, $C_3$-$C_{12}$ cycloalkyl, or 3-to-15 membered heterocycloalkyl, wherein the aryl, and heteroaryl is optionally substituted with 1-4 groups independently selected from $R^{10}$, and the alkyl, heteroalkyl, cycloalkyl, and heterocycloalkyl is optionally substituted with 1-4 groups independently selected from oxo and $R^{10}$;

$R^3$ is halogen, cyano, —C(=O)OH, —C(=O)O($C_1$-$C_6$ alkyl), $C_1$-$C_6$ alkyl, $C_1$-$C_6$ alkenyl, —O($C_1$-$C_6$ alkyl), $C_3$-$C_6$ cycloalkyl, or $C_1$-$C_6$ haloalkyl;

each $R^4$ is independently hydrogen, halogen, $C_1$-$C_6$ alkyl, —O—$C_1$-$C_6$ alkyl, $C_1$-$C_6$ haloalkyl, or —O—($C_1$-$C_6$ haloalkyl);

L is a bond, $C_1$-$C_2$ alkylene, or $C_3$-$C_6$ cycloalkylene, wherein said alkylene, or cycloalkylene is optionally substituted with 1 or 2 —OH groups;

each $R^5$ is independently hydrogen, cyano, halogen, $C_1$-$C_6$ alkyl, —O($C_1$-$C_6$ alkyl), $C_3$-$C_6$ cycloalkyl, $C_1$-$C_6$ haloalkyl, or —O($C_1$-$C_6$ haloalkyl);

each $R^6$ is independently selected from the group consisting of halogen, hydroxy, cyano, amino, $C_1$-$C_6$ alkyl, $C_1$-$C_6$ hydroxyalkyl, $C_1$-$C_6$ aminoalkyl, —O($C_1$-$C_6$ alkyl), —NH($C_1$-$C_6$ alkyl), —N($C_1$-$C_6$ alkyl)$_2$, $C_3$-$C_6$ cycloalkyl, —CH$_2$—($C_{3-6}$ cycloalkyl), —O—($C_{3-6}$ cycloalkyl), $C_1$-$C_6$ haloalkyl, and —O($C_1$-$C_6$ haloalkyl);

wherein if an $R^6$ is attached to a nitrogen atom, then it is selected from the group consisting of $C_1$-$C_6$ alkyl, $C_1$-$C_6$ hydroxyalkyl, $C_1$-$C_6$ aminoalkyl, $C_3$-$C_6$ cycloalkyl, —CH$_2$—($C_{3-6}$ cycloalkyl), and $C_1$-$C_6$ haloalkyl;

each $R^7$ is independently hydrogen or $C_1$-$C_6$ alkyl, wherein said alkyl is optionally substituted with 1-2 hydroxy groups;

$R^8$ is hydrogen, $C_1$-$C_{10}$ alkyl, $C_1$-$C_{10}$ heteroalkyl, $C_1$-$C_{10}$ alkenyl, $C_1$-$C_{10}$ alkynyl, $C_3$-$C_{12}$ cycloalkyl, 3- to 15-membered heterocycloalkyl, $C_6$-$C_{10}$ aryl, or 5- to 10-membered heteroaryl; wherein the aryl, and heteroaryl is optionally substituted with 1-6 groups independently selected from $R^{11}$, and the alkyl, heteroalkyl, alkenyl, alkynyl, cycloalkyl and heterocycloalkyl is optionally substituted with 1-6 groups independently selected from oxo and $R^{11}$;

or one $R^7$ and one $R^8$ bound to the same nitrogen atom come together to form a 3- to 15-membered heterocycloalkyl that is optionally substituted with 1-6 groups independently selected from oxo and $R^{11}$;

$R^9$ is hydrogen, —C(O)O$R^{12}$, —C(O)N($R^{12}$)$_2$, —S(O)$_2$$R^{12}$, —S(O)$_2$N($R^{12}$)$_2$, or $C_1$-$C_6$ alkyl;

each $R^{10}$ is independently selected from hydroxy, amino, cyano, fluoro, —C(=O)O$R^{12}$, —C(=O)N($R^{12}$)$_2$, $C_1$-$C_4$ alkyl, $C_1$-$C_4$ haloalkyl, —O($C_1$-$C_6$ alkyl), —NH($C_1$-$C_4$ alkyl), —N($C_1$-$C_4$ alkyl)$_2$, $C_3$-$C_6$ cycloalkyl, wherein said alkyl, haloalkyl or cycloalkyl is optionally substituted with 1-2 groups selected from hydroxy, amino, cyano, fluoro, —C(=O)O$R^{12}$, and —C(=O)N($R^{12}$)$_2$;

each $R^{11}$ is independently selected from the group consisting of halogen, hydroxy, amino, cyano, —S(=O)$_2$(R$^{13}$), —N(R$^{12}$)S(=O)$_2$(R$^{13}$), —S(=O)(R$^{13}$), —N(R$^{12}$)S(=O)(R$^{13}$), —C(=O)R$^{13}$, —N(R$^{12}$)C(=O)R$^{13}$, C$_1$-C$_6$ alkyl, —O(C$_1$-C$_6$ alkyl), —NH(C$_1$-C$_6$ alkyl), —N(C$_1$-C$_6$ alkyl)$_2$, C$_1$-C$_6$ haloalkyl, C$_2$-C$_6$ alkenyl, C$_2$-C$_6$ alkynyl, C$_3$-C$_8$ cycloalkyl, 3- to 10-membered heterocycloalkyl, C$_6$-C$_{10}$ aryl, and 5- to 10-membered heteroaryl, wherein the aryl, and heteroaryl is optionally substituted with 1-4 groups independently selected from R$^{14}$, and the alkyl, alkenyl, alkynyl, haloalkyl, cycloalkyl, and heterocycloalkyl is optionally substituted with 1-4 groups independently selected from oxo and R$^{14}$;

or two $R^{11}$ bound to the same carbon or nitrogen atom come together to form a C$_3$-C$_6$ cycloalkyl or 3- to 6-membered heterocycloalkyl, wherein the cycloalkyl, and heterocycloalkyl is optionally substituted with 1-4 groups independently selected from oxo and R$^{14}$;

each $R^{12}$ is independently hydrogen or C$_1$-C$_6$ alkyl;

each $R^{13}$ is independently hydroxy, amino, C$_1$-C$_6$ alkyl, —O(C$_1$-C$_6$ alkyl), —NH(C$_1$-C$_6$ alkyl), —N(C$_1$-C$_6$ alkyl)$_2$, C$_1$-C$_6$ haloalkyl, C$_3$-C$_6$ cycloalkyl, or 3- to 6-membered heterocycloalkyl; and each $R^{14}$ is independently cyano, amino, hydroxy, —C(=O)OR$^{12}$, —C(=O)N(R$^{12}$)$_2$, C$_1$-C$_6$ alkyl, —O(C$_1$-C$_6$ alkyl), —NR$^{12}$(C$_1$-C$_6$ alkyl), aryl, heteroaryl, C$_3$-C$_6$ cycloalkyl, or 3- to 6-membered heterocycloalkyl, wherein each alkyl is optionally substituted with 1-2 hydroxy groups.

In some embodiments, the compound (e.g., the compound of Formula (I)) has the structure of Formula (IIa):

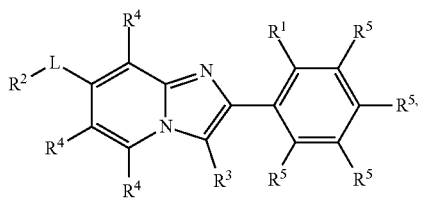

Formula (IIa)

or a pharmaceutically acceptable salt or solvate thereof.

In some embodiments, the compound (e.g., the compound of Formula (I)) has the structure of Formula (IIb):

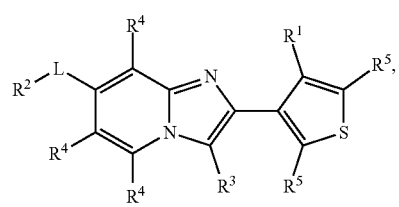

Formula (IIb)

or a pharmaceutically acceptable salt or solvate thereof.

In some embodiments, the compound (e.g., the compound of Formula (I)) has the structure of Formula (IIc):

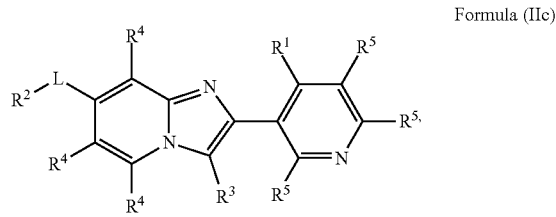

Formula (IIc)

or a pharmaceutically acceptable salt or solvate thereof.

In some embodiments, the compound (e.g., the compound of Formula (I)) has the structure of Formula (IId):

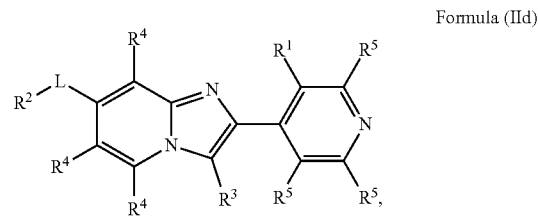

Formula (IId)

or a pharmaceutically acceptable salt or solvate thereof.

In some embodiments, the compound (e.g., the compound of Formula (I)) has the structure of Formula (III):

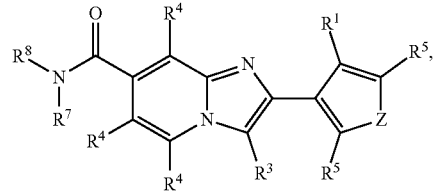

Formula (III)

or a pharmaceutically acceptable salt or solvate thereof.

In some embodiments, the compound (e.g., the compound of Formula (I)) has the structure of Formula (IVa):

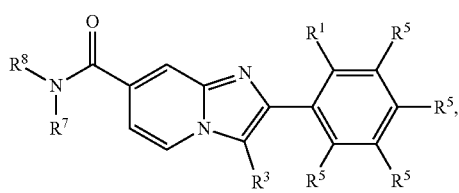

Formula (IVa)

or a pharmaceutically acceptable salt or solvate thereof.

In some embodiments, the compound (e.g., the compound of Formula (I)) has the structure of Formula (VIa):

Formula (VIa)

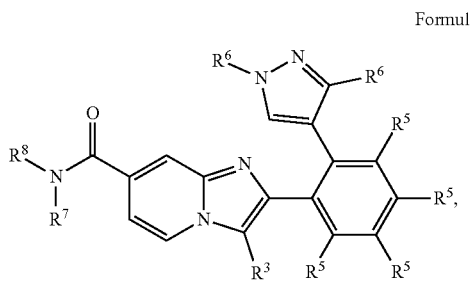

or a pharmaceutically acceptable salt or solvate thereof.

In some embodiments, the compound (e.g., the compound of Formula (I)) has the structure of Formula (VIIa):

Formula (VIIa)

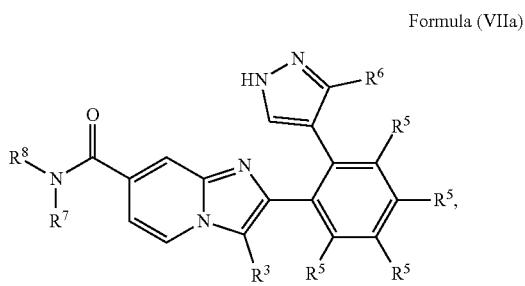

or a pharmaceutically acceptable salt or solvate thereof.

Also described herein is a pharmaceutical composition comprising a compound described herein, or a pharmaceutically acceptable salt or solvate thereof, and at least one pharmaceutically acceptable excipient. In some embodiments, the pharmaceutical composition is formulated for administration to a mammal by intravenous administration, subcutaneous administration, oral administration, inhalation, nasal administration, dermal administration, or ophthalmic administration. In some embodiments, the pharmaceutical composition is formulated for administration to a mammal by oral administration. In some embodiments, the pharmaceutical composition is in the form of a tablet, a pill, a capsule, a liquid, a suspension, a gel, a dispersion, a solution, an emulsion, an ointment, or a lotion. In some embodiments, the pharmaceutical composition is in the form of a tablet, a pill, or a capsule.

Also described herein is a method of treating a disease or condition in a mammal that would benefit from the modulation of neurokinin receptor 3 activity comprising administering a compound described herein, or a pharmaceutically acceptable salt or solvate thereof, to the mammal in need thereof. In some embodiments, the compound described herein, or a pharmaceutically acceptable salt or solvate thereof, is orally administered. In some embodiments, the disease or condition is migraine, medication overuse headache, cluster headache, general headache, trigeminal neuralgia, orofacial pain, or combinations thereof. In some embodiments, the disease or condition is migraine, medication overuse headache, cluster headache, general headache, or combinations thereof. In some embodiments, the disease or condition is migraine.

In any of the aforementioned aspects are further embodiments in which the effective amount of the compound of Formula (I), or a pharmaceutically acceptable salt thereof, is: (a) systemically administered to the mammal; and/or (b) administered orally to the mammal; and/or (c) intravenously administered to the mammal; and/or (d) administered by inhalation; and/or (e) administered by nasal administration; or and/or (f) administered by injection to the mammal; and/or (g) administered topically to the mammal; and/or (h) administered by ophthalmic administration; and/or (i) administered rectally to the mammal; and/or (j) administered non-systemically or locally to the mammal.

In any of the aforementioned aspects are further embodiments comprising single administrations of the effective amount of the compound, including further embodiments in which the compound is administered once a day to the mammal or the compound is administered to the mammal multiple times over the span of one day. In some embodiments, the compound is administered on a continuous dosing schedule. In some embodiments, the compound is administered on a continuous daily dosing schedule.

In any of the embodiments disclosed herein, the mammal is a human.

In some embodiments, compounds provided herein are orally administered to a human.

Articles of manufacture, which include packaging material, a compound of Formula (I), or a pharmaceutically acceptable salt or solvate thereof, within the packaging material, and a label that indicates that the compound or composition, or pharmaceutically acceptable salt, tautomers, pharmaceutically acceptable N-oxide, pharmaceutically active metabolite, pharmaceutically acceptable prodrug, or pharmaceutically acceptable solvate thereof, is used for modulating neurokinin receptor 3 proteins, or for the treatment, prevention or amelioration of one or more symptoms of a disease or condition that would benefit from modulating neurokinin receptor 3, are provided.

Other objects, features and advantages of the compounds, methods and compositions described herein will become apparent from the following detailed description. It should be understood, however, that the detailed description and the specific examples, while indicating specific embodiments, are given by way of illustration only, since various changes and modifications within the spirit and scope of the instant disclosure will become apparent to those skilled in the art from this detailed description.

INCORPORATION BY REFERENCE

All publications, patents, and patent applications mentioned in this specification are herein incorporated by reference to the same extent as if each individual publication, patent, or patent application was specifically and individually indicated to be incorporated by reference.

DETAILED DESCRIPTION OF THE INVENTION

Neurokinin receptor 3 (NK3) (also known as tachykinin receptor 3) is encoded by the TACR3 gene (also referred to herein as NK3 gene). Compounds of Formula (I) detailed herein are NK3 modulators. In some embodiments, the compounds of Formula (I) detailed herein are NK3 antagonists. In some embodiments, a compound of Formula (I) may be utilized in the treatment of headache disorders and diseases, such as cluster headaches and migraines. The present disclosure demonstrates the efficacy of compounds of Formula (I) to act as NK3 modulators in well-known in vitro models.

Certain Terminology

Unless defined otherwise, all technical and scientific terms used herein have the same meaning as is commonly understood by one of skill in the art to which this invention belongs. All patents and publications referred to herein are incorporated by reference.

As used herein and in the appended claims, the singular forms "a," "an," and "the" include plural referents unless the context clearly dictates otherwise. Thus, for example, reference to "an agent" includes a plurality of such agents, and reference to "the cell" includes reference to one or more cells (or to a plurality of cells) and equivalents thereof known to those skilled in the art, and so forth. When ranges are used herein for physical properties, such as molecular weight, or chemical properties, such as chemical formulas, all combinations and subcombinations of ranges and specific embodiments therein are intended to be included.

The term "about" when referring to a number or a numerical range means that the number or numerical range referred to is an approximation within experimental variability (or within statistical experimental error), and thus the number or numerical range, in some instances, will vary between 1% and 15% of the stated number or numerical range.

The term "comprising" (and related terms such as "comprise" or "comprises" or "having" or "including") is not intended to exclude that in other certain embodiments, for example, an embodiment of any composition of matter, composition, method, or process, or the like, described herein, "consist of" or "consist essentially of" the described features.

As used in the specification and appended claims, unless specified to the contrary, the following terms have the meaning indicated below:

As used herein, $C_1$-$C_x$ includes $C_1$-$C_2$, $C_1$-$C_3$ ... $C_1$-$C_x$. By way of example only, a group designated as "$C_1$-$C_4$" indicates that there are one to four carbon atoms in the moiety, i.e., groups containing 1 carbon atom, 2 carbon atoms, 3 carbon atoms or 4 carbon atoms. Thus, by way of example only, "$C_1$-$C_4$ alkyl" indicates that there are one to four carbon atoms in the alkyl group, i.e., the alkyl group is selected from among methyl, ethyl, propyl, iso-propyl, n-butyl, iso-butyl, sec-butyl, and t-butyl.

"Alkyl" refers to an optionally substituted straight-chain, or optionally substituted branched-chain saturated hydrocarbon monoradical having from one to about ten carbon atoms, or more preferably, from one to six carbon atoms, wherein an $sp^3$-hybridized carbon of the alkyl residue is attached to the rest of the molecule by a single bond. Examples include, but are not limited to, methyl, ethyl, n-propyl, isopropyl, 2-methyl-1-propyl, 2-methyl-2-propyl, 2-methyl-1-butyl, 3-methyl-1-butyl, 2-methyl-3-butyl, 2,2-dimethyl-1-propyl, 2-methyl-1-pentyl, 3-methyl-1-pentyl, 4-methyl-1-pentyl, 2-methyl-2-pentyl, 3-methyl-2-pentyl, 4-methyl-2-pentyl, 2,2-dimethyl-1-butyl, 3,3-dimethyl-1-butyl, 2-ethyl-1-butyl, n-butyl, isobutyl, sec-butyl, t-butyl, n-pentyl, isopentyl, neopentyl, tert-amyl and hexyl, and longer alkyl groups, such as heptyl, octyl, and the like. Whenever it appears herein, a numerical range such as "$C_1$-$C_6$ alkyl" means that the alkyl group consists of 1 carbon atom, 2 carbon atoms, 3 carbon atoms, 4 carbon atoms, 5 carbon atoms or 6 carbon atoms, although the present definition also covers the occurrence of the term "alkyl" where no numerical range is designated. In some embodiments, the alkyl is a $C_1$-$C_{10}$ alkyl, a $C_1$-$C_9$ alkyl, a $C_1$-$C_8$ alkyl, a $C_1$-$C_7$ alkyl, a $C_1$-$C_6$ alkyl, a $C_1$-$C_5$ alkyl, a $C_1$-$C_4$ alkyl, a $C_1$-$C_3$ alkyl, a $C_1$-$C_2$ alkyl, or a $C_1$ alkyl. Unless stated otherwise specifically in the specification, an alkyl group is optionally substituted as described below by one or more of the following substituents: halo, cyano, nitro, oxo, thioxo, imino, oximo, trimethylsilanyl, —$OR^a$, —$SR^a$, —$OC(O)R^a$, —$OC(O)$—$OR^f$, —$N(R^a)_2$, —$N^+(R^a)_3$, —$C(O)R^a$, —$C(O)OR^a$, —$C(O)N(R^a)_2$, —$N(R^a)C(O)OR^f$, —$OC(O)$—$N(R^a)_2$, —$N(R^a)C(O)R^a$, —$N(R^a)S(O)_tR^f$ (where t is 1 or 2), —$S(O)_tOR^a$ (where t is 1 or 2), —$S(O)_tR^f$ (where t is 1 or 2) and —$S(O)_tN(R^a)_2$ (where t is 1 or 2) where each $R^a$ is independently hydrogen, alkyl, haloalkyl, cycloalkyl, aryl, aralkyl, heterocycloalkyl, heteroaryl or heteroarylalkyl, and each $R^f$ is independently alkyl, haloalkyl, cycloalkyl, aryl, aralkyl, heterocycloalkyl, heteroaryl or heteroarylalkyl.

"Alkenyl" refers to an optionally substituted straight-chain, or optionally substituted branched-chain hydrocarbon monoradical having one or more carbon-carbon double-bonds and having from two to about ten carbon atoms, more preferably two to about six carbon atoms, wherein an $sp^2$-hybridized carbon or an $sp^3$-hybridized carbon of the alkenyl residue is attached to the rest of the molecule by a single bond. The group may be in either the cis or trans conformation about the double bond(s), and should be understood to include both isomers. Examples include, but are not limited to ethenyl (—CH=CH$_2$), 1-propenyl (—CH$_2$CH=CH$_2$), isopropenyl (—C(CH$_3$)=CH$_2$), butenyl, 1,3-butadienyl and the like. Whenever it appears herein, a numerical range such as "$C_2$-$C_6$ alkenyl" means that the alkenyl group may consist of 2 carbon atoms, 3 carbon atoms, 4 carbon atoms, 5 carbon atoms or 6 carbon atoms, although the present definition also covers the occurrence of the term "alkenyl" where no numerical range is designated. In some embodiments, the alkenyl is a $C_2$-$C_{10}$ alkenyl, a $C_2$-$C_9$ alkenyl, a $C_2$-$C_8$ alkenyl, a $C_2$-$C_7$ alkenyl, a $C_2$-$C_6$ alkenyl, a $C_2$-$C_5$ alkenyl, a $C_2$-$C_4$ alkenyl, a $C_2$-$C_3$ alkenyl, or a $C_2$ alkenyl. Unless stated otherwise specifically in the specification, an alkenyl group is optionally substituted as described below, for example, with oxo, halogen, amino, nitrile, nitro, hydroxyl, haloalkyl, alkoxy, aryl, cycloalkyl, heterocycloalkyl, heteroaryl, and the like. Unless stated otherwise specifically in the specification, an alkenyl group is optionally substituted as described below by one or more of the following substituents: halo, cyano, nitro, oxo, thioxo, imino, oximo, trimethylsilanyl, —$OR^a$, —$SR^a$, —$OC(O)$—$R^f$, —$OC(O)$—$OR^f$, —$N(R^a)_2$, —$N^+(R^a)_3$, —$C(O)R^a$, —$C(O)OR^a$, —$C(O)N(R^a)_2$, —$N(R^a)C(O)OR^f$, —$OC(O)$—$N(R^a)_2$, —$N(R^a)C(O)R^f$, —$N(R^a)S(O)_tR^f$ (where t is 1 or 2), —$S(O)_tOR^a$ (where t is 1 or 2), —$S(O)_tR^f$ (where t is 1 or 2) and —$S(O)_tN(R^a)_2$ (where t is 1 or 2) where each $R^a$ is independently hydrogen, alkyl, haloalkyl, cycloalkyl, aryl, aralkyl, heterocycloalkyl, heteroaryl or heteroarylalkyl, and each $R^f$ is independently alkyl, haloalkyl, cycloalkyl, aryl, aralkyl, heterocycloalkyl, heteroaryl or heteroarylalkyl.

"Alkynyl" refers to an optionally substituted straight-chain or optionally substituted branched-chain hydrocarbon monoradical having one or more carbon-carbon triple-bonds and having from two to about ten carbon atoms, more preferably from two to about six carbon atoms, wherein an sp-hybridized carbon or an $sp^3$-hybridized carbon of the alkynyl residue is attached to the rest of the molecule by a single bond. Examples include, but are not limited to ethynyl, 2-propynyl, 2-butynyl, 1,3-butadiynyl and the like. Whenever it appears herein, a numerical range such as "$C_2$-$C_6$ alkynyl" means that the alkynyl group may consist of 2 carbon atoms, 3 carbon atoms, 4 carbon atoms, 5 carbon atoms or 6 carbon atoms, although the present definition also covers the occurrence of the term "alkynyl" where no numerical range is designated. In some embodiments, the alkynyl is a $C_2$-$C_{10}$ alkynyl, a $C_2$-$C_9$ alkynyl, a $C_2$-$C_8$ alkynyl, a $C_2$-$C_7$ alkynyl, a $C_2$-$C_6$ alkynyl, a $C_2$-$C_5$ alkynyl, a $C_2$-$C_4$ alkynyl, a $C_2$-$C_3$ alkynyl, or a $C_2$ alkynyl. Unless stated otherwise specifically in the specification, an alkynyl group is optionally substituted as described below by one or more of the following substituents: halo, cyano, nitro, oxo, thioxo, imino, oximo, trimethylsilanyl, —$OR^a$, —$SR^a$, —$OC(O)R^a$, —$OC(O)$—$OR^f$, —$N(R^a)_2$, —$N^+(R^a)_3$, —$C(O)R^a$, —$C(O)OR^a$, —$C(O)N(R^a)_2$, —$N(R^a)C(O)OR^f$, —$OC(O)$—$N(R^a)_2$, —$N(R^a)C(O)R^f$, —$N(R^a)S(O)_tR^f$ (where t is 1 or 2), —$S(O)_tOR^a$ (where t is 1 or 2), —$S(O)_tR$ (where t is 1 or 2) and —$S(O)_tN(R^a)_2$ (where t is 1 or 2) where each $R^a$ is independently hydrogen, alkyl, haloalkyl, cycloalkyl, aryl, aralkyl, heterocycloalkyl, heteroaryl or heteroarylalkyl, and each $R^f$ is independently alkyl, haloalkyl, cycloalkyl, aryl, aralkyl, heterocycloalkyl, heteroaryl or heteroarylalkyl.

"Alkylene" or "alkylene chain" refers to a straight or branched divalent hydrocarbon chain linking the rest of the molecule to a radical group, consisting solely of carbon and hydrogen, containing no unsaturation and having from one to twelve carbon atoms, for example, methylene, ethylene, propylene, n-butylene, and the like. The alkylene chain is attached to the rest of the molecule through a single bond and to the radical group through a single bond. The points of attachment of the alkylene chain to the rest of the molecule and to the radical group are through one carbon in the alkylene chain or through any two carbons within the chain. Unless stated otherwise specifically in the specification, an alkylene group is optionally substituted as described below by one or more of the following substituents: halo, cyano, nitro, oxo, thioxo, imino, oximo, trimethylsilanyl, —$OR^a$, —$SR^a$, —$OC(O)R^a$, —$OC(O)$—$OR^f$, —$N(R^a)_2$, —$N^+(R^a)_3$, —$C(O)R^a$, —$C(O)OR^a$, —$C(O)N(R^a)_2$, —$N(R^a)C(O)OR^f$, —$OC(O)$—$N(R^a)_2$, —$N(R^a)C(O)R^f$, —$N(R^a)S(O)_tR^f$ (where t is 1 or 2), —$S(O)_tOR^a$ (where t is 1 or 2), —$S(O)_tR$ (where t is 1 or 2) and —$S(O)_tN(R^a)_2$ (where t is 1 or 2) where each $R^a$ is independently hydrogen, alkyl, haloalkyl, cycloalkyl, aryl, aralkyl, heterocycloalkyl, heteroaryl or heteroarylalkyl, and each $R^f$ is independently alkyl, haloalkyl, cycloalkyl, aryl, aralkyl, heterocycloalkyl, heteroaryl or heteroarylalkyl.

"Alkenylene" or "alkenylene chain" refers to a straight or branched divalent hydrocarbon chain linking the rest of the molecule to a radical group, consisting solely of carbon and hydrogen, containing at least one carbon-carbon double bond, and having from two to twelve carbon atoms. The alkenylene chain is attached to the rest of the molecule through a single bond and to the radical group through a single bond. Unless stated otherwise specifically in the specification, an alkenylene group is optionally substituted as described below by one or more of the following substituents: halo, cyano, nitro, oxo, thioxo, imino, oximo, trimethylsilanyl, —$OR^a$, —$SR^a$, —$OC(O)$—RE, —$OC(O)$—$OR^f$, —$N(R^a)_2$, —$N^+(R^a)_3$, —$C(O)R^a$, —$C(O)OR^a$, —$C(O)N(R^a)_2$, —$N(R^a)C(O)OR^f$, —$OC(O)$—$N(R^a)_2$, —$N(R^a)C(O)R^f$, —$N(R^a)S(O)_tR^f$ (where t is 1 or 2), —$S(O)_tOR^a$ (where t is 1 or 2), —$S(O)_tR$ (where t is 1 or 2) and —$S(O)_tN(R^a)_2$ (where t is 1 or 2) where each $R^a$ is independently hydrogen, alkyl, haloalkyl, cycloalkyl, aryl, aralkyl, heterocycloalkyl, heteroaryl or heteroarylalkyl, and each $R^f$ is independently alkyl, haloalkyl, cycloalkyl, aryl, aralkyl, heterocycloalkyl, heteroaryl or heteroarylalkyl.

"Alkynylene" or "alkynylene chain" refers to a straight or branched divalent hydrocarbon chain linking the rest of the molecule to a radical group, consisting solely of carbon and hydrogen, containing at least one carbon-carbon triple bond, and having from two to twelve carbon atoms. The alkynylene chain is attached to the rest of the molecule through a single bond and to the radical group through a single bond. Unless stated otherwise specifically in the specification, an alkynylene group is optionally substituted as described below by one or more of the following substituents: halo, cyano, nitro, oxo, thioxo, imino, oximo, trimethylsilanyl, —$OR^a$, —$SR^a$, —$OC(O)R^a$, —$OC(O)$—$OR^f$, —$N(R^a)_2$, —$N^+(R^a)_3$, —$C(O)R^a$, —$C(O)OR^a$, —$C(O)N(R^a)_2$, —$N(R^a)C(O)OR^f$, —$OC(O)$—$N(R^a)_2$, —$N(R^a)C(O)R^f$, —$N(R^a)S(O)_tR^f$ (where t is 1 or 2), —$S(O)_tOR^a$ (where t is 1 or 2), —$S(O)_tR$ (where t is 1 or 2) and —$S(O)_tN(R^a)_2$ (where t is 1 or 2) where each $R^a$ is independently hydrogen, alkyl, haloalkyl, cycloalkyl, aryl, aralkyl, heterocycloalkyl, heteroaryl or heteroarylalkyl, and each $R^f$ is independently alkyl, haloalkyl, cycloalkyl, aryl, aralkyl, heterocycloalkyl, heteroaryl or heteroarylalkyl.

"Alkoxy" or "alkoxyl" refers to a radical bonded through an oxygen atom of the formula —O-alkyl, where alkyl is an alkyl chain as defined above.

"Aminoalkyl" refers to an alkyl radical, as defined above, that is substituted by one or more amino radicals, as defined above, e.g., aminomethyl, 1-aminoethyl, 2-aminoethyl, 2-aminopropyl, 3-aminopropyl, 1,2-diaminoethyl, 2,3-diaminopropyl, 2,3,4,5,6-pentaaminohexyl, and the like.

The term "aromatic" refers to a planar ring having a delocalized p-electron system containing 4n+2 p electrons, where n is an integer. The term "aromatic" includes both carbocyclic aryl ("aryl", e.g., phenyl) and heterocyclic aryl (or "heteroaryl" or "heteroaromatic") groups (e.g., pyridine). The term includes monocyclic or fused-ring polycyclic (i.e., rings which share adjacent pairs of carbon atoms) groups.

"Aryl" refers to a radical derived from an aromatic monocyclic or multicyclic hydrocarbon ring system by removing a hydrogen atom from a ring carbon atom. The aromatic monocyclic or multicyclic hydrocarbon ring system contains only hydrogen and carbon atoms unless otherwise specified (i.e., from 6 to 18 carbon atoms), where at least one of the rings in the ring system is fully unsaturated, (i.e., it contains a cyclic, delocalized (4n+2) π-electron system in accordance with the Hückel theory). The ring system from which aryl groups are derived include, but are not limited to, groups such as benzene, fluorene, indane, indene, tetralin and naphthalene. In some embodiments, the aryl is a $C_6$-$C_{10}$ aryl. In one aspect, aryl is phenyl or a naphthyl. In some embodiments, the aryl is a phenyl. In some embodiments, an aryl is a phenyl, naphthyl, indanyl, indenyl, or tetrahydronaphthyl. Unless stated otherwise specifically in the specification, the term "aryl" or the prefix "ar-" (such as in "aralkyl") is meant to include aryl radicals optionally substituted as described below by one or more substituents independently selected from alkyl, alkenyl, alkynyl, halo, haloalkyl, cyano, nitro, aryl, aralkyl, aralkenyl, aralkynyl, cycloalkyl, heterocycloalkyl, heteroaryl, heteroarylalkyl, —$R^b$—$OR^a$, —$R^b$—$SR^a$, —$R^b$OC(O)—$R^a$, —$R^b$—OC(O)—$OR^f$, —$R^b$—OC(O)—$N(R^a)_2$, —$R^b$—$N(R^a)_2$, —$R^b$—$N^+(R^a)_3$, —$R^b$—$C(O)R^a$, —$R^b$—$C(O)OR^a$, —$R^b$—$C(O)N(R^a)_2$, —$R^b$—O—$R^c$—$C(O)N(R^a)_2$, —$R^b$—$N(R^a)C(O)OR^f$, —$R^b$—$N(R^a)C(O)R^a$, —$R^b$—$N(R^a)S(O)_tR^f$ (where t is 1 or 2), —$R^b$—$S(O)_tOR^a$ (where t is 1 or 2), —$R^b$—$S(O)_tR^f$ (where t is 1 or 2) and —$R^b$—$S(O)_tN(R^a)_2$ (where t is 1 or 2), where each $R^a$ is independently hydrogen, alkyl, haloalkyl, cycloalkyl, cycloalkylalkyl, aryl (optionally substituted with one or more halo groups), aralkyl, heterocycloalkyl, heteroaryl or heteroarylalkyl, $R^f$ is independently alkyl, haloalkyl, cycloalkyl, cycloalkylalkyl, aryl (optionally substituted with one or more halo groups), aralkyl, heterocycloalkyl, heteroaryl or heteroarylalkyl, each $R^b$ is independently a direct bond or a straight or branched alkylene or alkenylene chain, and $R^c$ is a straight or branched alkylene or alkenylene chain.

An "arylene" refers to a divalent radical derived from an "aryl" group as described above linking the rest of the molecule to a radical group. The arylene is attached to the rest of the molecule through a single bond and to the radical group through a single bond. In some embodiments, the arylene is a phenylene. Unless stated otherwise specifically in the specification, an arylene group is optionally substituted as described above for an aryl group.

"Cycloalkyl" refers to a stable, partially or fully saturated, monocyclic or polycyclic carbocyclic ring, which may include fused (when fused with an aryl or a heteroaryl ring, the cycloalkyl is bonded through a non-aromatic ring atom), bridged ring systems, and/or spirocyclic ring systems. Representative cycloalkyls include, but are not limited to, cycloalkyls having from three to fifteen carbon atoms ($C_3$-$C_{15}$ cycloalkyl), from three to ten carbon atoms ($C_3$-$C_{10}$ cycloalkyl), from three to eight carbon atoms ($C_3$-$C_8$ cycloalkyl), from three to six carbon atoms ($C_3$-$C_6$ cycloalkyl), from three to five carbon atoms ($C_3$-$C_5$ cycloalkyl), or three to four carbon atoms ($C_3$-$C_4$ cycloalkyl). In some embodiments, the cycloalkyl is a 3- to 6-membered cycloalkyl. In some embodiments, the cycloalkyl is a 5- to 6-membered cycloalkyl. Monocyclic cycloalkyls include, for example, cyclopropyl, cyclobutyl, cyclopentyl, cyclohexyl, cycloheptyl, and cyclooctyl. Polycyclic cycloalkyls or carbocycles include, for example, adamantyl, norbornyl, decalinyl, bicyclo[1.1.1]pentyl, bicyclo[3.3.0]octane, bicyclo[4.3.0]nonane, cis-decalin, trans-decalin, bicyclo[2.1.1]hexane, bicyclo[2.2.1]heptane, bicyclo[2.2.2]octane, bicyclo[3.2.2]nonane, and bicyclo[3.3.2]decane, 7,7-dimethyl-bicyclo[2.2.1]heptanyl, and the like. Unless otherwise stated specifically in the specification, the term "cycloalkyl" is meant to include cycloalkyl radicals optionally substituted as described below by one or more substituents independently selected from alkyl, alkenyl, alkynyl, halo, haloalkyl, cyano, nitro, aryl, aralkyl, aralkenyl, aralkynyl, cycloalkyl, heterocycloalkyl, heteroaryl, heteroarylalkyl, —$R^b$—$OR^a$, —$R^b$—$SR^a$, —$R^b$—$OC(O)$—$R^a$, —$R^b$—$OC(O)$—$OR^f$, —$R^b$—$OC(O)$—$N(R^a)_2$, —$R^b$—$N(R^a)_2$, —$R^b$—$N^+(R^a)_3$, —$R^b$—$C(O)R^a$, —$R^b$—$C(O)OR^a$, —$R^b$—$C(O)N(R^a)_2$, —$R^b$—$O$—$R^c$—$C(O)N(R^a)_2$, —$R^b$—$N(R^a)C(O)OR^f$, —$R^b$—$N(R^a)C(O)R^a$, —$R^b$—$N(R^a)S(O)_tR^f$ (where t is 1 or 2), —$R^b$—$S(O)OR^a$ (where t is 1 or 2), —$R^b$—$S(O)_tR^f$ (where t is 1 or 2) and —$R^b$—$S(O)_tN(R^a)_2$ (where t is 1 or 2), where each $R^a$ is independently hydrogen, alkyl, haloalkyl, cycloalkyl, cycloalkylalkyl, aryl (optionally substituted with one or more halo groups), aralkyl, heterocycloalkyl, heteroaryl or heteroarylalkyl, $R^f$ is independently alkyl, haloalkyl, cycloalkyl, cycloalkylalkyl, aryl (optionally substituted with one or more halo groups), aralkyl, heterocycloalkyl, heteroaryl or heteroarylalkyl, each $R^b$ is independently a direct bond or a straight or branched alkylene or alkenylene chain, and $R^c$ is a straight or branched alkylene or alkenylene chain.

A "cycloalkylene" refers to a divalent radical derived from a "cycloalkyl" group as described above linking the rest of the molecule to a radical group. The cycloalkylene is attached to the rest of the molecule through a single bond and to the radical group through a single bond. Unless stated otherwise specifically in the specification, a cycloalkylene group is optionally substituted as described above for a cycloalkyl group.

"Halo" or "halogen" refers to bromo, chloro, fluoro or iodo. In some embodiments, halogen is fluoro or chloro. In some embodiments, halogen is fluoro.

"Haloalkyl" refers to an alkyl radical, as defined above, that is substituted by one or more halo radicals, e.g., trifluoromethyl, difluoromethyl, fluoromethyl, trichloromethyl, 2,2,2-trifluoroethyl, 1,2-difluoroethyl, 3-bromo-2-fluoropropyl, 1,2-dibromoethyl, and the like.

"Fluoroalkyl" refers to an alkyl radical, as defined above, that is substituted by one or more fluoro radicals, as defined above, for example, trifluoromethyl, difluoromethyl, fluoromethyl, 2,2,2-trifluoroethyl, 1-fluoromethyl-2-fluoroethyl, and the like.

"Haloalkoxy" or "haloalkoxyl" refers to an alkoxyl radical, as defined above, that is substituted by one or more halo radicals, as defined above.

"Fluoroalkoxy" or "fluoroalkoxyl" refers to an alkoxy radical, as defined above, that is substituted by one or more fluoro radicals, as defined above, for example, trifluoromethoxy, difluoromethoxy, fluoromethoxy, and the like.

"Hydroxyalkyl" refers to an alkyl radical, as defined above, that is substituted by one or more hydroxy radicals, as defined above, e.g., hydroxymethyl, 1-hydroxyethyl, 2-hydroxyethyl, 2-hydroxypropyl, 3-hydroxypropyl, 1,2-dihydroxyethyl, 2,3-dihydroxypropyl, 2,3,4,5,6-pentahydroxyhexyl, and the like.

"Heterocycloalkyl" refers to a stable 3- to 24-membered partially or fully saturated ring radical comprising 2 to 23 carbon atoms and from one to 8 heteroatoms selected from the group consisting of nitrogen, oxygen, and sulfur. Unless stated otherwise specifically in the specification, the heterocycloalkyl radical may be a monocyclic, bicyclic, tricyclic or tetracyclic ring system, which may include fused (when fused with an aryl or a heteroaryl ring, the heterocycloalkyl is bonded through a non-aromatic ring atom), bridged ring systems, and/or spirocyclic ring systems; and the nitrogen, carbon or sulfur atoms in the heterocycloalkyl radical may be optionally oxidized; the nitrogen atom may be optionally quaternized. In some embodiments, the heterocycloalkyl is a 3- to 8-membered heterocycloalkyl. In some embodiments, the heterocycloalkyl is a 3- to 6-membered heterocycloalkyl. In some embodiments, the heterocycloalkyl is a 5- to 6-membered heterocycloalkyl. Examples of such heterocycloalkyl radicals include, but are not limited to, aziridinyl, azetidinyl, dioxolanyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuryl, trithianyl, tetrahydropyranyl, thiomorpholinyl, thiamorpholinyl, 1-oxo-thiomorpholinyl, 1,1-dioxo-thiomorpholinyl, 1,3-dihydroisobenzofuran-1-yl, 3-oxo-1,3-dihydroisobenzofuran-1-yl, methyl-2-oxo-1,3-dioxol-4-yl, and 2-oxo-1,3-dioxol-4-yl. The term heterocycloalkyl also includes all ring forms of the carbohydrates, including but not limited to the monosaccharides, the disaccharides and the oligosaccharides. More preferably, heterocycloalkyls have from 2 to 10 carbons in the ring. It is understood that when referring to the number of carbon atoms in a heterocycloalkyl, the number of carbon atoms in the heterocycloalkyl is not the same as the total number of atoms (including the heteroatoms) that make up the heterocycloalkyl (i.e., skeletal atoms of the heterocycloalkyl ring). Unless stated otherwise specifically in the specification, the term "heterocycloalkyl" is meant to include heterocycloalkyl radicals as defined above that are optionally substituted by one or more substituents selected from alkyl, alkenyl, alkynyl, halo, fluoroalkyl, oxo, thioxo, cyano, nitro, aryl, aralkyl, aralkenyl, aralkynyl, cycloalkyl, heterocycloalkyl, heteroaryl, heteroarylalkyl, —R—OR$^a$, —R$^b$—SR$^a$, —R$^b$—OC(O)—R$^a$, —R$^b$—OC(O)—OR$^f$, —R$^b$—OC(O)—N(R$^a$)$_2$, —R$^b$—N(R$^a$)$_2$, —R$^b$—N$^+$(R$^a$)$_3$, —R$^b$—C(O)R$^a$, —R$^b$—C(O)OR$^a$, —R$^b$—C(O)N(R$^a$)$_2$, —R$^b$—O—R$^c$—C(O)N(R$^a$)$_2$, —R$^b$—N(R$^a$)C(O)OR$^f$, —R$^b$—N(R$^a$)C(O)R$^a$, —R$^b$—N(R$^a$)S(O)$_t$R$^f$ (where t is 1 or 2), —R$^b$—S(O)$_t$OR$^a$ (where t is 1 or 2), —R$^b$—S(O)$_t$R$^f$ (where t is 1 or 2) and —R$^b$—S(O)$_t$N(R$^a$)$_2$ (where t is 1 or 2), where each R$^a$ is independently hydrogen, alkyl, haloalkyl, cycloalkyl, cycloalkylalkyl, aryl (optionally substituted with one or more halo groups), aralkyl, heterocycloalkyl, heteroaryl or heteroarylalkyl, R is independently alkyl, haloalkyl, cycloalkyl, cycloalkylalkyl, aryl (optionally substituted with one or more halo groups), aralkyl, heterocycloalkyl, heteroaryl or heteroarylalkyl, each R$^b$ is independently a direct bond or a straight or branched alkylene or alkenylene chain, and R$^c$ is a straight or branched alkylene or alkenylene chain.

"N-heterocycloalkyl" refers to a heterocycloalkyl radical as defined above containing at least one nitrogen and where the point of attachment of the heterocycloalkyl radical to the rest of the molecule is through a nitrogen atom in the heterocycloalkyl radical. An N-heterocycloalkyl radical is optionally substituted as described above for heterocycloalkyl radicals.

"C-heterocycloalkyl" refers to a heterocycloalkyl radical as defined above and where the point of attachment of the heterocycloalkyl radical to the rest of the molecule is through a carbon atom in the heterocycloalkyl radical. A C-heterocycloalkyl radical is optionally substituted as described above for heterocycloalkyl radicals.

A "heterocycloalkylene" refers to a divalent radical derived from a "heterocycloalkyl" group as described above linking the rest of the molecule to a radical group. The heterocycloalkylene is attached to the rest of the molecule through a single bond and to the radical group through a single bond. Unless stated otherwise specifically in the specification, a heterocycloalkylene group is optionally substituted as described above for a heterocycloalkyl group.

"Heteroaryl" refers to a radical derived from a 5- to 18-membered aromatic ring radical that comprises one to seventeen carbon atoms and from one to six heteroatoms selected from nitrogen, oxygen and sulfur. As used herein, the heteroaryl radical is a monocyclic, bicyclic, tricyclic or tetracyclic ring system, wherein at least one of the rings in the ring system is fully unsaturated, i.e., it contains a cyclic, delocalized (4n+2) π-electron system in accordance with the Hückel theory. In some embodiments, the heteroaryl is a 5- to 10-membered heteroaryl. In some embodiments, the heteroaryl is a monocyclic heteroaryl, or a monocyclic 5- or 6-membered heteroaryl. In some embodiments, the heteroaryl is a 6,5-fused bicyclic heteroaryl. Illustrative examples of heteroaryl groups include monocyclic heteroaryls and bicyclic heteroaryls. Monocyclic heteroaryls include pyridinyl, imidazolyl, pyrimidinyl, pyrazolyl, triazolyl, pyrazinyl, tetrazolyl, furyl, thienyl, isoxazolyl, thiazolyl, oxazolyl, isothiazolyl, pyrrolyl, pyridazinyl, triazinyl, oxadiazolyl, thiadiazolyl, and furazanyl. Bicyclic heteroaryls include indolizinyl, indolyl, benzofuranyl, benzothiophenyl, indazolyl, benzimidazolyl, purinyl, quinolizinyl, quinolinyl, isoquinolinyl, cinnolinyl, phthalazinyl, quinazolinyl, quinoxalinyl, 1,8-naphthyridinyl, and pteridinyl. In some embodiments, a heteroaryl contains 0-4 N atoms in the ring. In some embodiments, a heteroaryl contains 1-4 N atoms in the ring. In some embodiments, a heteroaryl contains 0-4 N atoms, 0-1 O atoms, and 0-1 S atoms in the ring. In some embodiments, a heteroaryl contains 1-4 N atoms, 0-1 O atoms, and 0-1 S atoms in the ring. In some embodiments, heteroaryl is a $C_1$-$C_9$ heteroaryl. In some embodiments, monocyclic heteroaryl is a $C_1$-$C_5$ heteroaryl. In some embodiments, monocyclic heteroaryl is a 5-membered or 6-membered heteroaryl. In some embodiments, bicyclic heteroaryl is a $C_6$-$C_9$ heteroaryl. The heteroatom(s) in the heteroaryl radical is optionally oxidized. The carbon atom(s) in the heteroaryl is optionally oxidized. Two non-limiting examples of heteroaryl radicals that are oxidized and are encompassed by the term heteroaryl are pyridone and pyridine N-oxide. One or more nitrogen atoms, if present, are optionally quaternized. The heteroaryl is attached to the rest of the molecule through any atom of the ring(s). Unless stated otherwise specifically in the specification, the term "heteroaryl" is meant to include heteroaryl radicals as defined above that are optionally substituted by one or more substituents selected from alkyl, alkenyl, alkynyl, halo, haloalkyl, oxo, thioxo, cyano, nitro, aryl, aralkyl, aralkenyl, aralkynyl, cycloalkyl, heterocycloalkyl, heteroaryl, heteroarylalkyl, —R—OR$^a$, —R$^b$—SR$^a$, —R$^b$—OC(O)—R$^a$, —R$^b$—OC(O)—OR$^f$, —R$^b$—OC(O)—N(R$^a$)$_2$, —R$^b$—N(R$^a$)$_2$, —R$^b$—N$^+$(R$^a$)$_3$, —R$^b$—C(O)R$^a$, —R$^b$—C(O)OR$^a$, —R$^b$—C(O)N(R$^a$)$_2$, —R$^b$—O—R$^c$—C(O)N(R$^a$)$_2$, —R$^b$—N(R$^a$)C(O)OR$^f$, —R$^b$—N(R$^a$)C(O)R$^a$, —R$^b$—N(R$^a$)S(O)$_t$R$^f$ (where t is 1 or 2), —R$^b$—S(O)$_t$OR$^a$ (where t is 1 or 2), —R$^b$—S(O)$_t$R$^f$ (where t is 1 or 2) and —R$^b$—S(O)$_t$N(R$^a$)$_2$ (where t is 1 or 2), where each R$^a$ is independently hydrogen, alkyl, haloalkyl, cycloalkyl, cycloalkylalkyl, aryl (optionally substituted with one or more halo groups), aralkyl, heterocycloalkyl, heteroaryl or heteroarylalkyl, R is independently alkyl, haloalkyl, cycloalkyl, cycloalkylalkyl, aryl (optionally substituted with one or more halo groups), aralkyl, heterocycloalkyl, heteroaryl or heteroarylalkyl, each R$^b$ is independently a direct bond or a straight or branched alkylene or alkenylene chain, and R$^c$ is a straight or branched alkylene or alkenylene chain.

A "heteroarylene" refers to a divalent radical derived from a "heteroaryl" group as described above linking the rest of the molecule to a radical group. The heteroarylene is attached to the rest of the molecule through a single bond and to the radical group through a single bond. Unless stated otherwise specifically in the specification, a heteroarylene group is optionally substituted as described above for a heteroaryl group.

The term "optional" or "optionally" means that the subsequently described event or circumstance may or may not occur, and that the description includes instances where said event or circumstance occurs and instances in which it does not. For example, "optionally substituted alkyl" means either "alkyl" or "substituted alkyl" as defined above. Further, an optionally substituted group may be unsubstituted (e.g., —CH$_2$CH$_3$), fully substituted (e.g., —CF$_2$CF$_3$), mono-substituted (e.g., —CH$_2$CH$_2$F) or substituted at a level anywhere in-between fully substituted and mono-substituted (e.g., —CH$_2$CHF$_2$, —CH$_2$CF$_3$, —CF$_2$CH$_3$, —CFHCHF$_2$, etc.). It will be understood by those skilled in the art with respect to any group containing one or more substituents that such groups are not intended to introduce any substitution or substitution patterns (e.g., substituted alkyl includes optionally substituted cycloalkyl groups, which in turn are defined as including optionally substituted alkyl groups, potentially ad infinitum) that are sterically impractical and/or synthetically non-feasible.

The term "salt" or "pharmaceutically acceptable salt" refers to salts derived from a variety of organic and inorganic counter ions well known in the art. Pharmaceutically acceptable acid addition salts can be formed with inorganic acids and organic acids. Pharmaceutically acceptable base addition salts can be formed with inorganic and organic bases.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically acceptable excipient" or "pharmaceutically acceptable carrier" as used herein means a pharmaceutically acceptable material, composition or vehicle, such as a liquid or solid filler, diluent, excipient, solvent or encapsulating material. Each carrier must be "acceptable" in the sense of being compatible with the other ingredients of the formulation and not injurious to the patient.

The term "preventing" is art-recognized, and when used in relation to a condition, such as headache, is well understood in the art, and includes administration of a composition which reduces the frequency of, or delays the onset of, symptoms of a medical condition in a subject relative to a subject which does not receive the composition. Thus, prevention of headache includes, for example, reducing the number of patients suffering from headaches in a population of patients receiving a prophylactic treatment relative to an untreated control population. Prevention of a headache condition also includes, for example, reducing the number of diagnoses of the headache condition in a treated population versus an untreated control population, and/or delaying the onset of symptoms of the headache condition in a treated population versus an untreated control population.

As used herein, the phrase "therapeutically effective amount," means the amount of a compound that, when administered to a patient for treating a disease, is sufficient to treat the disease or condition. The "therapeutically effective amount" will vary depending on the compound, the disease and its severity and the age, weight, adsorption, distribution, metabolism and excretion etc., of the patient to be treated.

As used herein, "treatment" or "treating" refers to an approach for obtaining beneficial or desired results with respect to a disease, disorder, or medical condition including, but not limited to, a therapeutic benefit. In certain embodiments, treatment or treating involves administering a compound or composition described herein to a subject. A therapeutic benefit may include the eradication or amelioration of the underlying disorder being treated.

As used herein, "modulate" refers to alteration of the activity or the expression of target protein/gene in the presence of a composition, relative to the comparable conditions in the absence of the composition. As used herein, the term "modulate" can be up-regulation (e.g., activation or stimulation) or down-regulation (e.g., inhibition or suppression). For example, modulation may cause a change in cellular level of the target protein or a change in expression of the target gene, stability of protein, enzymatic modification (e.g., phosphorylation) of the target protein, binding characteristics (e.g., binding to a target transcription regulatory element), or any other biological, functional, or immunological properties of the target protein. The change in activity can arise from, for example, an increase or decrease in expression of the target gene, the stability of mRNA that encodes the target protein, translation efficiency, or from a change in other bioactivities of the target protein transcription factor (e.g., regulating expression of the target protein-responsive gene). The mode of action of a target gene/protein modulator can be direct, e.g., through binding to the target protein or to genes encoding the target protein. The change can also be indirect, e.g., through binding to and/or modifying (e.g., enzymatically) another molecule which otherwise modulates target gene/protein (e.g., a kinase that specifically phosphorylates target protein).

As used herein, the term "administer", "administered", "administration", or "to administer" refers to the step of giving (i.e. administering) a pharmaceutical composition to a subject, or alternatively a subject receiving a pharmaceutical composition. The pharmaceutical compositions described herein can be locally administered by various methods. For example, intramuscular, intradermal, subcutaneous administration, intrathecal administration, intraperitoneal administration, topical (transdermal), instillation, and implantation (for example, of a slow-release device such as polymeric implant or miniosmotic pump) can all be appropriate routes of administration.

The terms "subject," "individual," and "patient" may be used interchangeably and refer to humans, as well as non-human mammals (e.g., non-human primates, canines, equines, felines, porcines, bovines, ungulates, lagomorphs, rodents, and the like). In various embodiments, the subject can be a human (e.g., adult male, adult female, adolescent male, adolescent female, male child, female child) under the care of a physician or other health worker in a hospital, as an outpatient, or other clinical context. In certain embodiments, the subject may not be under the care or prescription of a physician or other health worker.

As used herein, the phrase "a subject in need thereof" refers to a subject, as described infra, that suffers from, or is at risk for, a pathology to be prophylactically or therapeutically treated with a therapeutic protein described herein.

The term "specificity," as used herein, refers to the ability of a protein binding domain, in particular, an immunoglobulin or an immunoglobulin fragment, such as a nanobody, to bind preferentially to one antigen versus a different antigen, and does not necessarily imply high affinity.

The term "agonism" as used herein refers to the activation of a receptor or enzyme by a modulator, or agonist, to produce a biological response.

The term "agonist" as used herein refers to a modulator that binds to a receptor or target enzyme and activates the receptor or enzyme to produce a biological response. By way of example, "NK3 agonist" can be used to refer to a compound that exhibits an $EC_{50}$ with respect to NK3 activity of no more than about 100 µM, as measured in the as measured in the inositol phosphate accumulation assay. In some embodiments, the term "agonist" includes full agonists or partial agonists.

The term "full agonist" refers to a modulator that binds to and activates a receptor or target enzyme with the maximum response that an agonist can elicit at the receptor or enzyme.

The term "partial agonist" refers to a modulator that binds to and activates a receptor or target enzyme, but has partial efficacy, that is, less than the maximal response, at the receptor or enzyme relative to a full agonist.

The term "positive allosteric modulator" refers to a modulator that binds to a site distinct from the orthosteric binding site and enhances or amplifies the effect of an agonist.

The term "antagonism" as used herein refers to the inactivation of a receptor or target enzyme by a modulator, or antagonist. Antagonism of a receptor, for example, is when a molecule binds to the receptor or target enzyme and does not allow activity to occur.

The term "antagonist" or "neutral antagonist" as used herein refers to a modulator that binds to a receptor or target enzyme and blocks a biological response. By way of example, NK3 antagonist can be used to refer to a compound that exhibits an $IC_{50}$ with respect to NK3 activity less than about 1 µM, about 2 µM, about 3 µM, about 4 µM, about 5 µM, about 6 µM, about 7 µM, about 8 µM, about 9 µM, or about 10 µM, as measured in the FLIPR calcium assay. In some embodiments, NK3 antagonist can be used to refer to a compound that exhibits an $IC_{50}$ with respect to NK3 activity less than about 10 µM as measured in the FLIPR calcium assay. In some embodiments, NK3 antagonist can be used to refer to a compound that exhibits an $IC_{50}$ with respect to NK3 activity less than about 1 µM as measured in the FLIPR calcium assay. An antagonist has no activity in the absence of an agonist or inverse agonist but can block the activity of either, causing no change in the biological response.

The term "inverse agonist" refers to a modulator that binds to the same receptor or target enzyme as an agonist but induces a pharmacological response opposite to that agonist, i.e., a decrease in biological response.

The term "negative allosteric modulator" refers to a modulator that binds to a site distinct from the orthosteric binding site and reduces or dampens the effect of an agonist.

As used herein, "EC50" is intended to refer to the concentration of a substance (e.g., a compound or a drug) that is required for 50% activation or enhancement of a biological process. In some instances, EC50 refers to the concentration of agonist that provokes a response halfway between the baseline and maximum response in an in vitro assay. In some embodiments as used herein, EC50 refers to the concentration of an agonist (e.g., a NK3 agonist) that is required for 50% activation of a receptor or target enzyme (e.g., NK3). Likewise, in some embodiments as used herein, "EC70" refers to the concentration of an agonist (e.g., a NK3 agonist) that is required for 70% activation of a receptor or target enzyme (e.g., NK3).

As used herein, "IC50" is intended to refer to the concentration of a substance (e.g., a compound or a drug) that is required for 50% inhibition of a biological process. For example, IC50 refers to the half maximal (50%) inhibitory concentration (IC) of a substance as determined in a suitable assay. In some instances, an IC50 is determined in an in vitro assay system. In some embodiments as used herein, IC50 refers to the concentration of a modulator (e.g., a NK3 antagonist) that is required for 50% inhibition of a receptor or a target enzyme (e.g., NK3).

The terms "subject," "individual," and "patient" are used interchangeably. These terms encompass mammals. Examples of mammals include, but are not limited to, any member of the Mammalian class: humans, non-human primates such as chimpanzees, and other apes and monkey species; farm animals such as cattle, horses, sheep, goats, swine; domestic animals such as rabbits, dogs, and cats; laboratory animals including rodents, such as rats, mice and guinea pigs, and the like. In some embodiment, the subject or mammal is a human.

NK3 Modulators

In some embodiments, a compound described herein, or a pharmaceutically acceptable salt or solvate thereof, is a therapeutic agent. In some embodiments, the compound described herein, or a pharmaceutically acceptable salt or solvate thereof, is an NK3 modulator. In some embodiments, the compound described herein, or a pharmaceutically acceptable salt or solvate thereof, modulates activity of an NK3 protein. In some embodiments, the compound described herein, or a pharmaceutically acceptable salt or solvate thereof, is an NK3 antagonist.

The methods of the present disclosure comprise administration of a compound described herein, or a pharmaceutically acceptable salt or solvate thereof, that may modulate activity of an NK3 protein. In some embodiments, at a therapeutically effective concentration, a compound described herein, or a pharmaceutically acceptable salt or solvate thereof, modulates NK3 protein activity by at least about 1%, at least about 2%, at least about 3%, at least about 4%, at least about 5%, at least about 10%, at least about 20%, at least about 30%, at least about 40%, at least about 50%, at least about 60%, at least about 70%, at least about 80%, at least about 90%, at least about 95%, at least about 99%, or about 100%, relative to NK3 protein activity in a standard.

NK3 signaling has distinct functions in the Central Nervous System (CNS), where its regulation of KNDy (kisspeptin, NKB, dynorphin) neurons in the hypothalamus regulates gonadotropin releasing hormone (GnRH) that ultimately controls pulsatile pituitary secretions of LH. See Uenoyama, Y., Nagae, M., Tsuchida, H., Inoue, N. & Tsukamura, H., *Role of KNDy Neurons Expressing Kisspeptin, Neurokinin B, and Dynorphin A as a GnRH Pulse Generator Controlling Mammalian Reproduction.* 12 FRONT. ENDOCRINOL. 724632 (2021); Depypere, H., Lademacher, C., Siddiqui, E. & Fraser, G. L. *Fezolinetant in the treatment of vasomotor symptoms associated with menopause,* 30 EXPERT OPIN. INVESTIG. DRUGS 681-694 (2021) (hereinafter "Depypere 2021"). To avoid unwanted side effects associated with affecting the secretions of these gonadotropins, in some embodiments, a compound described herein, or a pharmaceutically acceptable salt or solvate thereof, selectively modulates NK3 in peripheral tissues over NK3 in the CNS. In some embodiments, a compound described herein, or a pharmaceutically acceptable salt or solvate thereof, selectively modulates NK3 in the peripheral nervous system over NK3 in the CNS In some embodiments, administration of a compound described herein, or a pharmaceutically acceptable salt or solvate thereof, selectively modulates activity of the NK3 protein in peripheral tissues relative to the central nervous system. In some embodiments, administration of a compound described herein, or a pharmaceutically acceptable salt or solvate thereof, does not cause one or more pharmacological effects associated with NK3 modulation in the CNS. In some embodiments, administration of a compound described herein, or a pharmaceutically acceptable salt or solvate thereof, does not cause one or more pharmacological effects selected from thermoregulatory dysfunction, bone mineral density, paresthesia, thrombophlebitis, and change in gonadotropin levels (e.g., luteinizing hormone).

In some embodiments, a compound described herein, or a pharmaceutically acceptable salt or solvate thereof, is restricted to peripheral tissues. In some embodiments, a compound described herein, or a pharmaceutically acceptable salt or solvate thereof, is restricted to the peripheral nervous system. In some embodiments, a compound described herein, or a pharmaceutically acceptable salt or solvate thereof, does not substantially cross the blood brain barrier. In some embodiments, administration of a compound described herein, or a pharmaceutically acceptable salt or solvate thereof, results in a ratio of blood plasma concentration to brain tissue concentration in the subject of, for example, at least about 2:1, at least about 3:1, at least about 4:1, at least about 5:1, at least about 10:1, at least about 15:1, at least about 20:1, at least about 25:1, at least about 50:1, at least about 75:1, at least about 100:1, at least about 150:1, at least about 200:1, at least about 250:1, at least about 300:1, at least about 350:1, at least about 400:1, at least about 450:1, at least about 500:1, or at least about 1000:1. In some embodiments, administration of a compound described herein, or a pharmaceutically acceptable salt or solvate thereof, results in a ratio of blood plasma concentration to brain tissue concentration in the subject of at least about 10:1. In further embodiments, the administration of a compound described herein, or a pharmaceutically acceptable salt or solvate thereof, results in a ratio of blood plasma concentration to brain tissue concentration in the subject of at least about 50:1. In further embodiments, the administration of a compound described herein, or a pharmaceutically acceptable salt or solvate thereof, results in a ratio of blood plasma concentration to brain tissue concentration in the subject of at least about 100:1.

In some embodiments, administration of a compound described herein, or a pharmaceutically acceptable salt or solvate thereof, results in a ratio of blood plasma concentration to brain tissue concentration in the subject of, for example, from about 2:1 to about 1000:1, from about 2:1 to about 500:1, from about 2:1 to about 250:1, from about 2:1 to about 100:1, from about 2:1 to about 75:1, from about 2:1 to about 50:1, from about 2:1 to about 25:1, from about 2:1 to about 20:1, from about 2:1 to about 15:1, from about 2:1 to about 10:1, from about 2:1 to about 5:1, from about 2:1 to about 4:1, or from about 2:1 to about 3:1. In some embodiments, administration of a compound described herein, or a pharmaceutically acceptable salt or solvate thereof, results in a ratio of blood plasma concentration to brain tissue concentration in the subject of, for example, from about 4:1 to about 1000:1, from about 4:1 to about 500:1, from about 4:1 to about 250:1, from about 4:1 to about 100:1, from about 4:1 to about 75:1, from about 4:1 to about 50:1, from about 4:1 to about 25:1, from about 4:1 to about 20:1, from about 4:1 to about 15:1, from about 4:1 to about 10:1, or from about 4:1 to about 5:1. In some embodiments, administration of a compound described herein, or a pharmaceutically acceptable salt or solvate thereof, results in a ratio of blood plasma concentration to brain tissue concentration in the subject of, for example, from about 10:1 to about 1000:1, from about 10:1 to about 500:1, from about 10:1 to about 250:1, from about 10:1 to about 100:1, from about 10:1 to about 75:1, from about 10:1 to about 50:1, from about 10:1 to about 25:1, from about 10:1 to about 20:1, or from about 10:1 to about 15:1. In some embodiments, administration of a compound described herein, or a pharmaceutically acceptable salt or solvate thereof, results in a ratio of blood plasma concentration to brain tissue concentration in the subject of, for example, from about 2:1 to about 20:1.

In some instances, P-glycoprotein (P-gp) at the blood-brain barrier (BBB) is an efflux transporter that functions to actively pump small-molecule compounds from brain tissue to the blood stream. In some instances, in vitro P-gp substrate assessment is used to predict the in vivo relevance of P-gp-mediated efflux at the BBB. In some instances, central nervous system (CNS) drugs are not substrates of P-gp (efflux ratio<2) while peripherally restricted compounds are P-gp substrates (efflux ratio 2). In some embodiments, a compound described herein, or a pharmaceutically acceptable salt or solvate thereof, has an efflux ratio of at least 2, at least 3, at least 4, at least 5, at least 10, at least 15, at least 20, at least 25, at least 30, or more, as measured in a P-gp substrate assessment study.

In some embodiments, the compound described herein, or a pharmaceutically acceptable salt or solvate thereof, is a peripherally restricted NK3 modulator. In some embodiments, the compound described herein, or a pharmaceutically acceptable salt or solvate thereof, is a peripherally restricted NK3 modulator (e.g., does not accumulate to a clinically significant concentration in the brain). In some embodiments, the use of a peripherally restricted NK3 modulator minimizes or avoids unwanted side effects associated with NK3 modulation in the CNS (e.g., changes in gonadotropin levels such as LH). Such side effects include thermoregulatory dysfunction, change in bone mineral density, paresthesia, thrombophlebitis, and change in one or more gonadotropin levels. In some embodiments, administration of the NK3 modulators disclosed herein lack one or more of the following side effects: bone mineral density changes, paresthesia, thrombophlebitis, infertility, changes in sex drive, menstrual cycle abnormalities (e.g. delayed or blocked ovulation), changes in testosterone levels, testicular shrinkage, and changes in gonadotropin levels (e.g., luteinizing hormone). In some embodiments, administration of the compound described herein, or a pharmaceutically acceptable salt or solvate thereof, do not reduce LH levels in the subject.

In some embodiments, administration of a compound described herein, or a pharmaceutically acceptable salt or solvate thereof, does not reduce luteinizing hormone in the subject at the therapeutically effective amount. In some embodiments, administration of a therapeutically effective amount of a compound described herein, or a pharmaceutically acceptable salt or solvate thereof, reduces luteinizing hormone in the subject, for example, by less than 1%, less than 2%, less than 3%, less than 4%, less than 5%, less than 6%, less than 7%, less than 8%, less than 9%, less than 10%, less than 11%, less than 12%, less than 13%, less than 14%, less than 15%, less than 20%, less than 25%, less than 30%, less than 35%, less than 40%, less than 45%, or less than 50%. In some embodiments, administration of a therapeutically effective amount of a compound described herein, or a pharmaceutically acceptable salt or solvate thereof, reduces the concentration of luteinizing hormone a sample obtained from the subject, for example, by less than 1%, less than 2%, less than 3%, less than 4%, less than 5%, less than 6%, less than 7%, less than 8%, less than 9%, less than 10%, less than 11%, less than 12%, less than 13%, less than 14%, less than 15%, less than 20%, less than 25%, less than 30%, less than 35%, less than 40%, less than 45%, or less than 50%. In some embodiments, the administration of a compound described herein, or a pharmaceutically acceptable salt or solvate thereof, at the therapeutic level reduces luteinizing hormone in the subject by less than about 50%, less than about 45%, less than about 40%, less than about 35%, less than about 30%, less than about 25%, less than about 20%, less than about 15%, less than about 10%, less than about 9%, less than about 8, less than about 7%, less than about 6%, less than about 5%, less than about 4%, less than about 3%, less than about 2%, less than about 1%, or less than about 0.5%. In some embodiments, the sample comprises, for example, blood, blood plasma, urine, mucus, or saliva. The foregoing examples are merely exemplary and are not intended to limit the scope of the present disclosure.

In some embodiments, the compounds described herein (e.g., a compound of Formula (I)) selectively bind to NK3 over NK2. In some embodiments, the compounds described herein (e.g., a compound of Formula (I)) selectively bind to NK3 over NK1. In some embodiments, the compounds described herein (e.g., a compound of Formula (I)) selectively bind to NK3 over NK1 and NK2. In some embodiments, the compounds described herein (e.g., a compound of Formula (I)) selectively bind to NK3 over NK2 with at least 2-fold, at least 3-fold, at least 5-fold, at least 10-fold, at least 25-fold, at least 50-fold, at least 100-fold, or greater than 100-fold selectivity for NK3 over NK2. In some embodiments, the compounds described herein (e.g., a compound of Formula (I)) selectively bind to NK3 over NK1 with at least 2-fold, at least 3-fold, at least 5-fold, at least 10-fold, at least 25-fold, at least 50-fold, at least 100-fold, or greater than 100-fold selectivity for NK3 over NK1. In some embodiments, the compounds described herein (e.g., a compound of Formula (I)) selectively bind to NK3 over both NK1 and NK2 with at least 2-fold, at least 3-fold, at least 5-fold, at least 10-fold, at least 25-fold, at least 50-fold, at least 100-fold, or greater than 100-fold selectivity for NK3 over both NK1 and NK2.

In some embodiments, the compounds described herein (e.g., a compound of Formula (I)) selectively modulate the activity NK3 over the activity of NK2. In some embodiments, the compounds described herein (e.g., a compound of Formula (I)) selectively inhibit the activity NK3 over the activity of NK1. In some embodiments, the compounds described herein (e.g., a compound of Formula (I)) selectively inhibit the activity NK3 over the activity of both NK1 and NK2. In some embodiments, the compounds described herein (e.g., a compound of Formula (I)) selectively inhibit the activity NK3 over the activity of NK2. In some embodiments, the compounds described herein (e.g., a compound of Formula (I)) selectively modulate the activity NK3 over the activity of NK1. In some embodiments, NK2 is neurokinin receptor 2. In some embodiments, NK1 is neurokinin receptor 1. In some embodiments, the compounds described herein (e.g., a compound of Formula (I)) selectively inhibit the activity of NK3 over the activity of NK2 by at least 2-fold, at least 3-fold, at least 5-fold, at least 10-fold, at least 25-fold, at least 50-fold, at least 100-fold, or greater than 100-fold. In some embodiments, the compounds described herein (e.g., a compound of Formula (I)) selectively inhibit the activity of NK3 over the activity of NK2 by at least 2-fold, at least 3-fold, at least 5-fold, at least 10-fold, at least 25-fold, at least 50-fold, at least 100-fold, or greater than 100-fold. In some embodiments, the compounds described herein (e.g., a compound of Formula (I)) selectively inhibit the activity of NK3 over the activity of both NK1 and NK2 by at least 2-fold, at least 3-fold, at least 5-fold, at least 10-fold, at least 25-fold, at least 50-fold, at least 100-fold, or greater than 100-fold.

Treatment of Headache Disorders

Provided herein are methods for treating a disease or condition in a subject in need thereof, comprising administering to the subject a therapeutically effective amount of a compound described herein, or a pharmaceutically acceptable salt or solvate thereof. In some embodiments, the compound described herein, or a pharmaceutically acceptable salt or solvate thereof, modulates activity of a NK3 protein in a subject in need thereof. In some embodiments, the disease or condition is a headache disorder. In some embodiments, the disease or condition is selected from migraine, medication overuse headache, cluster headache, general headache, tension headache, caffeine headache, hormone headache, hemicrania continua, hypertension headache, rebound headache, post-traumatic headache, exertion headache, spinal headache, thunderclap headache, icepick headache, trigeminal neuralgia, orofacial pain (e.g., chronic orofacial pain), or a combination of two or more of these diseases or conditions. Non-limiting examples of said combinations include migraine and general headache, general headache and trigeminal neuralgia, and cluster headache and orofacial pain. In some embodiments, the disease or condition is selected from the group consisting of: migraine, medication overuse headache, cluster headache, general headache, trigeminal neuralgia, and orofacial pain. In further embodiments, the disease or condition is migraine. In some embodiments, the subject is a mammal. In some embodiments, the subject is a human.

In some embodiments, the compounds described herein, or a pharmaceutically acceptable salt or solvate thereof, are used in the preparation of medicaments for the prevention or treatment of diseases or conditions. In some embodiments, the compounds described herein, or a pharmaceutically acceptable salt or solvate thereof, are used in the preparation of medicaments for the prevention or treatment of headache disorders. In some embodiments, the compounds described herein, or a pharmaceutically acceptable salt or solvate thereof, are used in the preparation of medicaments for the prevention or treatment of a disease or condition selected from migraine, medication overuse headache, cluster headache, general headache, tension headache, caffeine headache, hormone headache, hemicrania continua, hypertension headache, rebound headache, post-traumatic headache, exertion headache, spinal headache, thunderclap headache, icepick headache, trigeminal neuralgia, orofacial pain, or a combination of two or more of these diseases or conditions.

Described herein in some embodiments is a compound of Formula (I) for use in treating or preventing a disease or condition. Described herein in some embodiments a compound of Formula (I) for use in treating or preventing a headache disorder. In some embodiments, the present disclosure provides a compound of Formula (I) for use in the treatment or prevention of a disease or condition selected from the group consisting of migraine, medication overuse headache, cluster headache, general headache, trigeminal neuralgia, and orofacial pain.

In some embodiments, compositions comprising a compound described herein, or a pharmaceutically acceptable salt or solvate thereof, and at least one pharmaceutically acceptable excipient, are administered for prophylactic and/or therapeutic treatments. In some embodiments, a compound described herein, or a pharmaceutically acceptable salt or solvate thereof, is administered to a patient already suffering from a headache disorder, in an amount sufficient to cure or at least partially arrest one or more symptoms of the headache disorder. Amounts effective for this use will depend on the severity and course of the disease or condition, previous therapy, the patient's health status, weight, and response to the drugs, and the judgment of the treating physician.

In some embodiments, administration of a compound described herein, or a pharmaceutically acceptable salt or solvate thereof, results in cessation or reduction of one or more symptoms of a headache disorder. In some embodiments, administration of a compound described herein, or a pharmaceutically acceptable salt or solvate thereof, results in cessation or reduction of one or more symptoms of a disease or condition selected from migraine, medication overuse headache, cluster headache, general headache, trigeminal neuralgia, and orofacial pain. In some embodiments, administration of a compound described herein, or a pharmaceutically acceptable salt or solvate thereof, results in cessation or reduction of one or more symptoms selected from pain, sensitivity to light, sensitivity to sound, sensitivity to smell, aura, nausea, vomiting, agitation, vertigo, lightheadedness, muscle stiffness, muscle spasm, swelling, numbness, scalp tenderness and nasal congestion. In some embodiments, administration of a compound described herein, or a pharmaceutically acceptable salt or solvate thereof, results in cessation or reduction of one or more symptoms selected from pain, sensitivity to light, sensitivity to sound, nausea, and vomiting. In some embodiments, administration of a compound described herein, or a pharmaceutically acceptable salt or solvate thereof, results in cessation or reduction of pain (e.g., pain associated with a headache disorder). In some embodiments, administration of a compound described herein, or a pharmaceutically acceptable salt or solvate thereof, results in freedom from pain.

In prophylactic applications, compositions comprising a compound described herein, or a pharmaceutically acceptable salt or solvate thereof, and at least one pharmaceutically acceptable excipient, are administered to a patient susceptible to or otherwise at risk of a disorder or condition (e.g. a headache disorder). Such an amount is defined to be a "prophylactically effective amount or dose." In this use, the precise amounts also depend on the patient's state of health, weight, and the like. When used in a patient, effective amounts for this use will depend on the severity and course of the disease, disorder or condition, previous therapy, the patient's health status and response to the drugs, and the judgment of the treating physician.

A compound described herein, or a pharmaceutically acceptable salt or solvate thereof, may be administered to the subject using different administration routes, including oral, transmucosal, topical, transdermal, inhalation, intravenous, subcutaneous, intradermal, intramuscular, intra-articular, perineural, intraventricular, intravenous, intraperitoneal, intranasal, and intraocular.

Compounds

Disclosed herein, in certain embodiments, is a compound of Formula (I):

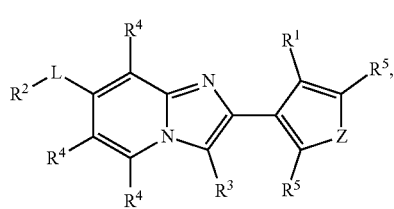

Formula (I)

or a pharmaceutically acceptable salt or solvate thereof, wherein:

Z is a bivalent group selected from —S—, —N=C($R^5$)—, —C($R^5$)=N—, or —C($R^5$)=C($R^5$)—;

$R^1$ is pyrazole, wherein said pyrazole is optionally substituted with 1-3 groups independently selected from $R^6$;

$R^2$ is $C_1$-$C_{10}$ alkyl, $C_1$-$C_{10}$ heteroalkyl, —C(=O)$OR^7$, —C(=O)N($R^8$)($R^7$), —N($R^8$)($R^7$), —C(=N$R^9$)N($R^8$)($R^7$), —N($R^7$)C(=N$R^9$)N($R^8$)($R^7$), $C_6$-$C_{10}$ aryl, 5- to 10-membered heteroaryl, $C_3$-$C_{12}$ cycloalkyl, or 3-to-15 membered heterocycloalkyl, wherein the aryl, and heteroaryl is optionally substituted with 1-4 groups independently selected from $R^{10}$, and the alkyl, heteroalkyl, cycloalkyl, and heterocycloalkyl is optionally substituted with 1-4 groups independently selected from oxo and $R^{10}$;

$R^3$ is halogen, cyano, —C(=O)OH, —C(=O)O($C_1$-$C_6$ alkyl), $C_1$-$C_6$ alkyl, $C_1$-$C_6$ alkenyl, —O($C_1$-$C_6$ alkyl), $C_3$-$C_6$ cycloalkyl, or $C_1$-$C_6$ haloalkyl;

each $R^4$ is independently hydrogen, halogen, $C_1$-$C_6$ alkyl, —O—$C_1$-$C_6$ alkyl, $C_1$-$C_6$ haloalkyl, or —O—($C_1$-$C_6$ haloalkyl);

L is a bond, $C_1$-$C_2$ alkylene, or $C_3$-$C_6$ cycloalkylene, wherein said alkylene, or cycloalkylene is optionally substituted with 1 or 2 —OH groups;

each $R^5$ is independently hydrogen, cyano, halogen, $C_1$-$C_6$ alkyl, —O($C_1$-$C_6$ alkyl), $C_3$-$C_6$ cycloalkyl, $C_1$-$C_6$ haloalkyl, or —O($C_1$-$C_6$ haloalkyl);

each $R^6$ is independently selected from the group consisting of halogen, hydroxy, cyano, amino, $C_1$-$C_6$ alkyl, $C_1$-$C_6$ hydroxyalkyl, $C_1$-$C_6$ aminoalkyl, —O($C_1$-$C_6$ alkyl), —NH($C_1$-$C_6$ alkyl), —N($C_1$-$C_6$ alkyl)$_2$, $C_3$-$C_6$ cycloalkyl, —CH$_2$—($C_{3-6}$ cycloalkyl), —O—($C_{3-6}$ cycloalkyl), $C_1$-$C_6$ haloalkyl, and —O($C_1$-$C_6$ haloalkyl);

wherein if an $R^6$ is attached to a nitrogen atom, then it is selected from the group consisting of $C_1$-$C_6$ alkyl, $C_1$-$C_6$ hydroxyalkyl, $C_1$-$C_6$ aminoalkyl, $C_3$-$C_6$ cycloalkyl, —CH$_2$—($C_{3-6}$ cycloalkyl), and $C_1$-$C_6$ haloalkyl;

each $R^7$ is independently hydrogen or $C_1$-$C_6$ alkyl, wherein said alkyl is optionally substituted with 1-2 hydroxy groups;

$R^8$ is hydrogen, $C_1$-$C_{10}$ alkyl, $C_1$-$C_{10}$ heteroalkyl, $C_1$-$C_{10}$ alkenyl, $C_1$-$C_{10}$ alkynyl, $C_3$-$C_{12}$ cycloalkyl, 3- to 15-membered heterocycloalkyl, $C_6$-$C_{10}$ aryl, or 5- to 10-membered heteroaryl; wherein the aryl, and heteroaryl is optionally substituted with 1-6 groups independently selected from $R^{11}$, and the alkyl, heteroalkyl, alkenyl, alkynyl, cycloalkyl and heterocycloalkyl is optionally substituted with 1-6 groups independently selected from oxo and $R^{11}$;

or one $R^7$ and one $R^8$ bound to the same nitrogen atom come together to form a 3- to 15-membered heterocycloalkyl that is optionally substituted with 1-6 groups independently selected from oxo and $R^{11}$;

$R^9$ is hydrogen, —C(O)$OR^{12}$, —C(O)N($R^{12}$)$_2$, —S(O)$_2$$R^{12}$, —S(O)$_2$N($R^{12}$)$_2$, or $C_1$-$C_6$ alkyl;

each $R^{10}$ is independently selected from hydroxy, amino, cyano, fluoro, —C(=O)$OR^{12}$, —C(=O)N($R^{12}$)$_2$, $C_1$-$C_4$ alkyl, $C_1$-$C_4$ haloalkyl, —O($C_1$-$C_6$ alkyl), —NH ($C_1$-$C_4$ alkyl), —N($C_1$-$C_4$ alkyl)$_2$, $C_3$-$C_6$ cycloalkyl, wherein said alkyl, haloalkyl or cycloalkyl is optionally substituted with 1-2 groups selected from hydroxy, amino, cyano, fluoro, —C(=O)$OR^{12}$, and —C(=O) N($R^{12}$)$_2$;

each $R^{11}$ is independently selected from the group consisting of halogen, hydroxy, amino, cyano, —S(=O)$_2$ ($R^{13}$), —N($R^{12}$)S(=O)$_2$($R^{13}$), —S(=O)($R^{13}$), —N($R^{12}$)S(=O)($R^{13}$), —C(=O)$R^{13}$, —N($R^{12}$)C (=O)$R^{13}$, $C_1$-$C_6$ alkyl, —O($C_1$-$C_6$ alkyl), —NH($C_1$-$C_6$ alkyl), —N($C_1$-$C_6$ alkyl)$_2$, $C_1$-$C_6$ haloalkyl, $C_2$-$C_6$ alkenyl, $C_2$-$C_6$ alkynyl, $C_3$-$C_8$ cycloalkyl, 3- to 10-membered heterocycloalkyl, $C_6$-$C_{10}$ aryl, and 5- to 10-membered heteroaryl, wherein the aryl, and heteroaryl is optionally substituted with 1-4 groups independently selected from $R^{14}$, and the alkyl, alkenyl, alkynyl, haloalkyl, cycloalkyl, and heterocycloalkyl is optionally substituted with 1-4 groups independently selected from oxo and $R^{14}$;

or two $R^{11}$ bound to the same carbon or nitrogen atom come together to form a $C_3$-$C_6$ cycloalkyl or 3- to 6-membered heterocycloalkyl, wherein the cycloalkyl, and heterocycloalkyl is optionally substituted with 1-4 groups independently selected from oxo and $R^{14}$;

each $R^{12}$ is independently hydrogen or $C_1$-$C_6$ alkyl;

each $R^{13}$ is independently hydroxy, amino, $C_1$-$C_6$ alkyl, —O($C_1$-$C_6$ alkyl), —NH($C_1$-$C_6$ alkyl), —N($C_1$-$C_6$ alkyl)$_2$, $C_1$-$C_6$ haloalkyl, $C_3$-$C_6$ cycloalkyl, or 3- to 6-membered heterocycloalkyl; and each $R^{14}$ is independently cyano, amino, hydroxy, —C(=O)O$R^{12}$, —C(=O)N($R^{12}$)$_2$, $C_1$-$C_6$ alkyl, —O($C_1$-$C_6$ alkyl), —N$R^{12}$($C_1$-$C_6$ alkyl), aryl, heteroaryl, $C_3$-$C_6$ cycloalkyl, or 3- to 6-membered heterocycloalkyl, wherein each alkyl is optionally substituted with 1-2 hydroxy groups.

For any and all of the embodiments, substituents are selected from among a subset of the listed alternatives. For example, in some embodiments of a compound of Formula (I), or a pharmaceutically acceptable salt or solvate thereof, Z is a bivalent group selected from —S—, —N=C($R^5$)—, —C($R^5$)=N—, or —C($R^5$)=C($R^5$)—. In some embodiments, Z is —S— or —C($R^5$)=C($R^5$)—. In some embodiments, Z is —N=C($R^5$)— or —C($R^5$)=N—. In some embodiments, Z is —S—. In some embodiments, Z is —C($R^5$)=C($R^5$)—. In some embodiments, Z is —C($R^5$)=N—. In some embodiments, Z is —N=C($R^5$)—.

In some embodiments of a compound of Formula (I), or a pharmaceutically acceptable salt or solvate thereof, Z is a bivalent group selected from —S—, —N=CH—, —CH=N—, or —CH=CH—. In some embodiments, Z is —S— or —CH=CH—. In some embodiments, Z is —N=CH— or —CH=N—. In some embodiments, Z is —S—. In some embodiments, Z is —CH=CH—. In some embodiments, Z is —CH=N—. In some embodiments, Z is —N=CH—.

In some embodiments of a compound of Formula (I), or a pharmaceutically acceptable salt or solvate thereof, $R^3$ is halogen, cyano, —C(=O)OH, $C_1$-$C_6$ alkyl, $C_1$-$C_6$ alkenyl, —O($C_1$-$C_6$ alkyl), $C_3$-$C_6$ cycloalkyl, or $C_1$-$C_6$ haloalkyl. In some embodiments, $R^3$ is halogen, cyano, $C_1$-$C_6$ alkyl, $C_3$-$C_6$ cycloalkyl, or $C_1$-$C_6$ haloalkyl. In some embodiments of a compound of Formula (I), or a pharmaceutically acceptable salt or solvate thereof, $R^3$ is fluoro, chloro, cyano, —C(=O)OH, $C_1$-$C_6$ alkyl, $C_1$-$C_6$ alkenyl, —O($C_1$-$C_6$ alkyl), $C_3$-$C_6$ cycloalkyl, or $C_1$-$C_6$ haloalkyl. In some embodiments of a compound of Formula (I), or a pharmaceutically acceptable salt or solvate thereof, $R^3$ is fluoro, chloro, cyano, —C(=O)OH, $C_1$-$C_4$ alkyl, $C_1$-$C_4$ alkenyl, —O($C_1$-$C_4$ alkyl), $C_3$-$C_4$ cycloalkyl, or $C_1$-$C_4$ haloalkyl. In some embodiments, $R^3$ is fluoro, chloro, cyano, methyl, ethyl, vinyl, —OMe, —C(=O)OH, trifluoromethyl, difluoromethyl, or cyclopropyl. In some embodiments, $R^3$ is chloro, cyano, methyl, or ethyl.

In some embodiments, the compound (e.g., the compound of Formula (I)) has the structure of Formula (IIa):

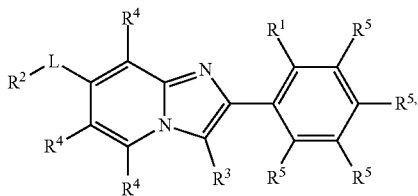

Formula (IIa)

or a pharmaceutically acceptable salt or solvate thereof.

In some embodiments, the compound (e.g., the compound of Formula (I)) has the structure of Formula (IIb):

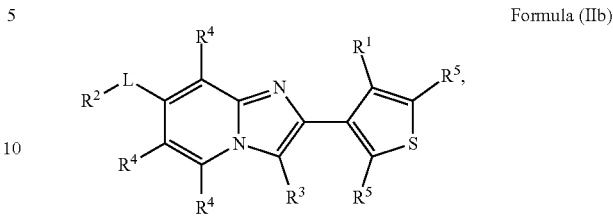

Formula (IIb)

or a pharmaceutically acceptable salt or solvate thereof.

In some embodiments, the compound (e.g., the compound of Formula (I)) has the structure of Formula (IIc):

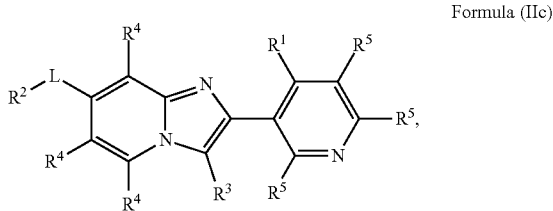

Formula (IIc)

or a pharmaceutically acceptable salt or solvate thereof.

In some embodiments, the compound (e.g., the compound of Formula (I)) has the structure of Formula (IId):

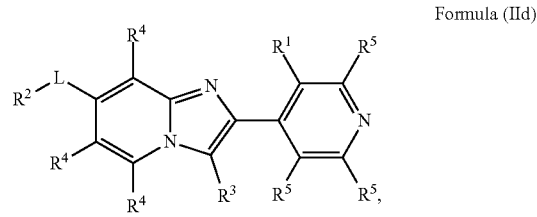

Formula (IId)

or a pharmaceutically acceptable salt or solvate thereof.

In some embodiments of a compound of Formula (IIa), Formula (IIb), Formula (IIc), or Formula (IId), or a pharmaceutically acceptable salt or solvate thereof, $R^3$ is halogen, cyano, —C(=O)OH, $C_1$-$C_6$ alkyl, $C_1$-$C_6$ alkenyl, —O($C_1$-$C_6$ alkyl), $C_3$-$C_6$ cycloalkyl, or $C_1$-$C_6$ haloalkyl. In some embodiments, $R^3$ is halogen, cyano, $C_1$-$C_6$ alkyl, $C_3$-$C_6$ cycloalkyl, or $C_1$-$C_6$ haloalkyl. In some embodiments, $R^3$ is fluoro, chloro, cyano, —C(=O)OH, $C_1$-$C_6$ alkyl, $C_1$-$C_6$ alkenyl, —O($C_1$-$C_6$ alkyl), $C_3$-$C_6$ cycloalkyl, or $C_1$-$C_6$ haloalkyl. In some embodiments, $R^3$ is fluoro, chloro, cyano, —C(=O)OH, $C_1$-$C_4$ alkyl, $C_1$-$C_4$ alkenyl, —O($C_1$-$C_4$ alkyl), $C_3$-$C_4$ cycloalkyl, or $C_1$-$C_4$ haloalkyl. In some embodiments, $R^3$ is fluoro, chloro, cyano, methyl, ethyl, vinyl, —OMe, —C(=O)OH, trifluoromethyl, difluoromethyl, or cyclopropyl. In some embodiments, $R^3$ is chloro, cyano, methyl, or ethyl.

In some embodiments of a compound of Formula (I), Formula (IIa), Formula (IIb), Formula (IIc), or Formula (IId), or a pharmaceutically acceptable salt or solvate thereof, L is a bond, $C_1$-$C_2$ alkylene, or $C_3$-$C_6$ cycloalkylene, wherein said alkylene, or cycloalkylene is optionally substituted with 1 or 2 —OH groups. In some embodiments, L is a bond or $C_1$-$C_2$ alkylene. In some embodiments, L is a bond, $C_1$-$C_2$ alkylene, or $C_3$-$C_4$ cycloalkylene. In some embodiments, L is a bond or $C_1$ alkylene. In some embodiments, L is a bond. In some embodiments, L is methylene. In some embodiments, L is ethylene. In some embodiments, L is cyclopropylene. In some embodiments, L is cyclobutylene.

In some embodiments of a compound of Formula (I), Formula (IIa), Formula (IIb), Formula (IIc), or Formula (IId), or a pharmaceutically acceptable salt or solvate thereof, L is optionally substituted with 1 or 2 —OH groups. In some embodiments, L is unsubstituted. In some embodiments, L is substituted with 1 or 2 —OH groups. In some embodiments, L is substituted with 1 —OH group.

In some embodiments of a compound of Formula (I), Formula (IIa), Formula (IIb), Formula (IIc), or Formula (IId), or a pharmaceutically acceptable salt or solvate thereof, -L-$R^2$ is —C(=O)$OR^7$ or —C(=O)$NR^7R^8$. In some embodiments, -L-$R^2$ is —C(=O)$OR^7$. In some embodiments, -L-$R^2$ is —C(=O)N($R^8$)($R^7$). In some embodiments, —C(=O)N($R^8$)($R^7$) is depicted as having the structure

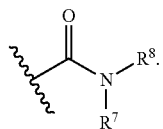

In some embodiments, —$R^2$ is —C(=O)$OR^7$ or —C(=O)$NR^7R^8$. In some embodiments, —$R^2$ is —C(=O)$OR^7$. In some embodiments, —$R^2$ is —C(=O)N($R^8$)($R^7$).

In some embodiments of a compound of Formula (I), Formula (IIa), Formula (IIb), Formula (IIc), or Formula (IId), or a pharmaceutically acceptable salt or solvate thereof, $R^2$ is $C_1$-$C_{10}$ alkyl, $C_1$-$C_{10}$ heteroalkyl, —C(=O)$OR^7$, —C(=O)N($R^8$)($R^7$), —N($R^8$)($R^7$), —C(=$NR^9$)N($R^8$)($R^7$), —N($R^7$)C(=$NR^9$)N($R^8$)($R^7$), $C_6$-$C_{10}$ aryl, 5- to 10-membered heteroaryl, $C_3$-$C_{12}$ cycloalkyl, or 3-to-15 membered heterocycloalkyl, wherein the aryl, and heteroaryl is optionally substituted with 1-4 groups independently selected from $R^{10}$, and the alkyl, heteroalkyl, cycloalkyl, and heterocycloalkyl is optionally substituted with 1-4 groups independently selected from oxo and $R^{10}$. In some embodiments, $R^2$ is —C(=O)$OR^7$, —C(=O)N($R^8$)($R^7$), —N($R^8$)($R^7$), —C(=$NR^9$)N($R^8$)($R^7$), or —N($R^7$)C(=$NR^9$)N($R^8$)($R^7$). In some embodiments, $R^2$ is —C(=O)$OR^7$, —C(=O)N($R^8$)($R^7$), or —C(=$NR^9$)N($R^8$)($R^7$). In some embodiments, $R^2$ is —C(=O)$OR^7$. In some embodiments, $R^2$ is —C(=O)N($R^8$)($R^7$). In some embodiments, $R^2$ is —C(=$NR^9$)N($R^8$)($R^7$). In some embodiments, $R^2$ is —C(=$NR^9$)N($R^8$)($R^7$). In some embodiments, $R^2$ is —N($R^8$)($R^7$). In some embodiments, $R^2$ is $C_1$-$C_{10}$ alkyl, $C_1$-$C_{10}$ heteroalkyl, $C_6$-$C_{10}$ aryl, 5- to 10-membered heteroaryl, $C_3$-$C_{12}$ cycloalkyl, or 3-to-15 membered heterocycloalkyl. In some embodiments, $R^2$ is $C_1$-$C_6$ alkyl, $C_1$-$C_6$ heteroalkyl, phenyl, 5- to 12-membered heteroaryl, $C_3$-$C_{10}$ cycloalkyl, or 3-to-12 membered heterocycloalkyl. In some embodiments, $R^2$ is $C_1$-$C_{10}$ alkyl, $C_1$-$C_{10}$ heteroalkyl, $C_6$-$C_{10}$ aryl, 5- to 10-membered heteroaryl, $C_3$-$C_{12}$ cycloalkyl, or 3-to-15 membered heterocycloalkyl. In some embodiments, $R^2$ is 5- to 10-membered heteroaryl or 3-to-15 membered heterocycloalkyl. In some embodiments, $R^2$ is 5- to 6-membered heteroaryl or 3-to-8 membered heterocycloalkyl. In some embodiments, $R^2$ is 5- to 10-membered heteroaryl. In some embodiments, $R^2$ is 5- to 6-membered heteroaryl. In some embodiments, $R^2$ is 3-to-15 membered heterocycloalkyl. In some embodiments, $R^2$ is 3-to-8 membered heterocycloalkyl. In some embodiments, $R^2$ is 3-to-6 membered heterocycloalkyl.

In some embodiments of a compound of Formula (I), Formula (IIa), Formula (IIb), Formula (IIc), or Formula (IId), or a pharmaceutically acceptable salt or solvate thereof, $R^2$ is optionally substituted with 1-4 groups independently selected from $R^{10}$. In some embodiments, $R^2$ is optionally substituted with 1-3 groups independently selected from $R^{10}$. In some embodiments, $R^2$ is optionally substituted with 1-2 groups independently selected from $R^{10}$. In some embodiments, $R^2$ is optionally substituted with 1 group selected from $R^{10}$. In some embodiments, $R^2$ is substituted with 1-4 groups independently selected from $R^{10}$. In some embodiments, $R^2$ is substituted with 1-3 groups independently selected from $R^{10}$. In some embodiments, $R^2$ is substituted with 1-2 groups independently selected from $R^{10}$. In some embodiments, $R^2$ is substituted with 1 group selected from $R^{10}$. In some embodiments, $R^2$ is substituted with 2 groups independently selected from $R^{10}$. In some embodiments, $R^2$ is substituted with 3 groups independently selected from $R^{10}$. In some embodiments, $R^2$ is substituted with 4 groups independently selected from $R^{10}$. In some embodiments, $R^2$ is unsubstituted. In some embodiments, $R^2$ is optionally substituted with 1-4 groups independently selected from oxo and $R^{10}$. In some embodiments, $R^2$ is optionally substituted with 1-3 groups independently selected from oxo and $R^{10}$. In some embodiments, $R^2$ is optionally substituted with 1-2 groups independently selected from oxo and $R^{10}$. In some embodiments, $R^2$ is optionally substituted with 1 group selected from oxo and $R^{10}$. In some embodiments, $R^2$ is substituted with 1-4 groups independently selected from oxo and $R^{10}$. In some embodiments, $R^2$ is substituted with 1-3 groups independently selected from oxo and $R^{10}$. In some embodiments, $R^2$ is substituted with 1-2 groups independently selected from oxo and $R^{10}$. In some embodiments, $R^2$ is substituted with 1 group selected from oxo and $R^{10}$. In some embodiments, $R^2$ is substituted with 2 groups independently selected from oxo and $R^{10}$. In some embodiments, $R^2$ is substituted with 3 groups independently selected from oxo and $R^{10}$. In some embodiments, $R^2$ is substituted with 4 groups selected from oxo and $R^{10}$.

In some embodiments of a compound of Formula (I), Formula (IIa), Formula (IIb), Formula (IIc), or Formula (IId), or a pharmaceutically acceptable salt or solvate thereof, each $R^{10}$ is independently selected from hydroxy, amino, cyano, fluoro, —C(=O)$OR^{12}$, —C(=O)N($R^{12}$)$_2$, $C_1$-$C_4$ alkyl, $C_1$-$C_4$ haloalkyl, —O($C_1$-$C_6$ alkyl), —NH($C_1$-$C_4$ alkyl), —N($C_1$-$C_4$ alkyl)$_2$, $C_3$-$C_6$ cycloalkyl, wherein said alkyl, haloalkyl or cycloalkyl is optionally substituted with 1-2 groups selected from hydroxy, amino, cyano, fluoro, —C(=O)$OR^{12}$, and —C(=O)N($R^{12}$)$_2$. In some embodiments, each $R^{10}$ is independently selected from hydroxy, amino, cyano, fluoro, —C(=O)OH, —C(=O)NH$_2$, $C_1$-$C_4$ alkyl, $C_1$-$C_4$ haloalkyl, $C_3$-$C_6$ cycloalkyl, wherein said alkyl, haloalkyl or cycloalkyl is optionally substituted with 1-2 groups selected from hydroxy, amino, cyano, fluoro, —C(=O)OH, and —C(=O)NH$_2$. In some embodiments, each $R^{10}$ is independently selected from hydroxy, amino, cyano, fluoro, —C(=O)OH, —C(=O)NH$_2$, $C_1$-$C_4$ alkyl, $C_1$-$C_4$ haloalkyl, $C_3$-$C_4$ cycloalkyl. In some embodiments, each $R^{10}$ is independently selected from hydroxy, amino, cyano, fluoro, —C(=O)OH, —C(=O)NH$_2$, methyl, ethyl, propyl, isopropyl, cyclopropyl, cyclobutyl, —OMe, —OEt, trifluoromethyl, and difluoromethyl. In some embodiments, each $R^{10}$ is independently selected from hydroxy, amino, cyano, fluoro, —C(=O)OH, —C(=O)NH$_2$, methyl, ethyl, cyclopropyl, cyclobutyl, and —OMe. In some embodiments, each $R^{10}$ is independently selected from hydroxy, fluoro, —C(=O)OH, —C(=O)NH$_2$, methyl, cyclobutyl, and —OMe. In some embodiments, each $R^{10}$ is independently selected from hydroxy, —C(=O)OH, methyl, and cyclobutyl. In some embodiments, each $R^{10}$ is hydroxy. In some embodiments, each $R^{10}$ is methyl. In some embodiments, each $R^{10}$ is —C(=O)OH. In some embodiments, each $R^{10}$ is cyclobutyl.

In some embodiments of a compound of Formula (I), Formula (IIa), Formula (IIb), Formula (IIc), or Formula (IId), or a pharmaceutically acceptable salt or solvate thereof, each $R^{10}$ is optionally substituted with 1-2 groups selected from hydroxy, amino, cyano, fluoro, —C(=O)OH, and —C(=O)NH$_2$. In some embodiments, each $R^{10}$ is optionally substituted with 1 group selected from hydroxy, amino, cyano, fluoro, —C(=O)OH, and —C(=O)NH$_2$. In some embodiments, each $R^{10}$ is optionally substituted with 1-2 groups selected from hydroxy, fluoro, and —C(=O)OH. In some embodiments, each $R^{10}$ is optionally substituted with 1-2 groups selected from hydroxy and —C(=O)OH. In some embodiments, each $R^{10}$ is unsubstituted. In some embodiments, at least one $R^{10}$ is unsubstituted. In some embodiments, at least one $R^{10}$ is substituted.

In some embodiments of a compound of Formula (I), Formula (IIa), Formula (IIb), Formula (IIc), or Formula (IId), or a pharmaceutically acceptable salt or solvate thereof:
-L-$R^2$ is —C(=O)O$R^7$ or —C(=O)N$R^7R^8$;
$R^3$ is halogen, cyano, $C_1$-$C_6$ alkyl, $C_3$-$C_6$ cycloalkyl or $C_1$-$C_6$ fluoroalkyl;
each $R^4$ is independently hydrogen or halogen;
each $R^5$ is independently hydrogen or halogen;
each $R^6$ is independently selected from the group consisting of halogen, cyano, $C_1$-$C_6$ alkyl, $C_3$-$C_6$ cycloalkyl, —CH$_2$—($C_{3-6}$ cycloalkyl), and $C_1$-$C_6$ haloalkyl, wherein when an $R^6$ is attached to a nitrogen atom, it is independently $C_1$-$C_6$ alkyl, $C_3$-$C_6$ cycloalkyl, —CH$_2$—($C_{3-6}$ cycloalkyl), or $C_1$-$C_6$ haloalkyl;
$R^7$ is hydrogen or $C_{1-6}$ alkyl;
$R^8$ is $C_1$-$C_{10}$ alkyl, $C_1$-$C_{10}$ heteroalkyl, $C_3$-$C_{12}$ cycloalkyl, or 3- to 15-membered heterocycloalkyl; wherein the alkyl, cycloalkyl and heterocycloalkyl is optionally substituted with 1-6 groups independently selected from oxo and $R^{11}$;
or one $R^7$ and one $R^8$ bound to the same nitrogen atom come together to form a 3- to 15-membered heterocycloalkyl that is optionally substituted with 1-6 groups independently selected from oxo and $R^{11}$;
each $R^{11}$ is independently selected from the group consisting of halogen, hydroxy, amino, cyano, —S(=O)$_2$($R^{13}$), —N($R^{12}$)S(=O)$_2$($R^{13}$), —S(=O)($R^{13}$), —N($R^{12}$)S(=O)($R^{13}$), —C(=O)$R^{13}$, —N($R^{12}$)C(=O)$R^{13}$, $C_1$-$C_6$ alkyl, —O($C_1$-$C_6$ alkyl), —NH($C_1$-$C_6$ alkyl), —N($C_1$-$C_6$ alkyl)$_2$, $C_1$-$C_6$ haloalkyl, $C_3$-$C_8$ cycloalkyl, 3- to 10-membered heterocycloalkyl, and 5- to 10-membered heteroaryl, wherein the heteroaryl is optionally substituted with 1-4 groups independently selected from $R^{14}$, and the alkyl, haloalkyl, cycloalkyl, and heterocycloalkyl is optionally substituted with 1-4 groups independently selected from oxo and $R^{14}$;
or two $R^{11}$ bound to the same carbon or nitrogen atom come together to form a $C_3$-$C_6$ cycloalkyl or 3- to 6-membered heterocycloalkyl, wherein the cycloalkyl, and heterocycloalkyl is optionally substituted with 1-4 groups independently selected from oxo and $R^{14}$;
each $R^{12}$ is independently hydrogen or $C_1$-$C_6$ alkyl;
each $R^{13}$ is independently hydroxy, amino, $C_1$-$C_6$ alkyl, —O($C_1$-$C_6$ alkyl), —NH($C_1$-$C_6$ alkyl), —N($C_1$-$C_6$ alkyl)$_2$, or $C_1$-$C_6$ haloalkyl; and
each $R^{14}$ is independently cyano, amino, hydroxy, —C(=O)O$R^{12}$, —C(=O)N($R^{12}$)$_2$, $C_1$-$C_6$ alkyl, —O($C_1$-$C_6$ alkyl), or —N$R^{12}$($C_1$-$C_6$ alkyl), wherein each alkyl is optionally substituted with 1-2 hydroxy groups.

In some embodiments, the compound (e.g., the compound of Formula (I)) has the structure of Formula (III):

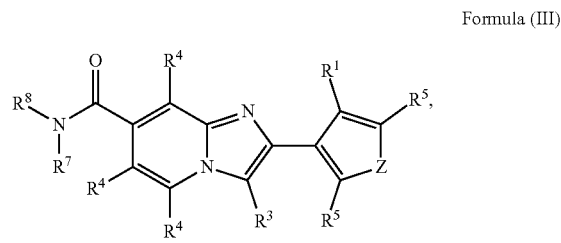

Formula (III)

or a pharmaceutically acceptable salt or solvate thereof.

In some embodiments of a compound of Formula (III), or a pharmaceutically acceptable salt or solvate thereof, Z is a bivalent group selected from —S—, —N=C($R^5$)—, —C($R^5$)=N—, or —C($R^5$)=C($R^5$)—. In some embodiments, Z is —S— or —C($R^5$)=C($R^5$)—. In some embodiments, Z is —N=C($R^5$)— or —C($R^5$)=N—. In some embodiments, Z is —S—. In some embodiments, Z is —C($R^5$)=C($R^5$)—. In some embodiments, Z is —C($R^5$)=N—. In some embodiments, Z is —N=C($R^5$)—.

In some embodiments, the compound (e.g., the compound of Formula (I)) has the structure of Formula (IIIa):

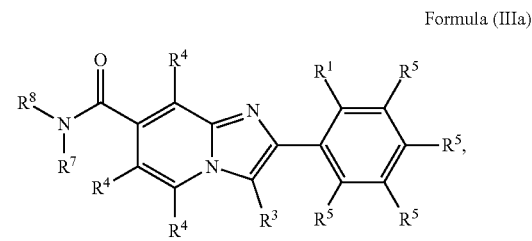

Formula (IIIa)

or a pharmaceutically acceptable salt or solvate thereof.

In some embodiments, the compound (e.g., the compound of Formula (I)) has the structure of Formula (IIIb):

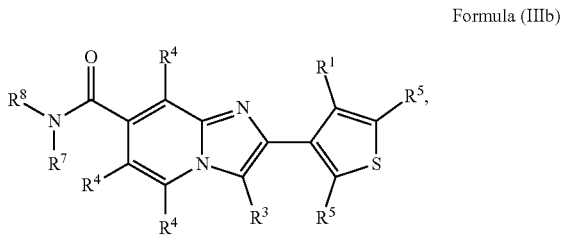

Formula (IIIb)

or a pharmaceutically acceptable salt or solvate thereof.

In some embodiments, the compound (e.g., the compound of Formula (I)) has the structure of Formula (IIIc):

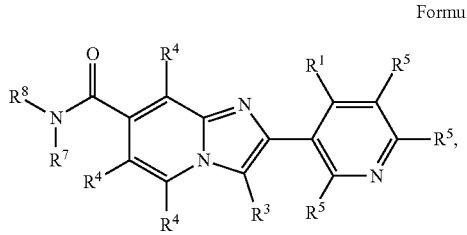

Formula (IIIc)

or a pharmaceutically acceptable salt or solvate thereof.

In some embodiments, the compound (e.g., the compound of Formula (I)) has the structure of Formula (IIId):

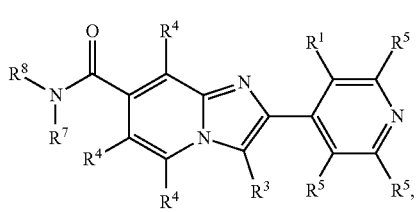

Formula (IIId)

or a pharmaceutically acceptable salt or solvate thereof.

In some embodiments of a compound of Formula (III), Formula (IIIa), Formula (IIIb), Formula (IIIc), or Formula (IIId), or a pharmaceutically acceptable salt or solvate thereof, $R^3$ is halogen, cyano, —C(=O)OH, $C_1$-$C_6$ alkyl, $C_1$-$C_6$ alkenyl, —O($C_1$-$C_6$ alkyl), $C_3$-$C_6$ cycloalkyl, or $C_1$-$C_6$ haloalkyl. In some embodiments, $R^3$ is fluoro, chloro, cyano, —C(=O)OH, $C_1$-$C_6$ alkyl, $C_1$-$C_6$ alkenyl, —O($C_1$-$C_6$ alkyl), $C_3$-$C_6$ cycloalkyl, or $C_1$-$C_6$ haloalkyl. In some embodiments, $R^3$ is fluoro, chloro, cyano, —C(=O)OH, $C_1$-$C_4$ alkyl, $C_1$-$C_4$ alkenyl, —O($C_1$-$C_4$ alkyl), $C_3$-$C_4$ cycloalkyl, or $C_1$-$C_4$ haloalkyl. In some embodiments, $R^3$ is halogen, cyano, $C_1$-$C_6$ alkyl, $C_3$-$C_6$ cycloalkyl, or $C_1$-$C_6$ haloalkyl. In some embodiments, $R^3$ is fluoro, chloro, cyano, methyl, ethyl, vinyl, —OMe, —C(=O)OH, trifluoromethyl, difluoromethyl, or cyclopropyl. In some embodiments, $R^3$ is chloro, cyano, methyl, or ethyl. In some embodiments, $R^3$ is chloro or cyano. In some embodiments, $R^3$ is chloro. In some embodiments, $R^3$ is cyano.

In some embodiments of a compound of Formula (I), Formula (IIa), Formula (IIb), Formula (IIc), Formula (IId), Formula (III), Formula (IIIa), Formula (IIIb), Formula (IIIc), or Formula (IIId), or a pharmaceutically acceptable salt or solvate thereof, each $R^5$ is independently hydrogen, cyano, halogen, $C_1$-$C_6$ alkyl, —O($C_1$-$C_6$ alkyl), $C_3$-$C_6$ cycloalkyl, $C_1$-$C_6$ haloalkyl, or —O($C_1$-$C_6$ haloalkyl). In some embodiments, each $R^5$ is independently hydrogen, cyano, halogen, $C_1$-$C_6$ alkyl, —O($C_1$-$C_6$ alkyl), $C_3$-$C_6$ cycloalkyl, or $C_1$-$C_6$ haloalkyl. In some embodiments, each $R^5$ is independently hydrogen, cyano, halogen, $C_1$-$C_4$ alkyl, —O($C_1$-$C_4$ alkyl), $C_3$-$C_4$ cycloalkyl, or $C_1$-$C_4$ haloalkyl. In some embodiments, each $R^5$ is independently hydrogen, cyano, halogen, methyl, ethyl, propyl, isopropyl, —OMe, —OEt, cyclopropyl, cyclobutyl, trifluoromethyl, or difluoromethyl. In some embodiments, each $R^5$ is independently hydrogen, cyano, fluoro, chloro, methyl, —OMe, cyclopropyl, trifluoromethyl, or difluoromethyl. In some embodiments, each $R^5$ is independently hydrogen or fluoro. In some embodiments, each $R^5$ is hydrogen. In some embodiments, each $R^5$ is fluoro. In some embodiments, each $R^5$ is independently hydrogen or halogen.

In some embodiments of a compound of Formula (I), Formula (IIa), Formula (IIb), Formula (IIc), Formula (IId), Formula (III), Formula (IIIa), Formula (IIIb), Formula (IIIc), or Formula (IIId), or a pharmaceutically acceptable salt or solvate thereof, each $R^4$ is independently hydrogen, halogen, $C_1$-$C_6$ alkyl, —O—$C_1$-$C_6$ alkyl, $C_1$-$C_6$ haloalkyl, or —O—($C_1$-$C_6$ haloalkyl). In some embodiments, each $R^4$ is independently hydrogen, halogen, $C_1$-$C_4$ alkyl, —O—$C_1$-$C_4$ alkyl, $C_1$-$C_4$ haloalkyl, or —O—($C_1$-$C_4$ haloalkyl). In some embodiments, each $R^4$ is independently hydrogen, halogen, methyl, ethyl, propyl, isopropyl, trifluoromethyl, difluoromethyl, trifluoroethyl, —O-(trifluoromethyl), —O-(difluoromethyl), —O-(trifluoroethyl), —OMe, or —OEt. In some embodiments, each $R^4$ is independently hydrogen, fluoro, chloro, methyl, ethyl, propyl, isopropyl, trifluoromethyl, difluoromethyl, —O-(trifluoromethyl), —OMe, or —OEt. In some embodiments, each $R^4$ is independently hydrogen, fluoro, trifluoromethyl, methyl, or —OMe. In some embodiments, each $R^4$ is independently hydrogen, fluoro or methyl. In some embodiments, one $R^4$ is fluoro, methyl, or —OMe, and the other $R^4$ are each hydrogen. In some embodiments, each $R^4$ is hydrogen. In some embodiments, each $R^4$ is independently hydrogen or halogen.

In some embodiments, the compound (e.g., the compound of Formula (I)) has the structure of Formula (IV):

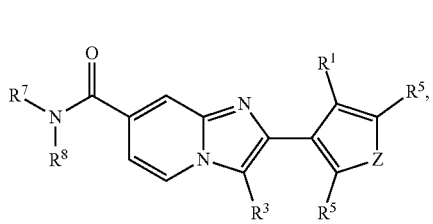

Formula (IV)

or a pharmaceutically acceptable salt or solvate thereof.

In some embodiments of a compound of Formula (IV), or a pharmaceutically acceptable salt or solvate thereof, Z is a bivalent group selected from —S—, —N=C($R^5$)—, —C($R^5$)=N—, or —C($R^5$)=C($R^5$)—. In some embodiments, Z is —S— or —C($R^5$)=C($R^5$)—. In some embodiments, Z is —N=C($R^5$)— or —C($R^5$)=N—. In some embodiments, Z is —S—. In some embodiments, Z is —C($R^5$)=C($R^5$)—. In some embodiments, Z is —C($R^5$)=N—. In some embodiments, Z is —N=C($R^5$)—.

In some embodiments of a compound of Formula (IV), or a pharmaceutically acceptable salt or solvate thereof, Z is a bivalent group selected from —S—, —N=CH—, —CH=N—, or —CH=CH—. In some embodiments, Z is —S— or —CH=CH—. In some embodiments, Z is —N=CH— or —CH=N—. In some embodiments, Z is —S—. In some embodiments, Z is —CH=CH—. In some embodiments, Z is —CH=N—. In some embodiments, Z is —N=CH—.

In some embodiments, the compound (e.g., the compound of Formula (I)) has the structure of Formula (IVa):

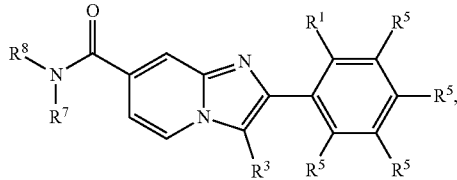

Formula (IVa)

or a pharmaceutically acceptable salt or solvate thereof.

In some embodiments, the compound (e.g., the compound of Formula (I)) has the structure of Formula (IVb):

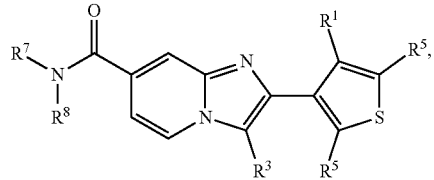

Formula (IVb)

or a pharmaceutically acceptable salt or solvate thereof.

In some embodiments, the compound (e.g., the compound of Formula (I)) has the structure of Formula (IVc):

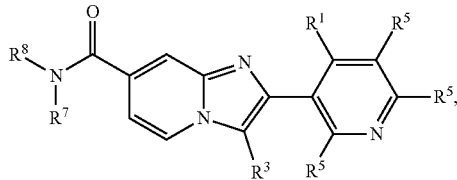

Formula (IVc)

or a pharmaceutically acceptable salt or solvate thereof.

In some embodiments, the compound (e.g., the compound of Formula (I)) has the structure of Formula (IVd):

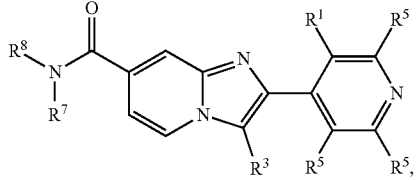

Formula (IVd)

or a pharmaceutically acceptable salt or solvate thereof.

In some embodiments of a compound of Formula (IV), Formula (IVa), Formula (IVb), Formula (IVc), or Formula (IVd), or a pharmaceutically acceptable salt or solvate thereof, $R^3$ is halogen, cyano, —C(=O)OH, $C_1$-$C_6$ alkyl, $C_1$-$C_6$ alkenyl, —O($C_1$-$C_6$ alkyl), $C_3$-$C_6$ cycloalkyl, or $C_1$-$C_6$ haloalkyl. In some embodiments, $R^3$ is fluoro, chloro, cyano, —C(=O)OH, $C_1$-$C_6$ alkyl, $C_1$-$C_6$ alkenyl, —O($C_1$-$C_6$ alkyl), $C_3$-$C_6$ cycloalkyl, or $C_1$-$C_6$ haloalkyl. In some embodiments, $R^3$ is fluoro, chloro, cyano, —C(=O)OH, $C_1$-$C_4$ alkyl, $C_1$-$C_4$ alkenyl, —O($C_1$-$C_4$ alkyl), $C_3$-$C_4$ cycloalkyl, or $C_1$-$C_4$ haloalkyl. In some embodiments, $R^3$ is halogen, cyano, $C_1$-$C_6$ alkyl, $C_3$-$C_6$ cycloalkyl, or $C_1$-$C_6$ haloalkyl. In some embodiments, $R^3$ is fluoro, chloro, cyano, methyl, ethyl, vinyl, —OMe, —C(=O)OH, trifluoromethyl, difluoromethyl, or cyclopropyl. In some embodiments, $R^3$ is chloro, cyano, methyl, or ethyl.

In some embodiments of a compound of Formula (IV), Formula (IVa), Formula (IVb), Formula (IVc), or Formula (IVd), or a pharmaceutically acceptable salt or solvate thereof, each $R^5$ is independently hydrogen, cyano, halogen, $C_1$-$C_6$ alkyl, —O($C_1$-$C_6$ alkyl), $C_3$-$C_6$ cycloalkyl, $C_1$-$C_6$ haloalkyl, or —O($C_1$-$C_6$ haloalkyl). In some embodiments, each $R^5$ is independently hydrogen, cyano, halogen, $C_1$-$C_6$ alkyl, —O($C_1$-$C_6$ alkyl), $C_3$-$C_6$ cycloalkyl, or $C_1$-$C_6$ haloalkyl. In some embodiments, each $R^5$ is independently hydrogen, cyano, halogen, $C_1$-$C_4$ alkyl, —O($C_1$-$C_4$ alkyl), $C_3$-$C_4$ cycloalkyl, or $C_1$-$C_4$ haloalkyl. In some embodiments, each $R^5$ is independently hydrogen, cyano, halogen, methyl, ethyl, propyl, isopropyl, —OMe, —OEt, cyclopropyl, cyclobutyl, trifluoromethyl, or difluoromethyl. In some embodiments, each $R^5$ is independently hydrogen, cyano, fluoro, chloro, methyl, —OMe, cyclopropyl, trifluoromethyl, or difluoromethyl. In some embodiments, each $R^5$ is independently hydrogen or fluoro. In some embodiments, each $R^5$ is hydrogen. In some embodiments, each $R^5$ is independently hydrogen or halogen.

In some embodiments of a compound of Formula (I), Formula (IIa), Formula (IIb), Formula (IIc), Formula (IId), Formula (III), Formula (IIIa), Formula (IIIb), Formula (IIIc), Formula (IIId), Formula (IV), Formula (IVa), Formula (IVb), Formula (IVc), or Formula (IVd), or a pharmaceutically acceptable salt or solvate thereof, $R^1$ is pyrazole, wherein said pyrazole is optionally substituted with 1-3 groups independently selected from $R^6$. In some embodiments, $R^1$ is pyrazole.

In some embodiments of a compound of Formula (I), Formula (IIa), Formula (IIb), Formula (IIc), Formula (IId), Formula (III), Formula (IIIa), Formula (IIIb), Formula (IIIc), Formula (IIId), Formula (IV), Formula (IVa), Formula (IVb), Formula (IVc), or Formula (IVd), or a pharmaceutically acceptable salt or solvate thereof, $R^1$ is optionally substituted with 1-3 groups independently selected from $R^6$. In some embodiments, $R^1$ is optionally substituted with 1-2 groups independently selected from $R^6$. In some embodiments, $R^1$ is unsubstituted. In some embodiments, $R^1$ is substituted with 1 group selected from $R^6$. In some embodiments, $R^1$ is substituted with 2 groups independently selected from $R^6$. In some embodiments, $R^1$ is substituted with 1-2 groups independently selected from $R^6$.

In some embodiments of a compound of Formula (I), Formula (IIa), Formula (IIb), Formula (IIc), Formula (IId), Formula (III), Formula (IIIa), Formula (IIIb), Formula (IIIc), Formula (IIId), Formula (IV), Formula (IVa), Formula (IVb), Formula (IVc), or Formula (IVd), or a pharmaceutically acceptable salt or solvate thereof, $R^1$ is optionally substituted with 1-3 RP groups independently selected from the group consisting of methyl, ethyl, cyano, fluoro, chloro, —OMe, cyclopropyl, —CH$_2$-cyclopropyl, trifluoromethyl, and difluoromethyl; wherein when an $R^6$ is attached to a nitrogen atom, it is selected from the group consisting of methyl, ethyl, cyclopropyl, —CH$_2$-cyclopropyl, trifluoromethyl, trifluoroethyl, and difluoromethyl. In some embodiments, $R^1$ is optionally substituted with 1-2 $R^6$ groups independently selected from the group consisting of methyl, cyano, fluoro, chloro, —OMe, cyclopropyl, —CH$_2$-cyclopropyl, and difluoromethyl; wherein when an $R^6$ is attached to a nitrogen atom, it is methyl, cyclopropyl, or —CH$_2$-cyclopropyl.

In some embodiments of a compound of Formula (I), Formula (IIa), Formula (IIb), Formula (IIc), Formula (IId), Formula (III), Formula (IIIa), Formula (IIIb), Formula (IIIc), Formula (IIId), Formula (IV), Formula (IVa), Formula (IVb), Formula (IVc), or Formula (IVd), or a pharmaceutically acceptable salt or solvate thereof, $R^1$ is

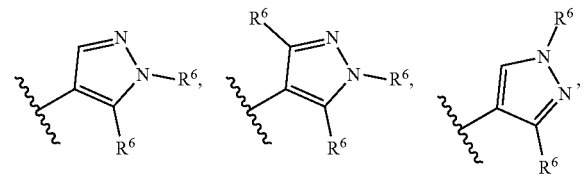

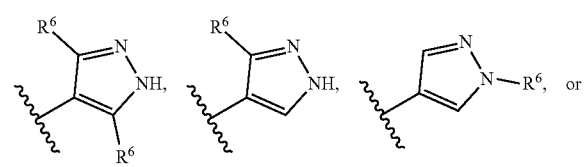

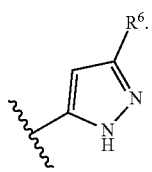

In some embodiments, $R^1$ is

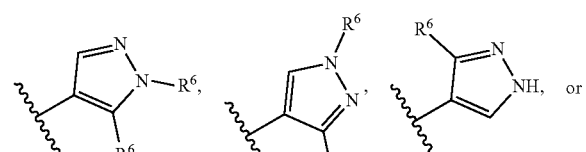

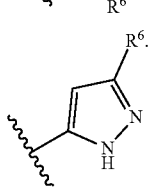

In some embodiments, $R^1$ is

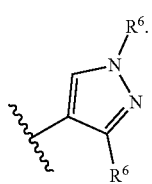

In some embodiments, $R^1$ is

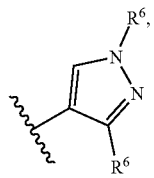

wherein each $R^6$ is independently fluoro, chloro, cyano, cyclopropyl, —CH$_2$-cyclopropyl, or methyl; wherein when an $R^6$ is attached to a nitrogen atom, it is methyl, cyclopropyl, or —CH$_2$-cyclopropyl. In some embodiments, $R^1$ is

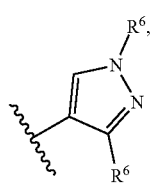

wherein each $R^6$ is independently fluoro, chloro, cyano, or methyl; wherein when an $R^6$ is attached to a nitrogen atom, it is methyl. In some embodiments, $R^1$ is

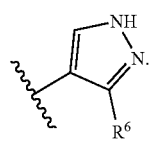

In some embodiments, $R^1$ is

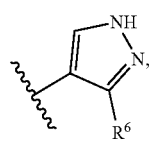

wherein $R^6$ is fluoro, chloro, cyano, cyclopropyl, —CH$_2$-cyclopropyl, or methyl. In some embodiments, $R^1$ is

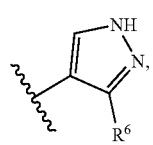

wherein $R^6$ is fluoro, chloro, cyano, or methyl. In some embodiments, $R^1$ is In some embodiments, $R^1$ is

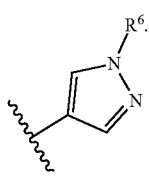

In some embodiments, $R^1$ is

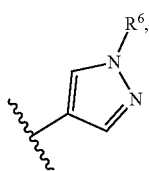

wherein $R^6$ is methyl, cyclopropyl, or —CH$_2$-cyclopropyl.

In some embodiments, $R^1$ is

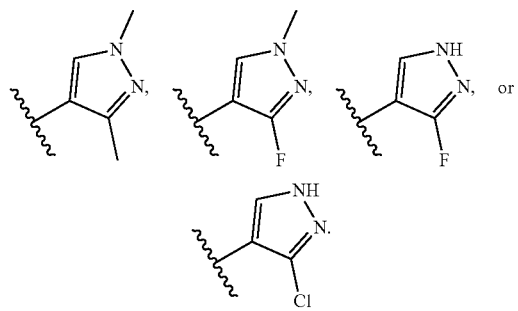

In some embodiments, $R^1$ is

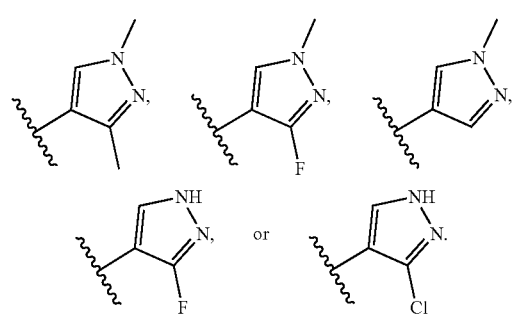

In some embodiments, $R^1$ is

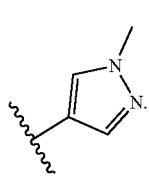 [SMILES: *c1cnn(C)c1]

In some embodiments, $R^1$ is

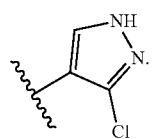 [SMILES: *c1c[nH]nc1Cl]

In some embodiments, $R^1$ is

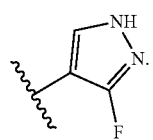

In some embodiments, $R^1$ is

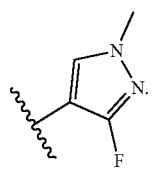 [SMILES: *c1cn(C)nc1F]

In some embodiments, $R^1$ is

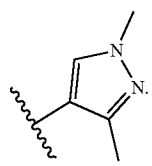 [SMILES: *c1cn(C)nc1C]

In some embodiments, the compound (e.g., the compound of Formula (I)) has the structure of Formula (VI):

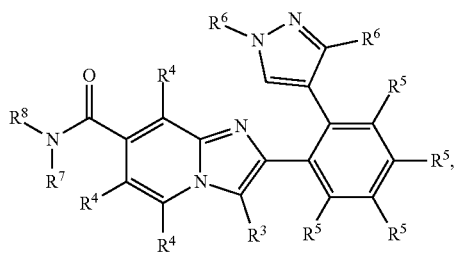

Formula (VI)

or a pharmaceutically acceptable salt or solvate thereof.

In some embodiments, the compound (e.g., the compound of Formula (I)) has the structure of Formula (VII):

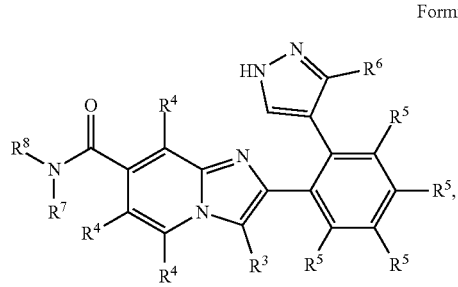

Formula (VII)

or a pharmaceutically acceptable salt or solvate thereof.

In some embodiments of a compound of Formula (VI) or Formula (VII), or a pharmaceutically acceptable salt or solvate thereof, $R^3$ is halogen, cyano, —C(=O)OH, $C_1$-$C_6$ alkyl, $C_1$-$C_6$ alkenyl, —O($C_1$-$C_6$ alkyl), $C_3$-$C_6$ cycloalkyl, or $C_1$-$C_6$ haloalkyl. In some embodiments, $R^3$ is fluoro, chloro, cyano, —C(=O)OH, $C_1$-$C_6$ alkyl, $C_1$-$C_6$ alkenyl, —O($C_1$-$C_6$ alkyl), $C_3$-$C_6$ cycloalkyl, or $C_1$-$C_6$ haloalkyl. In some embodiments, $R^3$ is fluoro, chloro, cyano, —C(=O)OH, $C_1$-$C_4$ alkyl, $C_1$-$C_4$ alkenyl, —O($C_1$-$C_4$ alkyl), $C_3$-$C_4$ cycloalkyl, or $C_1$-$C_4$ haloalkyl. In some embodiments, $R^3$ is halogen, cyano, $C_1$-$C_6$ alkyl, $C_3$-$C_6$ cycloalkyl, or $C_1$-$C_6$ haloalkyl. In some embodiments, $R^3$ is fluoro, chloro, cyano, methyl, ethyl, vinyl, —OMe, —C(=O)OH, trifluoromethyl, difluoromethyl, or cyclopropyl. In some embodiments, $R^3$ is chloro, cyano, methyl, or ethyl.

In some embodiments of a compound of Formula (VI) or Formula (VII), or a pharmaceutically acceptable salt or solvate thereof, each $R^5$ is independently hydrogen, cyano, halogen, $C_1$-$C_6$ alkyl, —O($C_1$-$C_6$ alkyl), $C_3$-$C_6$ cycloalkyl, $C_1$-$C_6$ haloalkyl, or —O($C_1$-$C_6$ haloalkyl). In some embodiments, each $R^5$ is independently hydrogen, cyano, halogen, $C_1$-$C_6$ alkyl, —O($C_1$-$C_6$ alkyl), $C_3$-$C_6$ cycloalkyl, or $C_1$-$C_6$ haloalkyl. In some embodiments, each $R^5$ is independently hydrogen, cyano, halogen, $C_1$-$C_4$ alkyl, —O($C_1$-$C_4$ alkyl), $C_3$-$C_4$ cycloalkyl, or $C_1$-$C_4$ haloalkyl. In some embodiments, each $R^5$ is independently hydrogen, cyano, halogen, methyl, ethyl, propyl, isopropyl, —OMe, —OEt, cyclopropyl, cyclobutyl, trifluoromethyl, or difluoromethyl. In some embodiments, each $R^5$ is independently hydrogen, cyano, fluoro, chloro, methyl, —OMe, cyclopropyl, trifluoromethyl, or difluoromethyl. In some embodiments, each $R^5$ is independently hydrogen or fluoro. In some embodiments, each $R^5$ is hydrogen.

In some embodiments of a compound of Formula (VI) or Formula (VII), or a pharmaceutically acceptable salt or solvate thereof, each $R^4$ is independently hydrogen, halogen, $C_1$-$C_6$ alkyl, —O—$C_1$-$C_6$ alkyl, $C_1$-$C_6$ haloalkyl, or —O—($C_1$-$C_6$ haloalkyl). In some embodiments, each $R^4$ is independently hydrogen, halogen, $C_1$-$C_4$ alkyl, —O—$C_1$-$C_4$ alkyl, $C_1$-$C_4$ haloalkyl, or —O—($C_1$-$C_4$ haloalkyl). In some embodiments, each $R^4$ is independently hydrogen, halogen, methyl, ethyl, propyl, isopropyl, trifluoromethyl, difluoromethyl, trifluoroethyl, —O-(trifluoromethyl), —O-(difluoromethyl), —O-(trifluoroethyl), —OMe, or —OEt. In some embodiments, each $R^4$ is independently hydrogen, fluoro, chloro, methyl, ethyl, propyl, isopropyl, trifluoromethyl, difluoromethyl, —O-(trifluoromethyl), —OMe, or —OEt. In some embodiments, each $R^4$ is independently hydrogen, fluoro, trifluoromethyl, methyl, or —OMe. In some embodiments, each $R^4$ is independently hydrogen, fluoro or methyl. In some embodiments, one $R^4$ is fluoro, methyl, or —OMe, and the other $R^4$ are each hydrogen. In some embodiments, each $R^4$ is hydrogen. In some embodiments, each $R^4$ is independently hydrogen or halogen.

In some embodiments of a compound of Formula (VI) or Formula (VII), or a pharmaceutically acceptable salt of solvate thereof:
$R^3$ is halogen, cyano, or $C_1$-$C_6$ alkyl;
each $R^4$ is independently hydrogen or halogen;
each $R^5$ is independently hydrogen or halogen;
each $R^6$ is independently selected from the group consisting of halogen, cyano, $C_1$-$C_6$ alkyl, $C_3$-$C_6$ cycloalkyl, —$CH_2$—($C_{3-6}$ cycloalkyl), and $C_1$-$C_6$ haloalkyl;
$R^7$ is hydrogen or $C_{1-6}$ alkyl;
$R^8$ is $C_1$-$C_{10}$ alkyl, $C_1$-$C_{10}$ heteroalkyl, $C_3$-$C_{12}$ cycloalkyl, or 3- to 15-membered heterocycloalkyl; wherein the alkyl, cycloalkyl and heterocycloalkyl is optionally substituted with 1-6 groups independently selected from oxo and $R^{11}$;
or one $R^7$ and one $R^8$ bound to the same nitrogen atom come together to form a 3- to 15-membered heterocycloalkyl that is optionally substituted with 1-6 groups independently selected from oxo and $R^{11}$;
each $R^{11}$ is independently selected from the group consisting of halogen, hydroxy, amino, cyano, —S(=O)$_2$ ($R^{13}$), —N($R^{12}$)S(=O)$_2$($R^{13}$), —S(=O)($R^{13}$), —N($R^{12}$)S(=O)($R^{13}$), —C(=O)$R^{13}$, —N($R^{12}$)C (=O)$R^{13}$, $C_1$-$C_6$ alkyl, —O($C_1$-$C_6$ alkyl), —NH($C_1$-$C_6$ alkyl), —N($C_1$-$C_6$ alkyl)$_2$, $C_1$-$C_6$ haloalkyl, $C_3$-$C_8$ cycloalkyl, 3- to 10-membered heterocycloalkyl, and 5- to 10-membered heteroaryl, wherein the heteroaryl is optionally substituted with 1-4 groups independently selected from $R^{14}$, and the alkyl, haloalkyl, cycloalkyl, and heterocycloalkyl is optionally substituted with 1-4 groups independently selected from oxo and $R^{14}$;
or two $R^{11}$ bound to the same carbon or nitrogen atom come together to form a $C_3$-$C_6$ cycloalkyl or 3- to 6-membered heterocycloalkyl, wherein the cycloalkyl, and heterocycloalkyl is optionally substituted with 1-4 groups independently selected from oxo and $R^{14}$;
each $R^{12}$ is independently hydrogen or $C_1$-$C_6$ alkyl;
each $R^{13}$ is independently hydroxy, amino, $C_1$-$C_6$ alkyl, —O($C_1$-$C_6$ alkyl), —NH($C_1$-$C_6$ alkyl), —N($C_1$-$C_6$ alkyl)$_2$, or $C_1$-$C_6$ haloalkyl; and
each $R^{14}$ is independently cyano, amino, hydroxy, —C(=O)O$R^{12}$, —C(=O)N($R^{12}$)$_2$, $C_1$-$C_6$ alkyl, —O($C_1$-$C_6$ alkyl), or —N$R^{12}$($C_1$-$C_6$ alkyl), wherein each alkyl is optionally substituted with 1-2 hydroxy groups.

In some embodiments, the compound (e.g., the compound of Formula (I)) has the structure of Formula (VIa):

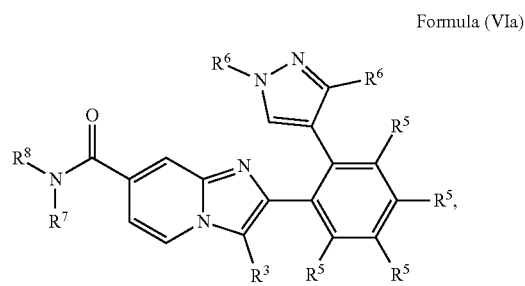

Formula (VIa)

or a pharmaceutically acceptable salt or solvate thereof, wherein:

$R^3$ is halogen, cyano, —C(═O)OH, —C(═O)O($C_1$-$C_6$ alkyl), $C_1$-$C_6$ alkyl, $C_1$-$C_6$ alkenyl, —O($C_1$-$C_6$ alkyl), $C_3$-$C_6$ cycloalkyl, or $C_1$-$C_6$ haloalkyl;

each $R^5$ is independently hydrogen, cyano, halogen, $C_1$-$C_6$ alkyl, —O($C_1$-$C_6$ alkyl), $C_3$-$C_6$ each $R^6$ is independently selected from the group consisting of halogen, hydroxy, cyano, amino, $C_1$-$C_6$ alkyl, $C_1$-$C_6$ hydroxyalkyl, $C_1$-$C_6$ aminoalkyl, —O($C_1$-$C_6$ alkyl), —NH($C_1$-$C_6$ alkyl), —N($C_1$-$C_6$ alkyl)$_2$, $C_3$-$C_6$ cycloalkyl, —CH$_2$—($C_{3-6}$ cycloalkyl), —O—($C_{3-6}$ cycloalkyl), $C_1$-$C_6$ haloalkyl, and —O($C_1$-$C_6$ haloalkyl);

wherein if an $R^6$ is attached to a nitrogen atom, then it is selected from the group consisting of $C_1$-$C_6$ alkyl, $C_1$-$C_6$ hydroxyalkyl, $C_1$-$C_6$ aminoalkyl, $C_3$-$C_6$ cycloalkyl, —CH$_2$—($C_{3-6}$ cycloalkyl), and $C_1$-$C_6$ haloalkyl;

each $R^7$ is independently hydrogen or $C_1$-$C_6$ alkyl, wherein said alkyl is optionally substituted with 1-2 hydroxy groups;

$R^8$ is hydrogen, $C_1$-$C_{10}$ alkyl, $C_1$-$C_{10}$ heteroalkyl, $C_1$-$C_{10}$ alkenyl, $C_1$-$C_{10}$ alkynyl, $C_3$-$C_{12}$ cycloalkyl, 3- to 15-membered heterocycloalkyl, $C_6$-$C_{10}$ aryl, or 5- to 10-membered heteroaryl; wherein the aryl, and heteroaryl is optionally substituted with 1-6 groups independently selected from $R^{11}$, and the alkyl, heteroalkyl, alkenyl, alkynyl, cycloalkyl and heterocycloalkyl is optionally substituted with 1-6 groups independently selected from oxo and $R^{11}$;

each $R^{11}$ is independently selected from the group consisting of halogen, hydroxy, amino, cyano, —S(═O)$_2$(R$^{13}$), —N(R$^{12}$)S(═O)$_2$(R$^{13}$), —S(═O)(R$^{13}$), —N(R$^{12}$)S(═O)(R$^{13}$), —C(═O)R$^{13}$, —N(R$^{12}$)C(═O)R$^{13}$, $C_1$-$C_6$ alkyl, —O($C_1$-$C_6$ alkyl), —NH($C_1$-$C_6$ alkyl), —N($C_1$-$C_6$ alkyl)$_2$, $C_1$-$C_6$ haloalkyl, $C_2$-$C_6$ alkenyl, $C_2$-$C_6$ alkynyl, $C_3$-$C_8$ cycloalkyl, 3- to 10-membered heterocycloalkyl, $C_6$-$C_{10}$ aryl, and 5- to 10-membered heteroaryl, wherein the aryl, and heteroaryl is optionally substituted with 1-4 groups independently selected from $R^{14}$, and the alkyl, alkenyl, alkynyl, haloalkyl, cycloalkyl, and heterocycloalkyl is optionally substituted with 1-4 groups independently selected from oxo and $R^{14}$;

or two $R^{11}$ bound to the same carbon or nitrogen atom come together to form a $C_3$-$C_6$ cycloalkyl or 3- to 6-membered heterocycloalkyl, wherein the cycloalkyl, and heterocycloalkyl is optionally substituted with 1-4 groups independently selected from oxo and $R^{14}$;

each $R^{12}$ is independently hydrogen or $C_1$-$C_6$ alkyl;

each $R^{13}$ is independently hydroxy, amino, $C_1$-$C_6$ alkyl, —O($C_1$-$C_6$ alkyl), —NH($C_1$-$C_6$ alkyl), —N($C_1$-$C_6$ alkyl)$_2$, $C_1$-$C_6$ haloalkyl, $C_3$-$C_6$ cycloalkyl, or 3- to 6-membered heterocycloalkyl; and each $R^{14}$ is independently cyano, amino, hydroxy, —C(═O)OR$^{12}$, —C(═O)N(R$^{12}$)$_2$, $C_1$-$C_6$ alkyl, —O($C_1$-$C_6$ alkyl), —NR$^{12}$($C_1$-$C_6$ alkyl), aryl, heteroaryl, $C_3$-$C_6$ cycloalkyl, or 3- to 6-membered heterocycloalkyl, wherein each alkyl is optionally substituted with 1-2 hydroxy groups.

In some embodiments, the compound (e.g., the compound of Formula (I)) has the structure of Formula (VIIa):

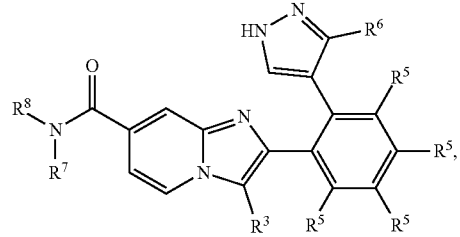

Formula (VIIa)

or a pharmaceutically acceptable salt or solvate thereof, wherein:

$R^3$ is halogen, cyano, —C(═O)OH, —C(═O)O($C_1$-$C_6$ alkyl), $C_1$-$C_6$ alkyl, $C_1$-$C_6$ alkenyl, —O($C_1$-$C_6$ alkyl), $C_3$-$C_6$ cycloalkyl, or $C_1$-$C_6$ haloalkyl;

each $R^5$ is independently hydrogen, cyano, halogen, $C_1$-$C_6$ alkyl, —O($C_1$-$C_6$ alkyl), $C_3$-$C_6$ cycloalkyl, $C_1$-$C_6$ haloalkyl, or —O($C_1$-$C_6$ haloalkyl);

$R^6$ is selected from the group consisting of halogen, hydroxy, cyano, amino, $C_1$-$C_6$ alkyl, $C_1$-$C_6$ hydroxyalkyl, $C_1$-$C_6$ aminoalkyl, —O($C_1$-$C_6$ alkyl), —NH($C_1$-$C_6$ alkyl), —N($C_1$-$C_6$ alkyl)$_2$, $C_3$-$C_6$ cycloalkyl, —CH$_2$—($C_{3-6}$ cycloalkyl), —O—($C_{3-6}$ cycloalkyl), $C_1$-$C_6$ haloalkyl, and —O($C_1$-$C_6$ haloalkyl);

$R^7$ is hydrogen or $C_1$-$C_6$ alkyl, wherein said alkyl is optionally substituted with 1-2 hydroxy groups;

$R^8$ is hydrogen, $C_1$-$C_{10}$ alkyl, $C_1$-$C_{10}$ heteroalkyl, $C_1$-$C_{10}$ alkenyl, $C_1$-$C_{10}$ alkynyl, $C_3$-$C_{12}$ cycloalkyl, 3- to 15-membered heterocycloalkyl, $C_6$-$C_{10}$ aryl, or 5- to 10-membered heteroaryl; wherein the aryl, and heteroaryl is optionally substituted with 1-6 groups independently selected from $R^{11}$, and the alkyl, heteroalkyl, alkenyl, alkynyl, cycloalkyl and heterocycloalkyl is optionally substituted with 1-6 groups independently selected from oxo and $R^{11}$;

or one $R^7$ and one $R^8$ bound to the same nitrogen atom come together to form a 3- to 15-membered heterocycloalkyl that is optionally substituted with 1-6 groups independently selected from oxo and $R^{11}$;

each $R^{11}$ is independently selected from the group consisting of halogen, hydroxy, amino, cyano, —S(═O)$_2$(R$^{13}$), —N(R$^{12}$)S(═O)$_2$(R$^{13}$), —S(═O)(R$^{13}$), —N(R$^{12}$)S(═O)(R$^{13}$), —C(═O)R$^{13}$, —N(R$^{12}$)C(═O)R$^{13}$, $C_1$-$C_6$ alkyl, —O($C_1$-$C_6$ alkyl), —NH($C_1$-$C_6$ alkyl), —N($C_1$-$C_6$ alkyl)$_2$, $C_1$-$C_6$ haloalkyl, $C_2$-$C_6$ alkenyl, $C_2$-$C_6$ alkynyl, $C_3$-$C_8$ cycloalkyl, 3- to 10-membered heterocycloalkyl, $C_6$-$C_{10}$ aryl, and 5- to 10-membered heteroaryl, wherein the aryl, and heteroaryl is optionally substituted with 1-4 groups independently selected from $R^{14}$, and the alkyl, alkenyl, alkynyl, haloalkyl, cycloalkyl, and heterocycloalkyl is optionally substituted with 1-4 groups independently selected from oxo and $R^{14}$;

or two $R^{11}$ bound to the same carbon or nitrogen atom come together to form a $C_3$-$C_6$ cycloalkyl or 3- to 6-membered heterocycloalkyl, wherein the cycloalkyl, and heterocycloalkyl is optionally substituted with 1-4 groups independently selected from oxo and $R^{14}$;

each $R^{12}$ is independently hydrogen or $C_1$-$C_6$ alkyl;

each $R^{13}$ is independently hydroxy, amino, $C_1$-$C_6$ alkyl, —O($C_1$-$C_6$ alkyl), —NH($C_1$-$C_6$ alkyl), —N($C_1$-$C_6$ alkyl)$_2$, $C_1$-$C_6$ haloalkyl, $C_3$-$C_6$ cycloalkyl, or 3- to 6-membered heterocycloalkyl; and each $R^{14}$ is independently cyano, amino, hydroxy, —C(=O)O$R^{12}$, —C(=O)N($R^{12}$)$_2$, $C_1$-$C_6$ alkyl, —O($C_1$-$C_6$ alkyl), —N$R^{12}$($C_1$-$C_6$ alkyl), aryl, heteroaryl, $C_3$-$C_6$ cycloalkyl, or 3- to 6-membered heterocycloalkyl, wherein each alkyl is optionally substituted with 1-2 hydroxy groups.

In some embodiments of a compound of Formula (VI), Formula (VII), Formula (VIa) or Formula (VIIa), or a pharmaceutically acceptable salt or solvate thereof, $R^3$ is halogen, cyano, —C(=O)OH, $C_1$-$C_6$ alkyl, $C_1$-$C_6$ alkenyl, —O($C_1$-$C_6$ alkyl), $C_3$-$C_6$ cycloalkyl, or $C_1$-$C_6$ haloalkyl. In some embodiments, $R^3$ is fluoro, chloro, cyano, —C(=O)OH, $C_1$-$C_6$ alkyl, $C_1$-$C_6$ alkenyl, —O($C_1$-$C_6$ alkyl), $C_3$-$C_6$ cycloalkyl, or $C_1$-$C_6$ haloalkyl. In some embodiments, $R^3$ is fluoro, chloro, cyano, —C(=O)OH, $C_1$-$C_4$ alkyl, $C_1$-$C_4$ alkenyl, —O($C_1$-$C_4$ alkyl), $C_3$-$C_4$ cycloalkyl, or $C_1$-$C_4$ haloalkyl. In some embodiments, $R^3$ is halogen, cyano, $C_1$-$C_6$ alkyl, $C_3$-$C_6$ cycloalkyl, or $C_1$-$C_6$ haloalkyl. In some embodiments, $R^3$ is fluoro, chloro, cyano, methyl, ethyl, vinyl, —OMe, —C(=O)OH, trifluoromethyl, difluoromethyl, or cyclopropyl. In some embodiments, $R^3$ is chloro, cyano, methyl, or ethyl.

In some embodiments of a compound of Formula (VI), Formula (VII), Formula (VIa) or Formula (VIIa), or a pharmaceutically acceptable salt or solvate thereof, each $R^5$ is independently hydrogen, cyano, halogen, $C_1$-$C_6$ alkyl, —O($C_1$-$C_6$ alkyl), $C_3$-$C_6$ cycloalkyl, $C_1$-$C_6$ haloalkyl, or —O($C_1$-$C_6$ haloalkyl). In some embodiments, each $R^5$ is independently hydrogen, cyano, halogen, $C_1$-$C_6$ alkyl, —O($C_1$-$C_6$ alkyl), $C_3$-$C_6$ cycloalkyl, or $C_1$-$C_6$ haloalkyl. In some embodiments, each $R^5$ is independently hydrogen, cyano, halogen, $C_1$-$C_4$ alkyl, —O($C_1$-$C_4$ alkyl), $C_3$-$C_4$ cycloalkyl, or $C_1$-$C_4$ haloalkyl. In some embodiments, each $R^5$ is independently hydrogen, cyano, halogen, methyl, ethyl, propyl, isopropyl, —OMe, —OEt, cyclopropyl, cyclobutyl, trifluoromethyl, or difluoromethyl. In some embodiments, each $R^5$ is independently hydrogen, cyano, fluoro, chloro, methyl, —OMe, cyclopropyl, trifluoromethyl, or difluoromethyl. In some embodiments, each $R^5$ is independently hydrogen or fluoro. In some embodiments, each $R^5$ is independently hydrogen or halogen. In some embodiments, each $R^5$ is hydrogen.

In some embodiments of a compound of Formula (I), Formula (IIa), Formula (IIb), Formula (IIc), Formula (IId), Formula (III), Formula (IIIa), Formula (IIIb), Formula (IIIc), Formula (IIId), Formula (IV), Formula (IVa), Formula (IVb), Formula (IVc), Formula (IVd), Formula (VI), Formula (VIa), or Formula (VIIa), or a pharmaceutically acceptable salt or solvate thereof, $R^3$ is halogen, cyano, —C(=O)OH, —C(=O)O($C_1$-$C_6$ alkyl), $C_1$-$C_6$ alkyl, $C_1$-$C_6$ alkenyl, —O($C_1$-$C_6$ alkyl), $C_3$-$C_6$ cycloalkyl, or $C_1$-$C_6$ haloalkyl. In some embodiments, $R^3$ is halogen, cyano, $C_1$-$C_6$ alkyl, $C_3$-$C_6$ cycloalkyl, or $C_1$-$C_6$ haloalkyl. In some embodiments, $R^3$ is halogen, cyano, $C_1$-$C_6$ alkyl, or $C_1$-$C_6$ haloalkyl. In some embodiments, $R^3$ is halogen, cyano, or $C_1$-$C_6$ alkyl. In some embodiments, $R^3$ is chloro, fluoro, cyano, —C(=O)OH, —C(=O)($C_1$-$C_6$ alkyl), $C_1$-$C_6$ alkyl, $C_1$-$C_6$ alkenyl, —O($C_1$-$C_6$ alkyl), $C_3$-$C_6$ cycloalkyl, or $C_1$-$C_6$ haloalkyl. In some embodiments, $R^3$ is halogen, cyano, —C(=O)OH, —C(=O)O($C_1$-$C_4$ alkyl), $C_1$-$C_4$ alkyl, $C_1$-$C_4$ alkenyl, —O($C_1$-$C_4$ alkyl), $C_3$-$C_4$ cycloalkyl, or $C_1$-$C_4$ haloalkyl. In some embodiments, $R^3$ is chloro, fluoro, cyano, —C(=O)OH, $C_1$-$C_4$ alkyl, $C_1$-$C_4$ alkenyl, —O($C_1$-$C_4$ alkyl), $C_3$-$C_4$ cycloalkyl, or $C_1$-$C_4$ haloalkyl. In some embodiments, $R^3$ is fluoro, chloro, cyano, methyl, ethyl, vinyl, —OMe, —C(=O)OH, trifluoromethyl, difluoromethyl, or cyclopropyl. In some embodiments, $R^3$ is chloro, cyano, methyl, or ethyl. In some embodiments, $R^3$ is chloro. In some embodiments, $R^3$ is cyano. In some embodiments, $R^3$ is methyl. In some embodiments, $R^3$ is ethyl. In some embodiments, $R^3$ is vinyl. In some embodiments, $R^3$ is —OMe. In some embodiments, $R^3$ is cyclopropyl.

In some embodiments of a compound of Formula (I), Formula (IIa), Formula (IIb), Formula (IIc), Formula (IId), Formula (III), Formula (IIIa), Formula (IIIb), Formula (IIIc), Formula (IIId), Formula (IV), Formula (IVa), Formula (IVb), Formula (IVc), Formula (IVd), Formula (VI), Formula (VIa), Formula (VII), or Formula (VIIa), or a pharmaceutically acceptable salt or solvate thereof, each $R^6$ is independently selected from the group consisting of halogen, hydroxy, cyano, amino, $C_1$-$C_6$ alkyl, $C_1$-$C_6$ hydroxyalkyl, $C_1$-$C_6$ aminoalkyl, —O($C_1$-$C_6$ alkyl), —NH($C_1$-$C_6$ alkyl), —N($C_1$-$C_6$ alkyl)$_2$, $C_3$-$C_6$ cycloalkyl, —CH$_2$—($C_{3-6}$ cycloalkyl), —O—($C_{3-6}$ cycloalkyl), $C_1$-$C_6$ haloalkyl, and —O($C_1$-$C_6$ haloalkyl); wherein if an $R^6$ is attached to a nitrogen atom, then it is selected from the group consisting of $C_1$-$C_6$ alkyl, $C_1$-$C_6$ hydroxyalkyl, $C_1$-$C_6$ aminoalkyl, $C_3$-$C_6$ cycloalkyl, —CH$_2$—($C_{3-6}$ cycloalkyl), and $C_1$-$C_6$ haloalkyl. In some embodiments, each $R^6$ is independently selected from the group consisting of halogen, hydroxy, cyano, amino, $C_1$-$C_6$ alkyl, $C_1$-$C_6$ hydroxyalkyl, —O($C_1$-$C_6$ alkyl), $C_3$-$C_6$ cycloalkyl, —CH$_2$—($C_{3-6}$ cycloalkyl), $C_1$-$C_6$ haloalkyl, and —O($C_1$-$C_6$ haloalkyl); wherein if an $R^6$ is attached to a nitrogen atom, then it is selected from the group consisting of $C_1$-$C_6$ alkyl, $C_1$-$C_6$ hydroxyalkyl, $C_3$-$C_6$ cycloalkyl, —CH$_2$—($C_{3-6}$ cycloalkyl), and $C_1$-$C_6$ haloalkyl. In some embodiments, each $R^6$ is independently selected from the group consisting of halogen, cyano, $C_1$-$C_6$ alkyl, $C_3$-$C_6$ cycloalkyl, —CH$_2$—($C_{3-6}$ cycloalkyl), and $C_1$-$C_6$ haloalkyl; wherein if an $R^6$ is attached to a nitrogen atom, then it is selected from the group consisting of $C_1$-$C_6$ alkyl, $C_3$-$C_6$ cycloalkyl, —CH$_2$—($C_{3-6}$ cycloalkyl), and $C_1$-$C_6$ haloalkyl.

In some embodiments of a compound of Formula (I), Formula (IIa), Formula (IIb), Formula (IIc), Formula (IId), Formula (III), Formula (IIIa), Formula (IIIb), Formula (IIIc), Formula (IIId), Formula (IV), Formula (IVa), Formula (IVb), Formula (IVc), Formula (IVd), Formula (VI), Formula (VIa), Formula (VII), or Formula (VIIa), or a pharmaceutically acceptable salt or solvate thereof, each $R^6$ is independently selected from the group consisting of halogen, hydroxy, cyano, $C_1$-$C_4$ alkyl, —O($C_1$-$C_4$ alkyl), —NH($C_1$-$C_4$ alkyl), —N($C_1$-$C_4$ alkyl)$_2$, $C_3$-$C_4$ cycloalkyl, $C_1$-$C_4$ haloalkyl, and —O($C_1$-$C_4$ haloalkyl); wherein if an $R^6$ is attached to a nitrogen atom, then it is selected from the group consisting of $C_1$-$C_4$ alkyl, $C_3$-$C_4$ cycloalkyl, and $C_1$-$C_4$ haloalkyl. In some embodiments, each $R^6$ is independently selected from the group consisting of halogen, hydroxy, cyano, $C_1$-$C_4$ alkyl, —O($C_1$-$C_4$ alkyl), $C_3$-$C_4$ cycloalkyl, and $C_1$-$C_4$ haloalkyl; wherein if an $R^6$ is attached to a nitrogen atom, then it is selected from the group consisting of $C_1$-$C_4$ alkyl, $C_3$-$C_4$ cycloalkyl, and $C_1$-$C_4$ haloalkyl. In some embodiment, each $R^6$ is independently halogen, cyano, $C_{1-6}$ alkyl, $C_{1-6}$ fluoroalkyl, $C_{3-6}$ cycloalkyl, or —CH$_2$—($C_{3-6}$ cycloalkyl); wherein when an $R^6$ is attached to a nitrogen atom, it is $C_{1-6}$ alkyl, $C_{1-6}$ fluoroalkyl, $C_{3-6}$ cycloalkyl, or —CH$_2$—($C_{3-6}$ cycloalkyl). In some embodiments, each $R^6$ is independently selected from the group consisting of methyl, ethyl, cyano, fluoro, chloro, —OMe, trifluoromethyl, and difluoromethyl; wherein when an $R^6$ is attached to a nitrogen atom, it is selected from the group consisting of methyl, ethyl, trifluoromethyl, and difluoromethyl. In some embodiments, each $R^6$ is independently fluoro, chloro, cyano, cyclopropyl, —CH$_2$-cyclopropyl, or methyl; wherein when an $R^6$ is attached to a nitrogen atom, it is methyl, cyclopropyl, or —$CH_2$-cyclopropyl. In some embodiments, each $R^6$ is independently selected from the group consisting of methyl, cyano, fluoro, —OMe, and difluoromethyl; wherein when an $R^6$ is attached to a nitrogen atom, it is methyl. In some embodiments, each $R^6$ is methyl. In some embodiments, each $R^6$ is methyl or fluoro; wherein when an $R^6$ is attached to a nitrogen atom, it is methyl. In some embodiments, each $R^6$ is fluoro. In some embodiments, each $R^6$ is chloro.

In some embodiments of a compound of Formula (I), Formula (IIa), Formula (IIb), Formula (IIc), Formula (IId), Formula (III), Formula (IIIa), Formula (IIIb), Formula (IIIc), Formula (IIId), Formula (IV), Formula (IVa), Formula (IVb), Formula (IVc), Formula (IVd), Formula (VI), Formula (VIa), Formula (VII), or Formula (VIIa), or a pharmaceutically acceptable salt or solvate thereof, each $R^7$ is independently hydrogen or $C_1$-$C_6$ alkyl. In some embodiments, each $R^7$ is independently hydrogen or $C_1$-$C_6$ alkyl, wherein said alkyl is optionally substituted with 1-2 hydroxy groups; $R^8$ is hydrogen, $C_1$-$C_{10}$ alkyl, $C_1$-$C_{10}$ heteroalkyl, $C_1$-$C_{10}$ alkenyl, $C_1$-$C_{10}$ alkynyl, $C_3$-$C_{12}$ cycloalkyl, 3- to 15-membered heterocycloalkyl, $C_6$-$C_{10}$ aryl, or 5- to 10-membered heteroaryl; wherein the aryl, and heteroaryl is optionally substituted with 1-6 groups independently selected from $R^{11}$, and the alkyl, heteroalkyl, alkenyl, alkynyl, cycloalkyl and heterocycloalkyl is optionally substituted with 1-6 groups independently selected from oxo and $R^{11}$; or one $R^7$ and one $R^8$ bound to the same nitrogen atom come together to form a 3- to 15-membered heterocycloalkyl that is optionally substituted with 1-6 groups independently selected from oxo and $R^{11}$. In some embodiments, each $R^7$ is hydrogen. In some embodiments, at least one $R^7$ is hydrogen. In some embodiments, one $R^7$ is hydrogen. In some embodiments, each $R^7$ is $C_1$-$C_6$ alkyl, wherein said alkyl is optionally substituted with 1-2 hydroxy groups. In some embodiments, at least one $R^7$ is $C_1$-$C_6$ alkyl, wherein said alkyl is optionally substituted with 1-2 hydroxy groups. In some embodiments, each $R^7$ is $C_1$-$C_4$ alkyl. In some embodiments, at least one $R^7$ is $C_1$-$C_4$ alkyl. In some embodiments, each $R^7$ is $C_1$-$C_4$ alkyl, wherein said alkyl is optionally substituted with 1 hydroxy groups. In some embodiments, at least one $R^7$ is $C_1$-$C_4$ alkyl, wherein said alkyl is optionally substituted with 1-2 hydroxy groups. In some embodiments, at least one $R^7$ is methyl. In some embodiments, at least one $R^7$ is 2-hydroxyethyl. In some embodiments, one $R^7$ is methyl. In some embodiments, one $R^7$ is 2-hydroxyethyl.

In some embodiments of a compound of Formula (I), Formula (IIa), Formula (IIb), Formula (IIc), Formula (IId), Formula (III), Formula (IIIa), Formula (IIIb), Formula (IIIc), Formula (IIId), Formula (IV), Formula (IVa), Formula (IVb), Formula (IVc), Formula (IVd), Formula (VI), Formula (VIa), Formula (VII), or Formula (VIIa), or a pharmaceutically acceptable salt or solvate thereof, $R^8$ is hydrogen, $C_1$-$C_{10}$ alkyl, $C_1$-$C_{10}$ heteroalkyl, $C_1$-$C_{10}$ alkenyl, $C_1$-$C_{10}$ alkynyl, $C_3$-$C_{12}$ cycloalkyl, 3- to 15-membered heterocycloalkyl, $C_6$-$C_{10}$ aryl, or 5- to 10-membered heteroaryl; wherein the aryl, and heteroaryl is optionally substituted with 1-6 groups independently selected from $R^{11}$, and the alkyl, heteroalkyl, alkenyl, alkynyl, cycloalkyl and heterocycloalkyl is optionally substituted with 1-6 groups independently selected from oxo and $R^{11}$. In some embodiments, $R^8$ is hydrogen, $C_1$-$C_{10}$ alkyl, $C_1$-$C_{10}$ heteroalkyl, $C_3$-$C_{12}$ cycloalkyl, 3- to 15-membered heterocycloalkyl, $C_6$-$C_{10}$ aryl, or 5- to 10-membered heteroaryl. In some embodiments, $R^8$ is hydrogen, $C_1$-$C_{10}$ alkyl, $C_1$-$C_{10}$ heteroalkyl, $C_3$-$C_{12}$ cycloalkyl, or 3- to 15-membered heterocycloalkyl. In some embodiments, $R^8$ is $C_1$-$C_{10}$ alkyl, $C_1$-$C_{10}$ heteroalkyl, $C_3$-$C_{12}$ cycloalkyl, or 3- to 15-membered heterocycloalkyl; wherein the alkyl, heteroalkyl, cycloalkyl or heterocycloalkyl is optionally substituted with 1-6 groups independently selected from oxo and $R^{11}$. In some embodiments, $R^8$ is hydrogen, $C_1$-$C_{10}$ alkyl, $C_3$-$C_{12}$ cycloalkyl, or 3- to 15-membered heterocycloalkyl. In some embodiments, $R^8$ is $C_1$-$C_{10}$ alkyl, $C_3$-$C_{12}$ cycloalkyl, or 3- to 15-membered heterocycloalkyl; wherein the alkyl, cycloalkyl or heterocycloalkyl is optionally substituted with 1-6 groups independently selected from oxo and $R^{11}$. In some embodiments, $R^8$ is hydrogen, $C_1$-$C_6$ alkyl, $C_3$-$C_{10}$ cycloalkyl, or 3- to 12-membered heterocycloalkyl. In some embodiments, $R^8$ is $C_1$-$C_6$ alkyl, $C_3$-$C_{10}$ cycloalkyl, or 3- to 12-membered heterocycloalkyl; wherein the alkyl, cycloalkyl or heterocycloalkyl is optionally substituted with 1-6 groups independently selected from oxo and $R^{11}$. In some embodiments, $R^8$ is hydrogen or $C_1$-$C_6$ alkyl. In some embodiments, $R^8$ is $C_1$-$C_{10}$ heteroalkyl. In some embodiments, $R^8$ is $C_1$-$C_{10}$ alkyl. In some embodiments, $R^8$ is $C_1$-$C_6$ alkyl. In some embodiments, $R^8$ is $C_3$-$C_{12}$ cycloalkyl or 3- to 15-membered heterocycloalkyl. In some embodiments, $R^8$ is $C_3$-$C_{12}$ cycloalkyl or 3- to 15-membered heterocycloalkyl; wherein the cycloalkyl or heterocycloalkyl is optionally substituted with 1-6 groups independently selected from oxo and $R^{11}$. In some embodiments, $R^8$ is $C_3$-$C_{12}$ cycloalkyl. In some embodiments, 3- to 15-membered heterocycloalkyl. In some embodiments, $R^8$ is $C_3$-$C_{10}$ cycloalkyl or 3- to 12-membered heterocycloalkyl. In some embodiments, $R^8$ is $C_3$-$C_{10}$ cycloalkyl or 3- to 12-membered heterocycloalkyl; wherein the cycloalkyl or heterocycloalkyl is optionally substituted with 1-6 groups independently selected from oxo and $R^{11}$. In some embodiments, $R^8$ is $C_3$-$C_{10}$ cycloalkyl. In some embodiments, $R^8$ is $C_3$-$C_{10}$ cycloalkyl; wherein the cycloalkyl is optionally substituted with 1-6 groups independently selected from oxo and $R^{11}$. In some embodiments, $R^8$ is 3- to 12-membered heterocycloalkyl. In some embodiments, $R^8$ is 3- to 12-membered heterocycloalkyl; wherein the heterocycloalkyl is optionally substituted with 1-6 groups independently selected from oxo and $R^{11}$. In some embodiments, $R^8$ is $C_1$-$C_{10}$ alkyl, monocyclic $C_3$-$C_{12}$ cycloalkyl, fused bicyclic $C_5$-$C_{12}$ cycloalkyl, bridged bicyclic $C_5$-$C_{12}$ cycloalkyl, spirocyclic bicyclic $C_5$-$C_{12}$ cycloalkyl, monocyclic 3- to 15-membered heterocycloalkyl, fused bicyclic 5- to 15-membered heterocycloalkyl, bridged bicyclic 5- to 15-membered heterocycloalkyl, or spirocyclic bicyclic 5- to 15-membered heterocycloalkyl. In some embodiments, $R^8$ is monocyclic $C_3$-$C_{10}$ cycloalkyl, fused bicyclic $C_5$-$C_{10}$ cycloalkyl, bridged bicyclic $C_5$-$C_{10}$ cycloalkyl, spirocyclic bicyclic $C_5$-$C_{10}$ cycloalkyl, monocyclic 3- to 12-membered heterocycloalkyl, fused bicyclic 5- to 12-membered heterocycloalkyl, bridged bicyclic 5- to 12-membered heterocycloalkyl, or spirocyclic bicyclic 5- to 12-membered heterocycloalkyl. In some embodiments, $R^8$ is monocyclic $C_3$-$C_{10}$ cycloalkyl, fused bicyclic $C_5$-$C_{10}$ cycloalkyl, bridged bicyclic $C_5$-$C_{10}$ cycloalkyl, spirocyclic bicyclic $C_5$-$C_{10}$ cycloalkyl, monocyclic 3- to 12-membered heterocycloalkyl, fused bicyclic 5- to 12-membered heterocycloalkyl, bridged bicyclic 5- to 12-membered heterocycloalkyl, or spirocyclic bicyclic 5- to 12-membered heterocycloalkyl; wherein the cycloalkyl or heterocycloalkyl is optionally substituted with 1-6 groups independently selected from oxo and $R^{11}$. In some embodiments, $R^8$ is $C_1$-$C_{10}$ alkyl, monocyclic $C_3$-$C_{10}$ cycloalkyl, fused bicyclic $C_5$-$C_{10}$ cycloalkyl, bridged bicyclic $C_5$-$C_{10}$ cycloalkyl, spirocyclic bicyclic $C_5$-$C_{10}$ cycloalkyl, monocyclic 3- to 12-membered heterocycloalkyl, fused bicyclic 5- to 12-membered heterocycloalkyl, bridged bicyclic 5- to 12-membered heterocycloalkyl, or spirocyclic bicyclic 5- to 12-membered heterocycloalkyl. In some embodiments, $R^8$ is monocyclic $C_3$-$C_{10}$ cycloalkyl, fused bicyclic $C_5$-$C_{10}$ cycloalkyl, bridged bicyclic $C_5$-$C_{10}$ cycloalkyl, spirocyclic bicyclic $C_5$-$C_{10}$ cycloalkyl, monocyclic 3- to 12-membered heterocycloalkyl, fused bicyclic 5- to 12-membered heterocycloalkyl, bridged bicyclic 5- to 12-membered heterocycloalkyl, or spirocyclic bicyclic 5- to 12-membered heterocycloalkyl. In some embodiments, $R^8$ is monocyclic $C_3$-$C_{10}$ cycloalkyl. In some embodiments, $R^8$ is monocyclic 5- to 12-membered heterocycloalkyl. In some embodiments, $R^8$ is monocyclic $C_3$-$C_6$ cycloalkyl. In some embodiments, $R^8$ is monocyclic 5- to 6-membered heterocycloalkyl. In some embodiments, $R^8$ is fused bicyclic $C_5$-$C_{12}$ cycloalkyl, bridged bicyclic $C_5$-$C_{12}$ cycloalkyl, spirocyclic bicyclic $C_5$-$C_{12}$ cycloalkyl, fused bicyclic 5- to 15-membered heterocycloalkyl, bridged bicyclic 5- to 15-membered heterocycloalkyl, or spirocyclic bicyclic 5- to 15-membered heterocycloalkyl. In some embodiments, $R^8$ is fused bicyclic $C_5$-$C_{10}$ cycloalkyl, bridged bicyclic $C_5$-$C_{10}$ cycloalkyl, spirocyclic bicyclic $C_5$-$C_{10}$ cycloalkyl, fused bicyclic 5- to 12-membered heterocycloalkyl, bridged bicyclic 5- to 12-membered heterocycloalkyl, or spirocyclic bicyclic 5- to 12-membered heterocycloalkyl. In some embodiments, $R^8$ is fused bicyclic $C_5$-$C_{10}$ cycloalkyl, bridged bicyclic $C_5$-$C_{10}$ cycloalkyl, spirocyclic bicyclic $C_5$-$C_{10}$ cycloalkyl, fused bicyclic 5- to 12-membered heterocycloalkyl, bridged bicyclic 5- to 12-membered heterocycloalkyl, or spirocyclic bicyclic 5- to 12-membered heterocycloalkyl; wherein the cycloalkyl or heterocycloalkyl is optionally substituted with 1-6 groups independently selected from oxo and $R^{11}$. In some embodiments, $R^8$ is fused bicyclic $C_5$-$C_{12}$ cycloalkyl, bridged bicyclic $C_5$-$C_{12}$ cycloalkyl, fused bicyclic 5- to 15-membered heterocycloalkyl, or bridged bicyclic 5- to 15-membered heterocycloalkyl. In some embodiments, $R^8$ is fused bicyclic $C_5$-$C_{12}$ cycloalkyl, bridged bicyclic $C_5$-$C_{12}$ cycloalkyl, fused bicyclic 5- to 15-membered heterocycloalkyl, or bridged bicyclic 5- to 15-membered heterocycloalkyl; wherein the cycloalkyl or heterocycloalkyl is optionally substituted with 1-6 groups independently selected from oxo and $R^{11}$. In some embodiments, $R^8$ is fused bicyclic $C_5$-$C_{10}$ cycloalkyl, bridged bicyclic $C_5$-$C_{10}$ cycloalkyl, fused bicyclic 5- to 12-membered heterocycloalkyl, or bridged bicyclic 5- to 12-membered heterocycloalkyl. In some embodiments, $R^8$ is fused bicyclic $C_5$-$C_{10}$ cycloalkyl, bridged bicyclic $C_5$-$C_{10}$ cycloalkyl, fused bicyclic 5- to 12-membered heterocycloalkyl, or bridged bicyclic 5- to 12-membered heterocycloalkyl; wherein the cycloalkyl or heterocycloalkyl is optionally substituted with 1-6 groups independently selected from oxo and $R^{11}$. In some embodiments, $R^8$ is spirocyclic bicyclic $C_5$-$C_{12}$ cycloalkyl, or spirocyclic bicyclic 5- to 15-membered heterocycloalkyl. In some embodiments, $R^8$ is spirocyclic bicyclic $C_5$-$C_{10}$ cycloalkyl, or spirocyclic bicyclic 5- to 12-membered heterocycloalkyl. In some embodiments, $R^8$ is spirocyclic bicyclic $C_5$-$C_{10}$ cycloalkyl, or spirocyclic bicyclic 5- to 12-membered heterocycloalkyl; wherein the cycloalkyl or heterocycloalkyl is optionally substituted with 1-6 groups independently selected from oxo and $R^{11}$. In some embodiments, $R^8$ is methyl.

In some embodiments of a compound of Formula (I), Formula (IIa), Formula (IIb), Formula (IIc), Formula (IId), Formula (III), Formula (IIIa), Formula (IIIb), Formula (IIIc), Formula (IIId), Formula (IV), Formula (IVa), Formula (IVb), Formula (IVc), Formula (IVd), Formula (VI), Formula (VIa), Formula (VII), or Formula (VIIa), or a pharmaceutically acceptable salt or solvate thereof, $R^8$ is optionally substituted with 1-6 groups independently selected from oxo and $R^{11}$. In some embodiments, $R^8$ is optionally substituted with 1-6 groups independently selected from $R^{11}$. In some embodiments, $R^8$ is optionally substituted with 1-4 groups independently selected from oxo and $R^{11}$. In some embodiments, $R^8$ is optionally substituted with 1-4 groups independently selected from $R^{11}$. In some embodiments, $R^8$ is optionally substituted with 1-2 groups independently selected from oxo and $R^{11}$. In some embodiments, $R^8$ is optionally substituted with 1-2 groups independently selected from $R^{11}$. In some embodiments, $R^8$ is unsubstituted. In some embodiments, $R^8$ is substituted with at least one group selected from oxo and $R^{11}$. In some embodiments, $R^8$ is substituted with at least one group selected from $R^{11}$. In some embodiments, $R^8$ is substituted with 1-6 groups independently selected from oxo and $R^{11}$. In some embodiments, $R^8$ is substituted with 1-6 groups independently selected from $R^{11}$. In some embodiments, $R^8$ is substituted with 1-4 groups independently selected from oxo and $R^{11}$. In some embodiments, $R^8$ is substituted with 1-4 groups independently selected from $R^{11}$. In some embodiments, $R^8$ is substituted with 1-2 groups independently selected from oxo and $R^{11}$. In some embodiments, $R^8$ is substituted with 1-2 groups independently selected from $R^{11}$.

In some embodiments of a compound of Formula (I), Formula (IIa), Formula (IIb), Formula (IIc), Formula (IId), Formula (III), Formula (IIIa), Formula (IIIb), Formula (IIIc), Formula (IIId), Formula (IV), Formula (IVa), Formula (IVb), Formula (IVc), Formula (IVd), Formula (VI), Formula (VIa), Formula (VII), or Formula (VIIa), or a pharmaceutically acceptable salt or solvate thereof, one $R^7$ and one $R^8$ bound to the same nitrogen atom come together to form a 3- to 15-membered heterocycloalkyl that is optionally substituted with 1-6 groups independently selected from oxo and $R^{11}$. In some embodiments, one $R^7$ and one $R^8$ bound to the same nitrogen atom come together to form a 3- to 12-membered heterocycloalkyl that is optionally substituted with 1-6 groups independently selected from oxo and $R^{11}$. In some embodiments, one $R^7$ and one $R^8$ bound to the same nitrogen atom come together to form a 3- to 12-membered heterocycloalkyl that is optionally substituted with 1-4 groups independently selected from oxo and $R^{11}$. In some embodiments, one $R^7$ and one $R^8$ bound to the same nitrogen atom come together to form a 3- to 12-membered heterocycloalkyl that is optionally substituted with 1-2 groups independently selected from oxo and $R^{11}$. In some embodiments, one $R^7$ and one $R^8$ bound to the same nitrogen atom come together to form a fused bicyclic 5- to 15-membered heterocycloalkyl, bridged bicyclic 5- to 15-membered heterocycloalkyl, or spirocyclic bicyclic 5- to 15-membered heterocycloalkyl. In some embodiments, one $R^7$ and one $R^8$ bound to the same nitrogen atom come together to form a fused bicyclic 5- to 12-membered heterocycloalkyl, bridged bicyclic 5- to 12-membered heterocycloalkyl, or spirocyclic bicyclic 5- to 12-membered heterocycloalkyl. In some embodiments, one $R^7$ and one $R^8$ bound to the same nitrogen atom come together to form a fused bicyclic 5- to 12-membered heterocycloalkyl, bridged bicyclic 5- to 12-membered heterocycloalkyl, or spirocyclic bicyclic 5- to 12-membered heterocycloalkyl; wherein the heterocycloalkyl is optionally substituted with 1-6 groups independently selected from oxo and $R^{11}$. In some embodiments, one $R^7$ and one $R^8$ bound to the same nitrogen atom come together to form a bridged bicyclic 5- to 15-membered heterocycloalkyl, or spirocyclic bicyclic 5- to 15-membered heterocycloalkyl. In some embodiments, one $R^7$ and one $R^8$ bound to the same nitrogen atom come together to form a bridged bicyclic 5- to 15-membered heterocycloalkyl, or spirocyclic bicyclic 5- to 15-membered heterocycloalkyl; wherein the heterocycloalkyl is optionally substituted with 1-6 groups independently selected from oxo and $R^{11}$. In some embodiments, one $R^7$ and one $R^8$ bound to the same nitrogen atom come together to form a bridged bicyclic 5- to 12-membered heterocycloalkyl, or spirocyclic bicyclic 5- to 12-membered heterocycloalkyl. In some embodiments, one $R^7$ and one $R^8$ bound to the same nitrogen atom come together to form a bridged bicyclic 5- to 12-membered heterocycloalkyl, or spirocyclic bicyclic 5- to 12-membered heterocycloalkyl; wherein the heterocycloalkyl is optionally substituted with 1-6 groups independently selected from oxo and $R^{11}$. In some embodiments, one $R^7$ and one $R^8$ bound to the same nitrogen atom come together to form a fused bicyclic 5- to 15-membered heterocycloalkyl. In some embodiments, one $R^7$ and one $R^8$ bound to the same nitrogen atom come together to form a fused bicyclic 5- to 12-membered heterocycloalkyl. In some embodiments, one $R^7$ and one $R^8$ bound to the same nitrogen atom come together to form a fused bicyclic 5- to 12-membered heterocycloalkyl; wherein the heterocycloalkyl is optionally substituted with 1-6 groups independently selected from oxo and $R^{11}$. In some embodiments, one $R^7$ and one $R^8$ bound to the same nitrogen atom come together to form a bridged bicyclic 5- to 15-membered heterocycloalkyl. In some embodiments, one $R^7$ and one $R^8$ bound to the same nitrogen atom come together to form a bridged bicyclic 5- to 12-membered heterocycloalkyl. In some embodiments, one $R^7$ and one $R^8$ bound to the same nitrogen atom come together to form a bridged bicyclic 5- to 12-membered heterocycloalkyl; wherein the heterocycloalkyl is optionally substituted with 1-6 groups independently selected from oxo and $R^{11}$. In some embodiments, one $R^7$ and one $R^8$ bound to the same nitrogen atom come together to form a spirocyclic bicyclic 5- to 15-membered heterocycloalkyl. In some embodiments, one $R^7$ and one $R^8$ bound to the same nitrogen atom come together to form a spirocyclic bicyclic 5- to 12-membered heterocycloalkyl. In some embodiments, one $R^7$ and one $R^8$ bound to the same nitrogen atom come together to form a spirocyclic bicyclic 5- to 12-membered heterocycloalkyl; wherein the heterocycloalkyl is optionally substituted with 1-6 groups independently selected from oxo and $R^{11}$. In some embodiments, $R^7$ and one $R^8$ bound to the same nitrogen atom come together to form a 5- to 7-membered heterocycloalkyl. In some embodiments, $R^7$ and one $R^8$ bound to the same nitrogen atom come together to form a 5- to 7-membered heterocycloalkyl; wherein the heterocycloalkyl is optionally substituted with 1-6 groups independently selected from oxo and $R^{11}$. In some embodiments, $R^7$ and one $R^8$ bound to the same nitrogen atom come together to form a diazepane ring. In some embodiments, $R^7$ and one $R^8$ bound to the same nitrogen atom come together to form a morpholine ring. In some embodiments, $R^7$ and one $R^8$ bound to the same nitrogen atom come together to form a piperidine ring. In some embodiments, $R^7$ and one $R^8$ bound to the same nitrogen atom come together to form a piperazine ring. In some embodiments, $R^7$ and one $R^8$ bound to the same nitrogen atom come together to form a pyrrolidine ring. In some embodiments, $R^7$ and one $R^8$ bound to the same nitrogen atom come together to form an azetidine ring. In some embodiments, $R^7$ and one $R^8$ bound to the same nitrogen atom come together to form an imidazolidine ring. In some embodiments, $R^7$ and one $R^8$ bound to the same nitrogen atom come together to form a heterocycloalkyl that is unsubstituted. In some embodiments, $R^7$ and one $R^8$ bound to the same nitrogen atom come together to form a heterocycloalkyl that is substituted with 1-4 groups independently selected from oxo and $R^{11}$. In some embodiments, $R^7$ and one $R^8$ bound to the same nitrogen atom come together to form a heterocycloalkyl that is substituted with 1-2 groups independently selected from oxo and $R^{11}$.

In some embodiments of a compound of Formula (I), Formula (IIa), Formula (IIb), Formula (IIc), Formula (IId), Formula (III), Formula (IIIa), Formula (IIIb), Formula (IIIc), Formula (IIId), Formula (IV), Formula (IVa), Formula (IVb), Formula (IVc), Formula (IVd), Formula (VI), Formula (VIa), Formula (VII), or Formula (VIIa), or a pharmaceutically acceptable salt or solvate thereof, each $R^{11}$ is independently selected from the group consisting of halogen, hydroxy, amino, cyano, —S(=O)$_2$($R^{13}$), —N($R^{12}$)S(=O)$_2$($R^{13}$), —S(=O)($R^{13}$), —N($R^{12}$)S(=O)($R^{13}$), —C(=O)$R^{13}$, —N($R^{12}$)C(=O)$R^{13}$, $C_1$-$C_6$ alkyl, —O($C_1$-$C_6$ alkyl), —NH($C_1$-$C_6$ alkyl), —N($C_1$-$C_6$ alkyl)$_2$, $C_1$-$C_6$ haloalkyl, $C_2$-$C_6$ alkenyl, $C_2$-$C_6$ alkynyl, $C_3$-$C_8$ cycloalkyl, 3- to 10-membered heterocycloalkyl, $C_6$-$C_{10}$ aryl, and 5- to 10-membered heteroaryl, wherein the aryl, and heteroaryl is optionally substituted with 1-4 groups independently selected from $R^{14}$, and the alkyl, alkenyl, alkynyl, haloalkyl, cycloalkyl, and heterocycloalkyl is optionally substituted with 1-4 groups independently selected from oxo and $R^{14}$; or two $R^{11}$ bound to the same carbon or nitrogen atom come together to form a $C_3$-$C_6$ cycloalkyl or 3- to 6-membered heterocycloalkyl, wherein the cycloalkyl, and heterocycloalkyl is optionally substituted with 1-4 groups independently selected from oxo and $R^{14}$. In some embodiments, each $R^{11}$ is independently selected from the group consisting of halogen, hydroxy, amino, cyano, —S(=O)$_2$($R^{13}$), —N($R^{12}$)S(=O)$_2$($R^{13}$), —S(=O)($R^{13}$), —N($R^{12}$)S(=O)($R^{13}$), —C(=O)$R^{13}$, —N($R^{12}$)C(=O)$R^{13}$, $C_1$-$C_6$ alkyl, —O($C_1$-$C_6$ alkyl), —NH($C_1$-$C_6$ alkyl), —N($C_1$-$C_6$ alkyl)$_2$, $C_1$-$C_6$ haloalkyl, $C_3$-$C_8$ cycloalkyl, 3- to 10-membered heterocycloalkyl, $C_6$ aryl, and 5- to 6-membered heteroaryl, wherein the aryl, and heteroaryl is optionally substituted with 1-4 groups independently selected from $R^{14}$, and the alkyl, haloalkyl, cycloalkyl, and heterocycloalkyl is optionally substituted with 1-4 groups independently selected from oxo and $R^{14}$; or two $R^{11}$ bound to the same carbon or nitrogen atom come together to form a $C_3$-$C_6$ cycloalkyl or 3- to 6-membered heterocycloalkyl, wherein the cycloalkyl, and heterocycloalkyl is optionally substituted with 1-4 groups independently selected from oxo and $R^{14}$. In some embodiments, each $R^{11}$ is independently selected from the group consisting of halogen, hydroxy, amino, cyano, —S(=O)$_2$($R^{13}$), —N($R^{12}$)S(=O)$_2$($R^{13}$), —S(=O)($R^{13}$), —N($R^{12}$)S(=O)($R^{13}$), —C(=O)$R^{13}$, —N($R^{12}$)C(=O)$R^{13}$, $C_1$-$C_6$ alkyl, —O($C_1$-$C_6$ alkyl), —NH($C_1$-$C_6$ alkyl), —N($C_1$-$C_6$ alkyl)$_2$, $C_1$-$C_6$ haloalkyl, $C_3$-$C_8$ cycloalkyl, 3- to 10-membered heterocycloalkyl, and 5- to 10-membered heteroaryl, wherein the heteroaryl is optionally substituted with 1-4 groups independently selected from $R^{14}$, and the alkyl, haloalkyl, cycloalkyl, and heterocycloalkyl is optionally substituted with 1-4 groups independently selected from oxo and $R^4$; or two $R^{11}$ bound to the same carbon or nitrogen atom come together to form a $C_3$-$C_6$ cycloalkyl or 3- to 6-membered heterocycloalkyl, wherein the cycloalkyl, and heterocycloalkyl is optionally substituted with 1-4 groups independently selected from oxo and $R^{14}$. In some embodiments, each $R^{11}$ is independently selected from the group consisting of halogen, hydroxy, amino, —S(=O)$_2$($R^{13}$), —N($R^{12}$)S(=O)$_2$($R^{13}$), —S(=O)($R^{13}$), —N($R^{12}$)S(=O)($R^{13}$), —N($R^{12}$)C(=O)$R^{13}$, $C_1$-$C_6$ alkyl, —O($C_1$-$C_6$ alkyl), $C_1$-$C_6$ haloalkyl, $C_3$-$C_8$ cycloalkyl, 3- to 10-membered heterocycloalkyl, and 5- to 6-membered heteroaryl, wherein the heteroaryl is optionally substituted with 1-4 groups independently selected from $R^{14}$, and the alkyl, haloalkyl, cycloalkyl, and heterocycloalkyl is optionally substituted with 1-4 groups independently selected from oxo and $R^{14}$; or two $R^{11}$ bound to the same carbon or nitrogen atom come together to form a $C_3$-$C_6$ cycloalkyl or 3- to 6-membered heterocycloalkyl, wherein the cycloalkyl, and heterocycloalkyl is optionally substituted with 1-4 groups independently selected from oxo and $R^{14}$. In some embodiments, each $R^{11}$ is independently selected from the group consisting of fluoro, hydroxy, amino, —S(=O)$_2$($R^{13}$), —N($R^{12}$)S(=O)$_2$($R^{13}$), —S(=O)($R^{13}$), —N($R^{12}$)S(=O)($R^{13}$), —N($R^{12}$)C(=O)$R^{13}$, $C_1$-$C_4$ alkyl, —O($C_1$-$C_4$ alkyl), $C_1$-$C_4$ haloalkyl, $C_3$-$C_6$ cycloalkyl, 3- to 6-membered heterocycloalkyl, and 5- to 6-membered heteroaryl, wherein the heteroaryl is optionally substituted with 1-4 groups independently selected from $R^{14}$, and the alkyl, haloalkyl, cycloalkyl, and heterocycloalkyl is optionally substituted with 1-4 groups independently selected from oxo and $R^{14}$; or two $R^{11}$ bound to the same carbon or nitrogen atom come together to form a $C_3$-$C_4$ cycloalkyl or 3- to 4-membered heterocycloalkyl, wherein the cycloalkyl, and heterocycloalkyl is optionally substituted with 1-4 groups independently selected from oxo and $R^{14}$. In some embodiments, each $R^{11}$ is independently selected from the group consisting of fluoro, hydroxy, amino, —S(=O)$_2$($R^{13}$), —N($R^{12}$)S(=O)$_2$($R^{13}$), —S(=O)($R^{13}$), —N($R^{12}$)S(=O)($R^{13}$), —N($R^{12}$)C(=O)$R^{13}$, $C_1$-$C_4$ alkyl, —O($C_1$-$C_4$ alkyl), $C_1$-$C_4$ haloalkyl, $C_3$-$C_6$ cycloalkyl, 3- to 6-membered heterocycloalkyl, and 5- to 6-membered heteroaryl, wherein the heteroaryl is optionally substituted with 1-4 groups independently selected from $R^{14}$, and the alkyl, haloalkyl, cycloalkyl, and heterocycloalkyl is optionally substituted with 1-2 groups independently selected from oxo and $R^{14}$; or two $R^{11}$ bound to the same carbon or nitrogen atom come together to form a $C_3$-$C_4$ cycloalkyl or 3- to 4-membered heterocycloalkyl, wherein the cycloalkyl, and heterocycloalkyl is optionally substituted with 1-2 groups independently selected from oxo and $R^{14}$. In some embodiments, each $R^{11}$ is independently selected from the group consisting of fluoro, hydroxy, amino, —S(=O)$_2$($R^{13}$), —N($R^{12}$)S(=O)$_2$($R^{13}$), —S(=O)($R^{13}$), —N($R^{12}$)S(=O)($R^{13}$), —N($R^{12}$)C(=O)$R^{13}$, $C_1$-$C_4$ alkyl, —O($C_1$-$C_4$ alkyl), $C_1$-$C_4$ haloalkyl, $C_3$-$C_6$ cycloalkyl, 3- to 6-membered heterocycloalkyl, and 5- to 6-membered heteroaryl; or two $R^{11}$ bound to the same carbon or nitrogen atom come together to form a $C_3$-$C_4$ cycloalkyl or 3- to 4-membered heterocycloalkyl. In some embodiments, each $R^{11}$ is independently selected from the group consisting of fluoro, hydroxy, amino, —S(=O)$_2$($R^{13}$), —N($R^{12}$)S(=O)$_2$($R^{13}$), —S(=O)($R^{13}$), —N($R^{12}$)S(=O)($R^{13}$), —N($R^{12}$)C(=O)$R^{13}$, $C_1$-$C_4$ alkyl, —O($C_1$-$C_4$ alkyl), $C_1$-$C_4$ haloalkyl, $C_3$-$C_6$ cycloalkyl, 3- to 6-membered heterocycloalkyl, and 5- to 6-membered heteroaryl.

In some embodiments of a compound of Formula (I), Formula (IIa), Formula (IIb), Formula (IIc), Formula (IId), Formula (III), Formula (IIIa), Formula (IIIb), Formula (IIIc), Formula (IIId), Formula (IV), Formula (IVa), Formula (IVb), Formula (IVc), Formula (IVd), Formula (VI), Formula (VIa), Formula (VII), or Formula (VIIa), or a pharmaceutically acceptable salt or solvate thereof, each $R^{11}$ is independently selected from the group consisting of halogen, hydroxy, amino, cyano, —S(=O)$_2$($R^{13}$), —N($R^{12}$)S(=O)$_2$($R^{13}$), —S(=O)($R^{13}$), —N($R^{12}$)S(=O)($R^{13}$), —C(=O)$R^{13}$, —N($R^{12}$)C(=O)$R^{13}$, $C_1$-$C_6$ alkyl, —O($C_1$-$C_6$ alkyl), —NH($C_1$-$C_6$ alkyl), —N($C_1$-$C_6$ alkyl)$_2$, $C_1$-$C_6$ haloalkyl, $C_3$-$C_8$ cycloalkyl, 3- to 10-membered heterocycloalkyl, and 5- to 10-membered heteroaryl, wherein the heteroaryl is optionally substituted with 1-4 groups independently selected from $R^{14}$, and the alkyl, haloalkyl, cycloalkyl, and heterocycloalkyl is optionally substituted with 1-4 groups independently selected from oxo and $R^{14}$; or two $R^{11}$ bound to the same carbon or nitrogen atom come together to form a $C_3$-$C_6$ cycloalkyl or 3- to 6-membered heterocycloalkyl, wherein the cycloalkyl, and heterocycloalkyl is optionally substituted with 1-4 groups independently selected from oxo and $R^{14}$.

In some embodiments of a compound of Formula (I), Formula (IIa), Formula (IIb), Formula (IIc), Formula (IId), Formula (III), Formula (IIIa), Formula (IIIb), Formula (IIIc), Formula (IIId), Formula (IV), Formula (IVa), Formula (IVb), Formula (IVc), Formula (IVd), Formula (VI), Formula (VIa), Formula (VII), or Formula (VIIa), or a pharmaceutically acceptable salt or solvate thereof, $R^9$ is hydrogen, —C(O)O$R^{12}$, —C(O)N($R^{12}$)$_2$, —S(O)$_2R^{12}$, —S(O)$_2$N($R^{12}$)$_2$, or $C_1$-$C_6$ alkyl. In some embodiments, $R^9$ is hydrogen, —C(O)N($R^{12}$)$_2$, —S(O)$_2R^{12}$, —S(O)$_2$N($R^{12}$)$_2$, or $C_1$-$C_6$ alkyl. In some embodiments, $R^9$ is hydrogen. In some embodiments, $R^9$ is $C_1$-$C_6$ alkyl. In some embodiments, $R^9$ is $C_1$-$C_4$ alkyl. In some embodiments, $R^9$ is methyl. In some embodiments, $R^9$ is —C(O)N($R^{12}$)$_2$, —S(O)$_2R^{12}$, or —S(O)$_2$N($R^{12}$)$_2$. In some embodiments, $R^9$ is —C(O)N($R^{12}$)$_2$. In some embodiments, $R^9$ is —S(O)$_2R^{12}$. In some embodiments, $R^9$ is —S(O)$_2$N($R^{12}$)$_2$.

In some embodiments of a compound of Formula (I), Formula (IIa), Formula (IIb), Formula (IIc), Formula (IId), Formula (III), Formula (IIIa), Formula (IIIb), Formula (IIIc), Formula (IIId), Formula (IV), Formula (IVa), Formula (IVb), Formula (IVc), Formula (IVd), Formula (VI), Formula (VIa), Formula (VII), or Formula (VIIa), or a pharmaceutically acceptable salt or solvate thereof, each $R^{12}$ is independently hydrogen or $C_1$-$C_6$ alkyl. In some embodiments, each $R^{12}$ is hydrogen. In some embodiments, at least one $R^{12}$ is hydrogen. In some embodiments, one $R^{12}$ is hydrogen. In some embodiments, each $R^{12}$ is $C_1$-$C_6$ alkyl. In some embodiments, at least one $R^{12}$ is $C_1$-$C_6$ alkyl. In some embodiments, one $R^{12}$ is $C_1$-$C_6$ alkyl. In some embodiments, each $R^{12}$ is $C_1$-$C_4$ alkyl. In some embodiments, at least one $R^{12}$ is $C_1$-$C_4$ alkyl. In some embodiments, one $R^{12}$ is $C_1$-$C_4$ alkyl. In some embodiments, each $R^{12}$ is methyl. In some embodiments, at least one $R^{12}$ is methyl. In some embodiments, one $R^{12}$ is methyl.

In some embodiments of a compound of Formula (I), Formula (IIa), Formula (IIb), Formula (IIc), Formula (IId), Formula (III), Formula (IIIa), Formula (IIIb), Formula (IIIc), Formula (IIId), Formula (IV), Formula (IVa), Formula (IVb), Formula (IVc), Formula (IVd), Formula (VI), Formula (VIa), Formula (VII), or Formula (VIIa), or a pharmaceutically acceptable salt or solvate thereof, each $R^{13}$ is independently hydroxy, amino, $C_1$-$C_6$ alkyl, —O($C_1$-$C_6$ alkyl), —NH($C_1$-$C_6$ alkyl), —N($C_1$-$C_6$ alkyl)$_2$, $C_1$-$C_6$ haloalkyl, $C_3$-$C_6$ cycloalkyl, or 3- to 6-membered heterocycloalkyl. In some embodiments, each $R^{13}$ is independently hydroxy, amino, $C_1$-$C_6$ alkyl, —O($C_1$-$C_6$ alkyl), $C_3$-$C_6$ cycloalkyl, or 3- to 6-membered heterocycloalkyl. In some embodiments, each $R^{13}$ is independently hydroxy, amino, $C_1$-$C_4$ alkyl, —O($C_1$-$C_4$ alkyl), $C_3$-$C_4$ cycloalkyl, or 3- to 4-membered heterocycloalkyl. In some embodiments, each $R^{13}$ is independently hydroxy, amino, methyl, ethyl, —OMe, —OEt, or cyclopropyl. In some embodiments, each $R^{13}$ is independently hydroxy, amino, methyl, ethyl, or —OMe. In some embodiments, each $R^{13}$ is independently hydroxy, amino, or methyl. In some embodiments, at least one $R^{13}$ is hydroxy. In some embodiments, at least one $R^{13}$ is amino. In some embodiments, at least one $R^{13}$ is methyl. In some embodiments, at least one $R^{13}$ is —OMe. In some embodiments, one $R^{13}$ is hydroxy. In some embodiments, one $R^{13}$ is amino. In some embodiments, one $R^{13}$ is methyl. In some embodiments, one $R^{13}$ is —OMe.

In some embodiments of a compound of Formula (I), Formula (IIa), Formula (IIb), Formula (IIc), Formula (IId), Formula (III), Formula (IIIa), Formula (IIIb), Formula (IIIc), Formula (IIId), Formula (IV), Formula (IVa), Formula (IVb), Formula (IVc), Formula (IVd), Formula (VI), Formula (VIa), Formula (VII), or Formula (VIIa), or a pharmaceutically acceptable salt or solvate thereof, each $R^{13}$ is independently hydroxy, amino, $C_1$-$C_6$ alkyl, —O($C_1$-$C_6$ alkyl), —NH($C_1$-$C_6$ alkyl), —N($C_1$-$C_6$ alkyl)$_2$, or $C_1$-$C_6$ haloalkyl.

In some embodiments of a compound of Formula (I), Formula (IIa), Formula (IIb), Formula (IIc), Formula (IId), Formula (III), Formula (IIIa), Formula (IIIb), Formula (IIIc), Formula (IIId), Formula (IV), Formula (IVa), Formula (IVb), Formula (IVc), Formula (IVd), Formula (VI), Formula (VIa), Formula (VII), or Formula (VIIa), or a pharmaceutically acceptable salt or solvate thereof, each occurrence of $R^{14}$ is independently cyano, amino, hydroxy, —C(=O)O$R^{12}$, —C(=O)N($R^{12}$)$_2$, $C_1$-$C_6$ alkyl, —O($C_1$-$C_6$ alkyl), —N$R^{12}$($C_1$-$C_6$ alkyl), aryl, heteroaryl, $C_3$-$C_6$ cycloalkyl, or 3- to 6-membered heterocycloalkyl, wherein each alkyl is optionally substituted with 1-2 hydroxy groups.

In some embodiments of a compound of Formula (I), Formula (IIa), Formula (IIb), Formula (IIc), Formula (IId), Formula (III), Formula (IIIa), Formula (IIIb), Formula (IIIc), Formula (IIId), Formula (IV), Formula (IVa), Formula (IVb), Formula (IVc), Formula (IVd), Formula (VI), Formula (VIa), Formula (VII), or Formula (VIIa), or a pharmaceutically acceptable salt or solvate thereof, each $R^{14}$ is independently cyano, amino, hydroxy, —C(=O)O$R^{12}$, —C(=O)N($R^{12}$)$_2$, $C_1$-$C_6$ alkyl, —O($C_1$-$C_6$ alkyl), —N$R^{12}$($C_1$-$C_6$ alkyl), aryl, heteroaryl, $C_3$-$C_6$ cycloalkyl, or 3- to 6-membered heterocycloalkyl, wherein each alkyl is optionally substituted with 1-2 hydroxy groups. In some embodiments, each $R^{14}$ is independently amino, hydroxy, —C(=O)O$R^{12}$, —C(=O)N($R^{12}$)$_2$, $C_1$-$C_6$ alkyl, —O($C_1$-$C_6$ alkyl), 5- to 6-membered heteroaryl, $C_3$-$C_6$ cycloalkyl, or 3- to 6-membered heterocycloalkyl, wherein each alkyl is optionally substituted with 1-2 hydroxy groups. In some embodiments, each $R^{14}$ is independently amino, hydroxy, —C(=O)OH, —C(=O)NH$_2$, $C_1$-$C_6$ alkyl, —O($C_1$-$C_6$ alkyl), 5- to 6-membered heteroaryl, $C_3$-$C_6$ cycloalkyl, or 3- to 6-membered heterocycloalkyl, wherein each alkyl is optionally substituted with 1-2 hydroxy groups. In some embodiments, each $R^{14}$ is independently amino, hydroxy, —C(=O)OH, —C(=O)NH$_2$, $C_1$-$C_4$ alkyl, —O($C_1$-$C_4$ alkyl), 5-membered heteroaryl, $C_3$-$C_6$ cycloalkyl, or 3- to 6-membered heterocycloalkyl, wherein each alkyl is optionally substituted with 1-2 hydroxy groups. In some embodiments, each $R^{14}$ is independently amino, hydroxy, —C(=O)OH, —C(=O)NH$_2$, $C_1$-$C_4$ alkyl, —O($C_1$-$C_4$ alkyl), or 5-membered heteroaryl, wherein each alkyl is optionally substituted with 1-2 hydroxy groups. In some embodiments, at least one $R^{14}$ is amino. In some embodiments, at least one $R^{14}$ is hydroxy. In some embodiments, at least one $R^{14}$ is methyl. In some embodiments, at least one $R^{14}$ is $C_1$-$C_4$ alkyl. In some embodiments, at least one $R^{14}$ is methyl. In some embodiments, at least one $R^{14}$ is $C_1$-$C_4$ alkyl substituted with 1-2 hydroxy groups. In some embodiments, at least one $R^{14}$ is —C(=O)O$R^{12}$. In some embodiments, at least one $R^{14}$ is —C(=O)N($R^{12}$)$_2$. In some embodiments, at least one $R^{14}$ is —C(=O)OH. In some embodiments, at least one $R^{14}$ is —C(=O)NH$_2$. In some embodiments, at least one $R^{14}$ is —O($C_1$-$C_4$ alkyl). In some embodiments, at least one $R^{14}$ is —OMe.

In some embodiments of a compound of Formula (I), Formula (IIa), Formula (IIb), Formula (IIc), Formula (IId), Formula (III), Formula (IIIa), Formula (IIIb), Formula (IIIc), Formula (IIId), Formula (IV), Formula (IVa), Formula (IVb), Formula (IVc), Formula (IVd), Formula (VI), Formula (VIa), Formula (VII), or Formula (VIIa), or a pharmaceutically acceptable salt or solvate thereof, each $R^{11}$ is independently selected from the group consisting of halogen, hydroxy, amino, cyano, —S(=O)$_2$($R^{13}$), —N($R^{12}$)S(=O)$_2$($R^{13}$), —S(=O)($R^{13}$), —N($R^{12}$)S(=O)($R^{13}$), —C(=O)$R^{13}$, —N($R^{12}$)C(=O)$R^{13}$, $C_1$-$C_6$ alkyl, —O($C_1$-$C_6$ alkyl), —NH($C_1$-$C_6$ alkyl), —N($C_1$-$C_6$ alkyl)$_2$, $C_1$-$C_6$ haloalkyl, $C_3$-$C_8$ cycloalkyl, 3- to 10-membered heterocycloalkyl, $C_6$ aryl, and 5- to 6-membered heteroaryl, wherein the aryl, and heteroaryl is optionally substituted with 1-4 groups independently selected from $R^{14}$, and the alkyl, haloalkyl, cycloalkyl, and heterocycloalkyl is optionally substituted with 1-4 groups independently selected from oxo and $R^4$; or two $R^{11}$ bound to the same carbon or nitrogen atom come together to form a $C_3$-$C_6$ cycloalkyl or 3- to 6-membered heterocycloalkyl, wherein the cycloalkyl, and heterocycloalkyl is optionally substituted with 1-4 groups independently selected from oxo and $R^{14}$; and each occurrence of $R^{14}$ is independently cyano, amino, hydroxy, —C(=O)O$R^{12}$, —C(=O)N($R^{12}$)$_2$, $C_1$-$C_6$ alkyl, —O($C_1$-$C_6$ alkyl), —N$R^{12}$($C_1$-$C_6$ alkyl), aryl, heteroaryl, $C_3$-$C_6$ cycloalkyl, or 3- to 6-membered heterocycloalkyl, wherein each alkyl is optionally substituted with 1-2 hydroxy groups.

In some embodiments of a compound of Formula (I), Formula (IIa), Formula (IIb), Formula (IIc), Formula (IId), Formula (III), Formula (IIIa), Formula (IIIb), Formula (IIIc), Formula (IIId), Formula (IV), Formula (IVa), Formula (IVb), Formula (IVc), Formula (IVd), Formula (VI), Formula (VIa), Formula (VII), or Formula (VIIa), or a pharmaceutically acceptable salt or solvate thereof, each $R^{11}$ is independently selected from the group consisting of halogen, hydroxy, amino, cyano, —S(=O)$_2$($R^{13}$), —N($R^{12}$)S(=O)$_2$($R^{13}$), —S(=O)($R^{13}$), —N($R^{12}$)S(=O)($R^{13}$), —C(=O)$R^{13}$, —N($R^{12}$)C(=O)$R^{13}$, $C_1$-$C_6$ alkyl, —O($C_1$-$C_6$ alkyl), —NH($C_1$-$C_6$ alkyl), —N($C_1$-$C_6$ alkyl)$_2$, $C_1$-$C_6$ haloalkyl, $C_3$-$C_8$ cycloalkyl, 3- to 10-membered heterocycloalkyl, $C_6$ aryl, and 5- to 6-membered heteroaryl, wherein the aryl, and heteroaryl is optionally substituted with 1-4 groups independently selected from $R^{14}$, and the alkyl, haloalkyl, cycloalkyl, and heterocycloalkyl is optionally substituted with 1-4 groups independently selected from oxo and $R^4$; or two $R^{11}$ bound to the same carbon or nitrogen atom come together to form a $C_3$-$C_6$ cycloalkyl or 3- to 6-membered heterocycloalkyl, wherein the cycloalkyl, and heterocycloalkyl is optionally substituted with 1-4 groups independently selected from oxo and $R^{14}$; and each occurrence of $R^{14}$ is independently cyano, amino, hydroxy, —C(=O)O$R^{12}$, —C(=O)N($R^{12}$)$_2$, $C_1$-$C_6$ alkyl, —O($C_1$-$C_6$ alkyl), —N$R^{12}$($C_1$-$C_6$ alkyl), aryl, heteroaryl, $C_3$-$C_6$ cycloalkyl, or 3- to 6-membered heterocycloalkyl, wherein each alkyl is optionally substituted with 1-2 hydroxy groups.

In some embodiments of a compound of Formula (I), Formula (IIa), Formula (IIb), Formula (IIc), Formula (IId), Formula (III), Formula (IIIa), Formula (IIIb), Formula (IIIc), Formula (IIId), Formula (IV), Formula (IVa), Formula (IVb), Formula (IVc), Formula (IVd), Formula (VI), Formula (VIa), Formula (VII), or Formula (VIIa), or a pharmaceutically acceptable salt or solvate thereof, -L-$R^2$ is

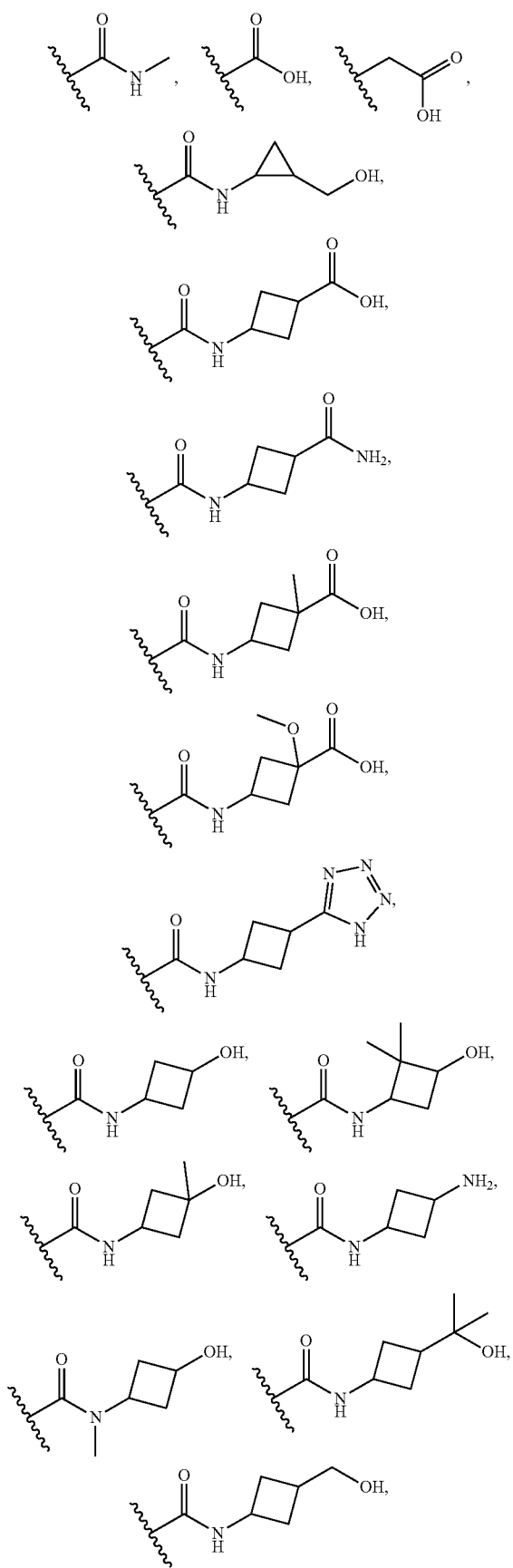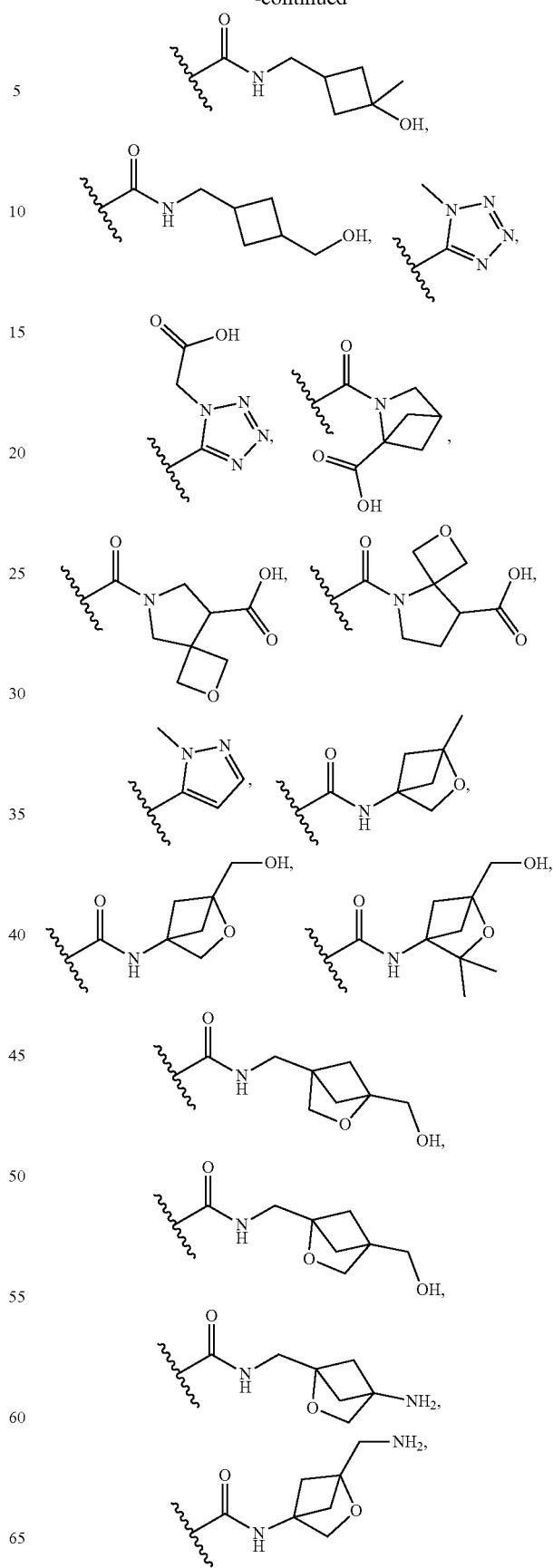

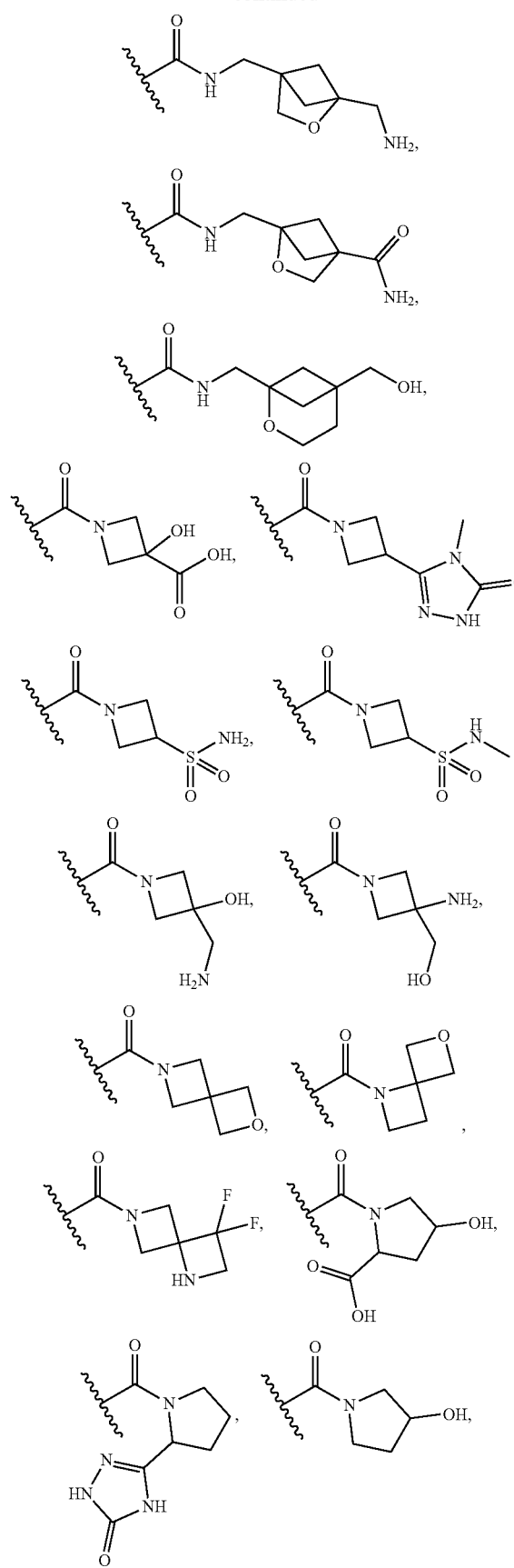

-continued
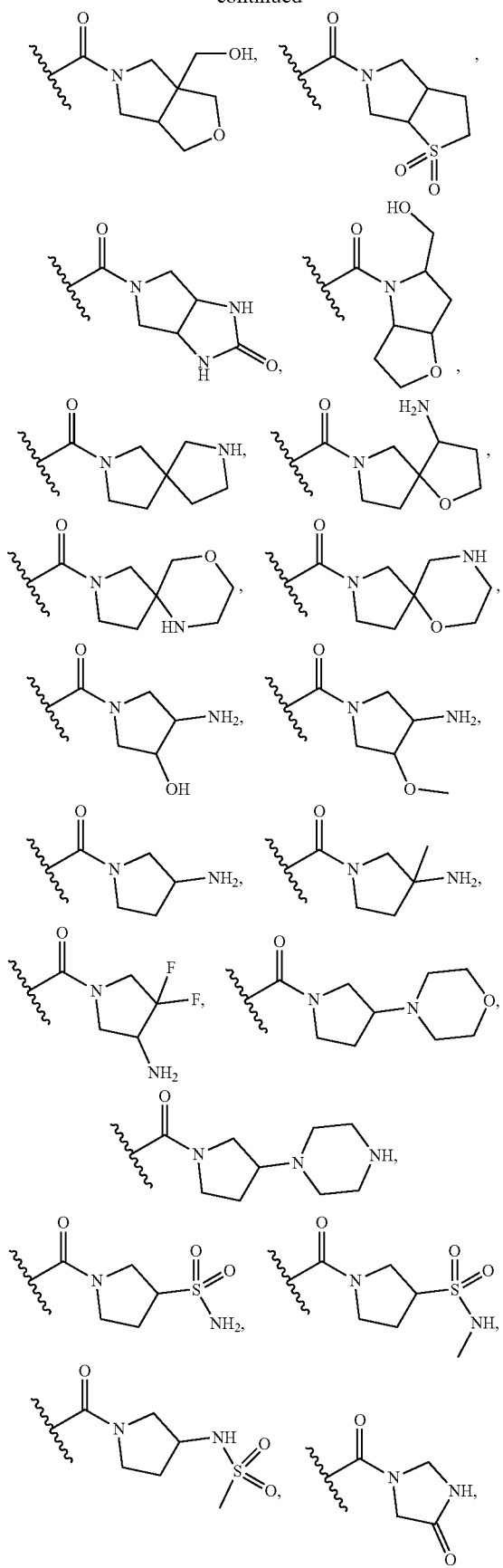
-continued
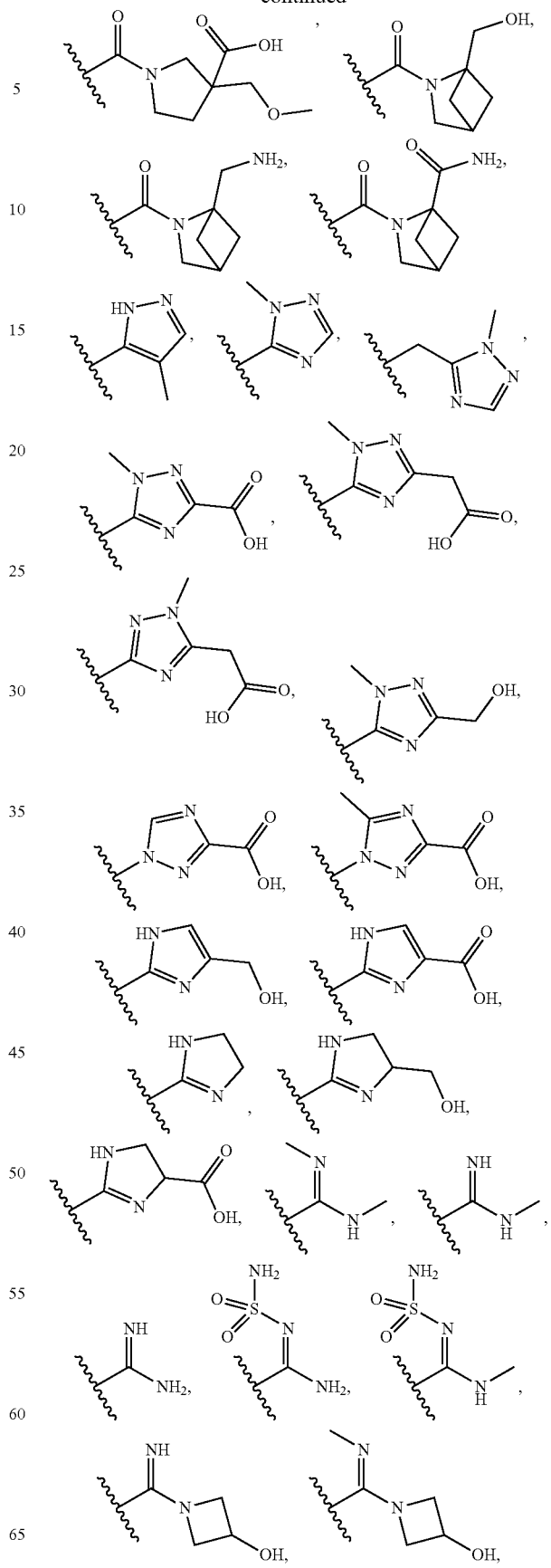

-continued
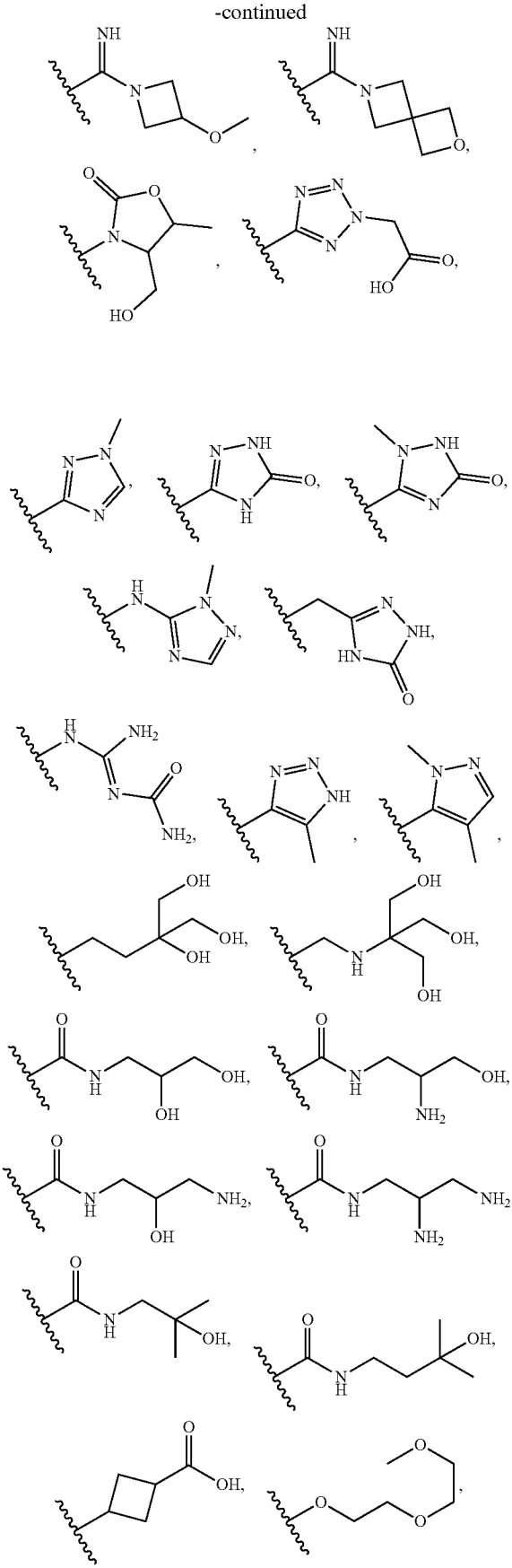
-continued
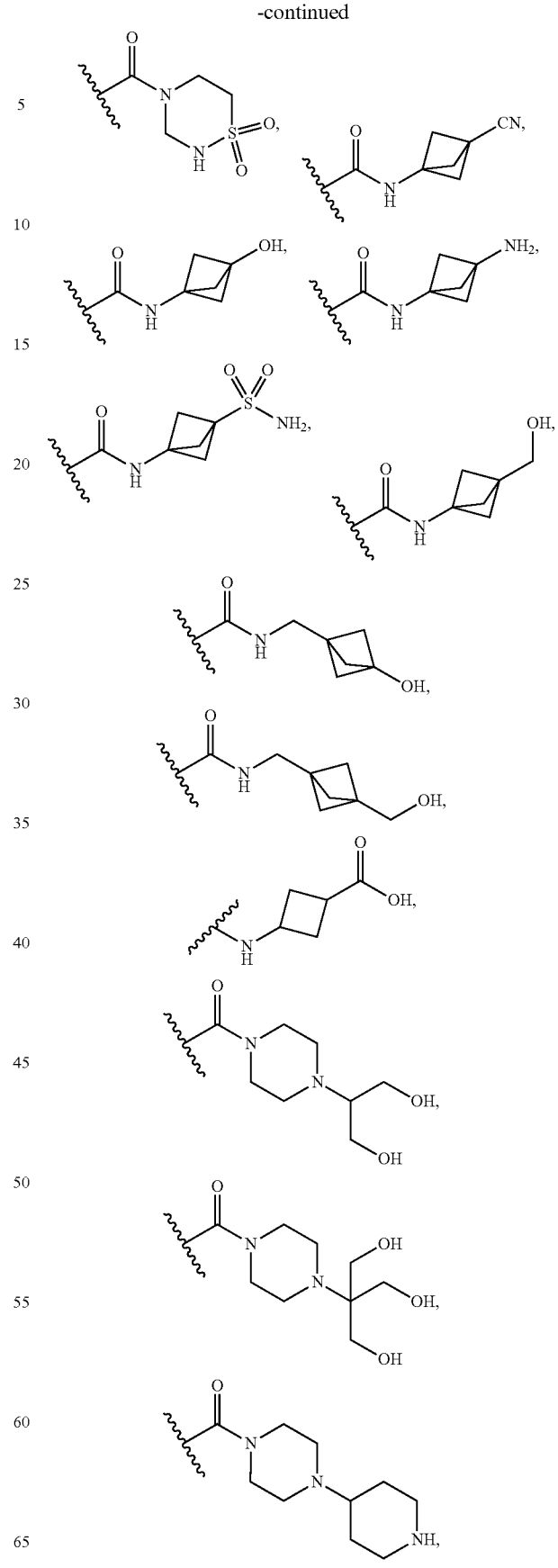

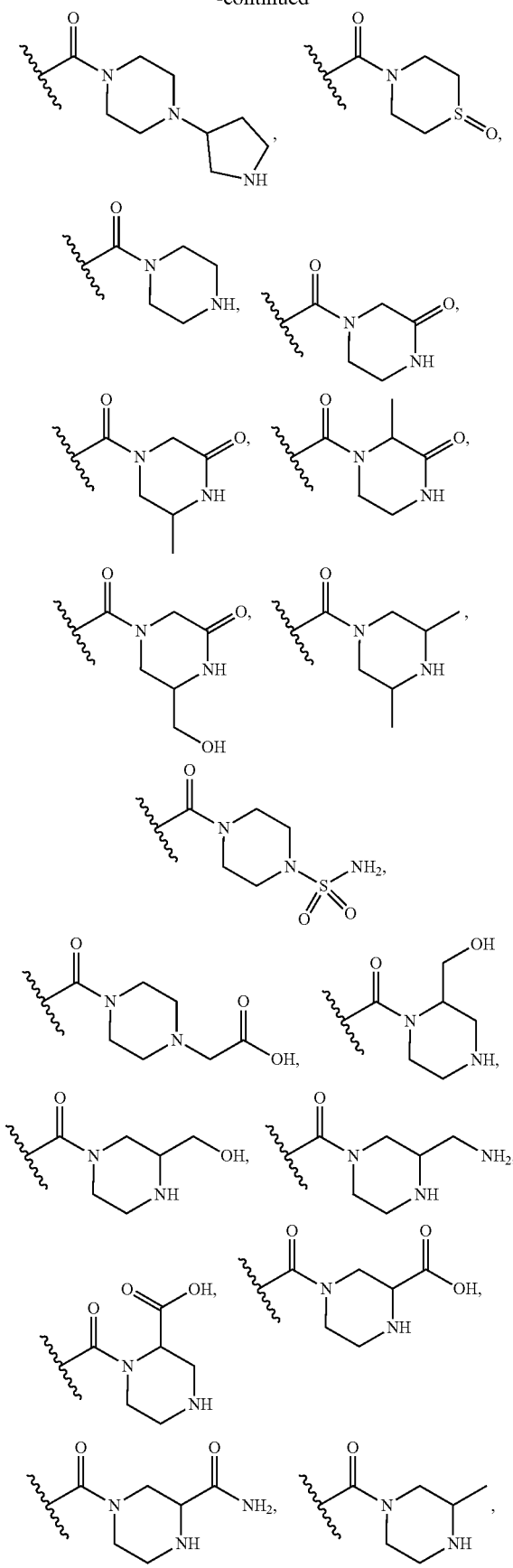
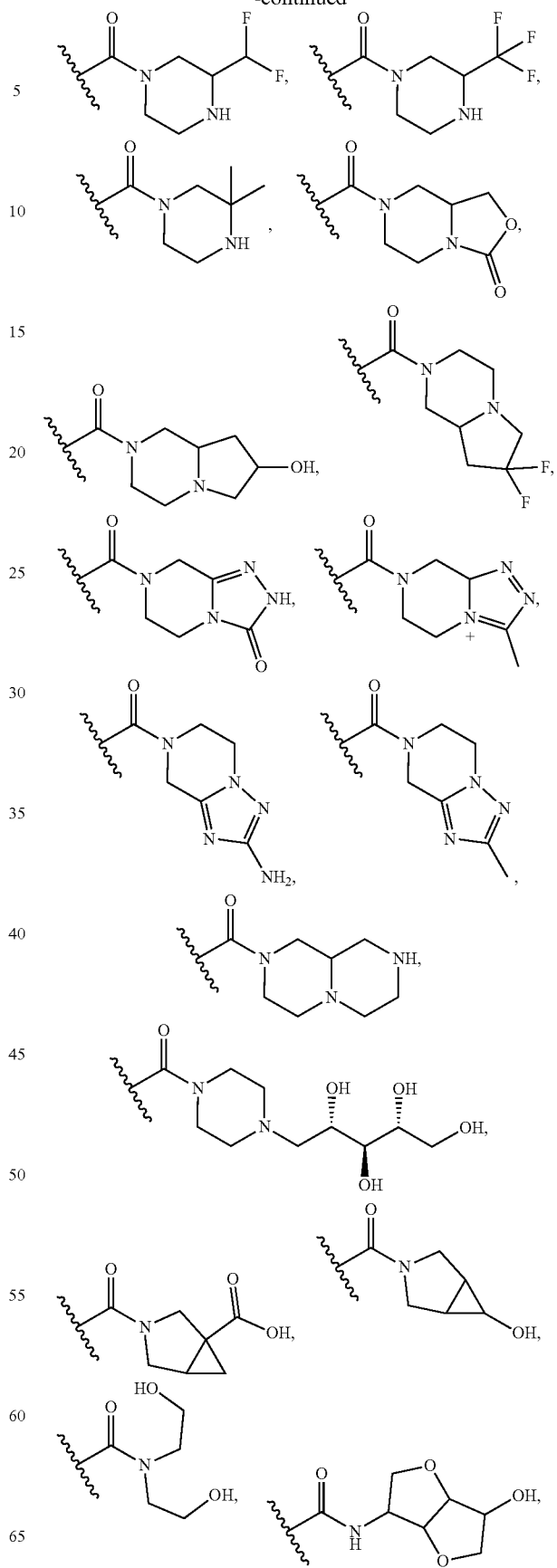

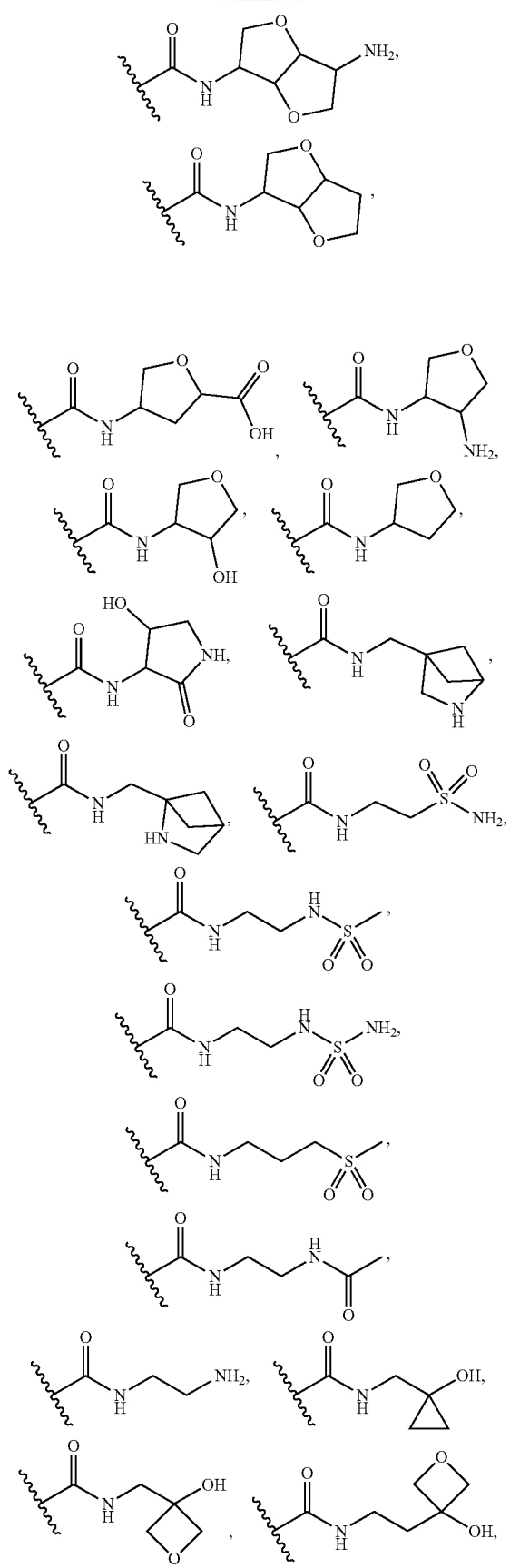
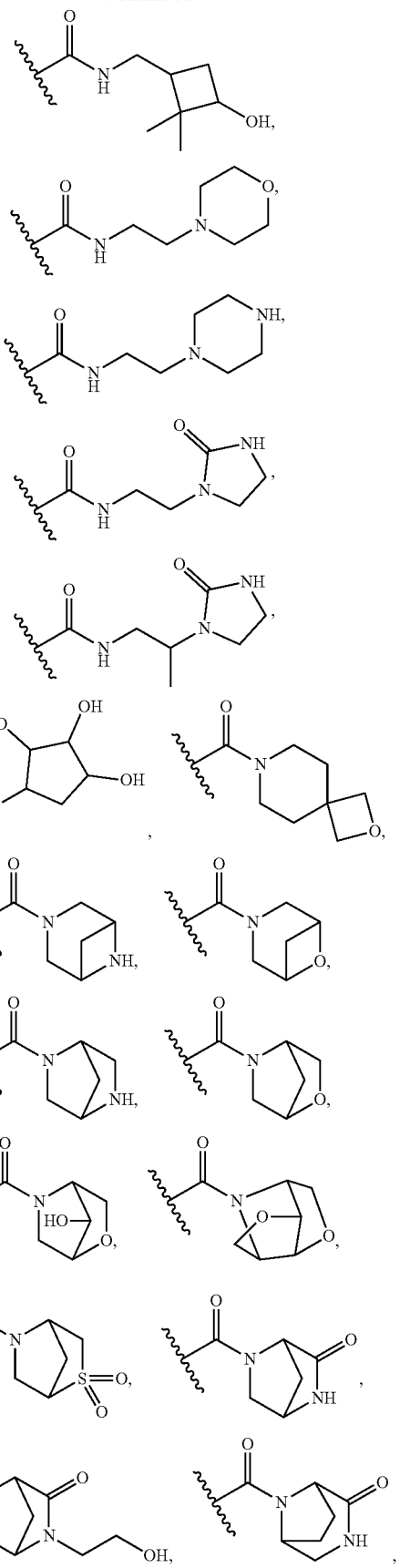

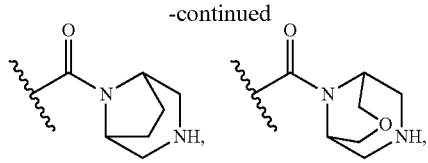
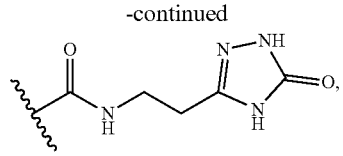
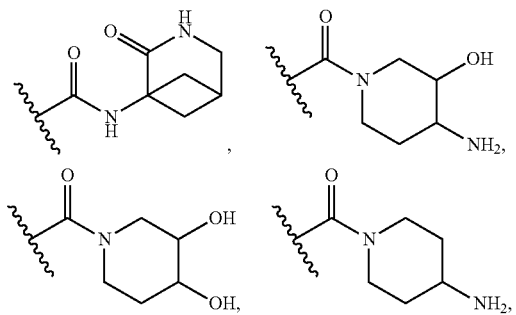
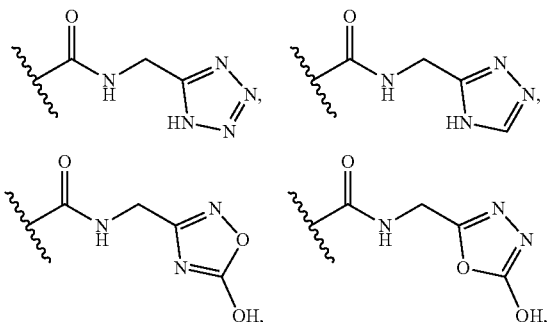
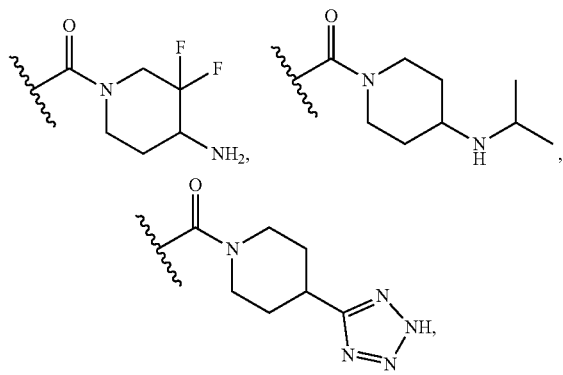
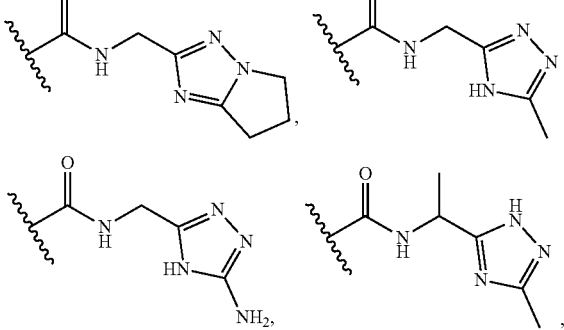
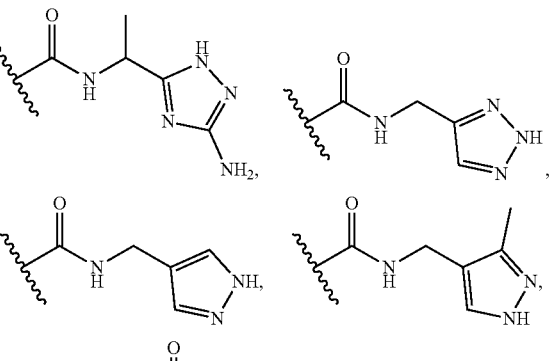
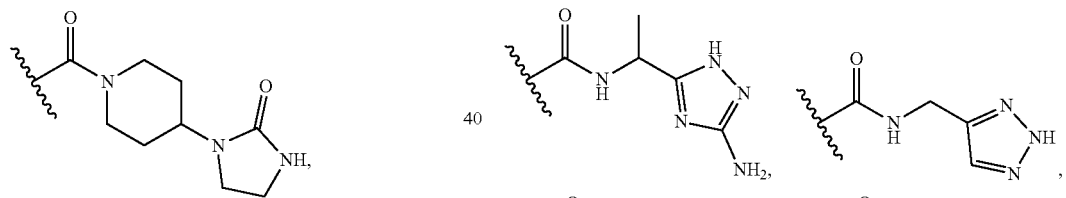
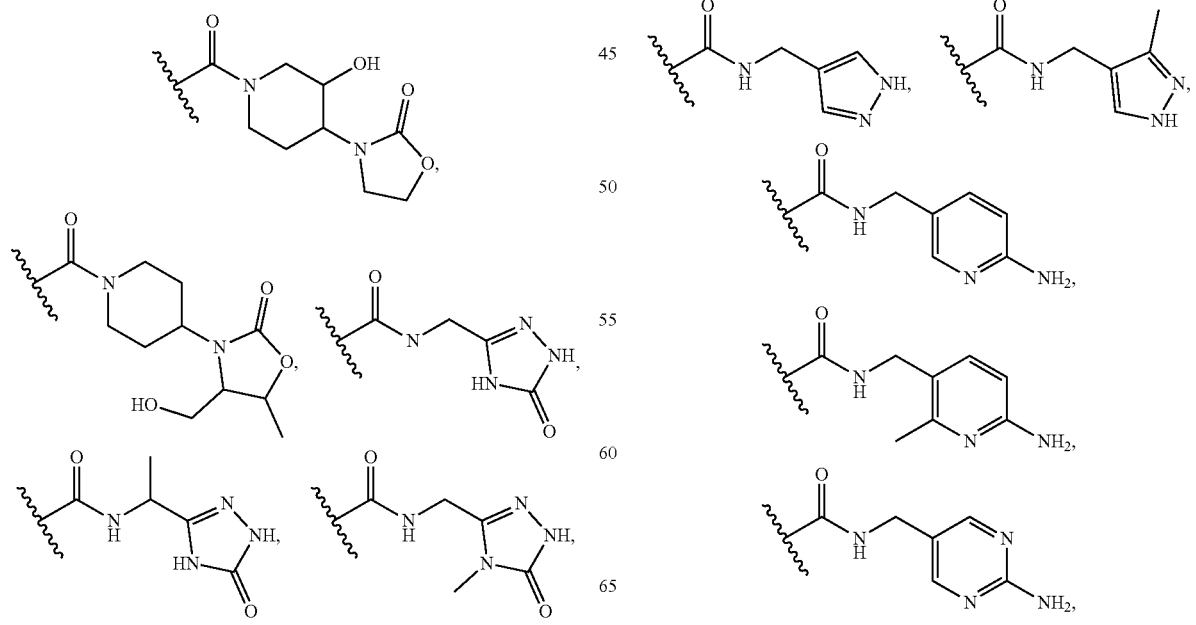
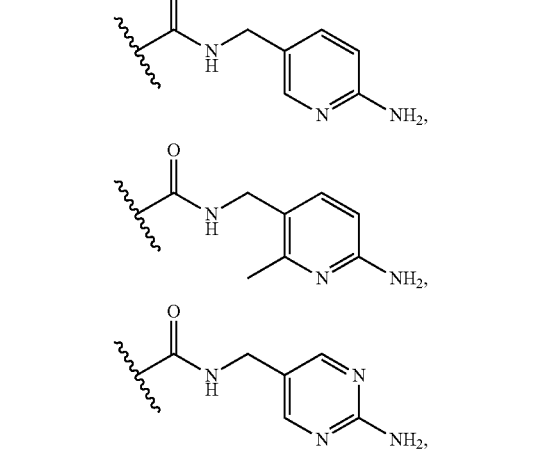

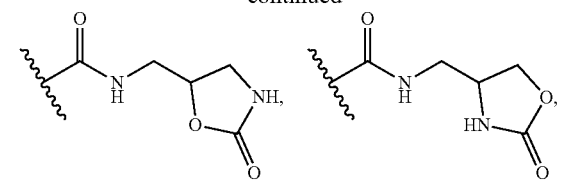
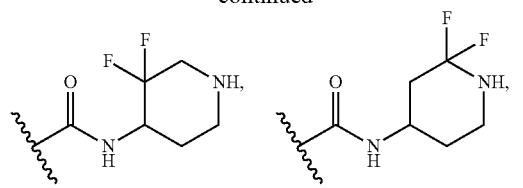

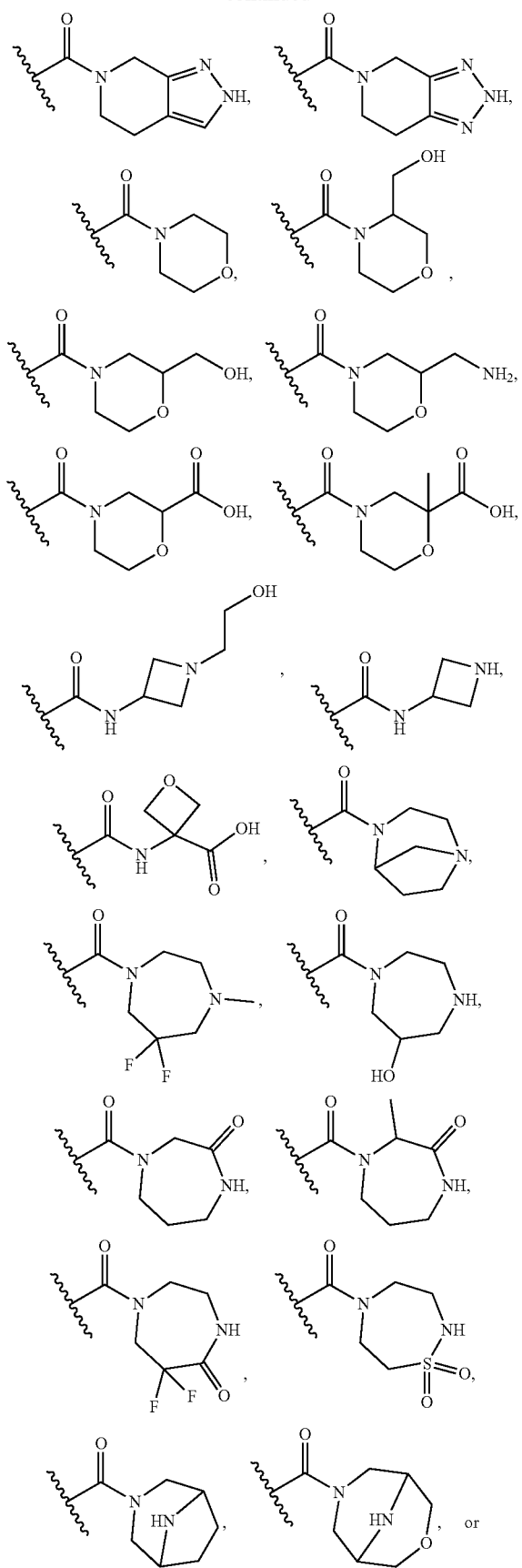
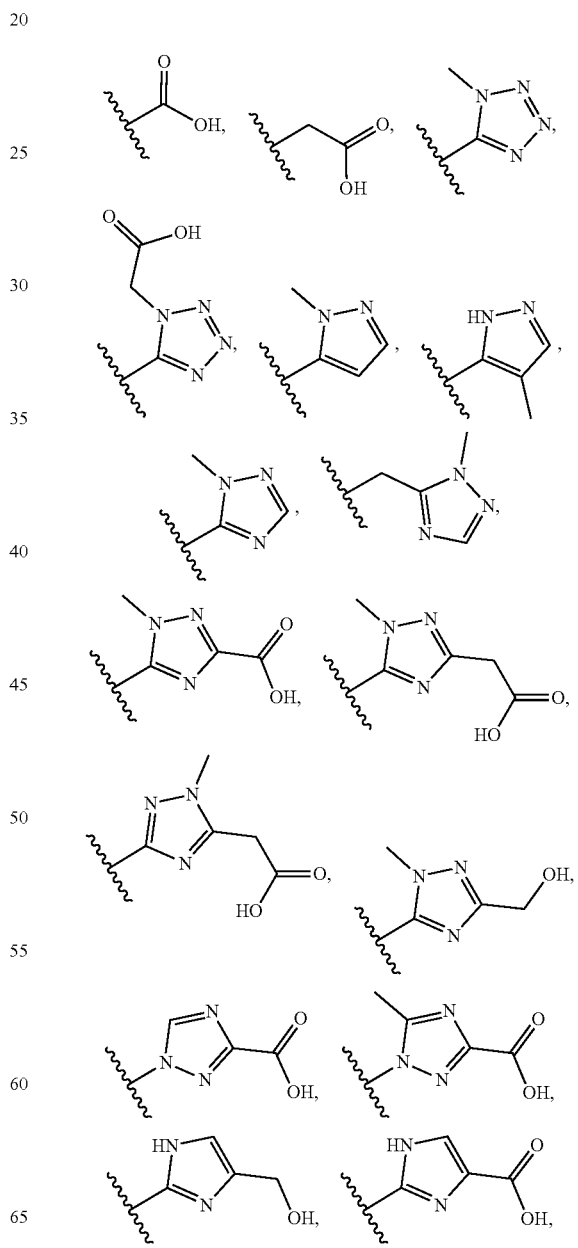
In some embodiments of a compound of Formula (I), Formula (IIa), Formula (IIb), Formula (IIc), Formula (IId), Formula (III), Formula (IIIa), Formula (IIIb), Formula (IIIc), Formula (IIId), Formula (IV), Formula (IVa), Formula (IVb), Formula (IVc), Formula (IVd), Formula (VI), Formula (VIa), Formula (VII), or Formula (VIIa), or a pharmaceutically acceptable salt or solvate thereof, -L-R² is -continued
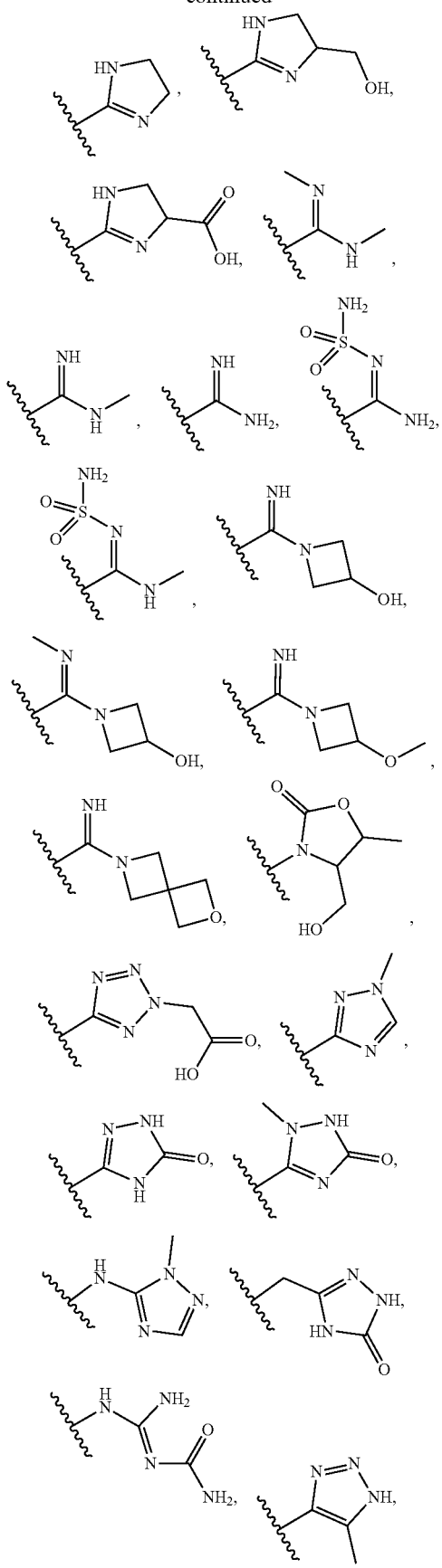
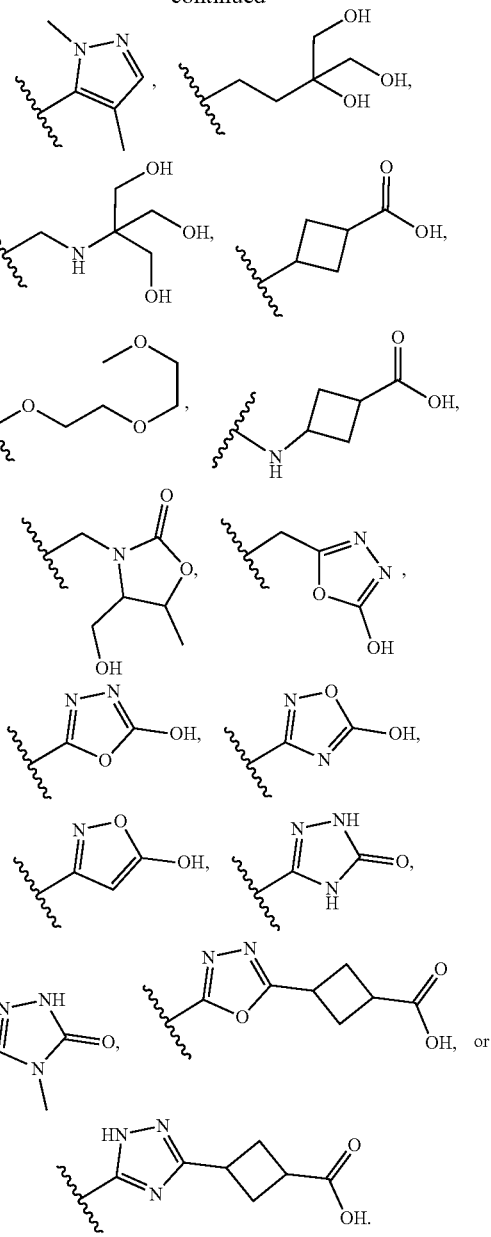
In some embodiments, -L-R² is -continued
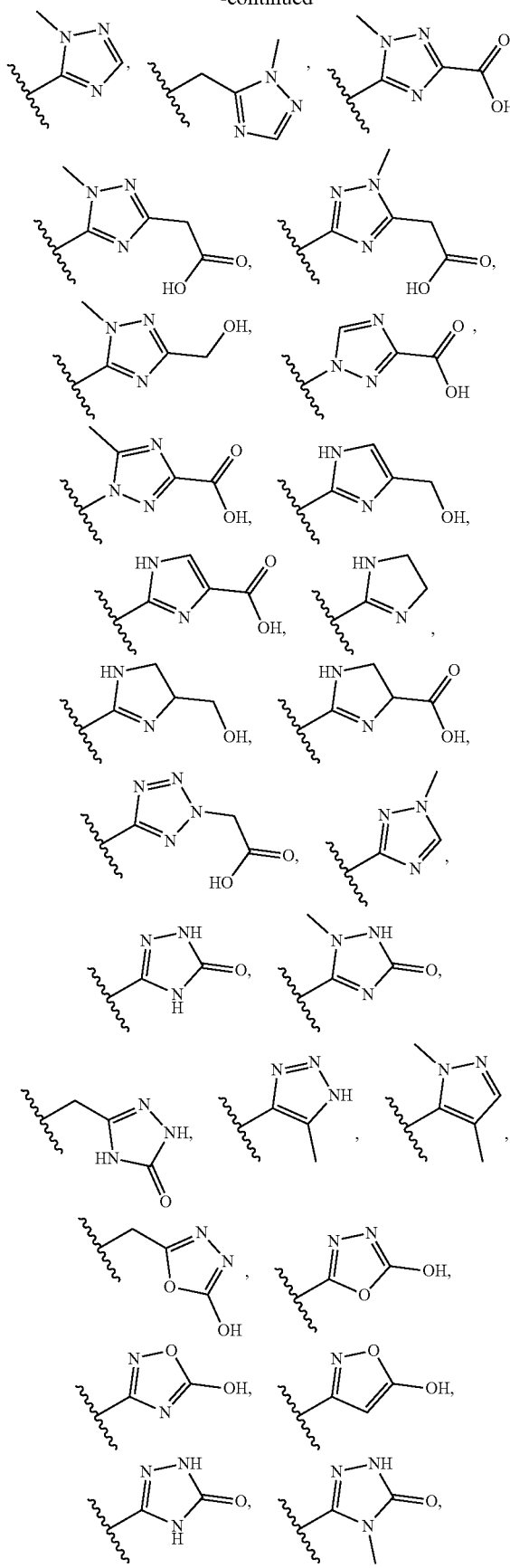
-continued
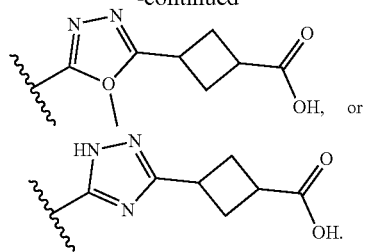
In some embodiments, -L-R² is
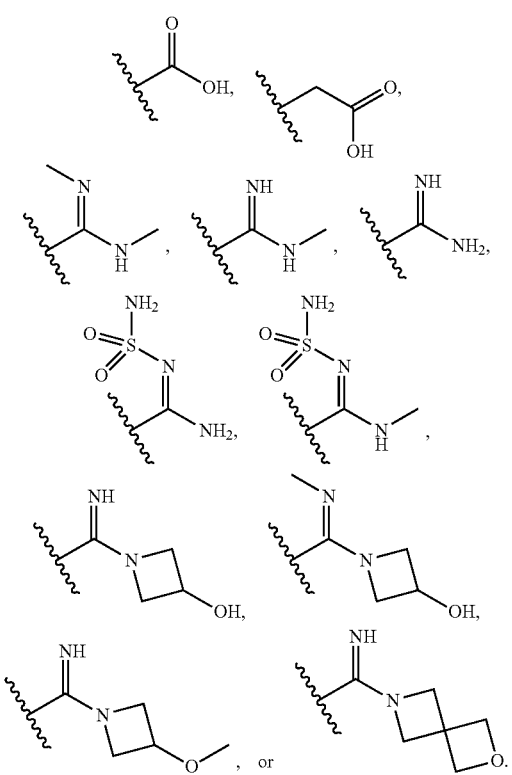
In some embodiments, -L-R² is
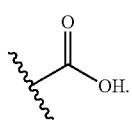
In some embodiments, -L-R² is
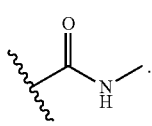
In some embodiments of a compound of Formula (III), Formula (IIIa), Formula (IIIb), Formula (IIIc), Formula (IIId), Formula (IV), Formula (IVa), Formula (IVb), Formula (IVc), Formula (IVd), Formula (VI), Formula (VIa), Formula (VII), or Formula (VIIa) or a pharmaceutically acceptable salt or solvate thereof,
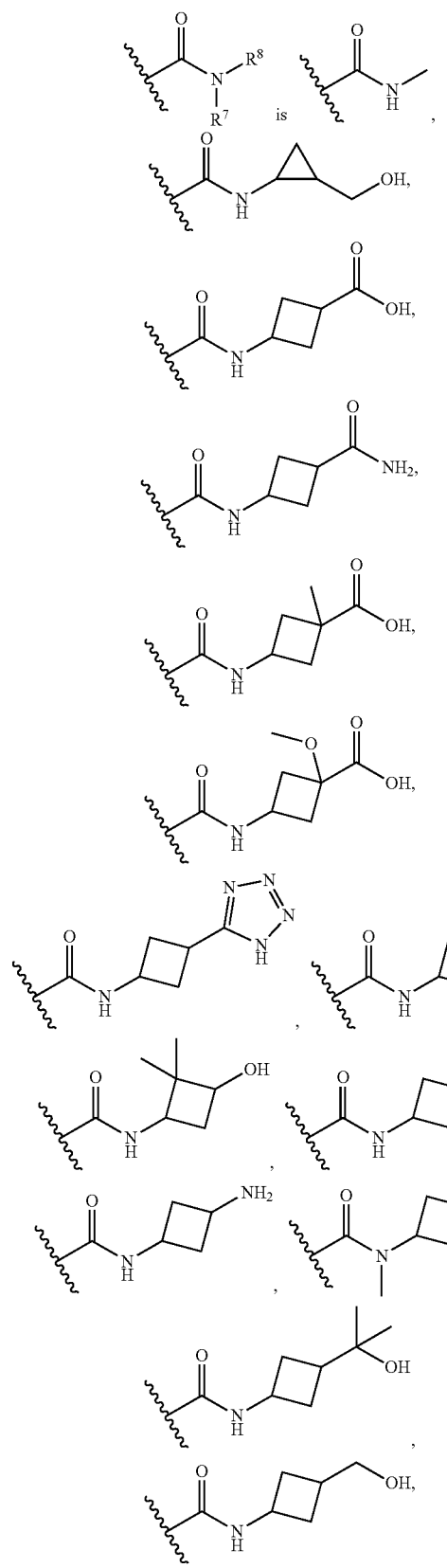
-continued
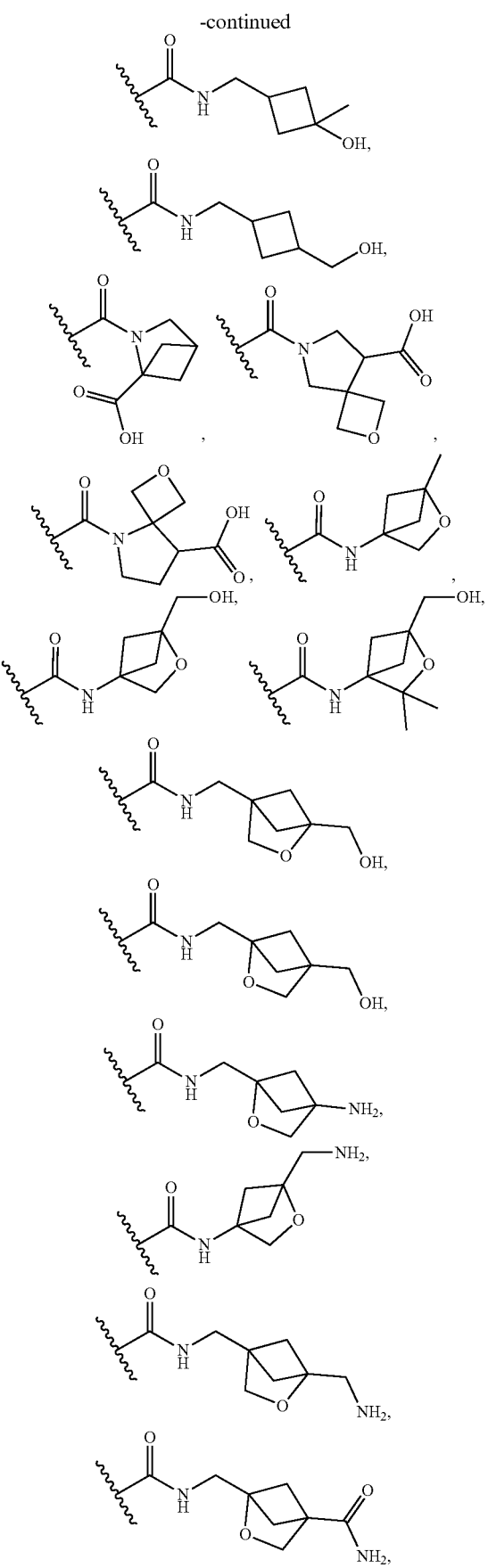

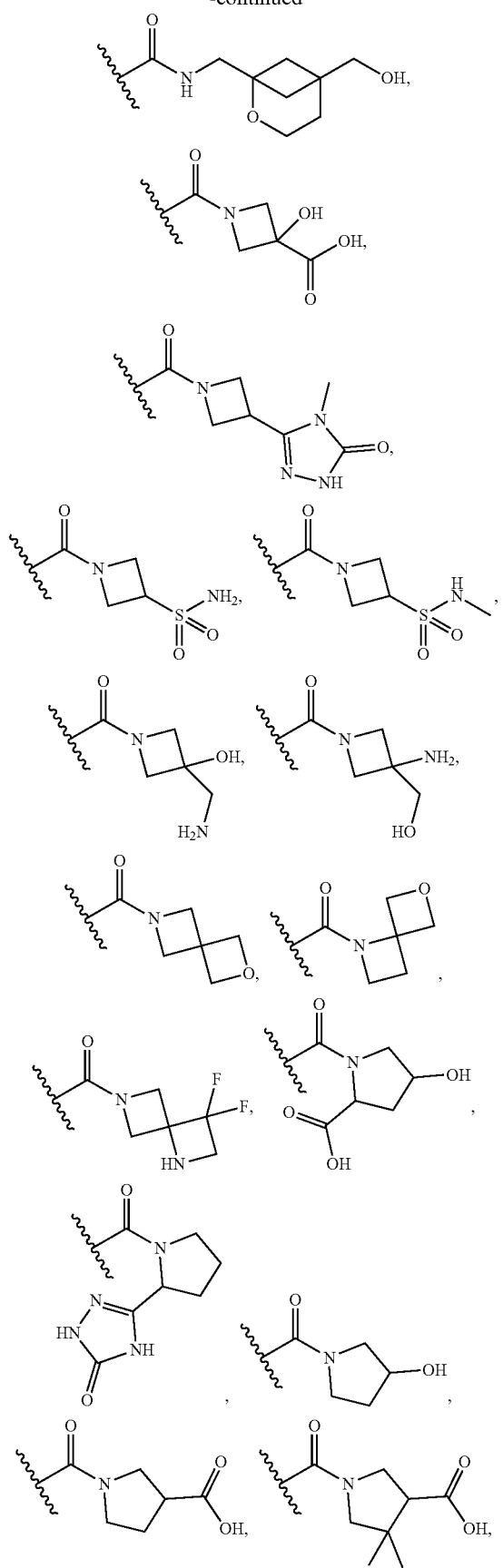
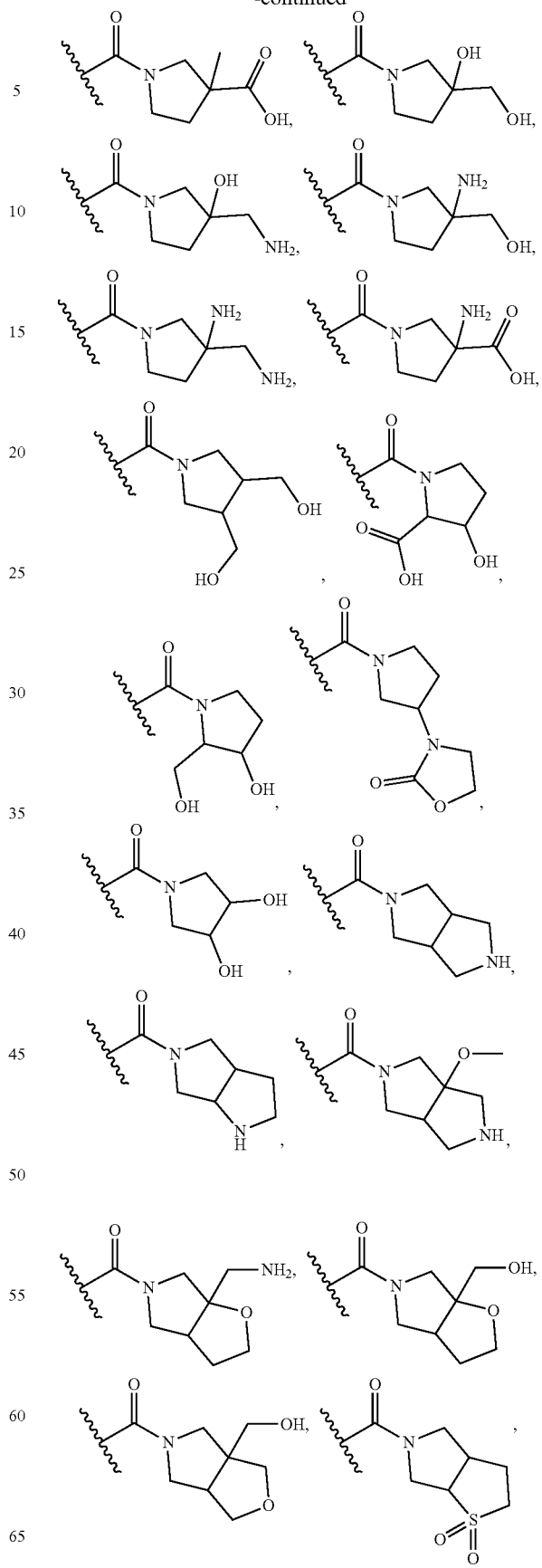

81
-continued
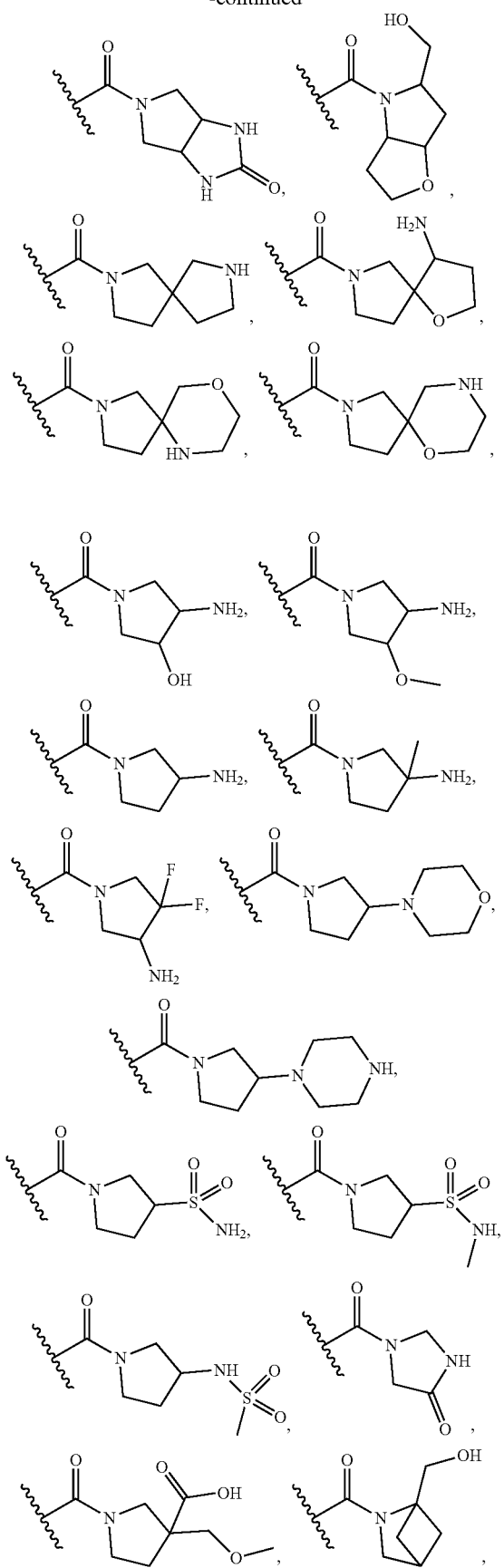
82
-continued
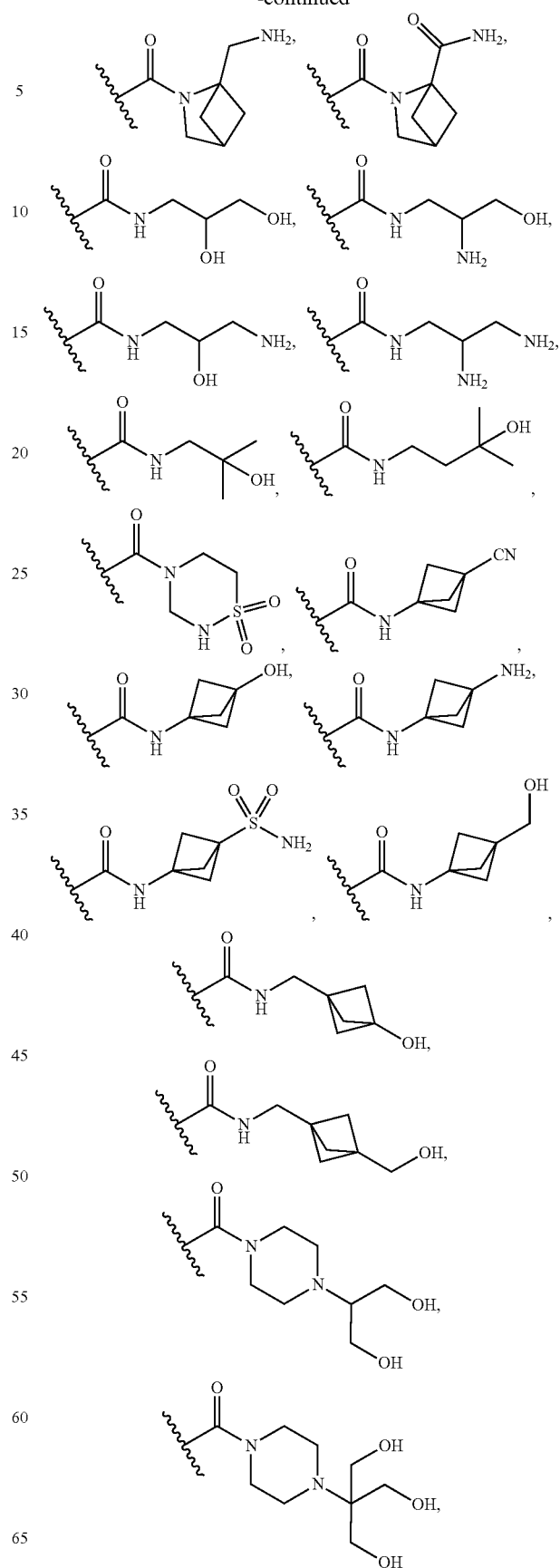

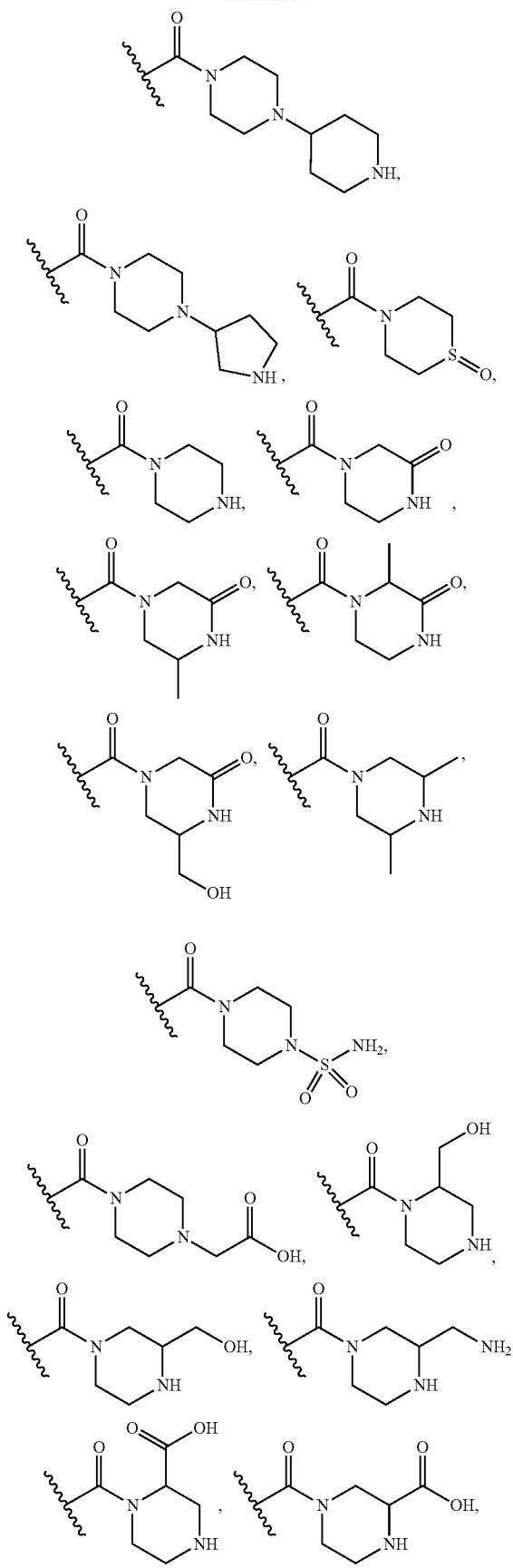
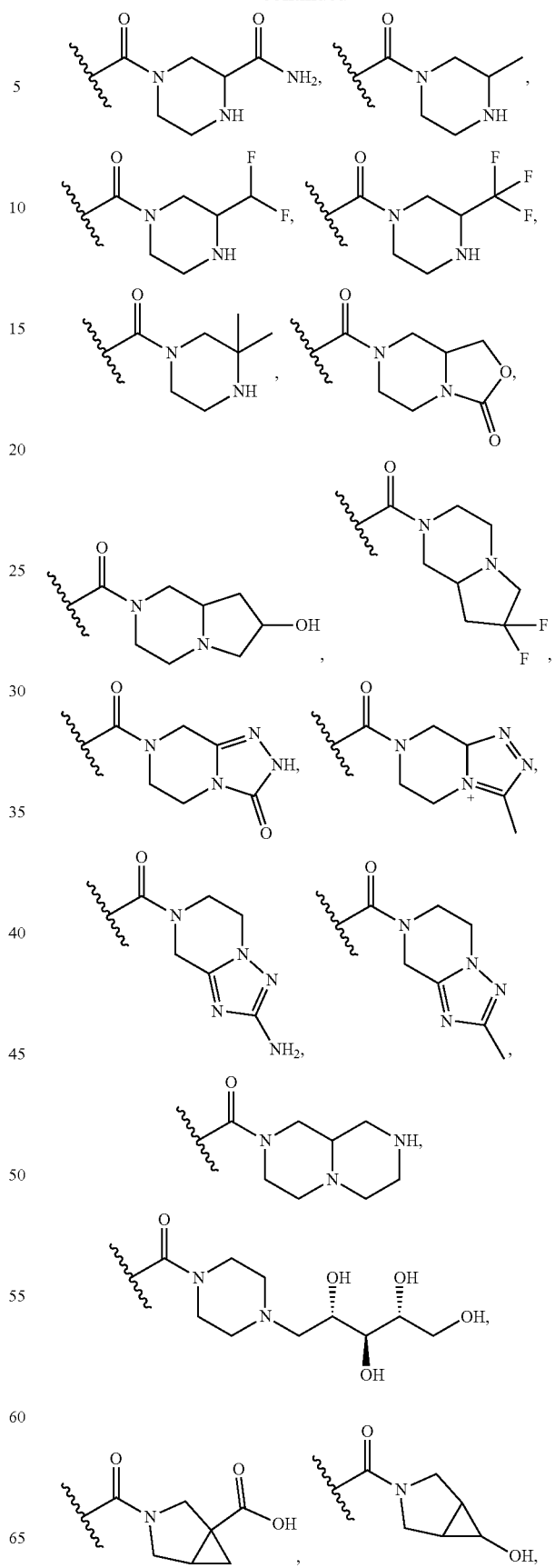

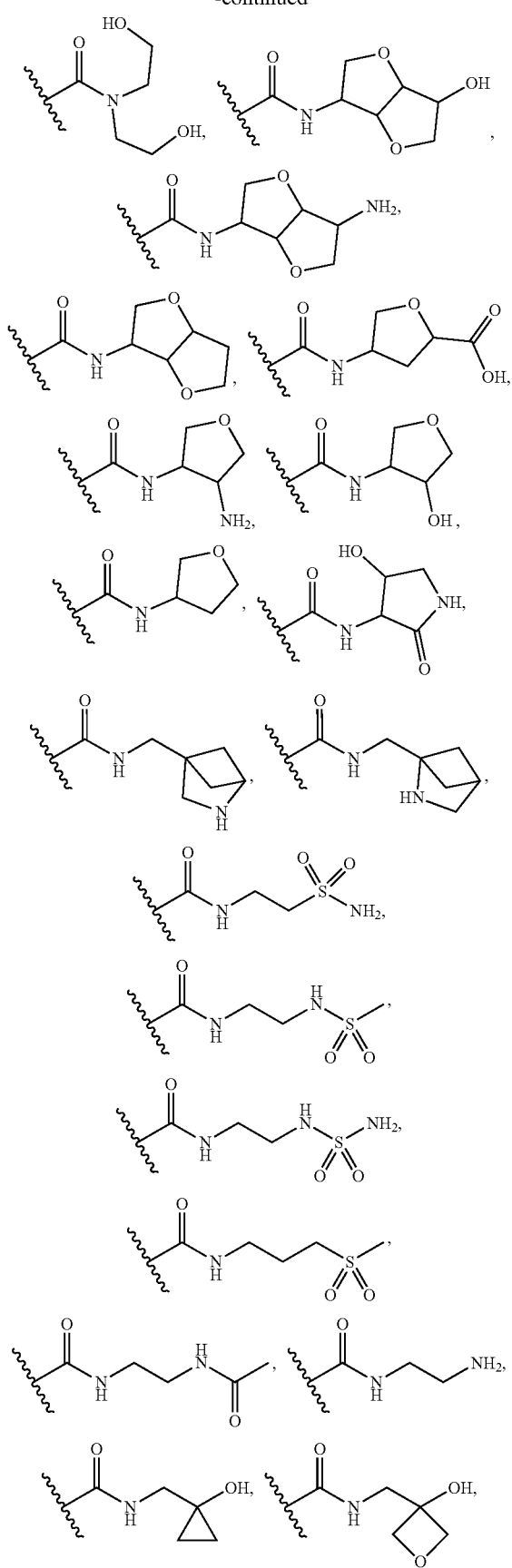
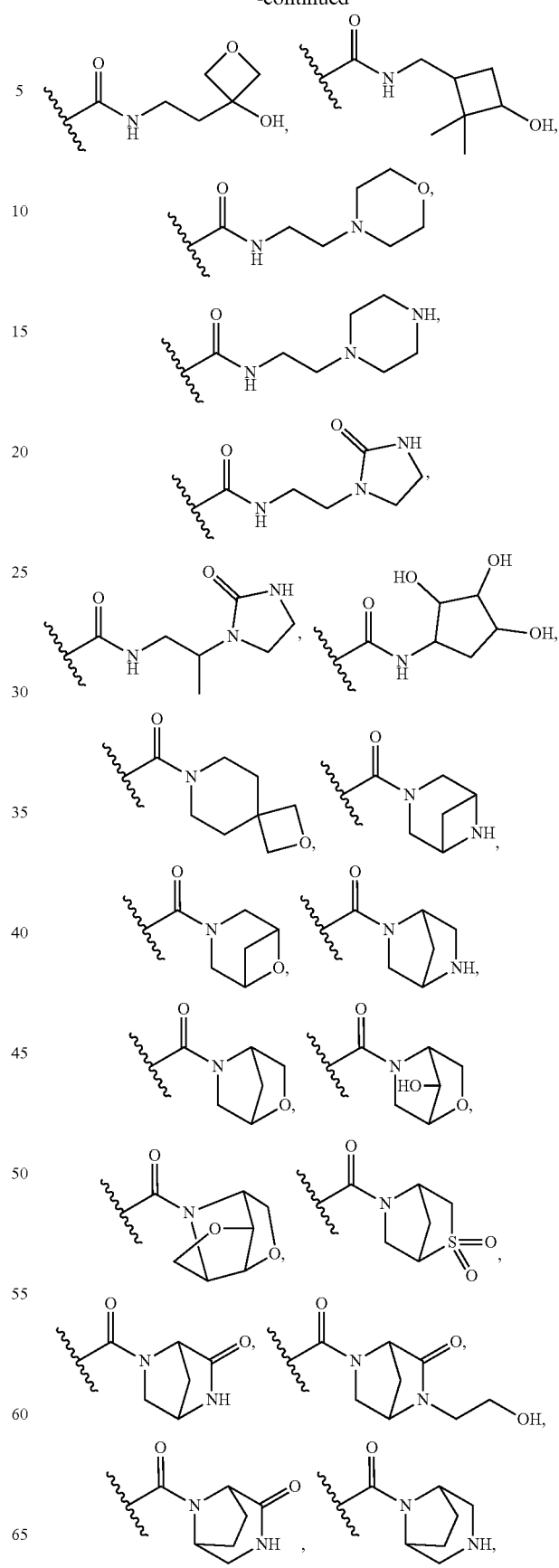

-continued
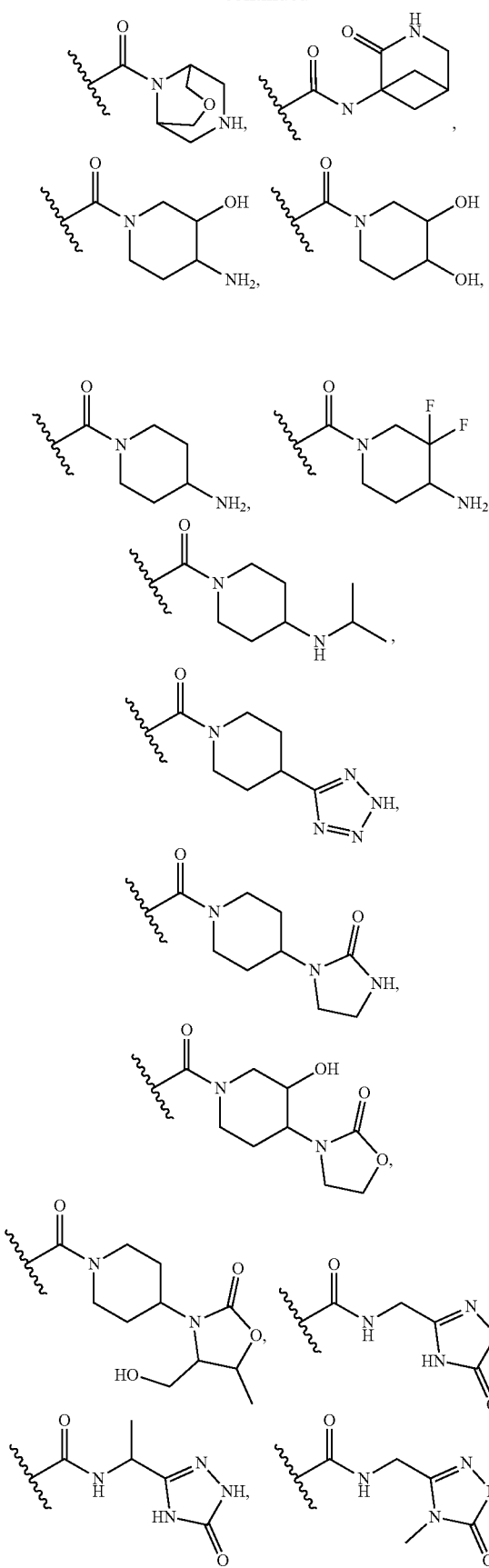
-continued
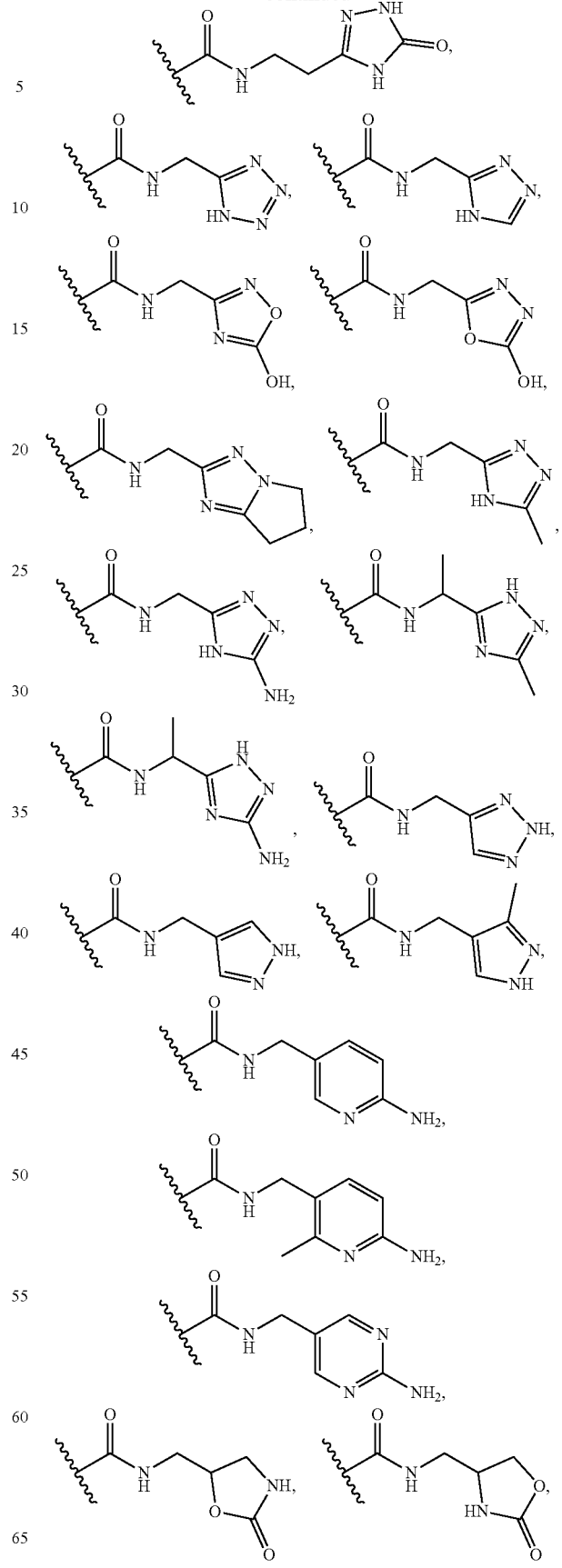

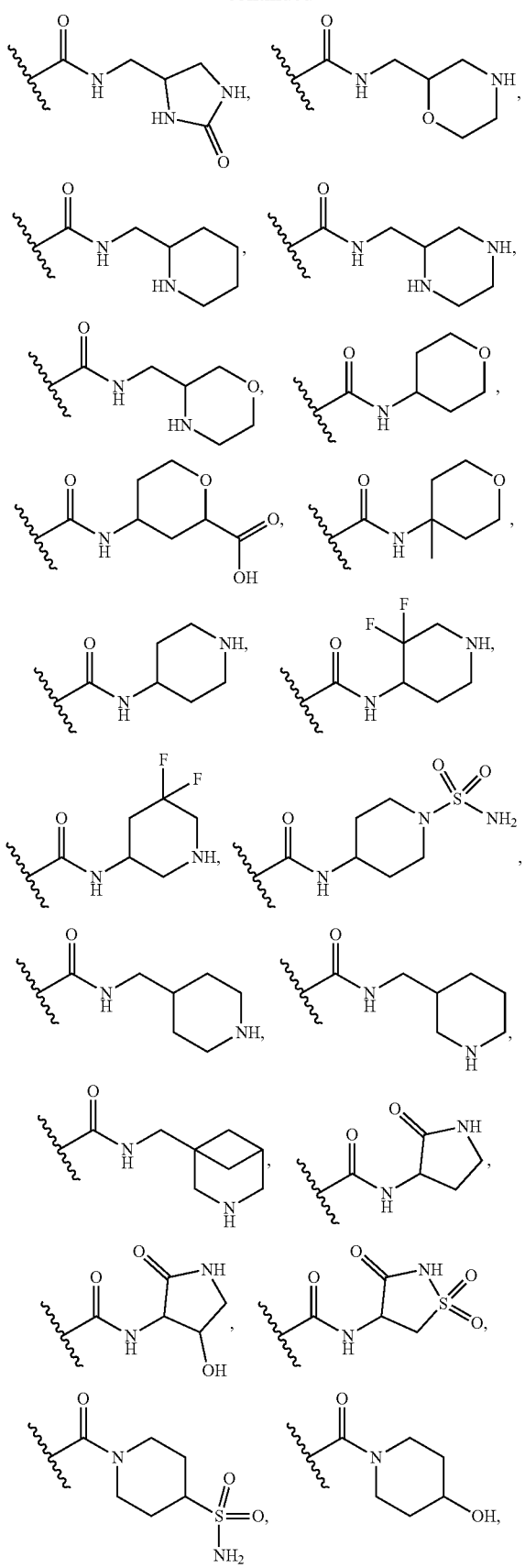
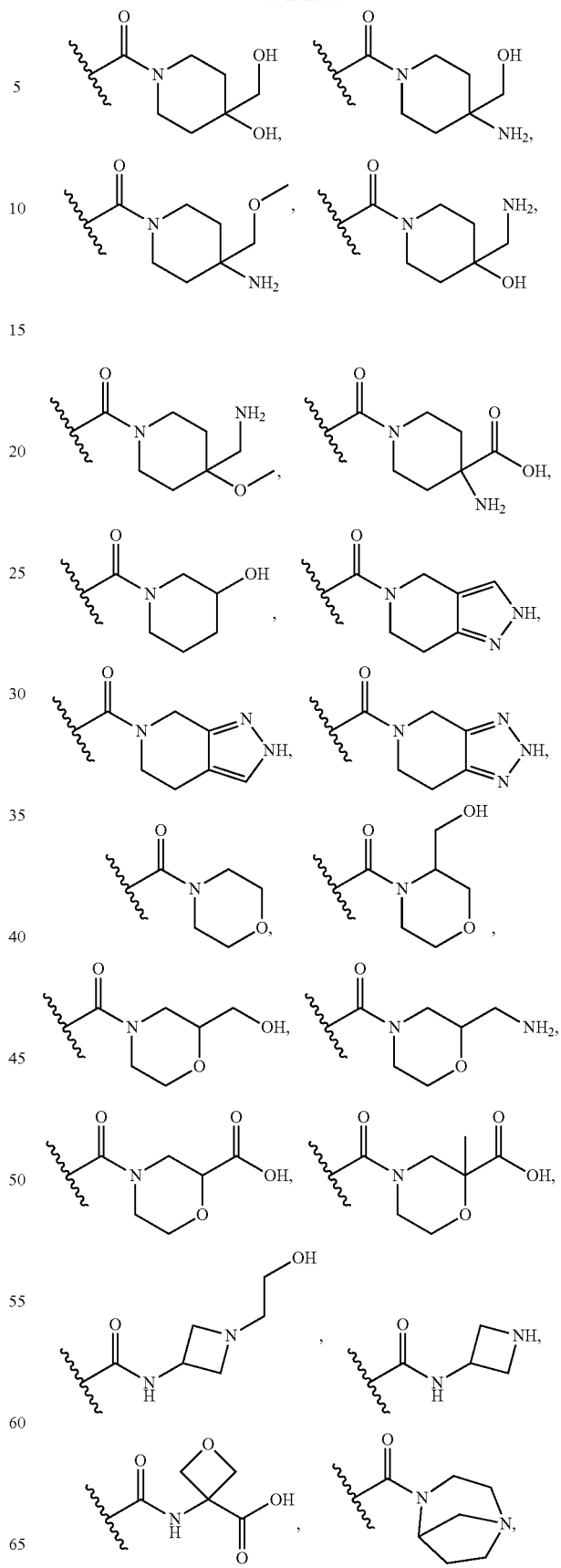

In some embodiments of a compound of Formula (I), Formula (Ia), Formula (IIb), Formula (IIc), Formula (IId), Formula (III), Formula (IIa), Formula (IIIb), Formula (IIIc), Formula (IIId), Formula (IV), Formula (IVa), Formula (IVb), Formula (IVc), Formula (IVd), Formula (VI), Formula (VIa), Formula (VII), or Formula (VIIa), or a pharmaceutically acceptable salt or solvate thereof, -L-R² is -continued
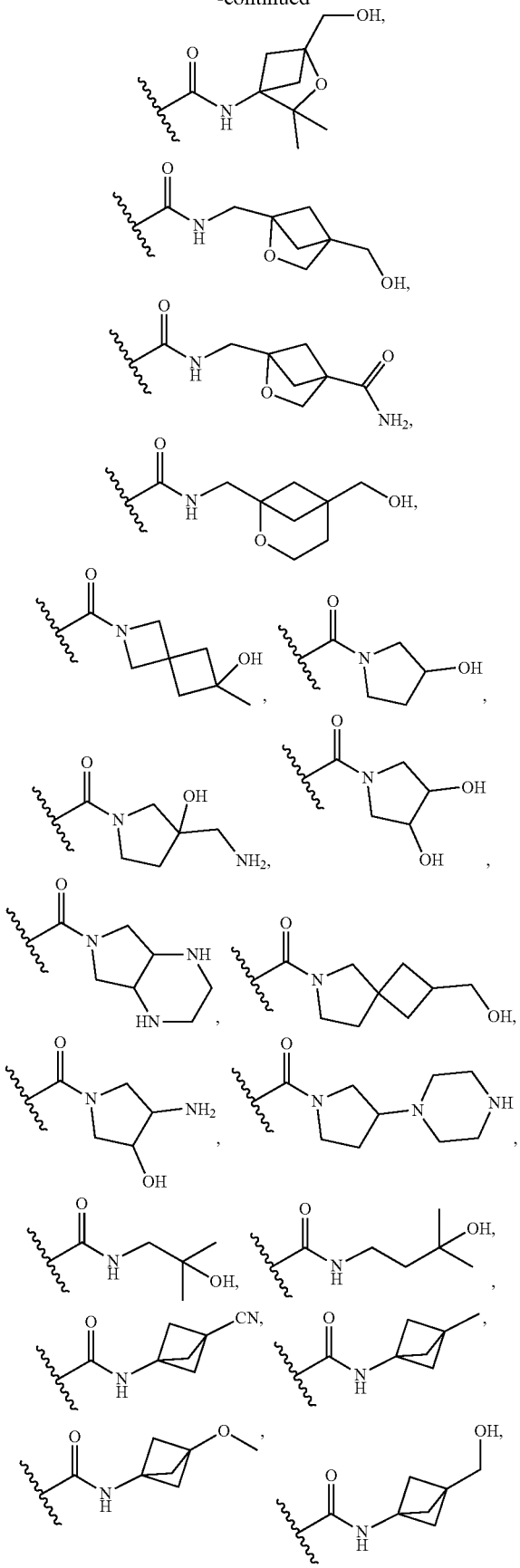
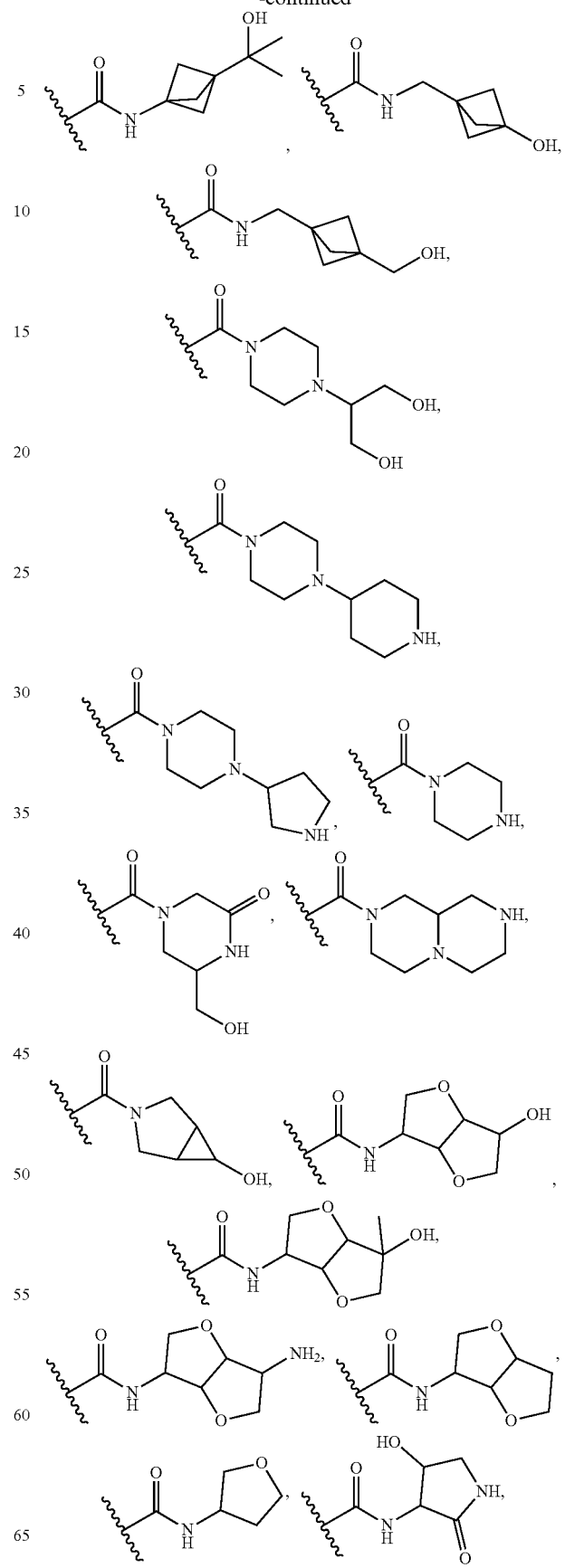

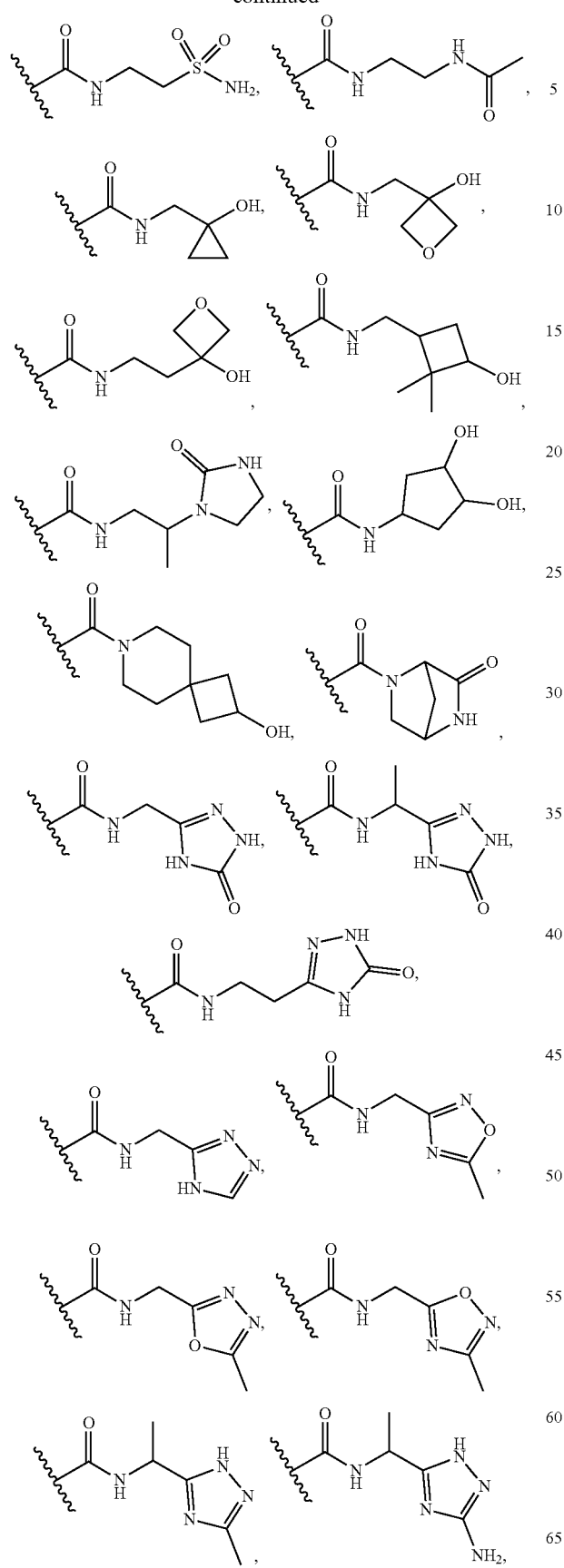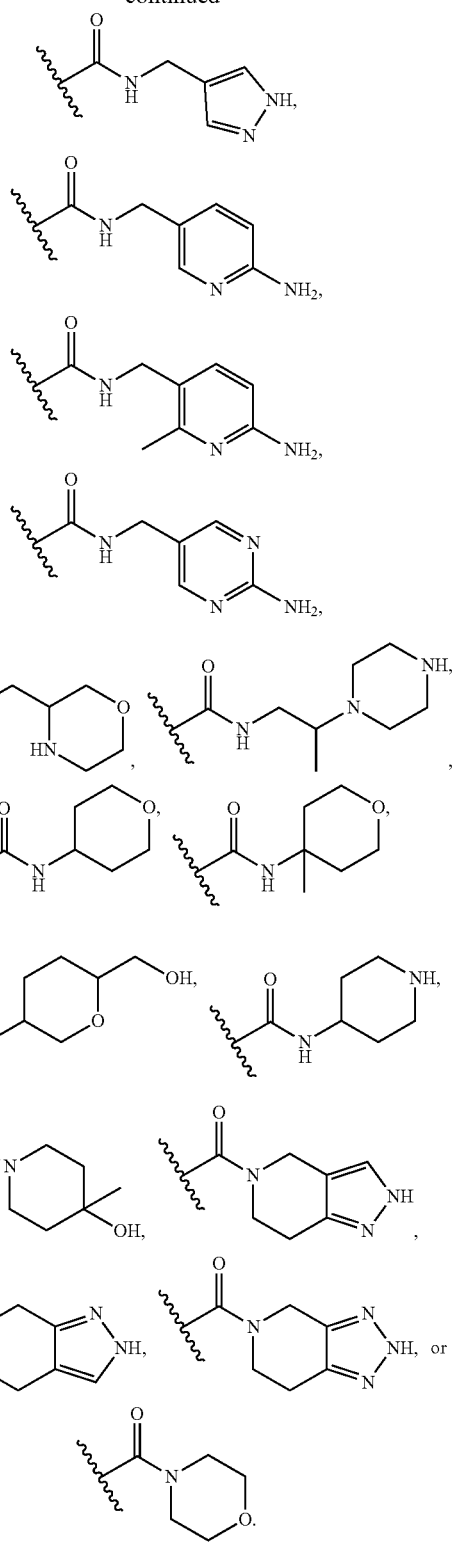
In some embodiments of a compound of Formula (III), Formula (IIIa), Formula (IIIb), Formula (IIIc), Formula (IIId), Formula (IV), Formula (IVa), Formula (IVb), Formula (IVc), Formula (IVd), Formula (VI), Formula (VIa), Formula (VII), or Formula (VIIa) or a pharmaceutically acceptable salt or solvate thereof,

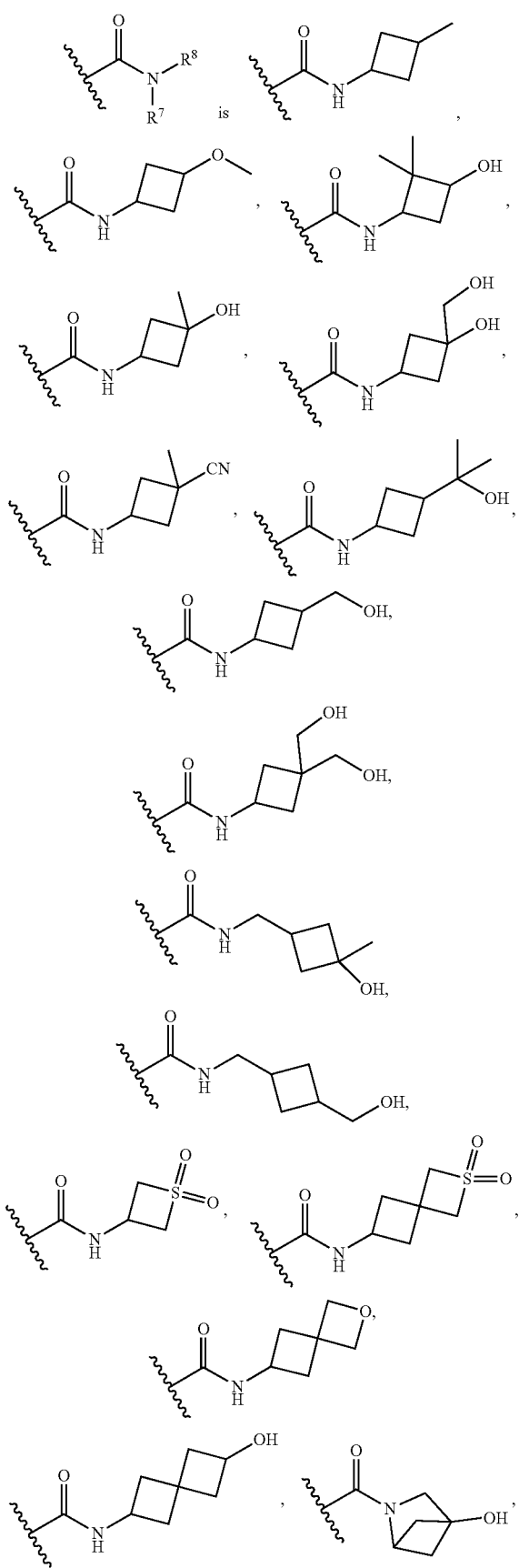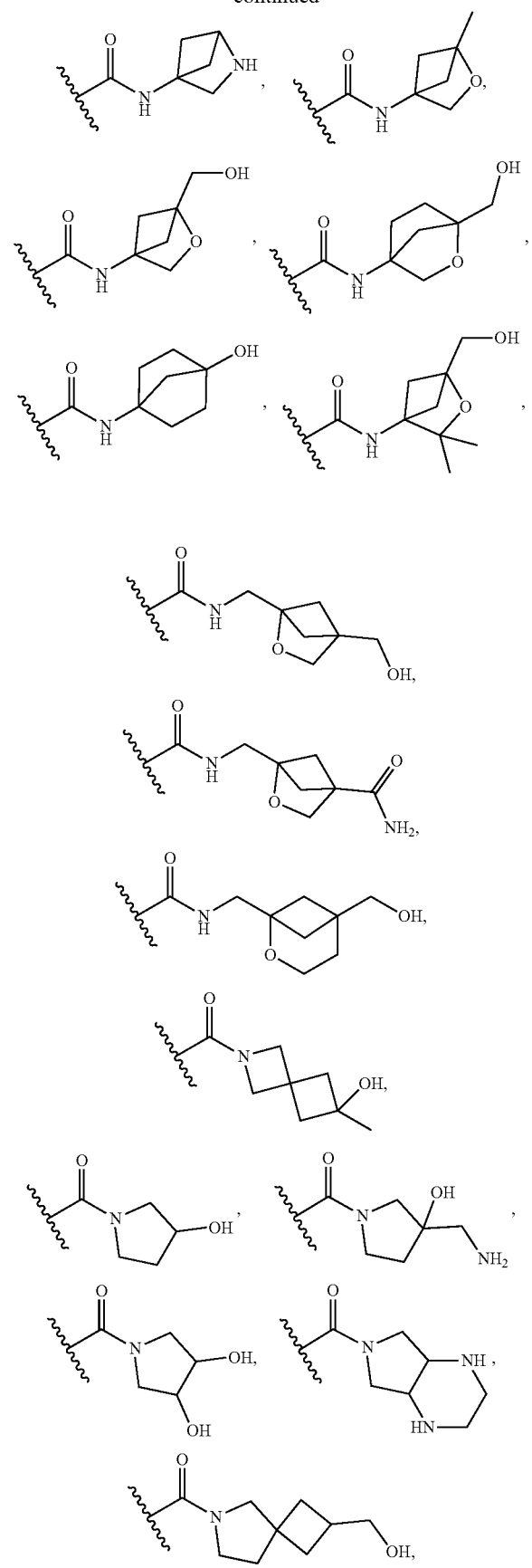

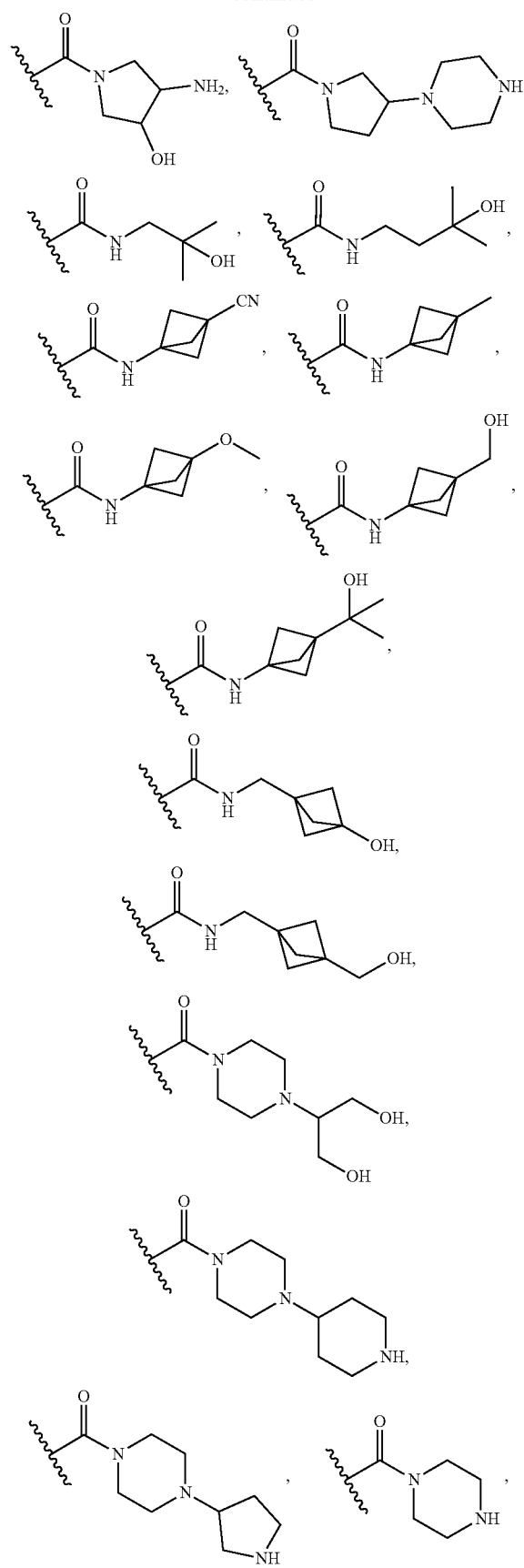
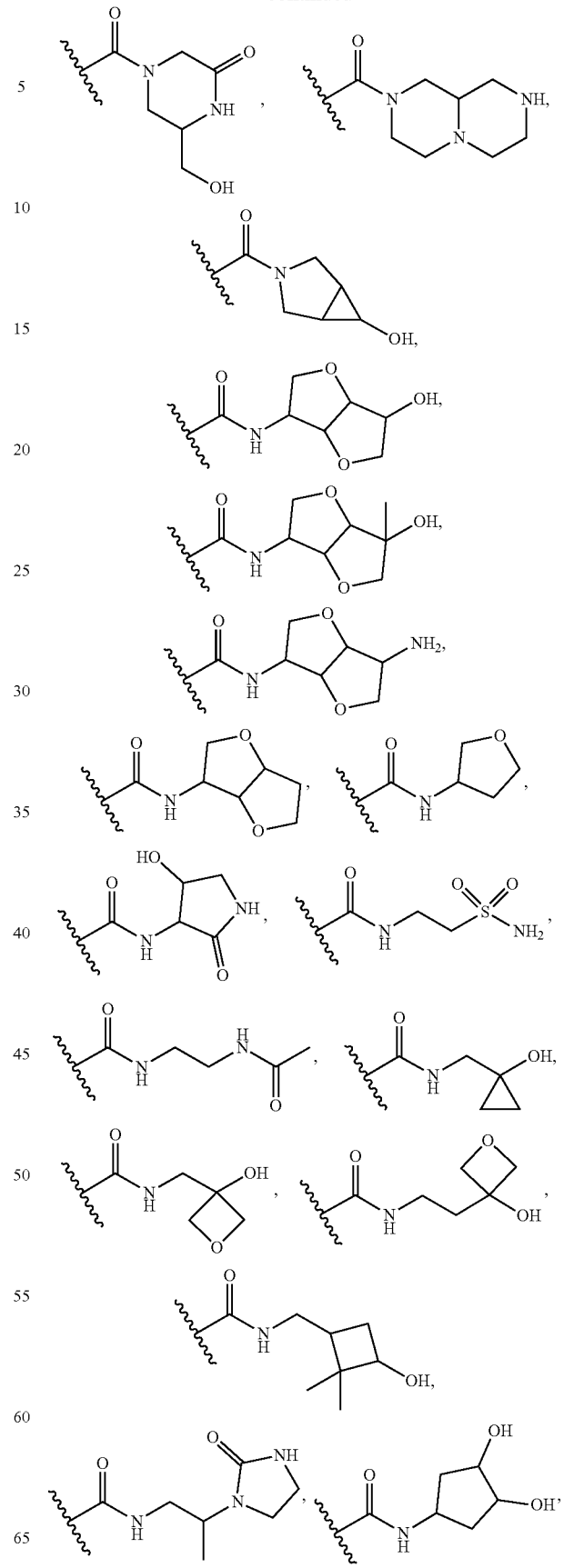

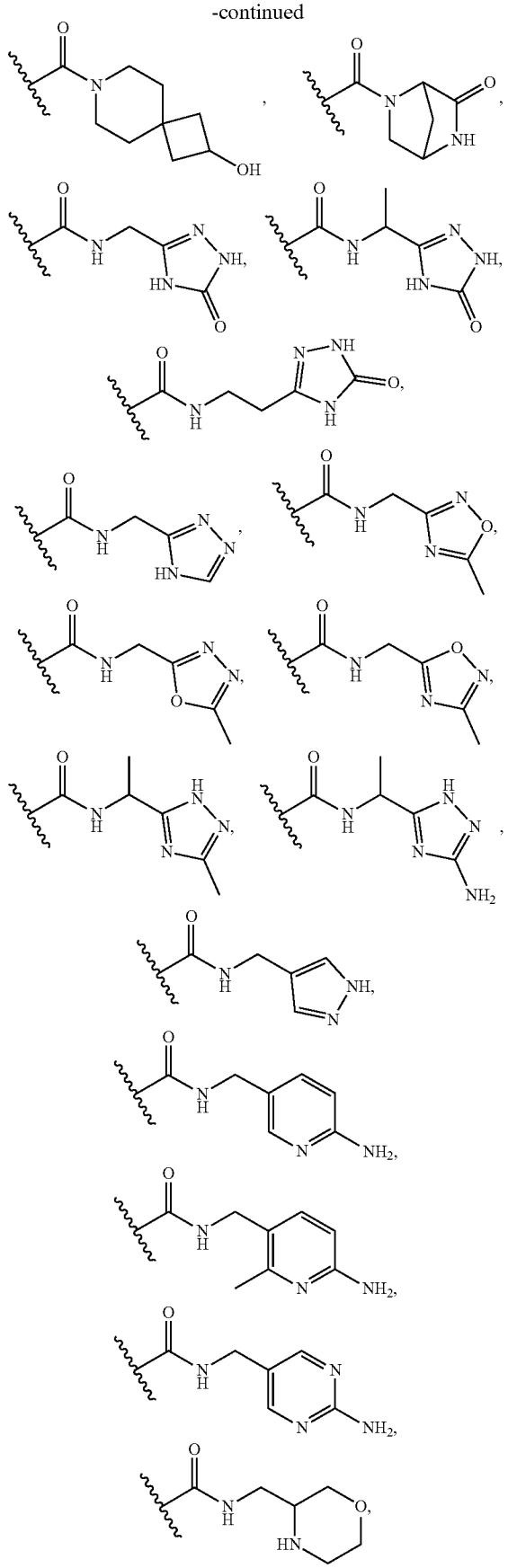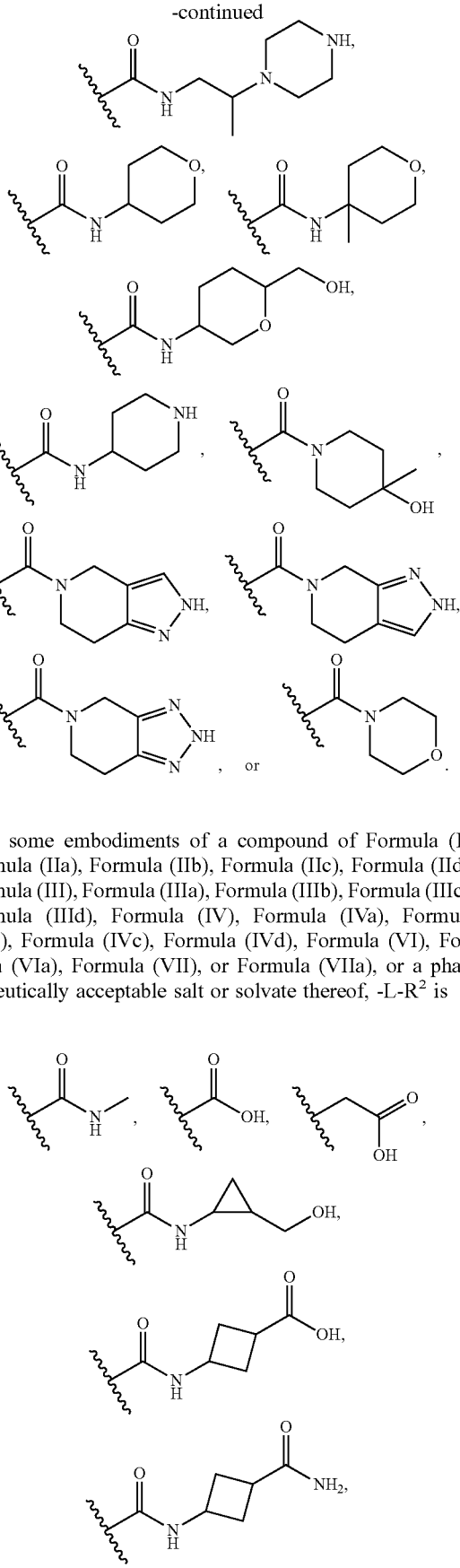
In some embodiments of a compound of Formula (I), Formula (IIa), Formula (IIb), Formula (IIc), Formula (IId), Formula (III), Formula (IIIa), Formula (IIIb), Formula (IIIc), Formula (IIId), Formula (IV), Formula (IVa), Formula (IVb), Formula (IVc), Formula (IVd), Formula (VI), Formula (VIa), Formula (VII), or Formula (VIIa), or a pharmaceutically acceptable salt or solvate thereof, -L-R² is

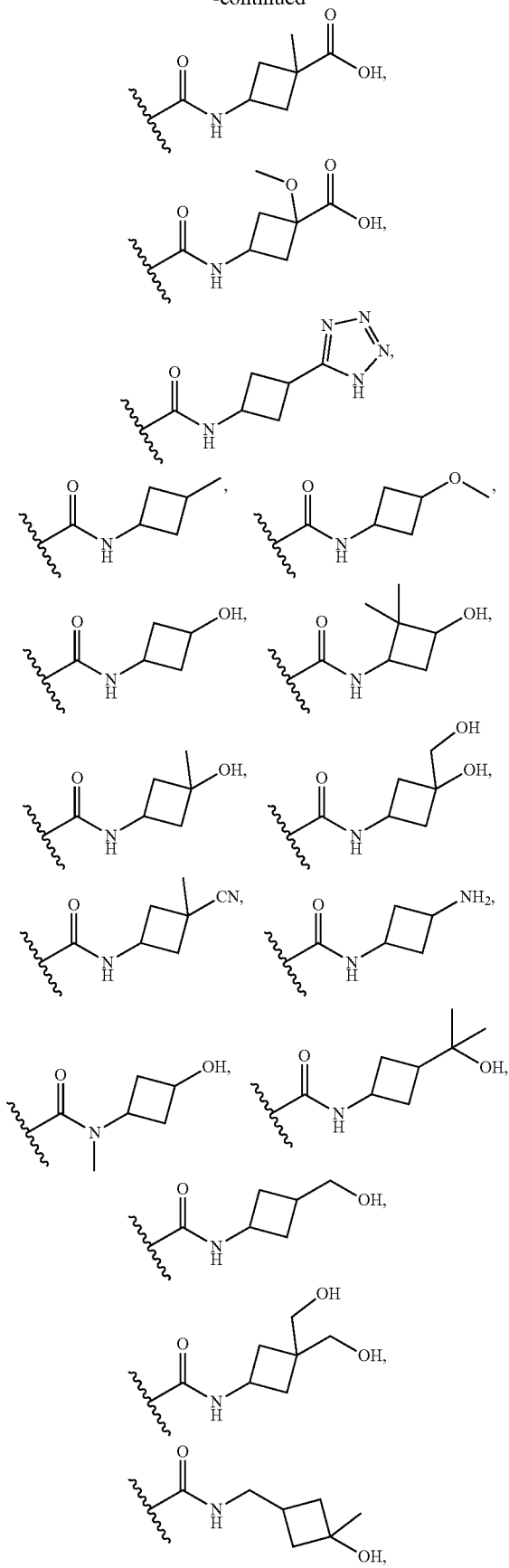
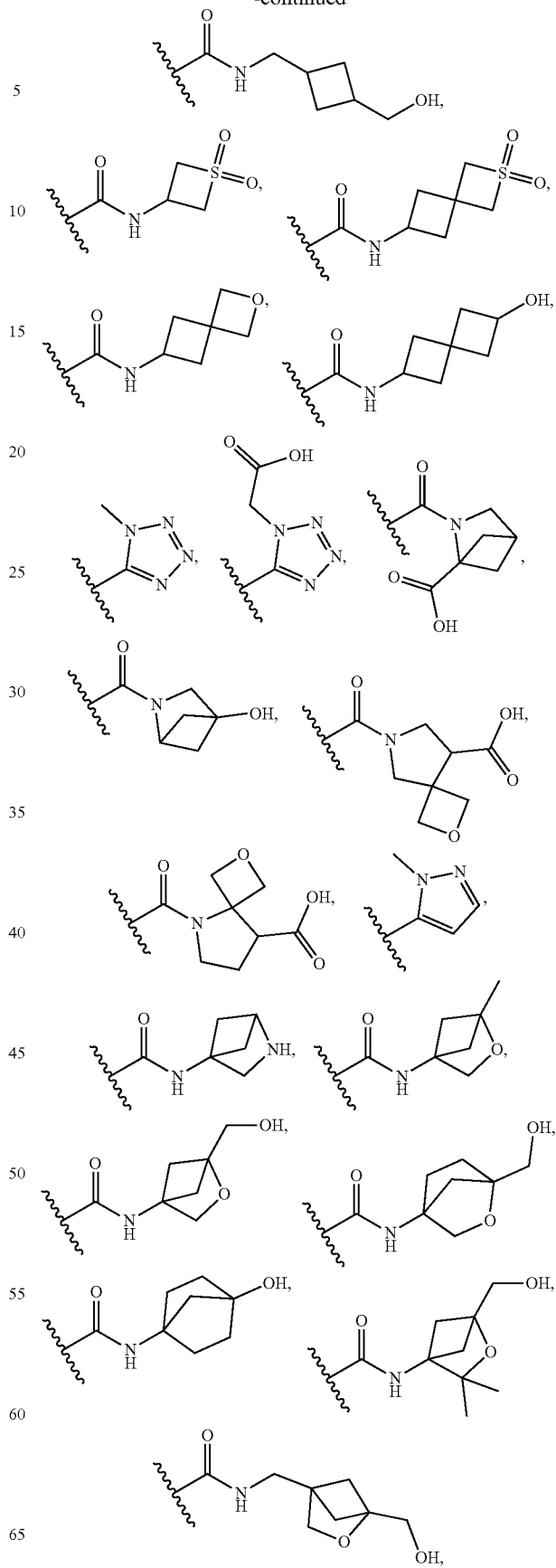

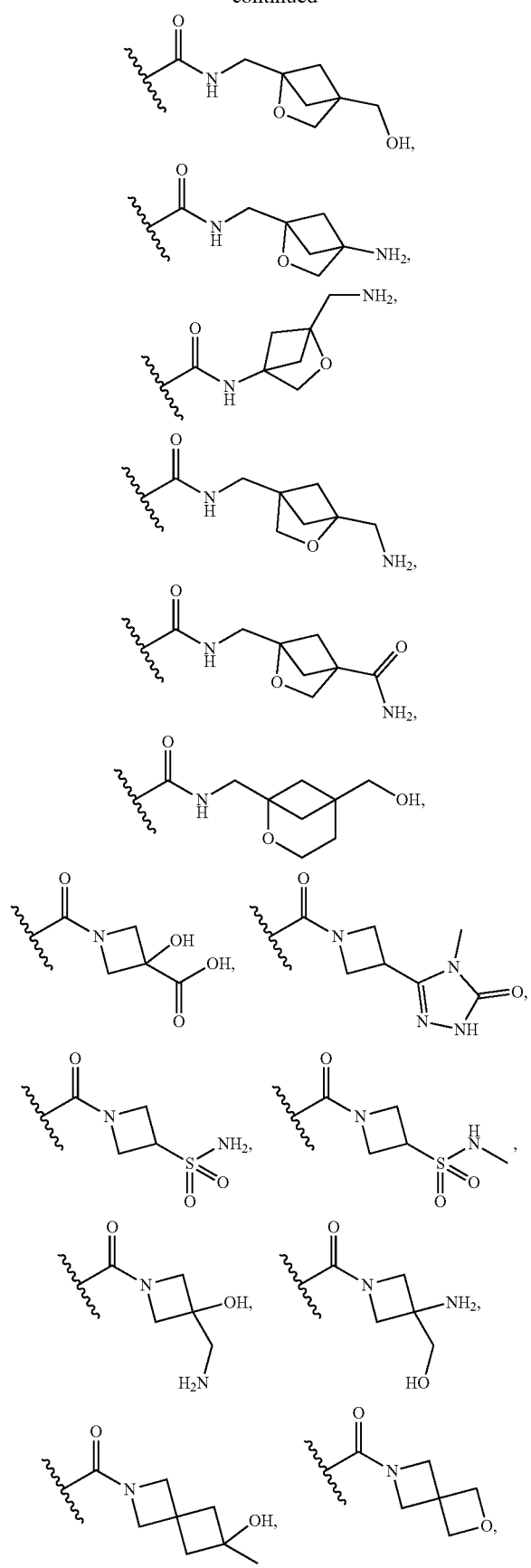
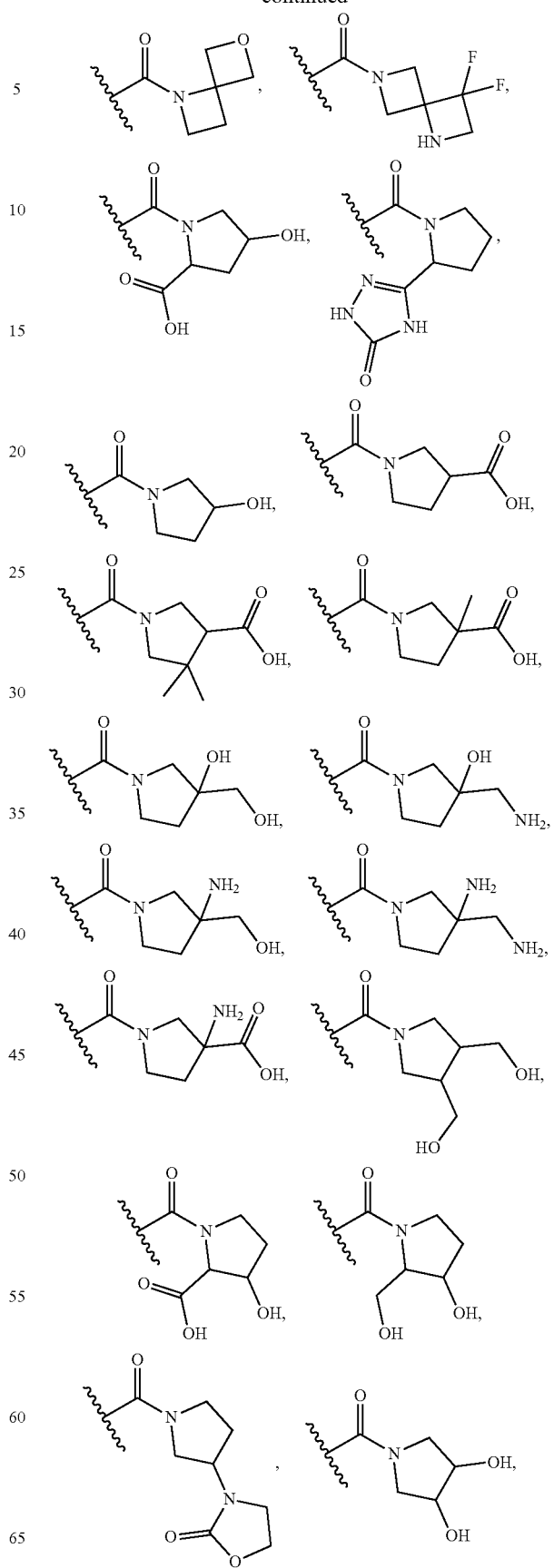

-continued
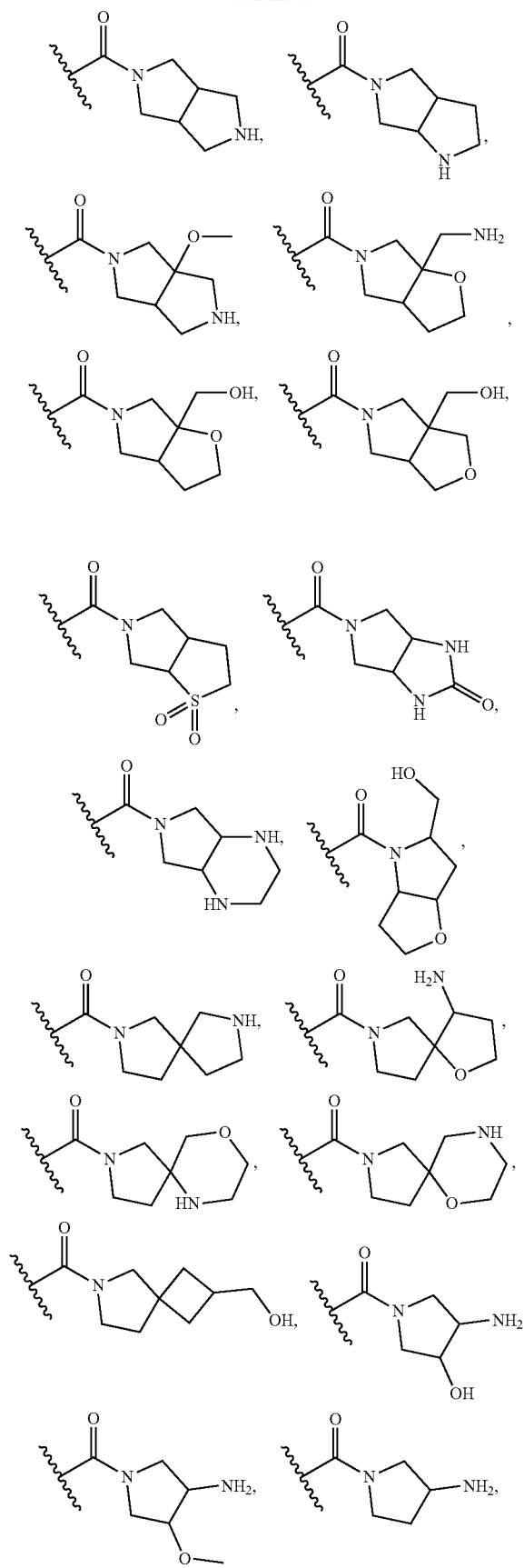
-continued
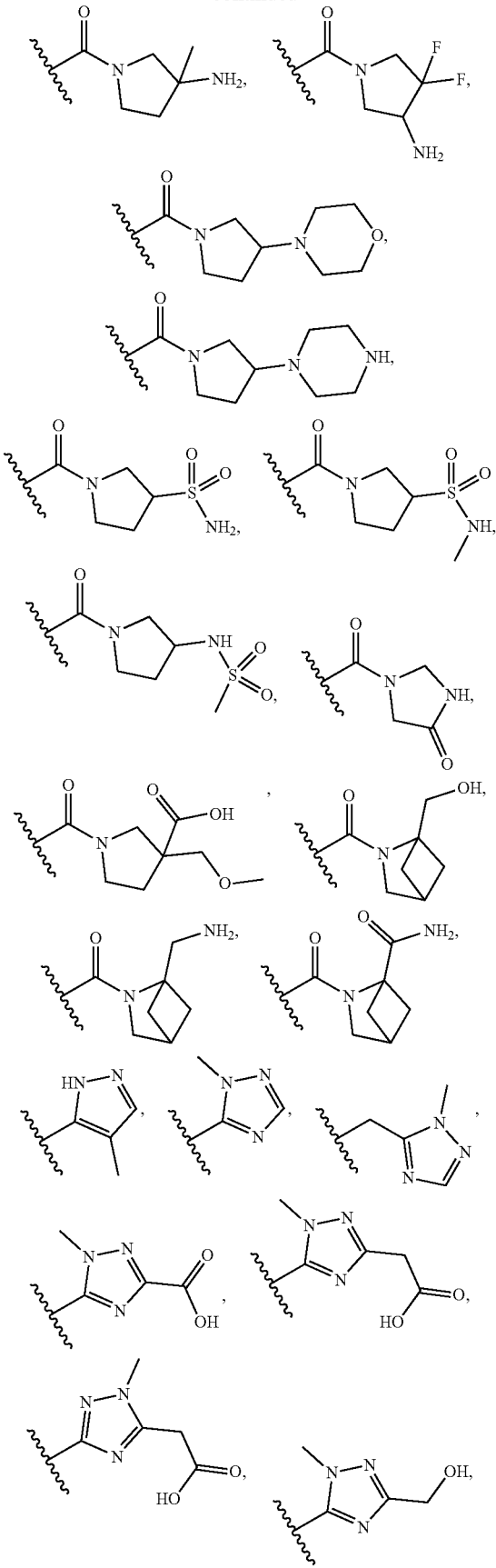

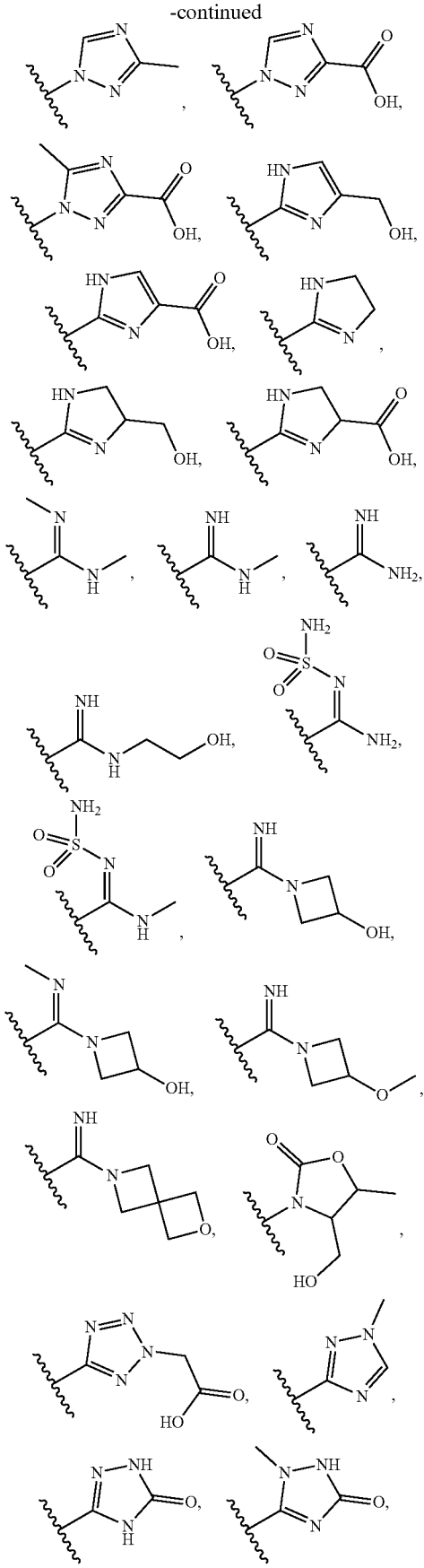
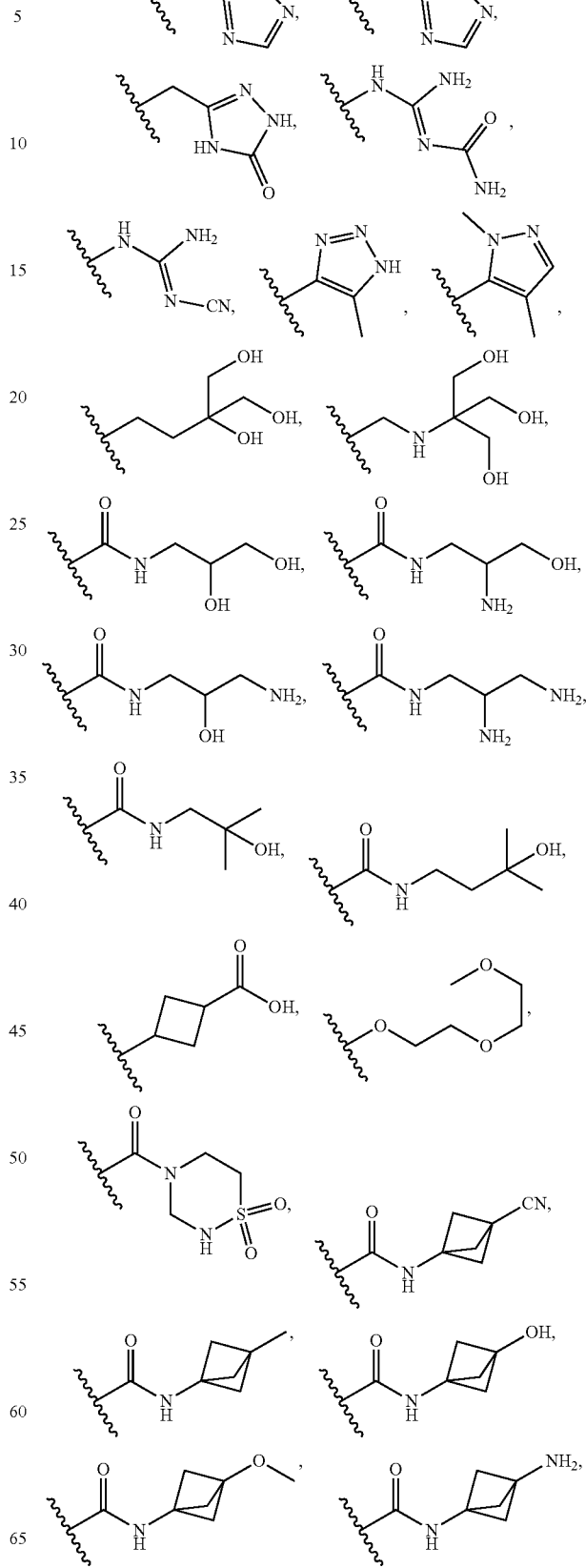

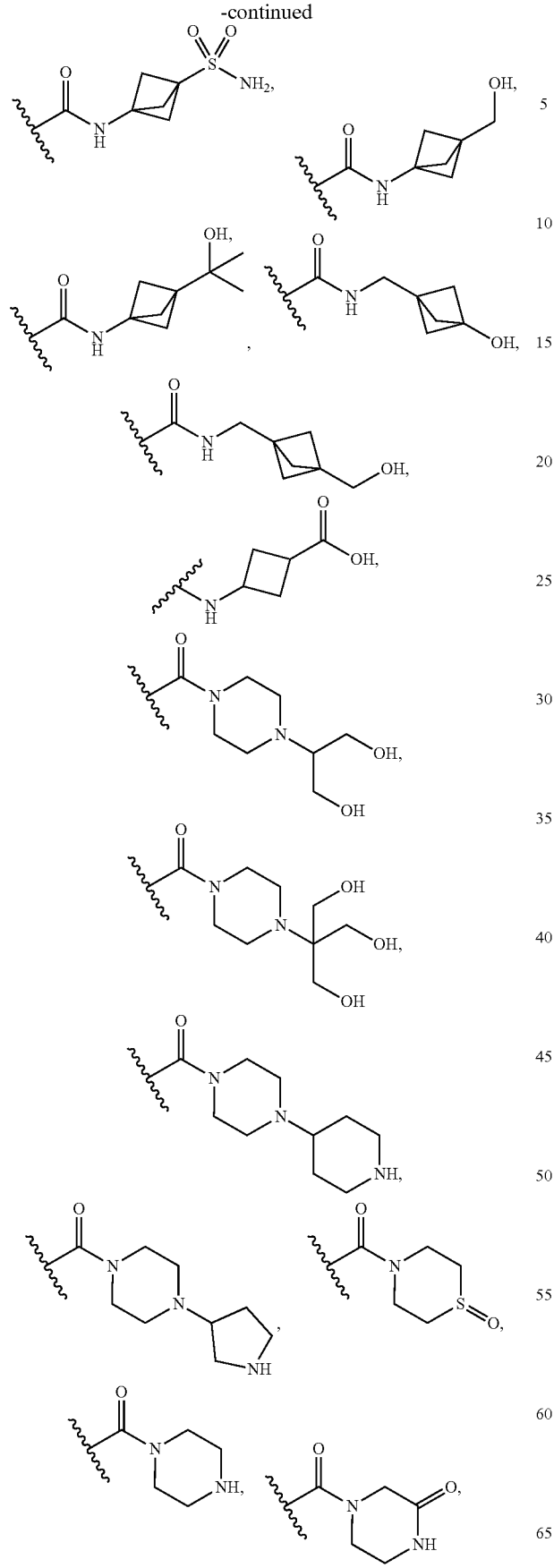
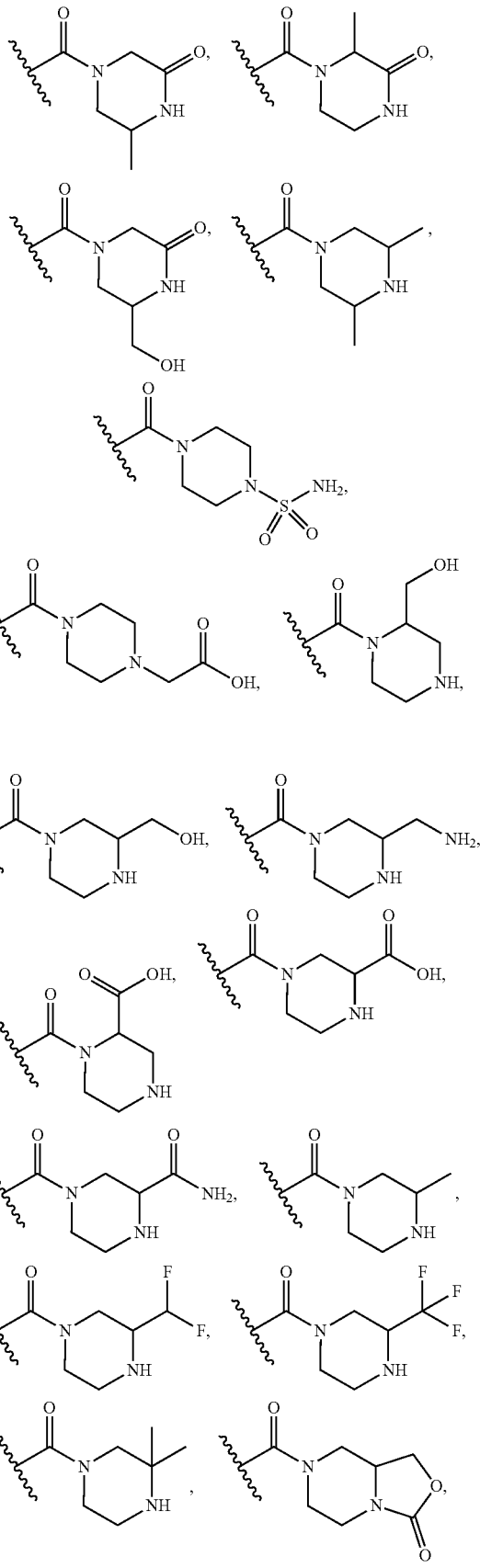

-continued
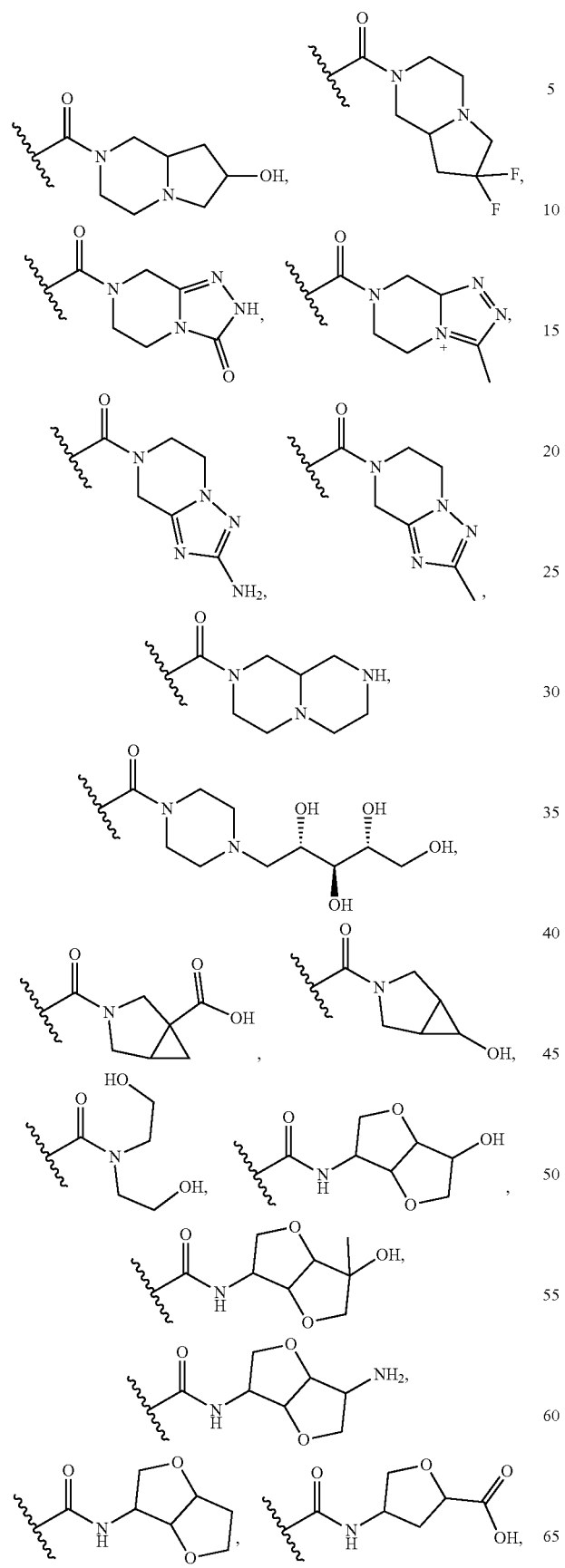
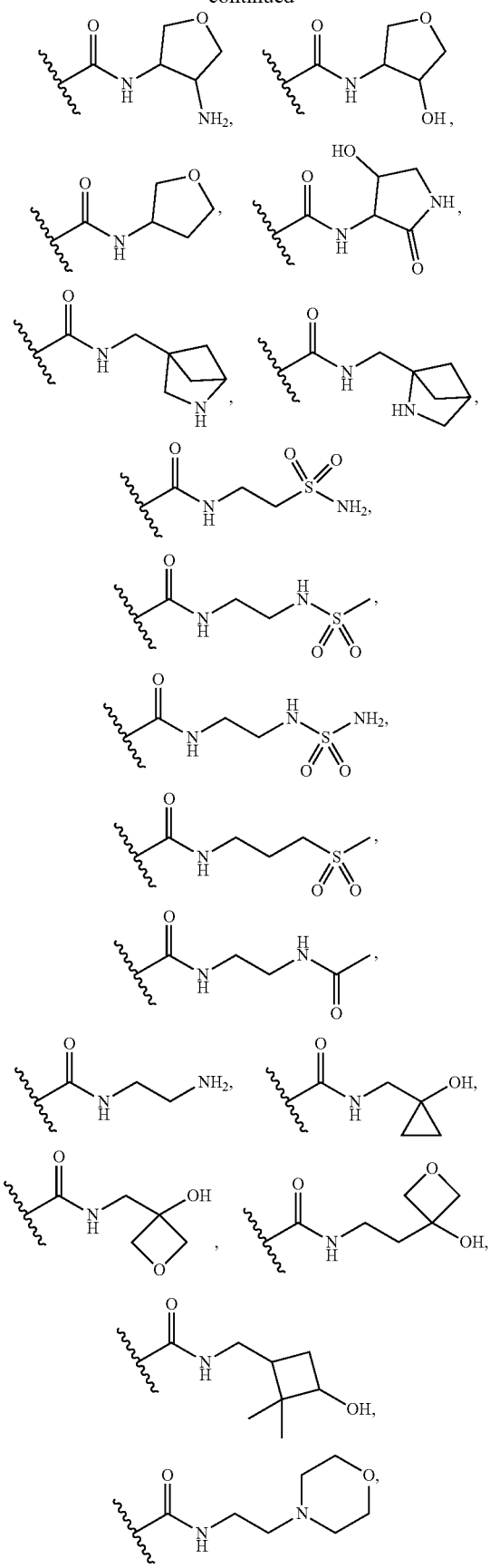

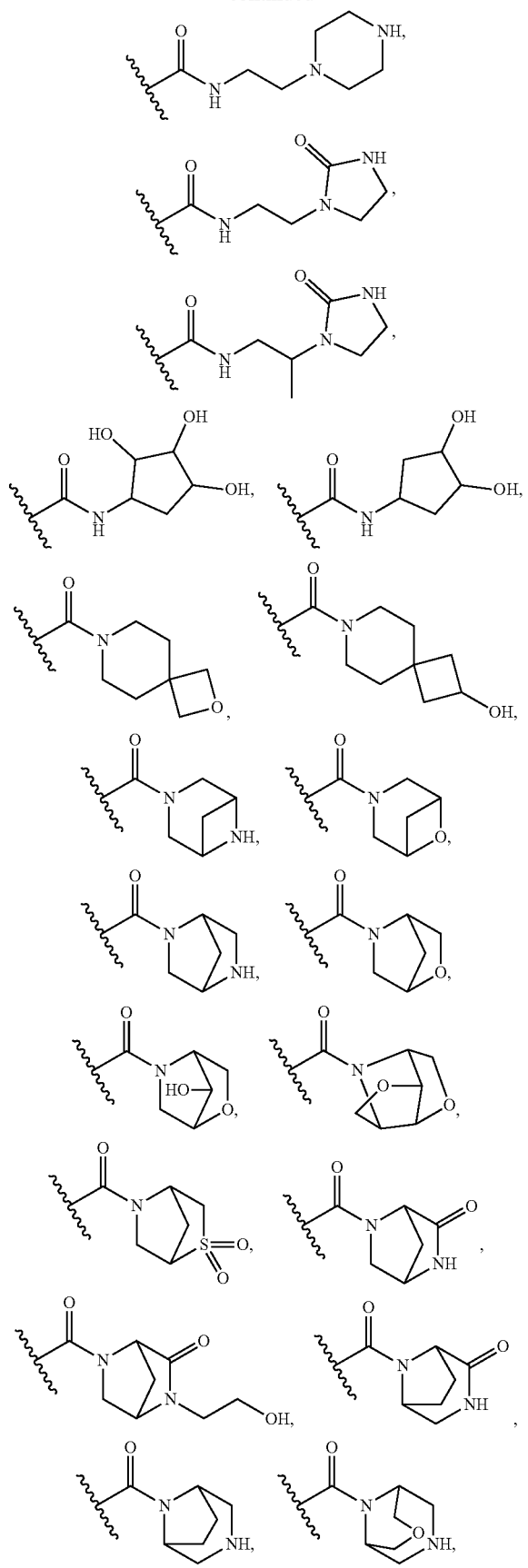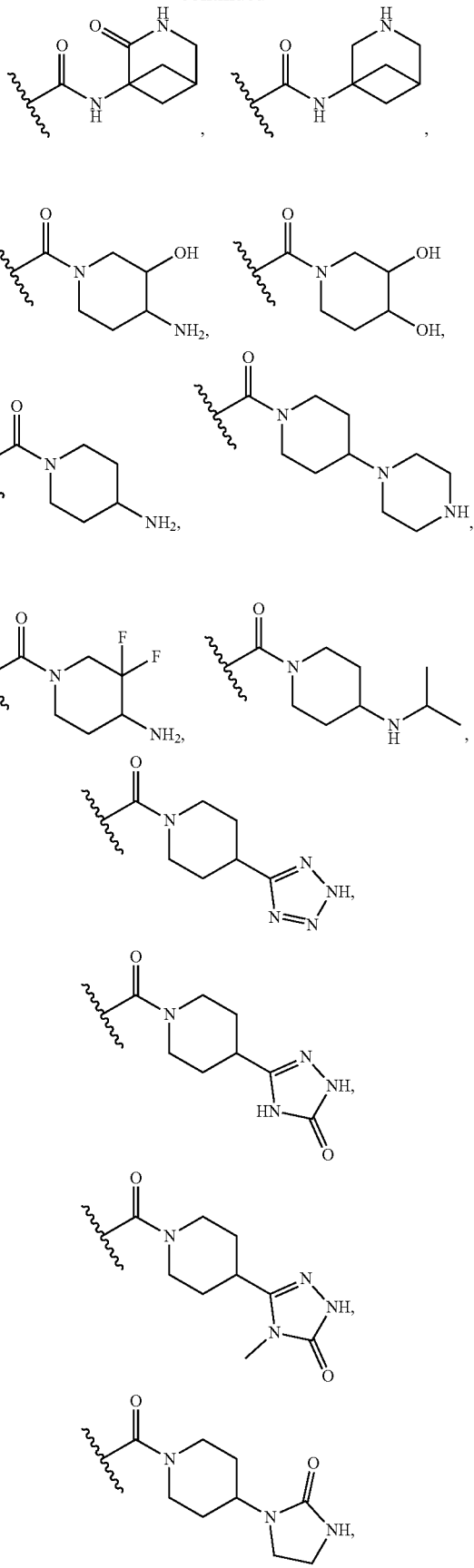

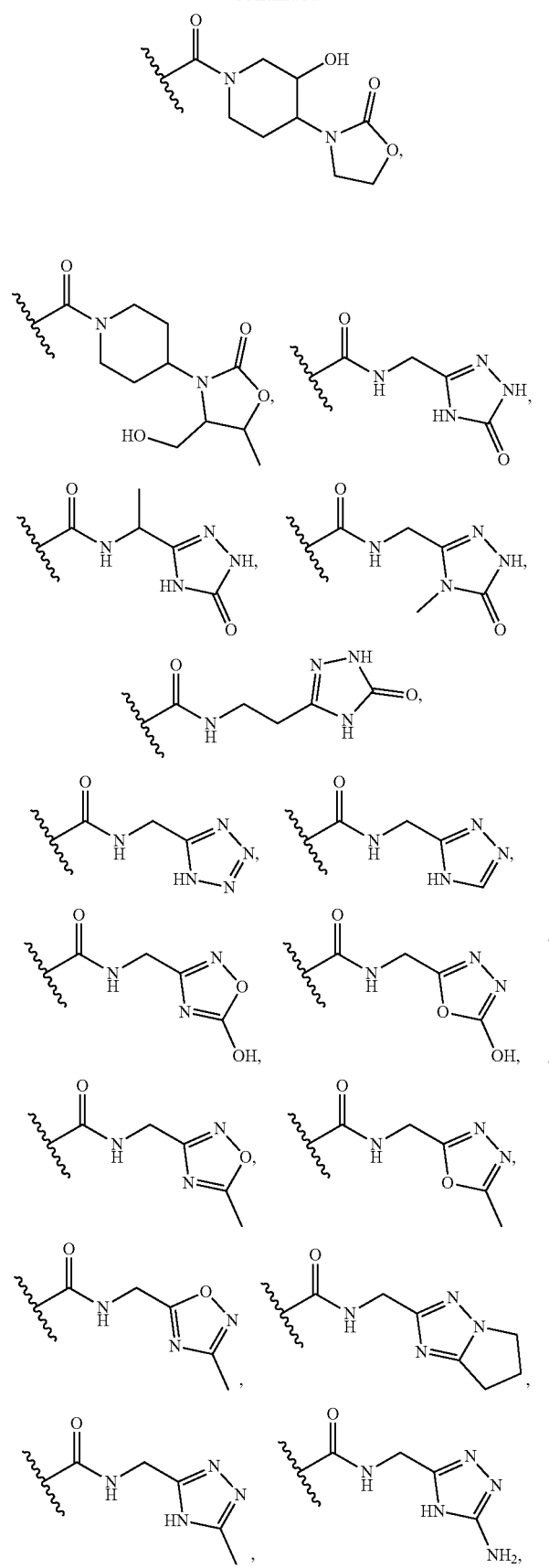
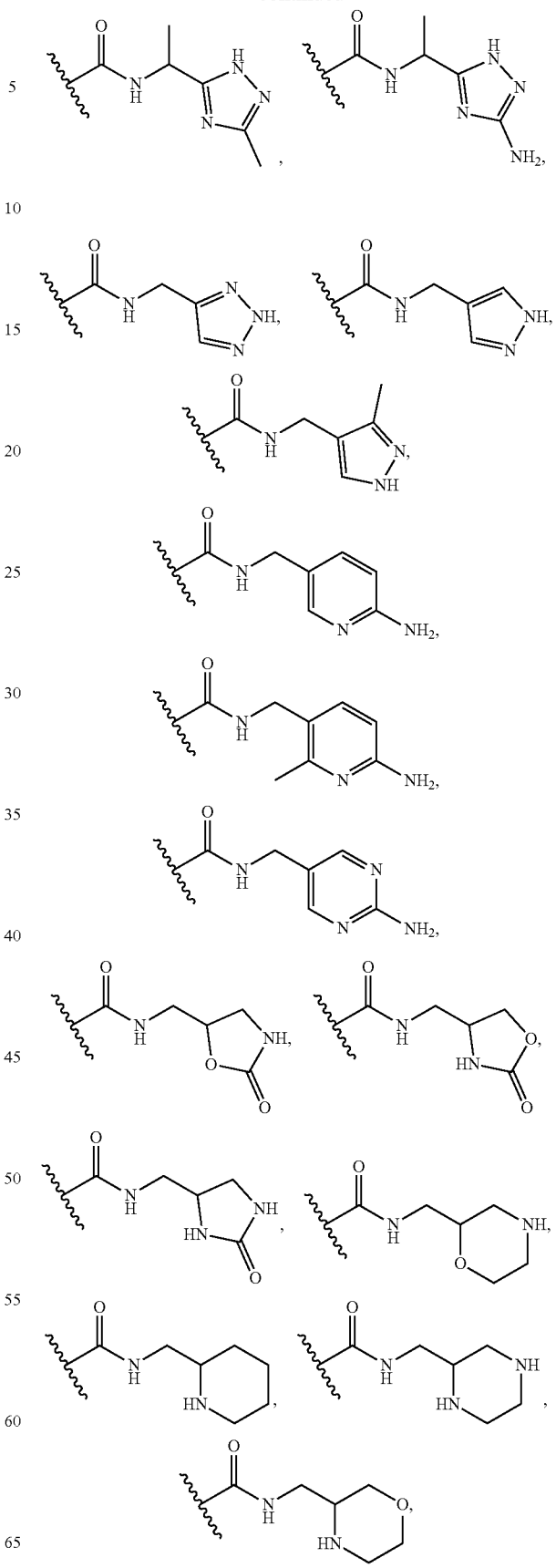

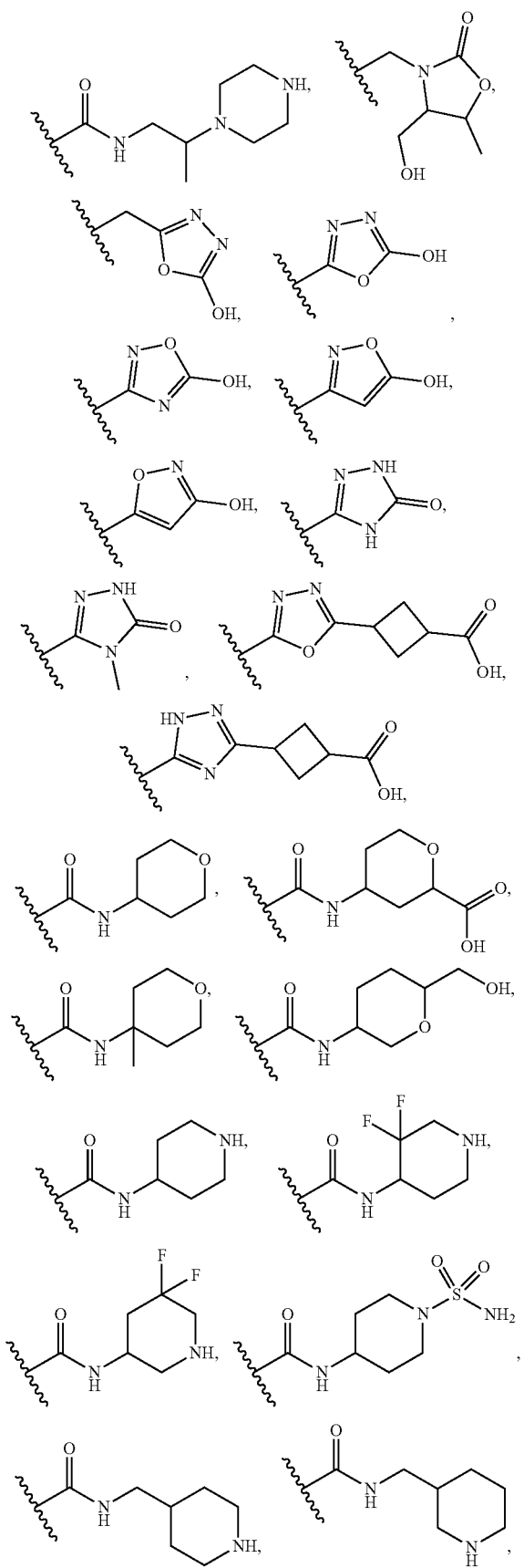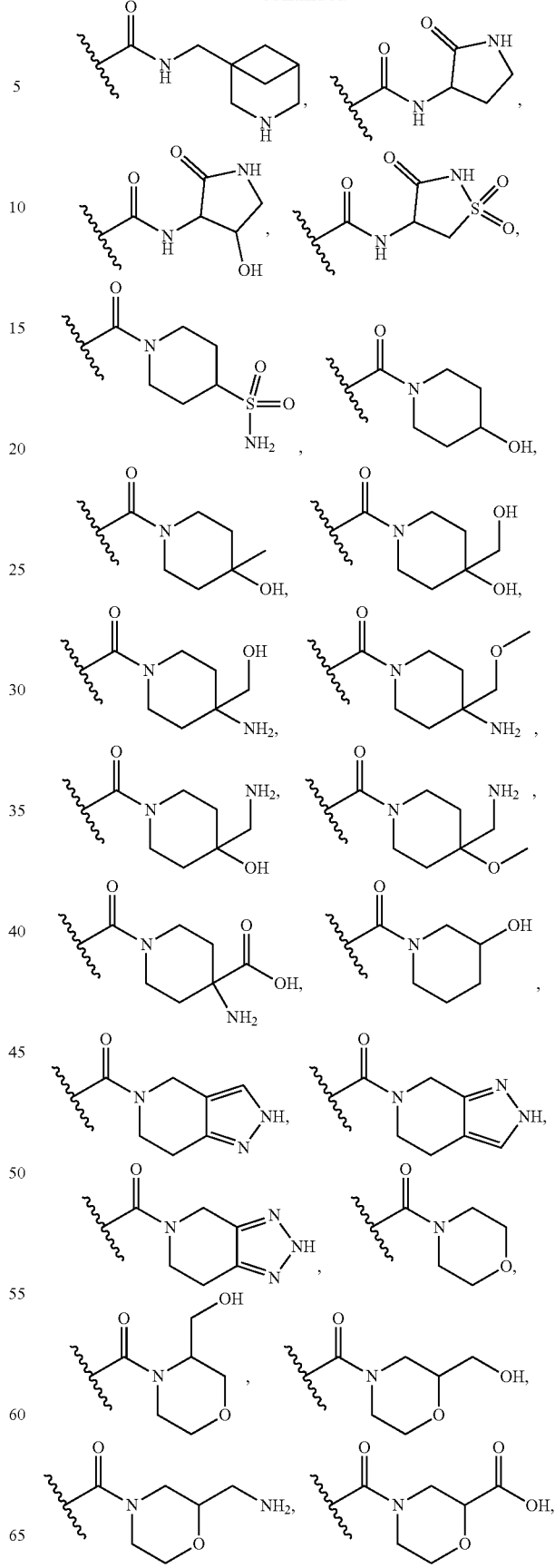

-L-R² is
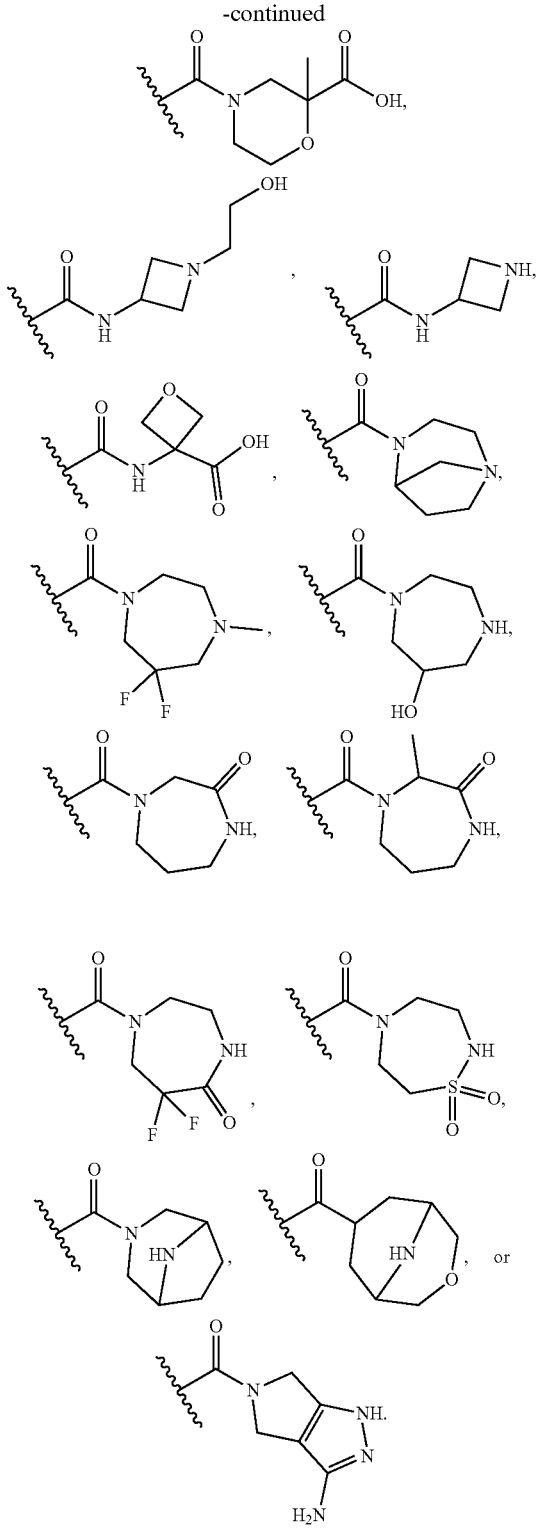
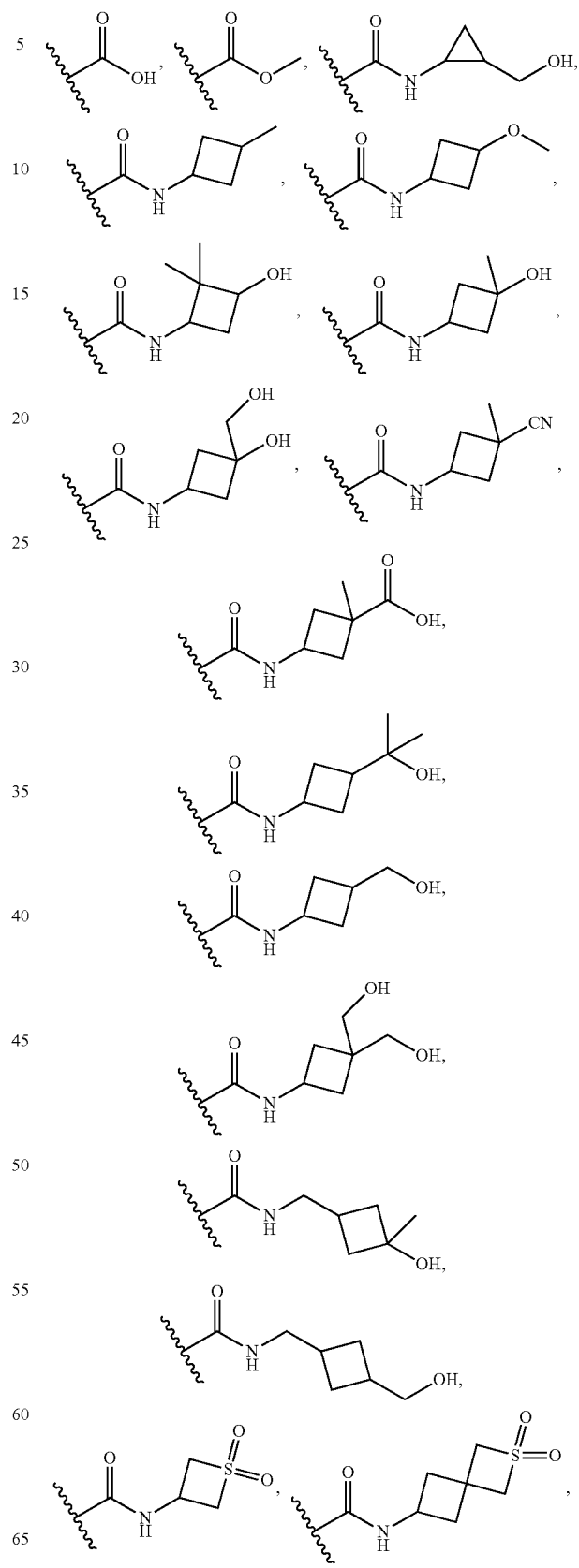
In some embodiments of a compound of Formula (I), Formula (IIa), Formula (IIb), Formula (IIc), Formula (IId), Formula (III), Formula (IIIa), Formula (IIIb), Formula (IIIc), Formula (IIId), Formula (IV), Formula (IVa), Formula (IVb), Formula (IVc), Formula (IVd), Formula (VI), Formula (VIa), Formula (VII), or Formula (VIIa), or a pharmaceutically acceptable salt or solvate thereof,

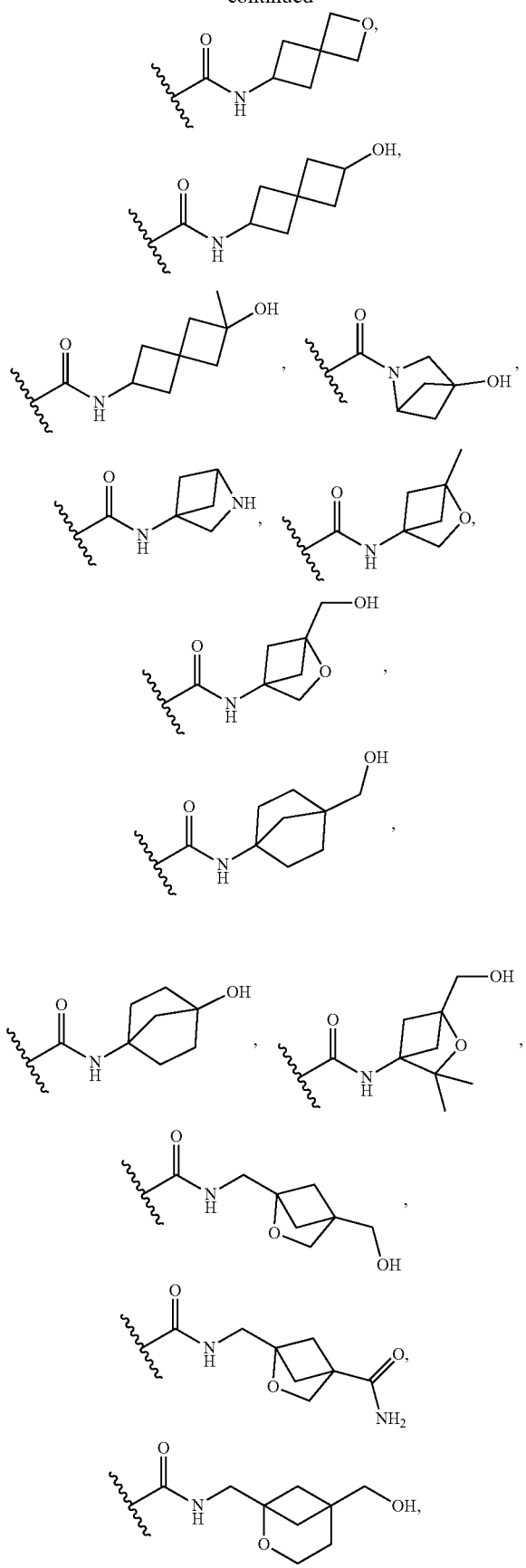
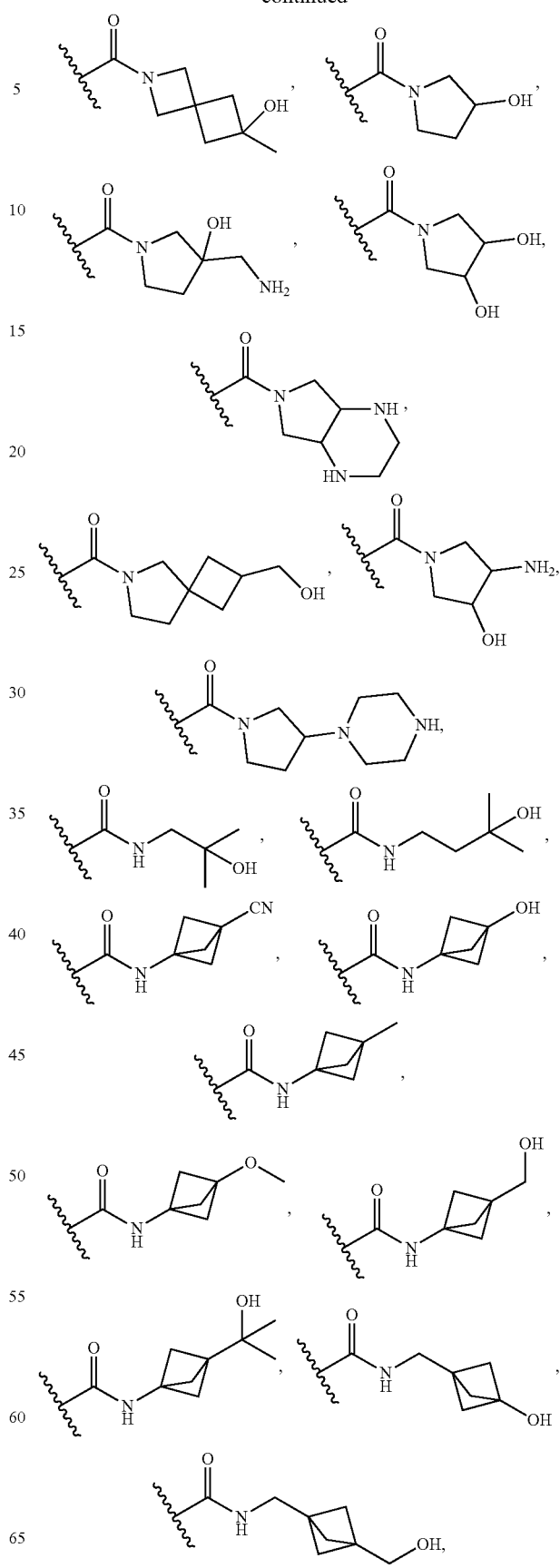

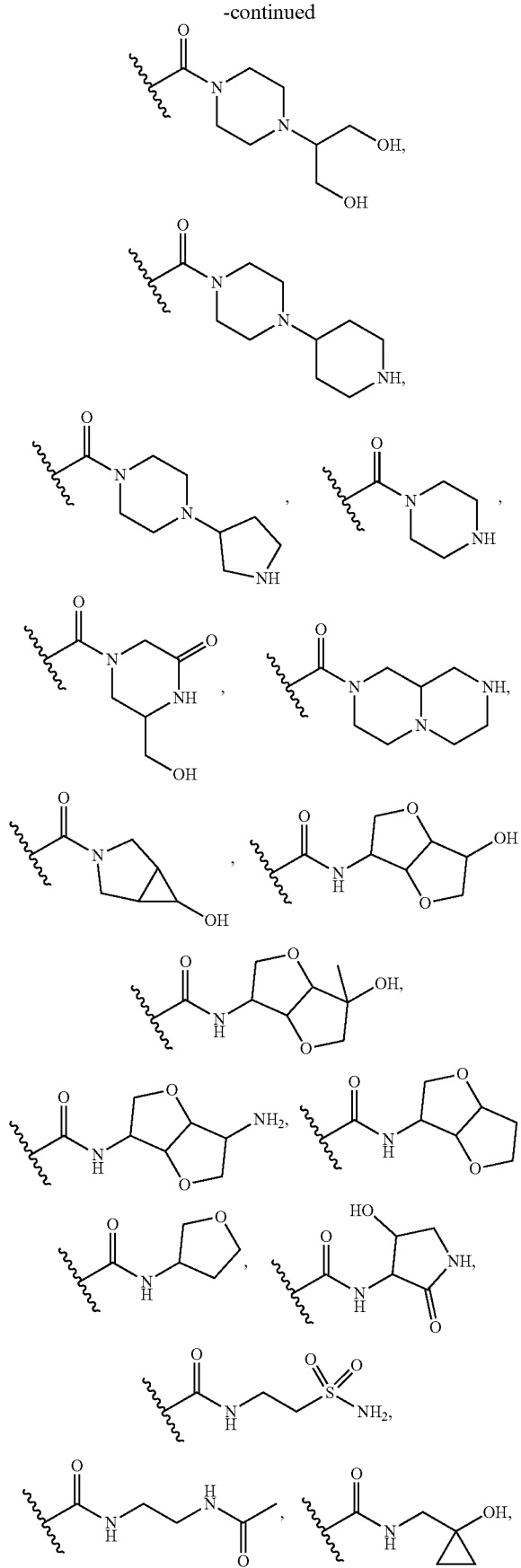
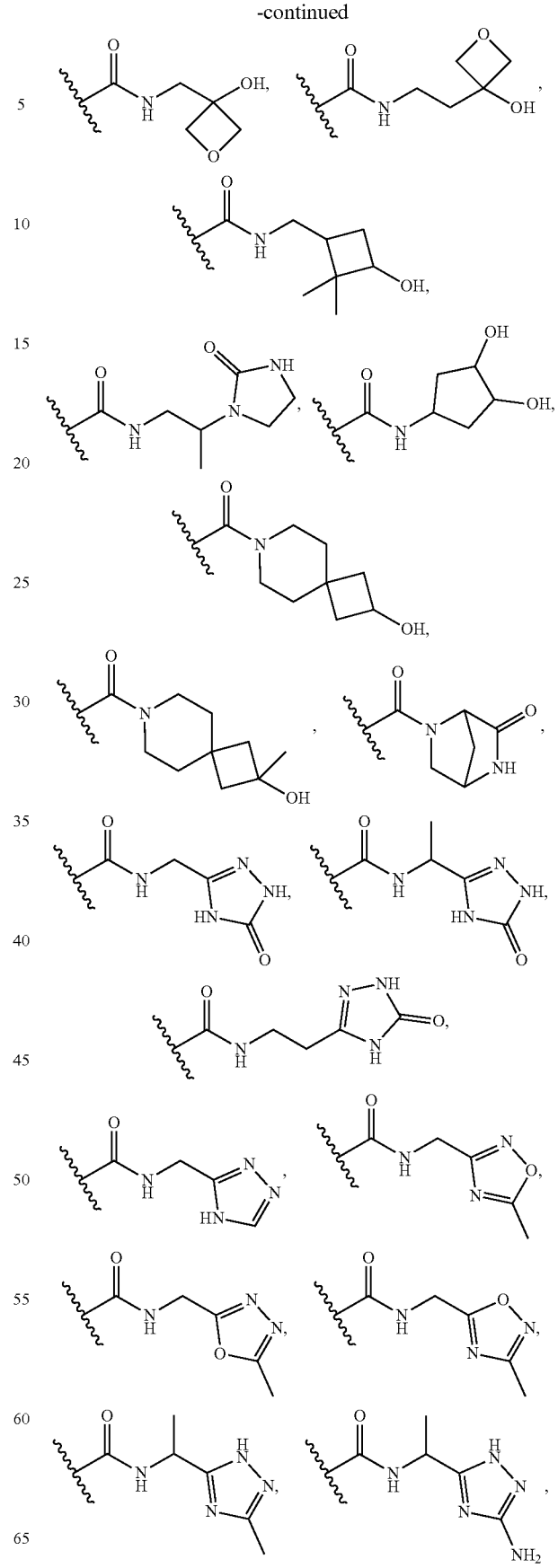

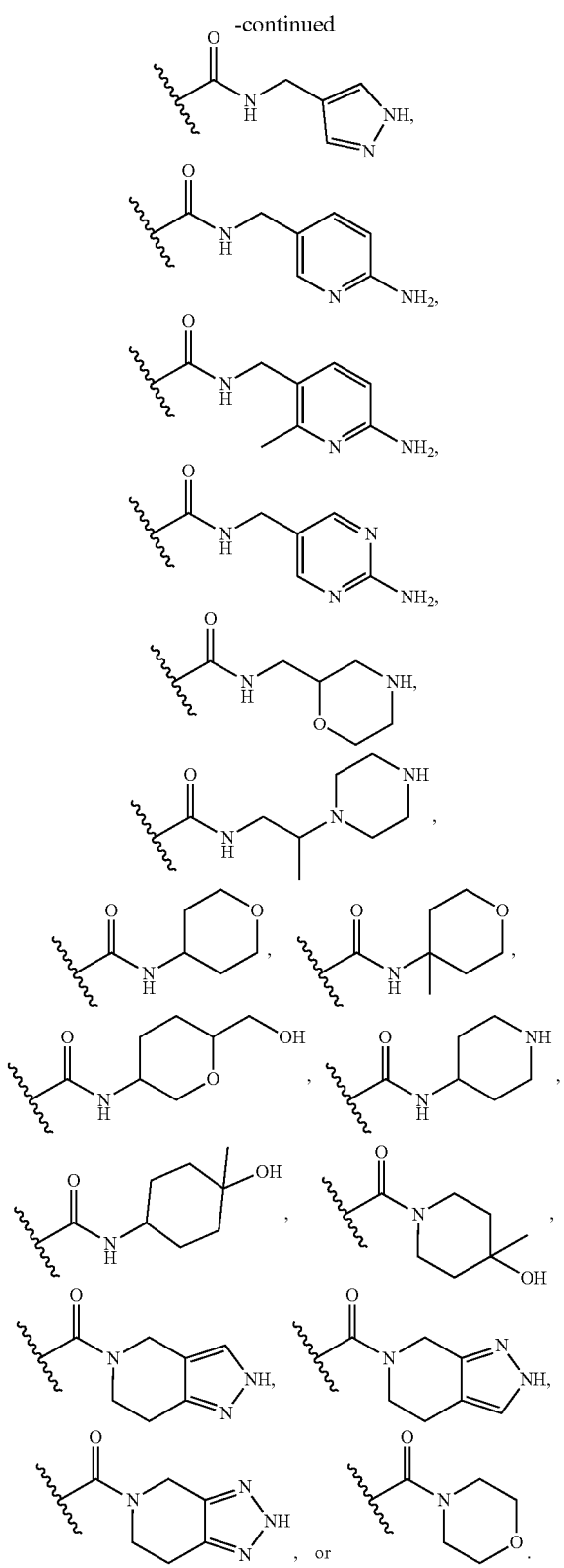
In some embodiments of a compound of Formula (I), Formula (IIa), Formula (IIb), Formula (IIc), Formula (IId), Formula (III), Formula (IIa), Formula (IIIb), Formula (IIIc), Formula (IIId), Formula (IV), Formula (IVa), Formula (IVb), Formula (IVc), Formula (IVd), Formula (VI), Formula (VIa), Formula (VII), or Formula (VIIa), or a pharmaceutically acceptable salt or solvate thereof,
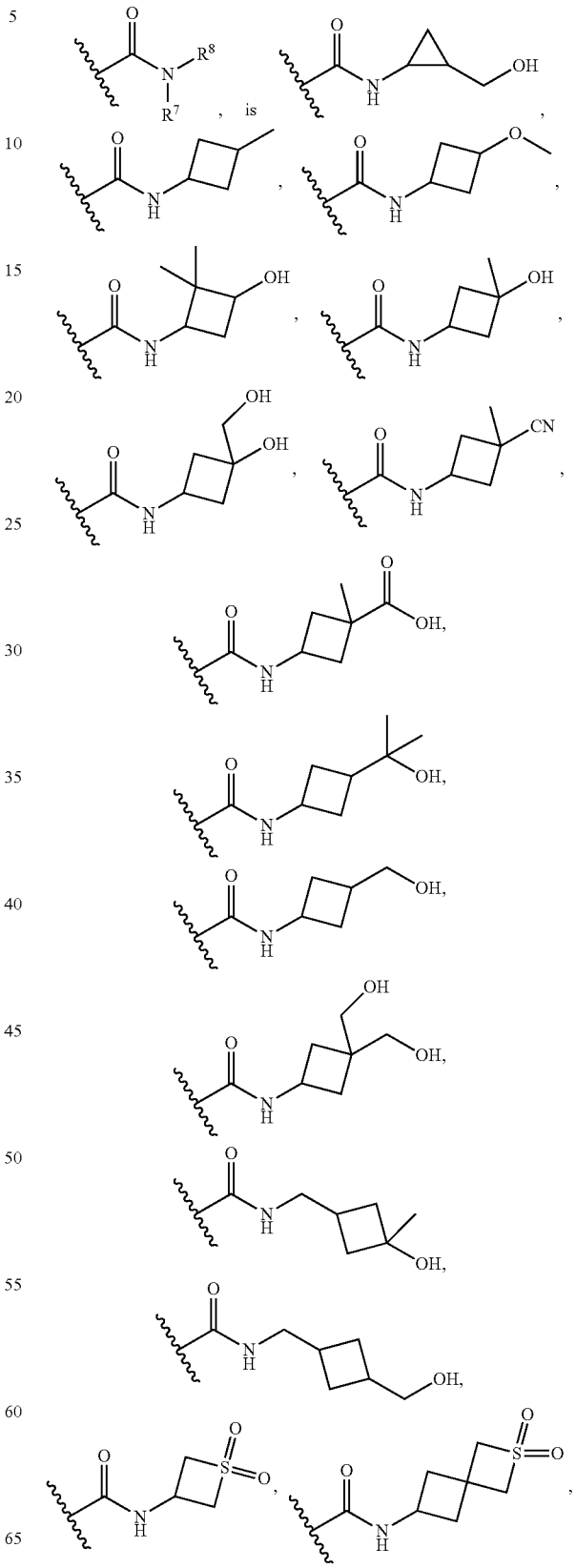

129
-continued
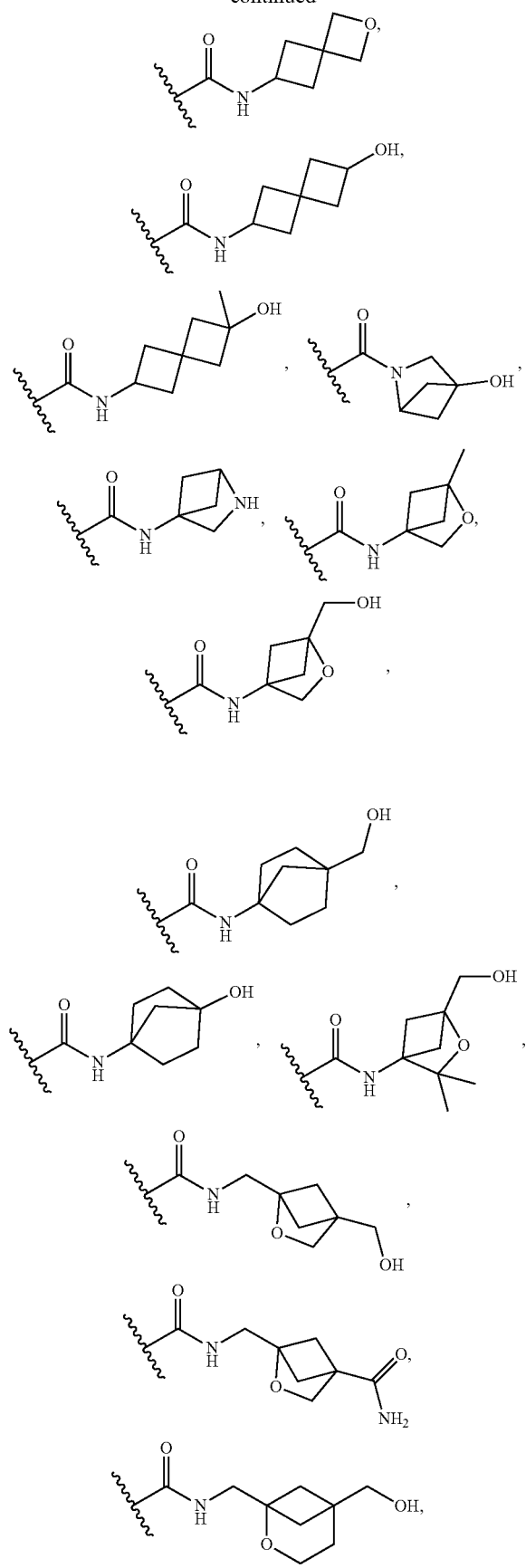
130
-continued
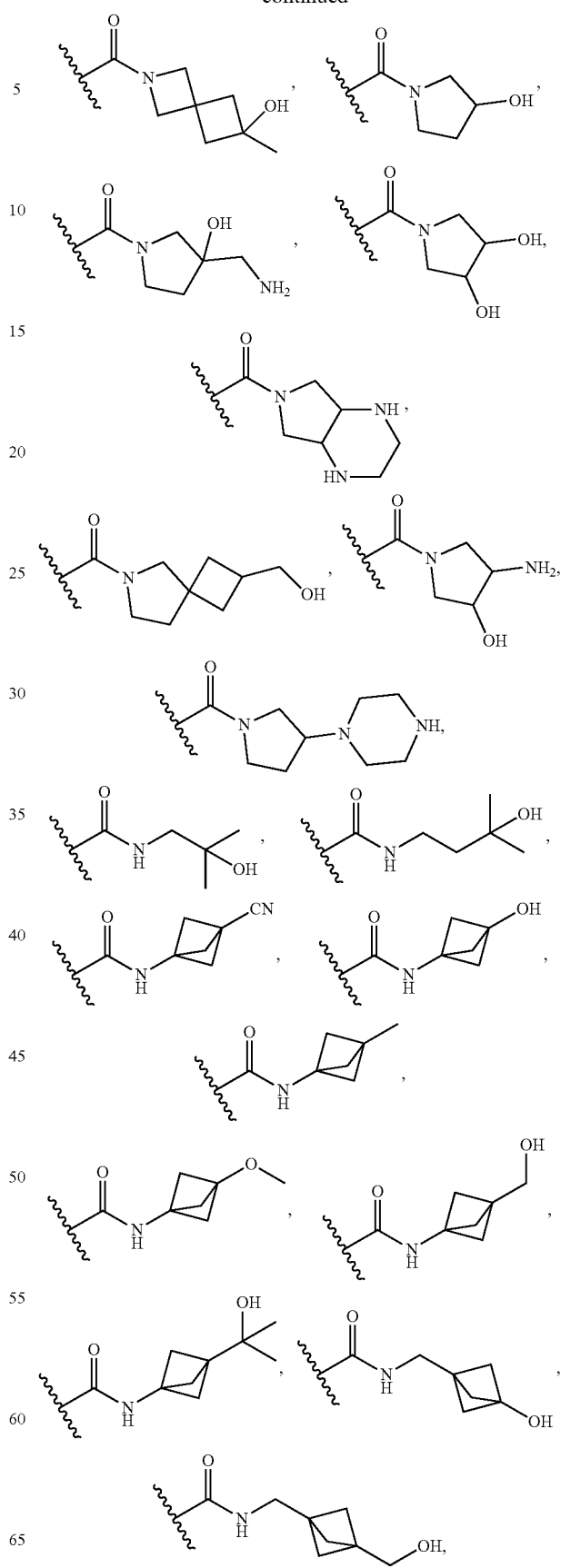

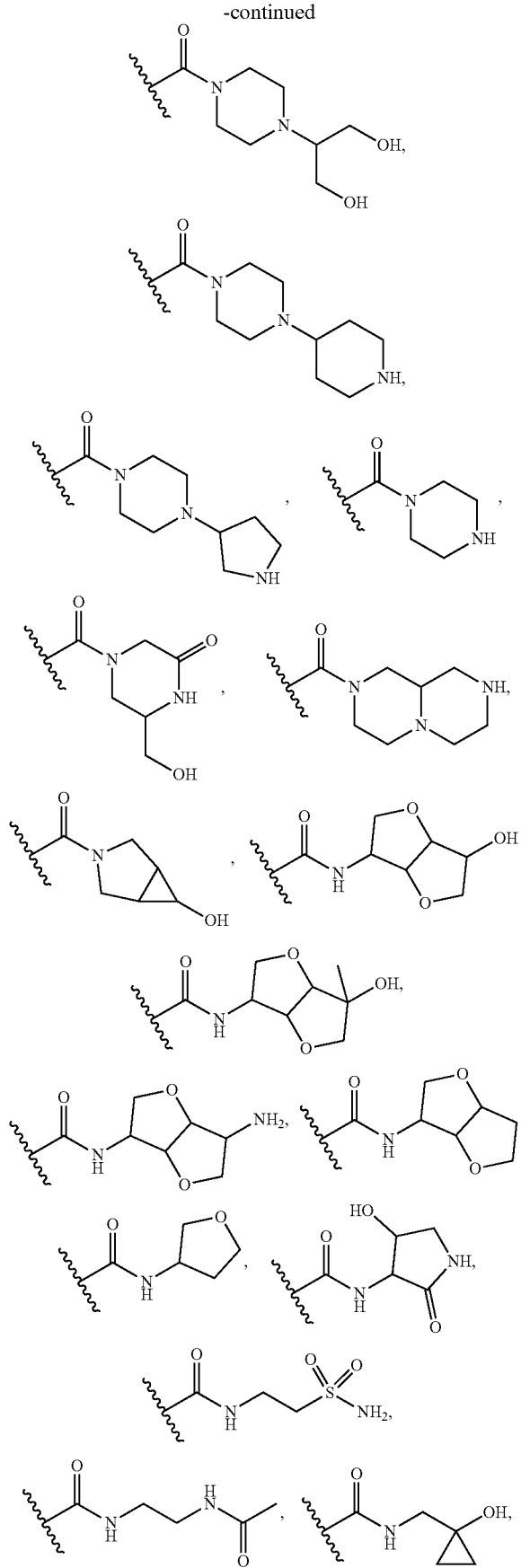
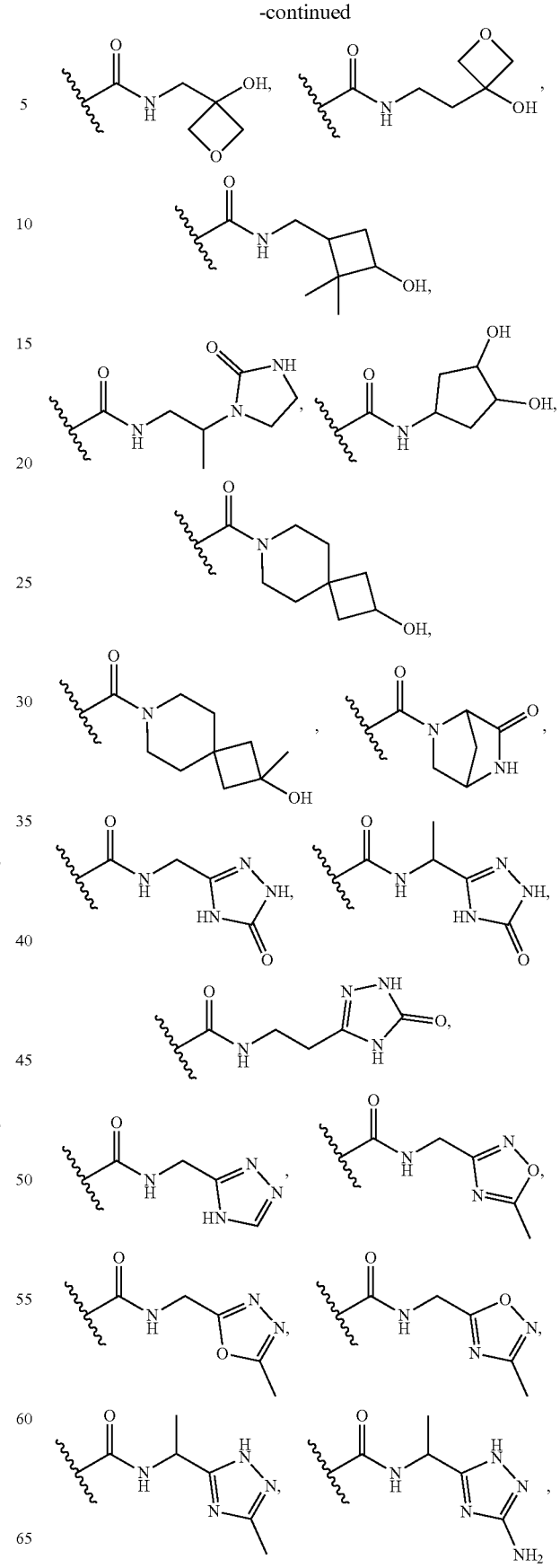

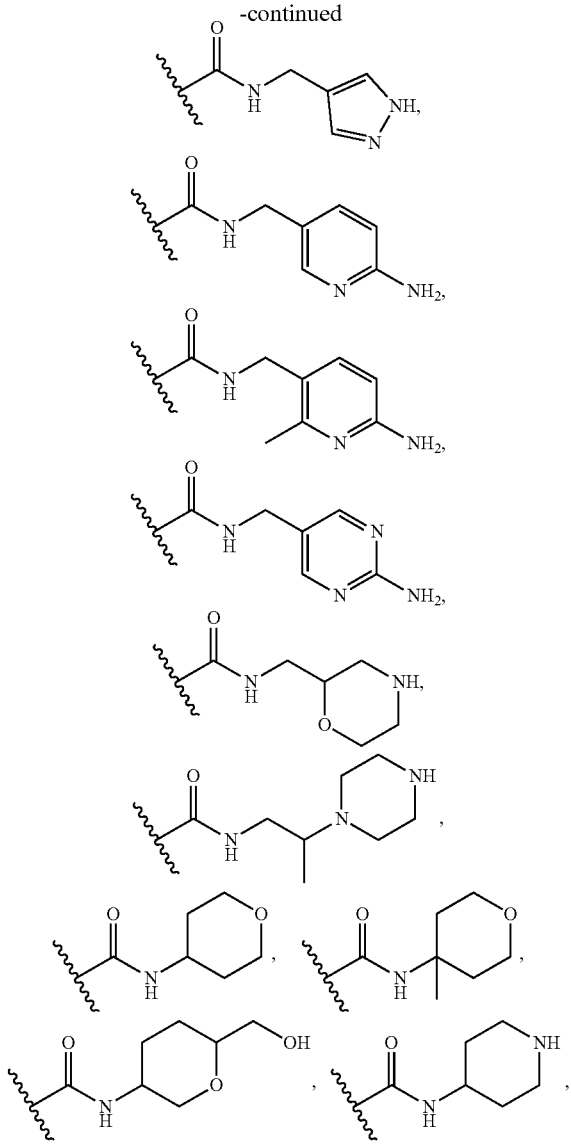

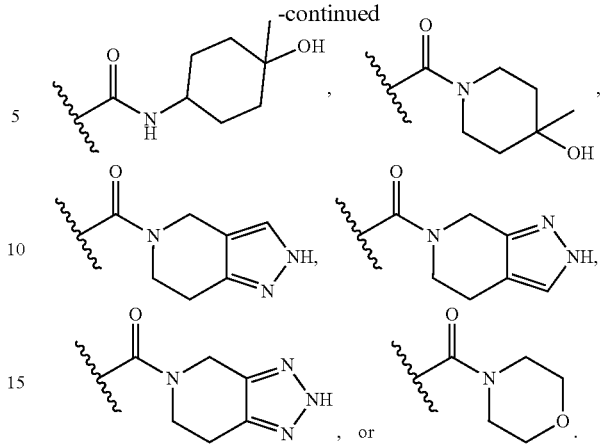

Any combination of the groups described above for the various variables is contemplated herein. Throughout the specification, groups and substituents thereof are chosen by one skilled in the field to provide stable moieties and compounds.

In some embodiments, the compound is a compound as prepared or described in the Examples provided herein. In some embodiments, the compound is a compound described in Table 1.

Further Forms of Compounds

Furthermore, in some embodiments, the compounds described herein exist as "geometric isomers." In some embodiments, the compounds described herein possess one or more double bonds. The compounds presented herein include all cis, trans, syn, anti, entgegen (E), and zusammen (Z) isomers as well as the corresponding mixtures thereof. In some situations, compounds exist as tautomers.

A "tautomer" refers to a molecule wherein a proton shift from one atom of a molecule to another atom of the same molecule is possible. In certain embodiments, the compounds presented herein exist as tautomers. In circumstances where tautomerization is possible, a chemical equilibrium of the tautomers will exist. The exact ratio of the tautomers depends on several factors, including physical state, temperature, solvent, and pH. Some examples of tautomeric equilibrium include:

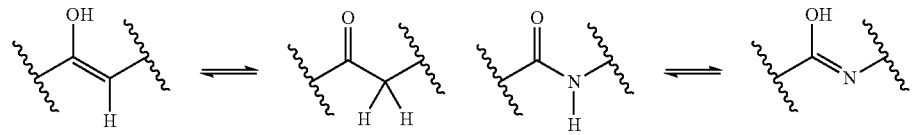

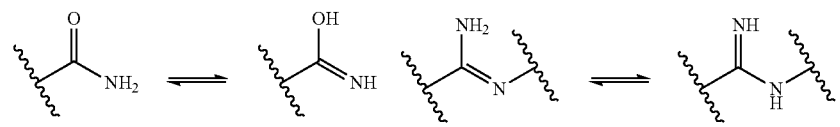

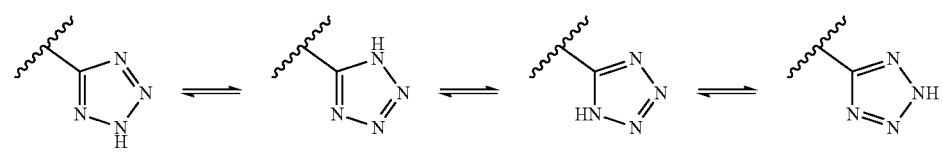

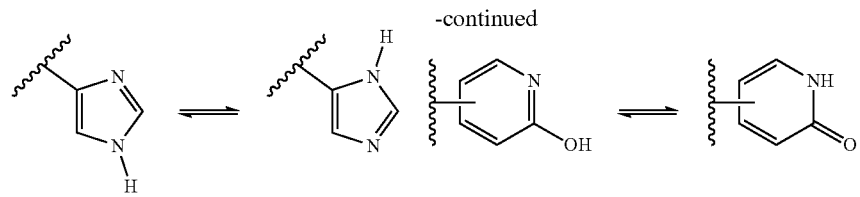

In some situations, the compounds described herein possess one or more chiral centers and each center exists in the (R)-configuration or (S)-configuration. The compounds described herein include all diastereomeric, enantiomeric, and epimeric forms as well as the corresponding mixtures thereof. In additional embodiments of the compounds and methods provided herein, mixtures of enantiomers and/or diastereoisomers, resulting from a single preparative step, combination, or interconversion are useful for the applications described herein. In some embodiments, the compounds described herein are prepared as optically pure enantiomers by chiral chromatographic resolution of the racemic mixture. In some embodiments, the compounds described herein are prepared as their individual stereoisomers by reacting a racemic mixture of the compound with an optically active resolving agent to form a pair of diastereoisomeric compounds, separating the diastereomers and recovering the optically pure enantiomers. In some embodiments, dissociable complexes are preferred (e.g., crystalline diastereomeric salts). In some embodiments, the diastereomers have distinct physical properties (e.g., melting points, boiling points, solubilities, reactivity, etc.) and are separated by taking advantage of these dissimilarities. In some embodiments, the diastereomers are separated by chiral chromatography, or preferably, by separation/resolution techniques based upon differences in solubility. In some embodiments, the optically pure enantiomer is then recovered, along with the resolving agent, by any practical means that would not result in racemization.

The term "positional isomer" refers to structural isomers around a central ring, such as ortho-, meta-, and para-isomers around a benzene ring.

The methods and formulations described herein include the use of N-oxides (if appropriate), crystalline forms (also known as polymorphs), or pharmaceutically acceptable salts of compounds described herein, as well as active metabolites of these compounds having the same type of activity.

"Pharmaceutically acceptable salt" includes both acid and base addition salts. A pharmaceutically acceptable salt of any one of the compounds described herein is intended to encompass any and all pharmaceutically suitable salt forms. Preferred pharmaceutically acceptable salts of the compounds described herein are pharmaceutically acceptable acid addition salts and pharmaceutically acceptable base addition salts.

"Pharmaceutically acceptable acid addition salt" refers to those salts which retain the biological effectiveness and properties of the free bases, which are not biologically or otherwise undesirable, and which are formed with inorganic acids such as hydrochloric acid, hydrobromic acid, sulfuric acid, nitric acid, phosphoric acid, hydroiodic acid, hydrofluoric acid, phosphorous acid, and the like. Also included are salts that are formed with organic acids such as aliphatic mono- and dicarboxylic acids, phenyl-substituted alkanoic acids, hydroxy alkanoic acids, alkanedioic acids, aromatic acids, aliphatic and aromatic sulfonic acids, etc. and include, for example, acetic acid, trifluoroacetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like. Exemplary salts thus include sulfates, pyrosulfates, bisulfates, sulfites, bisulfites, nitrates, phosphates, monohydrogenphosphates, dihydrogenphosphates, metaphosphates, pyrophosphates, chlorides, bromides, iodides, acetates, trifluoroacetates, propionates, caprylates, isobutyrates, oxalates, malonates, succinate suberates, sebacates, fumarates, maleates, mandelates, benzoates, chlorobenzoates, methylbenzoates, dinitrobenzoates, phthalates, benzenesulfonates, toluenesulfonates, phenylacetates, citrates, lactates, malates, tartrates, methanesulfonates, and the like. Also contemplated are salts of amino acids, such as arginates, gluconates, and galacturonates (see, for example, Berge S. M. et al., "Pharmaceutical Salts," *Journal of Pharmaceutical Science*, 66:1-19 (1997). Acid addition salts of basic compounds are prepared by contacting the free base forms with a sufficient amount of the desired acid to produce the salt.

"Pharmaceutically acceptable base addition salt" refers to those salts that retain the biological effectiveness and properties of the free acids, which are not biologically or otherwise undesirable. These salts are prepared from addition of an inorganic base or an organic base to the free acid. In some embodiments, pharmaceutically acceptable base addition salts are formed with metals or amines, such as alkali and alkaline earth metals or organic amines. Salts derived from inorganic bases include, but are not limited to, sodium, potassium, lithium, ammonium, calcium, magnesium, iron, zinc, copper, manganese, aluminum salts and the like. Salts derived from organic bases include, but are not limited to, salts of primary, secondary, and tertiary amines, substituted amines including naturally occurring substituted amines, cyclic amines and basic ion exchange resins, for example, isopropylamine, trimethylamine, diethylamine, triethylamine, tripropylamine, ethanolamine, diethanolamine, 2-dimethylaminoethanol, 2-diethylaminoethanol, dicyclohexylamine, lysine, arginine, histidine, caffeine, procaine, N,N-dibenzylethylenediamine, chloroprocaine, hydrabamine, choline, betaine, ethylenediamine, ethylenedianiline, N-methylglucamine, glucosamine, methylglucamine, theobromine, purines, piperazine, piperidine, N-ethylpiperidine, polyamine resins and the like. See Berge et al., supra.

"Prodrug" is meant to indicate a compound that is, in some embodiments, converted under physiological conditions or by solvolysis to an active compound described herein. Thus, the term prodrug refers to a precursor of an active compound that is pharmaceutically acceptable. A prodrug is typically inactive when administered to a subject, but is converted in vivo to an active compound, for example, by hydrolysis. The prodrug compound often offers advantages of solubility, tissue compatibility or delayed release in a mammalian organism (see, e.g., Bundgard, H., Design of Prodrugs (1985), pp. 7-9, 21-24 (Elsevier, Amsterdam).

A discussion of prodrugs is provided in Higuchi, T., et al., "Pro-drugs as Novel Delivery Systems," A.C.S. Symposium Series, Vol. 14, and in Bioreversible Carriers in Drug Design, ed. Edward B. Roche, American Pharmaceutical Association and Pergamon Press, 1987.

The term "prodrug" is also meant to include any covalently bonded carriers, which release the active compound in vivo when such prodrug is administered to a mammalian subject. Prodrugs of an active compound, as described herein, are prepared by modifying functional groups present in the active compound in such a way that the modifications are cleaved, either in routine manipulation or in vivo, to the parent active compound. Prodrugs include compounds wherein a hydroxy, amino, carboxy, or mercapto group is bonded to any group that, when the prodrug of the active compound is administered to a mammalian subject, cleaves to form a free hydroxy, free amino, free carboxy, or free mercapto group, respectively. Examples of prodrugs include, but are not limited to, acetate, formate and benzoate derivatives of alcohol or amine functional groups in the active compounds and the like.

"Pharmaceutically acceptable solvate" refers to a composition of matter that is the solvent addition form. In some embodiments, solvates contain either stoichiometric or non-stoichiometric amounts of a solvent, and are formed during the process of making with pharmaceutically acceptable solvents such as water, ethanol, and the like. "Hydrates" are formed when the solvent is water, or "alcoholates" are formed when the solvent is alcohol. Solvates of compounds described herein are conveniently prepared or formed during the processes described herein. The compounds provided herein optionally exist in unsolvated as well as solvated forms.

The compounds disclosed herein, in some embodiments, are used in different enriched isotopic forms, e.g., enriched in the content of $^2$H, $^3$H, $^{11}$C, $^{13}$C and/or $^{14}$C. In some embodiments, the compound is deuterated in at least one position. Such deuterated forms can be made by the procedure described in U.S. Pat. Nos. 5,846,514 and 6,334,997. As described in U.S. Pat. Nos. 5,846,514 and 6,334,997, deuteration can improve the metabolic stability and or efficacy, thus increasing the duration of action of drugs.

Unless otherwise stated, structures depicted herein are intended to include compounds which differ only in the presence of one or more isotopically enriched atoms. For example, compounds having the present structures except for the replacement of a hydrogen by a deuterium or tritium, or the replacement of a carbon by $^{13}$C- or $^{14}$C-enriched carbon are within the scope of the present disclosure.

The compounds of the present disclosure optionally contain unnatural proportions of atomic isotopes at one or more atoms that constitute such compounds. For example, the compounds may be labeled with isotopes, such as for example, deuterium ($^2$H), tritium ($^3$H), iodine-125 ($^{125}$I) or carbon-14 ($^{14}$C). Isotopic substitution with $^2$H, $^3$H, $^{11}$C, $^{13}$C, $^{14}$C, $^{15}$C, $^{12}$N, $^{13}$N, $^{15}$N, $^{16}$N, $^{17}$O, $^{18}$O, $^{14}$F, $^{15}$F, $^{16}$F, $^{17}$F, $^{18}$F, $^{33}$S, $^{34}$S, $^{35}$S, $^{36}$S, $^{35}$Cl, $^{37}$Cl, $^{79}$Br, $^{81}$Br, $^{125}$I are all contemplated. All isotopic variations of the compounds of the present invention, whether radioactive or not, are encompassed within the scope of the present invention.

In certain embodiments, the compounds disclosed herein have some or all of the $^1$H atoms replaced with $^2$H atoms. The methods of synthesis for deuterium-containing compounds are known in the art. In some embodiments deuterium substituted compounds are synthesized using various methods such as described in: Dean, Dennis C.; Editor. Recent Advances in the Synthesis and Applications of Radiolabeled Compounds for Drug Discovery and Development. [In: Curr., Pharm. Des., 2000; 6(10)] 2000, 110 pp; George W.; Varma, Rajender S. The Synthesis of Radiolabeled Compounds via Organometallic Intermediates, Tetrahedron, 1989, 45(21), 6601-21; and Evans, E. Anthony. Synthesis of radiolabeled compounds, J. Radioanal. Chem., 1981, 64(1-2), 9-32.

In some embodiments, the compounds described herein are labeled by other means, including, but not limited to, the use of chromophores or fluorescent moieties, bioluminescent labels, or chemiluminescent labels.

In certain embodiments, the compounds described herein, or a pharmaceutically acceptable salt, solvate, stereoisomer, or prodrug thereof, as described herein are substantially pure, in that it contains less than about 5%, or less than about 1%, or less than about 0.1% of other organic small molecules, such as contaminating intermediates or by-products that are created, for example, in one or more of the steps of a synthesis method.

Preparation of the Compounds

Compounds described herein are synthesized using standard synthetic techniques or using methods known in the art in combination with methods described herein.

Unless otherwise indicated, conventional methods of mass spectroscopy, NMR, HPLC, protein chemistry, biochemistry, recombinant DNA techniques and pharmacology are employed.

Compounds are prepared using standard organic chemistry techniques such as those described in, for example, March's Advanced Organic Chemistry, 6th Edition, John Wiley and Sons, Inc. Alternative reaction conditions for the synthetic transformations described herein may be employed such as variation of solvent, reaction temperature, reaction time, as well as different chemical reagents and other reaction conditions.

In some embodiments, compounds described herein are prepared as described as outlined in the Examples.

Pharmaceutical Compositions

In some aspects, the present disclosure provides a pharmaceutical composition comprising a compound of Formula (I) and at least one pharmaceutically acceptable excipient.

A compound of Formula (I) may be formulated in any suitable pharmaceutical formulation. A pharmaceutical formulation of the present disclosure typically contains an active ingredient (e.g., compound of Formula (I)), and one or more pharmaceutically acceptable excipients or carriers, including but not limited to: inert solid diluents and fillers, diluents, sterile aqueous solution and various organic solvents, permeation enhancers, antioxidants, solubilizers, and adjuvants. Preparations for such pharmaceutical composition are well-known in the art. See, e.g., Anderson, Philip O.; Knoben, James E.; Troutman, William G, eds., Handbook of Clinical Drug Data, Tenth Edition, McGraw-Hill, 2002; Pratt and Taylor, eds., Principles of Drug Action, Third Edition, Churchill Livingston, New York, 1990; Katzung, ed., Basic and Clinical Pharmacology, Ninth Edition, McGraw Hill, 2003; Goodman and Gilman, eds., The Pharmacological Basis of Therapeutics, Tenth Edition, McGraw Hill, 2001; Remington's Pharmaceutical Sciences, 20th Ed., Lippincott Williams & Wilkins., 2000; Martindale, The Extra Pharmacopoeia, Thirty-Second Edition (The Pharmaceutical Press, London, 1999).

The amount of a therapeutic agent of the present disclosure will be dependent on the mammal being treated, the severity of the disorder or condition, the rate of administration, the disposition of the therapeutic protein and the discretion of the prescribing physician.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

Combination Therapies

In certain embodiments, it is appropriate to administer at least one compound described herein, or a pharmaceutically acceptable salt, solvate, stereoisomer, or prodrug thereof, in combination with one or more other therapeutic agents (e.g., additional therapeutic agents). In some embodiments, a compound described herein, or a pharmaceutically acceptable salt or solvate thereof, is administered in combination with one or more other therapeutic agents (e.g., additional therapeutic agents) used to treat migraine. In some embodiments, the one or more other therapeutic agents (e.g., additional therapeutic agents) comprise: beta blockers such as propranolol, nadolol, timolol, metoprolol, and atenolol; antidepressants such as amitriptyline and venlafaxine; anticonvulsants such as valproate and topiramate; phenothiazine anti-emetics such as prochlorperazine; non-phenothiazine anti-emetics such as metoclopramide; non-steroidal anti-inflammatory drugs (NSAIDS) such as aspirin, ibuprofen, and naproxen; acetaminophen; caffeine; ergots such as ergotamine and dihydroergotamine (DHE); ditans such as lasmiditan; triptans such as almotriptan, eletriptan, frovatriptan, naratriptan, rizatriptan, sumatriptan and zolmitriptan; calcitonin gene-related peptide (CGRP) receptor antagonists such as ubrogepant, rimegepant, atogepant, and zavegepant; CGRP antibodies such as erenumab, fremanezumab, galcanezumab and eptinezumab; and combinations thereof.

NON-LIMITING EMBODIMENTS

Below are listed some non-limiting embodiments of the present disclosure:

Embodiment 1. A compound of Formula (I):

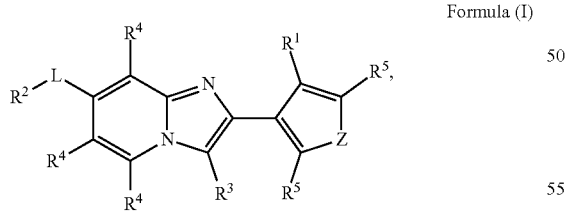

Formula (I)

or a pharmaceutically acceptable salt or solvate thereof, wherein:

Z is a bivalent group selected from —S—, —N=C($R^5$)—, —C($R^5$)=N—, or —C($R^5$)=C($R^5$)—;

$R^1$ is pyrazole, wherein said pyrazole is optionally substituted with 1-3 groups independently selected from $R^6$;

$R^2$ is $C_1$-$C_{10}$ alkyl, $C_1$-$C_{10}$ heteroalkyl, —C(=O)O$R^7$, —C(=O)N($R^8$)($R^7$), —N($R^8$)($R^7$), —C(=N$R^9$)N($R^8$)($R^7$), —N($R^7$)C(=N$R^9$)N($R^8$)($R^7$), $C_6$-$C_{10}$ aryl, 5- to 10-membered heteroaryl, $C_3$-$C_{12}$ cycloalkyl, or 3-to-15 membered heterocycloalkyl, wherein the aryl, and heteroaryl is optionally substituted with 1-4 groups independently selected from $R^{10}$, and the alkyl, heteroalkyl, cycloalkyl, and heterocycloalkyl is optionally substituted with 1-4 groups independently selected from oxo and $R^{10}$;

$R^3$ is halogen, cyano, —C(=O)OH, —C(=O)O($C_1$-$C_6$ alkyl), $C_1$-$C_6$ alkyl, $C_1$-$C_6$ alkenyl, —O($C_1$-$C_6$ alkyl), $C_3$-$C_6$ cycloalkyl, or $C_1$-$C_6$ haloalkyl;

each $R^4$ is independently hydrogen, halogen, $C_1$-$C_6$ alkyl, —O—$C_1$-$C_6$ alkyl, $C_1$-$C_6$ haloalkyl, or —O—($C_1$-$C_6$ haloalkyl);

L is a bond, $C_1$-$C_2$ alkylene, or $C_3$-$C_6$ cycloalkylene, wherein said alkylene, or cycloalkylene is optionally substituted with 1 or 2 —OH groups;

each $R^5$ is independently hydrogen, cyano, halogen, $C_1$-$C_6$ alkyl, —O($C_1$-$C_6$ alkyl), $C_3$-$C_6$ cycloalkyl, $C_1$-$C_6$ haloalkyl, or —O($C_1$-$C_6$ haloalkyl);

each $R^6$ is independently selected from the group consisting of halogen, hydroxy, cyano, amino, $C_1$-$C_6$ alkyl, $C_1$-$C_6$ hydroxyalkyl, $C_1$-$C_6$ aminoalkyl, —O($C_1$-$C_6$ alkyl), —NH($C_1$-$C_6$ alkyl), —N($C_1$-$C_6$ alkyl)$_2$, $C_3$-$C_6$ cycloalkyl, —CH$_2$—($C_{3-6}$ cycloalkyl), —O—($C_{3-6}$ cycloalkyl), $C_1$-$C_6$ haloalkyl, and —O($C_1$-$C_6$ haloalkyl);

wherein if an $R^6$ is attached to a nitrogen atom, then it is selected from the group consisting of $C_1$-$C_6$ alkyl, $C_1$-$C_6$ hydroxyalkyl, $C_1$-$C_6$ aminoalkyl, $C_3$-$C_6$ cycloalkyl, —CH$_2$—($C_{3-6}$ cycloalkyl), and $C_1$-$C_6$ haloalkyl;

each $R^7$ is independently hydrogen or $C_1$-$C_6$ alkyl, wherein said alkyl is optionally substituted with 1-2 hydroxy groups;

$R^8$ is hydrogen, $C_1$-$C_{10}$ alkyl, $C_1$-$C_{10}$ heteroalkyl, $C_1$-$C_{10}$ alkenyl, $C_1$-$C_{10}$ alkynyl, $C_3$-$C_{12}$ cycloalkyl, 3- to 15-membered heterocycloalkyl, $C_6$-$C_{10}$ aryl, or 5- to 10-membered heteroaryl; wherein the aryl, and heteroaryl is optionally substituted with 1-6 groups independently selected from $R^{11}$, and the alkyl, heteroalkyl, alkenyl, alkynyl, cycloalkyl and heterocycloalkyl is optionally substituted with 1-6 groups independently selected from oxo and $R^{11}$;

or one $R^7$ and one $R^8$ bound to the same nitrogen atom come together to form a 3- to 15-membered heterocycloalkyl that is optionally substituted with 1-6 groups independently selected from oxo and $R^{11}$;

$R^9$ is hydrogen, —C(O)O$R^{12}$, —C(O)N($R^{12}$)$_2$, —S(O)$_2$ $R^{12}$, —S(O)$_2$N($R^{12}$)$_2$, or $C_1$-$C_6$ alkyl;

each $R^{10}$ is independently selected from hydroxy, amino, cyano, fluoro, —C(=O)O$R^{12}$, —C(=O)N($R^{12}$)$_2$, $C_1$-$C_4$ alkyl, $C_1$-$C_4$ haloalkyl, —O($C_1$-$C_6$ alkyl), —NH($C_1$-$C_4$ alkyl), —N($C_1$-$C_4$ alkyl)$_2$, $C_3$-$C_6$ cycloalkyl, wherein said alkyl, haloalkyl or cycloalkyl is optionally substituted with 1-2 groups selected from hydroxy, amino, cyano, fluoro, —C(=O)O$R^{12}$, and —C(=O)N($R^{12}$)$_2$;

each $R^{11}$ is independently selected from the group consisting of halogen, hydroxy, amino, cyano, —S(=O)$_2$($R^{13}$), —N($R^{12}$)S(=O)$_2$($R^{13}$), —S(=O)($R^{13}$), —N($R^{12}$)S(=O)($R^{13}$), —C(=O)$R^{13}$, —N($R^{12}$)C(=O)$R^{13}$, $C_1$-$C_6$ alkyl, —O($C_1$-$C_6$ alkyl), —NH($C_1$-$C_6$ alkyl), —N($C_1$-$C_6$ alkyl)$_2$, $C_1$-$C_6$ haloalkyl, $C_2$-$C_6$ alkenyl, $C_2$-$C_6$ alkynyl, $C_3$-$C_8$ cycloalkyl, 3- to 10-membered heterocycloalkyl, $C_6$-$C_{10}$ aryl, and 5- to 10-membered heteroaryl, wherein the aryl, and heteroaryl is optionally substituted with 1-4 groups independently selected from R$^{14}$, and the alkyl, alkenyl, alkynyl, haloalkyl, cycloalkyl, and heterocycloalkyl is optionally substituted with 1-4 groups independently selected from oxo and R$^{14}$;

or two R$^{11}$ bound to the same carbon or nitrogen atom come together to form a C$_3$-C$_6$ cycloalkyl or 3- to 6-membered heterocycloalkyl, wherein the cycloalkyl, and heterocycloalkyl is optionally substituted with 1-4 groups independently selected from oxo and R$^{14}$;

each R$^{12}$ is independently hydrogen or C$_1$-C$_6$ alkyl;

each R$^{13}$ is independently hydroxy, amino, C$_1$-C$_6$ alkyl, —O(C$_1$-C$_6$ alkyl), —NH(C$_1$-C$_6$ alkyl), —N(C$_1$-C$_6$ alkyl)$_2$, C$_1$-C$_6$ haloalkyl, C$_3$-C$_6$ cycloalkyl, or 3- to 6-membered heterocycloalkyl; and each R$^{14}$ is independently cyano, amino, hydroxy, —C(=O)OR$^{12}$, —C(=O)N(R$^{12}$)$_2$, C$_1$-C$_6$ alkyl, —O(C$_1$-C$_6$ alkyl), —NR$^{12}$(C$_1$-C$_6$ alkyl), aryl, heteroaryl, C$_3$-C$_6$ cycloalkyl, or 3- to 6-membered heterocycloalkyl, wherein each alkyl is optionally substituted with 1-2 hydroxy groups.

Embodiment 2. The compound of Embodiment 1, or a pharmaceutically acceptable salt or solvate thereof, wherein:

R$^3$ is fluoro, chloro, cyano, methyl, ethyl, vinyl, —OMe, —C(=O)OH, trifluoromethyl, difluoromethyl, or cyclopropyl.

Embodiment 3. The compound of Embodiment 1 or 2, or a pharmaceutically acceptable salt or solvate thereof, wherein:

R$^3$ is chloro, cyano, methyl, or ethyl.

Embodiment 4. The compound of any one of Embodiments 1 to 3, or a pharmaceutically acceptable salt or solvate thereof, wherein:

one R$^4$ is fluoro, methyl, or —OMe, and the other R$^4$ are each hydrogen.

Embodiment 5. The compound of any one of Embodiments 1 to 3, or a pharmaceutically acceptable salt or solvate thereof, wherein:

each R$^4$ is hydrogen.

Embodiment 6. The compound of any one of Embodiments 1 to 5, or a pharmaceutically acceptable salt or solvate thereof, wherein:

Z is —C(R$^5$)=C(R$^5$)— or —S—.

Embodiment 7. The compound of Embodiment 6, having the structure of Formula (IIa):

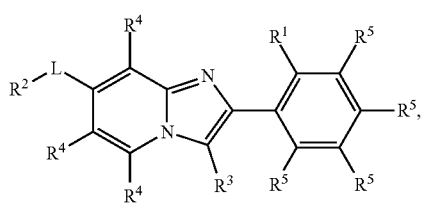

Formula (IIa)

or a pharmaceutically acceptable salt or solvate thereof.

Embodiment 8. The compound of Embodiment 6, having the structure of Formula (IIb):

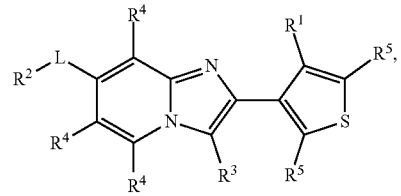

Formula (IIb)

or a pharmaceutically acceptable salt or solvate thereof.

Embodiment 9. The compound of any one of Embodiments 1 to 5, or a pharmaceutically acceptable salt or solvate thereof, wherein:

Z is —N=C(R$^5$)— or —C(R$^5$)=N—.

Embodiment 10. The compound of Embodiment 9, having the structure of Formula (IIc):

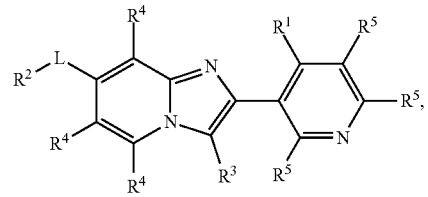

Formula (IIc)

or a pharmaceutically acceptable salt or solvate thereof.

Embodiment 11. The compound of Embodiment 9, having the structure of Formula (IId):

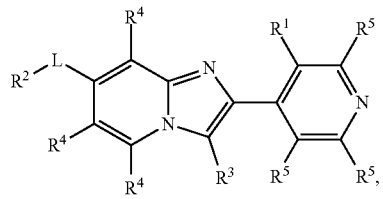

Formula (IId)

or a pharmaceutically acceptable salt or solvate thereof.

Embodiment 12. The compound of any one of Embodiments 1 to 11, or a pharmaceutically acceptable salt or solvate thereof, wherein:

L is a bond or C$_1$ alkylene.

Embodiment 13. The compound of any one of Embodiments 1 to 12, or a pharmaceutically acceptable salt or solvate thereof, wherein:

R$^2$ is —C(O)(OR$^7$).

Embodiment 14. The compound of any one of Embodiments 1 to 12, or a pharmaceutically acceptable salt or solvate thereof, wherein:

R$^2$ is 5- to 10-membered heteroaryl or 3-to-15 membered heterocycloalkyl.

Embodiment 15. The compound of any one of Embodiments 1 to 12, or a pharmaceutically acceptable salt or solvate thereof, wherein:

R$^2$ is 5- to 6-membered heteroaryl or 3-to-8 membered heterocycloalkyl.

Embodiment 16. The compound of Embodiment 1 having a structure of Formula (III):

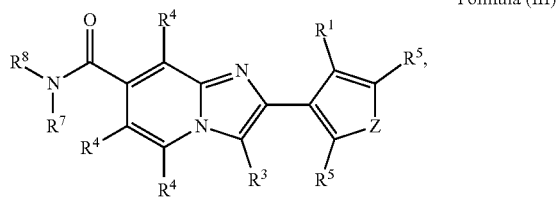

Formula (III)

or a pharmaceutically acceptable salt or solvate thereof.

Embodiment 17. The compound of Embodiment 16 having the structure of Formula (IVa):

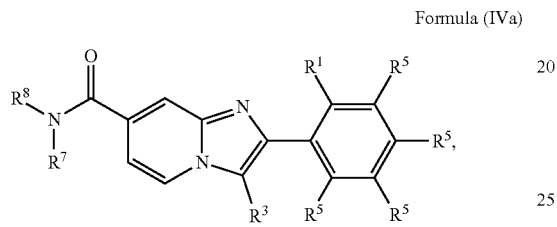

Formula (IVa)

or a pharmaceutically acceptable salt or solvate thereof.

Embodiment 18. The compound of any one of Embodiments 1 to 17, or a pharmaceutically acceptable salt or solvate thereof, wherein:

$R^1$ is optionally substituted with 1-3 $R^6$ groups independently selected from the group consisting of methyl, ethyl, cyano, fluoro, chloro, —OMe, trifluoromethyl, and difluoromethyl; wherein when an $R^6$ is attached to a nitrogen atom, it is selected from the group consisting of methyl, ethyl, trifluoromethyl, trifluoroethyl, and difluoromethyl.

Embodiment 19. The compound of any one of Embodiments 1 to 18, or a pharmaceutically acceptable salt or solvate thereof, wherein:

$R^1$ is

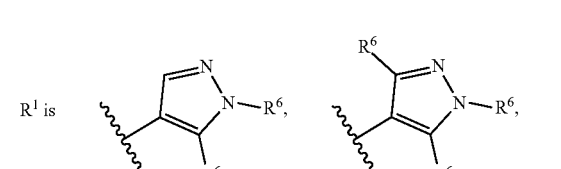

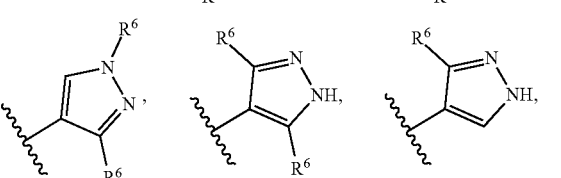

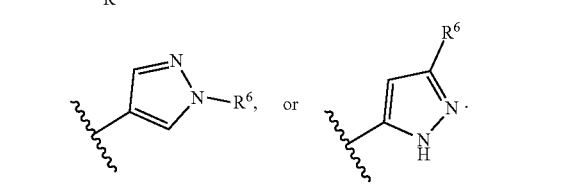

Embodiment 20. The compound of any one of Embodiments 1 to 19, or a pharmaceutically acceptable salt or solvate thereof, wherein:

$R^1$ is optionally substituted with 1-2 $R^6$ groups independently selected from the group consisting of methyl, cyano, fluoro, chloro, —OMe, and difluoromethyl; wherein when an $R^6$ is attached to a nitrogen atom, it is methyl.

Embodiment 21. The compound of Embodiment 19, or a pharmaceutically acceptable salt or solvate thereof, wherein:

$R^1$ is

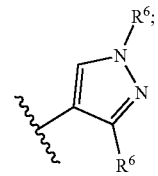

and each $R^6$ is independently fluoro, chloro, cyano, or methyl; wherein when an $R^6$ is attached to a nitrogen atom, it is methyl.

Embodiment 22. The compound of Embodiment 19, or a pharmaceutically acceptable salt or solvate thereof, wherein:

$R^1$ is

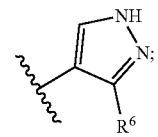

and $R^6$ is independently fluoro, chloro, cyano, or methyl.

Embodiment 23. The compound of Embodiment 1 having a structure of Formula (VIa):

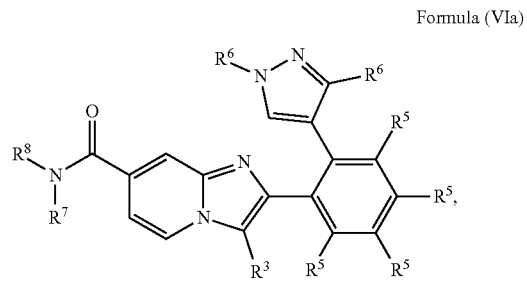

Formula (VIa)

or a pharmaceutically acceptable salt or solvate thereof.

Embodiment 24. The compound of Embodiment 1 having a structure of Formula (VIIa):

Formula (VIIa)

[Chemical structure of Formula (VIIa) showing a fused imidazopyridine core with an HN-pyrazole group bearing R⁶, a phenyl ring with R⁵ substituents, an amide group with R⁷ and R⁸ on nitrogen, and R³ substituent]

or a pharmaceutically acceptable salt or solvate thereof.

Embodiment 25. The compound of any one of Embodiments 1 to 24, or a pharmaceutically acceptable salt or solvate thereof, wherein:
each $R^5$ is independently hydrogen or fluoro.

Embodiment 26. The compound of any one of Embodiments 1 to 25, or a pharmaceutically acceptable salt or solvate thereof, wherein:
each $R^5$ is hydrogen.

Embodiment 27. The compound of any one of Embodiments 1 to 13 or 16 to 26, or a pharmaceutically acceptable salt or solvate thereof, wherein:
$R^7$ is hydrogen.

Embodiment 28. The compound of any one of Embodiments 1 to 12 or 16 to 27, or a pharmaceutically acceptable salt or solvate thereof, wherein:
$R^8$ is $C_1$-$C_{10}$ alkyl, $C_1$-$C_{10}$ heteroalkyl, $C_3$-$C_{12}$ cycloalkyl, or 3- to 15-membered heterocycloalkyl.

Embodiment 29. The compound of Embodiment 28, or a pharmaceutically acceptable salt or solvate thereof, wherein:
$R^8$ is $C_1$-$C_{10}$ alkyl, $C_3$-$C_{12}$ cycloalkyl, or 3- to 15-membered heterocycloalkyl.

Embodiment 30. The compound of Embodiment 28 or 29, or a pharmaceutically acceptable salt or solvate thereof, wherein:
$R^8$ is $C_3$-$C_{10}$ cycloalkyl, or 3- to 12-membered heterocycloalkyl.

Embodiment 31. The compound of any one of Embodiments 28 to 30, or a pharmaceutically acceptable salt or solvate thereof, wherein:
$R^8$ is monocyclic $C_3$-$C_{10}$ cycloalkyl, fused bicyclic $C_5$-$C_{10}$ cycloalkyl, bridged bicyclic $C_5$-$C_{10}$ cycloalkyl, spirocyclic bicyclic $C_5$-$C_{10}$ cycloalkyl, monocyclic 3- to 12-membered heterocycloalkyl, fused bicyclic 5- to 12-membered heterocycloalkyl, bridged bicyclic 5- to 12-membered heterocycloalkyl, or spirocyclic bicyclic 5- to 12-membered heterocycloalkyl.

Embodiment 32. The compound of any one of Embodiments 28 to 31, or a pharmaceutically acceptable salt or solvate thereof, wherein:
$R^8$ is fused bicyclic $C_5$-$C_{10}$ cycloalkyl, bridged bicyclic $C_5$-$C_{10}$ cycloalkyl, spirocyclic bicyclic $C_5$-$C_{10}$ cycloalkyl, fused bicyclic 5- to 12-membered heterocycloalkyl, bridged bicyclic 5- to 12-membered heterocycloalkyl, or spirocyclic bicyclic 5- to 12-membered heterocycloalkyl.

Embodiment 33. The compound of any one of Embodiments 28 to 32, or a pharmaceutically acceptable salt or solvate thereof, wherein:
$R^8$ is spirocyclic bicyclic $C_5$-$C_{10}$ cycloalkyl, or spirocyclic bicyclic 5- to 12-membered heterocycloalkyl.

Embodiment 34. The compound of any one of Embodiments 1 to 12 or 16 to 26, or a pharmaceutically acceptable salt or solvate thereof, wherein:
one $R^7$ and one $R^8$ bound to the same nitrogen atom come together to form a 3- to 15-membered heterocycloalkyl that is optionally substituted with 1-6 groups independently selected from oxo and $R^{11}$.

Embodiment 35. The compound of Embodiment 34, or a pharmaceutically acceptable salt or solvate thereof, wherein:
one $R^7$ and one $R^8$ bound to the same nitrogen atom come together to form a fused bicyclic 5- to 12-membered heterocycloalkyl, bridged bicyclic 5- to 12-membered heterocycloalkyl, or spirocyclic bicyclic 5- to 12-membered heterocycloalkyl.

Embodiment 36. The compound of Embodiment 34 or 35, or a pharmaceutically acceptable salt or solvate thereof, wherein:
one $R^7$ and one $R^8$ bound to the same nitrogen atom come together to form a bridged bicyclic 5- to 12-membered heterocycloalkyl, or spirocyclic bicyclic 5- to 12-membered heterocycloalkyl.

Embodiment 37. The compound of any one of Embodiments 34 to 36, or a pharmaceutically acceptable salt or solvate thereof, wherein:
one $R^7$ and one $R^8$ bound to the same nitrogen atom come together to form a spirocyclic bicyclic 5- to 12-membered heterocycloalkyl.

Embodiment 38. The compound of any one of Embodiments 1 to 12 or 16 to 37, or a pharmaceutically acceptable salt or solvate thereof, wherein:
each $R^{11}$ is independently selected from the group consisting of halogen, hydroxy, amino, cyano, —S(=O)$_2$($R^{13}$), —N($R^{12}$)S(=O)$_2$($R^{13}$), —S(=O)($R^{13}$), —N($R^{12}$)S(=O)($R^{13}$), —C(=O)$R^{13}$, —N($R^{12}$)C(=O)$R^{13}$, $C_1$-$C_6$ alkyl, —O($C_1$-$C_6$ alkyl), —NH($C_1$-$C_6$ alkyl), —N($C_1$-$C_6$ alkyl)$_2$, $C_1$-$C_6$ haloalkyl, $C_3$-$C_8$ cycloalkyl, 3- to 10-membered heterocycloalkyl, $C_6$ aryl, and 5- to 6-membered heteroaryl, wherein the aryl, and heteroaryl is optionally substituted with 1-4 groups independently selected from $R^{14}$, and the alkyl, haloalkyl, cycloalkyl, and heterocycloalkyl is optionally substituted with 1-4 groups independently selected from oxo and $R^{14}$;
or two $R^{11}$ bound to the same carbon or nitrogen atom come together to form a $C_3$-$C_6$ cycloalkyl or 3- to 6-membered heterocycloalkyl, wherein the cycloalkyl, and heterocycloalkyl is optionally substituted with 1-4 groups independently selected from oxo and $R^{14}$; and
each occurrence of $R^{14}$ is independently cyano, amino, hydroxy, —C(=O)O$R^{12}$, —C(=O)N($R^{12}$)$_2$, $C_1$-$C_6$ alkyl, —O($C_1$-$C_6$ alkyl), —N$R^{12}$($C_1$-$C_6$ alkyl), aryl, heteroaryl, $C_3$-$C_6$ cycloalkyl, or 3- to 6-membered heterocycloalkyl, wherein each alkyl is optionally substituted with 1-2 hydroxy groups.

Embodiment 39. The compound of Embodiment 38, or a pharmaceutically acceptable salt or solvate thereof, wherein:
each $R^{11}$ is independently selected from the group consisting of fluoro, hydroxy, amino, —S(=O)$_2$($R^{13}$), —N($R^{12}$)S(=O)$_2$($R^{13}$), —S(=O)($R^{13}$), —N($R^{12}$)S(=O)($R^{13}$), —C(=O)$R^{13}$, —N($R^{12}$)C(=O)$R^{13}$, $C_1$-$C_6$ alkyl, —O($C_1$-$C_6$ alkyl), —NH($C_1$-

C₆ alkyl), $C_1$-$C_6$ haloalkyl, $C_3$-$C_8$ cycloalkyl, 3- to 10-membered heterocycloalkyl, phenyl, and 5- to 6-membered heteroaryl, wherein the phenyl, and heteroaryl is optionally substituted with 1-4 groups independently selected from $R^{14}$, and the alkyl, haloalkyl, cycloalkyl, and heterocycloalkyl is optionally substituted with 1-4 groups independently selected from oxo and $R^{14}$.

Embodiment 40. The compound of any one of Embodiments 1 to 11, or a pharmaceutically acceptable salt or solvate thereof, wherein:

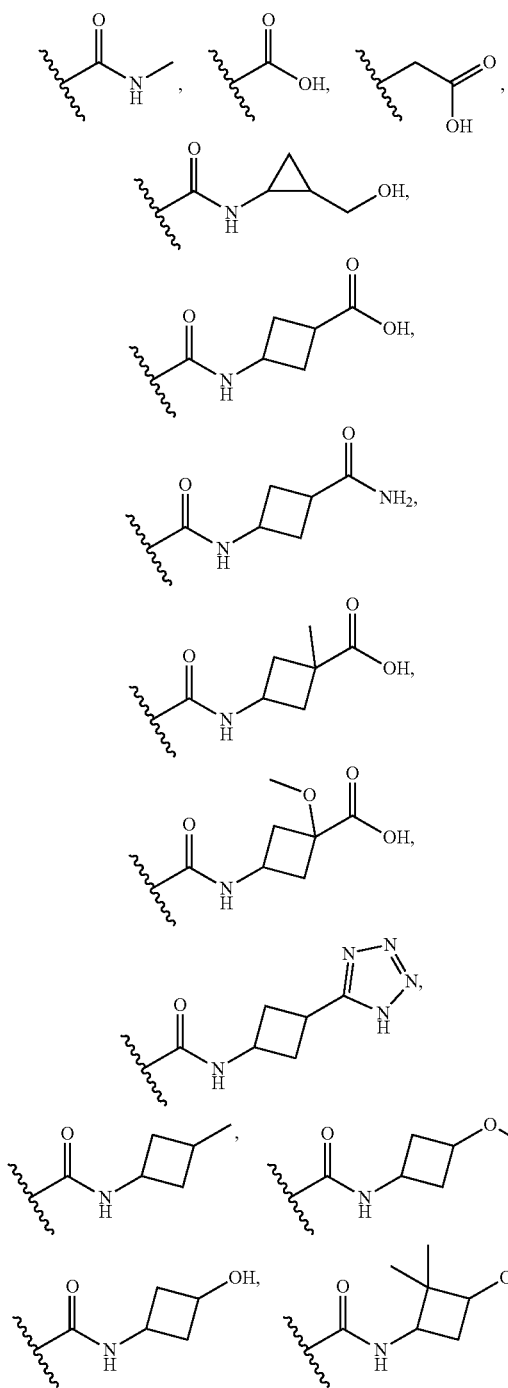
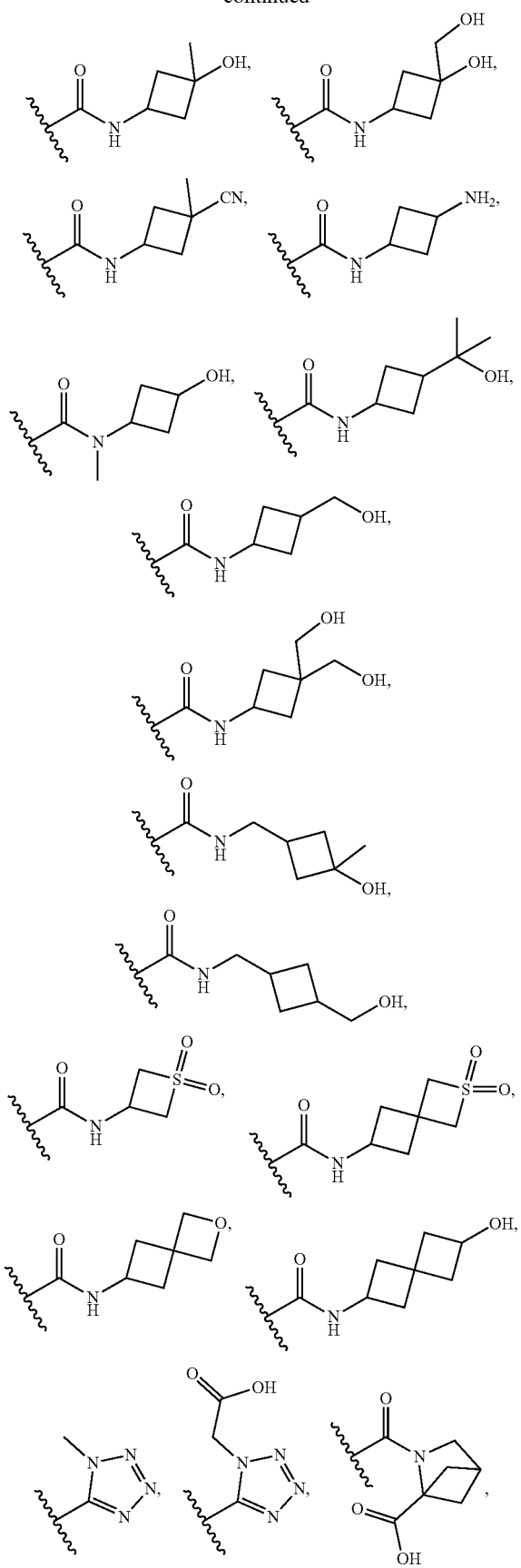

151
-continued
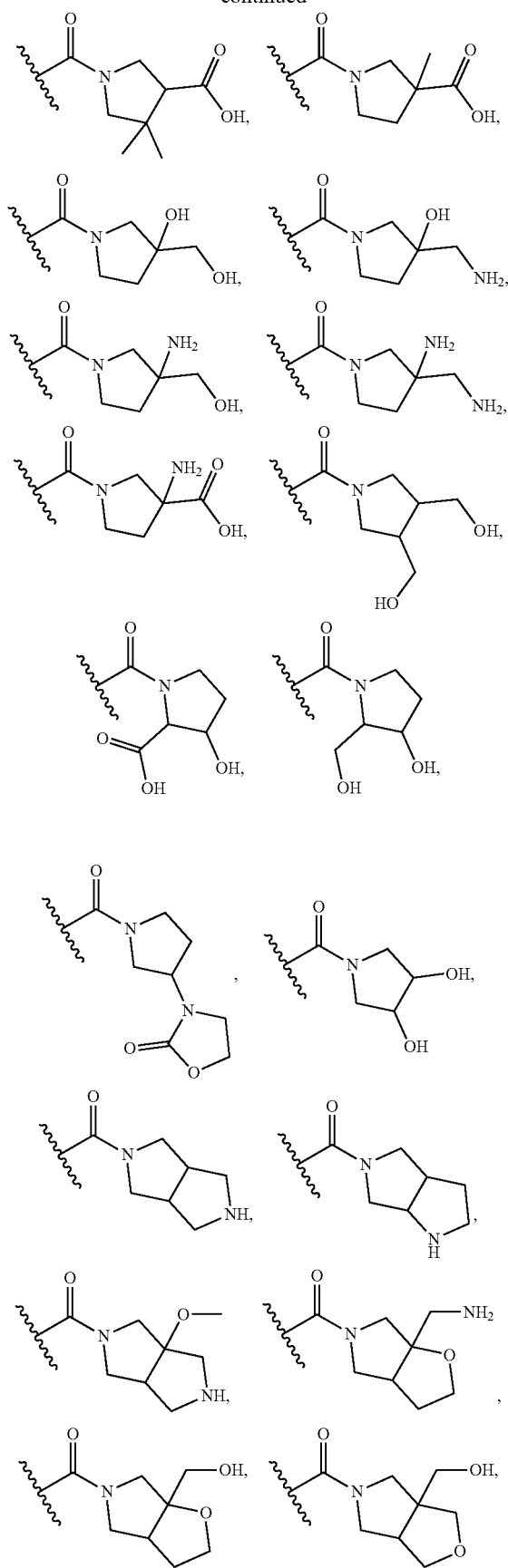
152
-continued
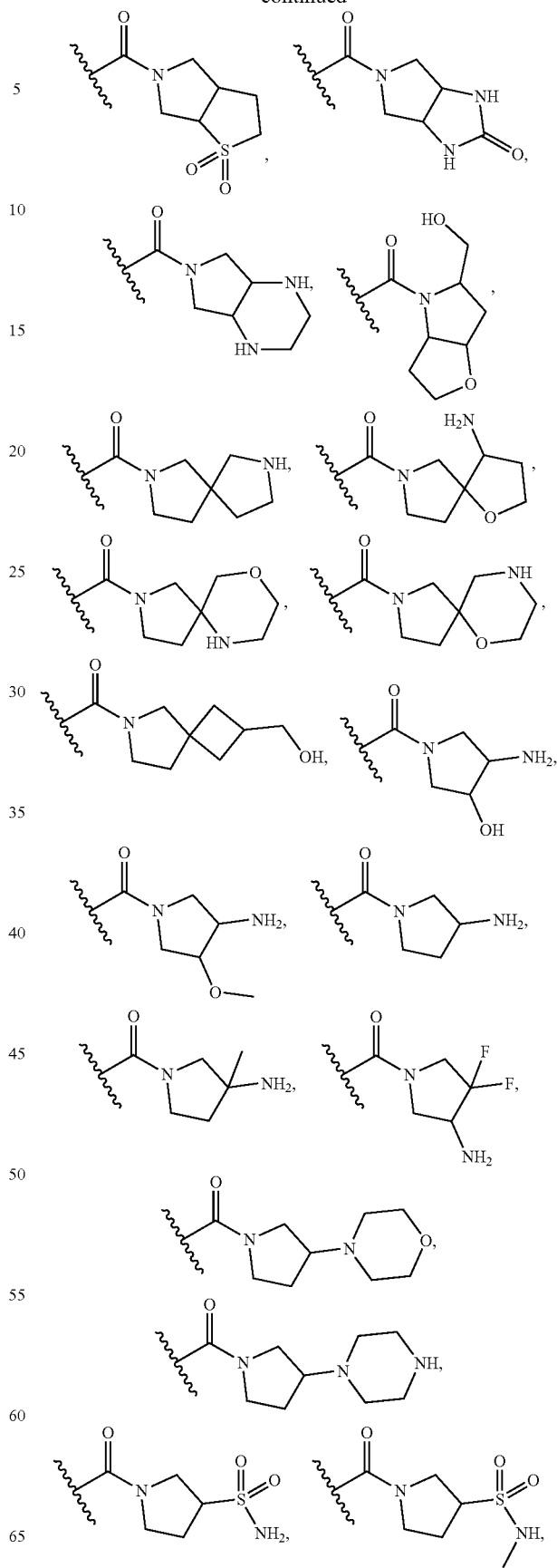

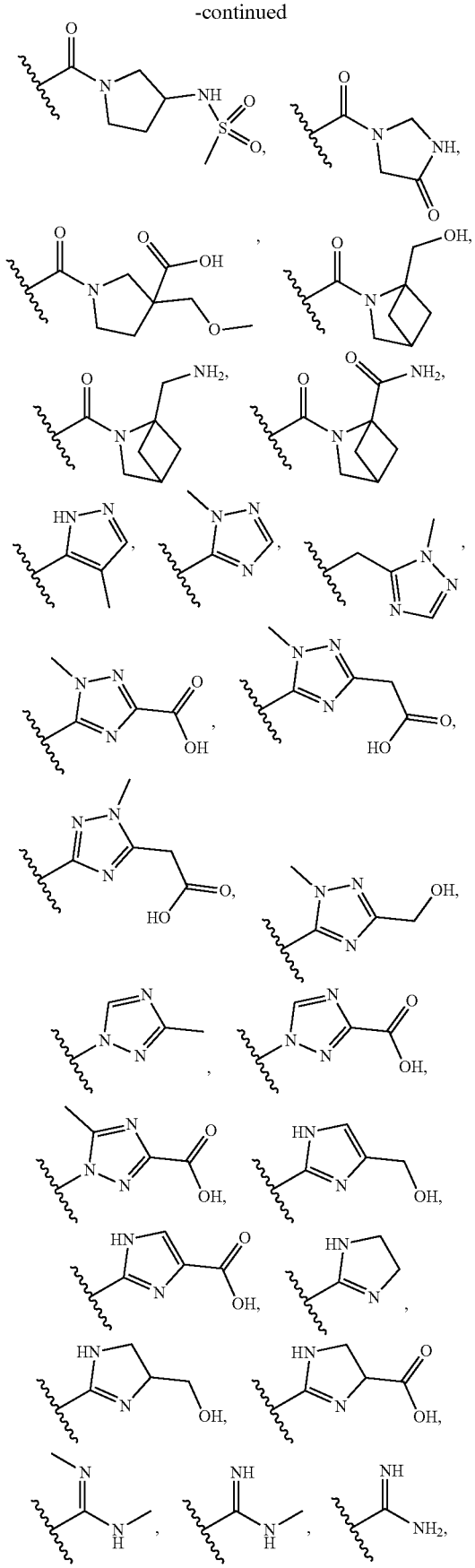
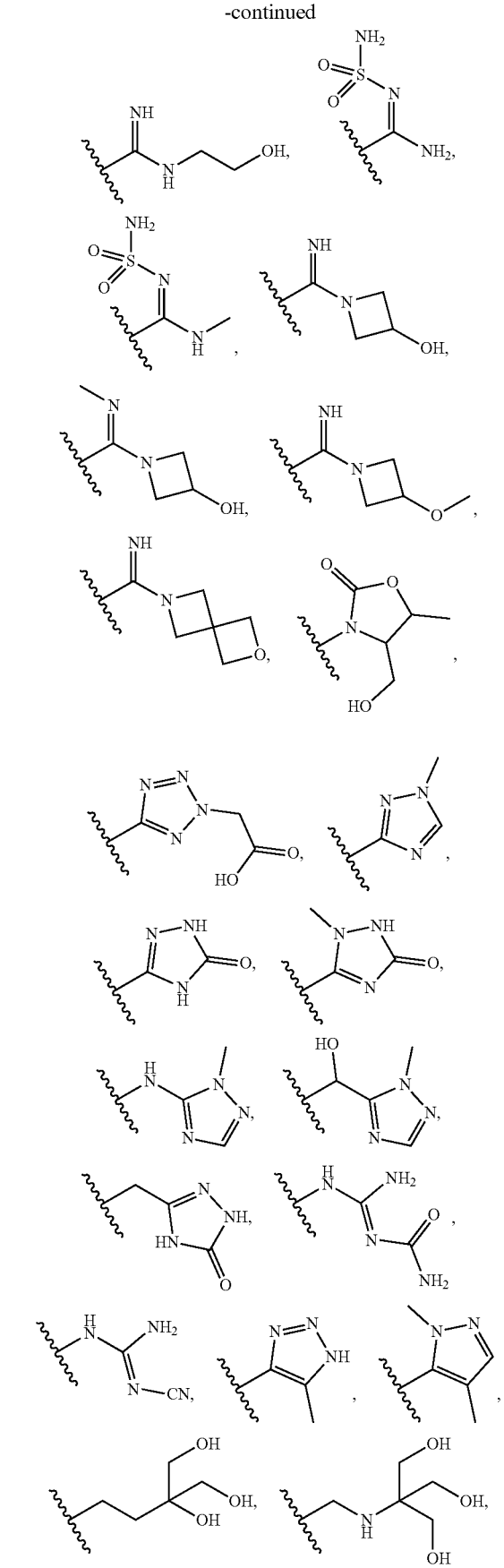

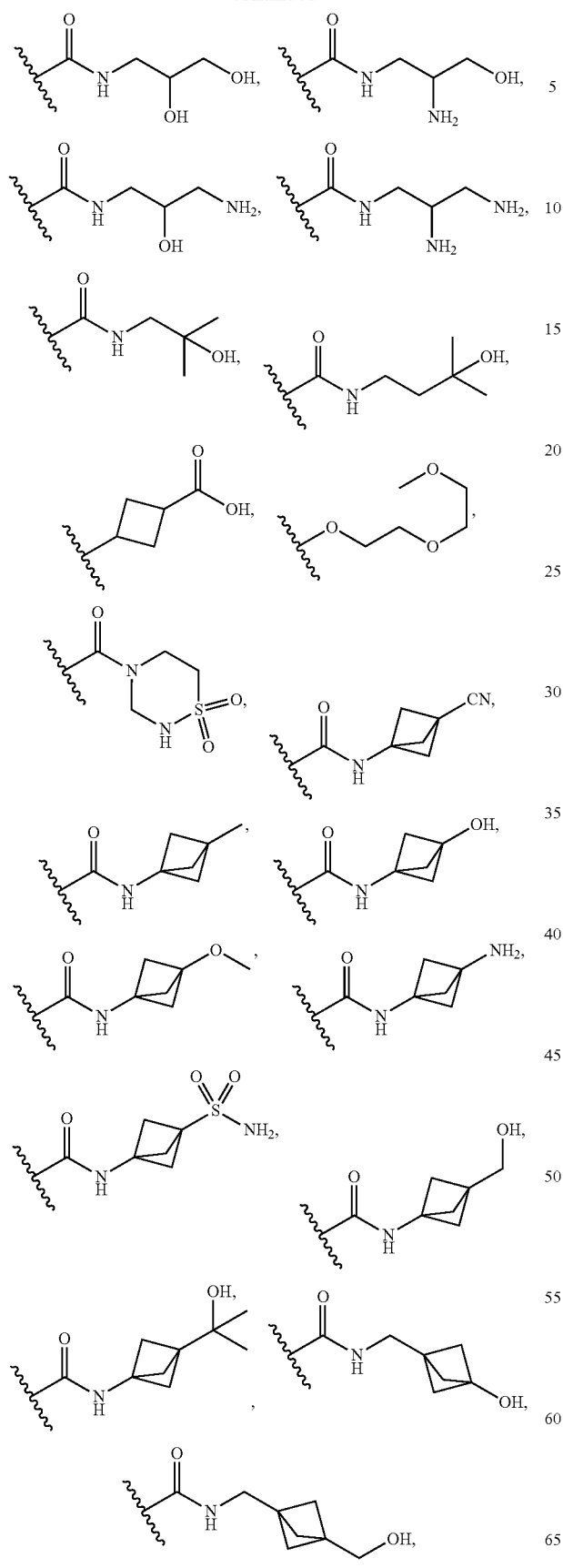
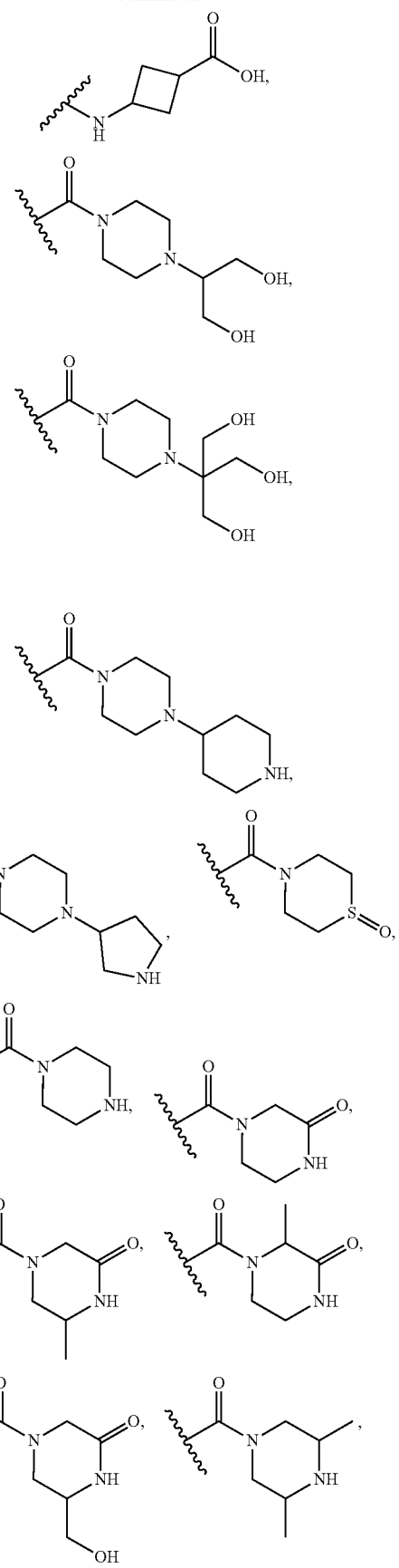

157
-continued
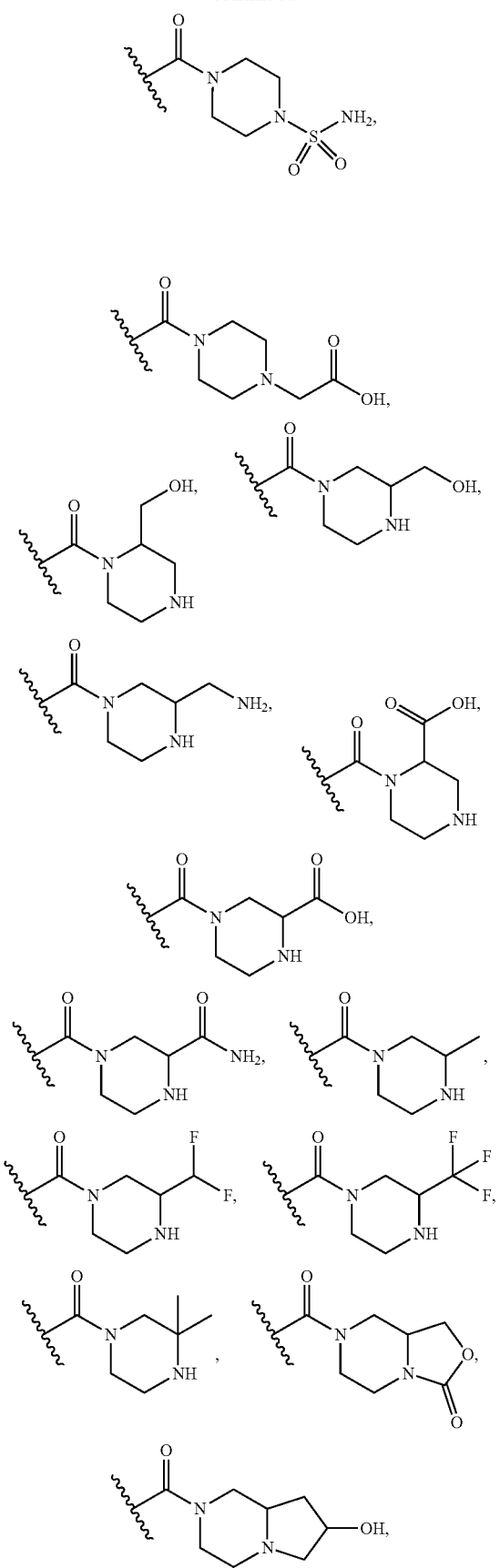
158
-continued
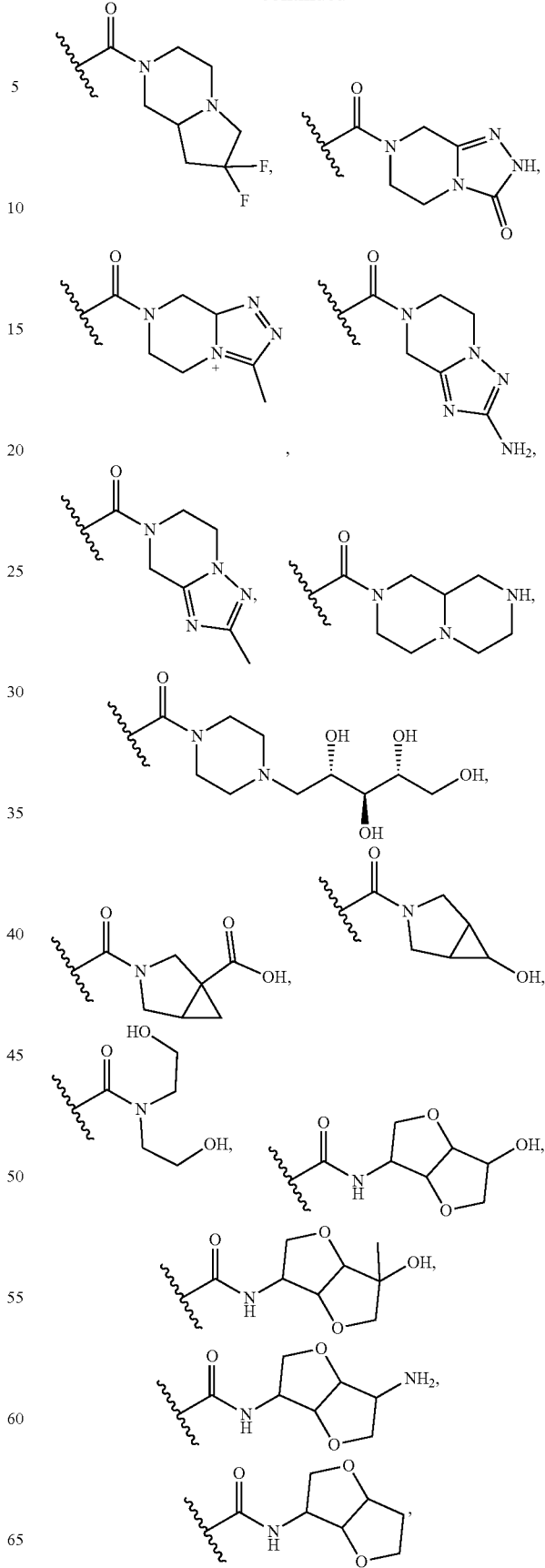

-continued
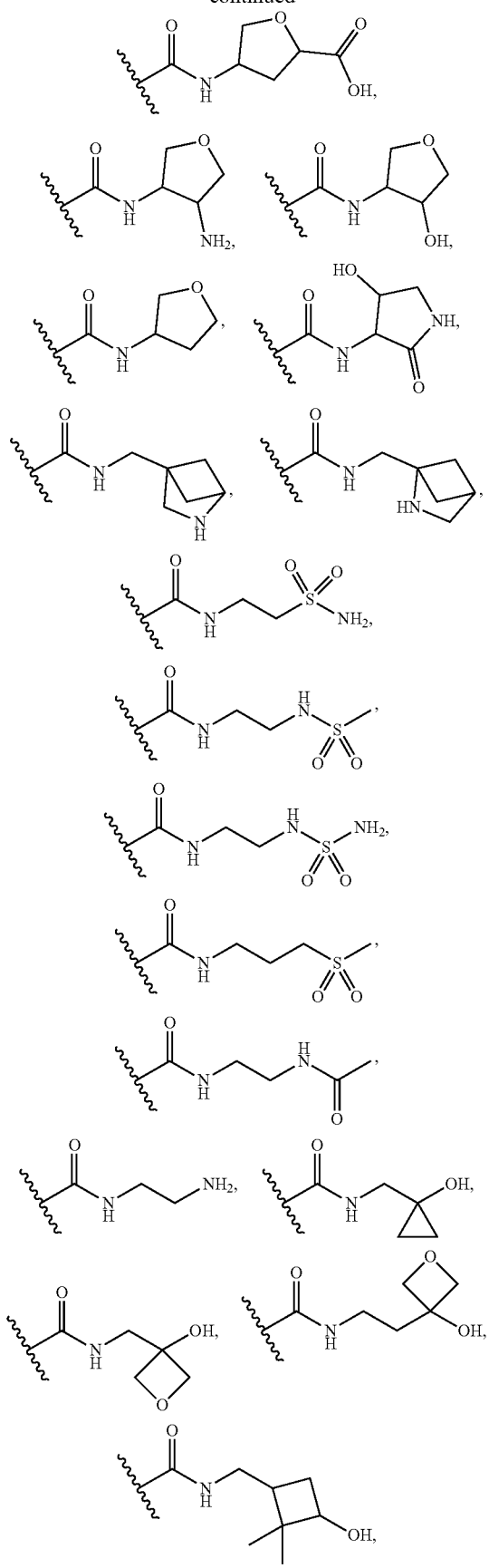
-continued
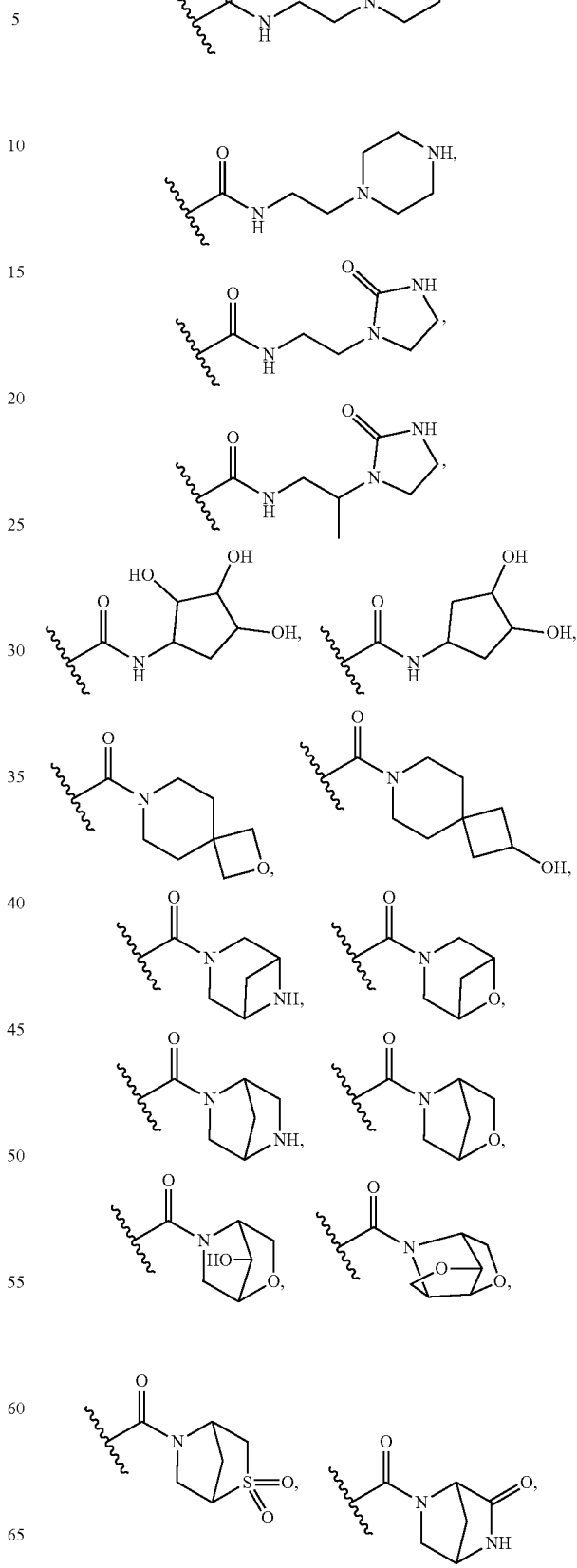

-continued
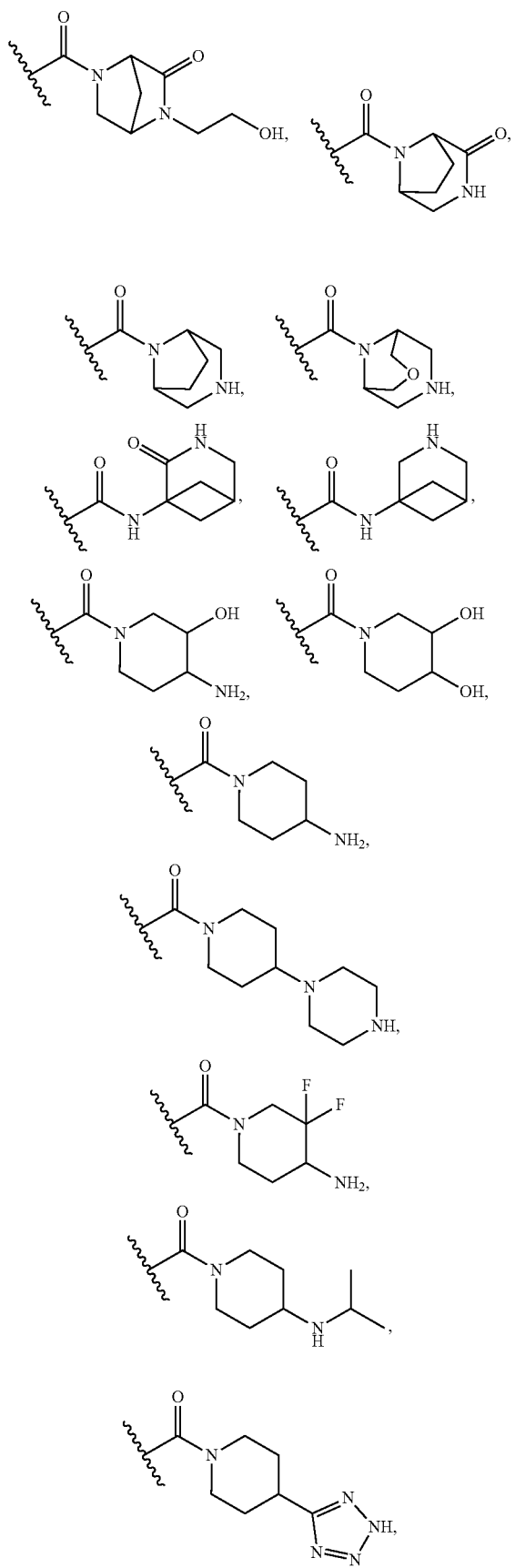
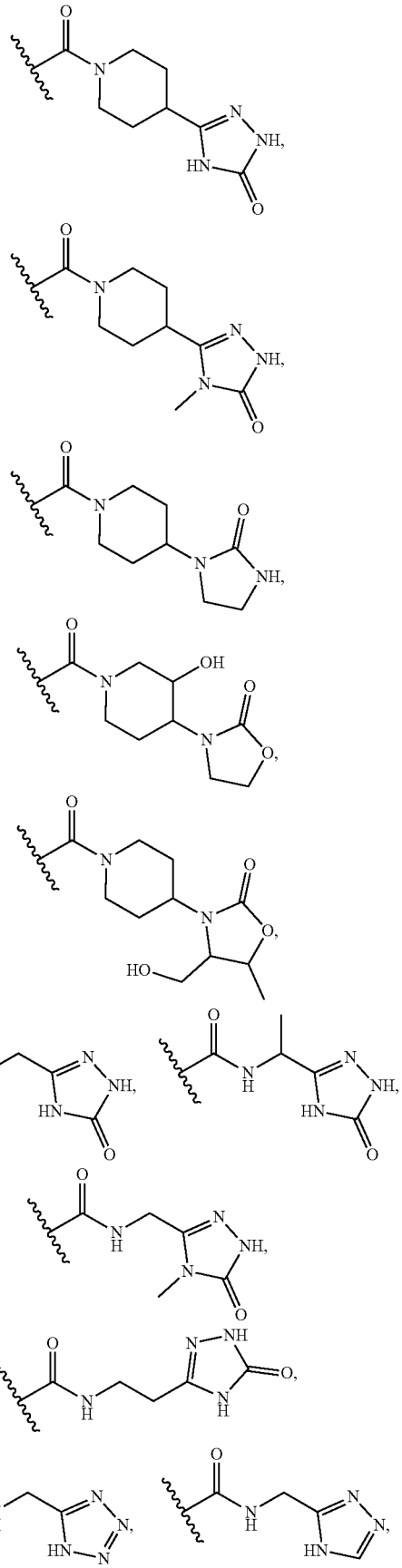

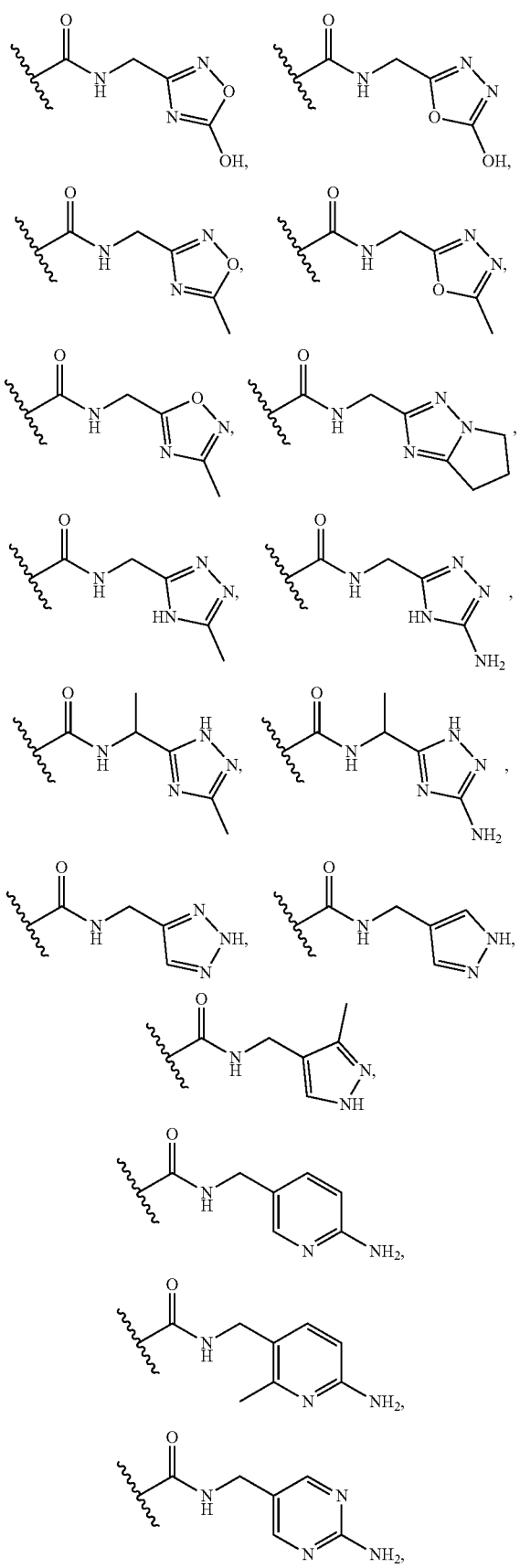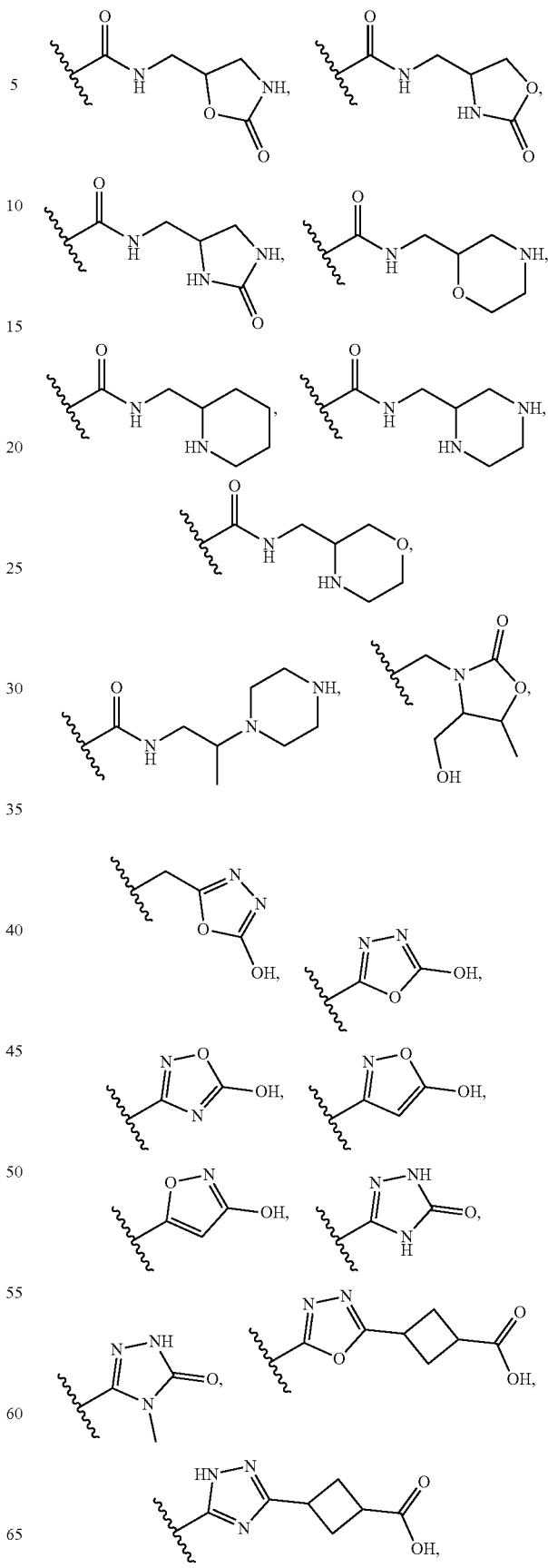

165
-continued
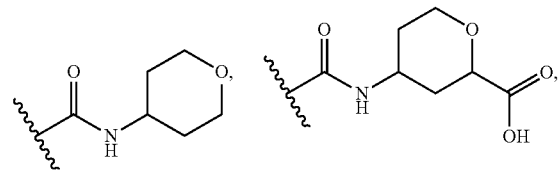
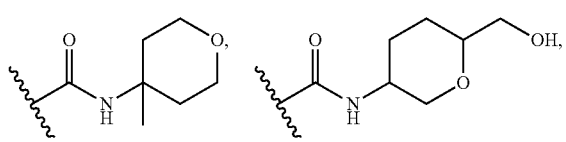
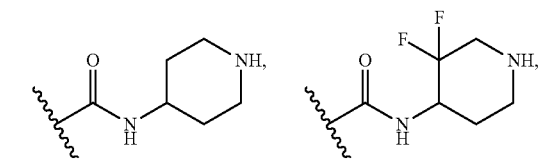
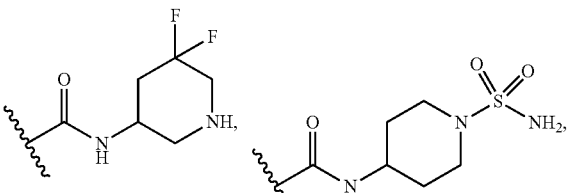
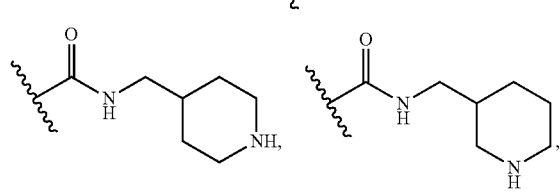
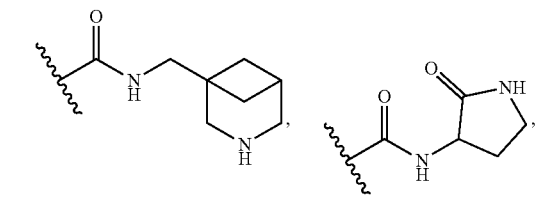
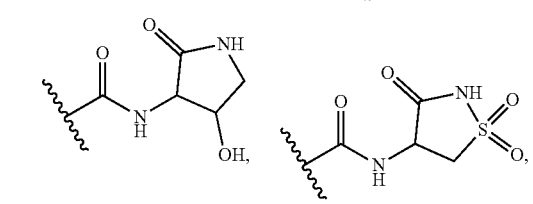
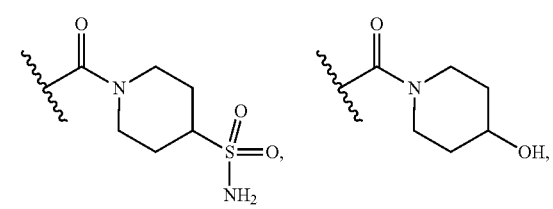
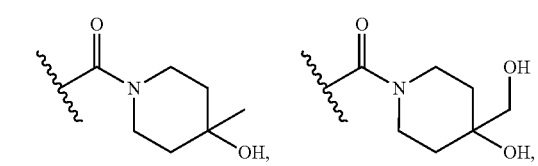
166
-continued
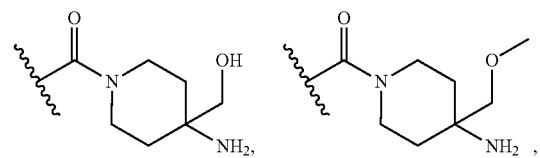
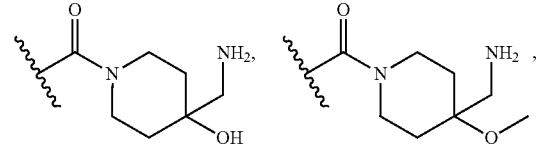
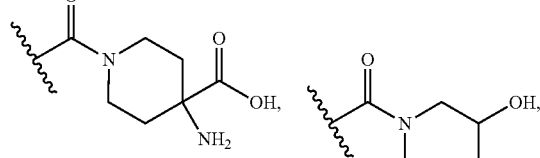
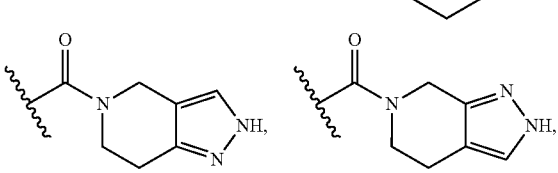
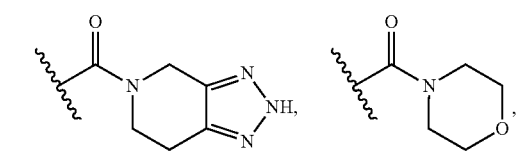
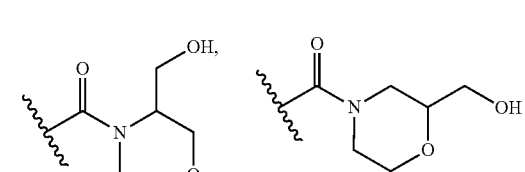
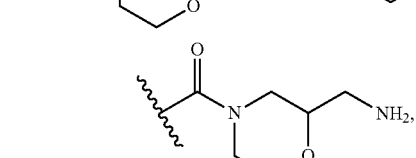
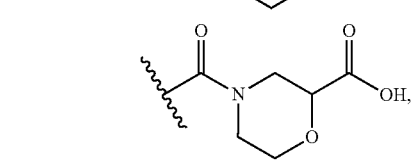
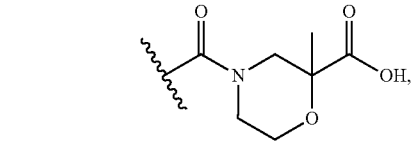
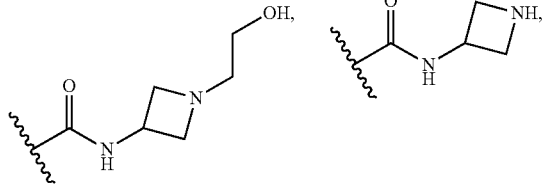

167
-continued
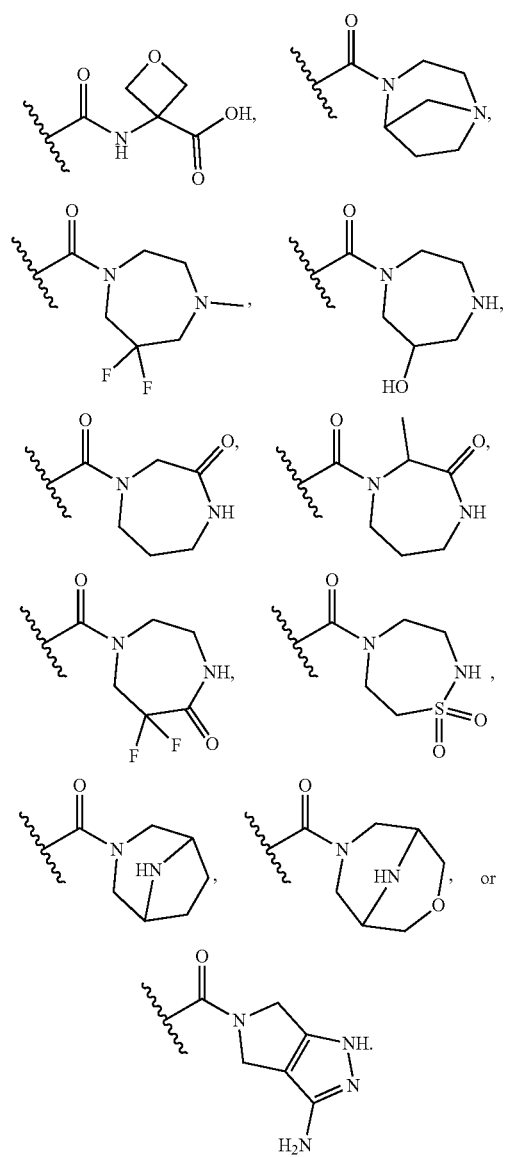
Embodiment 41. The compound of any one of Embodiments 1 to 11, or a pharmaceutically acceptable salt or solvate thereof, wherein:
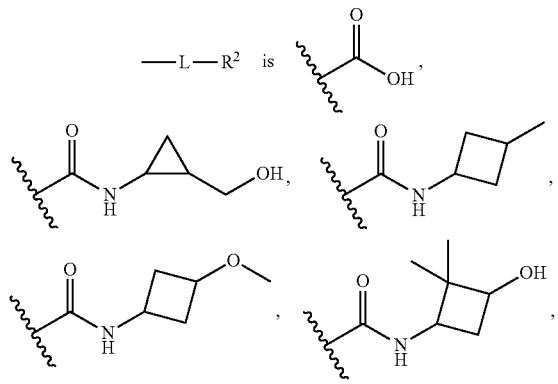
168
-continued
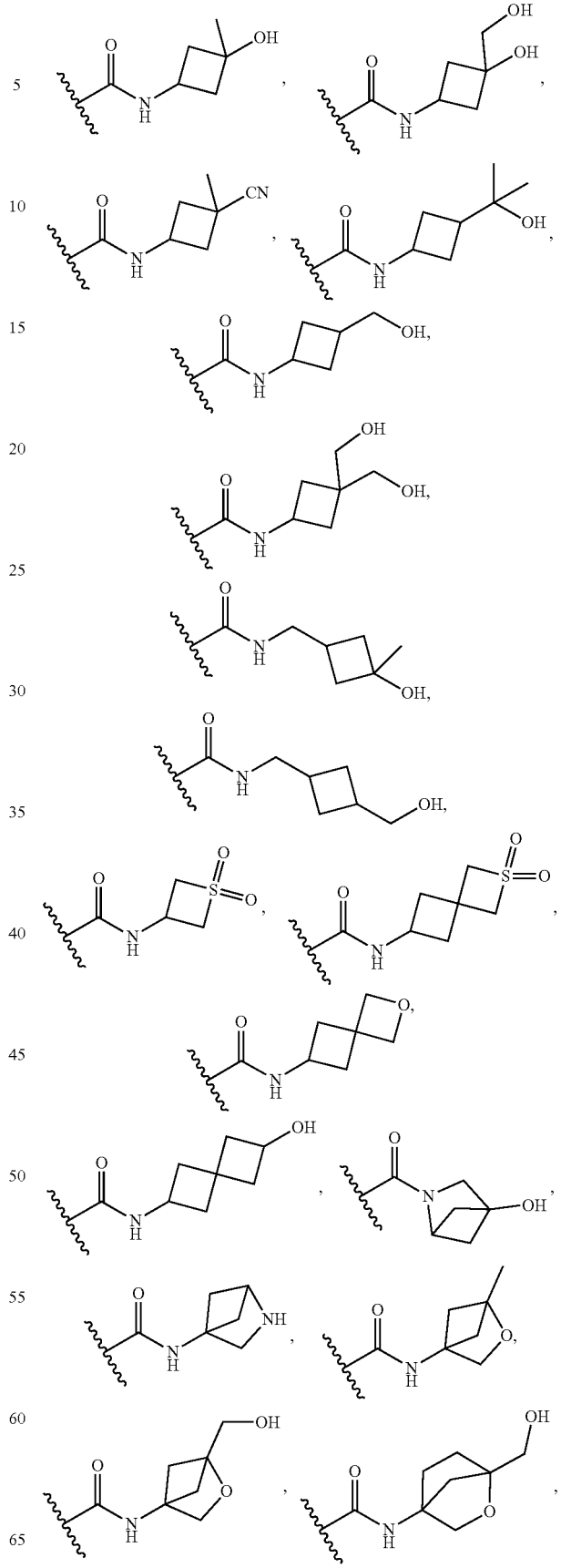

169
-continued
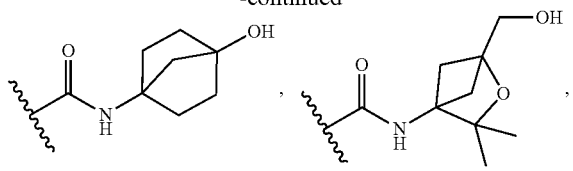
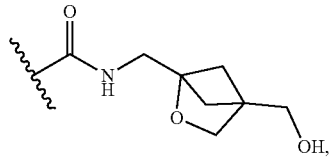
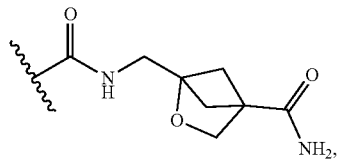
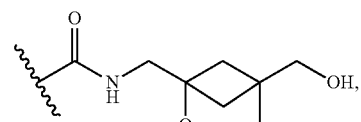
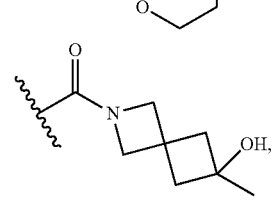
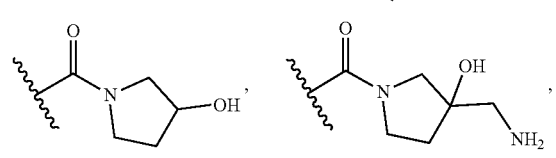
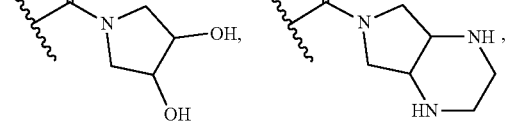
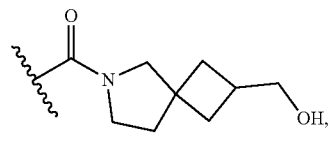
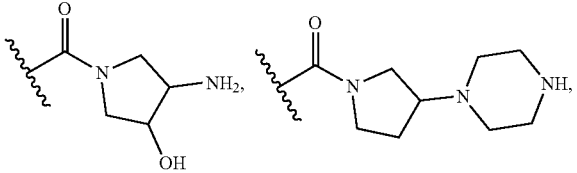
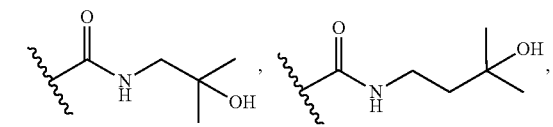
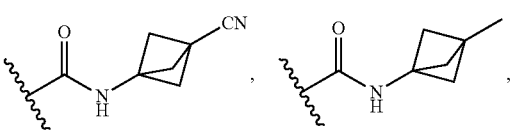
170
-continued
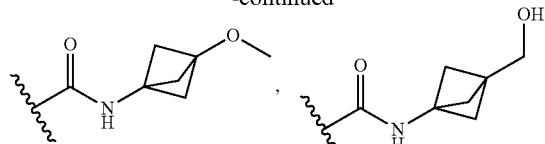
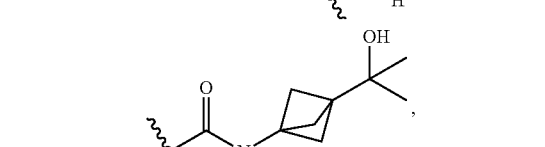
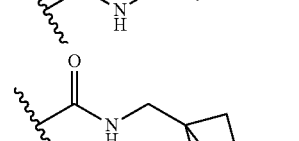
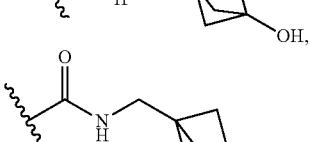
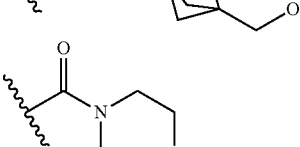
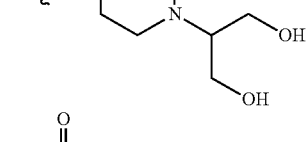
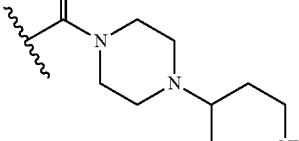
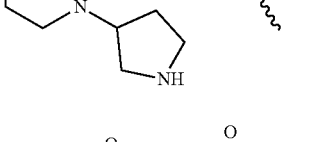
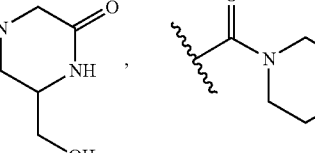
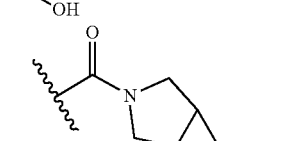
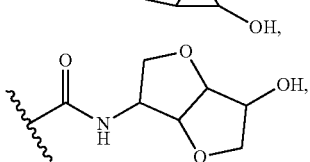

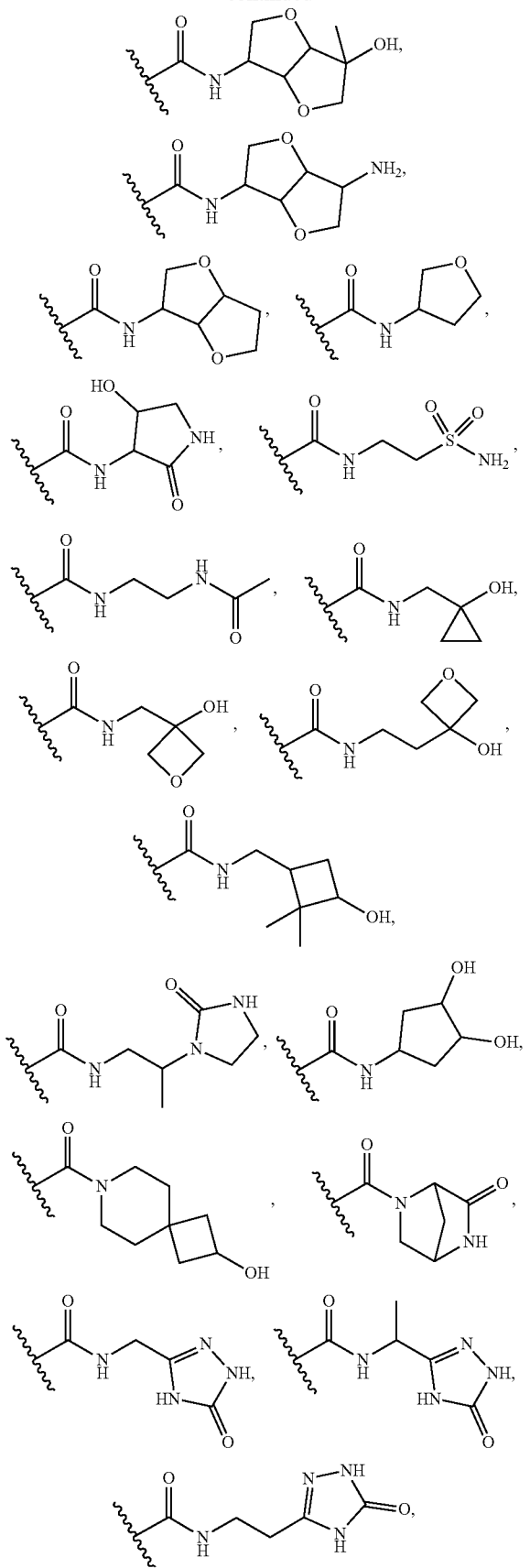
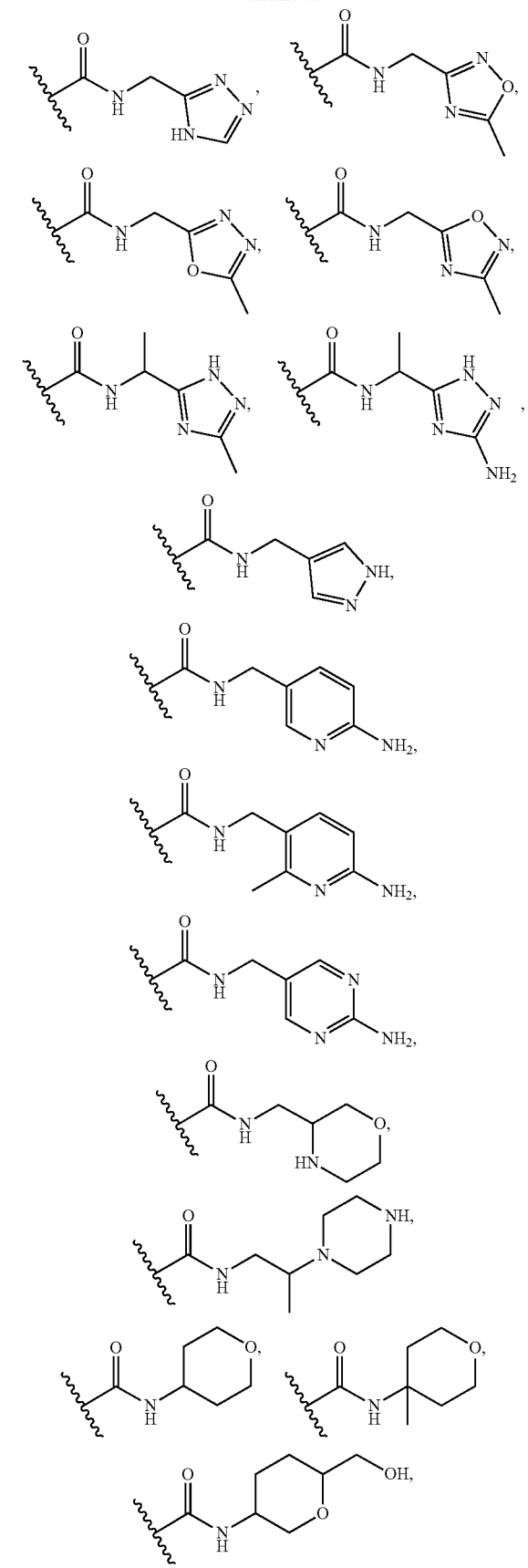

-continued

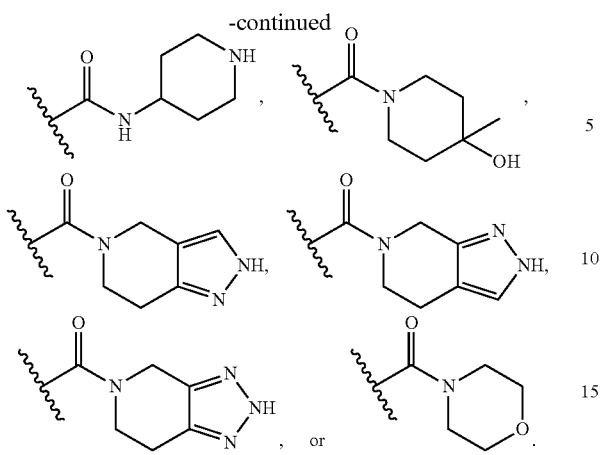

Embodiment 42. A compound described in Table 1, or a pharmaceutically acceptable salt or solvate thereof.

Embodiment 43. A pharmaceutical composition comprising a compound of any one of Embodiments 1 to 42, or a pharmaceutically acceptable salt or solvate thereof, and at least one pharmaceutically acceptable excipient.

Embodiment 44. A method for the treatment of a disease or disorder in a subject in need thereof, comprising administering to the subject a therapeutically effective amount of a compound of any one of Embodiments 1 to 42, or a pharmaceutically acceptable salt or solvate thereof, or the pharmaceutical composition of Embodiment 43.

Embodiment 45. The method of Embodiment 44, wherein the disease or disorder is a neurokinin receptor 3 (NK3)-dependent disease or disorder.

Embodiment 46. The method of Embodiment 44 or 45, wherein the disease or disorder is selected from the group consisting of migraine, medication overuse headache, cluster headache, general headache, trigeminal neuralgia, orofacial pain, and combinations thereof.

Embodiment 47. The method of any one of Embodiments 44 to 46, wherein the disease or disorder is selected from the group consisting of: migraine, medication overuse headache, cluster headache, general headache, and combinations thereof.

Embodiment 48. The method of any one of Embodiments 44 to 47, wherein the disease or disorder is migraine.

Embodiment 49. The method of any one of Embodiments 44 to 48, further comprising administration of a therapeutically effective amount of an additional therapeutic agent.

Embodiment 50. A compound of Formula (I):

Formula (I)

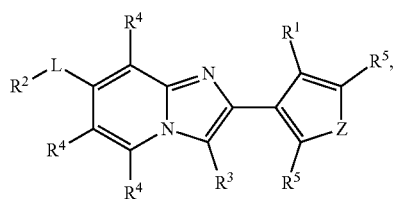

or a pharmaceutically acceptable salt or solvate thereof, wherein:

Z is a bivalent group selected from —S—, —N=C(R$^5$)—, —C(R$^5$)=N—, or —C(R$^5$)=C(R$^5$)—;

R$^1$ is pyrazole, wherein said pyrazole is optionally substituted with 1-3 groups independently selected from R$^6$;

R$^2$ is $C_1$-$C_{10}$ alkyl, $C_1$-$C_{10}$ heteroalkyl, —C(=O)OR$^7$, —C(=O)N(R$^8$)(R$^7$), —N(R$^8$)(R$^7$), —C(=NR$^9$)N(R$^8$)(R$^7$), —N(R$^7$)C(=NR$^9$)N(R$^8$)(R$^7$), $C_6$-$C_{10}$ aryl, 5- to 10-membered heteroaryl, $C_3$-$C_{12}$ cycloalkyl, or 3-to-15 membered heterocycloalkyl, wherein the aryl, and heteroaryl is optionally substituted with 1-4 groups independently selected from R$^{10}$, and the alkyl, heteroalkyl, cycloalkyl, and heterocycloalkyl is optionally substituted with 1-4 groups independently selected from oxo and R$^{10}$;

R$^3$ is halogen, cyano, —C(=O)OH, —C(=O)O($C_1$-$C_6$ alkyl), $C_1$-$C_6$ alkyl, $C_1$-$C_6$ alkenyl, —O($C_1$-$C_6$ alkyl), $C_3$-$C_6$ cycloalkyl, or $C_1$-$C_6$ haloalkyl;

each R$^4$ is independently hydrogen, halogen, $C_1$-$C_6$ alkyl, —O—$C_1$-$C_6$ alkyl, $C_1$-$C_6$ haloalkyl, or —O—($C_1$-$C_6$ haloalkyl);

L is a bond, $C_1$-$C_2$ alkylene, or $C_3$-$C_6$ cycloalkylene, wherein said alkylene, or cycloalkylene is optionally substituted with 1 or 2 —OH groups;

each R$^5$ is independently hydrogen, cyano, halogen, $C_1$-$C_6$ alkyl, —O($C_1$-$C_6$ alkyl), $C_3$-$C_6$ cycloalkyl, $C_1$-$C_6$ haloalkyl, or —O($C_1$-$C_6$ haloalkyl);

each R$^6$ is independently selected from the group consisting of halogen, hydroxy, cyano, amino, $C_1$-$C_6$ alkyl, $C_1$-$C_6$ hydroxyalkyl, $C_1$-$C_6$ aminoalkyl, —O($C_1$-$C_6$ alkyl), —NH($C_1$-$C_6$ alkyl), —N($C_1$-$C_6$ alkyl)$_2$, $C_3$-$C_6$ cycloalkyl, —CH$_2$—($C_{3-6}$ cycloalkyl), —O—($C_{3-6}$ cycloalkyl), $C_1$-$C_6$ haloalkyl, and —O($C_1$-$C_6$ haloalkyl);

wherein if an R$^6$ is attached to a nitrogen atom, then it is selected from the group consisting of $C_1$-$C_6$ alkyl, $C_1$-$C_6$ hydroxyalkyl, $C_1$-$C_6$ aminoalkyl, $C_3$-$C_6$ cycloalkyl, —CH$_2$—($C_{3-6}$ cycloalkyl), and $C_1$-$C_6$ haloalkyl;

each R$^7$ is independently hydrogen or $C_1$-$C_6$ alkyl, wherein said alkyl is optionally substituted with 1-2 hydroxy groups;

R$^8$ is hydrogen, $C_1$-$C_{10}$ alkyl, $C_1$-$C_{10}$ heteroalkyl, $C_1$-$C_{10}$ alkenyl, $C_1$-$C_{10}$ alkynyl, $C_3$-$C_{12}$ cycloalkyl, 3- to 15-membered heterocycloalkyl, $C_6$-$C_{10}$ aryl, or 5- to 10-membered heteroaryl; wherein the aryl, and heteroaryl is optionally substituted with 1-6 groups independently selected from R$^{11}$, and the alkyl, heteroalkyl, alkenyl, alkynyl, cycloalkyl and heterocycloalkyl is optionally substituted with 1-6 groups independently selected from oxo and R$^{11}$;

or one R$^7$ and one R$^8$ bound to the same nitrogen atom come together to form a 3- to 15-membered heterocycloalkyl that is optionally substituted with 1-6 groups independently selected from oxo and R$^{11}$;

R$^9$ is hydrogen, —C(O)OR$^{12}$, —C(O)N(R$^{12}$)$_2$, —S(O)$_2$R$^{12}$, —S(O)$_2$N(R$^{12}$)$_2$, or $C_1$-$C_6$ alkyl;

each R$^{10}$ is independently selected from hydroxy, amino, cyano, fluoro, —C(=O)OR$^{12}$, —C(=O)N(R$^{12}$)$_2$, $C_1$-$C_4$ alkyl, $C_1$-$C_4$ haloalkyl, —O($C_1$-$C_6$ alkyl), —NH($C_1$-$C_4$ alkyl), —N($C_1$-$C_4$ alkyl)$_2$, $C_3$-$C_6$ cycloalkyl, wherein said alkyl, haloalkyl or cycloalkyl is optionally substituted with 1-2 groups selected from hydroxy, amino, cyano, fluoro, —C(=O)OR$^{12}$, and —C(=O)N(R$^{12}$)$_2$;

each R$^{11}$ is independently selected from the group consisting of halogen, hydroxy, amino, cyano, —S(=O)$_2$(R$^{13}$), —N(R$^{12}$)S(=O)$_2$(R$^{13}$), —S(=O)(R$^{13}$), —N(R$^{12}$)S(=O)(R$^{13}$), —C(=O)R$^{13}$, —N(R$^{12}$)C(=O)R$^{13}$, C$_1$-C$_6$ alkyl, —O(C$_1$-C$_6$ alkyl), —NH(C$_1$-C$_6$ alkyl), —N(C$_1$-C$_6$ alkyl)$_2$, C$_1$-C$_6$ haloalkyl, C$_2$-C$_6$ alkenyl, C$_2$-C$_6$ alkynyl, C$_3$-C$_8$ cycloalkyl, 3- to 10-membered heterocycloalkyl, C$_6$-C$_{10}$ aryl, and 5- to 10-membered heteroaryl, wherein the aryl, and heteroaryl is optionally substituted with 1-4 groups independently selected from R$^{14}$, and the alkyl, alkenyl, alkynyl, haloalkyl, cycloalkyl, and heterocycloalkyl is optionally substituted with 1-4 groups independently selected from oxo and R$^{14}$;

or two R$^{11}$ bound to the same carbon or nitrogen atom come together to form a C$_3$-C$_6$ cycloalkyl or 3- to 6-membered heterocycloalkyl, wherein the cycloalkyl, and heterocycloalkyl is optionally substituted with 1-4 groups independently selected from oxo and R$^{14}$;

each R$^{12}$ is independently hydrogen or C$_1$-C$_6$ alkyl;

each R$^{13}$ is independently hydroxy, amino, C$_1$-C$_6$ alkyl, —O(C$_1$-C$_6$ alkyl), —NH(C$_1$-C$_6$ alkyl), —N(C$_1$-C$_6$ alkyl)$_2$, C$_1$-C$_6$ haloalkyl, C$_3$-C$_6$ cycloalkyl, or 3- to 6-membered heterocycloalkyl; and each R$^{14}$ is independently cyano, amino, hydroxy, —C(=O)OR$^{12}$, —C(=O)N(R$^{12}$)$_2$, C$_1$-C$_6$ alkyl, —O(C$_1$-C$_6$ alkyl), —NR$^{12}$(C$_1$-C$_6$ alkyl), aryl, heteroaryl, C$_3$-C$_6$ cycloalkyl, or 3- to 6-membered heterocycloalkyl, wherein each alkyl is optionally substituted with 1-2 hydroxy groups.

Embodiment 51. The compound of Embodiment 50, or a pharmaceutically acceptable salt or solvate thereof, wherein:
R$^3$ is halogen, cyano, C$_1$-C$_6$ alkyl, C$_3$-C$_6$ cycloalkyl, or C$_1$-C$_6$ haloalkyl.

Embodiment 52. The compound of Embodiment 50, or a pharmaceutically acceptable salt or solvate thereof, wherein:
R$^3$ is fluoro, chloro, cyano, methyl, ethyl, vinyl, —OMe, —C(=O)OH, trifluoromethyl, difluoromethyl, or cyclopropyl.

Embodiment 53. The compound of any one of Embodiments 50 to 52, or a pharmaceutically acceptable salt or solvate thereof, wherein:
R$^3$ is chloro, cyano, methyl, or ethyl.

Embodiment 54. The compound of any one of Embodiments 50 to 53, or a pharmaceutically acceptable salt or solvate thereof, wherein:
each R$^4$ is independently hydrogen, fluoro or methyl.

Embodiment 55. The compound of any one of Embodiments 50 to 53, or a pharmaceutically acceptable salt or solvate thereof, wherein:
each R$^4$ is hydrogen.

Embodiment 56. The compound of any one of Embodiments 50 to 55, or a pharmaceutically acceptable salt or solvate thereof, wherein:
Z is —C(R$^5$)=C(R$^5$)— or —S—.

Embodiment 57. The compound of Embodiment 56, having the structure of Formula (IIa):

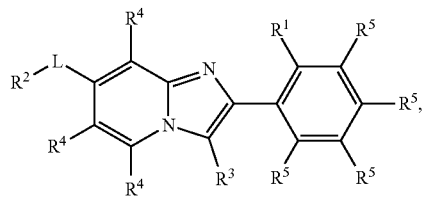

Formula (IIa)

or a pharmaceutically acceptable salt or solvate thereof.

Embodiment 58. The compound of Embodiment 56, having the structure of Formula (IIb):

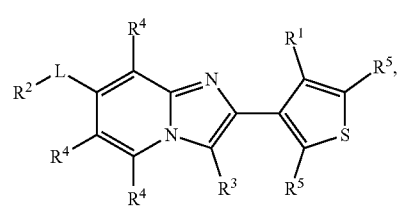

Formula (IIb)

or a pharmaceutically acceptable salt or solvate thereof.

Embodiment 59. The compound of any one of Embodiments 50-55, or a pharmaceutically acceptable salt or solvate thereof, wherein:
Z is —N=C(R$^5$)— or —C(R$^5$)=N—.

Embodiment 60. The compound of Embodiment 59, having the structure of Formula (IIc):

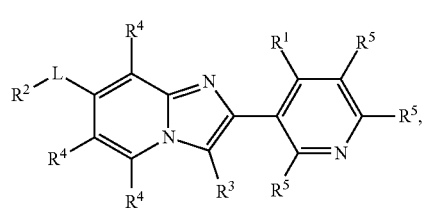

Formula (IIc)

or a pharmaceutically acceptable salt or solvate thereof.

Embodiment 61. The compound of Embodiment 59, having the structure of Formula (IId):

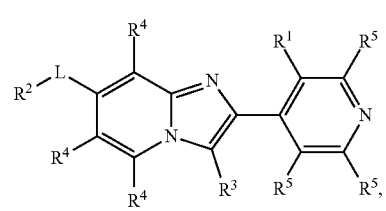

Formula (IId)

or a pharmaceutically acceptable salt or solvate thereof.

Embodiment 62. The compound of any one of Embodiments 50 to 61, or a pharmaceutically acceptable salt or solvate thereof, wherein:
L is a bond or C$_1$ alkylene.

Embodiment 63. The compound of any one of Embodiments 50 to 62, or a pharmaceutically acceptable salt or solvate thereof, wherein:
R$^2$ is —C(O)(OR$^7$) or —C(O)N(R$^8$)(R$^7$).

Embodiment 64. The compound of any one of Embodiments 50 to 62, or a pharmaceutically acceptable salt or solvate thereof, wherein:

R² is 5- to 10-membered heteroaryl or 3-to-15 membered heterocycloalkyl.

Embodiment 65. The compound of any one of Embodiments 50 to 62, or a pharmaceutically acceptable salt or solvate thereof, wherein:

R² is 5- to 6-membered heteroaryl or 3-to-8 membered heterocycloalkyl.

Embodiment 66. The compound of Embodiments 50 to 56, having a structure of Formula (III):

Formula (III)

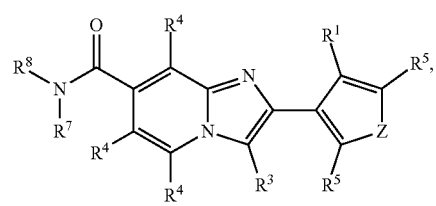

or a pharmaceutically acceptable salt or solvate thereof.

Embodiment 67. The compound of Embodiment 66 having the structure of Formula (IVa):

Formula (IVa)

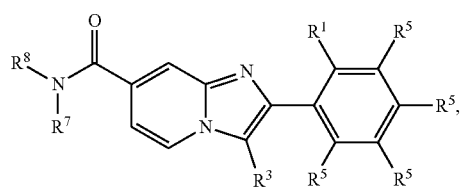

or a pharmaceutically acceptable salt or solvate thereof.

Embodiment 68. The compound of any one of Embodiments 50 to 67, or a pharmaceutically acceptable salt or solvate thereof, wherein:

R¹ is optionally substituted with 1-3 R⁶ groups independently selected from the group consisting of methyl, ethyl, cyano, fluoro, chloro, —OMe, cyclopropyl, —CH₂-cyclopropyl, trifluoromethyl, and difluoromethyl; wherein when an R⁶ is attached to a nitrogen atom, it is selected from the group consisting of methyl, ethyl, cyclopropyl, —CH₂-cyclopropyl, trifluoromethyl, trifluoroethyl, and difluoromethyl.

Embodiment 69. The compound of any one of Embodiments 50 to 68, or a pharmaceutically acceptable salt or solvate thereof, wherein:

R¹ is 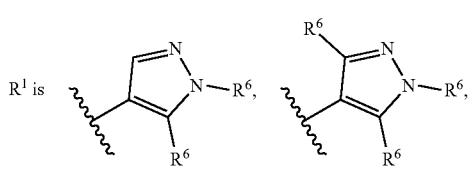

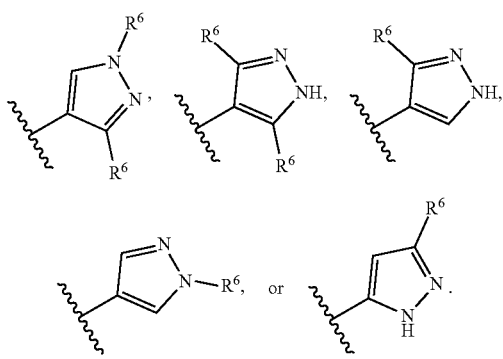

Embodiment 70. The compound of any one of Embodiments 50 to 69, or a pharmaceutically acceptable salt or solvate thereof, wherein:

R¹ is optionally substituted with 1-2 R⁶ groups independently selected from the group consisting of methyl, cyano, fluoro, chloro, —OMe, cyclopropyl, —CH₂-cyclopropyl, and difluoromethyl; wherein when an R⁶ is attached to a nitrogen atom, it is methyl, cyclopropyl, or —CH₂-cyclopropyl.

Embodiment 71. The compound of Embodiment 69, or a pharmaceutically acceptable salt or solvate thereof, wherein:

R¹ is

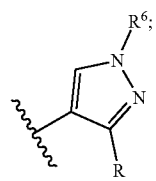

and each R⁶ is independently fluoro, chloro, cyano, cyclopropyl, —CH₂-cyclopropyl, or methyl; wherein when an R⁶ is attached to a nitrogen atom, it is methyl, cyclopropyl, or —CH₂-cyclopropyl.

Embodiment 72. The compound of Embodiment 69, or a pharmaceutically acceptable salt or solvate thereof, wherein:

R¹ is

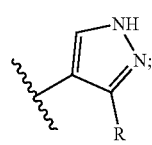

and

R⁶ is independently fluoro, chloro, cyano, cyclopropyl, —CH₂-cyclopropyl, or methyl.

Embodiment 73. The compound of Embodiment 69, or a pharmaceutically acceptable salt or solvate thereof, wherein:

$R^1$ is

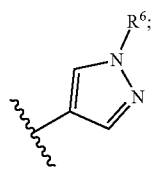

and $R^6$ is methyl, cyclopropyl, or —CH$_2$-cyclopropyl.

Embodiment 74. The compound of any one of Embodiments 50 to 53 having a structure of Formula (VIa):

Formula (VIa)

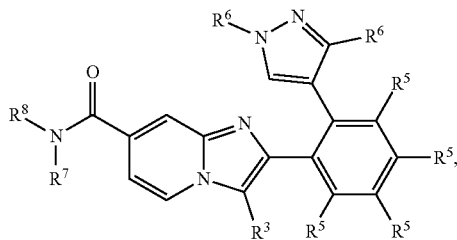

or a pharmaceutically acceptable salt or solvate thereof.

Embodiment 75. The compound of any one of Embodiments 50 to 53 having a structure of Formula (VIIa):

Formula (VIIa)

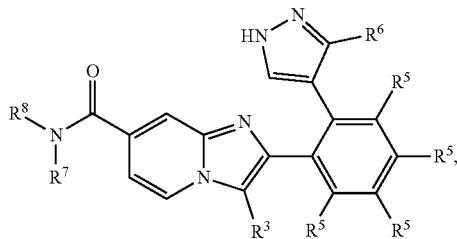

or a pharmaceutically acceptable salt or solvate thereof.

Embodiment 76. The compound of Embodiment 74 or 75, or a pharmaceutically acceptable salt or solvate thereof, wherein:
  each $R^6$ is independently halogen, cyano, $C_{1-6}$ alkyl, $C_{1-6}$ fluoroalkyl, $C_{3-6}$ cycloalkyl, or —CH$_2$—($C_{3-6}$ cycloalkyl); wherein when an $R^6$ is attached to a nitrogen atom, it is $C_{1-6}$ alkyl, $C_{1-6}$ fluoroalkyl, $C_{3-6}$ cycloalkyl, or —CH$_2$—($C_{3-6}$ cycloalkyl).

Embodiment 77. The compound of Embodiment 74 or 75, or a pharmaceutically acceptable salt or solvate thereof, wherein:
  each $R^6$ is independently fluoro, chloro, cyano, cyclopropyl, —CH$_2$-cyclopropyl, or methyl; wherein when an $R^6$ is attached to a nitrogen atom, it is methyl, cyclopropyl, or —CH$_2$-cyclopropyl.

Embodiment 78. The compound of any one of Embodiments 50 to 77, or a pharmaceutically acceptable salt or solvate thereof, wherein:
  each $R^5$ is independently hydrogen or fluoro.

Embodiment 79. The compound of Embodiment 78, or a pharmaceutically acceptable salt or solvate thereof, wherein:
  each $R^5$ is hydrogen.

Embodiment 80. The compound of any one of Embodiments 50 to 63 or 66 to 79, or a pharmaceutically acceptable salt or solvate thereof, wherein:
  each $R^7$ is independently hydrogen or $C_1$-$C_6$ alkyl.

Embodiment 81. The compound of any one of Embodiments 50 to 63 or 66 to 80, or a pharmaceutically acceptable salt or solvate thereof, wherein:
  $R^8$ is $C_1$-$C_{10}$ alkyl, $C_1$-$C_{10}$ heteroalkyl, $C_3$-$C_{12}$ cycloalkyl, or 3- to 15-membered heterocycloalkyl; wherein the alkyl, heteroalkyl, cycloalkyl or heterocycloalkyl is optionally substituted with 1-6 groups independently selected from oxo and $R^{11}$.

Embodiment 82. The compound of Embodiment 81, or a pharmaceutically acceptable salt or solvate thereof, wherein:
  $R^8$ is $C_1$-$C_{10}$ alkyl, $C_3$-$C_{12}$ cycloalkyl, or 3- to 15-membered heterocycloalkyl; wherein the alkyl, cycloalkyl or heterocycloalkyl is optionally substituted with 1-6 groups independently selected from oxo and $R^{11}$.

Embodiment 83. The compound of Embodiment 81 or 82, or a pharmaceutically acceptable salt or solvate thereof, wherein:
  $R^8$ is $C_3$-$C_{10}$ cycloalkyl, or 3- to 12-membered heterocycloalkyl; wherein the cycloalkyl or heterocycloalkyl is optionally substituted with 1-6 groups independently selected from oxo and $R^{11}$.

Embodiment 84. The compound of any one of Embodiments 81 to 83, or a pharmaceutically acceptable salt or solvate thereof, wherein:
  $R^8$ is monocyclic $C_3$-$C_{10}$ cycloalkyl, fused bicyclic $C_5$-$C_{10}$ cycloalkyl, bridged bicyclic $C_5$-$C_{10}$ cycloalkyl, spirocyclic bicyclic $C_5$-$C_{10}$ cycloalkyl, monocyclic 3- to 12-membered heterocycloalkyl, fused bicyclic 5- to 12-membered heterocycloalkyl, bridged bicyclic 5- to 12-membered heterocycloalkyl, or spirocyclic bicyclic 5- to 12-membered heterocycloalkyl; wherein the cycloalkyl or heterocycloalkyl is optionally substituted with 1-6 groups independently selected from oxo and $R^{11}$.

Embodiment 85. The compound of any one of Embodiments 81 to 84, or a pharmaceutically acceptable salt or solvate thereof, wherein:
  $R^8$ is fused bicyclic $C_5$-$C_{10}$ cycloalkyl, bridged bicyclic $C_5$-$C_{10}$ cycloalkyl, spirocyclic bicyclic $C_5$-$C_{10}$ cycloalkyl, fused bicyclic 5- to 12-membered heterocycloalkyl, bridged bicyclic 5- to 12-membered heterocycloalkyl, or spirocyclic bicyclic 5- to 12-membered heterocycloalkyl; wherein the cycloalkyl or heterocycloalkyl is optionally substituted with 1-6 groups independently selected from oxo and $R^{11}$.

Embodiment 86. The compound of any one of Embodiments 81 to 85, or a pharmaceutically acceptable salt or solvate thereof, wherein:
  $R^8$ is spirocyclic bicyclic $C_5$-$C_{10}$ cycloalkyl, or spirocyclic bicyclic 5- to 12-membered heterocycloalkyl; wherein the cycloalkyl or heterocycloalkyl is optionally substituted with 1-6 groups independently selected from oxo and $R^{11}$.

Embodiment 87. The compound of any one of Embodiments 50 to 62 or 66 to 79, or a pharmaceutically acceptable salt or solvate thereof, wherein:
  one $R^7$ and one $R^8$ bound to the same nitrogen atom come together to form a 3- to 15-membered heterocycloalkyl that is optionally substituted with 1-6 groups independently selected from oxo and $R^{11}$.

Embodiment 88. The compound of Embodiment 87, or a pharmaceutically acceptable salt or solvate thereof, wherein:
one $R^7$ and one $R^8$ bound to the same nitrogen atom come together to form a fused bicyclic 5- to 12-membered heterocycloalkyl, bridged bicyclic 5- to 12-membered heterocycloalkyl, or spirocyclic bicyclic 5- to 12-membered heterocycloalkyl; wherein the heterocycloalkyl is optionally substituted with 1-6 groups independently selected from oxo and $R^{11}$.

Embodiment 89. The compound of Embodiment 87 or 88, or a pharmaceutically acceptable salt or solvate thereof, wherein:
one $R^7$ and one $R^8$ bound to the same nitrogen atom come together to form a bridged bicyclic 5- to 12-membered heterocycloalkyl, or spirocyclic bicyclic 5- to 12-membered heterocycloalkyl; wherein the heterocycloalkyl is optionally substituted with 1-6 groups independently selected from oxo and $R^{11}$.

Embodiment 90. The compound of any one of Embodiments 87 to 89, or a pharmaceutically acceptable salt or solvate thereof, wherein:
one $R^7$ and one $R^8$ bound to the same nitrogen atom come together to form a spirocyclic bicyclic 5- to 12-membered heterocycloalkyl; wherein the heterocycloalkyl is optionally substituted with 1-6 groups independently selected from oxo and $R^{11}$.

Embodiment 91. The compound of any one of Embodiments 50 to 62 or 66 to 90, or a pharmaceutically acceptable salt or solvate thereof, wherein:
each $R^{11}$ is independently selected from the group consisting of halogen, hydroxy, amino, cyano, —S(=O)$_2$(R$^{13}$), —N(R$^{12}$)S(=O)$_2$(R$^{13}$), —S(=O)(R$^{13}$), —N(R$^{12}$)S(=O)(R$^{13}$), —C(=O)R$^{13}$, —N(R$^{12}$)C(=O)R$^{13}$, $C_1$-$C_6$ alkyl, —O($C_1$-$C_6$ alkyl), —NH($C_1$-$C_6$ alkyl), —N($C_1$-$C_6$ alkyl)$_2$, $C_1$-$C_6$ haloalkyl, $C_3$-$C_8$ cycloalkyl, 3- to 10-membered heterocycloalkyl, $C_6$ aryl, and 5- to 6-membered heteroaryl, wherein the aryl, and heteroaryl is optionally substituted with 1-4 groups independently selected from $R^{14}$, and the alkyl, haloalkyl, cycloalkyl, and heterocycloalkyl is optionally substituted with 1-4 groups independently selected from oxo and $R^{14}$;
or two $R^{11}$ bound to the same carbon or nitrogen atom come together to form a $C_3$-$C_6$ cycloalkyl or 3- to 6-membered heterocycloalkyl, wherein the cycloalkyl, and heterocycloalkyl is optionally substituted with 1-4 groups independently selected from oxo and $R^{14}$; and
each occurrence of $R^{14}$ is independently cyano, amino, hydroxy, —C(=O)OR$^{12}$, —C(=O)N(R$^{12}$)$_2$, $C_1$-$C_6$ alkyl, —O($C_1$-$C_6$ alkyl), —NR$^{12}$($C_1$-$C_6$ alkyl), aryl, heteroaryl, $C_3$-$C_6$ cycloalkyl, or 3- to 6-membered heterocycloalkyl, wherein each alkyl is optionally substituted with 1-2 hydroxy groups.

Embodiment 92. The compound of Embodiment 91, or a pharmaceutically acceptable salt or solvate thereof, wherein:
each $R^{11}$ is independently selected from the group consisting of fluoro, hydroxy, amino, —S(=O)$_2$(R$^{13}$), —N(R$^{12}$)S(=O)$_2$(R$^{13}$), —S(=O)(R$^{13}$), —N(R$^{12}$)S(=O)(R$^{13}$), —C(=O)R$^{13}$, —N(R$^{12}$)C(=O)R$^{13}$, $C_1$-$C_6$ alkyl, —O($C_1$-$C_6$ alkyl), —NH($C_1$-$C_6$ alkyl), $C_1$-$C_6$ haloalkyl, $C_3$-$C_8$ cycloalkyl, 3- to 10-membered heterocycloalkyl, phenyl, and 5- to 6-membered heteroaryl, wherein the phenyl, and heteroaryl is optionally substituted with 1-4 groups independently selected from $R^{14}$, and the alkyl, haloalkyl, cycloalkyl, and heterocycloalkyl is optionally substituted with 1-4 groups independently selected from oxo and $R^{14}$.

Embodiment 93. The compound of any one of Embodiments 50 to 62 or 66 to 90, or a pharmaceutically acceptable salt or solvate thereof, wherein:
each $R^{11}$ is independently selected from the group consisting of halogen, hydroxy, amino, cyano, —S(=O)$_2$(R$^{13}$), —N(R$^{12}$)S(=O)$_2$(R$^{13}$), —S(=O)(R$^{13}$), —N(R$^{12}$)S(=O)(R$^{13}$), —C(=O)R$^{13}$, —N(R$^{12}$)C(=O)R$^{13}$, $C_1$-$C_6$ alkyl, —O($C_1$-$C_6$ alkyl), —NH($C_1$-$C_6$ alkyl), —N($C_1$-$C_6$ alkyl)$_2$, $C_1$-$C_6$ haloalkyl, $C_3$-$C_8$ cycloalkyl, 3- to 10-membered heterocycloalkyl, and 5- to 10-membered heteroaryl, wherein the heteroaryl is optionally substituted with 1-4 groups independently selected from $R^{14}$, and the alkyl, haloalkyl, cycloalkyl, and heterocycloalkyl is optionally substituted with 1-4 groups independently selected from oxo and $R^{14}$;
or two $R^{11}$ bound to the same carbon or nitrogen atom come together to form a $C_3$-$C_6$ cycloalkyl or 3- to 6-membered heterocycloalkyl, wherein the cycloalkyl, and heterocycloalkyl is optionally substituted with 1-4 groups independently selected from oxo and $R^{14}$;
each $R^{12}$ is independently hydrogen or $C_1$-$C_6$ alkyl;
each $R^{13}$ is independently hydroxy, amino, $C_1$-$C_6$ alkyl, —O($C_1$-$C_6$ alkyl), —NH($C_1$-$C_6$ alkyl), —N($C_1$-$C_6$ alkyl)$_2$, or $C_1$-$C_6$ haloalkyl; and
each $R^{14}$ is independently cyano, amino, hydroxy, —C(=O)OR$^{12}$, —C(=O)N(R$^{12}$)$_2$, $C_1$-$C_6$ alkyl, —O($C_1$-$C_6$ alkyl), or —NR$^{12}$($C_1$-$C_6$ alkyl), wherein each alkyl is optionally substituted with 1-2 hydroxy groups.

Embodiment 94. The compound of any one of Embodiments 66 to 67 or 74 to 77, or a pharmaceutically acceptable salt or solvate thereof, wherein:

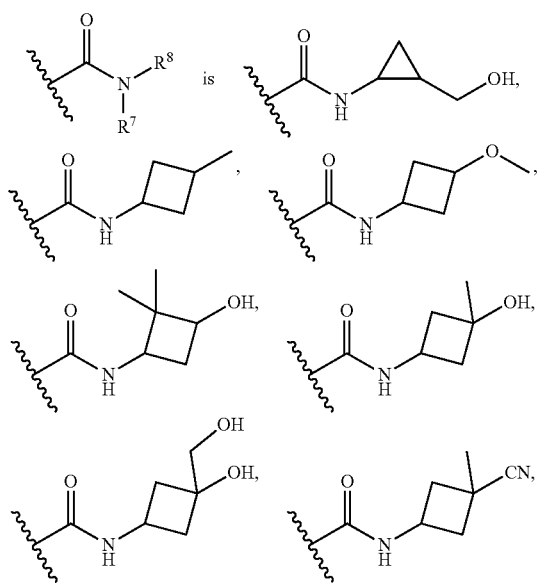

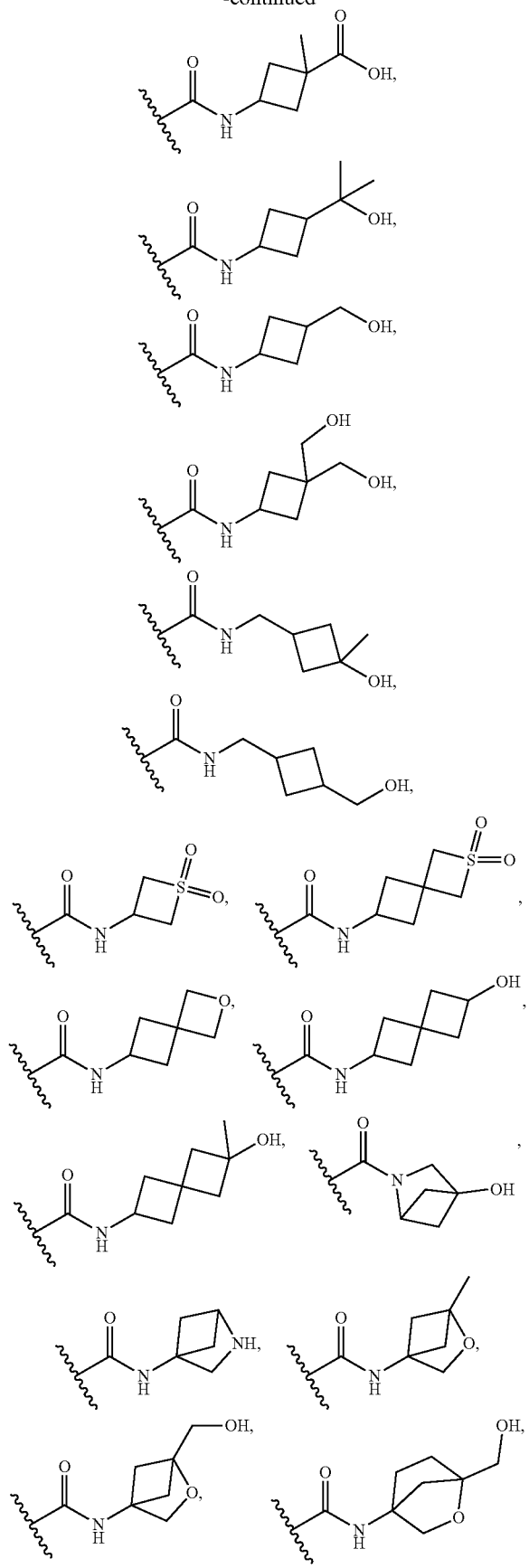
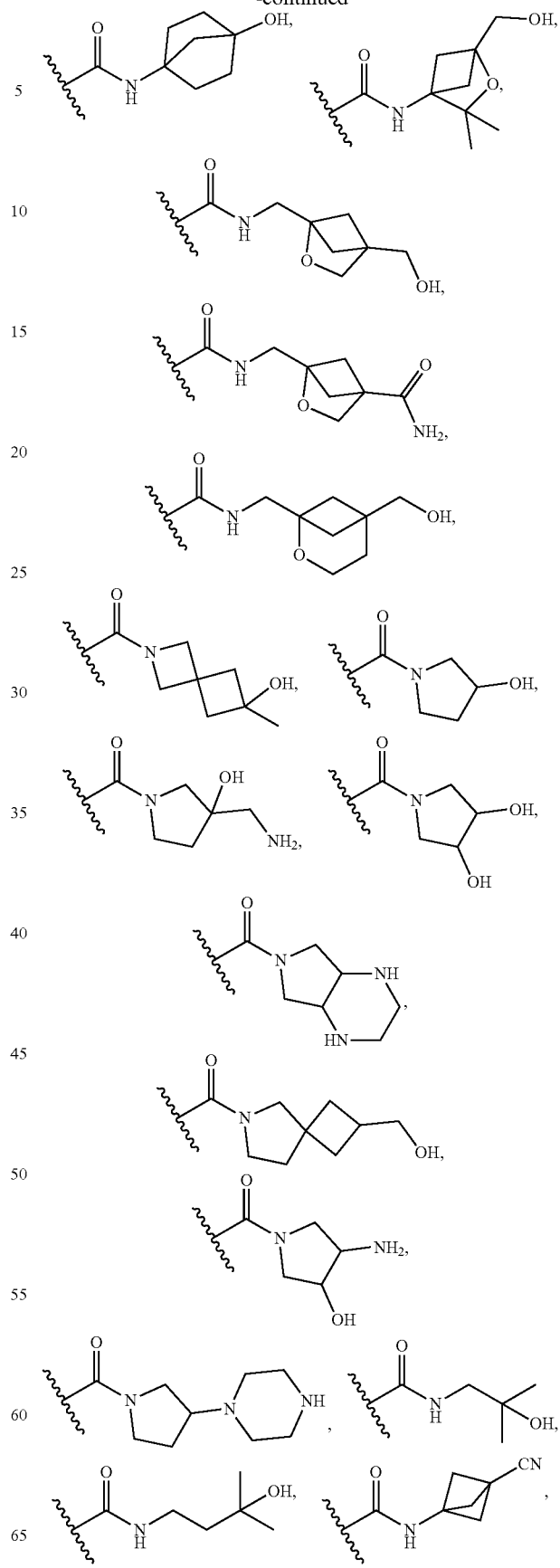

-continued
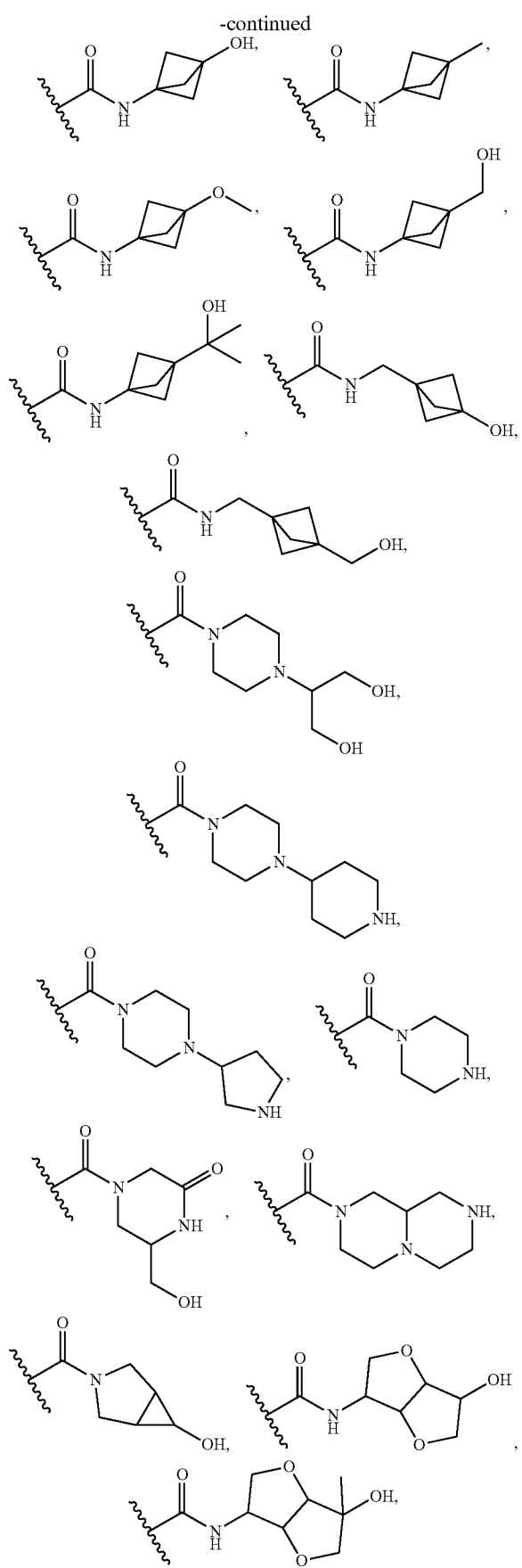
-continued
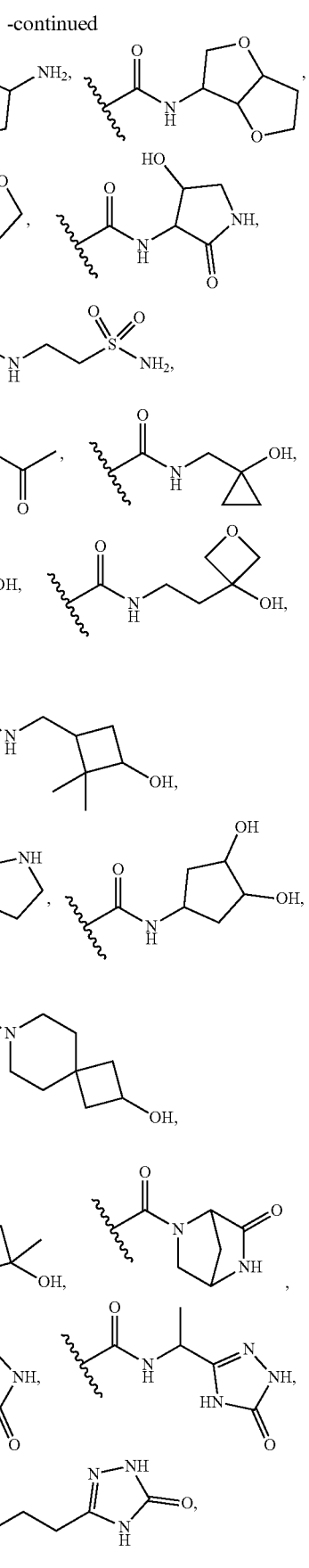

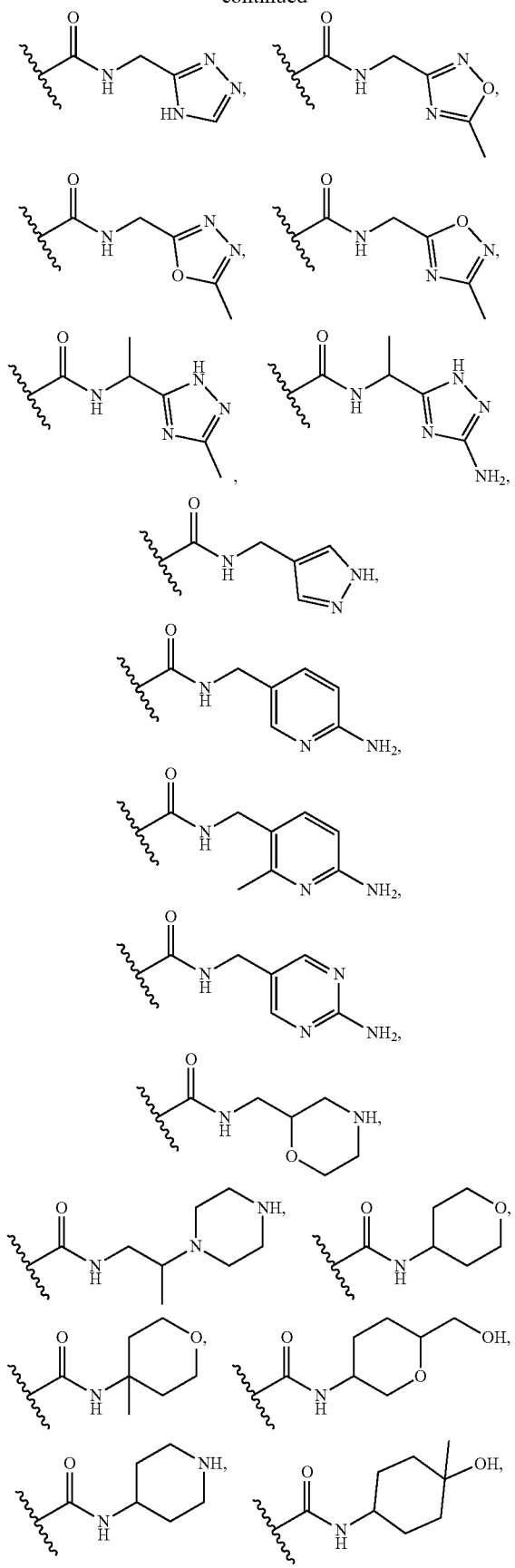
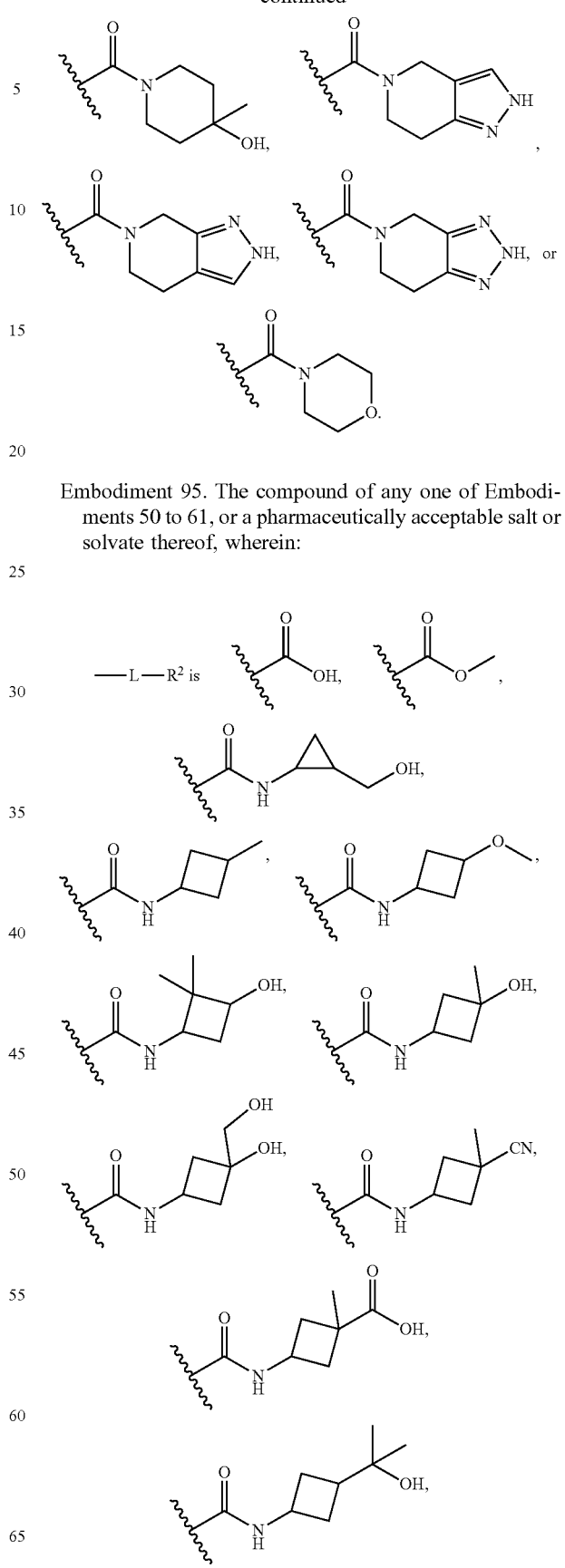
Embodiment 95. The compound of any one of Embodiments 50 to 61, or a pharmaceutically acceptable salt or solvate thereof, wherein:

-continued
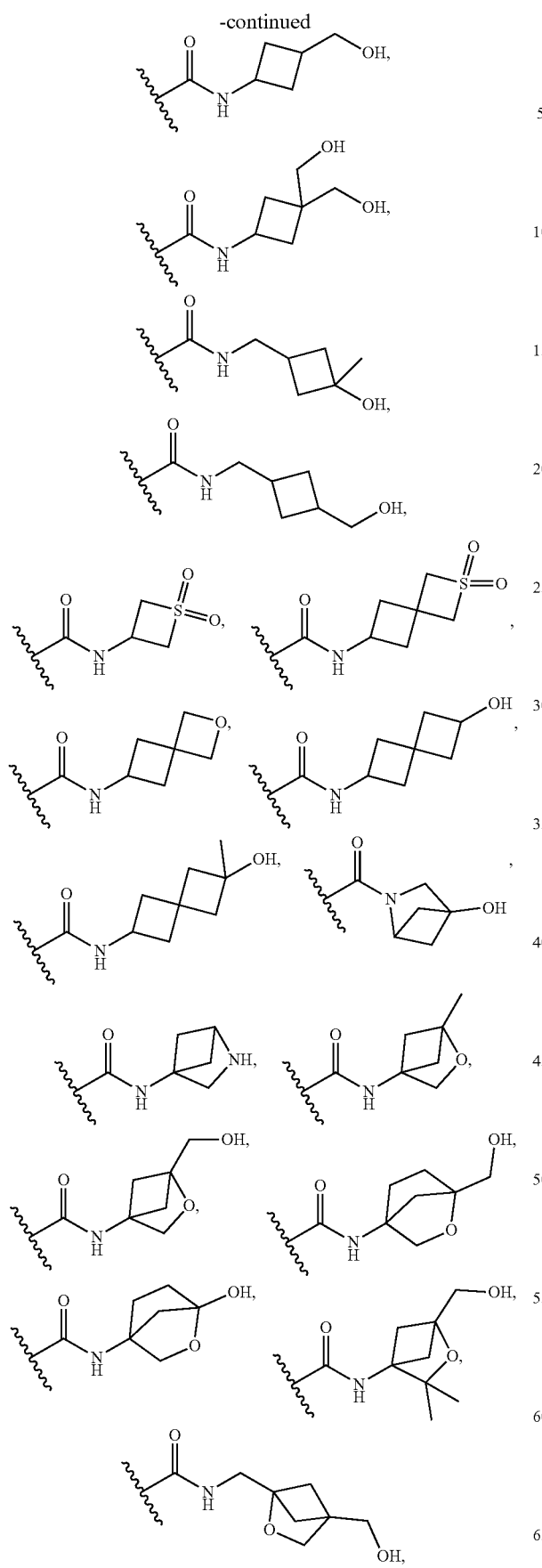
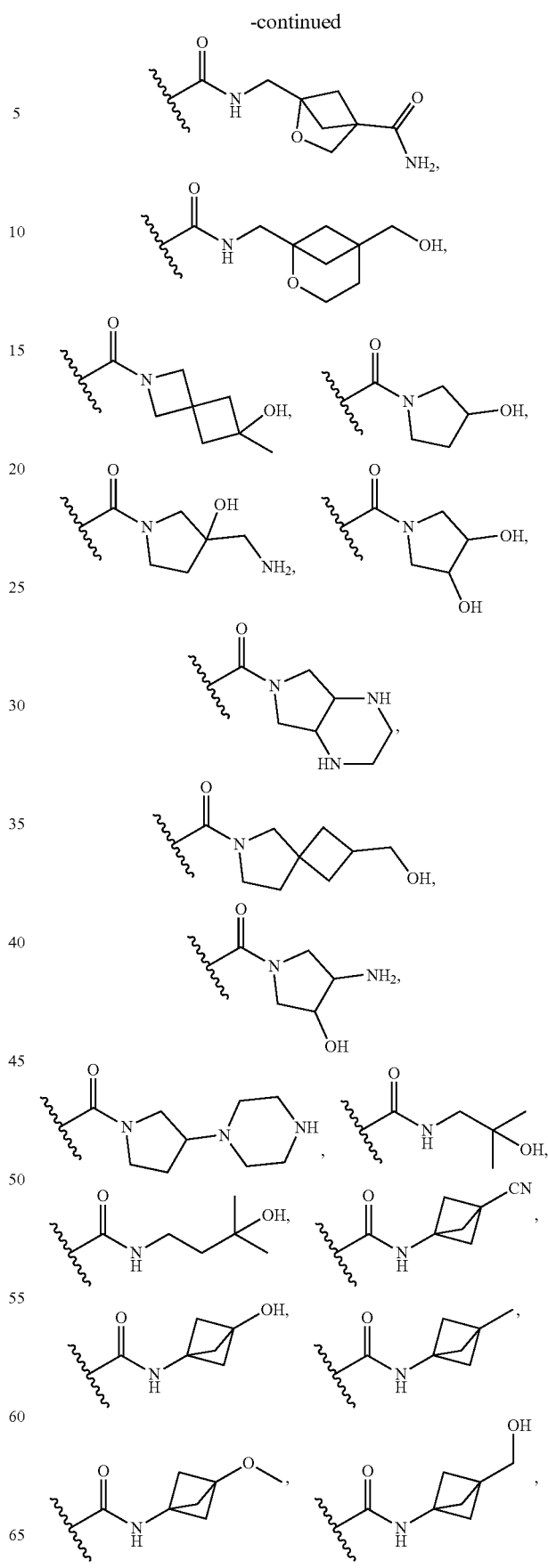

-continued
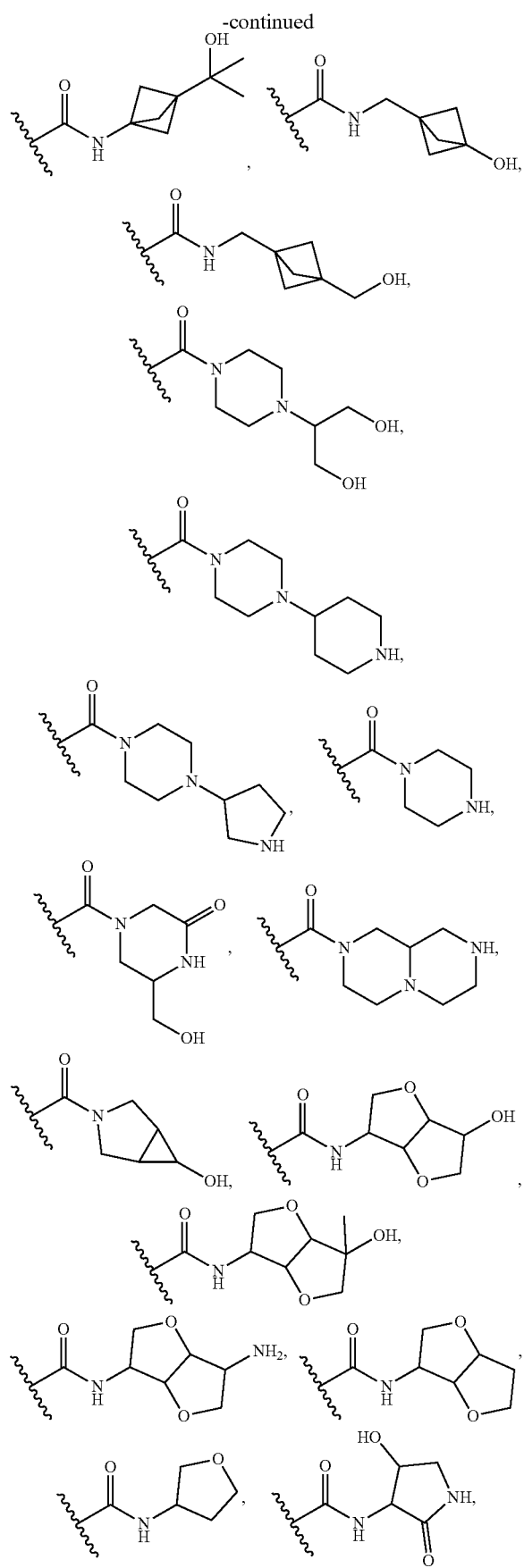
-continued
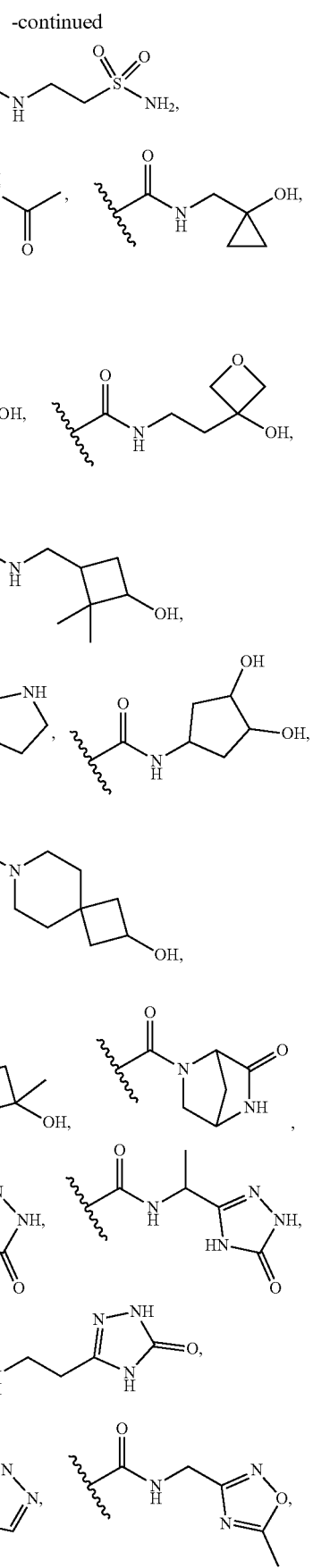

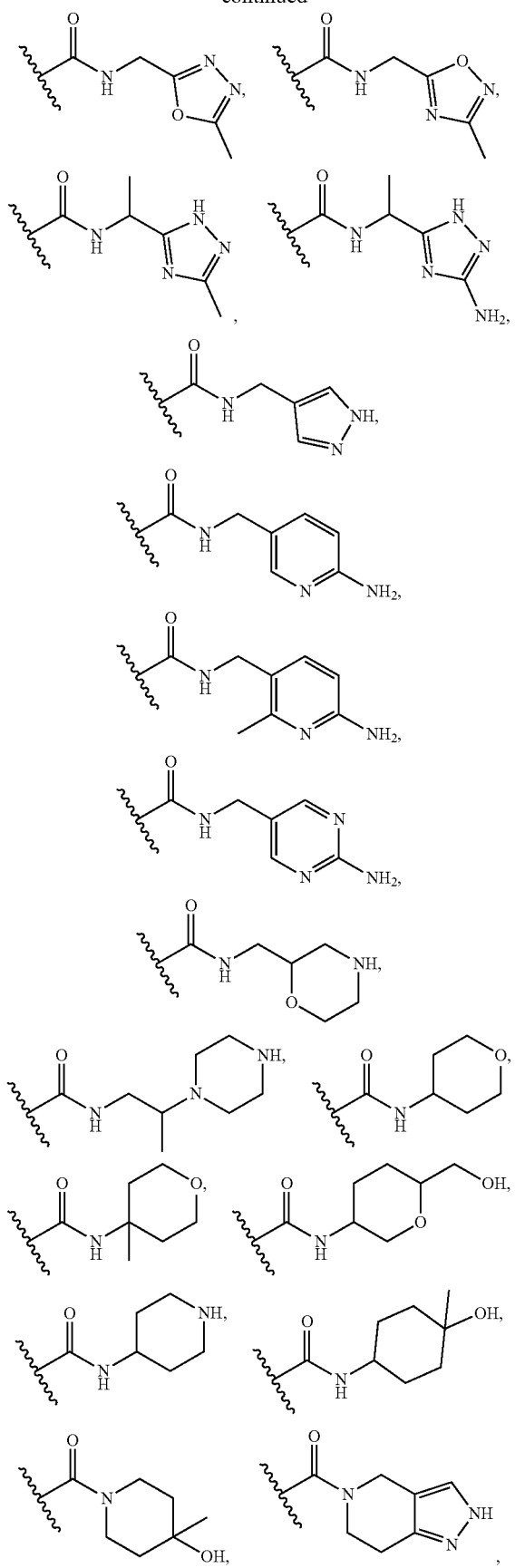

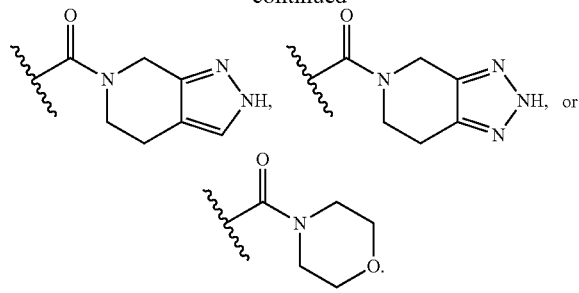

Embodiment 96. The compound of Embodiment 50, or a pharmaceutically acceptable salt or solvate thereof, wherein the compound is a compound depicted in Table 1.

Embodiment 97. A pharmaceutical composition comprising a compound of any one of Embodiments 50 to 96, or a pharmaceutically acceptable salt or solvate thereof, and at least one pharmaceutically acceptable excipient.

Embodiment 98. A method for the treatment of a disease or disorder in a subject in need thereof, comprising administering to the subject a therapeutically effective amount of a compound of any one of Embodiments 50 to 96, or a pharmaceutically acceptable salt or solvate thereof, or the pharmaceutical composition of Embodiment 97.

Embodiment 99. The method of Embodiment 98, wherein the disease or disorder is a neurokinin receptor 3 (NK3)-dependent disease or disorder.

Embodiment 100. The method of Embodiment 98 or 99, wherein the disease or disorder is selected from the group consisting of: migraine, medication overuse headache, cluster headache, general headache, trigeminal neuralgia, orofacial pain, and combinations thereof.

Embodiment 101. The method of any one of Embodiments 98 to 100, wherein the disease or disorder is selected from the group consisting of: migraine, medication overuse headache, cluster headache, general headache, and combinations thereof.

Embodiment 102. The method of any one of Embodiments 98 to 101, wherein the disease or disorder is migraine.

Embodiment 103. The method of any one of Embodiments 98 to 102, further comprising administration of a therapeutically effective amount of an additional therapeutic agent.

Embodiment 104. The method of Embodiment 103, wherein the additional therapeutic agent is selected from: beta blockers such as propranolol, nadolol, timolol, metoprolol, and atenolol; antidepressants such as amitriptyline and venlafaxine; anticonvulsants such as valproate and topiramate; phenothiazine anti-emetics such as prochlorperazine; non-phenothiazine anti-emetics such as metoclopramide; non-steroidal anti-inflammatory drugs (NSAIDS) such as aspirin, ibuprofen, and naproxen; acetaminophen; caffeine; ergots such as ergotamine and dihydroergotamine (DHE); ditans such as lasmiditan; triptans such as almotriptan, eletriptan, frovatriptan, naratriptan, rizatriptan, sumatriptan and zolmitriptan; calcitonin gene-related peptide (CGRP) receptor antagonists such as ubrogepant, rimegepant, atogepant, and zavegepant;

CGRP antibodies such as erenumab, fremanezumab, galcanezumab and eptinezumab; and combinations thereof.

EXAMPLES

The following examples are illustrative and non-limiting to the scope of the disclosure.

List of Abbreviations

As used above, and throughout the description of the invention, the following abbreviations, unless otherwise indicated, shall be understood to have the following meanings:
NK3 neurokinin receptor 3
NKB neurokinin B
FLIPR Fluorescence Imaging Plate Reader
eq equivalents
g, mg, μg gram(s), milligram(s), microgram(s)
h, hr(s) hour(s)
min(s) minute(s)
LCMS liquid chromatography-mass spectrometry
mL/μL/nL milliliter/microliter/nanoliter
mol/mmol/μmol mole/millimole/micromole
N normality, equivalent concentration
M molarity
NMR nuclear magnetic resonance
psi pound(s) per square inch
RFU relative fluorescence units
Ac acetyl
AcOH or HOAc acetic acid
OAc acetate
ACN or MeCN acetonitrile
Boc tert-butyloxycarbonyl
BPD bis(pinacolato)diboron
cataCXium A Pd G2 chloro[(di(1-adamantyl)-N-butylphosphine)-2-(2-aminobiphenyl)]palladium(II)
CMPI 2-chloro-N-methylpyridinium iodide
Cy cyclohexyl
$(Cy)_3$P-Pg-G3 or $PCy_3$-Pg-G3 [(tricyclohexylphosphine)-2-(2'-aminobiphenyl)]palladium(II) methanesulfonate
DAST diethylaminosulfur trifluoride
DCE dichloroethane
DCM dichloromethane
DIEA N,N-diisopropylethylamine
DME dimethoxyethane
DMF N,N-dimethylformamide
DMP Dess-Martin periodinane
DMSO dimethyl sulfoxide
dppf 1,1'-bis(diphenylphosphino)ferrocene
EDCI 1-ethyl-3-(3-dimethylaminopropyl)carbodiimide
Me methyl
$MeNH_2$ methylamine, methanamine
MeOH methanol
Et ethyl
EtOH ethanol
EtOAc, EA ethyl acetate
EtMgBr ethylmagnesium bromide
iPr isopropyl, 2-propyl
iPrOH, IPA isopropyl alcohol, isopropanol, 2-propanol
t-Bu tert-butyl
HATU 1-[bis(dimethylamino)methylene]-1H-1,2,3-triazolo[4,5-b]pyridinium 3-oxide hexafluorophosphate
MTBE methyl tert-butyl ether
NBS N-bromosuccinimide
NCS N-chlorosuccinimide
NMM N-methyl morpholine
NMO N-methyl morpholine N-oxide
Oxone potassium peroxymonosulfate
PE petroleum ether
Py pyridine
SEMCl 2-(trimethylsilyl)ethoxymethyl chloride
TBD triazabicyclodecene, 1,5,7-triazabicyclo[4.4.0]dec-5-ene
Tf trifluoromethanesulfonyl
TfOH trifluoromethanesulfonic acid
TFA trifluoroacetic acid
THF tetrahydrofuran
TMS trimethylsilyl
TBS tert-butyldimethylsilyl
Ts tosyl, p-toluenesulfonyl
TsOH, PTSA tosylic acid, p-toluenesulfonic acid

I. Chemical Synthesis

Unless otherwise noted, reagents and solvents were used as received from commercial suppliers. Anhydrous solvents and oven-dried glassware were used for synthetic transformations sensitive to moisture and/or oxygen. Yields were not optimized. Reaction times are approximate and were not optimized. Column chromatography and thin layer chromatography (TLC) were performed on silica gel unless otherwise noted.

Example 1: Methyl 2-(2-bromophenyl)imidazo[1,2-a]pyridine-7-carboxylate (1-1)

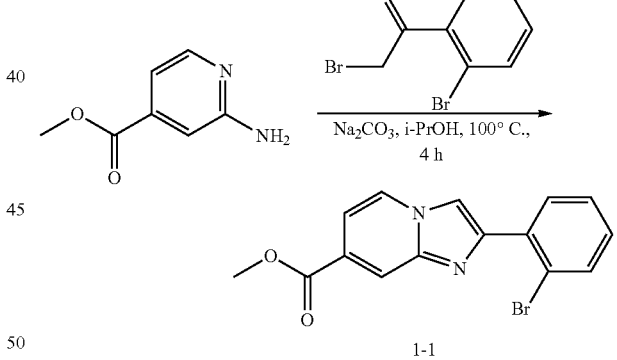

Step 1: methyl 2-(2-bromophenyl)imidazo[1,2-a]pyridine-7-carboxylate (1-1): To a solution of methyl 2-aminoisonicotinate (0.87 g, 5.7 mmol, 1 eq) in i-PrOH (10 mL) was added 2-bromo-1-(2-bromophenyl)ethan-1-one (1.6 g, 5.7 mmol, 1 eq) and $Na_2CO_3$ (0.61 g, 5.7 mmol, 1 eq). The mixture was stirred at 100° C. for 4 hrs. The reaction mixture was filtered and the filtrate was concentrated under reduced pressure. The residue was purified by flash silica gel chromatography (ISCO®; 40 g SepaFlash® Silica Flash Column, Eluent of 0~15% Ethyl acetate/Petroleum ether gradient @ 100 mL/min) to give 1-1 (1.1 g, 58% yield) as a yellow solid. LCMS: $(ES^+)$ m/z $(M+H)^+$=333.1. $^1$H NMR (400 MHz, $CDCl_3$) δ=8.32 (s, 2H) 8.03-8.18 (m, 2H) 7.62 (d, J=8.0 Hz, 1H) 7.32-7.43 (m, 2H) 7.11-7.18 (m, 1H) 3.90 (s, 3H).

Example 2: 3-chloro-2-(2-(1,3-dimethyl-1H-pyrazol-4-yl)phenyl)-N-((3R,3aR,6R,6aR)-6-hydroxyhexahydrofuro[3,2-b]furan-3-yl)imidazo[1,2-a]pyridine-7-carboxamide (Compound 7)

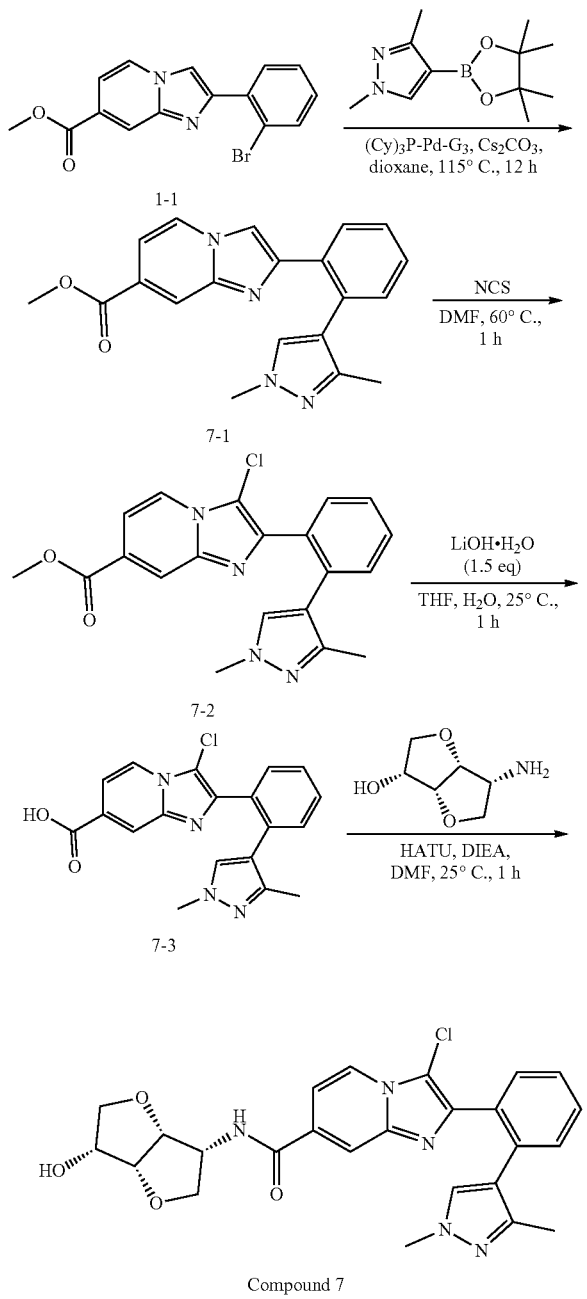

Compound 7

Step 1: methyl 2-(2-(1,3-dimethyl-1H-pyrazol-4-yl)phenyl)imidazo[1,2-a]pyridine-7-carboxylate (7-1): To a solution of 1-1 (27 g, 0.81 mol, 1 eq) and 1,3-dimethyl-4-(4,4,5,5-tetramethyl-1,3,2-dioxaborolan-2-yl)pyrazole (27 g, 0.12 mol, 1.5 eq) in dioxane (250 mL) was added $(Cy)_3$P-Pd-G3 (6.0 g, 8.1 mol, 0.1 eq) and $Cs_2CO_3$ (80 g, 0.24 mol, 3 eq). The mixture was stirred at 115° C. for 12 hrs under $N_2$. The reaction mixture was filtered to remove the insoluble. The filter liquor was concentrated under reduced pressure. The residue was purified by flash silica gel chromatography (ISCO®; 120 g SepaFlash® Silica Flash Column, Eluent of 0~100% Ethyl acetate/Petroleum ether gradient @ 100 mL/min, PE/EA=1/1, Rf=0.1) to give 7-1 (27 g, 94 yield) as brown solid. LCMS: (ES$^+$) m/z (M+H)$^+$=347.1. $^1$H NMR (400 MHz, CDCl$_3$) δ ppm 1.92 (s, 3H) 3.91 (s, 3H) 3.96 (s, 3H) 7.05 (s, 1H) 7.27 (d, J=3.76 Hz, 2H) 7.31-7.40 (m, 2H) 7.47 (td, J=7.58, 1.38 Hz, 1H) 7.96 (dd, J=7.08, 0.68 Hz, 1H) 8.22 (dd, J=7.82, 1.18 Hz, 1H) 8.35 (s, 1H)

Step 2: methyl 3-chloro-2-(2-(1,3-dimethyl-1H-pyrazol-4-yl)phenyl)imidazo[1,2-a]pyridine-7-carboxylate (7-2): To a solution of 7-1 (27 g, 78 mmol, 1 eq) in DMF (250 mL) was added NCS (12 g, 93 mmol, 1.2 eq). The mixture was stirred at 60° C. for 1 hr. The reaction mixture was diluted with H$_2$O (100 mL) and extracted with EA (100 mL×3). The combined organic layers were washed with saturated sodium chloride aqueous solution (100 mL×2), dried over anhydrous Na$_2$SO$_4$, filtered and concentrated under reduced pressure to give a residue. The residue was purified by flash silica gel chromatography (ISCO®; 120 g SepaFlash® Silica Flash Column, Eluent of 0~100% Ethyl acetate/Petroleum ether gradient @ 100 mL/min, PE/EA=0/1, Rf=0.4) to give 7-2 (15 g, 38 mmol, 97% purity) as a yellow solid. LCMS: (ES$^+$) m/z (M+H)$^+$=381.2. $^1$H NMR (400 MHz, CD$_3$OD) δ ppm 1.90 (s, 3H), 3.69 (s, 3H), 3.98 (s, 3H), 7.22 (s, 1H), 7.46 (dd, J=16.70, 7.68 Hz, 2H), 7.51-7.56 (m, 1H), 7.57-7.62 (m, 2H), 8.25 (s, 1H), 8.32 (d, J=7.26 Hz, 1H).

Step 3: 3-chloro-2-(2-(1,3-dimethyl-1H-pyrazol-4-yl)phenyl)imidazo[1,2-a]pyridine-7-carboxylic acid (7-3): To a solution of 7-2 (14 g, 37 mmol, 1 eq) in THF (60 mL) and H$_2$O (60 mL) was added LiOH·H$_2$O (3.1 g, 74 mmol, 2 eq). The mixture was stirred at 25° C. for 1 hr. The reaction mixture was adjusted to pH=5 with 2 N HCl. Then the reaction mixture was filtered and the filter cake was dried in vacuo. The crude product was purified by re-crystallization from H$_2$O (50 mL) at 25° C. to give 7-3 (15 g, 32 mmol, 88% yield, 2HCl) as a yellow solid. LCMS: (ES$^+$) m/z (M+H)$^+$ =367.0. $^1$H NMR (400 MHz, CD$_3$OD) δ ppm 1.91 (s, 3H), 3.69 (s, 3H), 7.22 (s, 1H), 7.41-7.50 (m, 2H), 7.53 (d, J=7.52 Hz, 1H), 7.60 (dd, J=6.50, 5.12 Hz, 2H), 8.25 (s, 1H), 8.30 (d, J=7.14 Hz, 1H).

Step 4: 3-chloro-2-(2-(1,3-dimethyl-1H-pyrazol-4-yl)phenyl)-N-((3R,3aR,6R,6aR)-6-hydroxyhexahydrofuro[3,2-b]furan-3-yl)imidazo[1,2-a]pyridine-7-carboxamide (Compound 7): To a solution of (3R,3aR,6R,6aR)-6-aminohexahydrofuro[3,2-b]furan-3-ol (2 g, 14 mmol, 1 eq) and 7-3 (5.9 g, 14 mmol, 1 eq) in DMF (20 mL) was added HATU (6.3 g, 16 mmol, 1.2 eq) and DIEA (7.1 g, 55 mmol, 9.6 mL, 4 eq). The mixture was stirred at 25° C. for 1 hr. The reaction mixture was diluted with H$_2$O (100 mL) and extracted with EA (100 mL×3). The combined organic layers were washed with saturated brine (100 mL×2), dried over anhydrous Na$_2$SO$_4$, filtered and concentrated under reduced pressure to give a residue. The crude product was purified by reversed-phase HPLC (column: Phenomenex luna C18 (250×70 mm, 10 μm); mobile phase: [water (0.1% NH$_4$HCO$_3$)-ACN]; gradient: 17%-47% B over 20 min) to give Compound 7 (2.5 g, 35% yield) as off-white solid. LCMS: (ES+) m/z (M−H)$^+$=494.1. $^1$H NMR (400 MHz, CD$_3$OD) δ ppm 1.88 (s, 3H) 3.64-3.68 (m, 1H) 3.69 (s, 3H) 3.73-3.81 (m, 1H) 3.96 (dd, J=8.88, 6.12 Hz, 1H) 4.16-4.24 (m, 1H) 4.29-4.37 (m, 1H) 4.59 (t, J=4.64 Hz, 1H) 4.62-4.70 (m, 2H) 7.23 (s, 1H) 7.40-7.44 (m, 2H) 7.45-7.55 (m, 3H) 7.59 (d, J=7.50 Hz, 1H) 8.10 (s, 1H) 8.30 (d, J=7.14 Hz, 1H).

Example 3: 3-chloro-2-(2-(1,3-dimethyl-1H-pyrazol-4-yl)-4-fluorophenyl)-N-((3R,3aR,6R,6aR)-6-hydroxyhexahydrofuro[3,2-b]furan-3-yl)imidazo[1,2-a]pyridine-7-carboxamide (Compound 16)

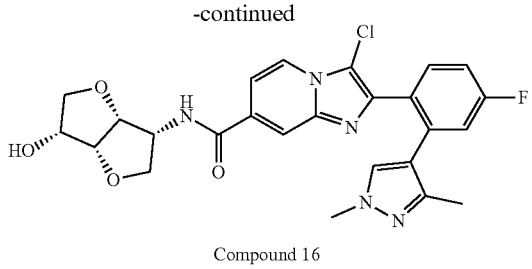

Compound 16

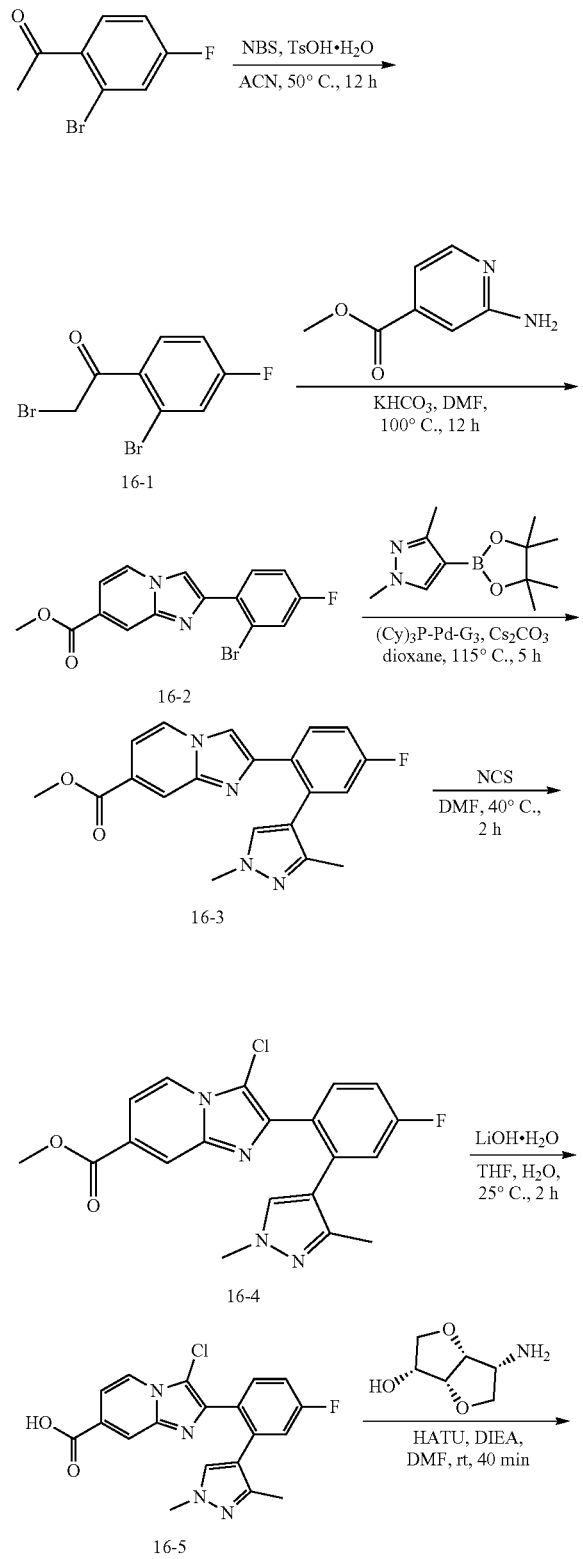

Step 1: 2-bromo-1-(2-bromo-4-fluorophenyl)ethan-1-one (16-1): To a solution of 1-(2-bromo-4-fluoro-phenyl)ethanone (5.0 g, 23 mmol, 1.0 eq) in ACN (100 mL) was added TsOH·H$_2$O (5.3 g, 28 mmol, 1.2 eq) and NBS (4.5 g, 25 mmol, 1.1 eq). The mixture was stirred at 50° C. for 12 hours. The reaction mixture was diluted with H$_2$O (100 mL) and extracted with EtOAc (100 mL×3). The combined organic layers were washed with saturated brine (100 mL×2), dried over Na$_2$SO$_4$, filtered and concentrated under reduced pressure to give a residue. The residue was purified by column chromatography (SiO$_2$, Petroleum ether/Ethyl acetate=1/0 to 10/1) to give 16-1 (6.3 g, 18 mmol, 79% yield, 85% purity) as a colorless oil. $^1$H NMR (400 MHz, CD$_3$OD) δ=7.75-7.70 (m, 1H), 7.56-7.52 (m, 1H), 7.28-7.23 (m, 1H), 4.61 (s, 2H).

Step 2: methyl 2-(2-bromo-4-fluorophenyl)imidazo[1,2-a]pyridine-7-carboxylate (16-2): To a solution of 16-1 (2.0 g, 6.8 mmol, 1.0 eq) and methyl 2-aminoisonicotinate (1.1 g, 7.4 mmol, 1.1 eq) in DMF (20 mL) was added KHCO$_3$ (0.74 g, 7.4 mmol, 1.1 eq). The mixture was stirred at 100° C. for 12 hours. The reaction mixture was diluted with H$_2$O (100 mL) and extracted with EtOAc (100 mL×3). The combined organic layers were washed with saturated brine (100 mL×2), dried over Na$_2$SO$_4$, filtered and concentrated under reduced pressure to give a residue. The residue was purified by column chromatography (SiO$_2$, Petroleum ether/Ethyl acetate=1/0 to 3/1) to give 16-2 (1.2 g, 3.2 mmol, 47% yield, 92% purity) as a yellow solid. LCMS: (ES+) m/z (M+H)$^+$= 350.7

Step 3: methyl 2-(2-(1,3-dimethyl-1H-pyrazol-4-yl)-4-fluorophenyl)imidazo[1,2-a]pyridine-7-carboxylate (16-3): To a solution of 16-2 (1.2 g, 3.4 mmol, 1.0 eq) and 1,3-dimethyl-4-(4,4,5,5-tetramethyl-1,3,2-dioxaborolan-2-yl)-1H-pyrazole (1.0 g, 4.5 mmol, 1.3 eq) in dioxane (15 mL) was added Cs$_2$CO$_3$ (3.4 g, 10 mmol, 3.0 eq) and (Cy)$_3$P Pd G3 (0.25 g, 0.34 mmol, 0.10 eq). The mixture was degassed and purged with N$_2$ for three times and the mixture was stirred at 115° C. for 5 hours under N$_2$ atmosphere. The reaction mixture was diluted with H$_2$O (100 mL) and extracted with EtOAc (100 mL×3). The combined organic layers were washed with saturated brine (100 mL×2), dried over Na$_2$SO$_4$, filtered and concentrated under reduced pressure to give a residue. The residue was purified by column chromatography (SiO$_2$, Petroleum ether/Ethyl acetate=1/0 to 1/3) to give 16-3 (1.2 g, 2.8 mmol, 82% yield, 85% purity) as a yellow oil. LCMS: (ES+) m/z (M+H)$^+$=365.0.

Step 4: methyl 3-chloro-2-(2-(1,3-dimethyl-1H-pyrazol-4-yl)-4-fluorophenyl)imidazo[1,2-a]pyridine-7-carboxylate (16-4): To a solution of 16-3 (1.2 g, 3.3 mmol, 1.0 eq) in DMF (20 mL) was added NCS (0.44 g, 3.3 mmol, 1.0 eq). The mixture was stirred at 40° C. for 2 hours. The reaction mixture was diluted with H$_2$O (100 mL) and extracted with EtOAc (100 mL×3). The combined organic layers were washed with saturated brine (100 mL×2), dried over Na₂SO₄, filtered and concentrated under reduced pressure to give 16-4 (1.3 g, crude) as a yellow oil. LCMS: (ES+) m/z (M+H)⁺=399.1.

Step 5: 3-chloro-2-(2-(1,3-dimethyl-1H-pyrazol-4-yl)-4-fluorophenyl)imidazo[1,2-a]pyridine-7-carboxylic acid (16-5): To a solution of 16-4 (1.3 g, 3.3 mmol, 1.0 eq) in MeOH (5.0 mL), H₂O (5.0 mL), THF (5.0 mL) was added LiOH·H₂O (0.69 g, 16 mmol, 5.0 eq). The mixture was stirred at 25° C. for 2 hours. The reaction mixture was adjusted pH to 4 by addition 1N HCl. The reaction mixture was diluted with H₂O (100 mL) and extracted with EtOAc (100 mL×3). The combined organic layers were washed with saturated brine (100 mL×2), dried over Na₂SO₄, filtered and concentrated under reduced pressure to give a residue. The crude product was purified by reversed-phase HPLC (0.1% FA condition) (330 g Flash Column Welch Ultimate XB_C18 20-40 µm; 120 A, 100 mL/min, H₂O+ACN, 5-35% 20 min; 35% 5 min, Biotage Prime) to give 16-5 (0.60 g, 1.6 mmol, 48% yield, 100% purity) as a yellow solid. LCMS: (ES+) m/z (M+H)⁺=384.9.

Step 6: 3-chloro-2-(2-(1,3-dimethyl-1H-pyrazol-4-yl)-4-fluorophenyl)-N-((3R,3aR,6R,6aR)-6-hydroxyhexahydrofuro[3,2-b]furan-3-yl)imidazo[1,2-a]pyridine-7-carboxamide (Compound 16): To a solution of 16-5 (0.15 g, 0.39 mmol, 1.0 eq) in DMF (2 mL) was added HATU (0.30 g, 0.78 mmol, 2.0 eq) and DIEA (0.25 g, 2.0 mmol, 0.34 mL, 5.0 eq). The mixture was stirred at 25° C. for 10 min. Then the (3R,3aR,6R,6aR)-6-aminohexahydrofuro[3,2-b]furan-3-ol (62 mg, 0.43 mmol, 1.1 eq) was added to the mixture, and the mixture was stirred at 25° C. for 30 min. The reaction mixture was diluted with H₂O (30 mL) and extracted with EtOAc (50 mL×3). The combined organic layers were washed with saturated brine (50 mL×2), dried over Na₂SO₄, filtered and concentrated under reduced pressure to give a residue. The crude product was purified by reversed-phase HPLC (neutral condition) (40 g Flash Column Welch Ultimate XB_C18 20-40 µm; 120 A, 100 mL/min, H₂O+ACN, 5-45% 20 min; 45%, 5 min, Biotage Prime) to give Compound 16 (0.12 g, 0.23 mmol, 58% yield, 97% purity) as a white solid. LCMS: (ES+) m/z (M+H)⁺=512.2. ¹H NMR (400 MHz, CD₃OD) δ=8.31 (d, J=7.2 Hz, 1H), 8.10 (s, 1H), 7.64-7.57 (m, 1H), 7.53-7.47 (m, 1H), 7.27 (s, 1H), 7.25-7.17 (m, 2H), 4.69-4.62 (m, 2H), 4.59 (t, J=4.8 Hz, 1H), 4.37-4.30 (m, 1H), 4.23-4.16 (m, 1H), 3.98-3.93 (m, 1H), 3.80-3.74 (m, 1H), 3.69 (s, 3H), 3.68-3.65 (m, 1H), 1.89 (s, 3H).

Example 4: 2-(2-(1,3-dimethyl-1H-pyrazol-4-yl)-6-fluorophenyl)-N-((3R,3aR,6R,6aR)-6-hydroxyhexahydrofuro[3,2-b]furan-3-yl)-3-methylimidazo[1,2-a]pyridine-7-carboxamide (Compound 17)

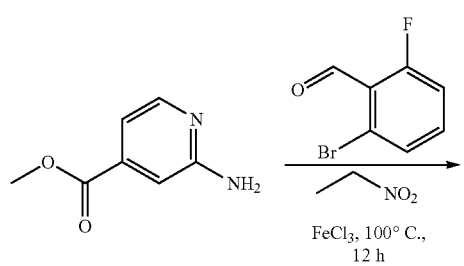

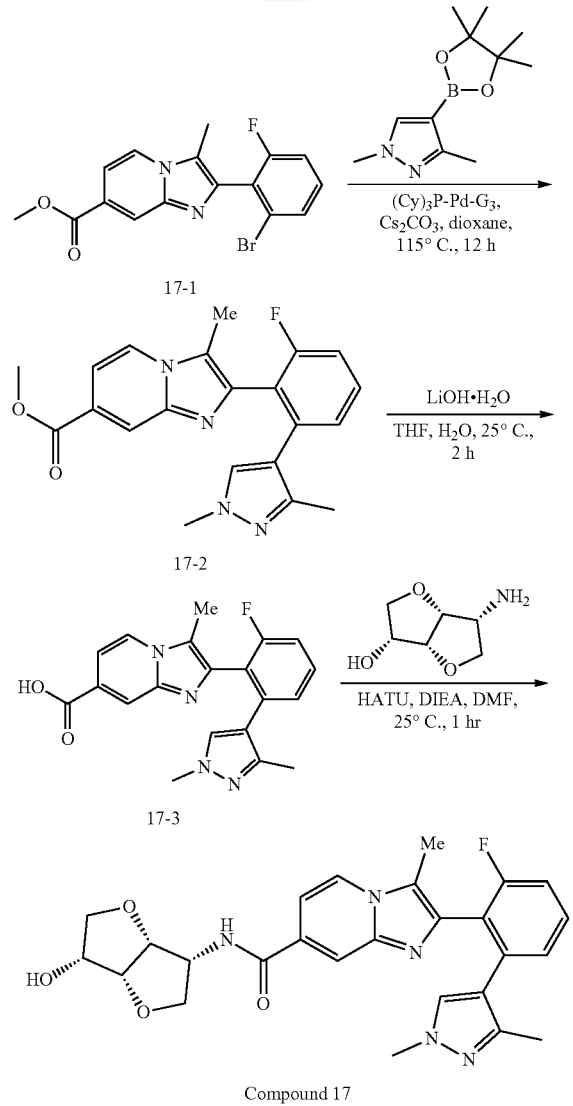

Step 1: methyl 2-(2-bromo-6-fluorophenyl)-3-methylimidazo[1,2-a]pyridine-7-carboxylate (17-1): To a solution of methyl 2-aminopyridine-4-carboxylate (2.0 g, 13 mmol, 1.0 eq) and 2-bromo-6-fluoro-benzaldehyde (2.7 g, 13 mmol, 1.0 eq) in 1-nitroethane (22 g, 0.29 mol, 21 mL, 22 eq) was added FeCl₃ (0.21 g, 1.3 mmol, 76 µL, 0.1 eq). The mixture was stirred at 100° C. for 12 hrs under air. The reaction mixture was diluted with H₂O (50 mL) and extracted with EtOAc (100 mL×3). The combined organic layers were washed with saturated brine (80 mL×2), dried over Na₂SO₄, filtered and concentrated under reduced pressure to give a residue. The residue was purified by flash silica gel chromatography (ISCO®; 20 g SepaFlash® Silica Flash Column, Eluent of 0~25% Ethyl acetate/Petroleum ether gradient @ 100 mL/min; PE/EA=1/1, Rf=0.59) to give 17-1 (2.2 g, 44% yield) as yellow solid. LCMS: (ES+) m/z (M+H)⁺=364.6. ¹H NMR (400 MHz, CDCl₃) δ=2.29-2.39 (m, 3H) 3.90 (s, 3H) 7.04-7.14 (m, 1H) 7.14-7.31 (m, 1H) 7.35-7.55 (m, 2H) 7.79-7.96 (m, 1H) 8.33 (s, 1H).

Step 2: methyl 2-(2-(1,3-dimethyl-1H-pyrazol-4-yl)-6-fluorophenyl)-3-methylimidazo[1,2-a]pyridine-7-carboxylate (17-2): A mixture of 17-1 (0.5 g, 1.4 mmol, 1.0 eq), 1,3-dimethyl-4-(4,4,5,5-tetramethyl-1,3,2-dioxaborolan-2-yl)pyrazole (0.61 g, 2.8 mmol, 2.0 eq), (Cy)₃P Pd G₃ (0.10 g, 0.14 mmol, 0.1 eq), Cs₂CO₃ (1.4 g, 4.1 mmol, 3.0 eq) in dioxane (8 mL) was degassed and purged with N₂ for 3 times. The mixture was stirred at 115° C. for 12 hrs under N₂ atmosphere. The mixture was concentrated to give a residue. The residue was purified by flash silica gel chromatography (ISCO®; 12 g SepaFlash® Silica Flash Column, Eluent of 0~80% Ethyl acetate/Petroleum ether gradient @ 100 mL/min; PE/EA=1/1, Rf=0.1) to give 17-2 (0.4 g, 74% yield, 97% purity) as yellow oil. LCMS: (ES+) m/z (M+H)⁺= 379.2. ¹H NMR (400 MHz, CDCl₃) δ=2.03-2.05 (m, 3H) 2.09-2.17 (m, 3H) 3.62-3.71 (m, 3H) 3.89-4.07 (m, 3H) 6.90-7.04 (m, 1H) 7.07-7.24 (m, 2H) 7.34-7.54 (m, 2H) 7.80-7.86 (m, 1H) 8.36 (s, 1H).

Step 3: 2-(2-(1,3-dimethyl-1H-pyrazol-4-yl)-6-fluorophenyl)-3-methylimidazo[1,2-a]pyridine-7-carboxylic acid (17-3): To a solution of 17-2 (0.4 g, 1.1 mmol, 1.0 eq) in THF (1.5 mL) and H₂O (1.5 mL) was added LiOH·H₂O (0.13 g, 3.2 mmol, 3.0 eq). The mixture was stirred at 25° C. for 2 hrs. The reaction mixture was added 2 M HCl until pH=5 and concentrated under reduced pressure to give 17-3 (0.5 g, crude) as yellow oil. LCMS: (ES+) m/z (M+H)⁺=365.1.

Step 4: 2-(2-(1,3-dimethyl-1H-pyrazol-4-yl)-6-fluorophenyl)-N-((3R,3aR,6R,6aR)-6-hydroxyhexahydrofuro[3,2-b]furan-3-yl)-3-methylimidazo[1,2-a]pyridine-7-carboxamide (Compound 17): To a solution of 17-3 (0.15 g, 0.34 mmol, 1.0 eq) and (3R,3aR,6R,6aR)-3-amino-2,3,3a,5,6,6a-hexahydrofuro[3,2-b]furan-6-ol (69 mg, 0.38 mmol, 1.1 eq) in DMF (2 mL) was added HATU (0.26 g, 0.69 mmol, 2.0 eq) and DIEA (0.22 g, 1.7 mmol, 5.0 eq). The mixture was stirred at 25° C. for 1 hour. The mixture was concentrated to give a residue. The residue was purified by prep-HPLC (column: Waters xbridge 150×25 mm×10 μm; mobile phase: [water (0.1% NH₄HCO₃)-ACN]; B %: 16%-46%, 10 min) to give Compound 17 (0.1 g, 59% yield) as white solid. LCMS: (ES+) m/z (M+H)⁺=492.3. ¹H NMR (400 MHz, CD₃OD) δ=1.85-2.02 (m, 3H) 2.12-2.26 (m, 3H) 3.51-3.66 (m, 3H) 3.66-3.73 (m, 1H) 3.73-3.82 (m, 1H) 3.91-4.04 (m, 1H) 4.11-4.28 (m, 1H) 4.28-4.42 (m, 1H) 4.51-4.61 (m, 1H) 4.62-4.74 (m, 2H) 7.05-7.15 (m, 1H) 7.15-7.30 (m, 2H) 7.33-7.45 (m, 1H) 7.46-7.60 (m, 1H) 8.01-8.13 (m, 1H) 8.22 (d, J=8.0 Hz, 1H).

Example 5: 3-chloro-2-(2-(1,3-dimethyl-1H-pyrazol-4-yl)-3-fluorophenyl)-N-((3R,3aR,6R,6aR)-6-hydroxyhexahydrofuro[3,2-b]furan-3-yl)imidazo[1,2-a]pyridine-7-carboxamide (Compound 18)

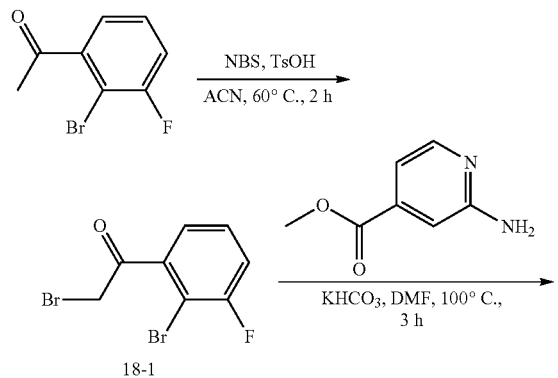

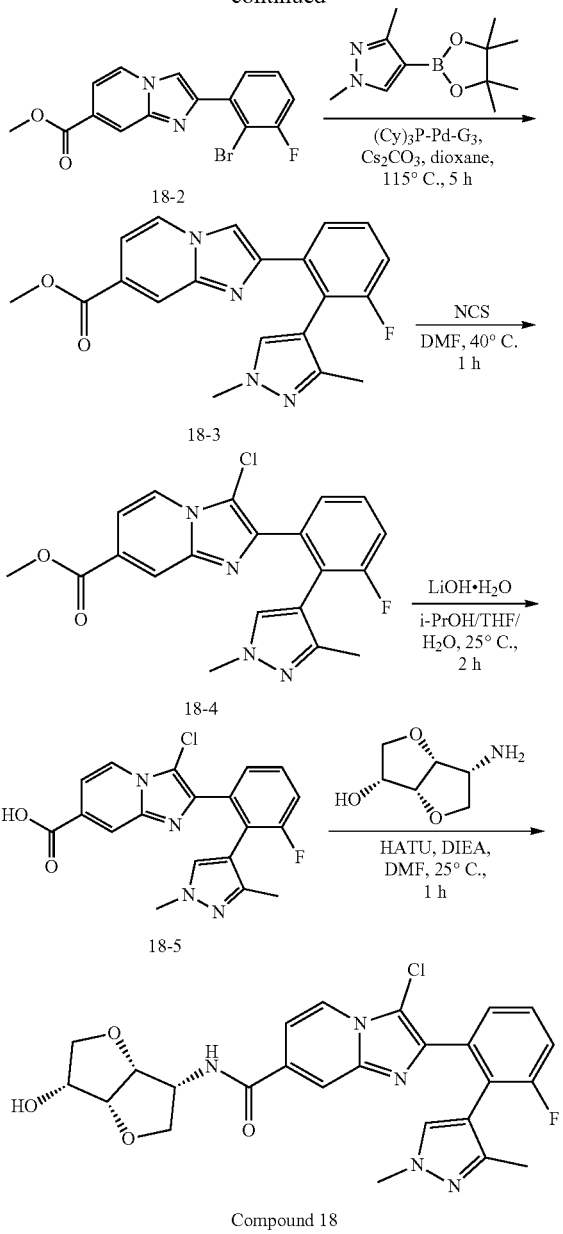

Compound 18

Step 1: 2-bromo-1-(2-bromo-3-fluorophenyl)ethan-1-one (18-1): To a solution of 1-(2-bromo-3-fluoro-phenyl)ethanone (0.50 g, 2.3 mmol, 1.0 eq) in ACN (5 mL) was added NBS (0.49 g, 2.8 mmol, 1.2 eq) and TsOH (0.60 g, 3.5 mmol, 1.5 eq) at 0° C. The mixture was stirred at 60° C. for 2 hours. The reaction mixture was quenched by addition water (50 mL), and then diluted with ethyl acetate (50 mL) and extracted with ethyl acetate (50 mL×3). The combined organic layers were washed with sat. brine (50 mL), dried over Na₂SO₄, filtered and concentrated under reduced pressure to give a residue. The residue was purified by column chromatography (SiO₂, Petroleum ether/Ethyl acetate=1:0 to 30:1) to give 18-1 (0.56 g, 1.6 mmol, 70% yield, 85% purity) as a yellow oil. ¹H NMR (400 MHz, CDCl₃) δ=7.41-7.30 (m, 1H), 7.25-7.10 (m, 2H), 4.40 (s, 2H).

Step 2: methyl 2-(2-bromo-3-fluorophenyl)imidazo[1,2-a]pyridine-7-carboxylate (18-2): To a solution of 18-1 (0.30 g, 0.86 mmol, 1.0 eq) and methyl 2-aminoisonicotinate (0.13 g, 0.86 mmol, 1.0 eq) in DMF (5 mL) was added KHCO$_3$ (86 mg, 0.86 mmol, 1.0 eq). The mixture was stirred at 100° C. for 3 hours. The reaction mixture was quenched by addition water (50 mL), and then diluted with ethyl acetate (50 mL) and extracted with ethyl acetate (50 mL×3). The combined organic layers were washed with sat. brine (100 mL), dried over Na$_2$SO$_4$, filtered and concentrated under reduced pressure to give a residue. The residue was purified by column chromatography (SiO$_2$, Petroleum ether/Ethyl acetate=1:0 to 5:1) to give 18-2 (0.30 g, 0.69 mmol, 80% yield, 80% purity) as a yellow oil. LCMS: (ES+) m/z (M+H)$^+$=350.9. $^1$H NMR (400 MHz, CDCl$_3$) δ=8.43 (s, 1H), 8.25-8.20 (m, 1H), 8.00-7.90 (m, 1H), 7.50-7.45 (m, 1H), 7.45-7.35 (m, 1H), 7.25-7.15 (m, 2H), 3.99 (s, 3H).

Step 3: methyl 2-(2-(1,3-dimethyl-1H-pyrazol-4-yl)-3-fluorophenyl)imidazo[1,2-a]pyridine-7-carboxylate (18-3): To a solution of 18-2 (0.30 g, 0.69 mmol, 1.0 eq) and 1,3-dimethyl-4-(4,4,5,5-tetramethyl-1,3,2-dioxaborolan-2-yl)-1H-pyrazole (0.23 g, 1.0 mmol, 1.5 eq) in dioxane (5 mL) was added Cs$_2$CO$_3$ (0.67 g, 2.1 mmol, 3.0 eq) and (Cy)$_3$P-Pd G3 (51 mg, 69 μmol, 0.1 eq). The mixture was degassed and purged with N$_2$ for three times, and then stirred at 115° C. under N$_2$ for 5 hours. The reaction mixture was quenched by addition water (50 mL), and then diluted with ethyl acetate (50 mL) and extracted with ethyl acetate (50 mL×3). The combined organic layers were washed with sat. brine (50 mL), dried over Na$_2$SO$_4$, filtered and concentrated under reduced pressure to give a residue. The residue was purified by column chromatography (SiO$_2$, Petroleum ether/Ethyl acetate=1:0 to 0:1) to give 18-3 (0.20 g, 0.54 mmol, 78% yield, 98% purity) as a yellow oil. LCMS: (ES+) m/z (M+H)$^+$=365.1.

Step 4: methyl 3-chloro-2-(2-(1,3-dimethyl-1H-pyrazol-4-yl)-3-fluorophenyl)imidazo[1,2-a]pyridine-7-carboxylate (18-4): To a solution of 18-3 (0.18 g, 0.49 mmol, 1.0 eq) in DMF (2 mL) was added NCS (66 mg, 0.49 mmol, 1.0 eq) at 0° C. The mixture was stirred at 40° C. for 1 hour. The reaction mixture was quenched by addition water (30 mL), and then diluted with ethyl acetate (30 mL) and extracted with ethyl acetate (30 mL×3). The combined organic layers were washed with sat. brine (20 mL), dried over Na$_2$SO$_4$, filtered and concentrated under reduced pressure to give 18-4 (0.18 g, crude) as a yellow oil. LCMS: (ES+) m/z (M+H)$^+$=399.1.

Step 5: 3-chloro-2-(2-(1,3-dimethyl-1H-pyrazol-4-yl)-3-fluorophenyl)imidazo[1,2-a]pyridine-7-carboxylic acid (18-5): To a solution of 18-4 (0.18 g, 0.45 mmol, 1.0 eq) in i-PrOH (0.5 mL), THF (0.5 mL) and H$_2$O (0.5 mL) was added LiOH·H$_2$O (47 mg, 1.1 mmol, 2.5 eq). The mixture was stirred at 25° C. for 2 hours. The reaction mixture was concentrated under reduced pressure to give a residue. The residue was purified by prep-HPLC (0.1% FA condition) to give 18-5 (0.17 g, 0.39 mmol, 86% yield, 98% purity, FA) as a yellow solid. LCMS: (ES+) m/z (M+H)$^+$=385.0. $^1$H NMR (400 MHz, CDCl$_3$) δ=8.47 (s, 1H), 8.10-8.00 (m, 1H), 7.65-7.55 (m, 1H), 7.50-7.40 (m, 2H), 7.35-7.25 (m, 1H), 7.25-7.20 (m, 1H), 3.81 (s, 3H), 1.98 (s, 3H).

Step 6: 3-chloro-2-(2-(1,3-dimethyl-1H-pyrazol-4-yl)-3-fluorophenyl)-N-((3R,3aR,6R,6aR)-6-hydroxyhexahydrofuro[3,2-b]furan-3-yl)imidazo[1,2-a]pyridine-7-carboxamide (Compound 18): To a solution of 18-5 (0.15 g, 0.39 mmol, 1.0 eq) in DMF (2 mL) was added HATU (0.30 g, 0.78 mmol, 2.0 eq) and DIEA (0.15 g, 1.2 mmol, 3.0 eq). The mixture was stirred at 25° C. for 0.2 hr. Then (3R,3aR,6R,6aR)-6-aminohexahydrofuro[3,2-b]furan-3-ol (57 mg, 0.39 mmol, 1.0 eq) was added to the solution and the mixture was stirred at 25° C. for 0.8 hour. The reaction mixture was concentrated under reduced pressure to give a residue. The residue was purified by prep-HPLC (column: Phenomenex luna C18 150×25 mm×10 μm; mobile phase: [water (FA)-ACN]; gradient: 18%-48% B over 11 min) to give Compound 18 (62 mg, 29% yield, 99% purity, FA) as a white solid. LCMS: (ES+) m/z (M+H)$^+$=512.1. $^1$H NMR (400 MHz, CD$_3$OD) δ=8.31 (d, J=7.2 Hz, 1H), 8.10 (s, 1H), 7.55-7.47 (m, 2H), 7.45-7.40 (m, 1H), 7.37-7.29 (m, 1H), 7.26 (s, 1H), 4.70-4.63 (m, 2H), 4.59 (d, J=4.8 Hz, 1H), 4.33 (q, J=5.2 Hz, 1H), 4.25-4.15 (m, 1H), 4.00-3.90 (m, 1H), 3.80-3.75 (m, 1H), 3.69 (s, 3H), 3.67-3.62 (m, 1H), 1.91 (s, 3H).

Example 6: 3-chloro-2-(2-(1,3-dimethyl-1H-pyrazol-4-yl)-4,6-difluorophenyl)-N-((3R,3aR,6R,6aR)-6-hydroxyhexahydrofuro[3,2-b]furan-3-yl)imidazo[1,2-a]pyridine-7-carboxamide (Compound 787)

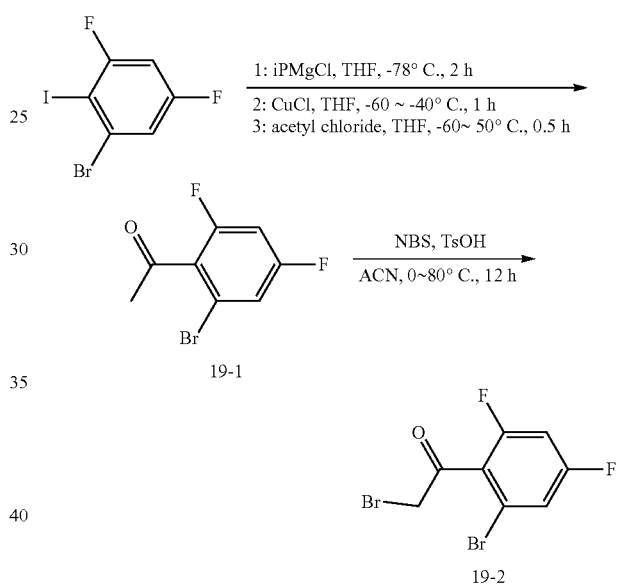

Step 1: 1-(2-bromo-4,6-difluorophenyl)ethan-1-one (19-1): A solution of 1-bromo-3,5-difluoro-2-iodo-benzene (50 g, 0.16 mol, 1 eq) in THF (50 mL) was degassed and purged with N$_2$ 3 times, then cooled to −78° C. and i-PrMgCl (2 M in THF, 94 mL, 1.2 eq) was added dropwise. The mixture was stirred for 2 hours. Then the temperature was raised to −60° C., and CuCl (11 g, 0.11 mol, 2.6 mL, 0.7 eq) was added. The solution was warmed to −40° C. over 1 hour, and then acetyl chloride (15 g, 0.19 mol, 13 mL, 1.2 eq) was added dropwise under N$_2$ atmosphere. After the temperature was warmed to 25° C., the solution was heated to 50° C. for 0.5 hour. The reaction mixture was quenched by addition of saturated aqueous NH$_4$Cl solution (200 mL) at 0° C., then extracted with EA (200 mL×3). The combined organic layers were washed with saturated aqueous sodium chloride solution (50 mL×2), dried over anhydrous Na$_2$SO$_4$, filtered and concentrated under reduced pressure to give a residue. The residue was purified by flash silica gel chromatography (ISCO®; 330 g SepaFlash® Silica Flash Column, Eluent of 0-5% Ethyl acetate/Petroleum ether gradient @ 100 mL/min) to give 19-1 (31 g, 84% yield) as a yellow oil. $^1$H NMR (400 MHz, CDCl$_3$) δ=7.18 (td, J=2, 8.0 Hz, 1H), 6.87 (dt, J=2.4, 9.0 Hz, 1H), 2.57 (d, J=1.2 Hz, 3H).

Step 2: 2-bromo-1-(2-bromo-4,6-difluorophenyl)ethan-1-one (19-2): A solution of 19-1 (25 g, 0.11 mol, 1 eq) in ACN (250 mL) was degassed and purged with N₂ 3 times, then NBS (28 g, 0.16 mol, 1.5 eq) and TsOH·H₂O (30 g, 0.16 mol, 1.5 eq) were added at 0° C. The mixture was stirred at 80° C. for 12 hours. The mixture was diluted with H₂O (300 mL) and extracted with EA (200 mL×3). The combined organic phase was washed with saturated brine (100 mL×2), dried with anhydrous Na₂SO₄, filtered and concentrated under reduced pressure to give a residue. The residue was purified by flash silica gel chromatography (ISCO®; 120 g SepaFlash® Silica Flash Column, Eluent of 0-5% Ethyl acetate/Petroleum ether gradient @ 100 mL/min) to give 19-2 (33 g, 75% yield) as a yellow oil. ¹H NMR (400 MHz, CDCl₃) δ=7.26-7.16 (m, 1H), 6.98-6.84 (m, 1H), 4.35 (s, 2H).

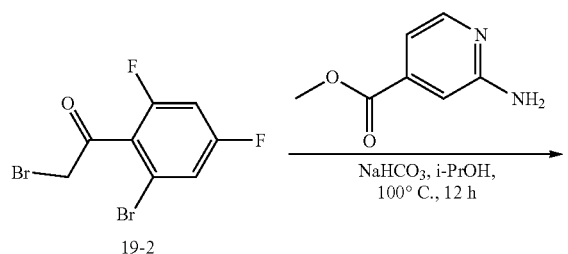

19-2

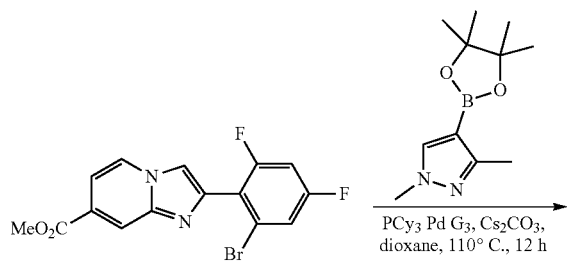

19-3

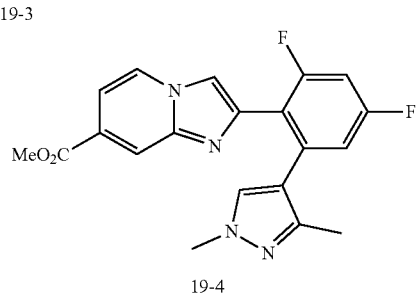

19-4

Step 3: methyl 2-(2-bromo-4,6-difluorophenyl)imidazo[1,2-a]pyridine-7-carboxylate (19-3): To a solution of 19-2 (33 g, 0.11 mol, 1 eq) and methyl 2-aminoisonicotinate (24 g, 0.16 mol, 1.5 eq) in i-PrOH (200 mL) was added NaHCO₃ (8.8 g, 0.11 mol, 4.1 mL, 1 eq). The mixture was degassed and purged with N₂ 3 times. The mixture was stirred at 100° C. for 12 hours. The mixture was diluted with H₂O (300 mL) and extracted with EA (200 mL×3). The combined organic layers were washed with saturated aqueous sodium chloride solution (100 mL×2), dried over anhydrous Na₂SO₄, filtered and concentrated under reduced pressure to give a residue. The residue was purified by flash silica gel chromatography (ISCO®; 120 g SepaFlash® Silica Flash Column, Eluent of 0~30% Ethyl acetate/Petroleum ether gradient @ 100 mL/min) to give 19-3 (35 g, 82% yield) a yellow solid. LCMS: (ES⁺) m/z (M+H)⁺=366.8. ¹H NMR (400 MHz, CDCl₃) δ=8.42 (s, 1H), 8.21 (d, J=6.8 Hz, 1H), 7.84 (s, 1H), 7.47 (dd, J=1.6, 7.2 Hz, 1H), 7.31 (td, J=2.1, 7.9 Hz, 1H), 6.95 (dt, J=2, 8 Hz, 1H), 3.98 (s, 3H).

Step 4: methyl 2-(2-(1,3-dimethyl-1H-pyrazol-4-yl)-4,6-difluorophenyl)imidazo[1,2-a]pyridine-7-carboxylate (19-4): A solution of 19-3 (35 g, 0.1 mol, 1 eq) and 1,3-dimethyl-4-(4,4,5,5-tetramethyl-1,3,2-dioxaborolan-2-yl)-1H-pyrazole (42 g, 0.2 mol, 2 eq) in dioxane (300 mL) was degassed and purged with N₂ 3 times. To the mixture was added Cs₂CO₃ (62 g, 0.19 mol, 2 eq) and [2-(2-aminophenyl)phenyl]-methylsulfonyloxy-palladium; dichloromethane; tricyclohexylphosphane (3.50 g, 4.8 mmol, 0.1 eq) under N₂ atmosphere. The mixture was stirred at 110° C. for 12 hours. The mixture was diluted with H₂O (500 mL) and extracted with EA (300 mL×3). The combined organic layers were washed with saturated aqueous sodium chloride solution (200 mL×2), dried over anhydrous Na₂SO₄, filtered and concentrated under reduced pressure to give a residue. The residue was purified by flash silica gel chromatography (ISCO®; 330 g SepaFlash® Silica Flash Column, Eluent of 0~70% Ethyl acetate/Petroleum ether gradient @ 100 mL/min) to give 19-4 (16 g, 43% yield) as a yellow solid. LCMS: (ES⁺) m/z (M+H)⁺=382.9.

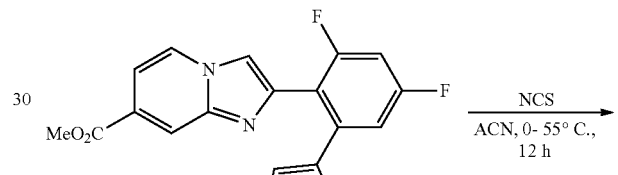

19-4

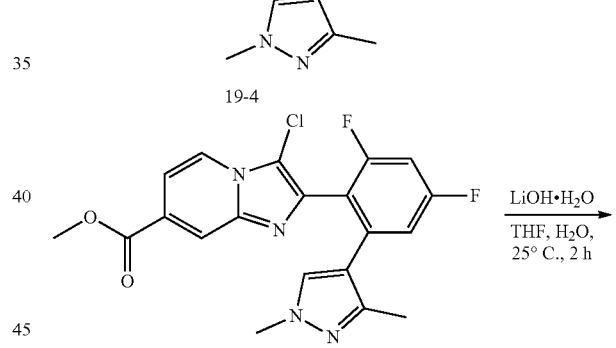

19-5

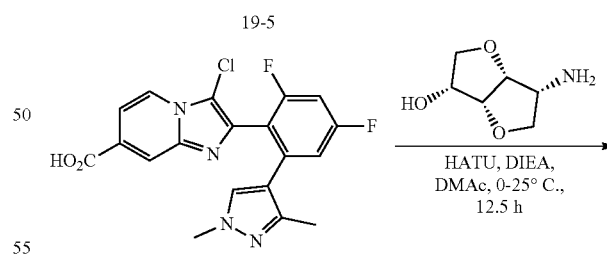

19-6

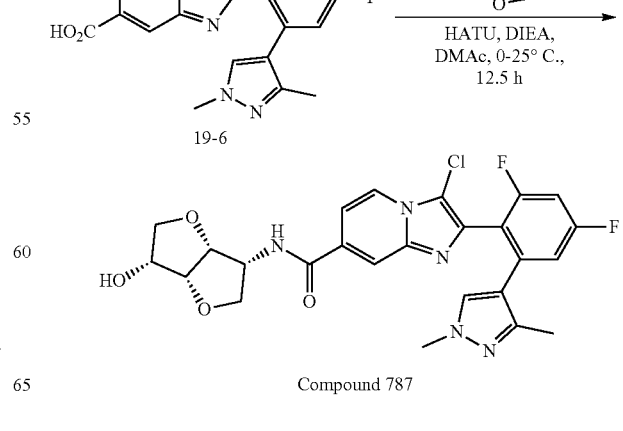

Compound 787

Step 5: methyl 3-chloro-2-(2-(1,3-dimethyl-1H-pyrazol-4-yl)-4,6-difluorophenyl)imidazo[1,2-a]pyridine-7-carboxylate (19-5): To a solution of 19-4 (16 g, 42 mmol, 1 eq) in ACN (200 mL) was added NCS (6.2 g, 46 mmol, 1.1 eq) at 0° C. The mixture was stirred at 55° C. for 12 hours. The mixture was diluted with H$_2$O (500 mL) and extracted with EA (300 mL×3). The combined organic layers were washed with saturated aqueous sodium chloride solution (200 mL×3), dried over anhydrous Na$_2$SO$_4$, filtered and concentrated under reduced pressure to give a residue. The residue was purified by flash silica gel chromatography (ISCO®; 330 g SepaFlash® Silica Flash Column, Eluent of 0~60% Ethyl acetate/Petroleum ether gradient @ 100 mL/min) to give 19-5 (16.6 g, 95% yield) as a yellow solid. LCMS: (ES$^+$) m/z (M+H)$^+$=416.9. $^1$H NMR (400 MHz, CD$_3$OD) δ=8.35 (d, J=7.2 Hz, 1H), 8.25 (s, 1H), 7.61 (dd, J=1.6, 7.2 Hz, 1H), 7.18 (s, 1H), 7.16-7.06 (m, 2H), 3.98 (s, 3H), 3.64 (s, 3H), 2.00 (s, 3H).

Step 6: 3-chloro-2-(2-(1,3-dimethyl-1H-pyrazol-4-yl)-4,6-difluorophenyl)imidazo[1,2-a]pyridine-7-carboxylic acid (19-6): To a solution of 19-5 (17 g, 40 mmol, 1 eq) in THF (80 mL) and H$_2$O (80 mL) was added LiOH·H$_2$O (3.3 g, 80 mmol, 2 eq) at 0° C. The mixture was stirred at 25° C. for 2 hours. The mixture was filtered and concentrated under reduced pressure to give a residue. The residue was purified by reversed-phase HPLC (Santai Technologies SepaFlash® cartridge 184.4×26.7 mm×40-60 µm; mobile phase: [A: water (0.1% FA), B: ACN]; B %: 45%-50%, 20 min) to give 19-6 (12 g, 67% yield) as a while solid. LCMS: (ES$^+$) m/z (M+H)$^+$=403. $^1$H NMR (400 MHz, METHANOL-d$_4$) δ=8.33 (d, J=7.2 Hz, 1H), 8.24 (s, 1H), 7.61 (dd, J=1.6, 7.2 Hz, 1H), 7.18 (s, 1H), 7.15-7.06 (m, 2H), 3.64 (s, 3H), 2.01 (s, 3H).

Step 7: 3-chloro-2-(2-(1,3-dimethyl-1H-pyrazol-4-yl)-4,6-difluorophenyl)-N-((3R,3aR,6R,6aR)-6-hydroxyhexahydrofuro[3,2-b]furan-3-yl)imidazo[1,2-a]pyridine-7-carboxamide (Compound 787): To a solution of 19-6 (3 g, 7.5 mmol, 1 eq) in DMAC (30 mL) was added HATU (5.7 g, 15 mmol, 2 eq) and DIPEA (3.9 g, 30 mmol, 5.2 mL, 4 eq) at 0° C. The mixture was stirred at 25° C. for 0.5 hour, then (3R,3aR,6R,6aR)-6-aminohexahydrofuro[3,2-b]furan-3-ol (1.4 g, 9.7 mmol, 1.3 eq) was added. The mixture was stirred at 25° C. for 12 hours. The mixture was filtered and concentrated under reduced pressure to give a residue. The residue was purified by prep-HPLC (column: Phenomenex luna C18 250×50 mm×10 µm; mobile phase: [A: water (0.1% FA), B: ACN]; B %: 25%-53%, 18 min) to give Compound 787 (1.9 g, 44% yield) as a white solid. LCMS: (ES$^+$) m/z (M+H)$^+$=530.1. $^1$H NMR (400 MHz, METHANOL-d$_4$) δ=8.35 (d, J=7.2 Hz, 1H), 8.10 (s, 1H), 7.52 (dd, J=1.6, 7.2 Hz, 1H), 7.18 (s, 1H), 7.16-7.05 (m, 2H), 4.70-4.61 (m, 2H), 4.59 (t, J=4.8 Hz, 1H), 4.37-4.29 (m, 1H), 4.24-4.15 (m, 1H), 3.95 (dd, J=6, 8.8 Hz, 1H), 3.81-3.73 (m, 1H), 3.70-3.60 (m, 4H), 1.99 (s, 3H).

Example 7: 3-chloro-2-(2-(3-chloro-1H-pyrazol-4-yl)-4,6-difluorophenyl)-N-(1-methyl-2-oxabicyclo[2.1.1]hexan-4-yl)imidazo[1,2-a]pyridine-7-carboxamide (Compound 788)

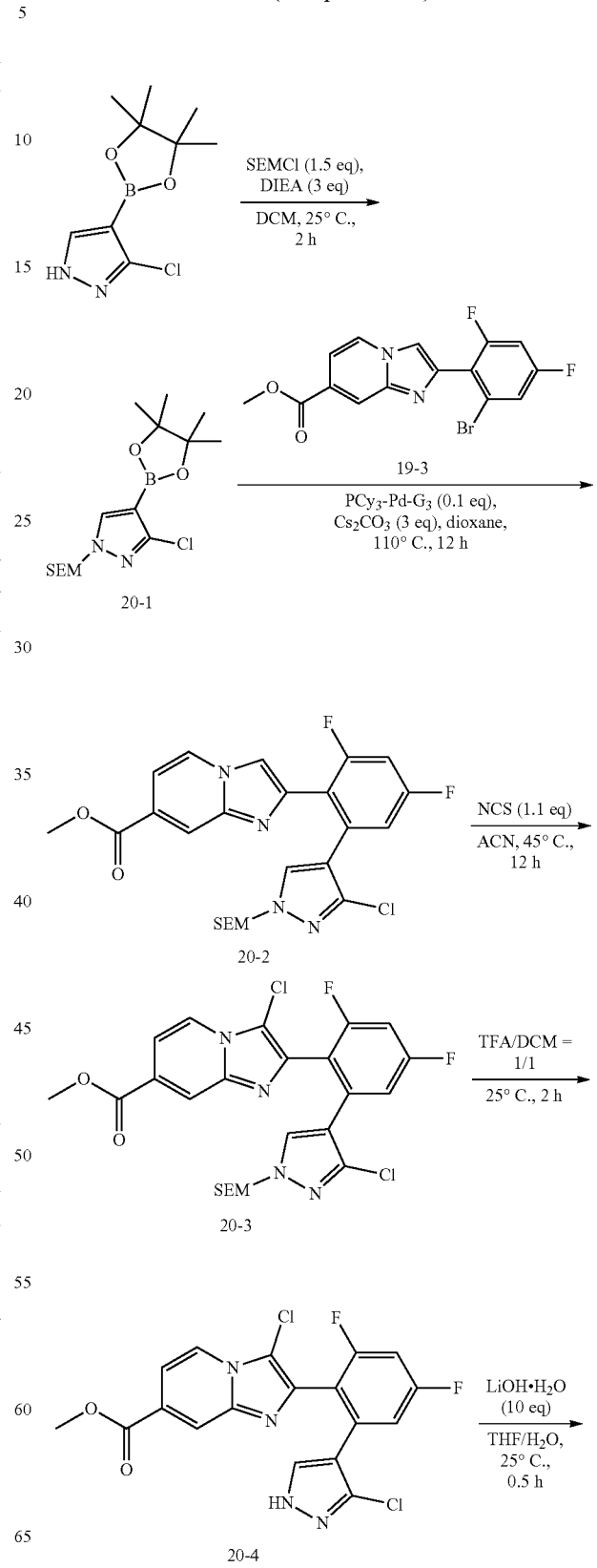

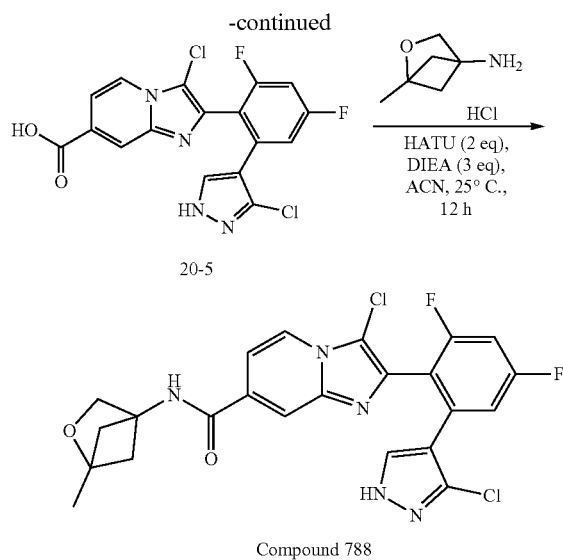

Step 1: 3-chloro-4-(4,4,5,5-tetramethyl-1,3,2-dioxaborolan-2-yl)-1-((2-(trimethylsilyl)ethoxy)methyl)-1H-pyrazole (20-1): To a solution of 3-chloro-4-(4,4,5,5-tetramethyl-1,3,2-dioxaborolan-2-yl)-1H-pyrazole (5.0 g, 22 mmol, 1.0 eq) in DCM (50 mL) was added DIEA (8.5 g, 66 mmol, 11.0 mL, 3.0 eq) and SEMCl (5.5 g, 33 mmol, 5.8 mL, 1.5 eq). The mixture was stirred at 25° C. for 2 hours. The reaction mixture was diluted with H$_2$O (100 mL) and extracted with EA (100 mL×2). The combined organic layers were washed with saturated brine (150 mL), dried over Na$_2$SO$_4$, filtered and concentrated under reduced pressure to give a residue. The residue was purified by flash silica gel chromatography (ISCO®; 80 g SepaFlash® Silica Flash Column, Eluent of 0~10% Ethyl acetate/Petroleum ether gradient @100 mL/min) to give 20-1 (6.0 g, 76% yield) as a yellow oil. $^1$H NMR (400 MHz, CD$_3$OD) δ=7.97 (s, 1H), 5.37 (s, 2H), 3.64-3.59 (t, J=7.6 Hz, 2H), 1.34 (s, 12H), 0.90 (t, J=7.6 Hz, 2H), 0.00 (s, 9H).

Step 2: methyl 2-(2-(3-chloro-1-((2-(trimethylsilyl)ethoxy)methyl)-1H-pyrazol-4-yl)-4,6-difluorophenyl)imidazo[1,2-a]pyridine-7-carboxylate (20-2): A solution of 19-3 (4.7 g, 13 mmol, 1.0 eq), 20-1 (6.0 g, 17 mmol, 1.3 eq) and Cs$_2$CO$_3$ (13.0 g, 38 mmol, 3.0 eq) in dioxane (50 mL) was degassed and purged with N$_2$ 3 times, then PCy$_3$-Pd-G$_3$ (0.9 mg, 1.3 mmol, 0.1 eq) was added to the reaction mixture under N$_2$ atmosphere. The mixture was stirred at 110° C. for 2 hours. The reaction mixture was diluted with H$_2$O (50 mL) and extracted with EA (50 mL×3). The combined organic layers were washed with saturated brine (50 mL×2), dried over Na$_2$SO$_4$, filtered and concentrated under reduced pressure to give a residue. The residue was purified by flash silica gel chromatography (ISCO®; 80 g SepaFlash® Silica Flash Column, Eluent of 20~30% Ethyl acetate/Petroleum ether gradient @ 100 mL/min) to give 20-2 (4.9 g, 74% yield) as a yellow oil. $^1$H NMR (400 MHz, CD$_3$OD) δ=8.55 (d, J=7.2 Hz, 1H), 8.23 (s, 1H), 8.04 (s, 1H), 7.52 (d, J=7.2 Hz, 1H), 7.39 (s, 1H), 7.24-7.20 (m, 2H), 5.46 (s, 2H), 4.02 (s, 3H), 3.58 (t, J=7.6 Hz, 2H), 0.88 (t, J=7.6 Hz, 2H), 0.00 (s, 9H).

Step 3: methyl 3-chloro-2-(2-(3-chloro-1-((2-(trimethylsilyl)ethoxy)methyl)-1H-pyrazol-4-yl)-4,6-difluorophenyl)imidazo[1,2-a]pyridine-7-carboxylate (20-3): To a solution of 20-2 (4.9 g, 9.4 mmol, 1.0 eq) in ACN (49 mL) was added NCS (1.5 g, 11 mmol, 1.2 eq). The mixture was stirred at 45° C. for 12 hours. The reaction mixture was diluted with H$_2$O (50 mL) and extracted with EA (50 mL×3). The combined organic layers were washed with saturated brine (60 mL), dried over Na$_2$SO$_4$, filtered and concentrated under reduced pressure to give a residue. The residue was purified by flash silica gel chromatography (ISCO®; 40 g SepaFlash® Silica Flash Column, Eluent of 15~15% Ethyl acetate/Petroleum ether gradient @ 100 mL/min) to give 20-3 (3.6 g, 66% yield) as a yellow oil. LCMS: (ES$^+$) m/z (M+H)$^+$=553.1. $^1$H NMR (400 MHz, CD$_3$OD) δ=8.44 (d, J=7.2 Hz, 1H), 8.30 (s, 1H), 7.68 (d, J=7.2 Hz, 1H), 7.56 (s, 1H), 7.32-7.28 (m, 2H), 5.45 (s, 2H), 4.04 (s, 3H), 3.55 (t, J=7.6 Hz, 2H), 0.86 (t, J=7.6 Hz, 2H), 0.00 (s, 9H).

Step 4: methyl 3-chloro-2-(2-(3-chloro-1H-pyrazol-4-yl)-4,6-difluorophenyl)imidazo[1,2-a]pyridine-7-carboxylate (20-4): To a solution of 20-3 (3.6 g, 6.3 mmol, 1.0 eq) in DCM (36 mL) was added TFA (0.5 mol, 36 mL, 77.0 eq). The mixture was stirred at 25° C. for 2 hours. The reaction mixture was concentrated under reduced pressure to give 20-4 (2.6 g, crude) as a yellow oil.

Step 5: 3-chloro-2-(2-(3-chloro-1H-pyrazol-4-yl)-4,6-difluorophenyl)imidazo[1,2-a]pyridine-7-carboxylic acid (20-5): To a solution of 20-4 (2.6 g, 6.1 mmol, 1.0 eq) in THF (26 mL) and H$_2$O (26 mL) was added LiOH·H$_2$O (2.6 g, 61 mmol, 10.0 eq). The mixture was stirred at 25° C. for 0.5 hour. The reaction mixture was adjusted to pH 5 by addition of 1 N aqueous HCl. The reaction mixture was filtered, and the residue concentrated under reduced pressure to give crude product. The crude product was triturated with MTBE (30 mL) at 25° C. for 10 min to give 2-5 (1.3 g, 52% yield) as a white solid. LCMS: (ES$^+$) m/z (M+H)$^+$=409.1. $^1$H NMR (400 MHz, CD$_3$OD) δ=8.36 (d, J=7.2 Hz, 1H), 8.24 (s, 1H), 7.62 (d, J=7.2 Hz, 1H), 7.34 (s, 1H), 7.26-7.14 (m, 2H).

Step 6: 3-chloro-2-(2-(3-chloro-1H-pyrazol-4-yl)-4,6-difluorophenyl)-N-(1-methyl-2-oxabicyclo[2.1.1]hexan-4-yl)imidazo[1,2-a]pyridine-7-carboxamide (Compound 788): To a solution of 20-5 (1.0 g, 2.0 mmol, 1.0 eq) in ACN (10 mL) was added HATU (1.5 g, 3.9 mmol, 2.0 eq) and DIEA (0.7 g, 5.9 mmol, 1.0 mL, 3.0 eq). The mixture was stirred at 25° C. for 0.5 hour. Then 1-methyl-2-oxabicyclo[2.1.1]hexan-4-amine hydrochloride (0.4 g, 2.4 mmol, 1.2 eq) was added. The mixture was stirred at 25° C. for 11.5 hr. The reaction mixture was quenched by addition H$_2$O (50 mL) and then extracted with EA (80 mL×3). The combined organic layers were washed with saturated brine (80 mL), dried over Na$_2$SO$_4$, filtered and concentrated under reduced pressure to give a residue. The residue was purified by prep-HPLC (column: Waters Xbridge BEH C18 250×50 mm×10 um; mobile phase: [A: water (0.5% NH$_4$HCO$_3$), B: ACN]; B %: 27%-57%, 10 min) to give Compound 788 (0.31 g, 33% yield) as a white solid. LCMS: (ES$^+$) m/z (M+H)$^+$=504.1. $^1$H NMR (400 MHz, CD$_3$OD) δ=8.37-8.36 (d, J=7.2 Hz, 1H), 8.07 (s, 1H), 7.52-7.50 (dd, J=7.2, 1.6 Hz, 1H), 7.35 (s, 1H), 7.24-7.15 (m, 2H), 3.91 (s, 2H), 2.11-2.06 (m, 2H), 2.03-1.98 (m, 2H), 1.46 (s, 3H).

213

Example 8: 3-chloro-N-(3-cyanobicyclo[1.1.1]pentan-1-yl)-2-(2,4-difluoro-6-(3-fluoro-1H-pyrazol-4-yl)phenyl)imidazo[1,2-a]pyridine-7-carboxamide (Compound 789)

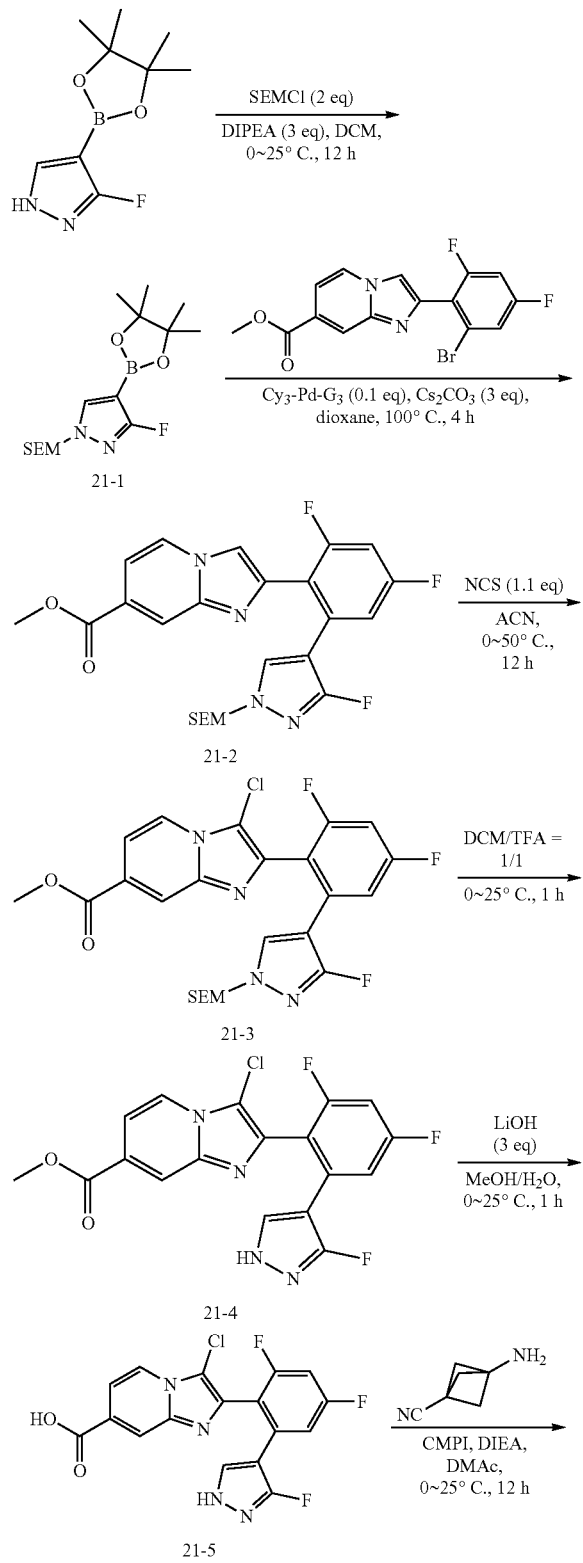

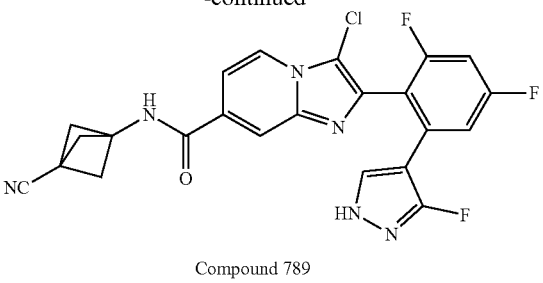

Compound 789

Step 1: 3-fluoro-4-(4,4,5,5-tetramethyl-1,3,2-dioxaborolan-2-yl)-1-((2-(trimethylsilyl)ethoxy)methyl)-1H-pyrazole (21-1): To a solution of 3-fluoro-4-(4,4,5,5-tetramethyl-1,3,2-dioxaborolan-2-yl)-1H-pyrazole (5 g, 24 mmol, 1 eq) in DCM (50 mL) was added the DIEA (9.1 g, 71 mmol, 12 mL, 3 eq) and SEM-Cl (5.9 g, 35 mmol, 6.3 mL, 1.5 eq) at 0° C. The mixture was stirred at 25° C. for 12 hours under $N_2$. The mixture was diluted with $H_2O$ (50 mL) and extracted with EA (50 mL×3). The combined organic layers were washed with saturated brine (50 mL×2), dried over $Na_2SO_4$, filtered and concentrated under reduced pressure to give residue. The residue was purified by flash silica gel chromatography (ISCO®; 40 g SepaFlash® Silica Flash Column, Eluent of 0~20% Ethyl acetate/Petroleum ether gradient @100 mL/min) to give 21-1 (6 g, 70% yield) as yellow oil. $^1$HNMR (400 MHz, $CDCl_3$) δ=7.70-7.61 (m, 1H), 5.37-5.25 (m, 2H), 3.66-3.59 (m, 2H), 0.93 (br t, J=8.4 Hz, 2H), 0.00 (s, 9H).

Step 2: methyl 2-(2,4-difluoro-6-(3-fluoro-1-((2-(trimethylsilyl)ethoxy)methyl)-1H-pyrazol-4-yl)phenyl)imidazo[1,2-a]pyridine-7-carboxylate (21-2): To a solution of 19-3 (5 g, 0.14 mol, 1 eq) and 21-1 (6 g, 0.18 mol, 1.3 eq) in dioxane (50 mL) was added the $Cs_2CO_3$ (13 g, 0.41 mol, 3 eq) and $Cy_3P$-Pd-$G_3$ (885.43 mg, 1.4 mmol, 0.1 eq) under $N_2$. The mixture was stirred at 100° C. for 4 hours under $N_2$. The mixture was diluted with $H_2O$ (60 mL) and extracted with EA (60 mL×3). The combined organic layers were washed with saturated brine (50 mL×2), dried over $Na_2SO_4$, filtered and concentrated under reduced pressure to give residue. The residue was purified by flash silica gel chromatography (ISCO®; 40 g SepaFlash® Silica Flash Column, Eluent of 0~40% Ethyl acetate/Petroleum ether gradient @ 100 mL/min) to give 21-2 (6 g, 74% yield) as yellow oil. $^1$HNMR (400 MHz, $CDCl_3$) δ=8.30 (s, 1H), 8.14 (d, J=7.1 Hz, 1H), 7.69 (s, 1H), 7.43 (d, J=7.2 Hz, 1H), 7.07 (d, J=9.2 Hz, 1H), 6.96 (d, J=2.4 Hz, 1H), 6.89 (br t, J=9.2 Hz, 1H), 5.27-5.10 (m, 2H), 3.96 (s, 3H), 3.60-3.45 (m, 2H), 0.88 (t, J=8.0 Hz, 2H), −0.02-−0.05 (m, 9H).

Step 3: methyl 3-chloro-2-(2,4-difluoro-6-(3-fluoro-1-((2-(trimethylsilyl)ethoxy)methyl)-1H-pyrazol-4-yl)phenyl)imidazo[1,2-a]pyridine-7-carboxylate (21-3): To a solution of 21-2 (7 g, 0.14 mol, 1 eq) in ACN (60 mL) was added NCS (2.1 g, 0.15 mol, 1.1 eq) at 0° C. The mixture was stirred at 50° C. for 12 hours under $N_2$. The mixture was diluted with $H_2O$ (60 mL) and extracted with EA (50 mL×3). The combined organic layers were washed with saturated brine (50 mL×2), dried over $Na_2SO_4$, filtered and concentrated under reduced pressure to give residue. The residue was purified by flash silica gel chromatography (ISCO®; 40 g SepaFlash® Silica Flash Column, Eluent of 0~10% Ethyl acetate/Petroleum ether gradient @ 100 mL/min) to give 21-3 (4 g, 60% yield) as yellow oil. $^1$HNMR (400 MHz, $CDCl_3$) δ=8.34 (s, 1H), 8.10 (d, J=7.2 Hz, 1H), 7.58 (dd, $J_1$=1.6 Hz, $J_2$=7.2 Hz, 1H), 7.10 (br d, J=8.4 Hz, 1H), 6.93

(dt, $J_1$=2.4 Hz, $J_2$=8.8 Hz, 1H), 6.86 (d, J=2.8 Hz, 1H), 5.27-5.08 (m, 2H), 3.99 (s, 3H), 3.64-3.47 (m, 2H), 0.96-0.83 (m, 2H), −0.02-−0.04 (m, 9H).

Step 4: methyl 3-chloro-2-(2,4-difluoro-6-(3-fluoro-1H-pyrazol-4-yl)phenyl)imidazo[1,2-a]pyridine-7-carboxylate (21-4): To a solution of 21-3 (4 g, 7.5 mmol, 1 eq) in DCM (10 mL) was added the TFA (14 g, 0.12 mol, 10 mL, 16 eq) at 0° C. The mixture was stirred at 25° C. for 1 hour. The mixture was diluted with $H_2O$ (50 mL) and extracted with EA (60 mL×3). The combined organic layers were washed with saturated brine (50 mL×2), dried over $Na_2SO_4$, filtered and concentrated under reduced pressure to give 21-4 (1.8 g, 56% yield) as yellow oil. LCMS:(ES+) m/z (M+H)$^+$=406.9.

Step 5: 3-chloro-2-(2,4-difluoro-6-(3-fluoro-1H-pyrazol-4-yl)phenyl)imidazo[1,2-a]pyridine-7-carboxylic acid (21-5): To a solution of 21-4 (1.8 g, 4.4 mmol, 1 eq) in MeOH (8 mL) and $H_2O$ (8 mL) was added the LiOH·$H_2O$ (0.55 g, 0.13 mol, 3 eq) at 0° C. The mixture was stirred at 25° C. for 1 hour. The reaction mixture was concentrated in vacuo to give a residue. The crude product was purified by reversed-phase HPLC (Column 80 g Flash Column Agela Flash Spherical C8 20-35 µm; 100 Å Flow rate 65 mL/min, Mobile phase: (A: $H_2O$ (0.1% $NH_4HCO_3$), B: ACN), Gradient B %: 15-30%, 40 min) to give 21-5 (1.0 g, 55% yield) as a white solid. LCMS:(ES+) m/z (M+H)$^+$=393.0. $^1$HNMR (400 MHz, $CD_3OD$) δ=8.30 (d, J=7.2 Hz, 1H), 8.19 (s, 1H), 7.68 (d, J=7.2 Hz, 1H), 7.24 (br d, J=9.6 Hz, 1H), 7.11 (dt, J1=2.4 Hz, J2=9.2 Hz, 1H), 7.01 (d, J=1.6 Hz, 1H).

Step 6: 3-chloro-N-(3-cyanobicyclo[1.1.1]pentan-1-yl)-2-(2,4-difluoro-6-(3-fluoro-1H-pyrazol-4-yl)phenyl)imidazo[1,2-a]pyridine-7-carboxamide (Compound 789): To a solution of 21-5 (0.5 g, 1.3 mmol, 1 eq) in DMAc (1 mL) was added DIEA (0.5 g, 3.8 mmol, 0.66 mL, 3 eq) and CMPI (0.65 g, 2.5 mmol, 2 eq) at 0° C. The mixture was stirred at 0° C. for 0.5 hr. Then 3-aminobicyclo[1.1.1]pentane-1-carbonitrile (0.21 g, 1.9 mmol, 1.5 eq) was added at 0° C. The mixture was stirred at 25° C. for 11.5 hours. The mixture was diluted with $H_2O$ (60 mL) and extracted with EA (50 mL×3). The combined organic layers were washed with saturated brine (50 mL×2), dried over $Na_2SO_4$, filtered and concentrated under reduced pressure to give residue. The crude product was purified by reversed-phase HPLC (Column 80 g Flash Column Agela Flash Spherical C8 20-35 µm; 100 A Flow rate 65 mL/min, Mobile phase (A: $H_2O$ (0.1% $NH_4HCO_3$), B: ACN), Gradient B %: 30-60%, 10 min) to give Compound 789 (0.22 g, 35% yield) as a white solid. LCMS:(ES+) m/z (M+H)$^+$=483.0. $^1$HNMR (400 MHz, $CD_3OD$) δ=8.40 (d, J=7.2 Hz, 1H), 8.06 (s, 1H), 7.51 (d, J=7.2 Hz, 1H), 7.24 (br d, J=4.0 Hz, 1H), 7.17-7.07 (m, 2H), 2.66 (s, 6H).

Example 9: 3-chloro-2-(2,4-difluoro-6-(3-fluoro-1H-pyrazol-4-yl)phenyl)-N-(1-methyl-2-oxabicyclo[2.1.1]hexan-4-yl)imidazo[1,2-a]pyridine-7-carboxamide (Compound 790)

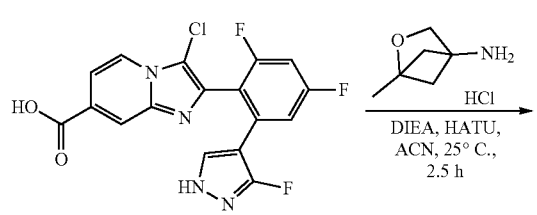

Compound 790

Step 1: 3-chloro-2-(2,4-difluoro-6-(3-fluoro-1H-pyrazol-4-yl)phenyl)-N-(1-methyl-2-oxabicyclo[2.1.1]hexan-4-yl)imidazo[1,2-a]pyridine-7-carboxamide (Compound 790): To a solution of 21-5 (0.35 g, 0.89 mmol, 1.0 eq) in ACN (4.0 mL) was added dropwise DIEA (0.35 g, 2.7 mmol, 0.47 µL, 3.0 eq) and HATU (0.51 g, 1.3 mmol, 1.5 eq). The mixture was stirred at 25° C. for 30 min, and then 1-methyl-2-oxabicyclo[2.1.1]hexan-4-amine hydrochloride (0.15 g, 0.98 mmol, 1.1 eq) was added. The resulting mixture was stirred at 25° C. for 2 hours. The reaction mixture was filtered, and the filtrate was concentrated under reduced pressure. The residue was purified by prep-HPLC (column: Waters Xbridge 150×25 mm×5 um; mobile phase: [water (0.1% $NH_3·H_2O$), B: ACN]; B %: 26%-56%, 12 min) to give Compound 790 (0.16 g, 36% yield) as a white solid. LCMS:(ES+) m/z (M+H)$^+$=488.1. $^1$HNMR (400 MHz, $CD_3OD$) δ=8.41 (d, J=7.2 Hz, 1H), 8.10 (s, 1H), 7.54 (d, J=7.2 Hz, 1H), 7.23 (dd, J=1.6, 8.2 Hz, 1H), 7.15 (s, 1H), 7.14-7.09 (m, 1H), 3.91 (s, 2H), 2.13-2.05 (m, 2H), 2.05-1.97 (m, 2H), 1.47 (s, 3H).

Example 10: 3-chloro-2-(2-fluoro-6-(3-fluoro-1-methyl-1H-pyrazol-4-yl)phenyl)-N-((1s,3s)-3-hydroxy-3-methylcyclobutyl)imidazo[1,2-a]pyridine-7-carboxamide (Compound 791)

Step 1: 2-bromo-1-(2-bromo-6-fluorophenyl)ethan-1-one (22-1): To a solution of 1-(2-bromo-6-fluorophenyl)ethan-1-one (20 g, 92 mmol, 1 eq) in ACN (200 mL) was added NBS (20 g, 0.11 mmol, 1.2 eq) and TsOH (24 g, 0.14 mol, 1.5 eq) at 0° C. The mixture was stirred at 60° C. for 12 hours. The reaction mixture was diluted with H₂O (300 mL) and extracted with EA (200 mL×3). The combined organic layers were washed with saturated brine (200 mL), dried over Na₂SO₄, filtered and concentrated under reduced pressure to give a residue. The residue was purified by flash silica gel chromatography (ISCO®; 220 g SepaFlash® Silica Flash Column, Eluent of 0~5% Ethyl acetate/Petroleum ether gradient @ 100 mL/min) to give 22-1 (33 g, 79% yield) as a yellow oil. ¹H NMR (400 MHz, CDCl₃) δ=7.45 (d, J=8.0 Hz, 1H), 7.32 (dt, J=6.0, 8.4 Hz, 1H), 7.17-7.11 (m, 1H), 4.39 (s, 2H).

Step 2: methyl 2-(2-bromo-6-fluorophenyl)imidazo[1,2-a]pyridine-7-carboxylate (22-2): To a solution of 22-1 (33 g, 73.60 mmol, 1 eq) and methyl 2-aminoisonicotinate (13 g, 88 mmol, 1.2 eq) in toluene (300 mL) was added NaHCO₃ (7.8 g, 88 mmol, 1 eq). The mixture was stirred at 110° C. for 12 hours. The reaction mixture was diluted with H₂O (400 mL) and extracted with EA (300 mL×3). The combined organic layers were washed with saturated brine (300 mL), dried over Na₂SO₄, filtered and concentrated under reduced pressure to give a residue. The residue was purified by flash silica gel chromatography (ISCO®; 330 g SepaFlash® Silica Flash Column, Eluent of 0~50% Ethyl acetate/Petroleum ether gradient @ 100 mL/min) to give 22-2 (16 g, 60% yield) as a yellow solid. LCMS: (ES⁺) m/z (M+H)⁺=349.8. ¹H NMR (400 MHz, CDCl₃) δ=8.57 (d, J=7.2 Hz, 1H), 8.28 (s, 1H), 8.16 (s, 1H), 7.59 (d, J=8.0 Hz, 1H), 7.49 (dd, J=1.6, 7.2 Hz, 1H), 7.40 (dt, J=6.0, 8.4 Hz, 1H), 7.32-7.19 (m, 1H), 3.98 (s, 3H).

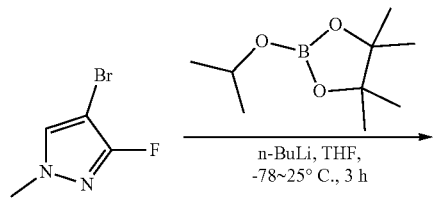

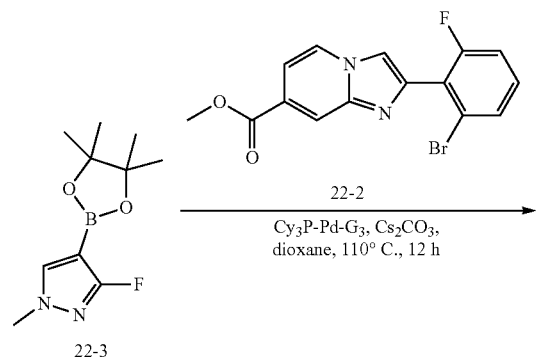

22-2
Cy₃P-Pd-G₃, Cs₂CO₃,
dioxane, 110° C., 12 h

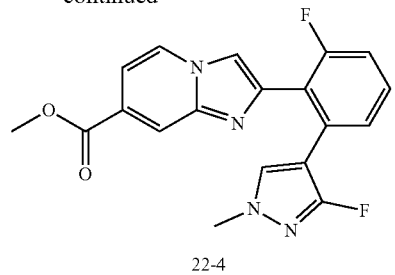

22-4

Step 3: 3-fluoro-1-methyl-4-(4,4,5,5-tetramethyl-1,3,2-dioxaborolan-2-yl)-1H-pyrazole (22-3): A mixture of 4-bromo-3-fluoro-1-methyl-1H-pyrazole (1.0 g, 5.6 mmol, 1 eq) and 2-isopropoxy-4,4,5,5-tetramethyl-1,3,2-dioxaborolane (3.1 g, 17 mmol, 3.4 mL, 3 eq) in THF (10 mL) was degassed and purged with N₂ 3 times, and then n-BuLi (2.5 M in n-hexane, 3.4 mL, 1.5 eq) was added dropwise at −78° C. under N₂ atmosphere. The mixture was stirred at −78° C. for 1 hour and at 25° C. for 2 hrs under N₂ atmosphere. The reaction mixture was quenched by addition of saturated aqueous NH₄Cl solution (20 mL) and extracted with EA (20 mL×3). The combined organic layers were washed with saturated brine (20 mL), dried over Na₂SO₄, filtered and concentrated under reduced pressure to give a residue. The residue was purified by flash silica gel chromatography (ISCO®; 20 g SepaFlash® Silica Flash Column, Eluent of 0~20% Ethyl acetate/Petroleum ether gradient @ 50 mL/min) to give 22-3 (0.5 g, 33% yield) as a yellow solid. LCMS: (ES⁺) m/z (M+H)⁺=227.1. ¹H NMR (400 MHz, CDCl₃) δ=7.44 (d, J=1.6 Hz, 1H), 3.76 (s, 3H), 1.32 (s, 12H).

Step 4: methyl 2-(2-fluoro-6-(3-fluoro-1-methyl-1H-pyrazol-4-yl)phenyl)imidazo[1,2-a]pyridine-7-carboxylate (22-4): To a solution of 22-3 (0.5 g, 1.9 mmol, 1.2 eq) and 22-2 (0.55 g, 1.6 mmol, 1 eq) in dioxane (10 mL) was added Cs₂CO₃ (1.5 g, 4.7 mmol, 3 eq) and Cy₃P Pd G3 (0.10 g, 0.16 mmol, 0.1 eq). The reaction mixture was degassed and purged with N₂ 3 times, then stirred at 110° C. for 12 hrs. The reaction mixture was diluted with H₂O (20 mL) and extracted with EA (20 mL×3). The combined organic layers were washed with saturated brine (20 mL), dried over Na₂SO₄, filtered and concentrated under reduced pressure to give a residue. The residue was purified by flash silica gel chromatography (ISCO®; 12 g SepaFlash® Silica Flash Column, Eluent of 0~50% Ethyl acetate/Petroleum ether gradient @ 50 mL/min) to give 22-4 (0.4 g, 62% yield) as a yellow solid. LCMS: (ES⁺) m/z (M+H)⁺=369.0. ¹H NMR (400 MHz, CD₃OD) δ=8.51 (d, J=7.2 Hz, 1H), 8.21 (s, 1H), 7.99 (s, 1H), 7.53-7.43 (m, 2H), 7.34 (br d, J=8.0 Hz, 1H), 7.20 (br s, 2H) 3.97 (s, 3H), 3.63 (s, 3H).

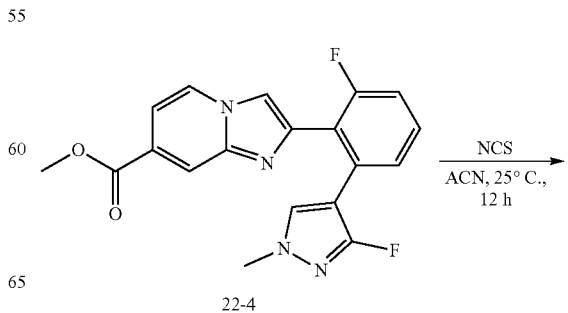

22-4
NCS
ACN, 25° C.,
12 h

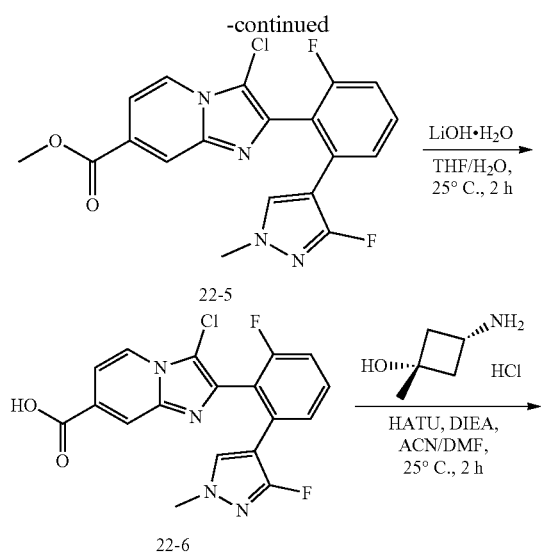

Step 5: methyl 3-chloro-2-(2-fluoro-6-(3-fluoro-1-methyl-1H-pyrazol-4-yl)phenyl)imidazo[1,2-a]pyridine-7-carboxylate (22-5): A solution of 22-4 (0.3 mg, 0.81 mmol, 1 eq) in ACN (1 mL) was added NCS (0.13 mg, 0.98 mmol, 1.2 eq) at 0° C. The mixture was stirred at 25° C. for 12 hr. The reaction mixture was diluted with H₂O (20 mL) and extracted with EA (20 mL×3). The combined organic layers were washed with saturated brine (20 mL), dried over Na₂SO₄, filtered and concentrated under reduced pressure to give a residue. The residue was purified by flash silica gel chromatography (ISCO®; 20 g SepaFlash® Silica Flash Column, Eluent of 0~50% Ethyl acetate/Petroleum ether gradient @ 50 mL/min) to give 22-5 (0.3 g, 91% yield) as a yellow oil. ¹H NMR (400 MHz, CD₃OD) δ=8.42 (d, J=7.2 Hz, 1H), 8.27 (s, 1H), 7.73-7.62 (m, 1H), 7.61 (s, 1H), 7.40 (br d, J=7.6 Hz, 1H), 7.28-7.20 (m, 1H), 7.17 (s, 1H), 3.99 (s, 3H), 3.61 (s, 3H).

Step 6: 3-chloro-2-(2-fluoro-6-(3-fluoro-1-methyl-1H-pyrazol-4-yl)phenyl)imidazo[1,2-a]pyridine-7-carboxylic acid (22-6): To a solution of 22-5 (0.3 g, 0.74 mmol, 1 eq) in THF (3 mL) and H₂O (1.5 mL) was added LiOH·H₂O (93 mg, 2.2 mmol, 3 eq) under 25° C. The mixture was stirred at 25° C. for 2 hr. The reaction mixture was adjusted to pH 7 with 2 N aqueous HCl. The reaction mixture was filtered and concentrated under vacuum to give 22-6 (0.3 g, crude) as a yellow solid.

Step 7: 3-chloro-2-(2-fluoro-6-(3-fluoro-1-methyl-1H-pyrazol-4-yl)phenyl)-N-((1s,3s)-3-hydroxy-3-methylcyclobutyl)imidazo[1,2-a]pyridine-7-carboxamide (Compound 791): To a solution of 22-6 (0.15 g, 0.36 mmol, 1 eq) in ACN (1.5 mL) and DMF (1.5 mL) was added HATU (0.22 g, 0.58 mmol, 1.5 eq), DIEA (0.25 g, 1.9 mmol, 0.34 mL, 5 eq), and (1s,3s)-3-amino-1-methylcyclobutan-1-ol hydrochloride (78 mg, 0.57 mmol, 1.5 eq) under 25° C. The mixture was stirred at 25° C. for 2 hr. The reaction mixture was poured into H₂O (40 mL) and extracted with EA (40 mL×3). The reaction mixture was adjusted to pH 7 with 2N aqueous HCl. The reaction mixture was filtered and concentrated under vacuum to give a residue. The residue was purified by prep-HPLC (column: Welch Xtimate C18 150× 25 mm×5 μm; mobile phase: [A: water (0.1% FA), B: ACN]; B %: 20%-40%, 15 min) to give Compound 791 (87 mg, 40% yield) as a white solid. LCMS: (ES⁺) m/z (M+H)⁺= 472.1. ¹H NMR (400 MHz, CD₃OD) δ=8.39 (d, J=7.2 Hz, 1H), 8.08 (s, 1H), 7.62-7.49 (m, 2H), 7.39 (d, J=7.6 Hz, 1H), 7.23 (t, J=8.8 Hz, 1H), 7.16 (d, J=1.6 Hz, 1H), 4.10 (quin, J=8.0 Hz, 1H), 3.60 (s, 3H), 2.59-2.43 (m, 2H), 2.25-2.09 (m, 2H), 1.40 (s, 3H).

Example 11: 3-chloro-2-(2-fluoro-6-(3-fluoro-1-methyl-1H-pyrazol-4-yl)phenyl)-N-(1-(hydroxymethyl)-2-oxabicyclo[2.2.1]heptan-4-yl)imidazo[1,2-a]pyridine-7-carboxamide, first eluting enantiomer, and 3-chloro-2-(2-fluoro-6-(3-fluoro-1-methyl-1H-pyrazol-4-yl)phenyl)-N-(1-(hydroxymethyl)-2-oxabicyclo[2.2.1]heptan-4-yl)imidazo[1,2-a]pyridine-7-carboxamide, second eluting enantiomer (Compound 920)

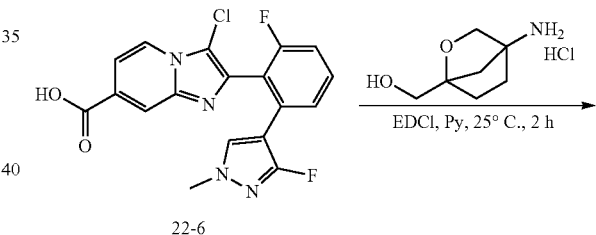

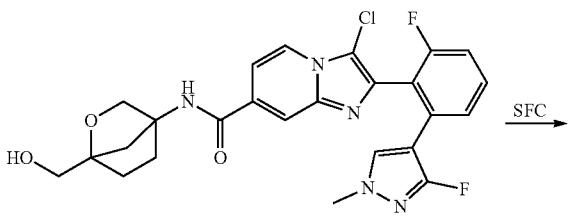

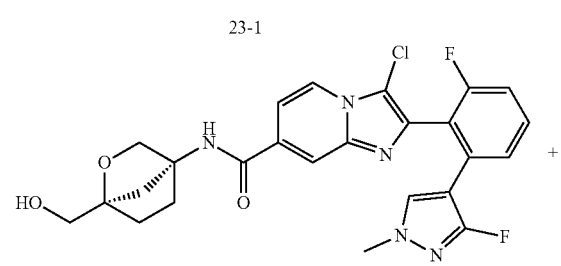

first eluting enantiomer
*sterochemistry abritarily assigned

-continued

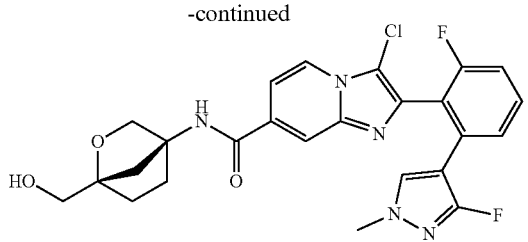

second eluting enantiomer
*sterochemistry abritarily assigned

Compound 920

Step 1: 3-chloro-2-(2-fluoro-6-(3-fluoro-1-methyl-1H-pyrazol-4-yl)phenyl)-N-(1-(hydroxymethyl)-2-oxabicyclo[2.2.1]heptan-4-yl)imidazo[1,2-a]pyridine-7-carboxamide (23-1): To a solution of 22-6 (0.20 g, 0.47 mmol, 1 eq, HCl salt) in pyridine (4 mL) was added EDCI (0.27 g, 1.4 mmol, 3 eq) and (4-amino-2-oxabicyclo[2.2.1]heptan-1-yl)methanol (92.90 mg, 0.52 mmol, 1.1 eq, HCl salt). The mixture was stirred at 25° C. for 2 hrs. The reaction mixture was diluted with water (10 mL), and then extracted with ethyl acetate (10 mL×3). The combined organic layers were washed with saturated brine (10 mL), dried over $Na_2SO_4$, filtered and concentrated under reduced pressure to give a residue. The residue was purified by flash silica gel chromatography (ISCO®; 20 g SepaFlash® Silica Flash Column, Eluent of 30~50% Ethyl acetate/Dichloromethane gradient @ 80 mL/min) and prep-HPLC (column: Santai Technologies SepaFlash® cartridge 184×21.4 mm, 40-60 μm; mobile phase: [A: water (0.1% FA), B: ACN]; B %: 30%-40%) to give 23-1 (0.14 g, 50% yield) as a yellow oil. LCMS: (ES+) m/z $(M+H)^+$=514.1.

Step 2: 3-chloro-2-(2-fluoro-6-(3-fluoro-1-methyl-1H-pyrazol-4-yl)phenyl)-N-(1-(hydroxymethyl)-2-oxabicyclo[2.2.1]heptan-4-yl)imidazo[1,2-a]pyridine-7-carboxamide, first eluting enantiomer, and 3-chloro-2-(2-fluoro-6-(3-fluoro-1-methyl-1H-pyrazol-4-yl)phenyl)-N-(1-(hydroxymethyl)-2-oxabicyclo[2.2.1]heptan-4-yl)imidazo[1,2-a]pyridine-7-carboxamide, second eluting enantiomer (Compound 920): 23-1 was purified by SFC (column: Phenomenex-Cellulose-2 (250 mm×30 mm, 10 um); mobile phase: [$CO_2$-MeOH (0.1% $NH_3 \cdot H_2O$)]; B %:55%, isocratic elution mode) to give Compound 920 (45.86 mg, 32% yield) as an off-white solid. LCMS: (ES+) m/z $(M+H)^+$=514.2. $^1$H NMR (400 MHz, $CD_3OD$) δ 9.21 (s, 1H), 8.20 (s, 1H), 7.58-7.52 (m, 3H), 7.41-7.39 (d, J=8.0 Hz, 1H), 6.96-6.95 (d, J=4.0 Hz, 2H), 6.94-6.86 (m, 1H), 2.99 (s, 3H), 2.74-2.71 (m, 2H), 2.69 (s, 3H), 2.1 (s, 3H), 0.92-0.88 (t, J=7.6 Hz, 3H).

Example 12: trans 3-chloro-2-(2-fluoro-6-(3-fluoro-1-methyl-1H-pyrazol-4-yl)phenyl)-N-(6-hydroxyspiro[3.3]heptan-2-yl)imidazo[1,2-a]pyridine-7-carboxamide (Compound 921)

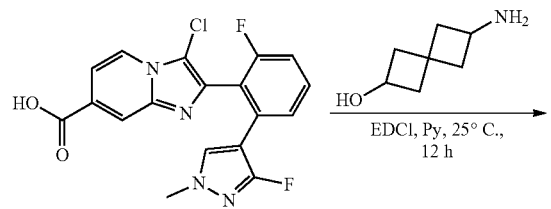

-continued

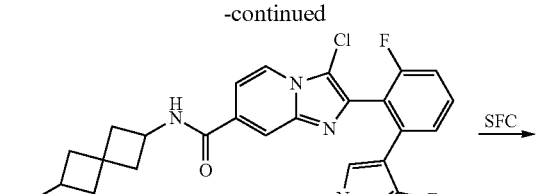

24-1

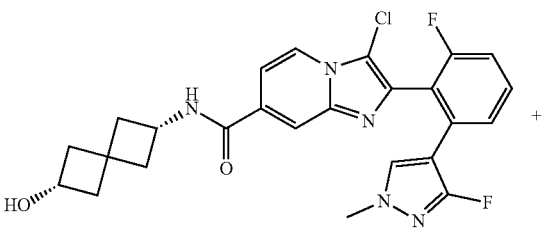

first eluting isomer
*sterochemistry abritarily assigned

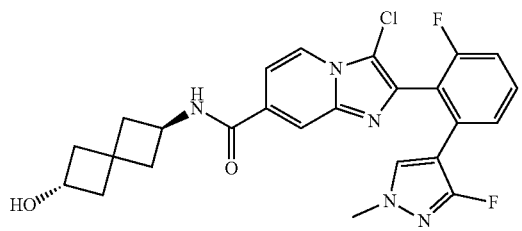

second eluting isomer
*sterochemistry abritarily assigned

Compound 921

Step 1: 3-chloro-2-(2-fluoro-6-(3-fluoro-1-methyl-1H-pyrazol-4-yl)phenyl)-N-(6-hydroxyspiro[3.3]heptan-2-yl)imidazo[1,2-a]pyridine-7-carboxamide (24-1): To a solution of 22-6 (0.20 g, 0.51 mmol, 1 eq) and 6-aminospiro[3.3]heptan-2-ol (78.52 mg, 0.62 mmol, 1.2 eq) in pyridine (3 mL) was added EDCI (0.30 g, 1.54 mmol, 3 eq). The mixture was stirred at 25° C. for 12 hrs. The reaction mixture was diluted with water (10 mL), and then extracted with ethyl acetate (20 mL×3). The combined organic layers were washed with saturated brine (10 mL), dried over $Na_2SO_4$, filtered and concentrated under reduced pressure to give a residue. The residue was purified by flash silica gel chromatography (ISCO®; 12 g SepaFlash® Silica Flash Column, Eluent of 80~100% Ethyl acetate/Petroleum ether gradient @ 50 mL/min) to give 24-1 (170 mg, 62% yield) as a yellow solid. LCMS: (ES$^+$) m/z $(M+H)^+$=498.0.

Step 2: Trans 3-chloro-2-(2-fluoro-6-(3-fluoro-1H-pyrazol-4-yl)phenyl)-N-(6-hydroxyspiro[3.3]heptan-2-yl)imidazo[1,2-a]pyridine-7-carboxamide (Compound 921): 24-1 (0.17 g, 0.34 mmol, 1 eq) was purified by SFC (column: DAICEL CHIRALPAK AD (250 mm×30 mm, 10 um); mobile phase: [A: $CO_2$; B: i-PrOH]; B %: 40%, isocratic elution mode) to give Compound 921 (22.9 mg, 13% yield) as a white solid. LCMS: (ES+) m/z $(M+H)^+$= 498.2. $^1$H NMR (400 MHz, DMSO) δ=8.83-8.31 (d, J=7.2 Hz, 1H), 8.46-8.44 (d, J=7.2 Hz, 1H), 8.18 (s, 1H), 7.65-7.56 (m, 1H), 7.52-7.51 (d, J=7.2 Hz, 1H), 7.38-7.36 (d, J=8.0 Hz, 1H), 7.33-7.31 (m, 1H), 5.12-4.70 (m, 1H), 4.45-4.21 (m, 1H), 4.07-3.88 (m, 1H), 3.58 (s, 3H), 2.43-2.27 (m, 2H), 2.26-2.15 (m, 2H), 2.14-1.99 (m, 2H), 1.91-1.73 (m, 2H).

Example 13: 33-chloro-2-(2,4-difluoro-6-(3-fluoro-1-methyl-1H-pyrazol-4-yl)phenyl)-N-((1s,3s)-3-hydroxy-3-(hydroxymethyl)cyclobutyl)imidazo[1,2-a]pyridine-7-carboxamide (Compound 922)

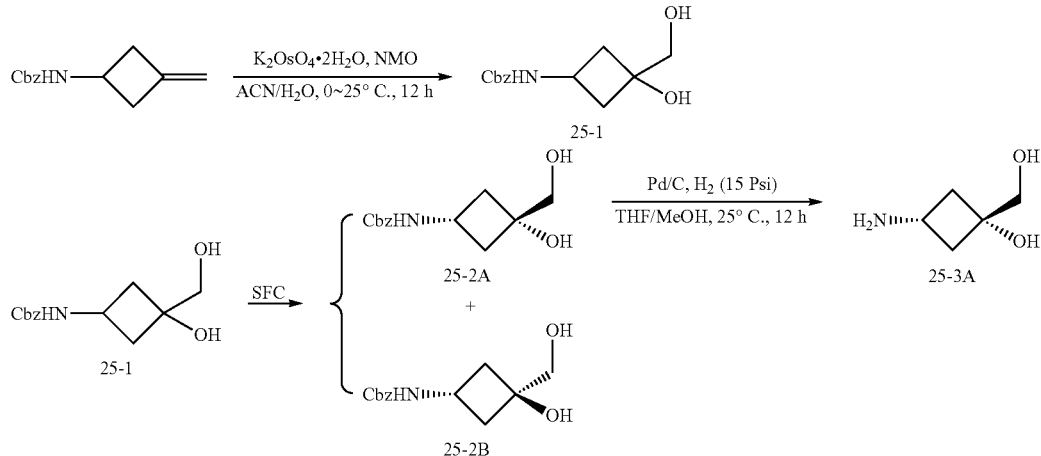

Step 1: Benzyl (3-hydroxy-3-(hydroxymethyl)cyclobutyl) carbamate (25-1): To a solution of benzyl (3-methylenecyclobutyl)carbamate (3 g, 13.81 mmol, 1 eq) in ACN (30 mL) and H$_2$O (10 mL) was added N-methyl morpholine N-oxide (7.28 g, 62.14 mmol, 4.5 eq) and potassium dioxido(dioxo) osmium dihydrate (0.51 g, 1.38 mmol, 0.1 eq) at 0° C. The mixture was stirred at 25° C. for 12 hrs. The reaction mixture was poured into saturated aqueous Na$_2$SO$_3$ solution (100 mL) and then extracted with EA (100 mL×3). The combined organic layers were washed with saturated brine (100 mL), dried over Na$_2$SO$_4$, filtered and concentrated in vacuo to give 3-1 (3.4 g, crude) as a yellow solid. $^1$H NMR (400 MHz, DMSO) δ=7.52-7.41 (m, 1H), 7.40-7.28 (m, 5H), 4.99 (s, 2H), 4.87-4.70 (m, 1H), 4.63-4.61 (td, J=14.8, 5.6 Hz, 1H), 4.12-3.51 (m, 1H), 3.24-3.22 (dd, J=19.2, 5.2 Hz, 2H), 2.38-2.29 (m, 1H), 2.06-1.93 (m, 2H), 1.84-1.82 (dt, J=8.8, 2.4 Hz, 1H).

Step 2: Benzyl ((1s,3s)-3-hydroxy-3-(hydroxymethyl)cyclobutyl)carbamate (25-2A) and benzyl ((1r,3r)-3-hydroxy-3-(hydroxymethyl)cyclobutyl)carbamate (25-2B): 25-1 (3.4 g, 13.53 mmol, 1 eq) was separated by SFC (column: DAICEL CHIRALCEL OX (250 mm×30 mm, 10 um); mobile phase: [A: CO$_2$, B: MeOH (0.1% NH$_3$·H$_2$O)]; B %: 25%, isocratic elution mode) to give 25-2A (1.29 g, 38% yield, RT=1.369 min) and 25-2B (1.28 g, 38% yield, RT=1.530 min) as a yellow solid. 25-2A: $^1$H NMR (400 MHz, DMSO) δ=7.49-7.47 (d, J=7.2 Hz, 1H), 7.40-7.22 (m, 5H), 4.98 (s, 2H), 4.82 (s, 1H), 4.63 (s, 1H), 3.60-3.45 (m, 1H), 3.25 (s, 2H), 2.40-2.28 (m, 2H), 1.83-1.81 (dt, J=9.2, 2.4 Hz, 2H). 25-2B: $^1$H NMR (400 MHz, DMSO) δ=7.49-7.47 (d, J=7.2 Hz, 1H), 7.40-7.22 (m, 5H), 4.98 (s, 2H), 4.82 (s, 1H), 4.63 (s, 1H), 3.60-3.45 (m, 1H), 3.25 (s, 2H), 2.40-2.28 (m, 2H), 1.83-1.81 (dt, J=9.2, 2.4 Hz, 2H).

Step 3: (1s,3s)-3-amino-1-(hydroxymethyl)cyclobutanol (25-3A): A mixture of 25-2A (1.8 g, 7.16 mmol, 1 eq) in MeOH (10 mL) and THF (10 mL) was degassed and purged with H$_2$ 3 times, then Pd/C (0.76 g, 0.72 mmol, 10% purity, 0.1 eq) was added. The mixture was degassed and purged with H$_2$ another 3 times, then stirred at 25° C. under H$_2$ (15 psi) for 12 hrs. The reaction mixture was filtered and the filtrate was concentrated under reduced pressure to give 25-3A (800 mg, crude) as a yellow oil. $^1$H NMR (400 MHz, CD$_3$OD) δ=3.43 (s, 2H), 2.99-2.92 (m, 1H), 2.50-2.48 (ddd, J=10.0, 7.2, 2.8 Hz, 2H), 1.84-1.68 (m, 2H).

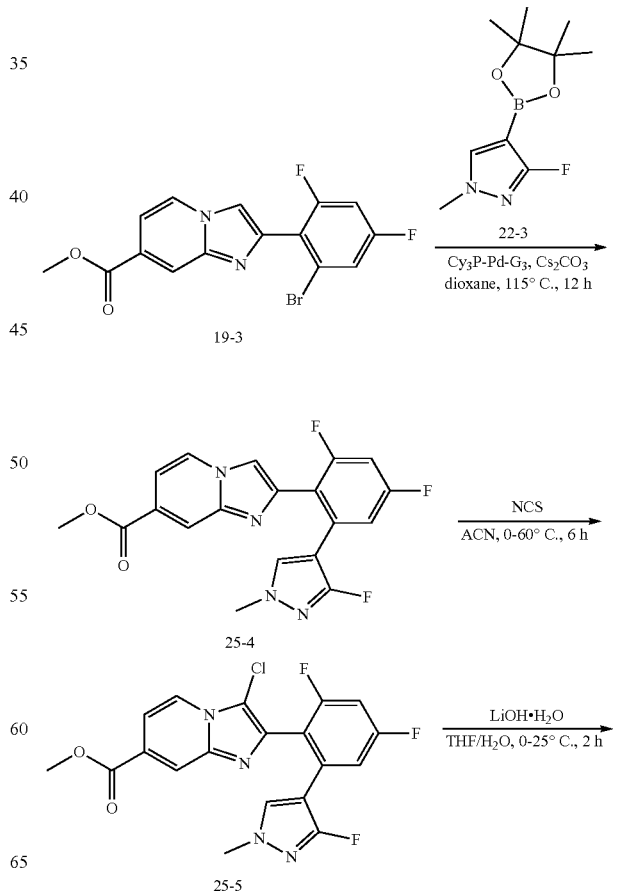

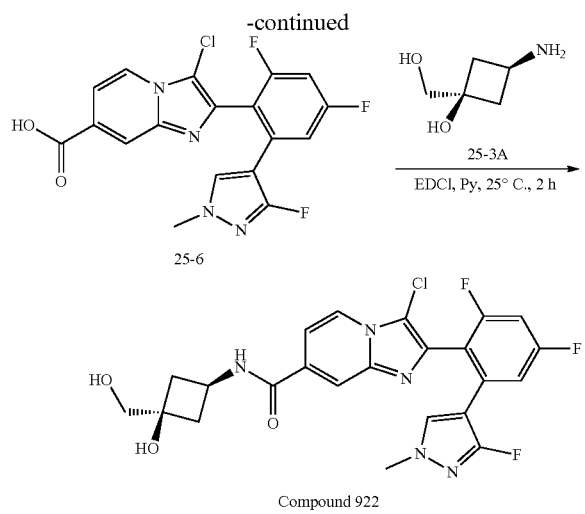

Step 4: Methyl 2-(2,4-difluoro-6-(3-fluoro-1-methyl-1H-pyrazol-4-yl)phenyl)imidazo[1,2-a]pyridine-7-carboxylate (25-4): A mixture of 19-3 (7 g, 19.07 mmol, 1 eq), 22-3 (10.77 g, 47.67 mmol, 2.5 eq), Cs$_2$CO$_3$ (18.64 g, 57.20 mmol, 3 eq), and PCy$_3$ Pd G3 (1.40 g, 1.91 mmol, 0.1 eq) in dioxane (70 mL) was degassed and purged with N$_2$ 3 times. The mixture was stirred at 115° C. for 12 hrs under N$_2$ atmosphere. The reaction mixture was filtered. The filtrate was diluted with water (100 mL), and then extracted with ethyl acetate (100 mL×3). The combined organic layers were washed with saturated brine (100 mL×3), dried over anhydrous sodium sulfate, filtered, and concentrated under reduced pressure to give a residue. The residue was purified by flash silica gel chromatography (ISCO®; 120 g SepaFlash® Silica Flash Column, Eluent of 30~70% Ethyl acetate/Petroleum ether gradient @ 100 mL/min) give 25-4 (4.8 g, 65% yield) as a yellow solid. $^1$H NMR (400 MHz, CD$_3$OD) δ=8.52 (d, J=7.2 Hz, 1H), 8.21 (s, 1H), 8.00 (s, 1H), 7.47 (dd, J=1.6, 7.2 Hz, 1H), 7.20-7.13 (m, 2H), 7.08 (dt, J=2.4, 9.2 Hz, 1H), 3.97 (s, 3H), 3.62 (s, 3H).

Step 5: Methyl 3-chloro-2-(2,4-difluoro-6-(3-fluoro-1-methyl-1H-pyrazol-4-yl)phenyl)imidazo[1,2-a]pyridine-7-carboxylate (25-5): To a solution of 25-4 (4.8 g, 12.42 mmol, 1 eq) in ACN (50 mL) was added NCS (1.99 g, 14.91 mmol, 1.2 eq) at 0° C. The mixture was stirred at 60° C. for 6 hrs. The reaction mixture was diluted with water (40 mL) and extracted with ethyl acetate (100 mL×3). The combined organic layers were washed with saturated brine (100 mL×3), dried over anhydrous sodium sulfate, filtered and concentrated under reduced pressure to give a residue. The residue was purified by flash silica gel chromatography (ISCO®; 120 g SepaFlash® Silica Flash Column, Eluent of 30~50% Ethyl acetate/Petroleum ether gradient @ 100 mL/min) to give 25-5 (3.8 g, 70% yield) as a yellow solid. LCMS: (ES$^+$) m/z (M+H)$^+$=421.1. $^1$H NMR (400 MHz, CD$_3$OD) δ=8.43 (d, J=7.2 Hz, 1H), 8.27 (s, 1H), 7.65 (d, J=7.2 Hz, 1H), 7.24-7.16 (m, 2H), 7.12 (dt, J=2.4, 9.2 Hz, 1H), 3.98 (s, 3H), 3.61 (s, 3H).

Step 6: 3-chloro-2-(2,4-difluoro-6-(3-fluoro-1-methyl-1H-pyrazol-4-yl)phenyl)imidazo[1,2-a]pyridine-7-carboxylic acid (25-6): To a solution of 25-5 (3.8 g, 9.03 mmol, 1 eq) in THF (40 mL) and H$_2$O (8 mL) was added LiOH·H$_2$O (1.14 g, 27.09 mmol, 3 eq). The mixture was stirred at 25° C. for 2 hrs. The reaction mixture was concentrated in vacuum to remove THF, and then diluted with H$_2$O (20 mL). The aqueous phase was adjusted to pH 4 by addition of 2N aqueous HCl at 0° C. so as to precipitate desired acid. The mixture was filtered and the filter cake was dried under reduced pressure to give 25-6 (2.85 g, 76% yield) as a yellow solid. $^1$H NMR (400 MHz, CD$_3$OD) δ=8.40 (d, J=7.2 Hz, 1H), 8.26 (s, 1H), 7.66 (d, J=7.2 Hz, 1H), 7.21 (d, J=10.0 Hz, 1H), 7.16 (s, 1H), 7.12 (t, J=9.2 Hz, 1H), 3.61 (s, 3H).

Step 7: 3-chloro-2-(2,4-difluoro-6-(3-fluoro-1-methyl-1H-pyrazol-4-yl)phenyl)-N-((1s,3s)-3-hydroxy-3-(hydroxymethyl)cyclobutyl)imidazo[1,2-a]pyridine-7-carboxamide (Compound 922): To a solution of 25-6 (80 mg, 0.19 mmol, 1 eq) and (1s,3s)-3-amino-1-(hydroxymethyl)cyclobutan-1-ol 25-3A (34.56 mg, 0.29 mmol, 1.5 eq) in pyridine (1 mL) was added EDCI (0.11 g, 0.59 mmol, 3 eq). The mixture was stirred at 25° C. for 2 hrs. The reaction mixture was filtered and the filtrate was purified by prep-HPLC (column: CD02-Waters Xbridge BEH C18 150×25×10 um; mobile phase: [A: water (0.05% NH$_4$HCO$_3$); B: ACN]; B %: 20%-50%, 10 min) to give Compound 922 (68.19 mg, 67% yield) as a white solid. LCMS: (ES+) m/z (M+H)$^+$=506.2. $^1$H NMR (400 MHz, CD$_3$OD) δ=8.41-8.39 (dd, J=0.8, 7.2 Hz, 1H), 8.17-8.02 (m, 1H), 7.56-7.54 (dd, J=1.6, 7.2 Hz, 1H), 7.25-7.15 (m, 2H), 7.14-7.09 (dt, J=2.4, 9.2 Hz, 1H), 4.12-4.08 (t, J=8 Hz, 1H), 3.60 (s, 3H), 3.55 (s, 2H), 2.68-2.63 (ddd, J=2.8, 7.6, 10 Hz, 2H), 2.18-2.10 (m, 2H).

Example 14: 3-chloro-2-(2,4-difluoro-6-(3-fluoro-1-methyl-1H-pyrazol-4-yl)phenyl)-N-((1r,3r)-3-hydroxy-3-(hydroxymethyl)cyclobutyl)imidazo[1,2-a]pyridine-7-carboxamide (Compound 923)

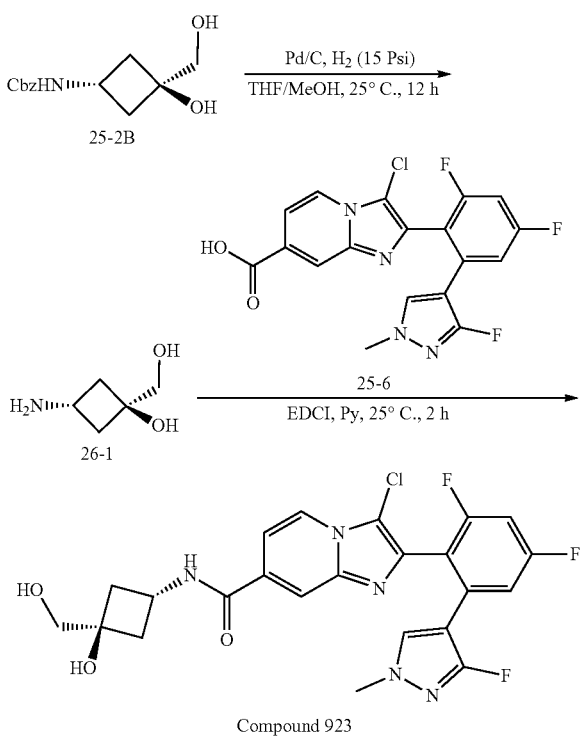

Step 1: (1r,3r)-3-amino-1-(hydroxymethyl)cyclobutan-1-ol (26-1): A mixture of benzyl ((1s,3s)-3-hydroxy-3-(hydroxymethyl)cyclobutyl)carbamate 25-2B (1.8 g, 7.16 mmol, 1 eq) in MeOH (10 mL) and THF (10 mL) was degassed and purged with H$_2$ 3 times, then Pd/C (0.76 g, 0.72 mmol, 10% purity, 0.1 eq) was added. The mixture was degassed and purged with H₂ another 3 times, then stirred at 25° C. under H₂ (15 psi) for 12 hrs. The reaction mixture was filtered and the filtrate was concentrated under reduced pressure to give 26-1 (800 mg, crude) as a yellow oil.

Step 2: 3-chloro-2-(2,4-difluoro-6-(3-fluoro-1-methyl-1H-pyrazol-4-yl)phenyl)-N-((1r,3r)-3-hydroxy-3-(hydroxymethyl)cyclobutyl)imidazo[1,2-a]pyridine-7-carboxamide (Compound 923): To a solution of 25-6 (0.10 g, 0.25 mmol, 1 eq) and 26-1 (43.20 mg, 0.37 mmol, 1.5 eq) in pyridine (1 mL) was added EDCI (141.39 mg, 0.74 mmol, 3 eq). The mixture was stirred at 25° C. for 2 hrs. The reaction mixture was filtered. The filtrate was concentrated in vacuo to give a residue. The residue was purified by prep-HPLC (column: CD02-Waters Xbridge BEH C18 150× 25×10 um; mobile phase: [A: water (0.05% NH₄HCO₃); B: ACN]; B %: 20%-50%, 10 min) to give Compound 923 (61.9 mg, 49% yield) as a white solid. LCMS: (ES⁺) m/z (M+H)⁺=506.2. ¹H NMR (400 MHz, CD₃OD) δ=8.40-8.39 (d, J=7.2 Hz, 1H), 8.08 (s, 1H), 7.55-7.53 (dd, J=1.6, 7.2 Hz, 1H), 7.26-7.15 (m, 2H), 7.13-7.08 (dt, J=2.4, 9.2 Hz, 1H), 4.71-4.63 (q, J=7.6 Hz, 1H), 3.60 (s, 3H), 3.49 (s, 2H), 2.42-2.35 (m, 2H), 2.34-2.27 (m, 2H).

Example 15: 3-chloro-2-(2-fluoro-6-(3-fluoro-1-methyl-1H-pyrazol-4-yl)phenyl)-N-((3S,6R)-6-(hydroxymethyl)tetrahydro-2H-pyran-3-yl)imidazo[1,2-a]pyridine-7-carboxamide (Compound 924)

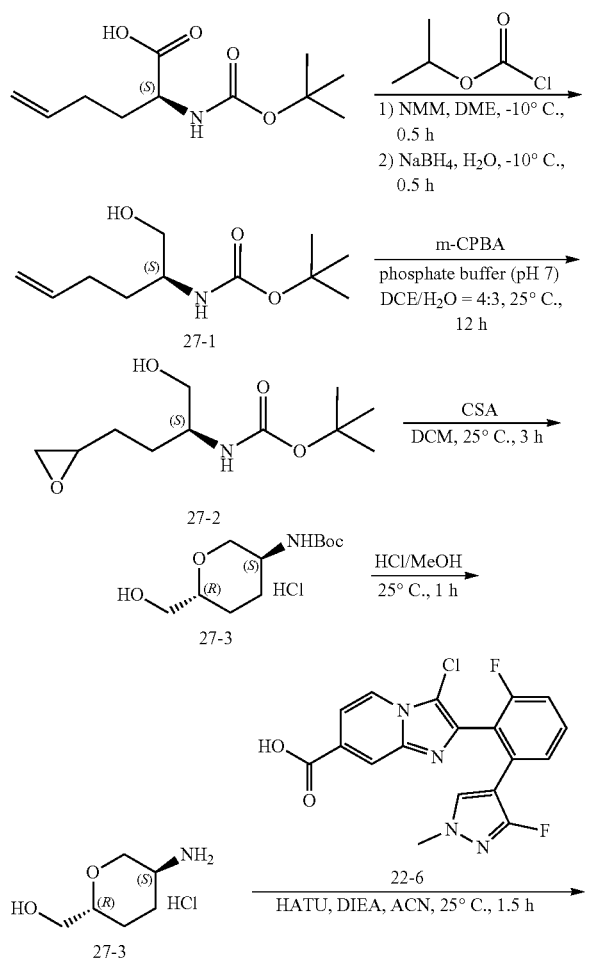

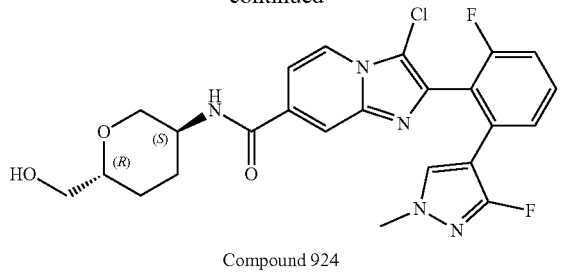

Compound 924

Step 1: Tert-butyl (S)-(1-hydroxyhex-5-en-2-yl)carbamate (27-1): To a cold (−10° C.) solution of (S)-2-((tert-butoxycarbonyl)amino)hex-5-enoic acid (2 g, 8.72 mmol, 1 eq) in DME (10 mL) was added NMM (882.33 mg, 8.72 mmol, 1 eq) and isopropyl carbonochloridate (1.19 g, 8.71 mmol, 1.14 mL, 1 eq). After stirring for 30 min., the precipitated N-methyl morpholine hydrochloride was removed by filtration. Then, a solution of NaBH₄ (570 mg, 15.07 mmol, 1.73 eq) in H₂O (5 mL) was added to the filtrate at once under N₂ atmosphere. The mixture was stirred at −10 for 30 min. The reaction mixture was quenched by addition saturated aqueous NH₄Cl (20 mL) at 0° C. under N₂, then extracted with ethyl acetate (30 mL×3). The combined organic layers were washed with saturated brine (20 mL×3), dried over anhydrous sodium sulfate, filtered and concentrated under reduced pressure to give 27-1 (1.4 g, 75% yield) as a colorless oil. LCMS: (ES⁺) m/z (M−56+H)⁺=160.2. ¹H NMR (400 MHz, CDCl₃) δ=5.82 (tdd, J=6.6, 10.2, 17.0 Hz, 1H), 5.12-4.93 (m, 2H), 4.74-4.50 (m, 1H), 3.78-3.62 (m, 3H), 2.23-2.09 (m, 2H), 1.70-1.60 (m, 1H), 1.58-1.51 (m, 1H), 1.46 (s, 9H).

Step 2: Tert-butyl ((2S)-1-hydroxy-4-(oxiran-2-yl)butan-2-yl)carbamate (27-2): To a solution of 27-1 (1 g, 4.64 mmol, 1 eq) in H₂O (30 mL) and DCE (40 mL) was added phosphate buffer (1 M in H₂O, 32 mL, 6.89 eq) and m-CPBA (3 g, 14.78 mmol, 85% purity, 3.18 eq). The reaction was stirred at 25° C. for 12 hrs. On completion, the mixture was quenched by addition of saturated aqueous Na₂SO₃ solution (100 mL), then extracted with DCM (50 mL×3). The combined organic layers were washed with saturated brine (30 mL), dried over Na₂SO₄, filtered and concentrated in vacuo to give a residue. The residue was purified by flash silica gel chromatography (ISCO®; 40 g SepaFlash® Silica Flash Column, Eluent of 50~80% EA/PE gradient @ 50 mL/min) to give 5-2 (0.8 g, 75% yield) as a colorless oil. ¹H NMR (400 MHz, CDCl₃) δ=4.85-4.55 (m, 1H), 3.76-3.66 (m, 2H), 3.63-3.56 (m, 1H), 2.95 (br d, J=2.8 Hz, 1H), 2.78 (q, J=4.0 Hz, 1H), 2.56-2.46 (m, 1H), 1.79-1.60 (m, 4H), 1.46 (s, 9H).

Step 3: Tert-butyl ((3S,6R)-6-(hydroxymethyl)tetrahydro-2H-pyran-3-yl)carbamate (27-3): To a solution of 27-2 (804 mg, 3.48 mmol, 1 eq) in DCM (10 mL) was added [rac-(1R,4S)-7,7-dimethyl-2-oxo-norbornan-1-yl]methanesulfonic acid (80.75 mg, 0.35 mmol, 0.1 eq). The mixture was stirred at 25° C. for 3 hrs. The reaction mixture was adjusted to pH 7 with saturated aqueous NaHCO₃ (20 mL), then extracted with ethyl acetate (30 mL×3). The combined organic layers were washed with saturated brine (20 mL×3), dried over anhydrous sodium sulfate, filtered and concentrated under reduced pressure to give a residue. The residue was purified by flash silica gel chromatography (ISCO®; 20 g SepaFlash® Silica Flash Column, Eluent of 90~100% EA/PE gradient @ 50 mL/min) to give 27-3 (0.16 g, 20% yield) as a white solid. ¹H NMR (400 MHz, CDCl₃) δ=4.25-

4.13 (m, 1H), 4.04-4.01 (m, 1H), 3.56-3.44 (m, 3H), 3.34-3.24 (m, 1H), 2.95 (t, J=10.6 Hz, 1H), 2.04 (br d, J=12.4 Hz, 1H), 1.55 (d, J=12.4 Hz, 1H), 1.45-1.41 (m, 1H), 1.37 (s, 9H), 1.28-1.22 (m, 1H).

Step 4: ((2R,5S)-5-aminotetrahydro-2H-pyran-2-yl)methanol hydrochloride (27-4): A solution of 27-3 (161 mg, 696.10 µmol, 1 eq) in 2 N HCl in MeOH (2 mL, 5.75 eq) was stirred at 25° C. for 1 hr. The reaction mixture was concentrated in vacuum to give 27-4 (0.1 g, 86% yield, HCl) as a white solid.

Step 5: 3-chloro-2-(2-fluoro-6-(3-fluoro-1-methyl-1H-pyrazol-4-yl)phenyl)-N-((3S,6R)-6-(hydroxymethyl)tetrahydro-2H-pyran-3-yl)imidazo[1,2-a]pyridine-7-carboxamide (Compound 924): To a solution of 22-6 (0.19 g, 0.49 mmol, 1 eq) in ACN (3 mL) was added HATU (0.28 g, 0.74 mmol, 1.5 eq) and DIEA (0.19 g, 1.49 mmol, 3 eq). The mixture was stirred at 25° C. for 0.5 h. Then 27-4 (100 mg, 0.59 mmol, 1.2 eq) was added to the mixture. The mixture was stirred at 25° C. for another 1 h. The reaction mixture was diluted with $H_2O$ (20 mL), then extracted with ethyl acetate (20 mL×3). The combined organic layers were washed with saturated brine (20 mL×3), dried over anhydrous sodium sulfate, filtered and concentrated under reduced pressure to give a residue. The residue was purified by flash silica gel chromatography (ISCO®; 12 g SepaFlash® Silica Flash Column, Eluent of 5~15% EtOH/EA gradient @ 50 mL/min) and SFC (column: Phenomenex-Cellulose-2 (250 mm×30 mm, 10 um); mobile phase: [A: $CO_2$, B: MeOH (0.1% $NH_3 \cdot H_2O$)]; B %: 55%, isocratic elution mode) to give Compound 924 (29 mg, 58% yield) as a white solid. LCMS: (ES+) m/z $(M+H)^+$=502.1. $^1$H NMR (400 MHz, DMSO) δ=8.54-8.39 (m, 2H), 8.20 (s, 1H), 7.60 (dt, J=5.8, 8.0 Hz, 1H), 7.53 (dd, J=1.6, 7.2 Hz, 1H), 7.41-7.29 (m, 3H), 4.64 (t, J=5.8 Hz, 1H), 3.97-3.83 (m, 2H), 3.58 (s, 3H), 3.44-3.37 (m, 1H), 3.25 (d, J=6.4 Hz, 1H), 3.19-3.11 (m, 1H), 1.99 (d, J=12.6 Hz, 1H), 1.79-1.69 (m, 1H), 1.62 (m, 1H), 1.40-1.23 (m, 1H).

Example 16: cis 3-chloro-2-(2-fluoro-6-(3-fluoro-1-methyl-1H-pyrazol-4-yl)phenyl)-N-(6-hydroxy-6-methylspiro[3.3]heptan-2-yl)imidazo[1,2-a]pyridine-7-carboxamide (Compound 928) and trans 3-chloro-2-(2-fluoro-6-(3-fluoro-1-methyl-1H-pyrazol-4-yl)phenyl)-N-(6-hydroxy-6-methylspiro[3.3]heptan-2-yl)imidazo[1,2-a]pyridine-7-carboxamide (Compound 929)

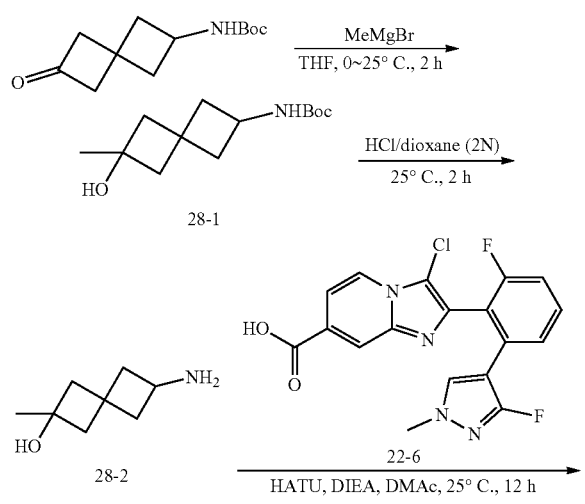

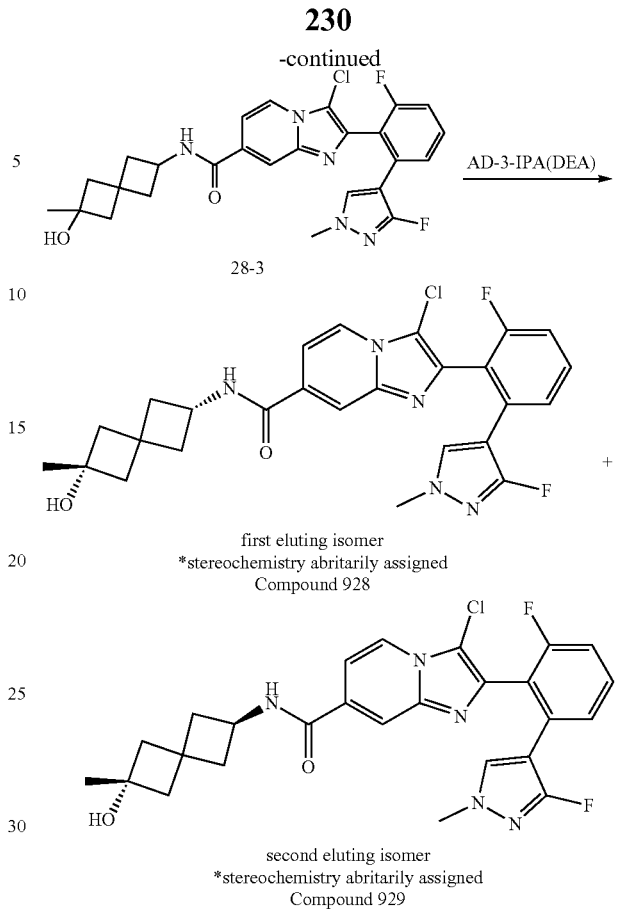

first eluting isomer
*stereochemistry abritarily assigned
Compound 928 second eluting isomer
*stereochemistry abritarily assigned
Compound 929

Step 1: Tert-butyl (6-hydroxy-6-methylspiro[3.3]heptan-2-yl)carbamate (6-1): To a solution of tert-butyl (6-oxospiro[3.3]heptan-2-yl)carbamate (3 g, 4.4 mmol, 1 eq) in THF (30 mL) was added MeMgBr (3 M in $Et_2O$, 8.9 mL, 2 eq) at 0° C. under $N_2$ atmosphere. The mixture was stirred at 0° C. for 0.5 hr. The mixture was warmed to 25° C. and stirred for another 1.5 hrs. The reaction mixture was quenched by addition of saturated aqueous $NH_4Cl$ (50 mL) at 0° C., then extracted with EA (40 mL×2). The combined organic layers were washed with saturated brine (30 mL×2), dried over $Na_2SO_4$, filtered and concentrated under reduced pressure to give a residue. The residue was purified by flash silica gel chromatography (ISCO®; 40 g SepaFlash® Silica Flash Column, Eluent of 0~20% Ethyl acetate/Petroleum ether gradient @ 80 mL/min) to give 28-1 (0.84 g, 26% yield) as a yellow solid. $^1$H NMR (400 MHz, $CD_3OD$) δ=3.94-3.81 (m, 1H), 2.42-2.32 (m, 1H), 2.31-2.22 (m, 1H), 2.15 (s, 2H), 2.11-2.05 (m, 1H), 2.03-1.95 (m, 2H), 1.94-1.86 (m, 2H), 1.42 (s, 9H), 1.27 (s, 3H).

Step 2: 6-amino-2-methylspiro[3.3]heptan-2-ol hydrochloride (28-2): A solution of 28-1 (0.84 g, 3.7 mmol, 1 eq) in 2 N HCl in dioxane (10 mL) was stirred at 25° C. for 2 hrs. The reaction mixture was concentrated under vacuum to give 28-2 (0.60 g, crude) as a yellow solid. $^1$H NMR (400 MHz, $CD_3OD$) δ=3.66-3.60 (m, 1H), 2.51-2.44 (m, 1H), 2.39 (ddd, J=5.4, 7.4, 12.0 Hz, 1H), 2.23-2.14 (m, 5H), 2.11-2.05 (m, 1H), 1.29 (s, 3H).

Step 3: 3-chloro-2-(2-fluoro-6-(3-fluoro-1-methyl-1H-pyrazol-4-yl)phenyl)-N-(6-hydroxy-6-methylspiro[3.3]heptan-2-yl)imidazo[1,2-a]pyridine-7-carboxamide (28-3): To a solution of 22-6 (300 mg, 0.7 mmol, 1 eq, HCl) in DMAc (3 mL) was added HATU (0.54 g, 1.4 mmol, 2 eq) and DIEA (0.6 mL, 3.5 mmol, 5 eq). The mixture was stirred at 25° C. for 0.5 hr. Then 28-2 (0.31 g, 1.06 mmol, 1.5 eq) was added to the mixture. The mixture was stirred at 25° C. for 11.5 hrs. The reaction mixture was adjusted to pH 7 with 2 N aqueous HCl. The reaction mixture was filtered. The filtrate was concentrated under vacuum to give a residue. The residue was purified by prep-HPLC (column: Santai Technologies SepaFlash® cartridge 257.4×31.2 mm, 40-60 μm; mobile phase: [A: water (0.1% $NH_3 \cdot H_2O$); B: ACN], B %: 20-40%, 30 min) to give 28-3 (0.13 g, 36% yield) as a yellow solid. LCMS: (ES+) m/z $(M+H)^+$=512.1. $^1$H NMR (400 MHz, $CD_3OD$) δ=8.39 (dd, J=0.8, 7.4 Hz, 1H), 8.06 (s, 1H), 7.62-7.49 (m, 2H), 7.39 (d, J=7.8 Hz, 1H), 7.27-7.20 (m, 1H), 7.16 (d, J=2.4 Hz, 1H), 4.40 (t, J=8.2 Hz, 1H), 2.58-2.47 (m, 1H), 2.46-2.38 (m, 1H), 2.27-2.22 (m, 2H), 2.22-2.12 (m, 3H), 2.10-2.03 (m, 1H), 1.31 (s, 3H).

Step 4: Cis 3-chloro-2-(2-fluoro-6-(3-fluoro-1-methyl-1H-pyrazol-4-yl)phenyl)-N-(6-hydroxy-6-methylspiro[3.3]heptan-2-yl)imidazo[1,2-a]pyridine-7-carboxamide (Compound 928) and trans 3-chloro-2-(2-fluoro-6-(3-fluoro-1-methyl-1H-pyrazol-4-yl)phenyl)-N-(6-hydroxy-6-methylspiro[3.3]heptan-2-yl)imidazo[1,2-a]pyridine-7-carboxamide (Compound 929): 3-chloro-2-(2-fluoro-6-(3-fluoro-1-methyl-1H-pyrazol-4-yl)phenyl)-N-(6-hydroxy-6-methylspiro[3.3]heptan-2-yl)imidazo[1,2-a]pyridine-7-carboxamide 28-3 (0.13 g, 0.25 mmol, 1 eq) was separated by SFC (column: DAICEL CHIRALPAK AD (250 mm×30 mm, 10 um); mobile phase: [A: $CO_2$, B: i-PrOH (0.1% $NH_3 \cdot H_2O$)]; B %: 50%, isocratic elution mode) to give Compound 928 (26.8 mg, 21% yield, RT=1.965 min on SFC_AD-3) and Compound 929 (34.74 mg, 27% yield, RT=2.251 min on SFC_AD-3) as a white solid. Compound 928: LCMS: (ES+) m/z $(M+H)^+$=512.2. $^1$H NMR (400 MHz, $CD_3OD$) δ=8.39 (d, J=7.2 Hz, 1H), 8.06 (s, 1H), 7.62-7.50 (m, 2H), 7.39 (d, J=7.8 Hz, 1H), 7.23 (t, J=9.0 Hz, 1H), 7.16 (d, J=2.2 Hz, 1H), 4.40 (t, J=8.2 Hz, 1H), 3.60 (s, 3H), 2.56-2.47 (m, 1H), 2.46-2.38 (m, 1H), 2.28-2.22 (m, 2H), 2.22-2.12 (m, 3H), 2.10-2.03 (m, 1H), 1.31 (s, 3H). Compound 929: LCMS: (ES+) m/z $(M+H)^+$=512.2. $^1$H NMR (400 MHz, $CD_3OD$) δ=8.39 (dd, J=0.8, 7.4 Hz, 1H), 8.06 (d, J=1.0 Hz, 1H), 7.61-7.50 (m, 2H), 7.39 (d, J=8.0 Hz, 1H), 7.27-7.20 (m, 1H), 7.16 (d, J=2.4 Hz, 1H), 4.40 (t, J=8.2 Hz, 1H), 3.60 (s, 3H), 2.56-2.48 (m, 1H), 2.47-2.37 (m, 1H), 2.29-2.22 (m, 2H), 2.22-2.13 (m, 3H), 2.10-2.04 (m, 1H), 1.31 (s, 3H).

Example 17: 3-cyano-2-(5-fluoro-2-(3-fluoro-1-methyl-1H-pyrazol-4-yl)phenyl)-N-(1-methyl-2-oxabicyclo[2.1.1]hexan-4-yl)imidazo[1,2-a]pyridine-7-carboxamide (Compound 931)

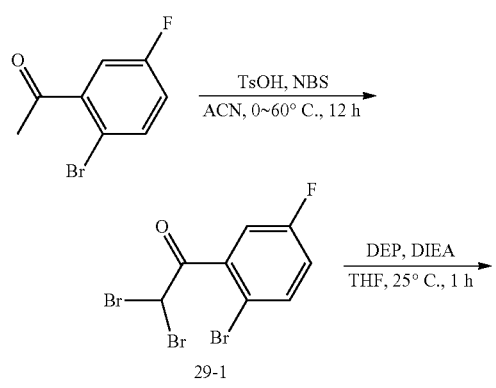

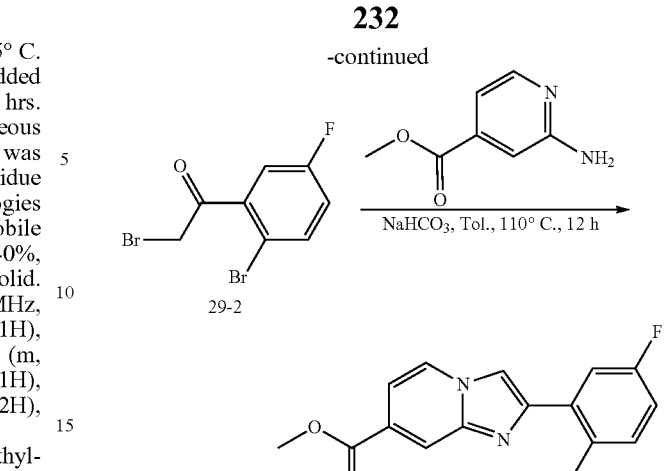

Step 1: 2,2-dibromo-1-(2-bromo-5-fluorophenyl)ethan-1-one (29-1): To a solution of 1-(2-bromo-5-fluorophenyl)ethan-1-one (22 g, 0.10 mol, 1 eq) in ACN (220 mL) was added NBS (45 g, 0.25 mol, 2.5 eq) and TsOH (43 g, 0.25 mol, 2.5 eq) at 0° C. The mixture was stirred at 60° C. for 12 hr. The reaction mixture was diluted with $H_2O$ (500 mL), then extracted with EtOAc (200 mL×3). The combined organic layers were washed with saturated brine (600 mL), dried over $Na_2SO_4$, filtered and concentrated under reduced pressure to give a residue. The residue was purified by flash silica gel chromatography (ISCO®; 220 g SepaFlash® Silica Flash Column, Eluent of 0~5% Ethyl acetate/Petroleum ether gradient @ 100 mL/min) to give 29-1 (33 g, 87% yield) as a yellow oil.

Step 2: 2-bromo-1-(2-bromo-5-fluorophenyl)ethan-1-one (29-2): To a solution of 29-1 (33 g, 87 mmol, 1 eq) in THF (320 mL) was added 1-ethoxyphosphonoyloxyethane (7.2 g, 52 mmol, 6.7 mL, 0.6 eq) and DIEA (6.8 g, 52 mmol, 9.1 mL, 0.6 eq). The mixture was stirred at 25° C. for 1 hr. The reaction mixture was diluted with $H_2O$ (500 mL) and extracted with EtOAc (200 mL×3). The combined organic layers were washed with saturated brine (600 mL), dried over $Na_2SO_4$, filtered and concentrated under reduced pressure to give a residue. The residue was purified by flash silica gel chromatography (ISCO®; 330 g SepaFlash® Silica Flash Column, Eluent of 0~6% Ethyl acetate/Petroleum ether gradient @ 100 mL/min) to give 29-2 (25 g, 97% yield) as a yellow oil. $^1$H NMR (400 MHz, $CD_3OD$) δ=7.73 (dd, J=4.8, 8.8 Hz, 1H), 7.44 (dd, J=3.0, 8.6 Hz, 1H), 7.24 (dt, J=3.0, 8.4 Hz, 1H), 4.63 (s, 2H).

Step 3: Methyl 2-(2-bromo-5-fluorophenyl)imidazo[1,2-a]pyridine-7-carboxylate (29-3): To a solution of 29-2 (25 g, 84 mmol, 1 eq) in toluene (300 mL) was added methyl 2-aminoisonicotinate (14 g, 93 mmol, 1.1 eq) and $NaHCO_3$ (14 g, 0.17 mol, 2 eq). The mixture was stirred at 110° C. for 12 hrs. The reaction mixture was diluted with $H_2O$ (500 mL) and extracted with EtOAc (200 mL×3). The combined organic layers were washed with saturated brine (600 mL), dried over $Na_2SO_4$, filtered and concentrated under reduced pressure to give a residue. The residue was purified by flash silica gel chromatography (ISCO®; 330 g SepaFlash® Silica Flash Column, Eluent of 20~30% Ethyl acetate/Petroleum ether gradient @ 100 mL/min) to give 29-3 (25 g, 85% yield) as a black solid. $^1$H NMR (400 MHz, $CD_3OD$) δ=8.63 (s, 1H), 8.57 (d, J=7.0 Hz, 1H), 8.28 (s, 1H), 7.78-7.71 (m, 2H), 7.50-7.45 (m, 1H), 7.10 (dt, J=3.0, 8.4 Hz, 1H), 3.98 (s 3H).

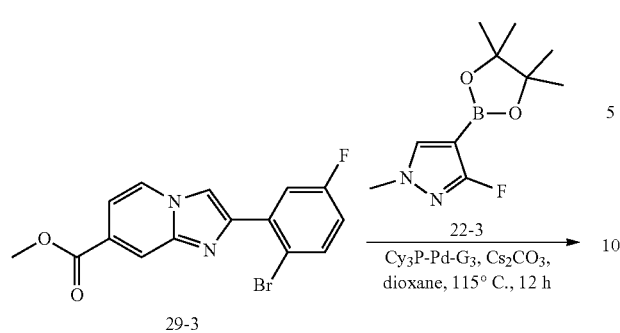

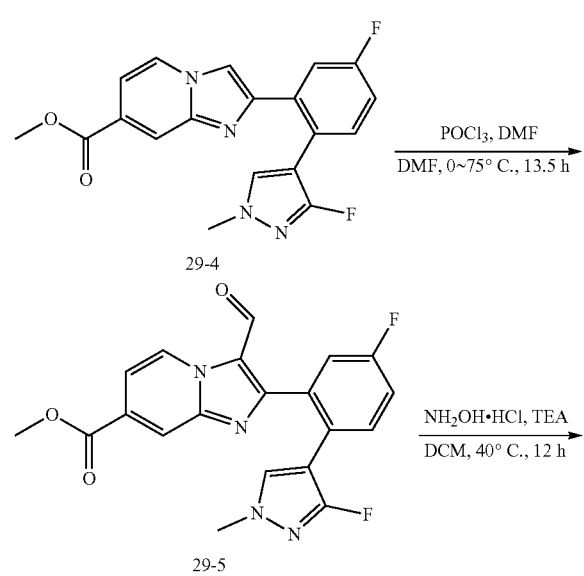

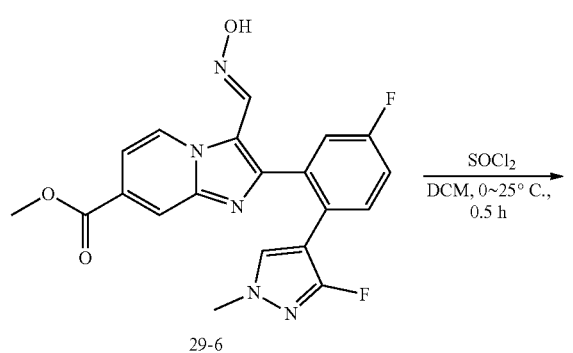

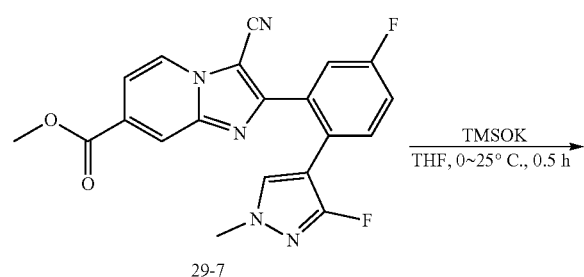

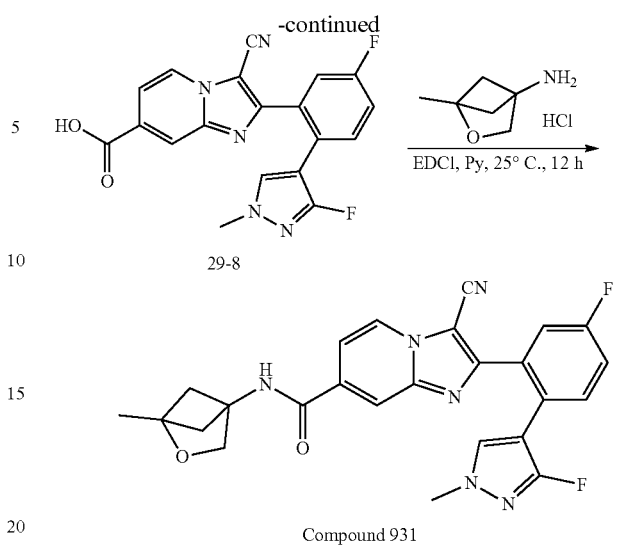

Compound 931

Step 4: Methyl 2-(5-fluoro-2-(3-fluoro-1-methyl-1H-pyrazol-4-yl)phenyl)imidazo[1,2-a]pyridine-7-carboxylate (29-4): A solution of 29-3 (5.0 g, 14 mmol, 1 eq), 22-3 (6.5 g, 28 mmol, 2 eq) and $Cs_2CO_3$ (14 g, 43 mmol, 3 eq) in dioxane (50 mL) was degassed and purged with $N_2$ 3 times. Then $Cy_3P$-Pd-$G_3$ (1.1 g, 1.4 mmol, 0.1 eq) was added to the reaction mixture under $N_2$ atmosphere. The mixture was stirred at 115° C. for 12 hrs. The reaction mixture was diluted with $H_2O$ (100 mL) and extracted with EtOAc (80 mL×3). The combined organic layers were washed with saturated brine (150 mL), dried over $Na_2SO_4$, filtered and concentrated under reduced pressure to give a residue. The residue was purified by flash silica gel chromatography (ISCO®; 80 g SepaFlash® Silica Flash Column, Eluent of 30~100% Ethyl acetate/Petroleum ether gradient @ 100 mL/min) to give 29-4 (3.9 g, 74% yield) as a yellow solid. $^1$H NMR (400 MHz, $CD_3OD$) δ=8.41 (d, J=7.0 Hz, 1H), 8.20 (s, 1H), 7.71 (s, 1H), 7.57 (dd, J=2.8, 9.8 Hz, 1H), 7.46 (d, J=2.4 Hz, 1H), 7.44-7.38 (m, 2H), 7.18 (dt, J=2.8, 8.4 Hz, 1H), 3.96 (s, 3H), 3.76 (s, 3H).

Step 5: Methyl 2-(5-fluoro-2-(3-fluoro-1-methyl-1H-pyrazol-4-yl)phenyl)-3-formylimidazo[1,2-a]pyridine-7-carboxylate (29-5): $POCl_3$ (9.4 g, 61 mmol, 5.7 mL, 15 eq) was added dropwise into DMF (4.5 g, 61 mmol, 4.7 mL, 15 eq) over 30 min, and the resulting mixture was stirred at 0° C. for 30 min (under $N_2$ atmosphere). On completion, the reaction mixture was warmed to 25° C. A solution of 29-4 (1.5 g, 4.1 mmol, 1 eq) in DMF (15 mL) was added to the mixture, and the mixture was stirred for 30 min. Then the mixture was stirred at 75° C. for 12 hrs. The mixture was poured into water (80 mL), adjusted to pH 7 by addition of saturated aqueous sodium carbonate, then extracted with EtOAc (80 mL×3). The combined organic layers were washed with saturated brine (150 mL), dried over $Na_2SO_4$, filtered and concentrated under reduced pressure to give 29-5 (1.4 g, crude) as a yellow solid. $^1$H NMR (400 MHz, DMSO) δ=9.63 (s, 1H), 9.53 (d, J=7.2 Hz, 1H), 8.36 (s, 1H), 7.73 (dd, J=1.4, 7.2 Hz, 1H), 7.61-7.52 (m, 3H), 7.48 (dt, J=2.8, 8.6 Hz, 1H), 3.94 (s, 3H), 3.61 (s, 3H).

Step 6: Methyl 2-(5-fluoro-2-(3-fluoro-1-methyl-1H-pyrazol-4-yl)phenyl)-3-((hi92ydroxyimino)methyl)imidazo[1,2-a]pyridine-7-carboxylate (29-6): To a solution of 29-5 (1.2 g, 3.0 mmol, 1 eq) in DCM (12 mL) was added TEA (2.5 g, 24 mmol, 8 eq) and hydroxylamine hydrochloride (1.05 g, 15.14 mmol, 5 eq). The mixture was stirred at 40°

C. for 12 hrs. The reaction mixture was diluted with H$_2$O (30 mL), then extracted with EtOAc (20 mL×3). The combined organic layers were washed with saturated brine (30 mL), dried over Na$_2$SO$_4$, filtered and concentrated under reduced pressure to give a residue. The residue was purified by flash silica gel chromatography (ISCO®; 40 g SepaFlash® Silica Flash Column, Eluent of 50~70% Ethyl acetate/Petroleum ether gradient @ 100 mL/min) to give 29-6 (1.0 g, 76% yield) as a yellow solid. LCMS: (ES+) m/z (M+H)$^+$=412.1.

Step 7: Methyl 3-cyano-2-(5-fluoro-2-(3-fluoro-1-methyl-1H-pyrazol-4-yl)phenyl)imidazo[1,2-a]pyridine-7-carboxylate (29-7): To a solution of 29-6 (1.0 g, 2.3 mmol, 1 eq) in DCM (10 mL) was added SOCl$_2$ (0.58 g, 4.9 mmol, 2.1 eq) at 0° C. The mixture was stirred at 25° C. for 0.5 hr. The reaction mixture was poured into saturated aqueous NaHCO$_3$ (30 mL), then extracted with EtOAc (20 mL×3). The combined organic layers were washed with saturated brine (30 mL), dried over Na$_2$SO$_4$, filtered and concentrated in vacuo to give 29-7 (5.3 g, 48% yield) as a yellow solid. $^1$H NMR (400 MHz, CD$_3$OD) δ=8.61 (d, J=7.0 Hz, 1H), 8.37 (s, 1H), 7.75 (dd, J=1.6, 7.2 Hz, 1H), 7.58 (dd, J=5.6, 8.6 Hz, 1H), 7.51-7.46 (m, 2H), 7.36 (dt, J=2.8, 8.4 Hz, 1H), 4.00 (s, 3H), 3.72 (s, 3H).

Step 8: 3-cyano-2-(5-fluoro-2-(3-fluoro-1-methyl-1H-pyrazol-4-yl)phenyl)imidazo[1,2-a]pyridine-7-carboxylic acid (29-8): To a solution of 29-7 (0.2 g, 0.51 mmol, 1 eq) in THF (3 mL) was added TMSOK (78 mg, 0.61 mmol, 1.2 eq) at 0° C. The mixture was stirred at 25° C. for 0.5 hr. The reaction mixture was adjusted to pH 7 by addition of 1 N aqueous HCl, then concentrated under reduced pressure to give 29-8 (0.19 g, crude) as a yellow solid.

Step 9: 3-cyano-2-(5-fluoro-2-(3-fluoro-1-methyl-1H-pyrazol-4-yl)phenyl)-N-(1-methyl-2-oxabicyclo[2.1.1]hexan-4-yl)imidazo[1,2-a]pyridine-7-carboxamide (Compound 931): To a solution of 29-8 (0.19 g, 0.5 mmol, 1 eq) in pyridine (3 mL) was added EDCI (0.19 g, 1.0 mmol, 2 eq) and 1-methyl-2-oxabicyclo[2.1.1]hexan-4-amine hydrochloride (90 mg, 0.60 mmol, 1.2 eq, HCl). The mixture was stirred at 25° C. for 12 hrs. The reaction mixture was diluted with H$_2$O (10 mL) and extracted with EtOAc (10 mL×3). The combined organic layers were washed with saturated brine (30 mL), dried over Na$_2$SO$_4$, filtered and concentrated under reduced pressure to give a residue. The residue was purified by prep-HPLC (column: CD02-Waters Xbridge BEH C18 150×25×10 um; mobile phase: [A: water (0.1% NH$_3$·H$_2$O); B: ACN]; B %: 27%-57%, 10 min) to give Compound 931 (0.11 g, 48% yield) as a white solid. LCMS: (ES$^+$) m/z (M+H)$^+$=475.2. $^1$H NMR (400 MHz, CD$_3$OD) δ=8.59 (d, J=7.0 Hz, 1H), 8.21 (s, 1H), 7.64 (dd, J=1.2, 7.0 Hz, 1H), 7.57 (dd, J=5.6, 8.6 Hz, 1H), 7.50-7.45 (m, 2H), 7.35 (dt, J=2.8, 8.4 Hz, 1H), 3.92 (s, 2H), 3.72 (s, 3H), 2.14-2.07 (m, 2H), 2.05-1.98 (m, 2H), 1.47 (s, 3H).

Example 18: 3-cyano-2-(2,3-difluoro-6-(3-fluoro-1-methyl-1H-pyrazol-4-yl)phenyl)-N-(1-methyl-2-oxabicyclo[2.1.1]hexan-4-yl)imidazo[1,2-a]pyridine-7-carboxamide (Compound 932)

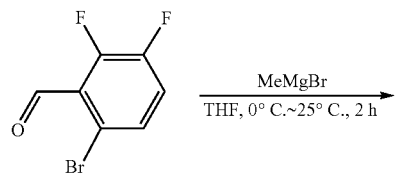

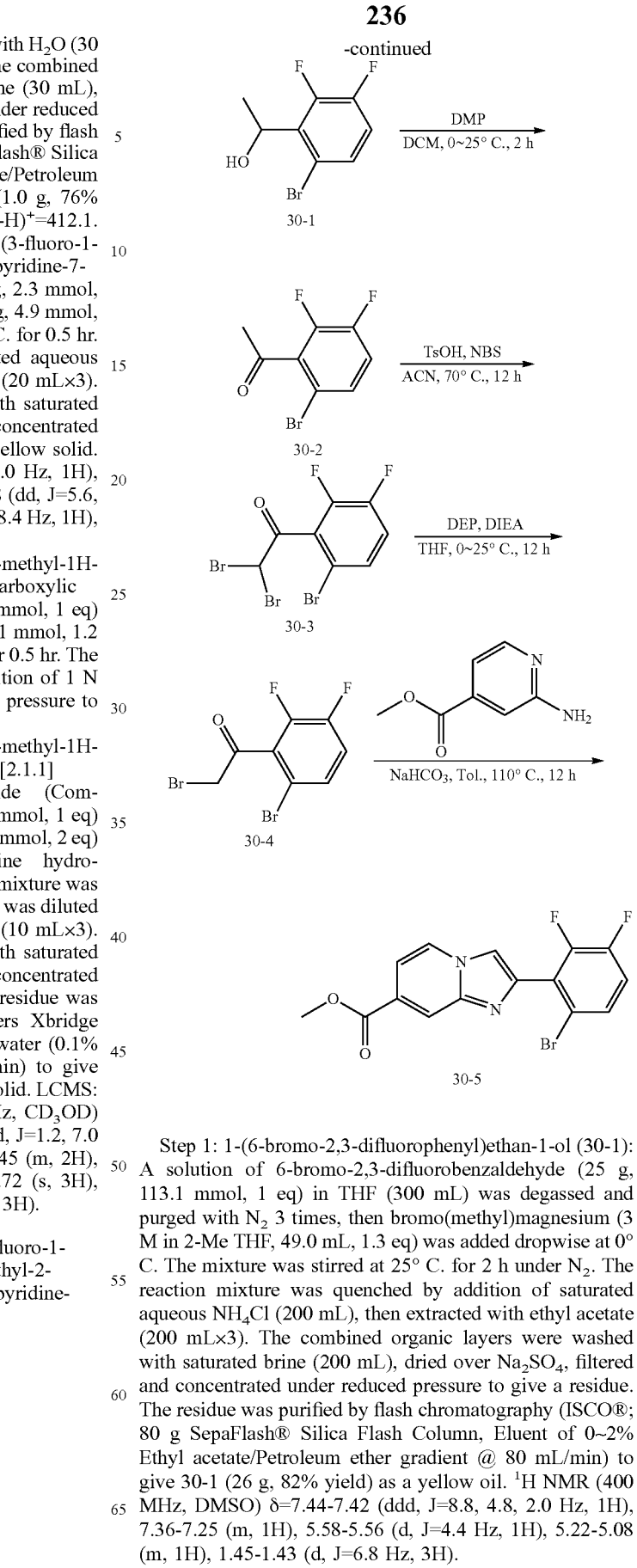

Step 1: 1-(6-bromo-2,3-difluorophenyl)ethan-1-ol (30-1): A solution of 6-bromo-2,3-difluorobenzaldehyde (25 g, 113.1 mmol, 1 eq) in THF (300 mL) was degassed and purged with N$_2$ 3 times, then bromo(methyl)magnesium (3 M in 2-Me THF, 49.0 mL, 1.3 eq) was added dropwise at 0° C. The mixture was stirred at 25° C. for 2 h under N$_2$. The reaction mixture was quenched by addition of saturated aqueous NH$_4$Cl (200 mL), then extracted with ethyl acetate (200 mL×3). The combined organic layers were washed with saturated brine (200 mL), dried over Na$_2$SO$_4$, filtered and concentrated under reduced pressure to give a residue. The residue was purified by flash chromatography (ISCO®; 80 g SepaFlash® Silica Flash Column, Eluent of 0~2% Ethyl acetate/Petroleum ether gradient @ 80 mL/min) to give 30-1 (26 g, 82% yield) as a yellow oil. $^1$H NMR (400 MHz, DMSO) δ=7.44-7.42 (ddd, J=8.8, 4.8, 2.0 Hz, 1H), 7.36-7.25 (m, 1H), 5.58-5.56 (d, J=4.4 Hz, 1H), 5.22-5.08 (m, 1H), 1.45-1.43 (d, J=6.8 Hz, 3H).

Step 2: 1-(6-bromo-2,3-difluorophenyl)ethan-1-one (30-2): To a solution of 30-1 (26 g, 109.7 mmol, 1 eq) in DCM (300 mL) was added DMP (60.5 g, 0.14 mol, 1.3 eq) at 0° C. The mixture was stirred at 25° C. for 2 hr. The reaction mixture was quenched by addition of saturated aqueous $Na_2SO_3$ (300 mL) and extracted with DCM (400 mL×3). The combined organic layers were washed with saturated brine (400 mL), dried over $Na_2SO_4$, filtered and concentrated under reduced pressure to give a residue. The residue was purified by flash chromatography (ISCO®; 80 g SepaFlash® Silica Flash Column, Eluent of 0~10% Ethyl acetate/ Petroleum ether gradient @ 80 mL/min) to give 30-2 (23.2 g, 810% yield) as a yellow oil. $^1$H NMR (400 MHz, DMSO) δ=7.64-7.56 (m, 1H), 7.56-7.44 (m, 1H), 2.58 (s, 3H).

Step 3: 2,2-dibromo-1-(6-bromo-2,3-difluorophenyl) ethan-1-one (30-3): To a solution of 30-2 (23.2 g, 84.0 mmol, 1 eq) in ACN (250 mL) was added NBS (44.8 g, 0.25 mol, 3 eq) and TsOH·$H_2O$ (47.9 g, 0.25 mol, 3 eq). The mixture was stirred at 70° C. for 12 hrs. The reaction mixture was quenched by addition of saturated aqueous $Na_2CO_3$ (300 mL), then extracted with ethyl acetate (300 mL×3). The combined organic layers were washed with saturated brine (300 mL), dried over $Na_2SO_4$, filtered and concentrated under reduced pressure to give a residue. The residue was purified by flash chromatography (ISCO®; 80 g SepaFlash® Silica Flash Column, Eluent of 0-3% Ethyl acetate/Petroleum ether gradient @ 80 mL/min) to give 30-3 (26.8 g, 81% yield) as a yellow oil. $^1$H NMR (400 MHz, $CDCl_3$) δ=7.34-7.32 (d, J=2.0 Hz, 1H), 7.21-7.15 (m, 1H), 6.51 (s, 1H).

Step 4: 2-bromo-1-(6-bromo-2,3-difluorophenyl)ethan-1-one (30-4): To a solution of 30-3 (26.8 g, 68.2 mmol, 1 eq) in THF (300 mL) was added 1-ethoxyphosphonoyloxy-ethane (4.71 g, 34.11 mmol, 4.39 mL, 0.5 eq) and DIEA (5.9 mL, 34.10 mmol, 0.5 eq) at 0° C. The mixture was stirred at 25° C. for 12 hrs. The reaction mixture was quenched by addition water (200 mL), and then extracted with ethyl acetate (200 mL×3). The combined organic layers were washed with saturated brine (200 mL), dried over $Na_2SO_4$, filtered and concentrated under reduced pressure to give a residue. The residue was purified by flash chromatography (ISCO®; 80 g SepaFlash® Silica Flash Column, Eluent of 0~2% Ethyl acetate/Petroleum ether gradient @80 mL/min) to give 30-4 (21.2 g, 99% yield) as a yellow oil. $^1$H NMR (400 MHz, $CDCl_3$) δ=7.40-7.38 (ddd, J=8.8, 4.0, 1.6 Hz, 1H), 7.20-7.18 (q, J=8.8 Hz, 1H), 4.37 (s, 2H).

Step 5: Methyl 2-(6-bromo-2,3-difluorophenyl)imidazo [1,2-a]pyridine-7-carboxylate (30-5): To a solution of 30-4 (17 g, 54.2 mmol, 1 eq) in toluene (200 mL) was added $NaHCO_3$ (9.10 g, 108.30 mmol, 2 eq) and methyl 2-aminoisonicotinate (9.10 g, 59.60 mmol, 1.1 eq). The mixture was stirred at 110° C. for 12 hrs. The reaction mixture was diluted with water (200 mL), then extracted with ethyl acetate (200 mL×3). The combined organic layers were washed with saturated brine (200 mL), dried over $Na_2SO_4$, filtered and concentrated under reduced pressure to give a residue. The residue was purified by flash chromatography (ISCO®; 80 g SepaFlash® Silica Flash Column, Eluent of 0~28% Ethyl acetate/Petroleum ether gradient @ 80 mL/min) to give 30-5 (18.7 g, 89% yield) as a yellow solid. LCMS: (ES+) m/z (M+H)$^+$=366.9. $^1$H NMR (400 MHz, $CD_3OD$) δ=8.60-8.58 (d, J=7.2 Hz, 1H), 8.29 (s, 1H), 8.23 (s, 1H), 7.60-7.58 (ddd, J=9.2, 4.4, 2.0 Hz, 1H), 7.52-7.50 (dd, J=7.2, 1.2 Hz, 1H), 7.40-7.31 (m, 1H), 3.98 (s, 3H).

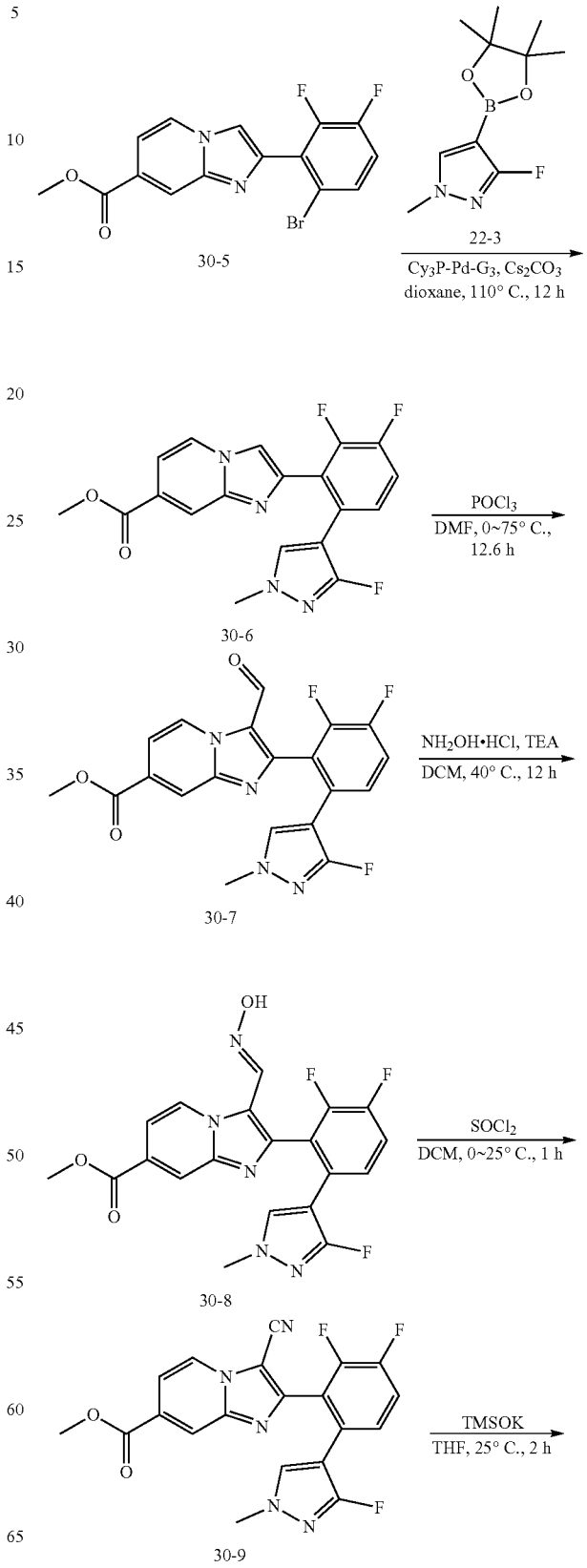

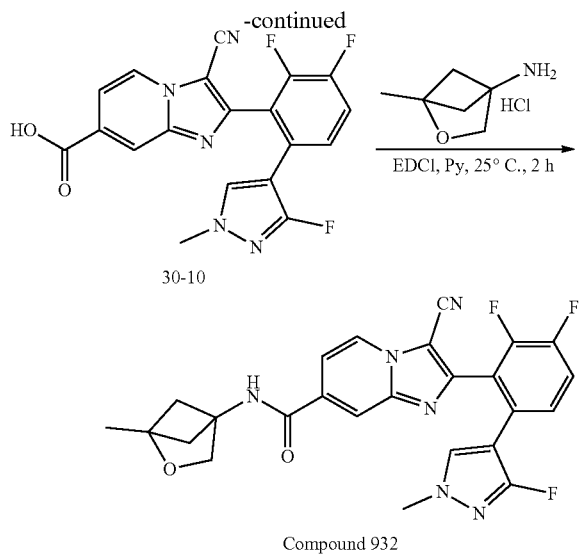

Compound 932

Step 6: Methyl 2-(2,3-difluoro-6-(3-fluoro-1-methyl-1H-pyrazol-4-yl)phenyl)imidazo[1,2-a]pyridine-7-carboxylate (30-6): To a solution of 30-5 (3.50 g, 9.50 mmol, 1 eq) and 22-3 (3.80 g, 14.30 mmol, 1.5 eq) in dioxane (100 mL) was added $Cs_2CO_3$ (9.30 g, 28.60 mmol, 3 eq). The reaction solution was degassed and purged with $N_2$ 3 times, then $Cy_3P$-Pd-$G_3$ (0.7 g, 0.95 mmol, 0.1 eq) was added. The mixture was degassed and purged with $N_2$ another 3 times, then stirred at 110° C. under $N_2$ for 12 hrs. The reaction mixture was diluted with water (100 mL), and then extracted with ethyl acetate (100 mL×3). The combined organic layers were washed with saturated brine (100 mL), dried over $Na_2SO_4$, filtered and concentrated under reduced pressure to give a residue. The residue was purified by flash silica gel chromatography (ISCO®; 80 g SepaFlash® Silica Flash Column, Eluent of 0-70 Ethyl acetate/Petroleum ether gradient @ 80 mL/min) to give 30-6 (2.8 g, 74% yield) as a yellow solid. LCMS: (ES+) m/z (M+H)$^+$=387.0. $^1$H NMR (400 MHz, $CD_3OD$) δ=8.53-8.51 (d, J=7.2 Hz, 1H), 8.22 (s, 1H), 8.03 (s, 1H), 7.48-7.46 (dd, J=7.2, 1.6 Hz, 1H), 7.45-7.37 (m, 1H), 7.34-7.28 (m, 1H), 7.22-7.20 (d, J=2.4 Hz, 1H), 3.97 (s, 3H), 3.63 (s, 3H).

Step 7: Methyl 2-(2,3-difluoro-6-(3-fluoro-1-methyl-1H-pyrazol-4-yl)phenyl)-3-formylimidazo[1,2-a]pyridine-7-carboxylate (30-7): $POCl_3$ (9.4 mL, 0.10 mol, 30 eq) was added dropwise into anhydrous DMF (7 mL) at 0° C. The reaction solution was degassed and purged with $N_2$ 3 times and stirred at 0° C. for 0.2 hr, then 25° C. for 0.2 hr. Then a solution of 30-6 (1.30 g, 3.40 mmol, 1 eq) in anhydrous DMF (14 mL) was added dropwise to the mixture at 0° C. The mixture was stirred at 25° C. for 0.2 hr, then warmed to 75° C. for another 12 hrs. The reaction mixture was quenched by addition of water (100 mL), adjusted to pH 7 by addition of saturated aqueous $NaHCO_3$ at 0° C., then extracted with ethyl acetate (200 mL×3). The combined organic layers were washed with saturated brine (200 mL), dried over $Na_2SO_4$, filtered and concentrated under reduced pressure to give 30-7 (1.2 g, crude) as a yellow solid. LCMS: (ES+) m/z (M+H)$^+$=415.1. $^1$H NMR (400 MHz, DMSO) δ=11.62 (s, 1H), 9.19-9.17 (d, J=7.2 Hz, 1H), 8.29-8.20 (m, 1H), 8.08 (s, 1H), 7.65-7.60 (m, 2H), 7.39-7.30 (m, 2H), 3.93 (s, 3H), 3.55 (s, 3H).

Step 8: Methyl 2-(2,3-difluoro-6-(3-fluoro-1-methyl-1H-pyrazol-4-yl)phenyl)-3-((hi96ydroxyimino)methyl)imidazo[1,2-a]pyridine-7-carboxylate (30-8): To a solution of 30-7 (1.20 g, 3.10 mmol, 1 eq) in DCM (20 mL) was added TEA (2.6 mL, 18.80 mmol, 6 eq) and hydroxylamine hydrochloride (0.33 g, 4.70 mmol, 1.5 eq). The mixture was stirred at 40° C. for 12 hrs. The reaction mixture was quenched by addition of water (80 mL), and then extracted with ethyl acetate (80 mL×3). The combined organic layers were washed with saturated brine (80 mL), dried over $Na_2SO_4$, filtered and concentrated under reduced pressure to give a residue. The residue was purified by flash silica gel chromatography (ISCO®; 40 g SepaFlash® Silica Flash Column, Eluent of 0-65% Ethyl acetate/Petroleum ether gradient @ 80 mL/min) to give 30-8 (1.1 g, 84% yield) as a yellow solid. LCMS: (ES+) m/z (M+H)$^+$=430.1. $^1$H NMR (400 MHz, DMSO) δ=11.62 (s, 1H), 9.18-9.16 (d, J=7.2 Hz, 1H), 8.28 (s, 1H), 8.08 (s, 1H), 7.70-7.62 (m, 2H), 7.38-7.36 (br dd, J=8.4, 4.4 Hz, 1H), 7.32-7.30 (d, J=2.0 Hz, 1H), 3.92 (s, 3H), 3.55 (s, 3H).

Step 9: Methyl 3-cyano-2-(2,3-difluoro-6-(3-fluoro-1-methyl-1H-pyrazol-4-yl)phenyl)imidazo[1,2-a]pyridine-7-carboxylate (30-9): To a solution of 30-8 (0.50 g, 1.20 mmol, 1 eq) in DCM (5 mL) was added thionyl chloride (0.83 g, 7.00 mmol, 6 eq) at 0° C. The mixture was stirred at 25° C. for 1 hr. The reaction mixture was quenched by addition of water (20 mL), adjusted to pH 7 by addition of saturated aqueous $NaHCO_3$ at 0° C., then extracted with ethyl acetate (50 mL×3). The combined organic layers were washed with saturated brine (30 mL), dried over $Na_2SO_4$, filtered and concentrated under reduced pressure to give 30-9 (465 mg, crude) as a yellow oil. LCMS: (ES+) m/z (M+H)$^+$=412.0. $^1$H NMR (400 MHz, DMSO) δ=8.85-8.83 (dd, J=7.2, 0.8 Hz, 1H), 8.38 (s, 1H), 7.80-7.70 (m, 1H), 7.67-7.65 (dd, J=7.2, 1.6 Hz, 1H), 7.49-7.47 (d, J=2.0 Hz, 1H), 7.43-7.41 (dd, J=8.4, 4.0 Hz, 1H), 3.94 (s, 3H), 3.60 (s, 3H).

Step 10: 3-cyano-2-(2,3-difluoro-6-(3-fluoro-1-methyl-1H-pyrazol-4-yl)phenyl)imidazo[1,2-a]pyridine-7-carboxylic acid (30-10): To a solution of 30-9 (0.46 g, 1.10 mmol, 1 eq) in THF (5 mL) was added TMSOK (0.21 g, 1.70 mmol, 1.5 eq). The mixture was stirred at 25° C. for 2 hrs. The reaction mixture was adjusted to pH 7 by addition of 1 N aqueous HCl at 0° C., then concentrated under reduced pressure to give 30-10 (440 mg, crude) as a yellow solid. LCMS: (ES+) m/z (M+H)$^+$=397.8.

Step 11: 3-cyano-2-(2,3-difluoro-6-(3-fluoro-1-methyl-1H-pyrazol-4-yl)phenyl)-N-(1-methyl-2-oxabicyclo[2.1.1]hexan-4-yl)imidazo[1,2-a]pyridine-7-carboxamide (Compound 932): To a solution of 30-10 (0.15 g, 0.38 mmol, 1 eq) in Py (3 mL) was added EDCI (0.22 g, 1.10 mmol, 3 eq) and 1-methyl-2-oxabicyclo[2.1.1]hexan-4-amine hydrochloride (56.5 mg, 0.38 mmol, 1 eq, HCl). The mixture was stirred at 25° C. for 2 hrs. The reaction mixture was diluted with water (20 mL), and then extracted with ethyl acetate (20 mL×3). The combined organic layers were washed with saturated brine (20 mL), dried over $Na_2SO_4$, filtered and concentrated under reduced pressure to give a residue. The residue was purified by prep-HPLC (column: CD02-Waters Xbridge BEH C18 150×25×10 um; mobile phase: [A: water (0.1% $NH_3·H_2O$); B: ACN]; B %: 28%-58%, 10 min) to give Compound 932 (36.21 mg, 19% yield) as a white solid. LCMS: (ES+) m/z (M+H)$^+$=493.3. $^1$H NMR (400 MHz, $CDCl_3$) δ=8.42-8.40 (d, J=7.2 Hz, 1H), 8.09 (s, 1H), 7.58-7.56 (dd, J=7.2, 1.6 Hz, 1H), 7.36 (q, J=8.4 Hz, 1H), 7.26-7.19 (m, 2H), 6.92 (s, 1H), 3.97 (s, 2H), 3.72 (s, 3H), 2.15-2.04 (m, 4H), 1.52 (s, 3H).

Example 19: (3-chloro-2-(2-fluoro-6-(1-methyl-1H-pyrazol-4-yl)phenyl)imidazo[1,2-a]pyridin-7-yl)(2-hydroxy-2-methyl-7-azaspiro[3.5]nonan-7-yl)methanone (Compound 915)

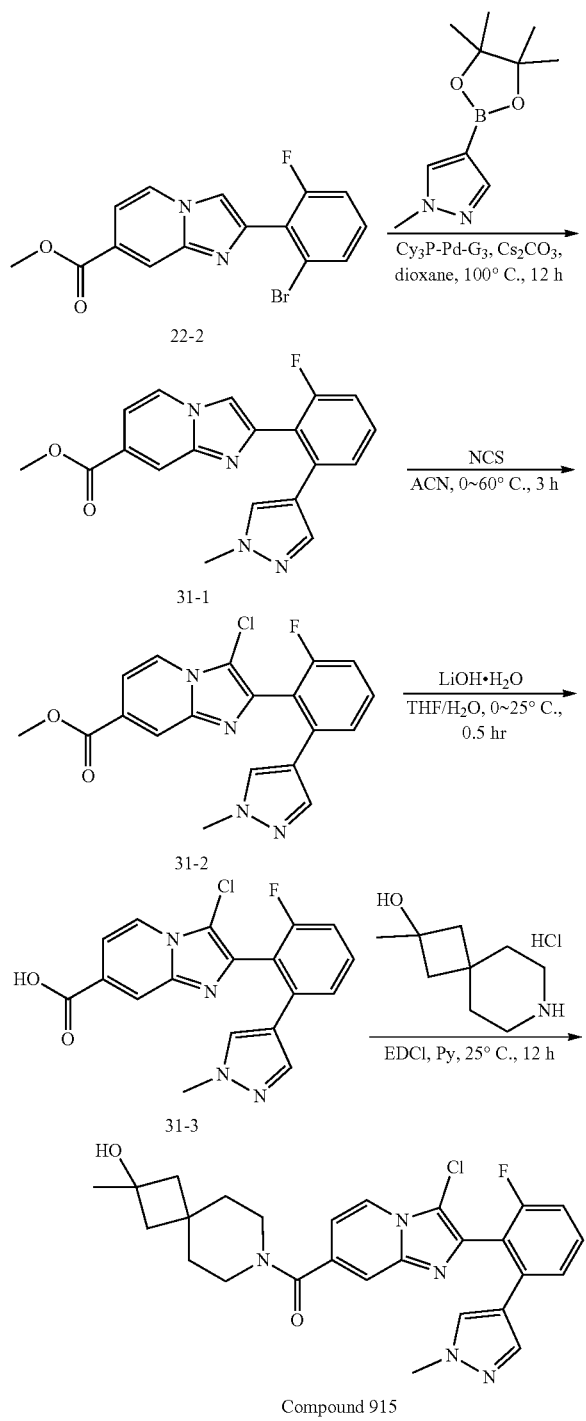

Step 1: Methyl 2-(2-fluoro-6-(1-methyl-1H-pyrazol-4-yl)phenyl)imidazo[1,2-a]pyridine-7-carboxylate (31-1): To a solution of 22-2 (2.2 g, 6.30 mmol, 1 eq) and 1-methyl-4-(4,4,5,5-tetramethyl-1,3,2-dioxaborolan-2-yl)-1H-pyrazole (1.97 g, 9.45 mmol, 1.5 eq) in dioxane (30 mL) was added Cs$_2$CO$_3$ (6.16 g, 18.90 mmol, 3 eq) and PCy$_3$ Pd G3 (0.46 g, 0.63 mmol, 0.1 eq). The reaction solution was degassed and purged with N$_2$ 3 times and stirred at 100° C. for 12 hrs. The mixture was diluted with H$_2$O (100 mL), and extracted with EA (100 mL×3). The combined organic layers were washed with saturated brine (80 mL), dried over anhydrous Na$_2$SO$_4$, filtered and concentrated under reduced pressure to give a residue. The residue was purified by flash silica gel chromatography (ISCO®; 120 g SepaFlash® Silica Flash Column, Eluent of 0~80% Petroleum ether/Ethyl acetate@ 100 mL/min) to give 31-1 (2 g, 88% yield) as a yellow solid. LCMS: (ES+) m/z (M+H)$^+$=351.2.

Step 2: Methyl 3-chloro-2-(2-fluoro-6-(1-methyl-1H-pyrazol-4-yl)phenyl)imidazo[1,2-a]pyridine-7-carboxylate (31-2): To a solution of 31-1 (2 g, 5.71 mmol, 1 eq) in ACN (25 mL) was added NCS (0.76 g, 5.71 mmol, 1 eq) at 0° C. The mixture was stirred at 60° C. for 3 hrs. The mixture was diluted with H$_2$O (100 mL), and extracted with EA (80 mL×3). The combined organic layers were washed with saturated brine (20 mL), dried over anhydrous Na$_2$SO$_4$, filtered and concentrated under reduced pressure to give a residue. The residue was purified by flash silica gel chromatography (ISCO®; 120 g SepaFlash® Silica Flash Column, Eluent of 0~80% Ethyl acetate/Petroleum ether gradient @ 120 mL/min) to give 31-2 (2.1 g, 95% yield) as a yellow oil. LCMS: (ES+) m/z (M+H)$^+$=385.0.

Step 3: 3-chloro-2-(2-fluoro-6-(1-methyl-1H-pyrazol-4-yl)phenyl)imidazo[1,2-a]pyridine-7-carboxylic acid (31-3): To a solution of 31-2 (2.10 g, 5.46 mmol, 1 eq) in THF (10 mL) and H$_2$O (10 mL) was added LiOH·H$_2$O (0.45 g, 10.92 mmol, 2 eq) at 0° C. The mixture was stirred at 25° C. for 0.5 hr. The mixture was concentrated in vacuo to remove THF, then diluted with water (50 mL). The solution was adjusted to pH 5 with 2 N aqueous HCl at 0° C. Some solid precipitated out. The solid was collected by filtration and trituration with PE (50 mL) at 25° C. for 10 min to give 31-3 (1.92 g, 86% yield, HCl) as a white solid LCMS: (ES+) m/z (M+H)$^+$=371.1. $^1$H NMR (400 MHz, CD$_3$OD) δ=8.39 (dd, J=0.6, 7.1 Hz, 1H), 8.30 (s, 1H), 7.65 (dd, J=1.5, 7.1 Hz, 1H), 7.55 (dt, J=5.8, 8.0 Hz, 1H), 7.44 (d, J=7.6 Hz, 1H), 7.39 (s, 1H), 7.22-7.13 (m, 1H), 7.06 (s, 1H), 3.74 (s, 3H).

Step 4: (3-chloro-2-(2-fluoro-6-(1-methyl-1H-pyrazol-4-yl)phenyl)imidazo[1,2-a]pyridin-7-yl)(2-hydroxy-2-methyl-7-azaspiro[3.5]nonan-7-yl)methanone (Compound 915): To a solution of 3-chloro-2-(2-fluoro-6-(1-methyl-1H-pyrazol-4-yl)phenyl)imidazo[1,2-a]pyridine-7-carboxylic acid 31-3 (100 mg, 0.24 mmol, 1 eq, HCl) in pyridine (1 mL) was added EDCI (0.14 g, 0.73 mmol, 3 eq) and 2-methyl-7-azaspiro[3.5]nonan-2-ol hydrochloride (51.80 mg, 0.27 mmol, 1.1 eq, HCl). The mixture was stirred at 25° C. for 12 hrs. The reaction mixture was diluted with H$_2$O (10 mL), then extracted with ethyl acetate (10 mL×3). The combined organic layers were washed with saturated brine (10 mL), dried over Na$_2$SO$_4$, filtered and concentrated under reduced pressure to give a residue. The residue was purified by prep-HPLC (column: CD02-Waters Xbridge BEH C18 150×25×10 um; mobile phase: [A: water (0.1% NH$_4$HCO$_3$); B: ACN]; B %: 23%-53%, 10 min) to give Compound 915 (72.81 mg, 58% yield) as a white solid. LCMS: (ES$^+$) m/z (M+H)$^+$=508.2. $^1$H NMR (400 MHz, CD$_3$OD) δ=8.41-8.39 (d, J=7.2 Hz, 1H), 7.67 (s, 1H), 7.54-7.52 (dd, J=8.0, 5.6 Hz, 1H), 7.45-7.39 (m, 2H), 7.20-7.12 (m, 2H), 7.05 (s, 1H), 3.75 (s, 3H), 3.69 (s, 2H), 3.45-3.43 (d, J=1.2 Hz, 2H), 2.05-1.93 (m, 4H), 1.82-1.59 (m, 4H), 1.35 (s, 3H).

Example 20: (3-chloro-2-(2,3-difluoro-6-(3-fluoro-1-methyl-1H-pyrazol-4-yl)phenyl)imidazo[1,2-a]pyridin-7-yl)(morpholino)methanone (Compound 933)

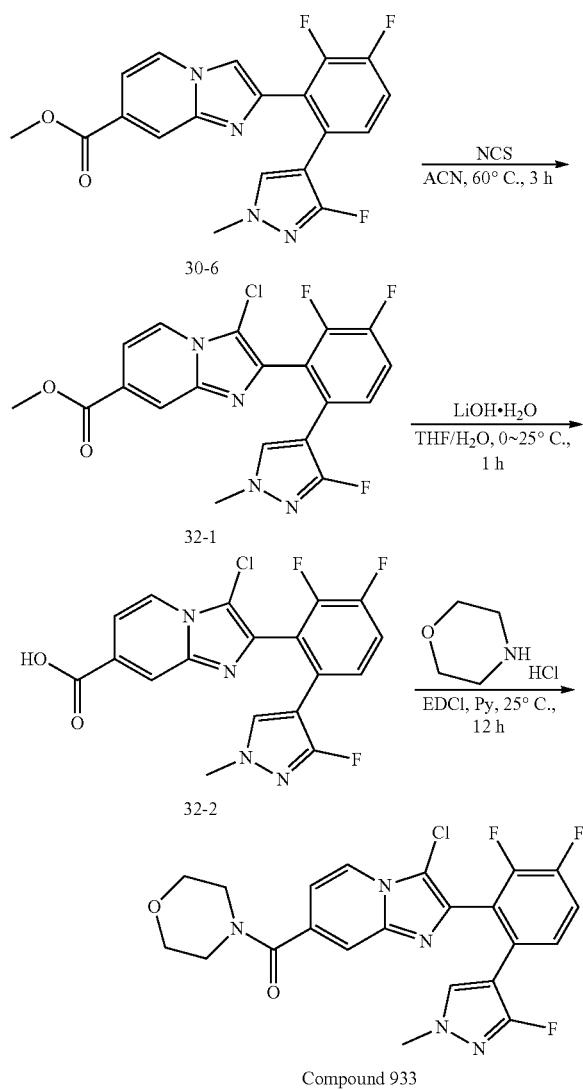

Step 1: Methyl 3-chloro-2-(2,3-difluoro-6-(3-fluoro-1-methyl-1H-pyrazol-4-yl)phenyl)imidazo[1,2-a]pyridine-7-carboxylate (32-1): To a solution of 30-6 (2.40 g, 6.20 mmol, 1 eq) in ACN (20 mL) was added NCS (0.99 g, 7.50 mmol, 1.2 eq). The mixture was stirred at 60° C. for 3 hrs. The reaction mixture was diluted with H₂O (100 mL), then extracted with EtOAc (100 mL×3). The combined organic layers were washed with saturated brine (50 mL×3), dried over Na₂SO₄, filtered and concentrated under reduced pressure to give a residue. The residue was purified by flash silica gel chromatography (ISCO®; 80 g SepaFlash® Silica Flash Column, Eluent of 25~45% Ethyl acetate/Petroleum ether gradient @ 100 m/min) to give 32-1 (2.2 g, 80% yield) as a yellow solid.

Step 2: 3-chloro-2-(2,3-difluoro-6-(3-fluoro-1-methyl-1H-pyrazol-4-yl)phenyl)imidazo[1,2-a]pyridine-7-carboxylic acid (32-2): To a solution of 32-1 (2.2 g, 5.2 mmol, 1 eq) in THF (10 mL) and H₂O (10 mL) was added LiOH·H₂O (0.66 g, 16 mmol, 3 eq) at 0° C. The mixture was stirred at 25° C. for 1 hr. The mixture was concentrated in vacuo to removed THF, and then diluted with water (30 mL). The clear solution was adjusted to pH 4 with 2 N aqueous HCl at 0° C., and then the mixture was filtered. The filter cake was collected to give 32-2 (0.8 g, 44% yield) as a yellow solid.

Step 3: (3-chloro-2-(2,3-difluoro-6-(3-fluoro-1-methyl-1H-pyrazol-4-yl)phenyl)imidazo[1,2-a]pyridin200-7-yl)(morpholino)methanone (Compound 933): To a solution of 32-2 (0.1 g, 0.25 mmol, 1 eq) in pyridine (2 mL) was added EDCI (94 mg, 0.49 mmol, 2 eq) and morpholine hydrochloride (36 mg, 0.30 mmol, 1.2 eq). The mixture was stirred at 25° C. for 12 hrs. The reaction mixture was adjusted to pH 7 by addition of 1 N aqueous HCl, then extracted with EtOAc (10 mL×3). The combined organic layers were washed with saturated brine (30 mL), dried over Na₂SO₄, filtered and concentrated under reduced pressure to give a residue. The residue was purified by prep-HPLC (column: CD01-Phenomenex luna C18 150×25×10 um; mobile phase: [A: water (0.05% FA); B: ACN]; B %: 29%-59%, 10 min) to give Compound 933 (54 mg, 42% yield) as a white solid. LCMS: (ES⁺) m/z (M+H)⁺=476.2. ¹H NMR (400 MHz, CD₃OD) δ=8.46 (dd, J=0.8, 7.2 Hz, 1H), 7.73 (s, 1H), 7.56-7.47 (m, 1H), 7.42-7.36 (m, 1H), 7.25-7.20 (m, 2H), 3.75 (d, J=5.6 Hz, 7H), 3.64 (s, 3H), 3.61 (s, 1H).

Example 21: 3-chloro-2-(2-fluoro-6-(1-methyl-1H-pyrazol-4-yl)phenyl)-N-((1r,4r)-4-hydroxy-4-methylcyclohexyl)imidazo[1,2-a]pyridine-7-carboxamide (Compound 918)

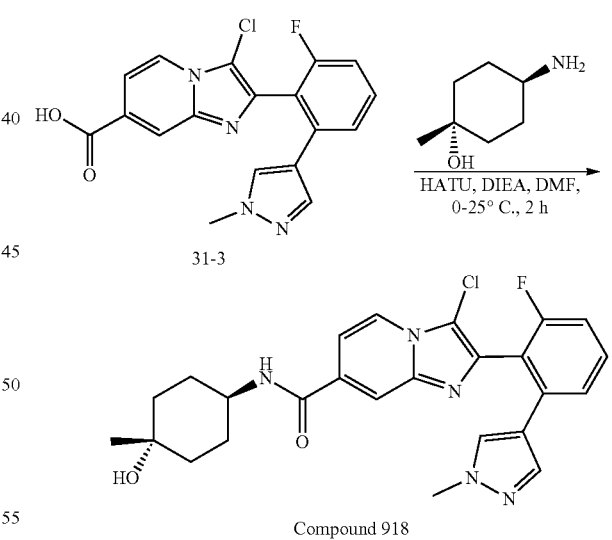

Step 1: 3-chloro-2-(2-fluoro-6-(1-methyl-1H-pyrazol-4-yl)phenyl)-N-((1r,4r)-4-hydroxy-4-methylcyclohexyl)imidazo[1,2-a]pyridine-7-carboxamide (Compound 918): To a solution of 31-3 (0.20 g, 0.54 mmol, 1 eq) in DMF (2 mL) was added HATU (0.41 g, 1.08 mmol, 2 eq) and DIEA (0.28 g, 2.16 mmol, 4 eq) at 0° C. The mixture was stirred at 25° C. for 0.5 hour under N₂ atmosphere, then 4-amino-1-methyl-cyclohexanol (0.11 g, 0.81 mmol, 1.50 eq) was added. The mixture was stirred at 25° C. for another 1.5 hours under N₂ atmosphere. The reaction mixture was filtered to remove some insoluble impurities. The filtrate was purified by prep-HPLC (column: CD02-Waters Xbridge BEH C18 150×25×10 um; mobile phase: [A: water (0.1% NH$_4$HCO$_3$); B: ACN]; B %: 21%-51%, 10 min) to give Compound 918 (141.28 mg, 54% yield) as a white solid. LCMS: (ES+) m/z (M+H)$^+$=482.1. $^1$H NMR (400 MHz, CD$_3$OD) δ (ppm)=8.39 (d, J=7.2 Hz, 1H), 8.11 (s, 1H), 7.59-7.50 (m, 2H), 7.47-7.37 (m, 2H), 7.17 (t, J=8.8 Hz, 1H), 7.02 (s, 1H), 4.01-3.92 (m, 1H), 3.74 (s, 3H), 2.01-1.92 (m, 2H), 1.80-1.71 (m, 2H), 1.68-1.56 (m, 4H), 1.30 (s, 3H).

Example 22: 3-cyano-2-(2-fluoro-6-(3-fluoro-1-methyl-1H-pyrazol-4-yl)phenyl)-N-((1r,3r)-3-hydroxy-3-methylcyclobutyl)imidazo[1,2-a]pyridine-7-carboxamide (Compound 925)

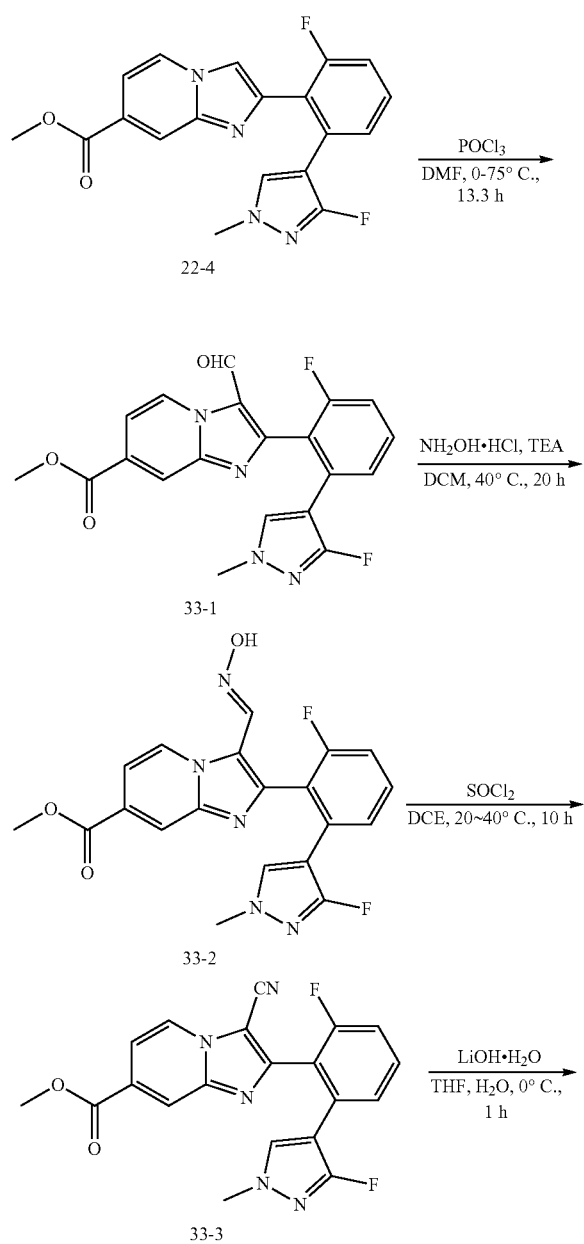

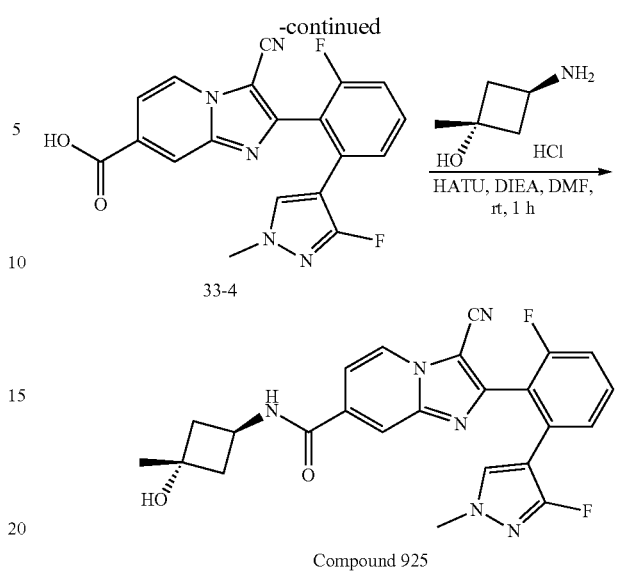

Compound 925

Step 1: Methyl 2-(2-fluoro-6-(3-fluoro-1-methyl-1H-pyrazol-4-yl)phenyl)-3-formylimidazo[1,2-a]pyridine-7-carboxylate (33-1): To a solution of DMF (20 mL) was added POCl$_3$ (16.65 g, 108.60 mmol, 10.12 mL) dropwise at 0° C. The mixture was stirred at 0° C. for 0.3 h, then at 25° C. for 0.5 h under N$_2$. A solution of 22-4 (4 g, 10.86 mmol) in DMF (20 mL) was added dropwise to the resulting mixture. The mixture was stirred at 25° C. for 0.5 h, then warmed to 75° C. and stirred for 12 h under N$_2$ atmosphere. The reaction mixture was quenched with saturated aqueous NaHCO$_3$ (200 mL) at 0° C., then extracted with ethyl acetate (200 mL×3). The combined organic layers were washed with saturated brine (300 mL×3), dried over anhydrous sodium sulfate, filtered and concentrated under reduced pressure to give 33-1 (6 g, crude) as yellow oil.

Step 2: Methyl 2-(2-fluoro-6-(3-fluoro-1-methyl-1H-pyrazol-4-yl)phenyl)-3-((h2O2ydroxyimino)methyl)imidazo[1,2-a]pyridine-7-carboxylate (33-2): To a solution of 33-1 (6 g, 15.14 mmol) in DCM (120 mL) was added NH$_2$OH·HCl (10.52 g, 151.38 mmol) and TEA (7.66 g, 75.69 mmol, 10.54 mL). The mixture was stirred at 40° C. for 20 hrs. The reaction mixture was poured into water (50 mL), then extracted with DCM (50 mL×2). The combined organic layers were dried over anhydrous sodium sulfate, filtered and concentrated under reduced pressure to give a residue. The residue was purified by flash silica gel chromatography (ISCO®; 80 g SepaFlash® Silica Flash Column, Eluent of 30~100% Ethyl acetate/Petroleum ether gradient @ 100 mL/min) to give 33-2 (4.75 g, 76% yield) as a yellow solid. LCMS: (ES$^+$) m/z (M+H)$^+$=412.0. $^1$H NMR (400 MHz, DMSO) δ=11.93 (s, 1H), 8.32 (d, J=7.2 Hz, 1H), 8.22 (s, 1H), 7.58-7.52 (m, 2H), 7.48 (dd, J=1.6, 7.2 Hz, 1H), 7.33 (d, J=8.0 Hz, 1H), 7.27 (t, J=9.2 Hz, 1H), 7.14 (d, J=2.0 Hz, 1H), 3.92 (s, 3H), 3.53 (s, 3H).

Step 3: Methyl 3-cyano-2-(2-fluoro-6-(3-fluoro-1-methyl-TH-pyrazol-4-yl)phenyl)imidazo[1,2-a]pyridine-7-carboxylate (33-3): To a mixture of 33-2 (4.47 g, 10.87 mmol) in DCE (60 mL) was added SOCl$_2$ (6.46 g, 54.33 mmol, 3.95 mL) at 20° C. The mixture was stirred at 40° C. for 10 hrs, then quenched by addition of saturated aqueous NaHCO$_3$ (100 mL) at 0° C. The reaction mixture was extracted with DCM (100 mL×2). The combined organic layers were washed with saturated brine (100 mL), dried over anhydrous sodium sulfate, filtered and concentrated under reduced pressure to give a residue. The residue was purified by flash silica gel chromatography (ISCO®; 80 g SepaFlash® Silica Flash Column, Eluent of 20-30% Ethyl acetate/Petroleum ether gradient @ 100 mL/min) to give 33-3 (3.7 g, 86% yield) as a yellow solid.

Step 4: 3-cyano-2-(2-fluoro-6-(3-fluoro-1-methyl-1H-pyrazol-4-yl)phenyl)imidazo[1,2-a]pyridine-7-carboxylic acid (33-4): To a solution of methyl 3-cyano-2-(2-fluoro-6-(3-fluoro-1-methyl-1H-pyrazol-4-yl)phenyl)imidazo[1,2-a] pyridine-7-carboxylate 33-3 (1.65 g, 4.19 mmol) in THF (16 mL) was added LiOH·H$_2$O (0.35 g, 8.39 mmol) in H$_2$O (3 mL) at 0° C. The mixture was stirred at 0° C. for 1 hr. The reaction mixture was diluted with H$_2$O (20 mL), adjusted to pH 5 with 1 N aqueous HCl, and extracted with ethyl acetate (20 mL×3). The combined organic layers were washed with saturated brine (40 mL), dried over anhydrous sodium sulfate, filtered and concentrated under reduced pressure to give 33-4 (2.09 g, 95.7% purity) as a white solid. LCMS: (ES$^+$) m/z (M+H)$^+$=380.0. $^1$H NMR (400 MHz, CD$_3$OD) δ=8.68 (d, J=7.2 Hz, 1H), 8.38 (s, 1H), 7.80 (d, J=6.8 Hz, 1H), 7.68-7.60 (m, 1H), 7.44 (d, J=8.0 Hz, 1H), 7.37 (d, J=1.6 Hz, 1H), 7.32 (t, J=9.2 Hz, 1H), 3.68 (s, 3H).

Step 5: 3-cyano-2-(2-fluoro-6-(3-fluoro-1-methyl-1H-pyrazol-4-yl)phenyl)-N-((1r,3r)-3-hydroxy-3-methylcyclobutyl)imidazo[1,2-a]pyridine-7-carboxamide (Compound 925): To a solution of 33-4 (0.15 g, 0.39 mmol, 1 eq) in DMF (4 mL) was added HATU (0.23 g, 0.59 mmol, 1.50 eq) and DIEA (0.15 g, 1.19 mmol, 0.21 mL, 3.00 eq) at 0° C. The mixture was stirred at 25° C. for 0.5 h. Then (1r,3r)-3-amino-1-methylcyclobutan-1-ol hydrochloride (0.06 g, 0.47 mmol, 1.20 eq) was added. The mixture was stirred at 25° C. for another 0.5 hr. The reaction mixture was filtered and the filtrate was concentrated under reduced pressure to give a residue. The residue was purified by prep-HPLC (column: CD02-Waters Xbridge BEH C18 150× 25×10 um; mobile phase: [A: water (0.1% NH$_4$HCO$_3$); B: ACN]; B %: 19%-49%, 10 min) to give Compound 925 (0.56 mg, 30% yield) as a white solid. LCMS: (ES+) m/z (M+H)$^+$=463.1. $^1$H NMR (400 MHz, CD$_3$OD) δ (ppm)= 8.66 (dd, J=0.8, 7.1 Hz, 1H), 8.22-8.14 (m, 1H), 7.68-7.59 (m, 2H), 7.42 (d, J=7.6 Hz, 1H), 7.36 (d, J=2.4 Hz, 1H), 7.33-7.26 (m, 1H), 4.62 (q, J=8.0 Hz, 1H), 3.66 (s, 3H), 2.55-2.42 (m, 2H), 2.23-2.14 (m, 2H), 1.40 (s, 3H).

Example 23: 3-cyano-2-(2-fluoro-6-(3-fluoro-1-methyl-1H-pyrazol-4-yl)phenyl)-N-((1r,4r)-4-hydroxy-4-methylcyclohexyl)imidazo[1,2-a]pyridine-7-carboxamide (Compound 930)

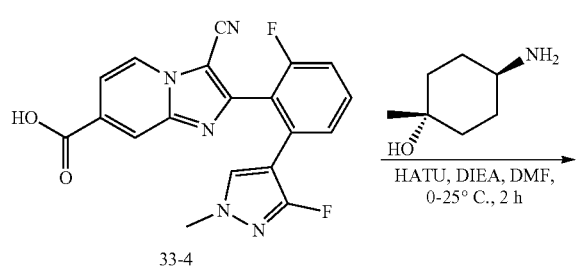

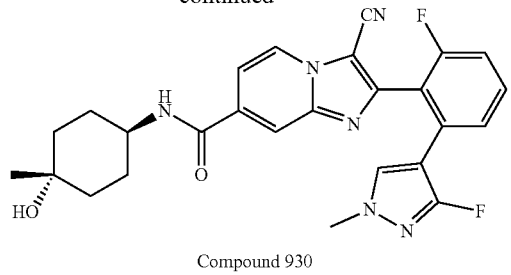

Compound 930

Step 1: 3-cyano-2-(2-fluoro-6-(3-fluoro-1-methyl-1H-pyrazol-4-yl)phenyl)-N-((1r,4r)-4-hydroxy-4-methylcyclohexyl)imidazo[1,2-a]pyridine-7-carboxamide (Compound 930): To a solution of 33-4 (0.15 g, 0.39 mmol, 1.00 eq) in DMF (2 mL) was added HATU (0.30 g, 0.79 mmol, 2.00 eq) and DIEA (0.20 g, 1.58 mmol, 0.28 mL, 4.00 eq) at 0° C. The mixture was stirred at 25° C. for 0.5 hours under N$_2$ atmosphere, then (1r,4r)-4-amino-1-methylcyclohexan-1-ol (0.08 g, 0.59 mmol, 1.50 eq) was added. The mixture was stirred at 25° C. for another 1.5 hours under N$_2$ atmosphere. The reaction mixture was filtered and the filtrate was concentrated under reduced pressure to give a residue. The residue was purified by prep-HPLC (column: CD02-Waters Xbridge BEH C18 150×25×10 um; mobile phase: [A: water (0.1% NH$_4$HCO$_3$); B: ACN]; B %: 22%-52%, 10 min) to give Compound 930 (85.7 mg, 44% yield) as a yellow solid. LCMS: (ES+) m/z (M+H)$^+$=491.1. $^1$H NMR (400 MHz, CD$_3$OD) δ (ppm)=8.65 (dd, J=0.8, 7.2 Hz, 1H), 8.17 (dd, J=0.8, 1.5 Hz, 1H), 7.67-7.59 (m, 2H), 7.42 (d, J=8.0 Hz, 1H), 7.36 (d, J=2.4 Hz, 1H), 7.33-7.26 (m, 1H), 4.01-3.90 (m, 1H), 3.66 (s, 3H), 2.00-1.92 (m, 2H), 1.78-1.72 (m, 2H), 1.65-1.56 (m, 4H), 1.29 (s, 3H).

Example 24: 3-cyano-2-(2-fluoro-6-(3-fluoro-1-methyl-1H-pyrazol-4-yl)phenyl)-N-(1-methyl-2-oxabicyclo[2.1.1]hexan-4-yl)imidazo[1,2-a]pyridine-7-carboxamide (Compound 845)

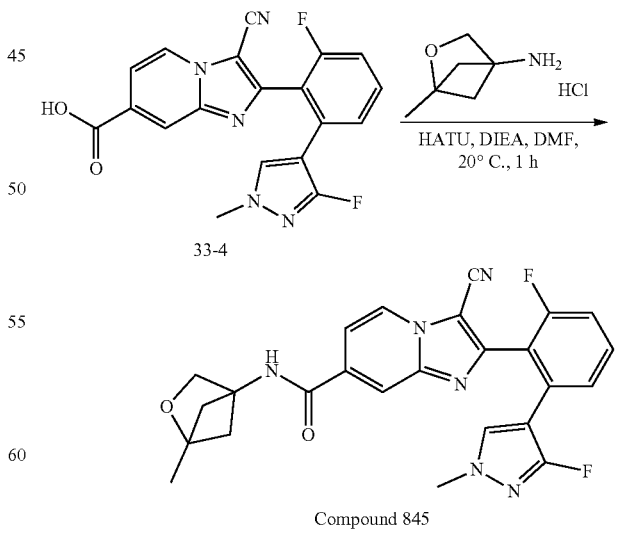

Compound 845

Step 1: 3-cyano-2-(2-fluoro-6-(3-fluoro-1-methyl-1H-pyrazol-4-yl)phenyl)-N-(1-methyl-2-oxabicyclo[2.1.1] hexan-4-yl)imidazo[1,2-a]pyridine-7-carboxamide (Compound 845): To a solution of 33-4 (0.16 g, 0.42 mmol, 1 eq), 1-methyl-2-oxabicyclo[2.1.1]hexan-4-amine hydrochloride (76 mg, 0.51 mmol, 1.2 eq) in DMF (1.6 mL) was added HATU (0.21 g, 0.55 mmol, 1.3 eq), DIEA (0.16 g, 1.3 mmol, 3 eq). The mixture was stirred at 20° C. for 1 hr. The reaction mixture was concentrated under vacuum to give a residue. The residue was purified by prep-HPLC (column: Phenomenex luna C18 150×25 mm×10 um; mobile phase: [A: water (0.1% FA); B: ACN]; B %: 26%-56%, 10 min) to give Compound 845 (0.11 g, 51% yield) as an off-white solid. LCMS: (ES+) m/z (M+H)+=475.0. $^1$H NMR (400 MHz, DMSO-$d_6$) δ=9.41 (s, 1H), 8.82 (d, J=7.2 Hz, 1H), 8.34 (s, 1H), 7.67 d, J=8.0 Hz, 2H), 7.47 (d, J=2.0 Hz, 1H), 7.45-7.37 (m, 2H), 3.78 (s, 2H), 3.61 (s, 3H), 2.06 (d, J=4.0 Hz, 2H), 1.86 (d, J=4.4 Hz, 2H), 1.40 (s, 3H).

The compounds in Table 1 were prepared according to the procedures described above using the appropriate intermediates and reagents.

TABLE 1

| Compound | Structure | LCMS (ES+) m/z |
|---|---|---|
| 7 | 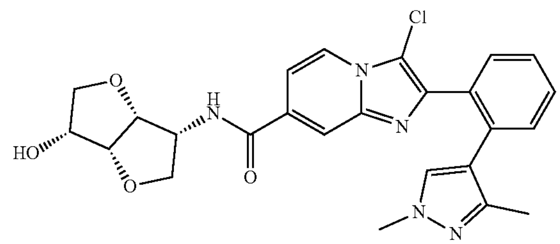 [SMILES: Cc1nn(C)cc1-c1ccccc1-c1nc2cc(C(=O)N[C@@H]3CO[C@H]4[C@@H]3OC[C@H]4O)ccn2c1Cl] | 494.1 |
| 16 | 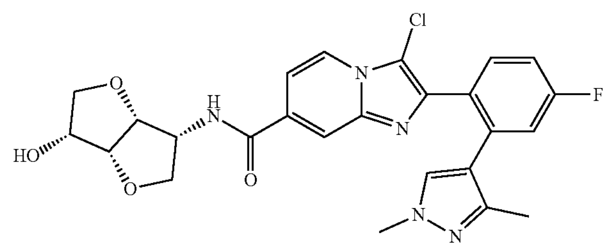 [SMILES: Cc1nn(C)cc1-c1cc(F)ccc1-c1nc2cc(C(=O)N[C@@H]3CO[C@H]4[C@@H]3OC[C@H]4O)ccn2c1Cl] | 512.2 |
| 17 | 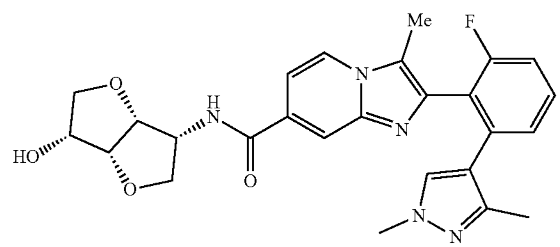 [SMILES: Cc1nn(C)cc1-c1cccc(F)c1-c1nc2cc(C(=O)N[C@@H]3CO[C@H]4[C@@H]3OC[C@H]4O)ccn2c1C] | 492.3 |
| 18 | 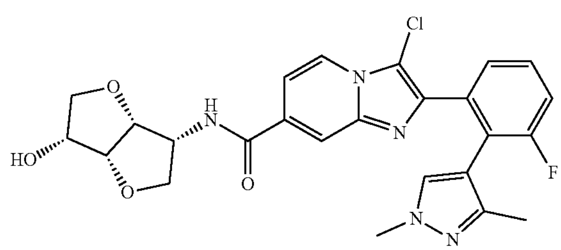 [SMILES: Cc1nn(C)cc1-c1c(F)cccc1-c1nc2cc(C(=O)N[C@@H]3CO[C@H]4[C@@H]3OC[C@H]4O)ccn2c1Cl] | 512.1 |
| 142 | 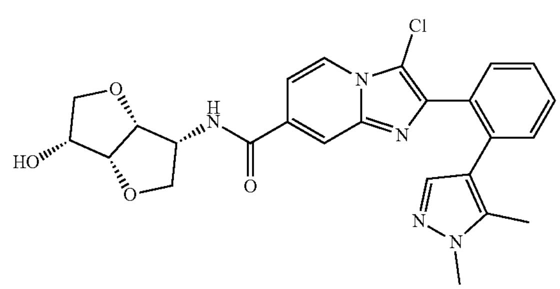 [SMILES: Cc1c(-c2ccccc2-c2nc3cc(C(=O)N[C@@H]4CO[C@H]5[C@@H]4OC[C@H]5O)ccn3c2Cl)cnn1C] | 494.2 |

TABLE 1-continued

| Compound | Structure | LCMS (ES+) m/z |
|---|---|---|
| 254 | 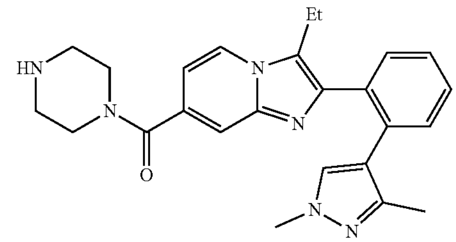 [SMILES: CCc1c(-c2ccccc2-c2cn(C)nc2C)nc2cc(C(=O)N3CCNCC3)ccn12] | 429.1 |
| 255 | 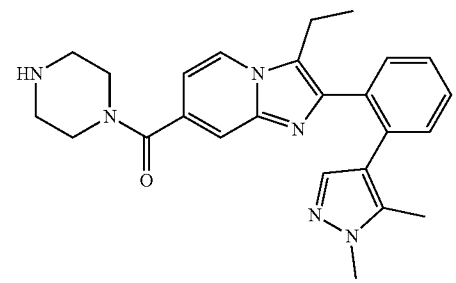 [SMILES: CCc1c(-c2ccccc2-c2cnn(C)c2C)nc2cc(C(=O)N3CCNCC3)ccn12] | 429.1 |
| 262 | 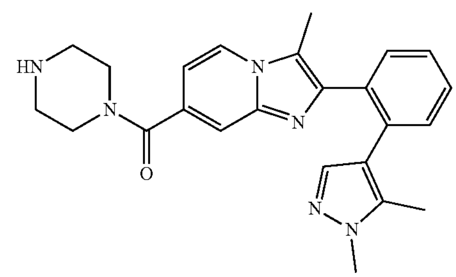 [SMILES: Cc1c(-c2ccccc2-c2nc3cc(C(=O)N4CCNCC4)ccn3c2C)cnn1C] | 415.1 |
| 264 | 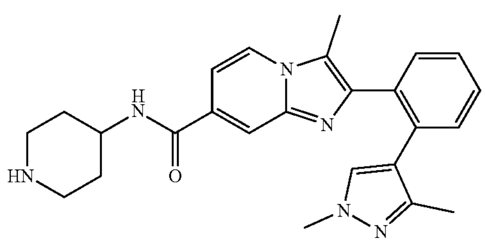 [SMILES: Cc1nn(C)cc1-c1ccccc1-c1nc2cc(C(=O)NC3CCNCC3)ccn2c1C] | 429.3 |
| 271 | 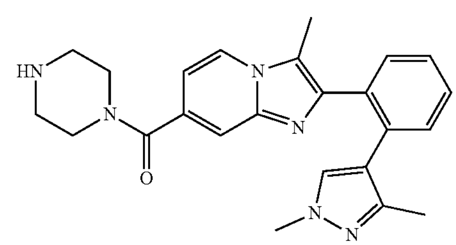 [SMILES: Cc1nn(C)cc1-c1ccccc1-c1nc2cc(C(=O)N3CCNCC3)ccn2c1C] | 415.1 |
| 284 | 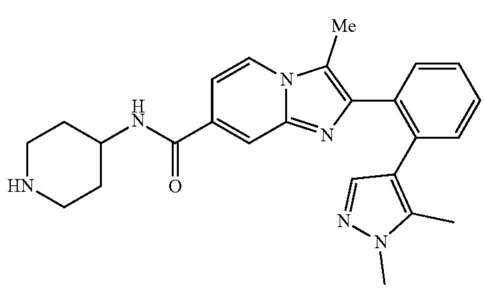 [SMILES: Cc1c(-c2ccccc2-c2nc3cc(C(=O)NC4CCNCC4)ccn3c2C)cnn1C] | 429.4 |

TABLE 1-continued
| Compound | Structure | LCMS (ES+) m/z |
|---|---|---|
| 289 | 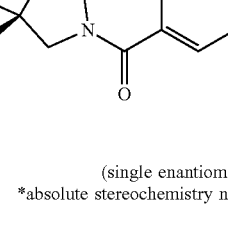 (single enantiomer) *absolute stereochemistry not determined | 445.1 |
| 295 | 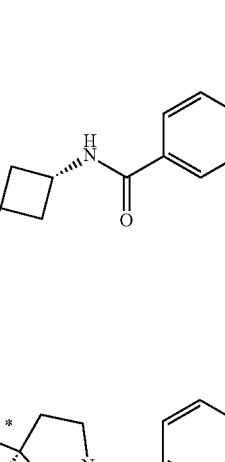 | 458.2 |
| 297 | 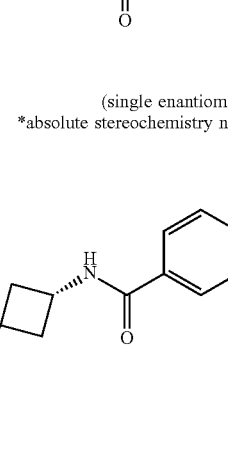 (single enantiomer) *absolute stereochemistry not determined | 445.1 |
| 298 | 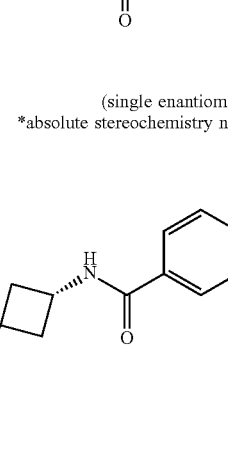 | 458.1 |
| 312 | 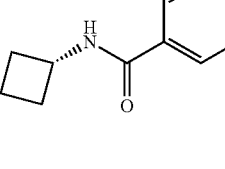 | 458.1 |

TABLE 1-continued

| Compound | Structure | LCMS (ES+) m/z |
|---|---|---|
| 313 | (single enantiomer) *absolute stereochemistry not determined | 445.3 |
| 314 | (single enantiomer) *absolute stereochemistry not determined | 445.3 |
| 317 | 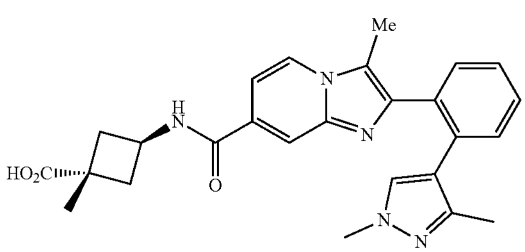 [SMILES: Cc1nn(C)cc1-c1ccccc1-c1nc2cc(C(=O)N[C@H]3C[C@](C)(C(=O)O)C3)ccn2c1C] | 458.1 |
| 425 | 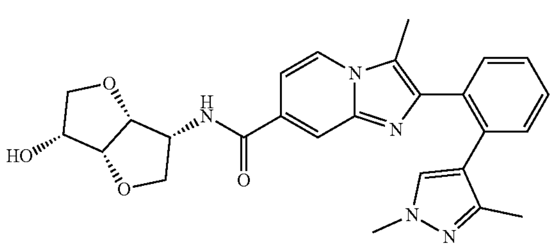 [SMILES: Cc1nn(C)cc1-c1ccccc1-c1nc2cc(C(=O)N[C@@H]3CO[C@H]4[C@@H]3OC[C@H]4O)ccn2c1C] | 474.1 |
| 430 | 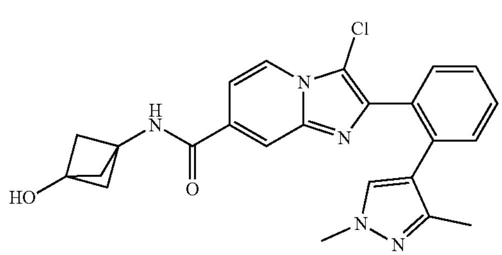 [SMILES: Cc1nn(C)cc1-c1ccccc1-c1nc2cc(C(=O)NC34CC(O)(C3)C4)ccn2c1Cl] | 448.2 |

TABLE 1-continued

| Compound | Structure | LCMS (ES+) m/z |
|---|---|---|
| 431 | 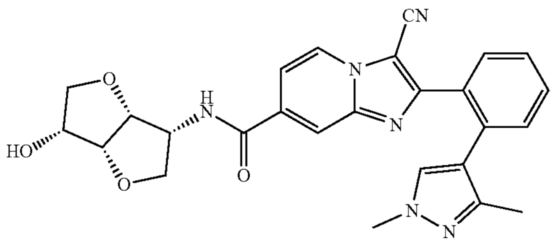 [SMILES: Cc1nn(C)cc1-c1ccccc1-c1nc2cc(C(=O)N[C@@H]3CO[C@H]4[C@@H]3OC[C@H]4O)ccn2c1C#N] | 485.1 |
| 434 | 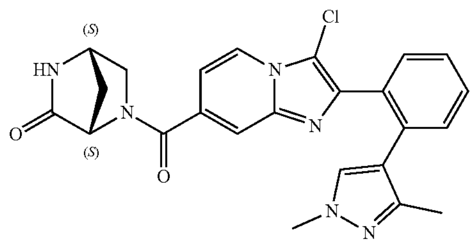 | 461.4 |
| 436 | 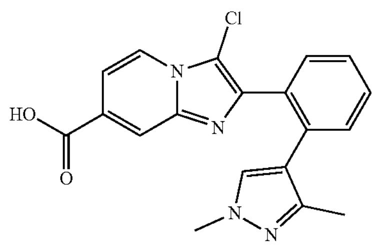 [SMILES: Cc1nn(C)cc1-c1ccccc1-c1nc2cc(C(=O)O)ccn2c1Cl] | 367.2 |
| 442 | 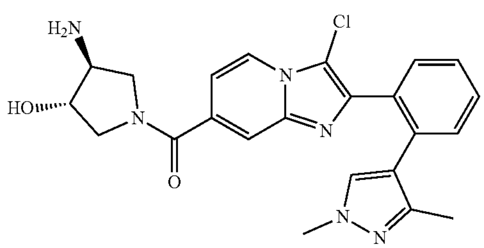 [SMILES: Cc1nn(C)cc1-c1ccccc1-c1nc2cc(C(=O)N3C[C@H](N)[C@@H](O)C3)ccn2c1Cl] | 451.3 |
| 443 | 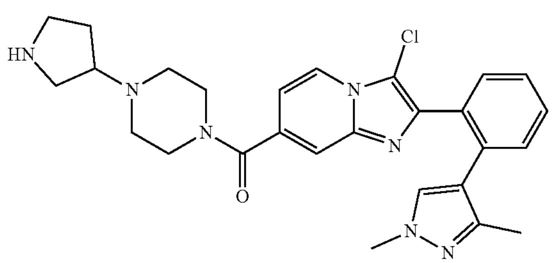 [SMILES: Cc1nn(C)cc1-c1ccccc1-c1nc2cc(C(=O)N3CCN(C4CCNC4)CC3)ccn2c1Cl] | 504.2 |
| 447 | 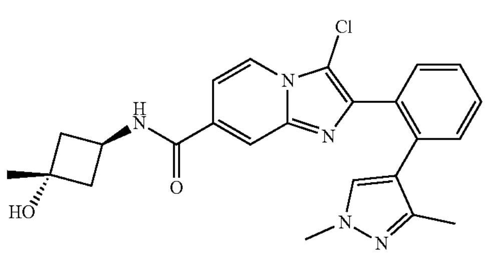 [SMILES: Cc1nn(C)cc1-c1ccccc1-c1nc2cc(C(=O)N[C@H]3C[C@](C)(O)C3)ccn2c1Cl] | 450.2 |

TABLE 1-continued

| Compound | Structure | LCMS (ES+) m/z |
|---|---|---|
| 448 | 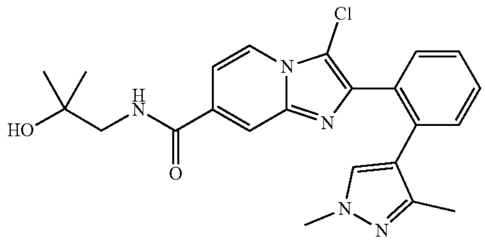 [SMILES: Cc1nn(C)cc1-c1ccccc1-c1nc2cc(C(=O)NCC(C)(C)O)ccn2c1Cl] | 438.2 |
| 451 | 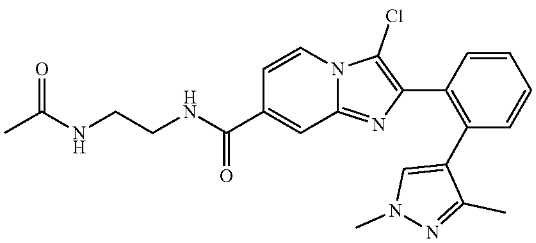 [SMILES: CC(=O)NCCNC(=O)c1ccn2c(Cl)c(-c3ccccc3-c3cn(C)nc3C)nc2c1] | 451.1 |
| 452 | 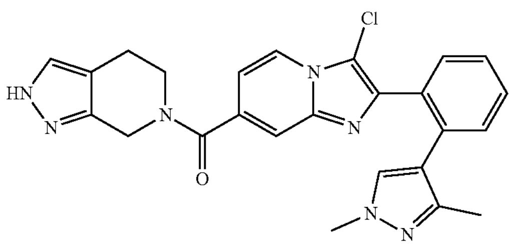 [SMILES: Cc1nn(C)cc1-c1ccccc1-c1nc2cc(C(=O)N3CCc4c[nH]nc4C3)ccn2c1Cl] | 472.1 |
| 455 | 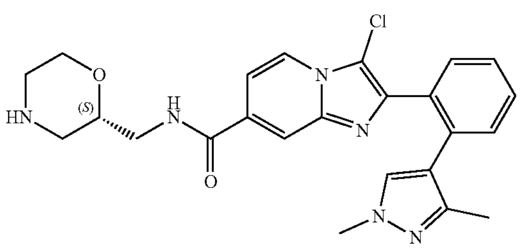 | 465.0 |
| 457 | (single enantiomer) *absolute stereochemistry not determined | 470.2 |
| 458 | (single enantiomer) *absolute stereochemistry not determined | 470.3 |

TABLE 1-continued
| Compound | Structure | LCMS (ES+) m/z |
|---|---|---|
| 459 | 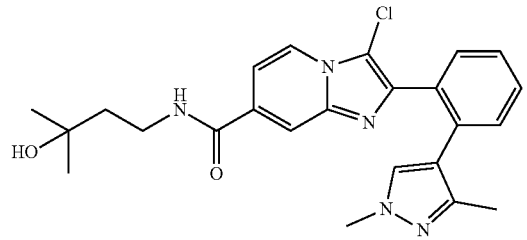 [SMILES: Cc1nn(C)cc1-c1ccccc1-c1nc2cc(C(=O)NCCC(C)(C)O)ccn2c1Cl] | 452.2 |
| 460 | 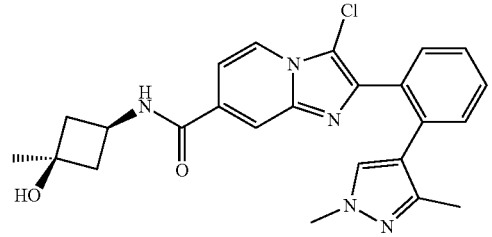 [SMILES: Cc1nn(C)cc1-c1ccccc1-c1nc2cc(C(=O)N[C@H]3C[C@@](C)(O)C3)ccn2c1Cl] | 450.2 |
| 461 | 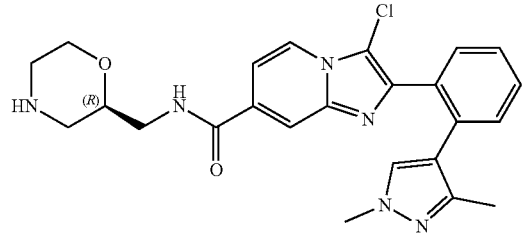 | 465.1 |
| 464 | 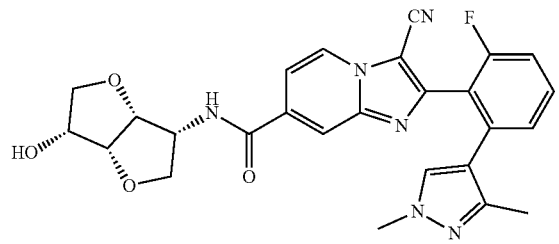 | 503.1 |
| 467 | 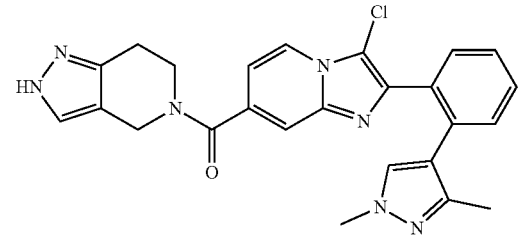 [SMILES: Cc1nn(C)cc1-c1ccccc1-c1nc2cc(C(=O)N3CCc4n[nH]cc4C3)ccn2c1Cl] | 472.2 |
| 468 | 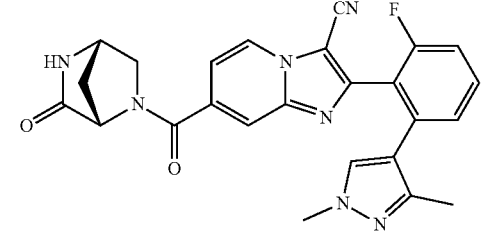 [SMILES: Cc1nn(C)cc1-c1cccc(F)c1-c1nc2cc(C(=O)N3C[C@@H]4C[C@H]3C(=O)N4)ccn2c1C#N] | 470.1 |

TABLE 1-continued

| Compound | Structure | LCMS (ES+) m/z |
|---|---|---|
| 470 | 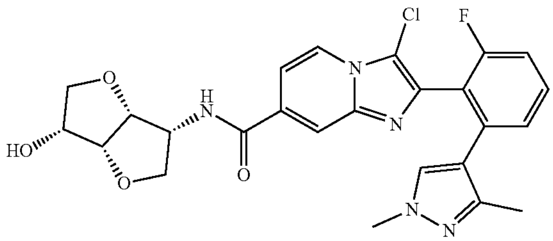 [SMILES: Cc1nn(C)cc1-c1cccc(F)c1-c1nc2cc(C(=O)N[C@@H]3CO[C@H]4[C@@H]3OC[C@H]4O)ccn2c1Cl] | 512.1 |
| 471 | 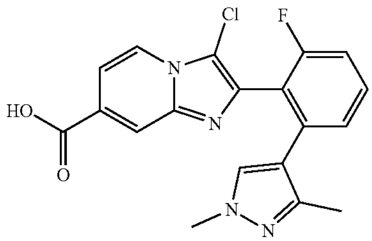 [SMILES: Cc1nn(C)cc1-c1cccc(F)c1-c1nc2cc(C(=O)O)ccn2c1Cl] | 385.0 |
| 472 | 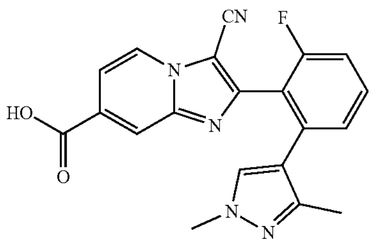 [SMILES: Cc1nn(C)cc1-c1cccc(F)c1-c1nc2cc(C(=O)O)ccn2c1C#N] | 376.1 |
| 473 | 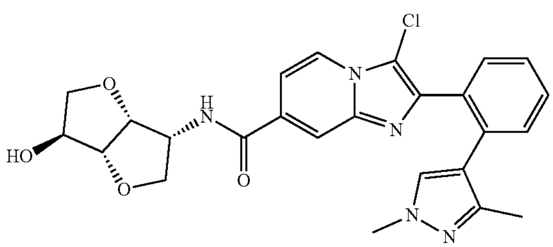 [SMILES: Cc1nn(C)cc1-c1ccccc1-c1nc2cc(C(=O)N[C@@H]3CO[C@H]4[C@@H]3OC[C@@H]4O)ccn2c1Cl] | 494.0 |
| 475 | 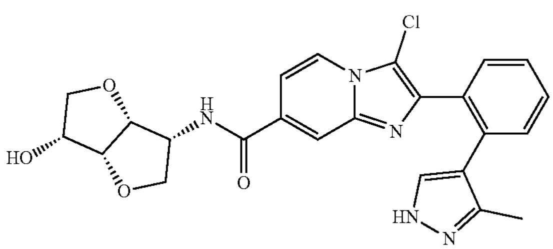 [SMILES: Cc1n[nH]cc1-c1ccccc1-c1nc2cc(C(=O)N[C@@H]3CO[C@H]4[C@@H]3OC[C@H]4O)ccn2c1Cl] | 480.2 |
| 476 | 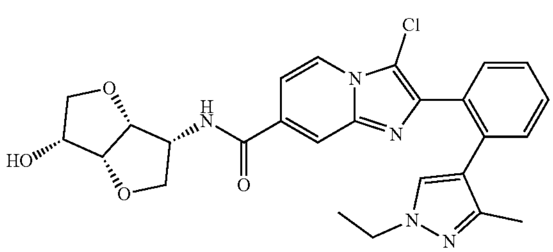 [SMILES: CCn1cc(-c2ccccc2-c2nc3cc(C(=O)N[C@@H]4CO[C@H]5[C@@H]4OC[C@H]5O)ccn3c2Cl)c(C)n1] | 508.2 |

TABLE 1-continued

| Compound | Structure | LCMS (ES+) m/z |
|---|---|---|
| 477 | 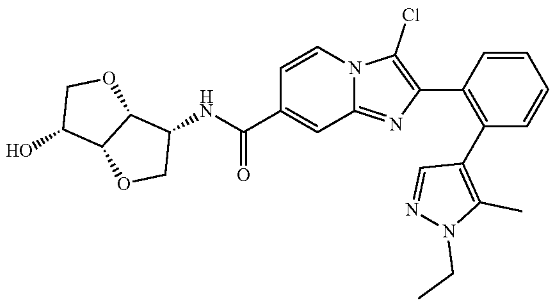 [SMILES: CCn1ncc(-c2ccccc2-c2nc3cc(C(=O)N[C@@H]4CO[C@H]5[C@@H]4OC[C@H]5O)ccn3c2Cl)c1C] | 508.1 |
| 478 | 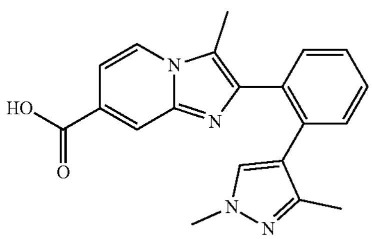 [SMILES: Cc1nn(C)cc1-c1ccccc1-c1nc2cc(C(=O)O)ccn2c1C] | 347.1 |
| 479 | 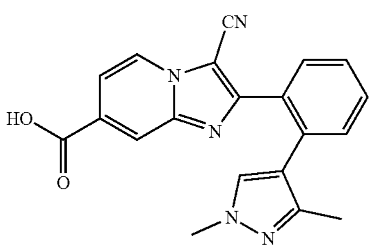 | 358.3 |
| 480 | (single enantiomer) *absolute stereochemistry not determined | 484.4 |
| 481 | (single enantiomer) *absolute stereochemistry not determined | 484.4 |

TABLE 1-continued

| Compound | Structure | LCMS (ES+) m/z |
|---|---|---|
| 486 | 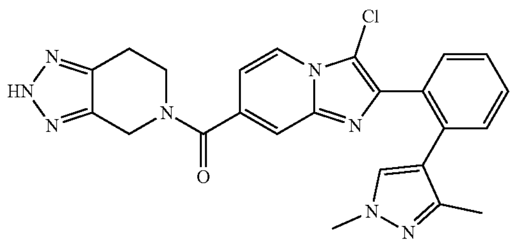 [SMILES: Cc1nn(C)cc1-c1ccccc1-c1nc2cc(C(=O)N3CCc4n[nH]nc4C3)ccn2c1Cl] | 473.2 |
| 487 | 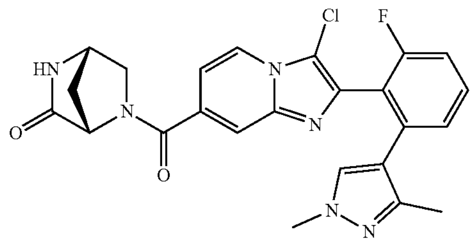 [SMILES: Cc1nn(C)cc1-c1cccc(F)c1-c1nc2cc(C(=O)N3C[C@@H]4C[C@H]3C(=O)N4)ccn2c1Cl] | 479.2 |
| 490 | 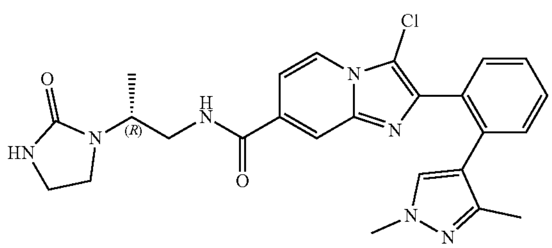 | 492.1 |
| 492 | 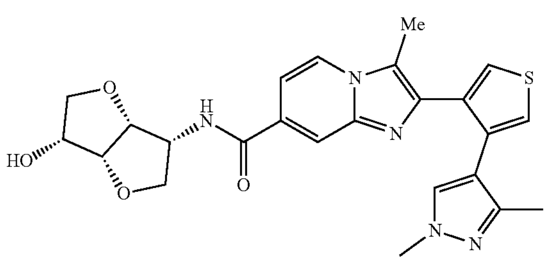 [SMILES: Cc1nn(C)cc1-c1cscc1-c1nc2cc(C(=O)N[C@@H]3CO[C@H]4[C@@H]3OC[C@H]4O)ccn2c1C] | 480.1 |
| 496 | 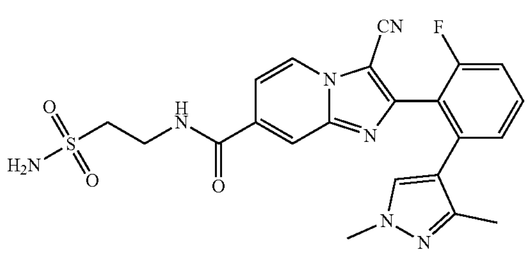 [SMILES: Cc1nn(C)cc1-c1cccc(F)c1-c1nc2cc(C(=O)NCCS(N)(=O)=O)ccn2c1C#N] | 482.2 |
| 497 | 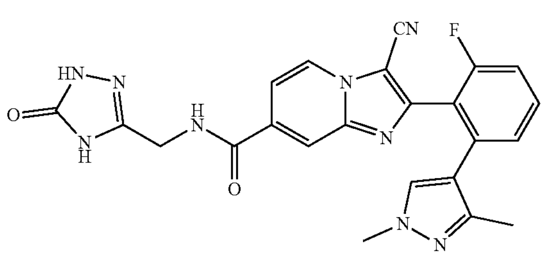 [SMILES: Cc1nn(C)cc1-c1cccc(F)c1-c1nc2cc(C(=O)NCc3n[nH]c(=O)[nH]3)ccn2c1C#N] | 472.2 |

TABLE 1-continued

| Compound | Structure | LCMS (ES+) m/z |
|---|---|---|
| 498 | 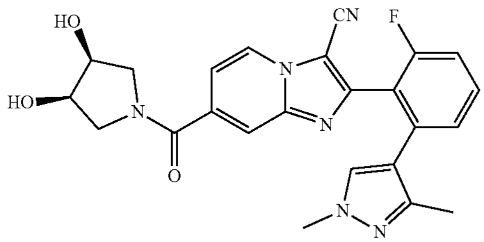 | 461.2 |
| 499 | 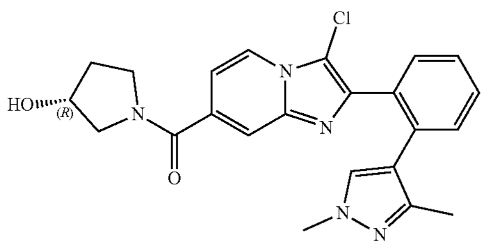 | 436.2 |
| 500 | 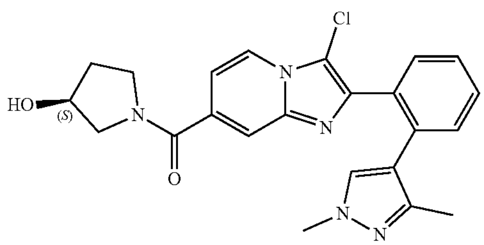 | 436.0 |
| 501 | 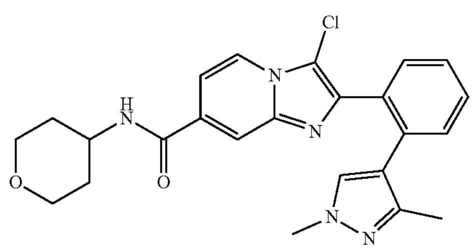 [SMILES: Cc1nn(C)cc1-c1ccccc1-c1nc2cc(C(=O)NC3CCOCC3)ccn2c1Cl] | 450.1 |
| 502 | 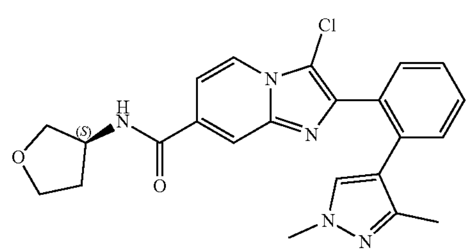 | 436.0 |
| 504 | 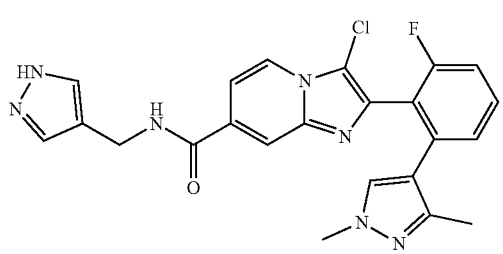 [SMILES: Cc1nn(C)cc1-c1cccc(F)c1-c1nc2cc(C(=O)NCc3cn[nH]c3)ccn2c1Cl] | 464.1 |

TABLE 1-continued

| Compound | Structure | LCMS (ES+) m/z |
|---|---|---|
| 505 | 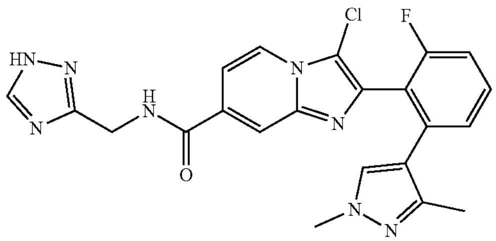 [SMILES: Cc1nn(C)cc1-c1cccc(F)c1-c1nc2cc(C(=O)NCc3nc[nH]n3)ccn2c1Cl] | 465.2 |
| 506 | 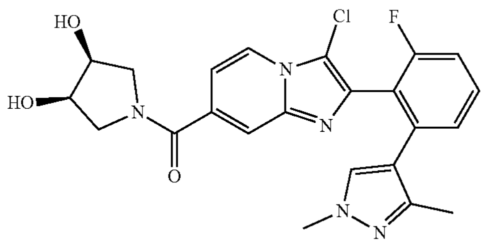 | 470.2 |
| 507 | 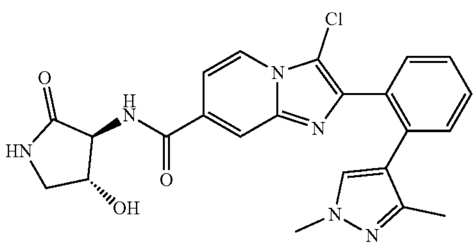 [SMILES: Cc1nn(C)cc1-c1ccccc1-c1nc2cc(C(=O)N[C@@H]3C(=O)NC[C@H]3O)ccn2c1Cl] | 465.1 |
| 508 | 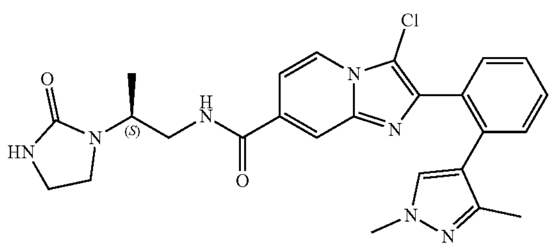 | 492.2 |
| 509 | 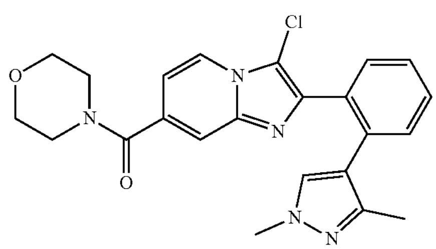 [SMILES: Cc1nn(C)cc1-c1ccccc1-c1nc2cc(C(=O)N3CCOCC3)ccn2c1Cl] | 436.0 |
| 511 | 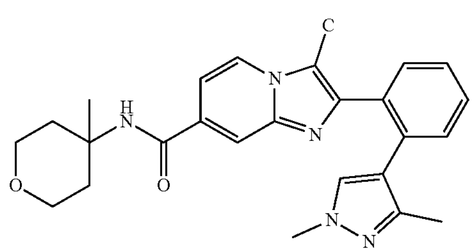 | 464.3 |

TABLE 1-continued
| Compound | Structure | LCMS (ES+) m/z |
|---|---|---|
| 516 | 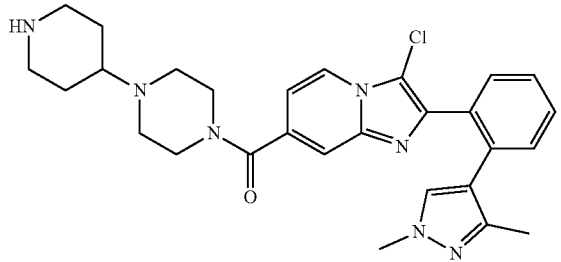 [SMILES: Cc1nn(C)cc1-c1ccccc1-c1nc2cc(C(=O)N3CCN(C4CCNCC4)CC3)ccn2c1Cl] | 518.1 |
| 517 | 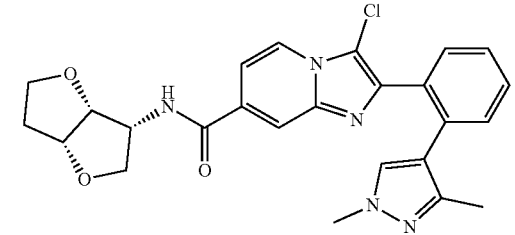 [SMILES: Cc1nn(C)cc1-c1ccccc1-c1nc2cc(C(=O)N[C@@H]3CO[C@@H]4CCO[C@H]34)ccn2c1Cl] | 478 |
| 518 | 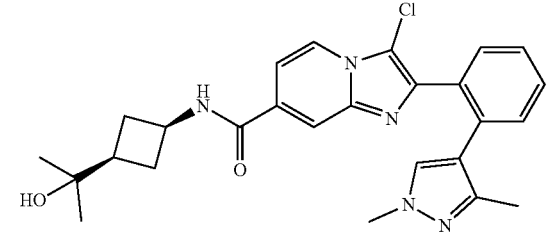 [SMILES: Cc1nn(C)cc1-c1ccccc1-c1nc2cc(C(=O)N[C@H]3C[C@@H](C(C)(C)O)C3)ccn2c1Cl] | 478.2 |
| 614 | 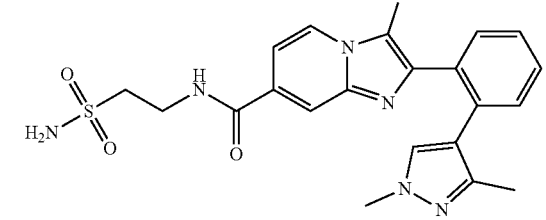 | 473.2 |
| 615 | 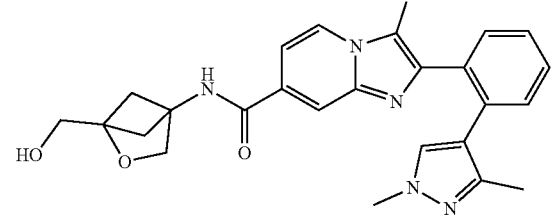 | 478.2 |
| 616 | 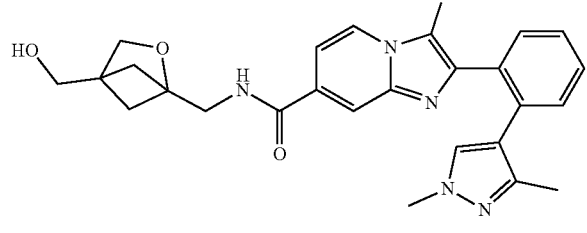 | 492.3 |

TABLE 1-continued

| Compound | Structure | LCMS (ES+) m/z |
|---|---|---|
| 617 | 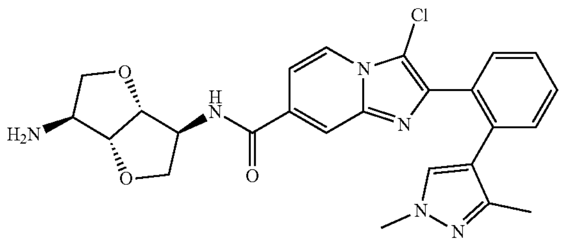 [SMILES: Cc1nn(C)cc1-c1ccccc1-c1nc2cc(C(=O)N[C@H]3CO[C@H]4[C@@H]3OC[C@@H]4N)ccn2c1Cl] | 493.3 |
| 619 | 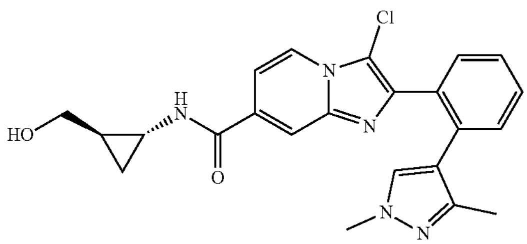 [SMILES: Cc1nn(C)cc1-c1ccccc1-c1nc2cc(C(=O)N[C@@H]3C[C@H]3CO)ccn2c1Cl] | 436.2 |
| 622 | 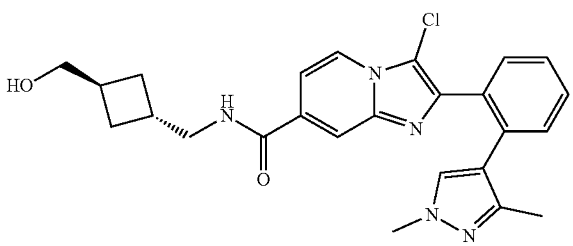 [SMILES: Cc1nn(C)cc1-c1ccccc1-c1nc2cc(C(=O)NC[C@H]3C[C@H](CO)C3)ccn2c1Cl] | 464.3 |
| 624 | 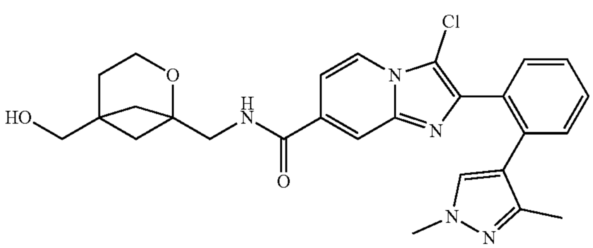 [SMILES: Cc1nn(C)cc1-c1ccccc1-c1nc2cc(C(=O)NCC34CC(CO)(CCO3)C4)ccn2c1Cl] | 506.3 |
| 625 | 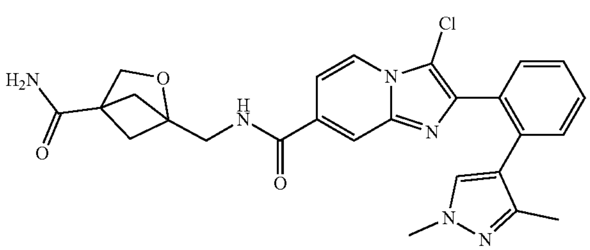 [SMILES: Cc1nn(C)cc1-c1ccccc1-c1nc2cc(C(=O)NCC34CC(C(N)=O)(CO3)C4)ccn2c1Cl] | 505.3 |
| 626 | 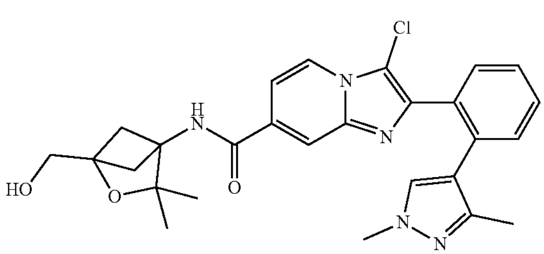 [SMILES: Cc1nn(C)cc1-c1ccccc1-c1nc2cc(C(=O)NC34CC(CO)(C3)OC4(C)C)ccn2c1Cl] | 506.3 |

TABLE 1-continued

| Compound | Structure | LCMS (ES+) m/z |
|---|---|---|
| 629 | 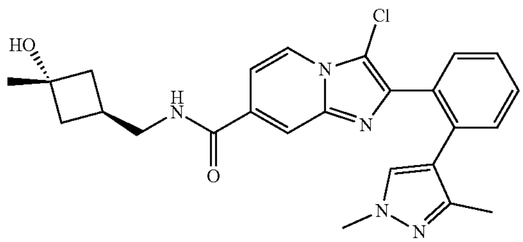 [SMILES: Cc1nn(C)cc1-c1ccccc1-c1nc2cc(C(=O)NC[C@H]3C[C@](C)(O)C3)ccn2c1Cl] | 464.3 |
| 631 | 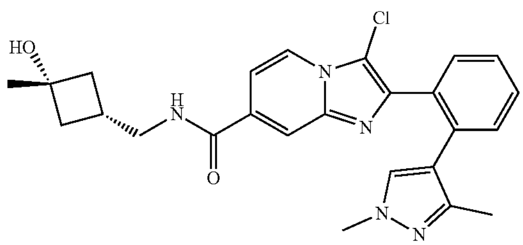 [SMILES: Cc1nn(C)cc1-c1ccccc1-c1nc2cc(C(=O)NC[C@H]3C[C@@](C)(O)C3)ccn2c1Cl] | 464.3 |
| 633 | 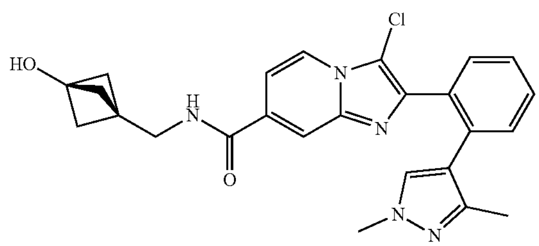 [SMILES: Cc1nn(C)cc1-c1ccccc1-c1nc2cc(C(=O)NC[C@]34C[C@](O)(C3)C4)ccn2c1Cl] | 462.3 |
| 635 | 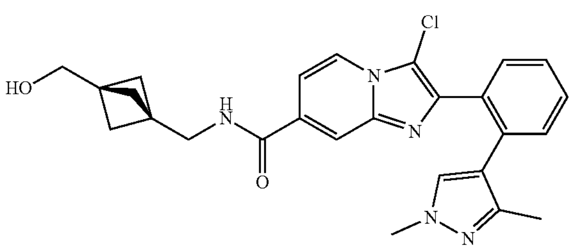 [SMILES: Cc1nn(C)cc1-c1ccccc1-c1nc2cc(C(=O)NC[C@]34C[C@](CO)(C3)C4)ccn2c1Cl] | 476.3 |
| 638 | 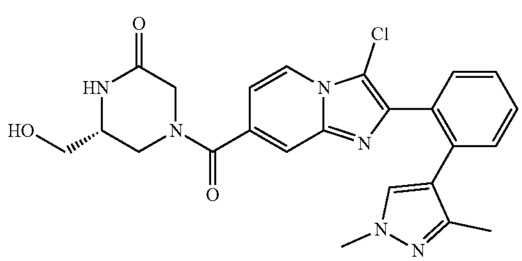 [SMILES: Cc1nn(C)cc1-c1ccccc1-c1nc2cc(C(=O)N3CC(=O)N[C@@H](CO)C3)ccn2c1Cl] | 479.3 |
| 639 | 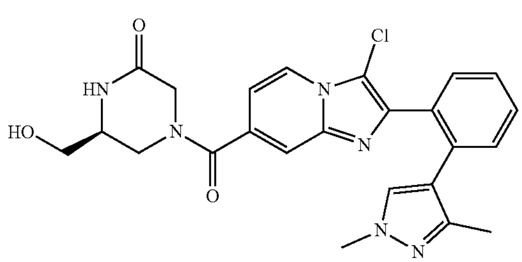 [SMILES: Cc1nn(C)cc1-c1ccccc1-c1nc2cc(C(=O)N3CC(=O)N[C@H](CO)C3)ccn2c1Cl] | 479.3 |

TABLE 1-continued
| Compound | Structure | LCMS (ES+) m/z |
|---|---|---|
| 641 | 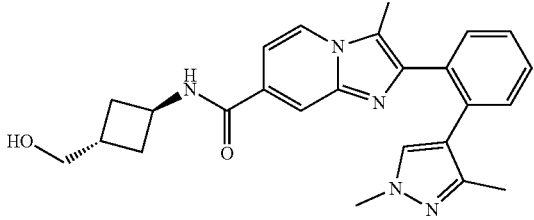 | 450.2 |
| 643 | 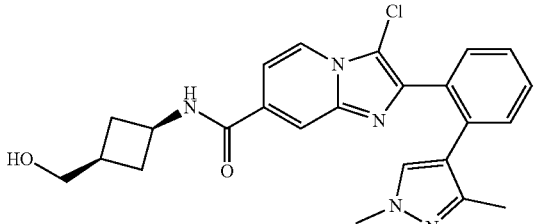 | 450.2 |
| 645 | 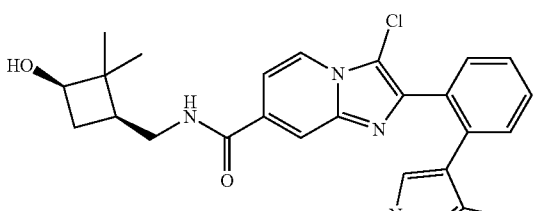 | 478.3 |
| 647 | 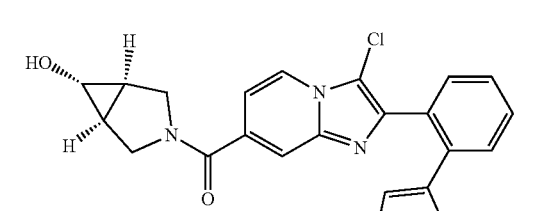 | 448.2 |
| 650 | 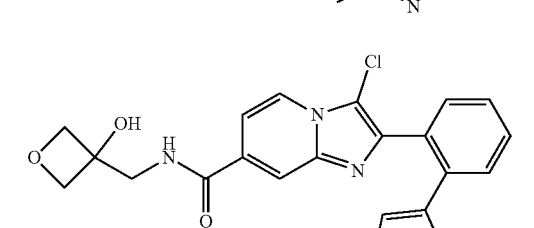 | 452.2 |
| 651 | 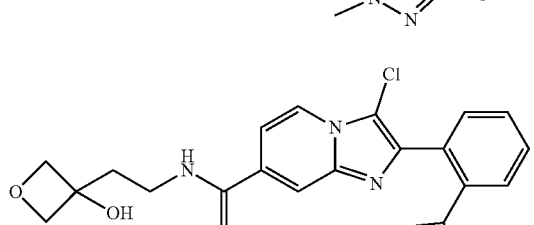 | 466.3 |

TABLE 1-continued
| Compound | Structure | LCMS (ES+) m/z |
|---|---|---|
| 652 | 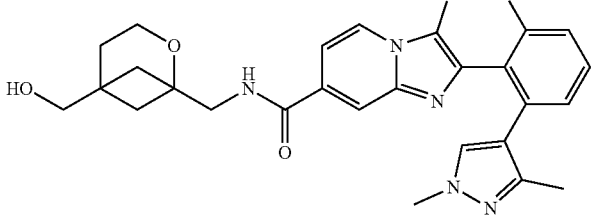 | 524.3 |
| 653 | 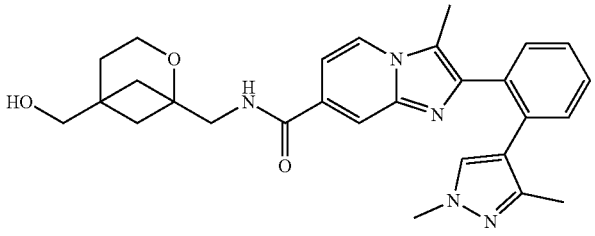 [SMILES: Cc1nn(C)cc1-c1ccccc1-c1nc2cc(C(=O)NCC34CC(CO)(CCO3)C4)ccn2c1C] | 486.3 |
| 654 | 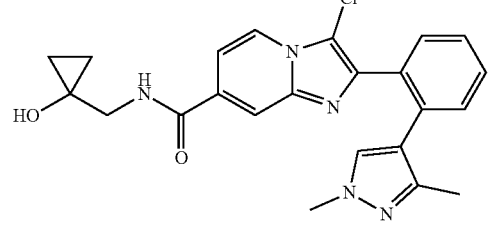 | 436.2 |
| 658 | 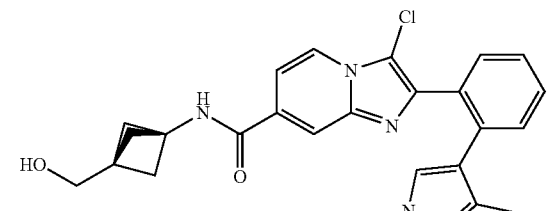 | 462.2 |
| 659 | 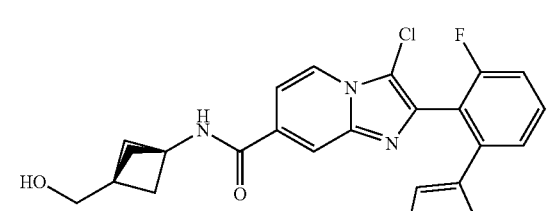 | 480.3 |
| 660 | 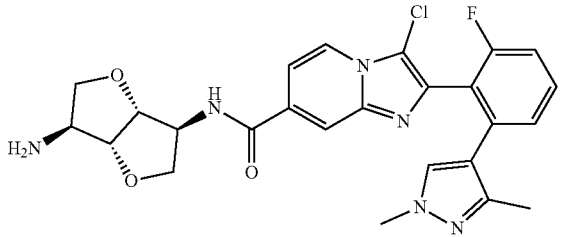 [SMILES: Cc1nn(C)cc1-c1cccc(F)c1-c1nc2cc(C(=O)N[C@H]3CO[C@H]4[C@@H]3OC[C@@H]4N)ccn2c1Cl] | 511.3 |

TABLE 1-continued
| Compound | Structure | LCMS (ES+) m/z |
|---|---|---|
| 661 | 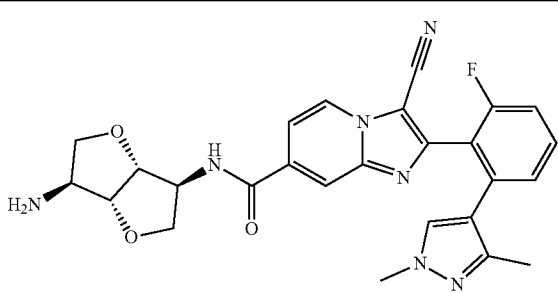 | 502.3 |
| 662 | 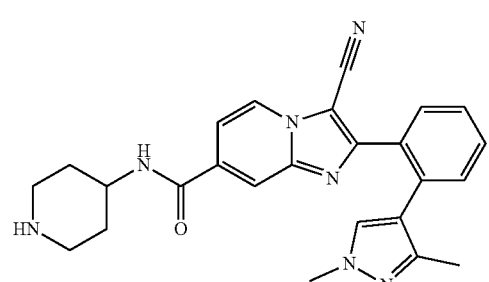 | 440.3 |
| 663 | 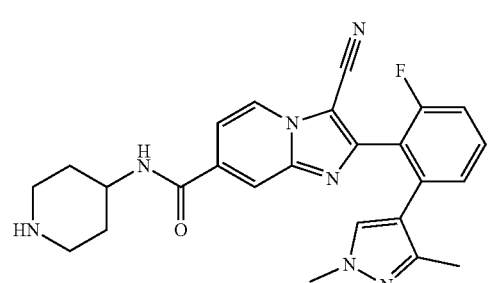 | 458.3 |
| 665 | 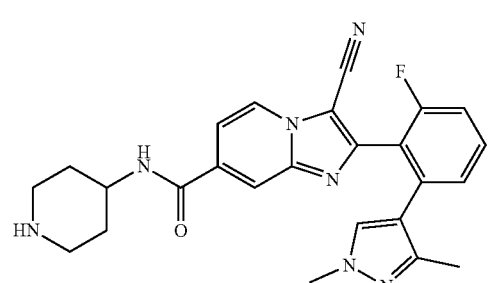 | 464.3 |
| 667 | 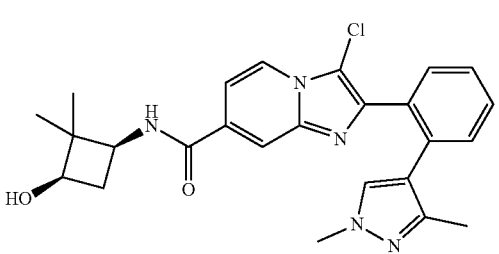 [SMILES: Cc1nn(C)cc1-c1ccccc1-c1nc2cc(C(=O)N[C@H]3C[C@@H](O)C3(C)C)ccn2c1Cl] | 464.3 |

TABLE 1-continued

| Compound | Structure | LCMS (ES+) m/z |
|---|---|---|
| 704 | 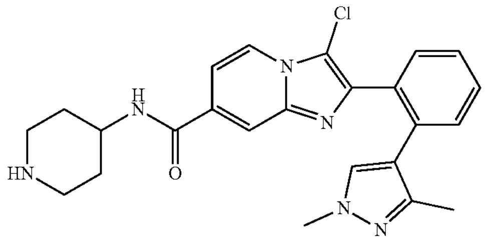 | 449.3 |
| 705 | 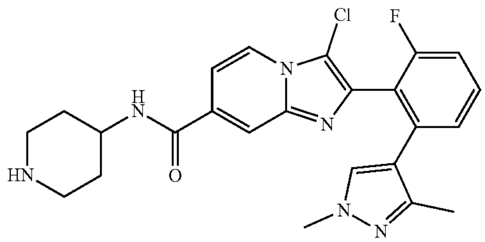 [SMILES: Cc1nn(C)cc1-c1cccc(F)c1-c1nc2cc(C(=O)NC3CCNCC3)ccn2c1Cl] | 467.3 |
| 747 | 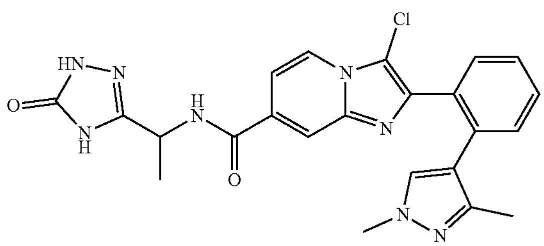 [SMILES: Cc1nn(C)cc1-c1ccccc1-c1nc2cc(C(=O)NC(C)c3n[nH]c(=O)[nH]3)ccn2c1Cl] | 477.3 |
| 748 | 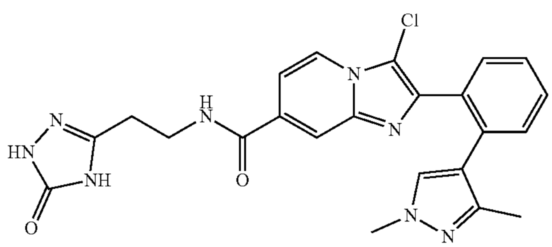 [SMILES: Cc1nn(C)cc1-c1ccccc1-c1nc2cc(C(=O)NCCc3n[nH]c(=O)[nH]3)ccn2c1Cl] | 477.3 |
| 750 | 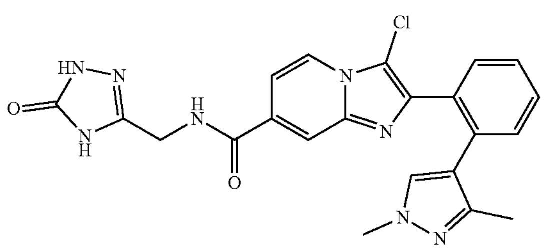 [SMILES: Cc1nn(C)cc1-c1ccccc1-c1nc2cc(C(=O)NCc3n[nH]c(=O)[nH]3)ccn2c1Cl] | 463.2 |
| 759 | 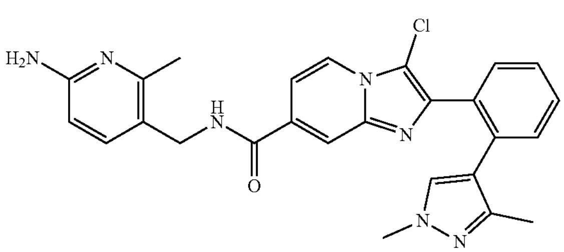 [SMILES: Cc1nc(N)ccc1CNC(=O)c1ccn2c(Cl)c(-c3ccccc3-c3cn(C)nc3C)nc2c1] | 486.3 |

TABLE 1-continued

| Compound | Structure | LCMS (ES+) m/z |
|---|---|---|
| 761 | 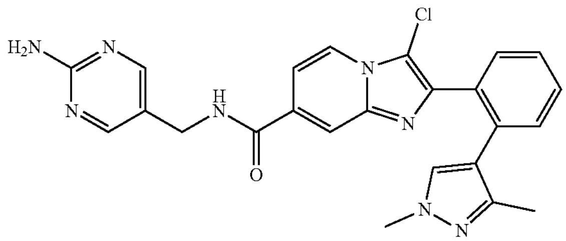 [SMILES: Cc1nn(C)cc1-c1ccccc1-c1nc2cc(C(=O)NCc3cnc(N)nc3)ccn2c1Cl] | 473.2 |
| 763 | 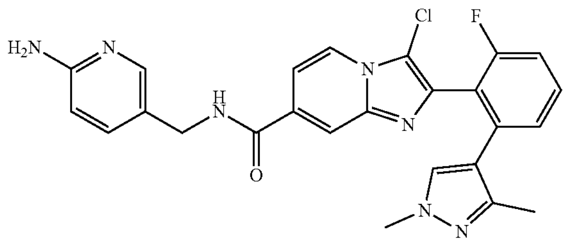 [SMILES: Cc1nn(C)cc1-c1cccc(F)c1-c1nc2cc(C(=O)NCc3ccc(N)nc3)ccn2c1Cl] | 490.2 |
| 764 | 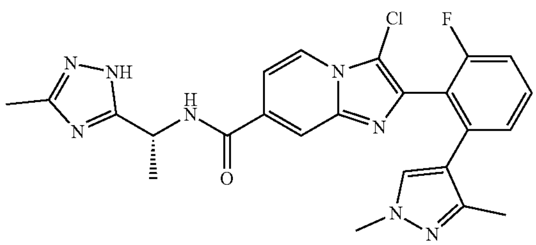 [SMILES: Cc1n[nH]c([C@@H](C)NC(=O)c2ccn3c(Cl)c(-c4c(F)cccc4-c4cn(C)nc4C)nc3c2)n1] | 493.3 |
| 765 | 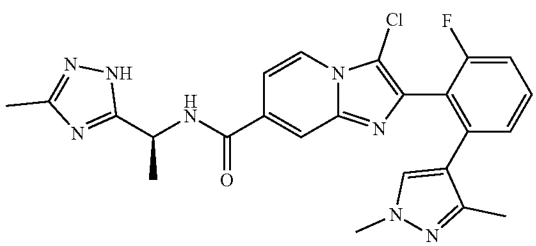 [SMILES: Cc1n[nH]c([C@H](C)NC(=O)c2ccn3c(Cl)c(-c4c(F)cccc4-c4cn(C)nc4C)nc3c2)n1] | 493.2 |
| 766 | 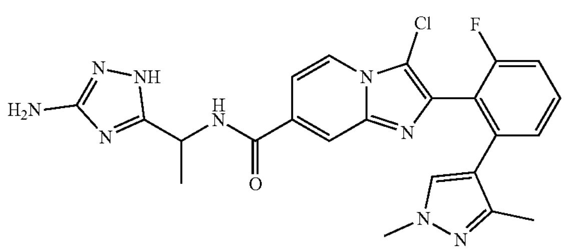 [SMILES: Cc1nn(C)cc1-c1cccc(F)c1-c1nc2cc(C(=O)NC(C)c3nc(N)n[nH]3)ccn2c1Cl] | 494.3 |
| 767 | 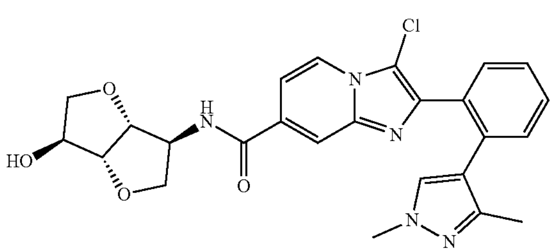 [SMILES: Cc1nn(C)cc1-c1ccccc1-c1nc2cc(C(=O)N[C@H]3CO[C@H]4[C@@H]3OC[C@@H]4O)ccn2c1Cl] | 494.2 |

TABLE 1-continued

| Compound | Structure | LCMS (ES+) m/z |
|---|---|---|
| 768 | 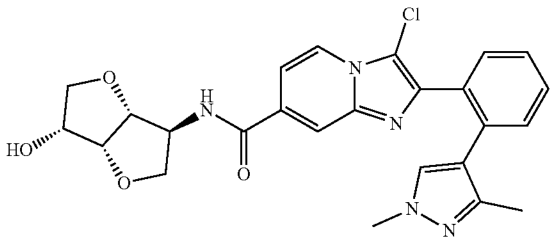 [SMILES: Cc1nn(C)cc1-c1ccccc1-c1nc2cc(C(=O)N[C@H]3CO[C@H]4[C@@H]3OC[C@H]4O)ccn2c1Cl] | 494.3 |
| 772 | 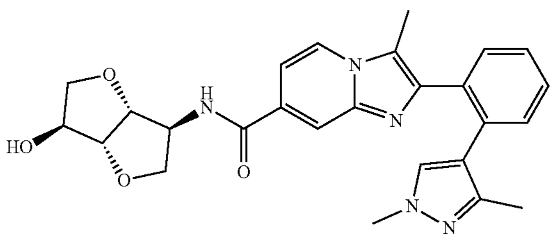 [SMILES: Cc1nn(C)cc1-c1ccccc1-c1nc2cc(C(=O)N[C@H]3CO[C@H]4[C@@H]3OC[C@@H]4O)ccn2c1C] | 474.3 |
| 773 | 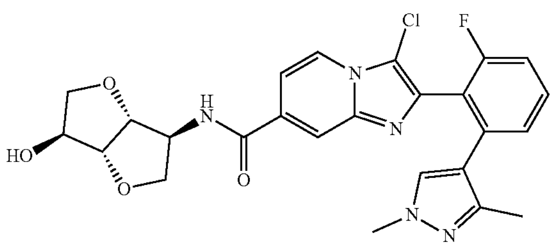 [SMILES: Cc1nn(C)cc1-c1cccc(F)c1-c1nc2cc(C(=O)N[C@H]3CO[C@H]4[C@@H]3OC[C@@H]4O)ccn2c1Cl] | 512.3 |
| 774 | 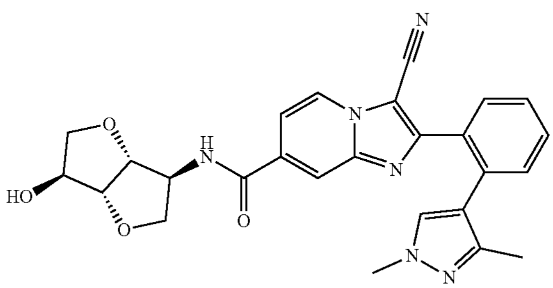 [SMILES: Cc1nn(C)cc1-c1ccccc1-c1nc2cc(C(=O)N[C@H]3CO[C@H]4[C@@H]3OC[C@@H]4O)ccn2c1C#N] | 485.3 |
| 775 | 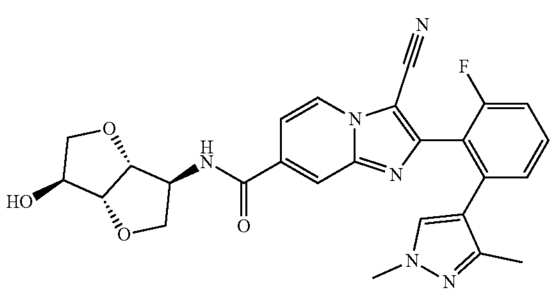 [SMILES: Cc1nn(C)cc1-c1cccc(F)c1-c1nc2cc(C(=O)N[C@H]3CO[C@H]4[C@@H]3OC[C@@H]4O)ccn2c1C#N] | 503.3 |
| 779 | 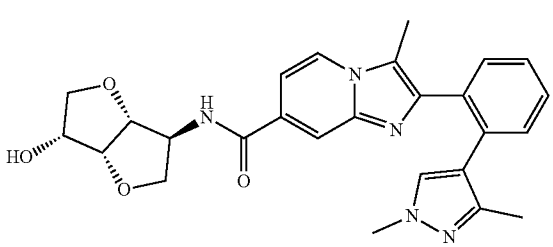 [SMILES: Cc1nn(C)cc1-c1ccccc1-c1nc2cc(C(=O)N[C@H]3CO[C@H]4[C@@H]3OC[C@H]4O)ccn2c1C] | 474.3 |

TABLE 1-continued
| Compound | Structure | LCMS (ES+) m/z |
|---|---|---|
| 780 | 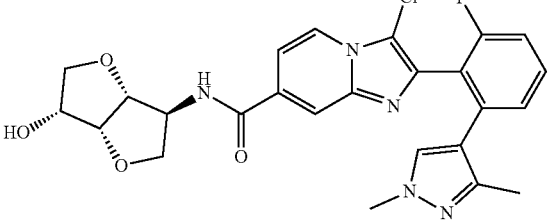 | 512.3 |
| 781 | 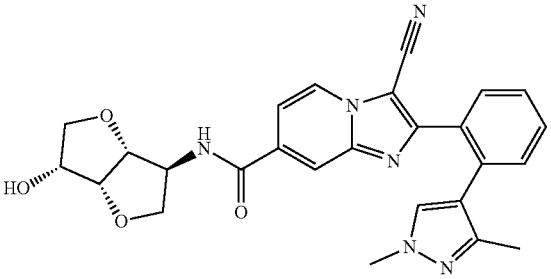 [SMILES: Cc1nn(C)cc1-c1ccccc1-c1nc2cc(C(=O)N[C@H]3CO[C@H]4[C@@H]3OC[C@H]4O)ccn2c1C#N] | 485.3 |
| 782 | 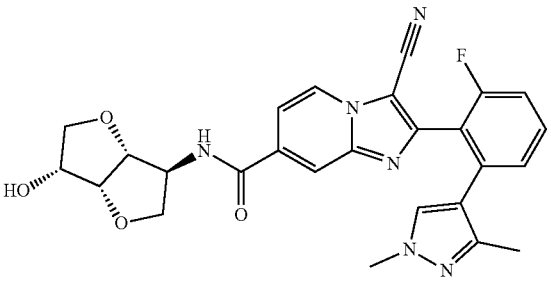 [SMILES: Cc1nn(C)cc1-c1cccc(F)c1-c1nc2cc(C(=O)N[C@H]3CO[C@H]4[C@@H]3OC[C@H]4O)ccn2c1C#N] | 503.2 |
| 783 | 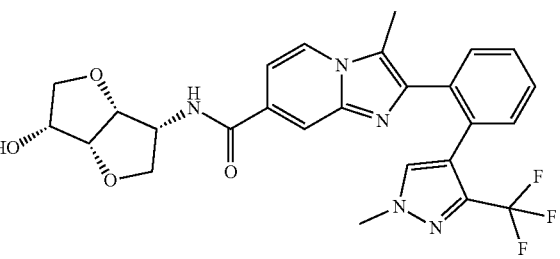 | 528.2 |
| 784 | 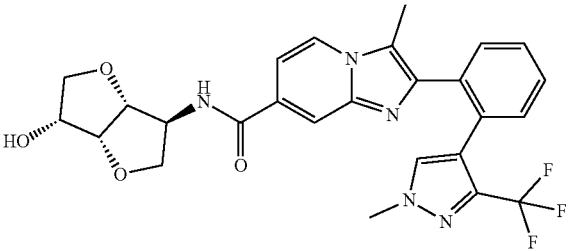 [SMILES: Cc1c(-c2ccccc2-c2cn(C)nc2C(F)(F)F)nc2cc(C(=O)N[C@H]3CO[C@H]4[C@@H]3OC[C@H]4O)ccn12] | 528.2 |

TABLE 1-continued
| Compound | Structure | LCMS (ES+) m/z |
|---|---|---|
| 785 | 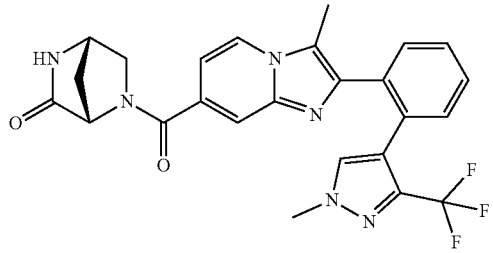 [SMILES: Cc1c(-c2ccccc2-c2cn(C)nc2C(F)(F)F)nc2cc(C(=O)N3C[C@@H]4C[C@H]3C(=O)N4)ccn12] | 495.2 |
| 786 | 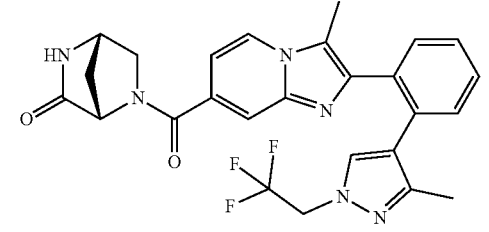 [SMILES: Cc1nn(CC(F)(F)F)cc1-c1ccccc1-c1nc2cc(C(=O)N3C[C@@H]4C[C@H]3C(=O)N4)ccn2c1C] | 509.3 |
| 787 | 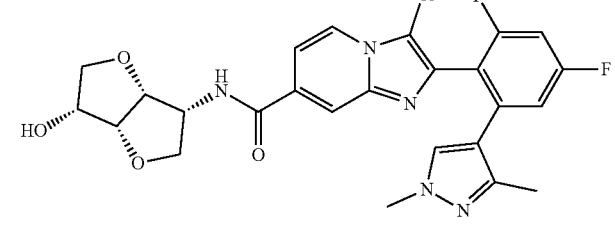 | 530.1 |
| 788 | 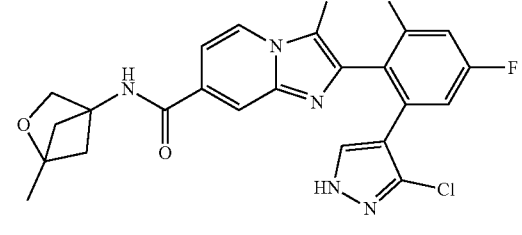 | 504.1 |
| 789 | 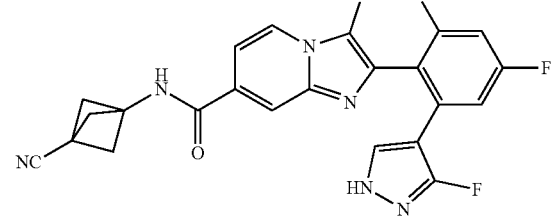 | 483.0 |
| 790 | 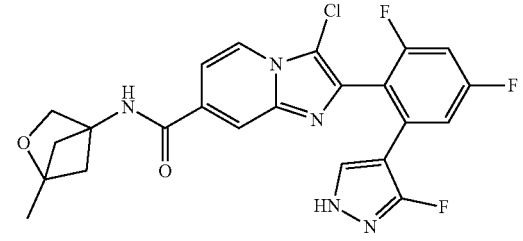 [SMILES: CC12CC(NC(=O)c3ccn4c(Cl)c(-c5c(F)cc(F)cc5-c5c[nH]nc5F)nc4c3)(CO1)C2] | 488.1 |

TABLE 1-continued

| Compound | Structure | LCMS (ES+) m/z |
|---|---|---|
| 791 | 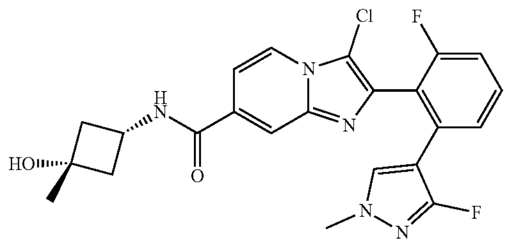 [SMILES: Cn1cc(-c2cccc(F)c2-c2nc3cc(C(=O)N[C@H]4C[C@@](C)(O)C4)ccn3c2Cl)c(F)n1] | 472.1 |
| 792 | 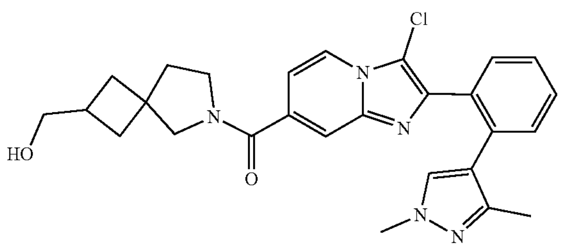 [SMILES: Cc1nn(C)cc1-c1ccccc1-c1nc2cc(C(=O)N3CCC4(CC(CO)C4)C3)ccn2c1Cl] | 490.3 |
| 793 | 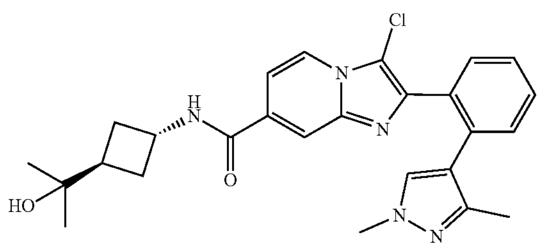 [SMILES: Cc1nn(C)cc1-c1ccccc1-c1nc2cc(C(=O)N[C@H]3C[C@H](C(C)(C)O)C3)ccn2c1Cl] | 478.3 |
| 794 | 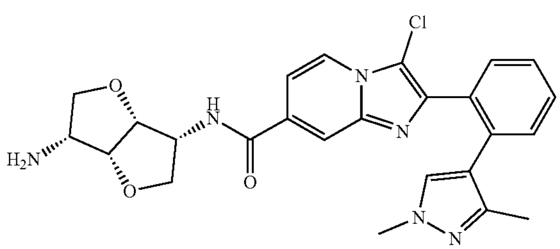 [SMILES: Cc1nn(C)cc1-c1ccccc1-c1nc2cc(C(=O)N[C@@H]3CO[C@H]4[C@@H]3OC[C@H]4N)ccn2c1Cl] | 493.2 |
| 795 | 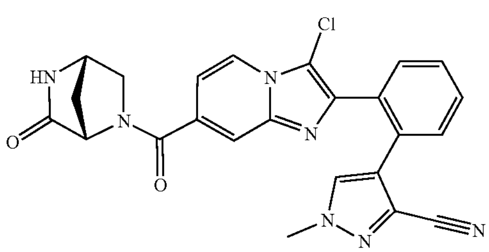 [SMILES: Cn1cc(-c2ccccc2-c2nc3cc(C(=O)N4C[C@@H]5C[C@H]4C(=O)N5)ccn3c2Cl)c(C#N)n1] | 472.2 |
| 796 | 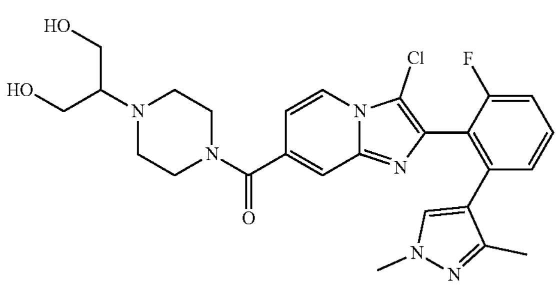 [SMILES: Cc1nn(C)cc1-c1cccc(F)c1-c1nc2cc(C(=O)N3CCN(C(CO)CO)CC3)ccn2c1Cl] | 527.3 |

TABLE 1-continued

| Compound | Structure | LCMS (ES+) m/z |
|---|---|---|
| 797 | 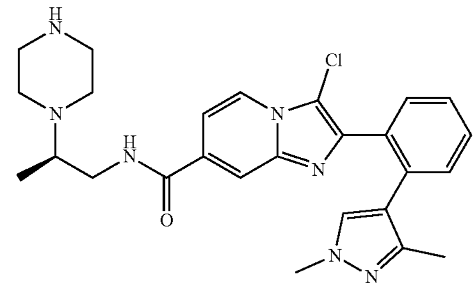 [SMILES: Cc1nn(C)cc1-c1ccccc1-c1nc2cc(C(=O)NC[C@@H](C)N3CCNCC3)ccn2c1Cl] | 492.3 |
| 798 | 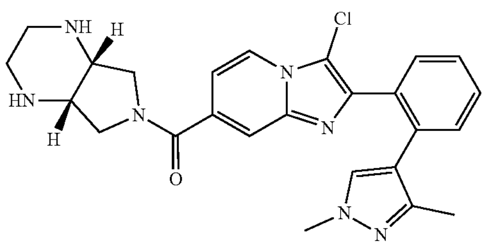 [SMILES: Cc1nn(C)cc1-c1ccccc1-c1nc2cc(C(=O)N3C[C@@H]4NCCN[C@@H]4C3)ccn2c1Cl] | 476.3 |
| 799 | 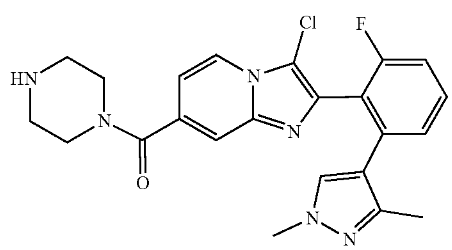 [SMILES: Cc1nn(C)cc1-c1cccc(F)c1-c1nc2cc(C(=O)N3CCNCC3)ccn2c1Cl] | 453.3 |
| 800 | 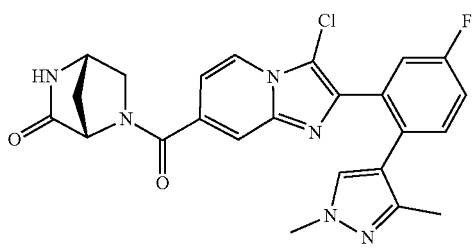 [SMILES: Cc1nn(C)cc1-c1ccc(F)cc1-c1nc2cc(C(=O)N3C[C@@H]4C[C@H]3C(=O)N4)ccn2c1Cl] | 479.1 |
| 801 | 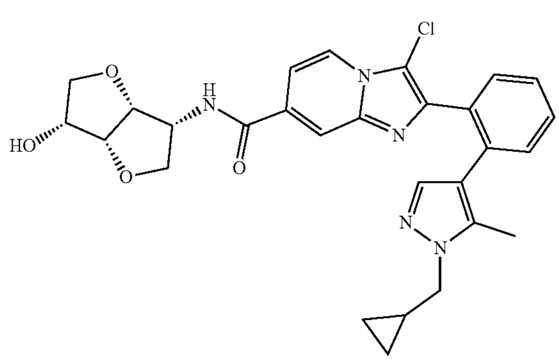 [SMILES: Cc1c(-c2ccccc2-c2nc3cc(C(=O)N[C@@H]4CO[C@H]5[C@@H]4OC[C@H]5O)ccn3c2Cl)cnn1CC1CC1] | 534.3 |

TABLE 1-continued

| Compound | Structure | LCMS (ES+) m/z |
|---|---|---|
| 802 | 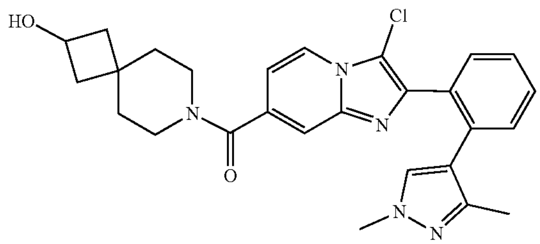 | 490.3 |
| 803 | 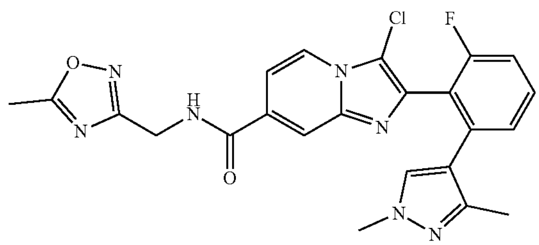 [SMILES: Cc1nc(CNC(=O)c2ccn3c(Cl)c(-c4c(F)cccc4-c4cn(C)nc4C)nc3c2)no1] | 480.1 |
| 804 | 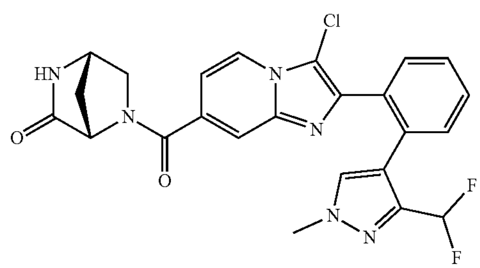 [SMILES: Cn1cc(-c2ccccc2-c2nc3cc(C(=O)N4C[C@@H]5C[C@H]4C(=O)N5)ccn3c2Cl)c(C(F)F)n1] | 497.2 |
| 805 | 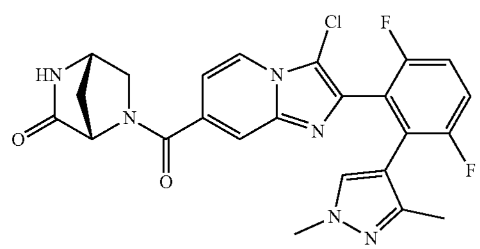 [SMILES: Cc1nn(C)cc1-c1c(F)ccc(F)c1-c1nc2cc(C(=O)N3C[C@@H]4C[C@H]3C(=O)N4)ccn2c1Cl] | 497.1 |
| 806 | 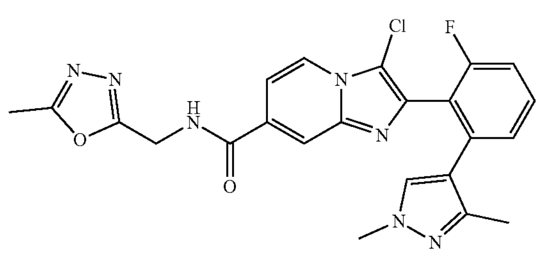 [SMILES: Cc1nnc(CNC(=O)c2ccn3c(Cl)c(-c4c(F)cccc4-c4cn(C)nc4C)nc3c2)o1] | 480.1 |
| 807 | 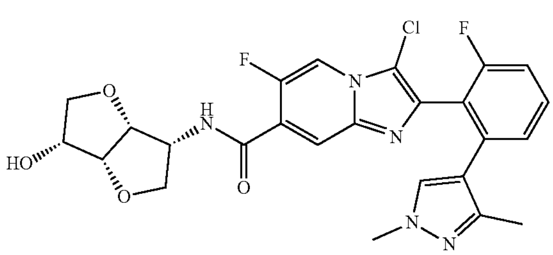 [SMILES: Cc1nn(C)cc1-c1cccc(F)c1-c1nc2cc(C(=O)N[C@@H]3CO[C@H]4[C@@H]3OC[C@H]4O)c(F)cn2c1Cl] | 530.2 |

TABLE 1-continued

| Compound | Structure | LCMS (ES+) m/z |
|---|---|---|
| 808 | 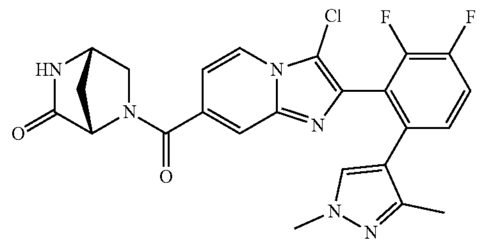 [SMILES: Cc1nn(C)cc1-c1ccc(F)c(F)c1-c1nc2cc(C(=O)N3C[C@@H]4C[C@H]3C(=O)N4)ccn2c1Cl] | 497.1 |
| 809 | 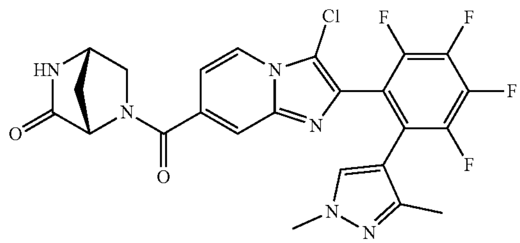 [SMILES: Cc1nn(C)cc1-c1c(F)c(F)c(F)c(F)c1-c1nc2cc(C(=O)N3C[C@@H]4C[C@H]3C(=O)N4)ccn2c1Cl] | 533.2 |
| 810 | 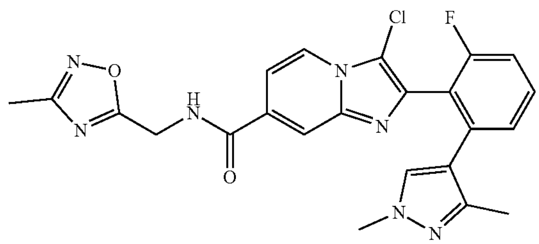 [SMILES: Cc1noc(CNC(=O)c2ccn3c(Cl)c(-c4c(F)cccc4-c4cn(C)nc4C)nc3c2)n1] | 480.1 |
| 811 | 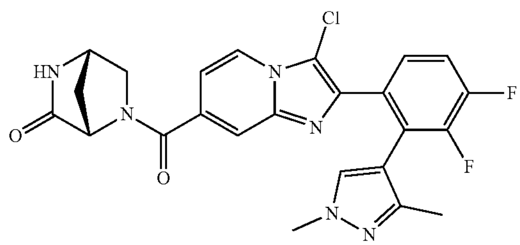 [SMILES: Cc1nn(C)cc1-c1c(-c2nc3cc(C(=O)N4C[C@@H]5C[C@H]4C(=O)N5)ccn3c2Cl)ccc(F)c1F] | 497.1 |
| 812 | 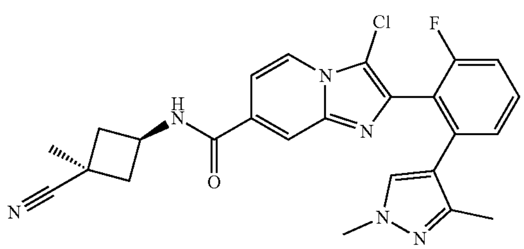 [SMILES: Cc1nn(C)cc1-c1cccc(F)c1-c1nc2cc(C(=O)N[C@H]3C[C@@](C)(C#N)C3)ccn2c1Cl] | 477.1 |
| 813 | 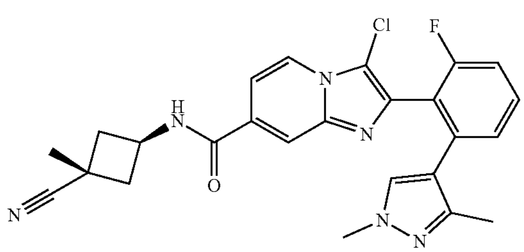 [SMILES: Cc1nn(C)cc1-c1cccc(F)c1-c1nc2cc(C(=O)N[C@H]3C[C@](C)(C#N)C3)ccn2c1Cl] | 477.1 |

TABLE 1-continued

| Compound | Structure | LCMS (ES+) m/z |
|---|---|---|
| 814 | 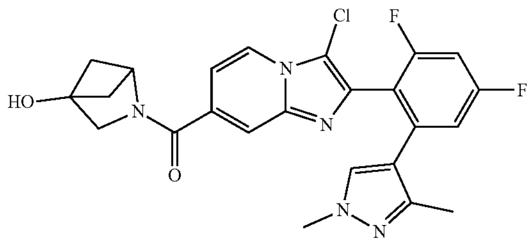 [SMILES: Cc1nn(C)cc1-c1cc(F)cc(F)c1-c1nc2cc(C(=O)N3CC4(O)CC3C4)ccn2c1Cl] | 484.2 |
| 815 | 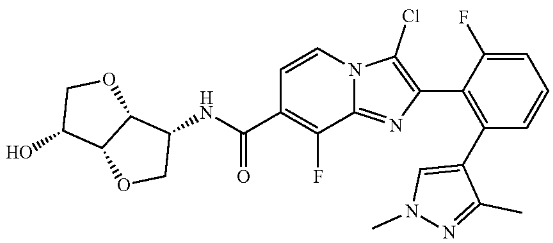 [SMILES: Cc1nn(C)cc1-c1cccc(F)c1-c1nc2c(F)c(C(=O)N[C@@H]3CO[C@H]4[C@@H]3OC[C@H]4O)ccn2c1Cl] | 530.2 |
| 816 | 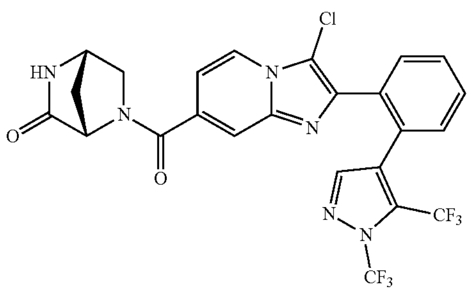 [SMILES: O=C1N[C@H]2C[C@@H]1N(C(=O)c1ccn3c(Cl)c(-c4ccccc4-c4cnn(C(F)(F)F)c4C(F)(F)F)nc3c1)C2] | 568.8 |
| 817 | 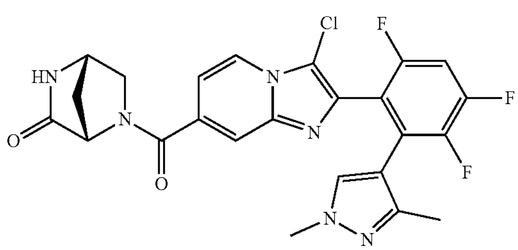 [SMILES: Cc1nn(C)cc1-c1c(F)c(F)cc(F)c1-c1nc2cc(C(=O)N3C[C@@H]4C[C@H]3C(=O)N4)ccn2c1Cl] | 515.0 |
| 818 | 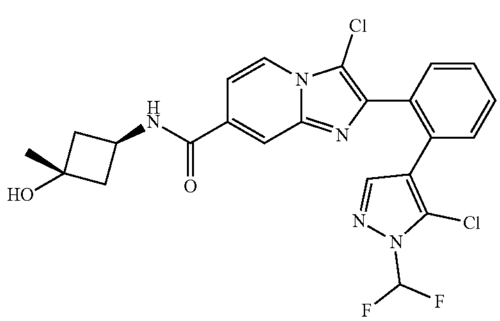 [SMILES: C[C@]1(O)C[C@H](NC(=O)c2ccn3c(Cl)c(-c4ccccc4-c4cnn(C(F)F)c4Cl)nc3c2)C1] | 506.0 |

TABLE 1-continued

| Compound | Structure | LCMS (ES+) m/z |
|---|---|---|
| 819 | 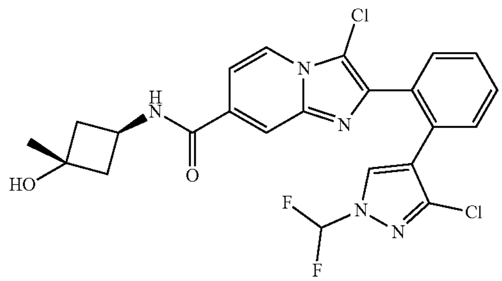 [SMILES: C[C@]1(O)C[C@H](NC(=O)c2ccn3c(Cl)c(-c4ccccc4-c4cn(C(F)F)nc4Cl)nc3c2)C1] | 506.0 |
| 820 | 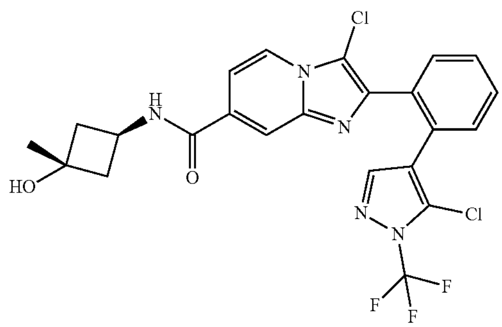 [SMILES: C[C@]1(O)C[C@H](NC(=O)c2ccn3c(Cl)c(-c4ccccc4-c4cnn(C(F)(F)F)c4Cl)nc3c2)C1] | 524.0 |
| 821 | 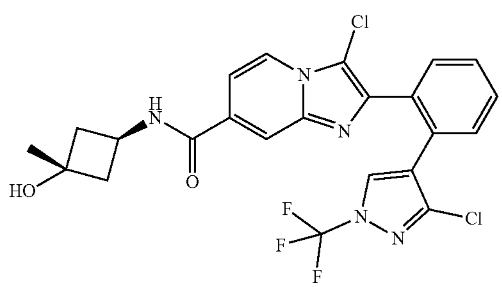 [SMILES: C[C@]1(O)C[C@H](NC(=O)c2ccn3c(Cl)c(-c4ccccc4-c4cn(C(F)(F)F)nc4Cl)nc3c2)C1] | 524.1 |
| 822 | 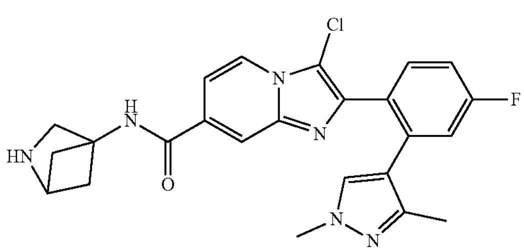 [SMILES: Cc1nn(C)cc1-c1cc(F)ccc1-c1nc2cc(C(=O)NC34CNC(C3)C4)ccn2c1Cl] | 465.2 |
| 823 | 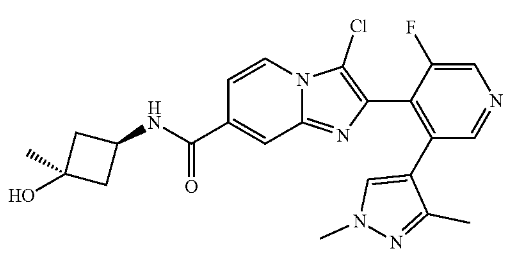 [SMILES: Cc1nn(C)cc1-c1cncc(F)c1-c1nc2cc(C(=O)N[C@H]3C[C@@](C)(O)C3)ccn2c1Cl] | 468.9 |

TABLE 1-continued

| Compound | Structure | LCMS (ES+) m/z |
|---|---|---|
| 824 | 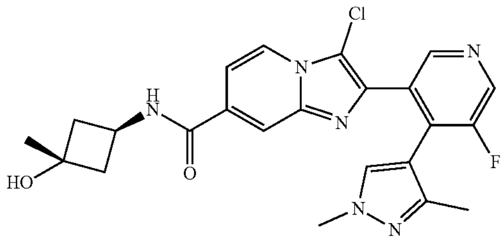 [SMILES: Cc1nn(C)cc1-c1c(F)cncc1-c1nc2cc(C(=O)N[C@H]3C[C@](C)(O)C3)ccn2c1Cl] | 469.0 |
| 825 | 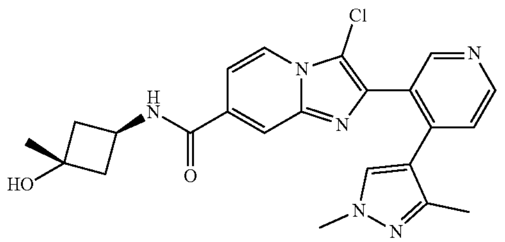 [SMILES: Cc1nn(C)cc1-c1ccncc1-c1nc2cc(C(=O)N[C@H]3C[C@](C)(O)C3)ccn2c1Cl] | 451.0 |
| 826 | 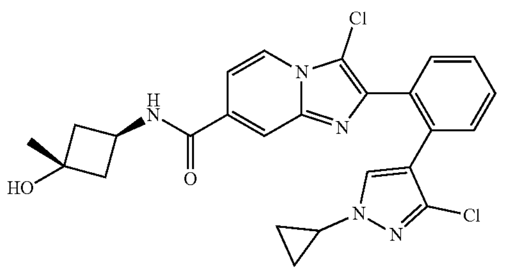 [SMILES: C[C@]1(O)C[C@H](NC(=O)c2ccn3c(Cl)c(-c4ccccc4-c4cn(C5CC5)nc4Cl)nc3c2)C1] | 496.0 |
| 827 | 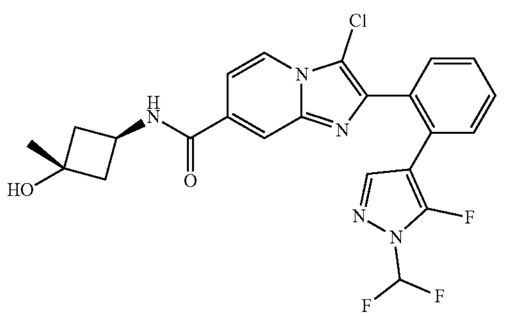 [SMILES: C[C@]1(O)C[C@H](NC(=O)c2ccn3c(Cl)c(-c4ccccc4-c4cnn(C(F)F)c4F)nc3c2)C1] | 490.0 |
| 828 | 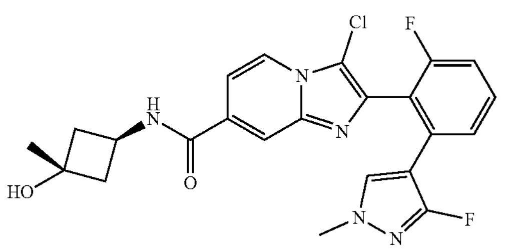 [SMILES: Cn1cc(-c2cccc(F)c2-c2nc3cc(C(=O)N[C@H]4C[C@](C)(O)C4)ccn3c2Cl)c(F)n1] | 472.1 |
| 829 | 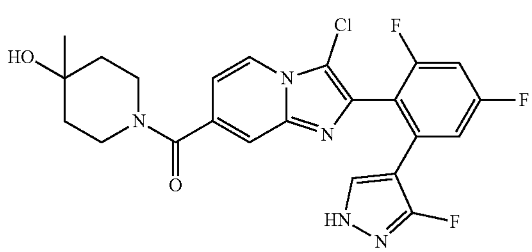 [SMILES: CC1(O)CCN(C(=O)c2ccn3c(Cl)c(-c4c(F)cc(F)cc4-c4c[nH]nc4F)nc3c2)CC1] | 490.2 |

TABLE 1-continued
| Compound | Structure | LCMS (ES+) m/z |
|---|---|---|
| 830 | 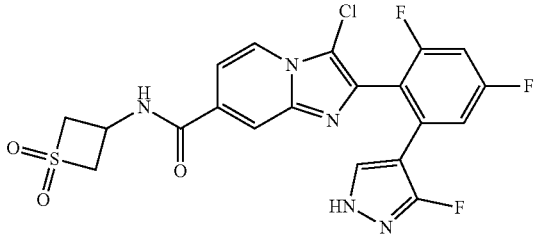 [SMILES: O=C(NC1CS(=O)(=O)C1)c1ccn2c(Cl)c(-c3c(F)cc(F)cc3-c3c[nH]nc3F)nc2c1] | 496.2 |
| 831 | 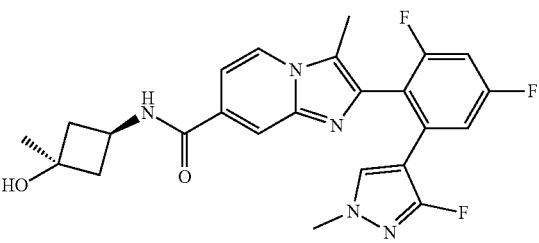 [SMILES: Cc1c(-c2c(F)cc(F)cc2-c2cn(C)nc2F)nc2cc(C(=O)N[C@H]3C[C@@](C)(O)C3)ccn12] | 470.1 |
| 832 | 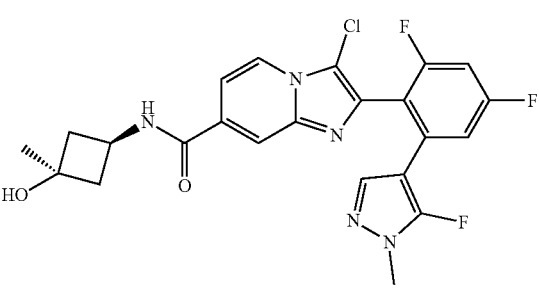 [SMILES: Cn1ncc(-c2cc(F)cc(F)c2-c2nc3cc(C(=O)N[C@H]4C[C@@](C)(O)C4)ccn3c2Cl)c1F] | 490.2 |
| 833 | 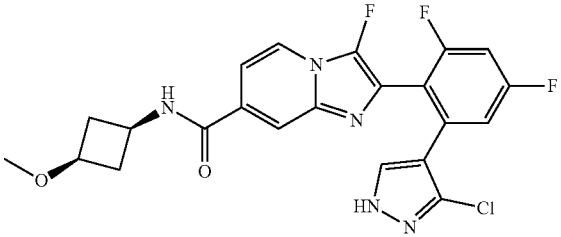 | 476.2 |
| 834 | 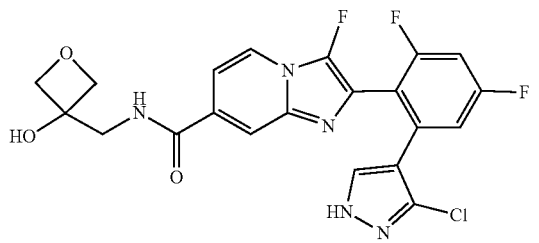 [SMILES: O=C(NCC1(O)COC1)c1ccn2c(F)c(-c3c(F)cc(F)cc3-c3c[nH]nc3Cl)nc2c1] | 478.2 |
| 835 | 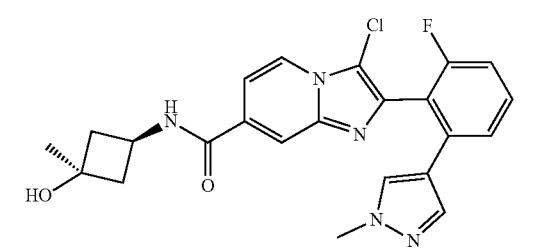 [SMILES: Cn1cc(-c2cccc(F)c2-c2nc3cc(C(=O)N[C@H]4C[C@@](C)(O)C4)ccn3c2Cl)cn1] | 454.0 |

TABLE 1-continued

| Compound | Structure | LCMS (ES+) m/z |
|---|---|---|
| 836 | 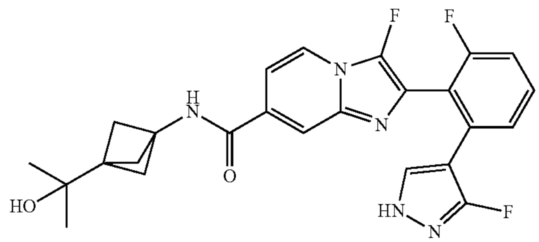 [SMILES: CC(C)(O)C12CC(NC(=O)c3ccn4c(F)c(-c5c(F)cccc5-c5c[nH]nc5F)nc4c3)(C1)C2] | 482.3 |
| 837 | 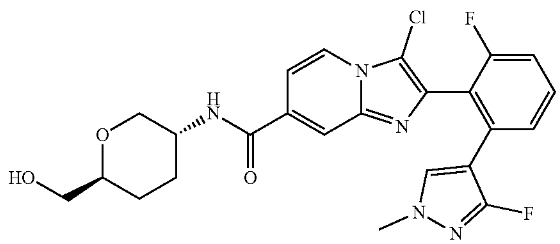 [SMILES: Cn1cc(-c2cccc(F)c2-c2nc3cc(C(=O)N[C@@H]4CC[C@@H](CO)OC4)ccn3c2Cl)c(F)n1] | 502.3 |
| 838 | 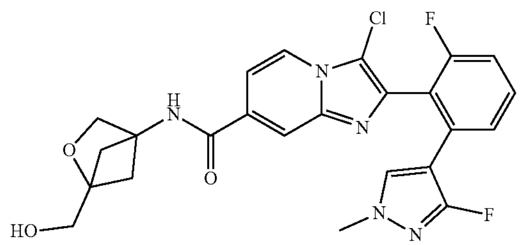 [SMILES: Cn1cc(-c2cccc(F)c2-c2nc3cc(C(=O)NC45COC(CO)(C4)C5)ccn3c2Cl)c(F)n1] | 500.2 |
| 839 | 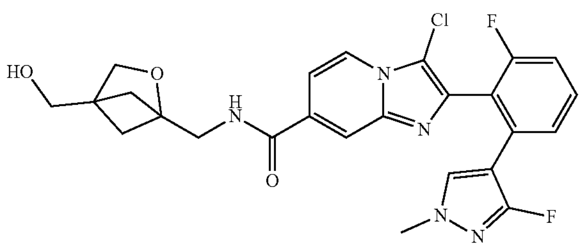 [SMILES: Cn1cc(-c2cccc(F)c2-c2nc3cc(C(=O)NCC45CC(CO)(CO4)C5)ccn3c2Cl)c(F)n1] | 514.3 |
| 840 | 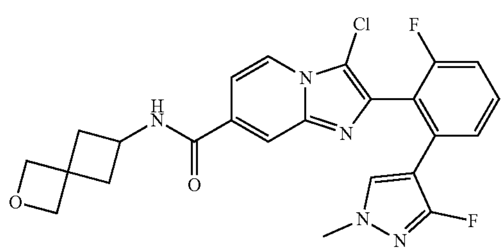 | 484.3 |
| 841 | 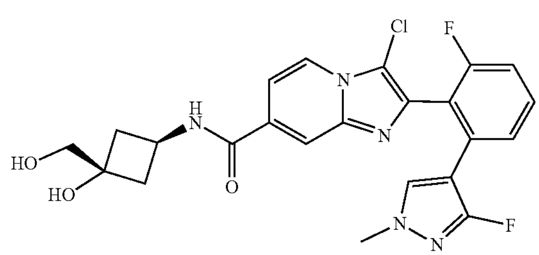 [SMILES: Cn1cc(-c2cccc(F)c2-c2nc3cc(C(=O)N[C@H]4C[C@@](O)(CO)C4)ccn3c2Cl)c(F)n1] | 488.2 |

TABLE 1-continued

| Compound | Structure | LCMS (ES+) m/z |
|---|---|---|
| 842 | 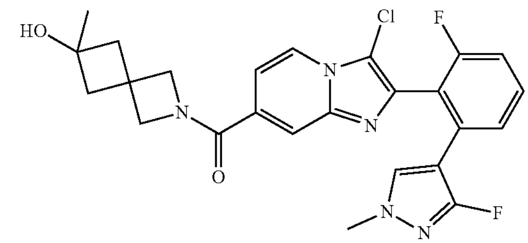 [SMILES: Cn1cc(-c2cccc(F)c2-c2nc3cc(C(=O)N4CC5(C4)CC(C)(O)C5)ccn3c2Cl)c(F)n1] | 498.0 |
| 843 | 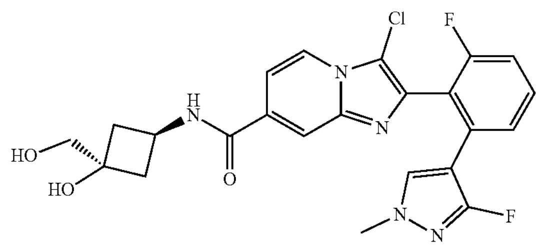 [SMILES: Cn1cc(-c2cccc(F)c2-c2nc3cc(C(=O)N[C@H]4C[C@](O)(CO)C4)ccn3c2Cl)c(F)n1] | 488.1 |
| 844 | 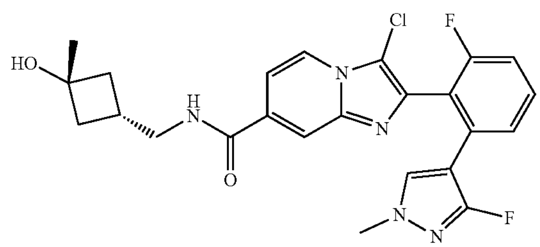 [SMILES: Cn1cc(-c2cccc(F)c2-c2nc3cc(C(=O)NC[C@H]4C[C@@](C)(O)C4)ccn3c2Cl)c(F)n1] | 486.3 |
| 845 | 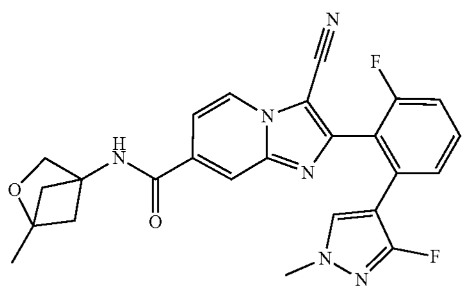 [SMILES: Cn1cc(-c2cccc(F)c2-c2nc3cc(C(=O)NC45COC(C)(C4)C5)ccn3c2C#N)c(F)n1] | 475.0 |
| 846 | 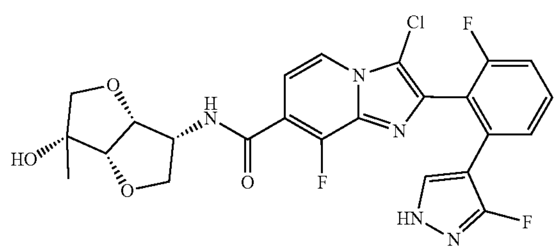 [SMILES: C[C@@]1(O)CO[C@@H]2[C@H](NC(=O)c3ccn4c(Cl)c(-c5c(F)cccc5-c5c[nH]nc5F)nc4c3F)CO[C@@H]21] | 516.2 |
| 847 | 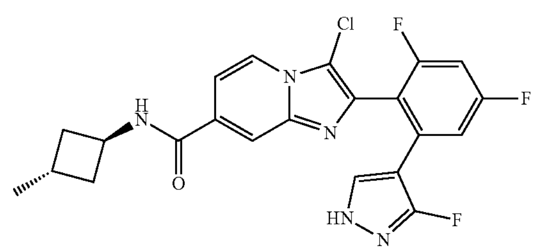 [SMILES: C[C@H]1C[C@H](NC(=O)c2ccn3c(Cl)c(-c4c(F)cc(F)cc4-c4c[nH]nc4F)nc3c2)C1] | 460.3 |

TABLE 1-continued
| Compound | Structure | LCMS (ES+) m/z |
|---|---|---|
| 848 | 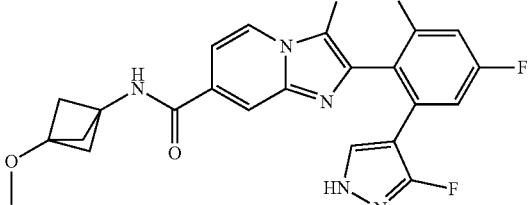 | 488.3 |
| 849 | 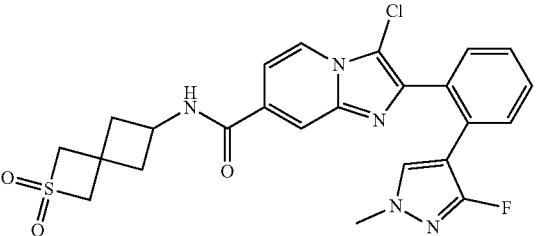 [SMILES: Cn1cc(-c2ccccc2-c2nc3cc(C(=O)NC4CC5(C4)CS(=O)(=O)C5)ccn3c2Cl)c(F)n1] | 514.3 |
| 850 | 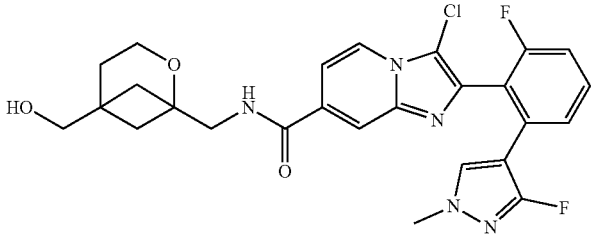 | 528.3 |
| 851 | 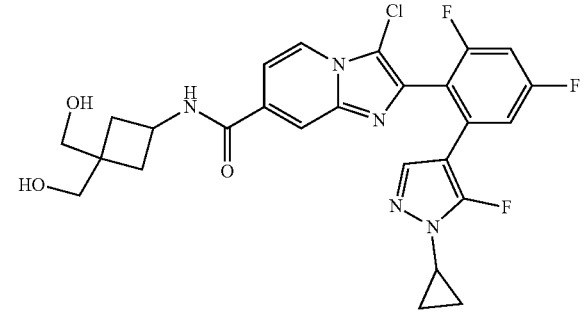 [SMILES: O=C(NC1CC(CO)(CO)C1)c1ccn2c(Cl)c(-c3c(F)cc(F)cc3-c3cnn(C4CC4)c3F)nc2c1] | 546.3 |
| 852 | 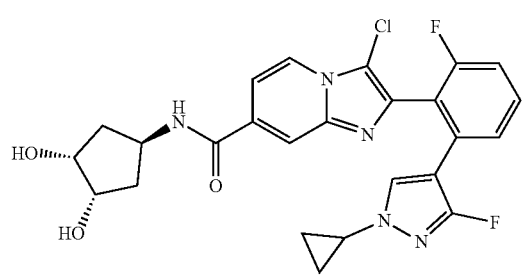 [SMILES: O=C(N[C@@H]1C[C@@H](O)[C@@H](O)C1)c1ccn2c(Cl)c(-c3c(F)cccc3-c3cn(C4CC4)nc3F)nc2c1] | 514.3 |
| 853 | 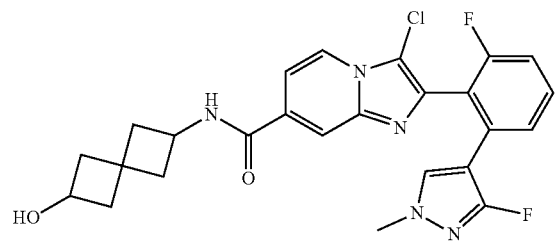 [SMILES: Cn1cc(-c2cccc(F)c2-c2nc3cc(C(=O)NC4CC5(CC(O)C5)C4)ccn3c2Cl)c(F)n1] | 498.3 |

TABLE 1-continued

| Compound | Structure | LCMS (ES+) m/z |
|---|---|---|
| 854 | 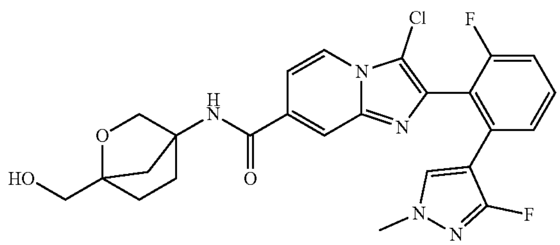 [SMILES: Cn1cc(-c2cccc(F)c2-c2nc3cc(C(=O)NC45CCC(CO)(C4)OC5)ccn3c2Cl)c(F)n1] | 514.3 |
| 855 | 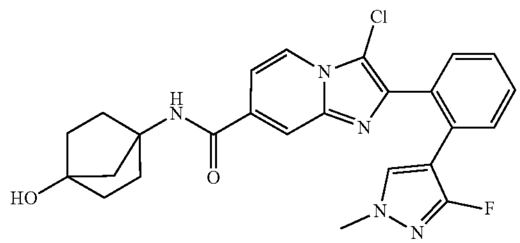 [SMILES: Cn1cc(-c2ccccc2-c2nc3cc(C(=O)NC45CCC(O)(CC4)C5)ccn3c2Cl)c(F)n1] | 480.3 |
| 856 | 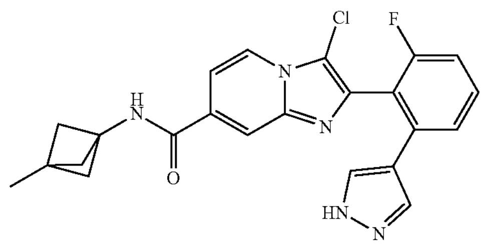 [SMILES: CC12CC(NC(=O)c3ccn4c(Cl)c(-c5c(F)cccc5-c5cn[nH]c5)nc4c3)(C1)C2] | 436.2 |
| 915 | 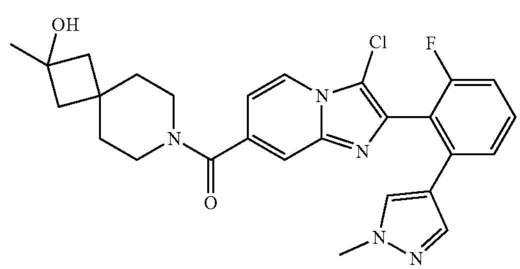 [SMILES: Cn1cc(-c2cccc(F)c2-c2nc3cc(C(=O)N4CCC5(CC4)CC(C)(O)C5)ccn3c2Cl)cn1] | 508.2 |
| 916 | 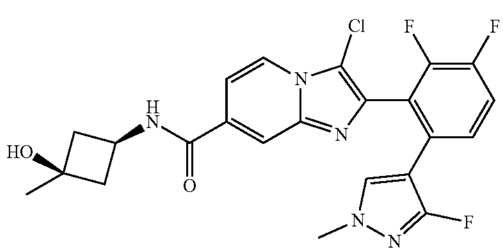 [SMILES: Cn1cc(-c2ccc(F)c(F)c2-c2nc3cc(C(=O)N[C@H]4C[C@@](C)(O)C4)ccn3c2Cl)c(F)n1] | 490.2 |
| 917 | 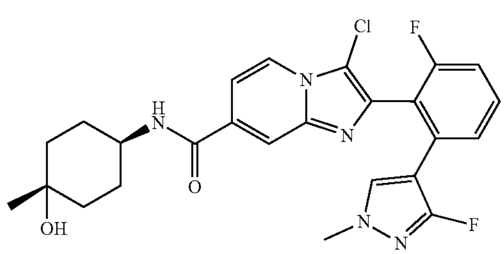 [SMILES: Cn1cc(-c2cccc(F)c2-c2nc3cc(C(=O)N[C@H]4CC[C@](C)(O)CC4)ccn3c2Cl)c(F)n1] | 500.2 |

TABLE 1-continued

| Compound | Structure | LCMS (ES+) m/z |
|---|---|---|
| 918 | 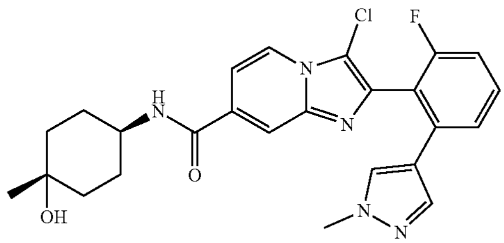 [SMILES: Cn1cc(-c2cccc(F)c2-c2nc3cc(C(=O)N[C@H]4CC[C@](C)(O)CC4)ccn3c2Cl)cn1] | 482.1 |
| 919 | 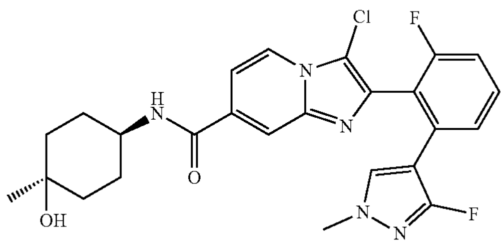 [SMILES: Cn1cc(-c2cccc(F)c2-c2nc3cc(C(=O)N[C@H]4CC[C@@](C)(O)CC4)ccn3c2Cl)c(F)n1] | 500.2 |
| 920 | 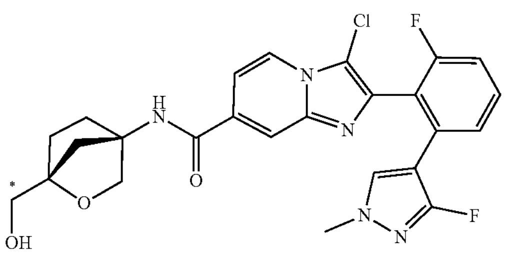 [SMILES: Cn1cc(-c2cccc(F)c2-c2nc3cc(C(=O)N[C@]45CC[C@](CO)(C4)OC5)ccn3c2Cl)c(F)n1] | 514.2 |
| 921 | 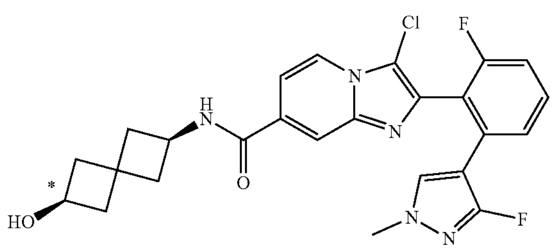 [SMILES: Cn1cc(-c2cccc(F)c2-c2nc3cc(C(=O)N[C@H]4CC5(C[C@@H](O)C5)C4)ccn3c2Cl)c(F)n1] | 498.2 |
| 922 | 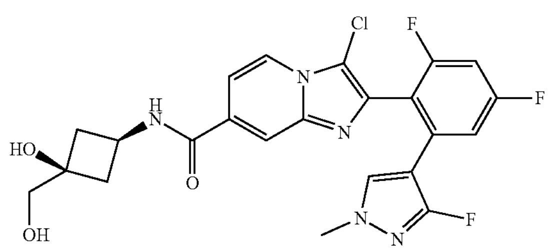 [SMILES: Cn1cc(-c2cc(F)cc(F)c2-c2nc3cc(C(=O)N[C@H]4C[C@](O)(CO)C4)ccn3c2Cl)c(F)n1] | 506.2 |
| 923 | 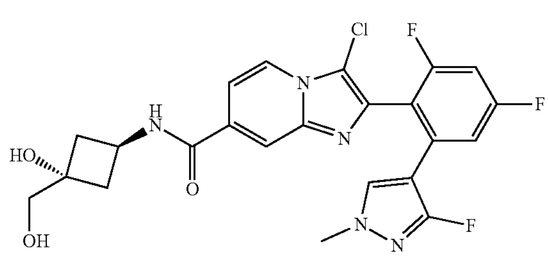 [SMILES: Cn1cc(-c2cc(F)cc(F)c2-c2nc3cc(C(=O)N[C@H]4C[C@@](O)(CO)C4)ccn3c2Cl)c(F)n1] | 506.2 |

TABLE 1-continued

| Compound | Structure | LCMS (ES+) m/z |
|---|---|---|
| 924 | 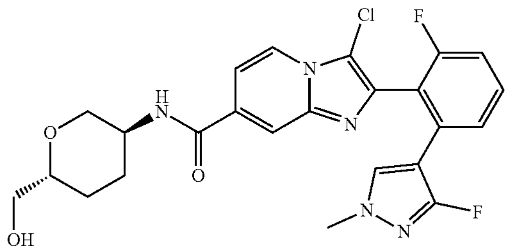 [SMILES: Cn1cc(-c2cccc(F)c2-c2nc3cc(C(=O)N[C@H]4CC[C@H](CO)OC4)ccn3c2Cl)c(F)n1] | 502.1 |
| 925 | 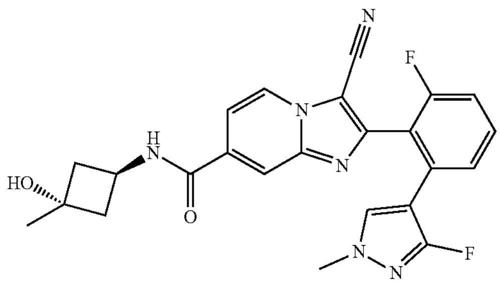 [SMILES: Cn1cc(-c2cccc(F)c2-c2nc3cc(C(=O)N[C@H]4C[C@](C)(O)C4)ccn3c2C#N)c(F)n1] | 463.1 |
| 926 | 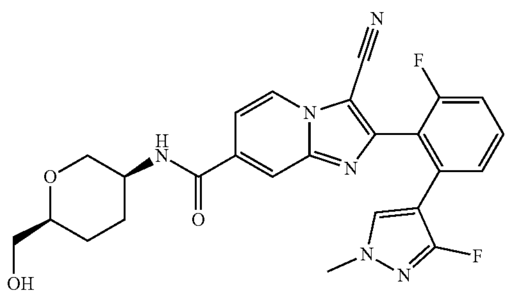 [SMILES: Cn1cc(-c2cccc(F)c2-c2nc3cc(C(=O)N[C@H]4CC[C@@H](CO)OC4)ccn3c2C#N)c(F)n1] | 493.3 |
| 927 | 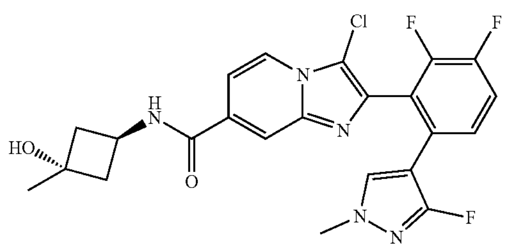 [SMILES: Cn1cc(-c2ccc(F)c(F)c2-c2nc3cc(C(=O)N[C@H]4C[C@](C)(O)C4)ccn3c2Cl)c(F)n1] | 490.2 |
| 928 | 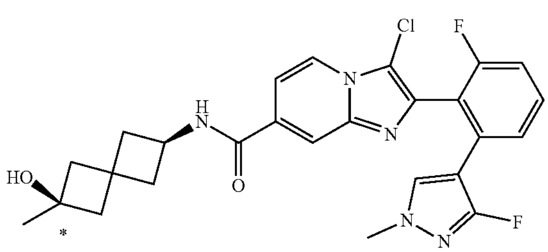 [SMILES: Cn1cc(-c2cccc(F)c2-c2nc3cc(C(=O)N[C@H]4CC5(C4)C[C@@](C)(O)C5)ccn3c2Cl)c(F)n1] | 512.2 |
| 929 | 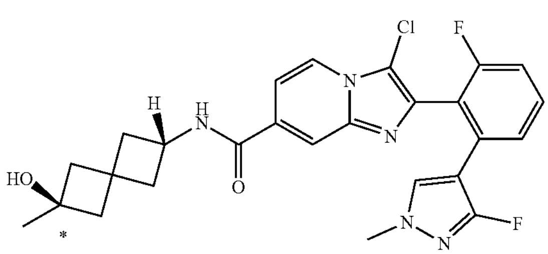 [SMILES: Cn1cc(-c2cccc(F)c2-c2nc3cc(C(=O)N[C@H]4CC5(C4)C[C@@](C)(O)C5)ccn3c2Cl)c(F)n1] | 512.2 |

TABLE 1-continued

| Compound | Structure | LCMS (ES+) m/z |
|---|---|---|
| 930 | 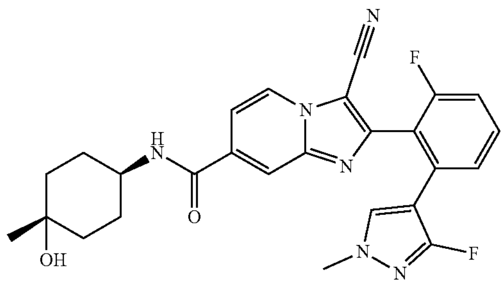 [SMILES: Cn1cc(-c2cccc(F)c2-c2nc3cc(C(=O)N[C@H]4CC[C@](C)(O)CC4)ccn3c2C#N)c(F)n1] | 491.1 |
| 931 | 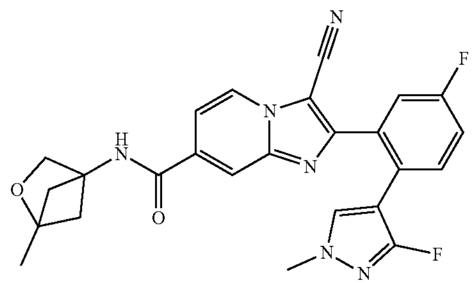 [SMILES: Cn1cc(-c2ccc(F)cc2-c2nc3cc(C(=O)NC45COC(C)(C4)C5)ccn3c2C#N)c(F)n1] | 475.2 |
| 932 | 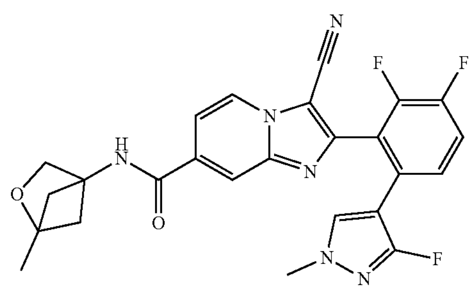 [SMILES: Cn1cc(-c2ccc(F)c(F)c2-c2nc3cc(C(=O)NC45COC(C)(C4)C5)ccn3c2C#N)c(F)n1] | 493.3 |
| 933 | 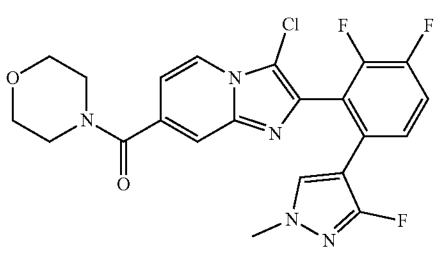 [SMILES: Cn1cc(-c2ccc(F)c(F)c2-c2nc3cc(C(=O)N4CCOCC4)ccn3c2Cl)c(F)n1] | 476.2 |
| 934 | 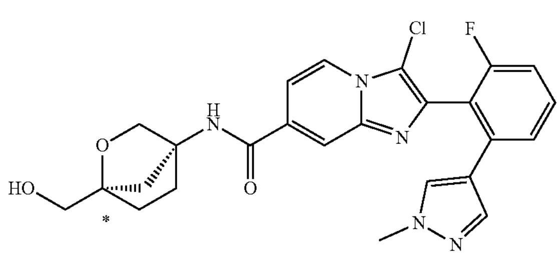 [SMILES: Cn1cc(-c2cccc(F)c2-c2nc3cc(C(=O)N[C@]45CC[C@](CO)(C4)OC5)ccn3c2Cl)cn1] | 496.1 |

TABLE 1-continued

| Compound | Structure | LCMS (ES+) m/z |
|---|---|---|
| 935 | 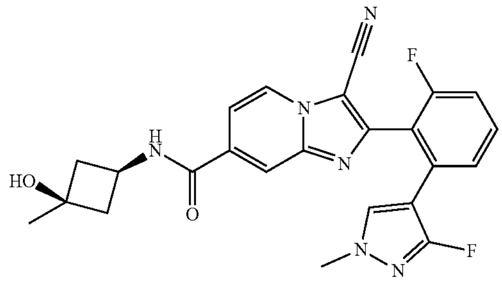 [SMILES: Cn1cc(-c2cccc(F)c2-c2nc3cc(C(=O)N[C@H]4C[C@@](C)(O)C4)ccn3c2C#N)c(F)n1] | 463.2 |

*absolute stereochemistry not determined for some compounds; i.e., all compounds are isolated as a single stereoisomer (diastereomer or enantiomer) but stereochemistry is arbitrarily drawn

*absolute stereochemistry not determined for some compounds; i.e., all compounds are isolated as a single stereoisomer (diastereomer or enantiomer) but stereochemistry is arbitrarily drawn II. In Vitro Assays of Compounds for Determining NK3 Modulation Activity Stable Cell Lines: A human recombinant NK3 Tachykinin Receptor stable cell line was purchased from GenScript (Genscript, Cat. #M00201; GenBank Accession Number NM 001059). The cell line was cultured according to manufacturer instructions, using 100 µg/mL Hygromycin B (Invitrogen, Cat. #D2650) for selective pressure. Cells were then collected using 0.05% Trypsin-EDTA (GIBCO, Cat. #25300) and frozen in a freezing media containing 90% FBS (Gibco, Cat. #10099-141) and 10% DMSO (Sigma, Cat. #D2650) at a density of $30 \times 10^6$ cells/mL. This bank of assay-ready frozen cells was later used in FLIPR assays to evaluate the potency and efficacy of NK3 antagonist test compounds.

FLIPR Calcium Assay: The FLIPR assay, used to measure changes in intracellular calcium levels, was performed in a 384-well plate format using the FLIPR Calcium 6 assay kit (Molecular Devices, Cat. #R8190). Assay-ready frozen cells expressing human NK3 (Genscript, Cat. #M00201) were thawed, washed, trypsinized, counted using a ViCell, and plated in cell growth media without Hygromycin at a density of $10 \times 10^5$ cells/well (40 µL/well).

Calculation of NKB $EC_{70}$: An $EC_{70}$ concentration of NKB needed to be determined for competition against test antagonists prior to the compound screen. NKB agonist (Phoenix Pharmaceuticals, Cat. #046-26) was diluted in DMSO at 1800 nM (6-fold the final concentration) and serially diluted to generate a 13-point dose response curve (3-fold serial dilution) using an ECHO. 20 µL of 1× stimulation buffer was added using the BRAVO. 10 µL of DMSO was added while on the FLIPR (described as the first addition), then the RFU signal was measured for 10 minutes. The NKB titration was added to the plate, then the RFU signal was measured for 10 minutes (described as the second addition) on the FLIPR. The EC70 concentration was determined by using a four-parameter fit on GraphPad Prism prior to performing the compound screen.

FLIPR Screen in Antagonist Mode: Test compounds were prepared at 60 µM (6-fold the final concentration) and spotted in 370 nL using the Janus and ECHO. 20 µL of assay buffer was added using the BRAVO. Calcium-sensitive dye was reconstituted in loading buffer (Molecular Devices, Cat. #R8190). Media was removed from the cell plate using a Bluecat Cell Washer, and 40 µL of dye was added to the cell plate using the Apricot. The plate was incubated for 2 hours at 37° C., 5% $CO_2$, then transferred to the FLIPR instrument. 10 µL of compound was added on the FLIPR (described as the first addition), then the RFU signal was measured for 10 minutes. $EC_{70}$ of NKB agonist was added to the entire plate (described as the second addition), and the RFU signal was measured for 10 minutes on the FLIPR. RFU (relative fluorescence units) signals for first baseline, first peak, second baseline, and second peak were measured using the FLIPR. RFU signal (second peak minus second baseline) for positive (Max, at 10 µM antagonist) and negative (Min, at 0 µM antagonist) controls were used to normalize data and generate values for % Activity. $IC_{50}$ and efficacy values were determined using a standard curve fitting equation on Dotmatics.

Results for exemplary compounds are shown in Table A, wherein $IC_{50}$ values are provided in units of nM.

TABLE A

| Cpd# | $IC_{50}$ |
|---|---|
| 7 | 1.21 |
| 142 | 6.60 |
| 264 | 10.67 |
| 271 | 20.31 |
| 295 | 131.4 |
| 298 | 26.78 |
| 312 | 41.68 |
| 317 | 7.03 |
| 425 | 3.16 |
| 430 | 2.30 |
| 431 | 4.03 |
| 434 | 1.47 |
| 436 | 67.46 |
| 442 | 15.08 |
| 443 | 11.30 |
| 447 | 3.19 |
| 448 | 6.01 |
| 451 | 7.13 |
| 452 | 2.79 |
| 455 | 1.74 |
| 459 | 1.86 |
| 460 | 2.55 |
| 461 | 3.41 |
| 464 | 2.90 |
| 468 | 4.27 |
| 470 | 1.41 |
| 473 | 2.26 |
| 475 | 5.74 |
| 476 | 3.31 |

TABLE A-continued

| Cpd# | IC$_{50}$ |
|---|---|
| 477 | 2.19 |
| 480 | 20.66 |
| 481 | 16.11 |
| 486 | 6.85 |
| 487 | 2.21 |
| 490 | 3.40 |
| 614 | 2.65 |
| 615 | 2.50 |
| 616 | 1.45 |
| 617 | 3.18 |
| 619 | 1.24 |
| 624 | 0.59 |
| 629 | 1.06 |
| 631 | 0.78 |
| 633 | 1.53 |
| 635 | 1.65 |
| 638 | 25.81 |
| 639 | 3.81 |
| 641 | 1.04 |
| 643 | 1.08 |
| 645 | 2.02 |
| 647 | 9.16 |
| 650 | 5.83 |
| 651 | 9.28 |
| 704 | 6.76 |
| 705 | 4.97 |
| 747 | 2.08 |
| 748 | 5.58 |
| 759 | 2.78 |
| 761 | 1.92 |
| 767 | 4.26 |
| 768 | 1.96 |
| 773 | 2.63 |
| 774 | 5.21 |
| 775 | 4.64 |
| 779 | 5.82 |
| 780 | 3.34 |
| 781 | 12.66 |
| 782 | 4.80 |
| 783 | 3.21 |
| 784 | 6.21 |
| 787 | 1.51 |
| 788 | 1.03 |
| 789 | 1.99 |
| 790 | 3.31 |
| 791 | 0.72 |
| 792 | 2.09 |
| 793 | 1.19 |
| 794 | 8.45 |
| 795 | 12.50 |
| 796 | 4.11 |
| 797 | 4.63 |
| 798 | 22.35 |
| 799 | 4.70 |
| 800 | 8.07 |
| 801 | 22.01 |
| 814 | 3.33 |
| 816 | 8.46 |
| 817 | 1.92 |
| 818 | 0.99 |
| 819 | 6.12 |
| 820 | 0.77 |
| 821 | 2.49 |
| 822 | 9.61 |
| 823 | 3.25 |
| 824 | 5.89 |
| 825 | 7.72 |
| 826 | 1.40 |
| 828 | 0.30 |
| 829 | 8.27 |
| 830 | 6.63 |
| 831 | 3.66 |
| 832 | 6.91 |
| 833 | 2.68 |
| 834 | 6.01 |
| 835 | 6.24 |
| 836 | 1.10 |
| 837 | 1.01 |
| 838 | 5.17 |
| 839 | 0.46 |
| 840 | 0.58 |
| 841 | 1.25 |
| 842 | 1.38 |
| 843 | 1.08 |
| 844 | 0.42 |
| 845 | 2.61 |
| 846 | 0.74 |
| 847 | 3.57 |
| 848 | 2.00 |
| 849 | 0.94 |
| 850 | 0.31 |
| 851 | 1.93 |
| 852 | 0.97 |
| 853 | 0.97 |
| 854 | 1.42 |
| 855 | 1.71 |
| 856 | 11.76 |
| 915 | 4.22 |
| 916 | 0.84 |
| 917 | 0.67 |
| 918 | 3.48 |
| 919 | 1.27 |
| 920 | 1.06 |
| 921 | 0.71 |
| 922 | 2.83 |
| 923 | 2.36 |
| 924 | 0.97 |
| 925 | 1.85 |
| 926 | 2.21 |
| 927 | 2.66 |
| 928 | 1.56 |
| 929 | 2.07 |
| 930 | 3.00 |
| 932 | 6.09 |
| 933 | 5.66 |
| 934 | 9.69 |

III. In Vivo Assay of Compounds for Determining Efficacy in a Rat Migraine Model An acute nitroglycerin (NTG) model was used to assess migraine efficacy in rats (for a review see: Sureda-Gibert, P, Neurobiol Pain. 2022 August-December; 12: 100105). Briefly, male Sprague Dawley rats, 8-weeks old (Charles River Laboratories), were pair-housed in a 12-h light cycle room upon facility arrival and left to acclimate for a minimum of 72 h. Animals were provided standard rodent chow (PicoLab Rodent Diet, 5053) and water ad libitum. Following the acclimation period, rats underwent a single behavioral testing apparatus acclimation. Rats were left to freely move and habituate for a minimum of 20 min. The testing apparatus used was a Multiple Configuration Animal Enclosure (Ugo Basile, 37000-007) placed on a self-standing table with a mesh-perforated bottom.

Periorbital threshold was measured using the up-down method (Chaplan, S. R., et al., J Neurosci Methods, 1994 July; 53(1):55-63), in which von Frey filaments (Ugo Basile, 37450-275) of increasing forces (0.4-15 g) were applied to the periorbital region until an application of a filament evoked a response, typically indicated by a rapid withdrawal response or paw swipe to the periorbital region. Once a response was observed, four more readings were obtained following the first change of direction to determine the withdrawal threshold close to 50%. The 50% threshold was then calculated using the following formula: 50% threshold $(g) = 10^{(X+kd)}/10^4$, where X=the value, in log units, of the final von Frey filament, k=tabular value for the response pattern, and d=the average increment, in log units, between von Frey filaments.

Following acclimation, a baseline assessment was performed, and rats were then randomized into balanced treatment groups using baseline periorbital threshold measurements. On the day of the experiment, rats (n=12/group) were weighed and administered 10 mg/kg NTG (2 mg/mL in 0.9% saline; Henry Schein, NDC-0517-4810-25) by intraperitoneal injection, immediately followed by their assigned compound treatment of either vehicle (0.25% methyl cellulose, 5% Tween 80, 0.02% sodium dodecyl sulfate (SDS) in Hanks' Buffered Salt Solution with $Ca^{2+}$ and $Mg^{2+}$), 10 mg/kg sumatriptan as a positive control (2 mg/mL in vehicle; Ambeed, A260899-1g) or 30 mg/kg test compound (10 mg/mL in vehicle).

Approximately 70 min post dosing, animals were placed in the behavioral testing apparatus and allowed to habituate to individual enclosures for a minimum of 20 min prior to von Frey assessment. Von Frey measurements were then recorded at 90 and 120. Upon final measurement, rats were immediately euthanized via $CO_2$ asphyxiation followed by exsanguination. Blood was collected in lithium-heparin serum-separating tubes (BD, 365985) and processed for serum collection. Serum samples were then stored at −80° C.

Migraine efficacy (%) was calculated by dividing the 50% threshold (g) following administration of test compound by the baseline 50% threshold (g) and then multiplying by 100. Results for exemplary compounds at 90 min are shown in Table B.

TABLE B

| Compound No. | Efficacy (%) |
|---|---|
| 7 | 81 |
| 16 | 82 |
| 787 | 70 |
| 845 | 92 |
| 915 | 92 |
| 920 | 100 |

IV. In Vitro Assay of Compounds for P-gp Substrate Assessment

P-glycoprotein (P-gp) at the blood-brain barrier (BBB) is an efflux transporter that functions to actively pump small-molecule compounds from brain tissue to the blood stream. In vitro P-gp substrate assessment is used to predict the in vivo relevance of P-gp-mediated efflux at the BBB. Typically, central nervous system (CNS) drugs are not substrates of P-gp (efflux ratio<2) while peripherally restricted compounds are P-gp substrates (efflux ratio≥2).

MDR1-MDCK II from passage 5-35 were used for P-gp substrate assessment studies. Briefly, test compounds were diluted with transport buffer (HBSS with 10 mM HEPES, pH 7.4) from stock solution to a concentration of 2.00 μM (DMSO<1%) and applied to the apical or basolateral side of the cell monolayer. Permeation of the test compounds from the A to B direction (Papp (AB)) or the B to A direction (Papp (BA)) was determined in duplicate over a 150-min incubation at 37° C. and 5% $CO_2$ with a relative humidity of 95%. Compounds were quantified by LC/MS/MS analysis based on the peak area ratio of analyte/internal standard. The efflux ratio of each compound was determined according to the following equation: Efflux Ratio=Papp (BA)/Papp (AB).

As shown in Table C, the Reference Compound (compound 1 from Y. Ding, et al. *ACS Combinatorial Science* 2018 20 (5), 251-255) is not a P-gp substrate (efflux ratio<2), whereas compounds of the present disclosure are P-gp substrates (efflux ratio≥2).

TABLE C

| Compound No. | Efflux Ratio |
|---|---|
| Reference Compound | 0.742 |
| 7 | 32.7 |
| 431 | 19.0 |
| 434 | 24.2 |
| 615 | 18.3 |
| 16 | 53.0 |
| 787 | 11.3 |
| 791 | 10.0 |
| 837 | 25.4 |
| 845 | 10.5 |
| 915 | 8.84 |
| 916 | 15.6 |
| 917 | 19.6 |
| 918 | 36.1 |
| 919 | 6.42 |
| 920 | 29.5 |
| 924 | 20.6 |
| 925 | 8.88 |
| 926 | 12.1 |
| 927 | 6.94 |
| 930 | 12.3 |
| 931 | 5.43 |
| 934 | 23.2 |

The examples and embodiments described herein are for illustrative purposes only and various modifications or changes suggested to persons skilled in the art are to be included within the spirit and purview of this application and scope of the appended claims.

What is claimed is:
1. A compound of Formula (I):

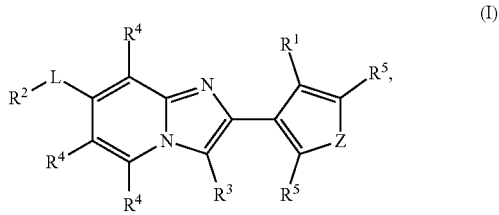

or a pharmaceutically acceptable salt or solvate thereof, wherein:

Z is a bivalent group selected from —S—, —N=C($R^5$)—, —C($R^5$)=N—, or —C($R^5$)=C($R^5$)—;

$R^1$ is pyrazole, wherein said pyrazole is optionally substituted with 1-3 groups independently selected from $R^6$;

$R^2$ is $C_1$-$C_{10}$ alkyl, $C_1$-$C_{10}$ heteroalkyl, —C(=O)$OR^7$, —C(=O)N($R^8$)($R^7$), —N($R^8$)($R^7$), —C(=N$R^9$)N($R^8$)($R^7$), —N($R^7$)C(=N$R^9$)N($R^8$)($R^7$), $C_6$-$C_{10}$ aryl, 5- to 10-membered heteroaryl, $C_3$-$C_{12}$ cycloalkyl, or 3-to-15 membered heterocycloalkyl, wherein the aryl, and heteroaryl is optionally substituted with 1-4 groups independently selected from $R^{10}$, and the alkyl, heteroalkyl, cycloalkyl, and heterocycloalkyl is optionally substituted with 1-4 groups independently selected from oxo and $R^{10}$;

$R^3$ is halogen, cyano, —C(=O)OH, —C(=O)O($C_1$-$C_6$ alkyl), $C_1$-$C_6$ alkyl, $C_1$-$C_6$ alkenyl, —O($C_1$-$C_6$ alkyl), $C_3$-$C_6$ cycloalkyl, or $C_1$-$C_6$ haloalkyl;

each $R^4$ is independently hydrogen, halogen, $C_1$-$C_6$ alkyl, —O—$C_1$-$C_6$ alkyl, $C_1$-$C_6$ haloalkyl, or —O—($C_1$-$C_6$ haloalkyl);

L is a bond, $C_1$-$C_2$ alkylene, or $C_3$-$C_6$ cycloalkylene, wherein said alkylene, or cycloalkylene is optionally substituted with 1 or 2 —OH groups;

each $R^5$ is independently hydrogen, cyano, halogen, $C_1$-$C_6$ alkyl, —O($C_1$-$C_6$ alkyl), $C_3$-$C_6$ cycloalkyl, $C_1$-$C_6$ haloalkyl, or —O($C_1$-$C_6$ haloalkyl);

each $R^6$ is independently selected from the group consisting of halogen, hydroxy, cyano, amino, $C_1$-$C_6$ alkyl, $C_1$-$C_6$ hydroxyalkyl, $C_1$-$C_6$ aminoalkyl, —O($C_1$-$C_6$ alkyl), —NH($C_1$-$C_6$ alkyl), —N($C_1$-$C_6$ alkyl)$_2$, $C_3$-$C_6$ cycloalkyl, —CH$_2$—($C_{3-6}$ cycloalkyl), —O—($C_{3-6}$ cycloalkyl), $C_1$-$C_6$ haloalkyl, and —O($C_1$-$C_6$ haloalkyl);

wherein if an $R^6$ is attached to a nitrogen atom, then it is selected from the group consisting of $C_1$-$C_6$ alkyl, $C_1$-$C_6$ hydroxyalkyl, $C_1$-$C_6$ aminoalkyl, $C_3$-$C_6$ cycloalkyl, —CH$_2$—($C_{3-6}$ cycloalkyl), and $C_1$-$C_6$ haloalkyl;

each $R^7$ is independently hydrogen or $C_1$-$C_6$ alkyl, wherein said alkyl is optionally substituted with 1-2 hydroxy groups;

$R^8$ is hydrogen, $C_1$-$C_{10}$ alkyl, $C_1$-$C_{10}$ heteroalkyl, $C_1$-$C_{10}$ alkenyl, $C_1$-$C_{10}$ alkynyl, $C_3$-$C_{12}$ cycloalkyl, 3- to 15-membered heterocycloalkyl, $C_6$-$C_{10}$ aryl, or 5- to 10-membered heteroaryl; wherein the aryl, and heteroaryl is optionally substituted with 1-6 groups independently selected from $R^{11}$, and the alkyl, heteroalkyl, alkenyl, alkynyl, cycloalkyl and heterocycloalkyl is optionally substituted with 1-6 groups independently selected from oxo and $R^{11}$;

or one $R^7$ and one $R^8$ bound to the same nitrogen atom come together to form a 3- to 15-membered heterocycloalkyl that is optionally substituted with 1-6 groups independently selected from oxo and $R^{11}$;

$R^9$ is hydrogen, —C(O)OR$^{12}$, —C(O)N(R$^{12}$)$_2$, —S(O)$_2$R$^{12}$, —S(O)$_2$N(R$^{12}$)$_2$, or $C_1$-$C_6$ alkyl;

each $R^{10}$ is independently selected from hydroxy, amino, cyano, fluoro, —C(=O)OR$^{12}$, —C(=O)N(R$^{12}$)$_2$, $C_1$-$C_4$ alkyl, $C_1$-$C_4$ haloalkyl, —O($C_1$-$C_6$ alkyl), —NH($C_1$-$C_4$ alkyl), —N($C_1$-$C_4$ alkyl)$_2$, $C_3$-$C_6$ cycloalkyl, wherein said alkyl, haloalkyl or cycloalkyl is optionally substituted with 1-2 groups selected from hydroxy, amino, cyano, fluoro, —C(=O)OR$^{12}$, and —C(=O)N(R$^{12}$)$_2$;

each $R^{11}$ is independently selected from the group consisting of halogen, hydroxy, amino, cyano, —S(=O)$_2$(R$^{13}$), —N(R$^{12}$)S(=O)$_2$(R$^{13}$), —S(=O)(R$^{13}$), —N(R$^{12}$)S(=O)(R$^{13}$), —C(=O)R$^{13}$, —N(R$^{12}$)C(=O)R$^{13}$, $C_1$-$C_6$ alkyl, —O($C_1$-$C_6$ alkyl), —NH($C_1$-$C_6$ alkyl), —N($C_1$-$C_6$ alkyl)$_2$, $C_1$-$C_6$ haloalkyl, $C_2$-$C_6$ alkenyl, $C_2$-$C_6$ alkynyl, $C_3$-$C_8$ cycloalkyl, 3- to 10-membered heterocycloalkyl, $C_6$-$C_{10}$ aryl, and 5- to 10-membered heteroaryl, wherein the aryl, and heteroaryl is optionally substituted with 1-4 groups independently selected from $R^{14}$, and the alkyl, alkenyl, alkynyl, haloalkyl, cycloalkyl, and heterocycloalkyl is optionally substituted with 1-4 groups independently selected from oxo and $R^{14}$;

or two $R^{11}$ bound to the same carbon or nitrogen atom come together to form a $C_3$-$C_6$ cycloalkyl or 3- to 6-membered heterocycloalkyl, wherein the cycloalkyl, and heterocycloalkyl is optionally substituted with 1-4 groups independently selected from oxo and $R^{14}$;

each $R^{12}$ is independently hydrogen or $C_1$-$C_6$ alkyl;

each $R^{13}$ is independently hydroxy, amino, $C_1$-$C_6$ alkyl, —O($C_1$-$C_6$ alkyl), —NH($C_1$-$C_6$ alkyl), —N($C_1$-$C_6$ alkyl)$_2$, $C_1$-$C_6$ haloalkyl, $C_3$-$C_6$ cycloalkyl, or 3- to 6-membered heterocycloalkyl; and each $R^{14}$ is independently cyano, amino, hydroxy, —C(=O)OR$^{12}$, —C(=O)N(R$^{12}$)$_2$, $C_1$-$C_6$ alkyl, —O($C_1$-$C_6$ alkyl), —NR$^{12}$($C_1$-$C_6$ alkyl), aryl, heteroaryl, $C_3$-$C_6$ cycloalkyl, or 3- to 6-membered heterocycloalkyl, wherein each alkyl is optionally substituted with 1-2 hydroxy groups.

2. The compound of claim 1, or a pharmaceutically acceptable salt or solvate thereof, wherein:

$R^3$ is halogen, cyano, $C_1$-$C_6$ alkyl, $C_3$-$C_6$ cycloalkyl, or $C_1$-$C_6$ haloalkyl.

3. The compound of claim 1, or a pharmaceutically acceptable salt or solvate thereof, wherein:

each $R^4$ is independently hydrogen, fluoro or methyl.

4. The compound of claim 1, having the structure of Formula (IIa):

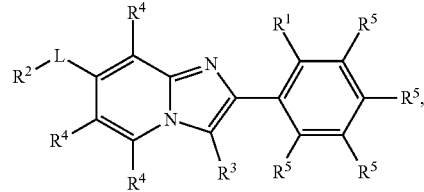

Formula (IIa)

or a pharmaceutically acceptable salt or solvate thereof.

5. The compound of claim 1, or a pharmaceutically acceptable salt or solvate thereof, wherein:

L is a bond or $C_1$ alkylene.

6. The compound of claim 1, or a pharmaceutically acceptable salt or solvate thereof, wherein:

$R^2$ is —C(O)(OR$^7$) or —C(O)N(R$^8$)(R$^7$).

7. The compound of claim 1, having the structure of Formula (IVa):

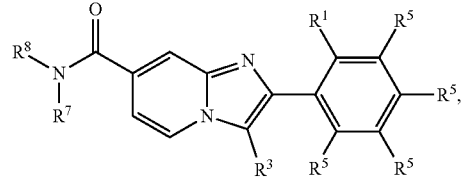

Formula (IVa)

or a pharmaceutically acceptable salt or solvate thereof.

8. The compound of claim 1, or a pharmaceutically acceptable salt or solvate thereof, wherein:

$R^1$ is

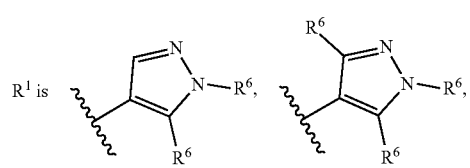

-continued

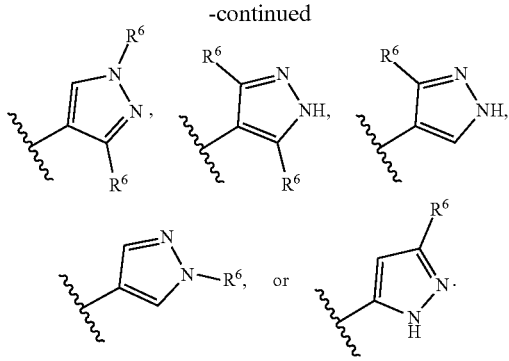

9. The compound of claim 1, having a structure of Formula (VIa):

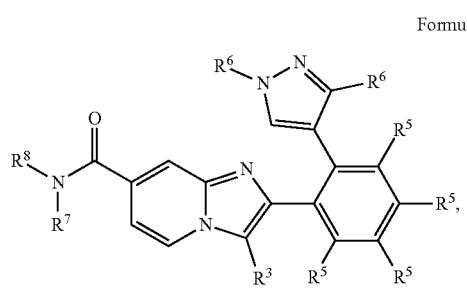

Formula (VIa)

or a pharmaceutically acceptable salt or solvate thereof.

10. The compound of claim 9, or a pharmaceutically acceptable salt or solvate thereof, wherein:
each $R^6$ is independently halogen, cyano, $C_{1-6}$ alkyl, $C_{1-6}$ fluoroalkyl, $C_{3-6}$ cycloalkyl, or —$CH_2$—($C_{3-6}$ cycloalkyl); wherein when an $R^6$ is attached to a nitrogen atom, it is $C_{1-6}$ alkyl, $C_{1-6}$ fluoroalkyl, $C_{3-6}$ cycloalkyl, or —$CH_2$—($C_{3-6}$ cycloalkyl).

11. The compound of claim 9, or a pharmaceutically acceptable salt or solvate thereof, wherein:
each $R^5$ is independently hydrogen or fluoro.

12. The compound of claim 1, or a pharmaceutically acceptable salt or solvate thereof, wherein:
$R^8$ is $C_1$-$C_{10}$ alkyl, $C_1$-$C_{10}$ heteroalkyl, $C_3$-$C_{12}$ cycloalkyl, or 3- to 15-membered heterocycloalkyl; wherein the alkyl, heteroalkyl, cycloalkyl or heterocycloalkyl is optionally substituted with 1-6 groups independently selected from oxo and $R^{11}$.

13. The compound of claim 12, or a pharmaceutically acceptable salt or solvate thereof, wherein:
$R^8$ is fused bicyclic $C_5$-$C_{10}$ cycloalkyl, bridged bicyclic $C_5$-$C_{10}$ cycloalkyl, spirocyclic bicyclic $C_5$-$C_{10}$ cycloalkyl, fused bicyclic 5- to 12-membered heterocycloalkyl, bridged bicyclic 5- to 12-membered heterocycloalkyl, or spirocyclic bicyclic 5- to 12-membered heterocycloalkyl; wherein the cycloalkyl or heterocycloalkyl is optionally substituted with 1-6 groups independently selected from oxo and $R^{11}$.

14. The compound of claim 1, or a pharmaceutically acceptable salt or solvate thereof, wherein:
one $R^7$ and one $R^8$ bound to the same nitrogen atom come together to form a 3- to 15-membered heterocycloalkyl that is optionally substituted with 1-6 groups independently selected from oxo and $R^{11}$.

15. The compound of claim 9, or a pharmaceutically acceptable salt or solvate thereof, wherein:

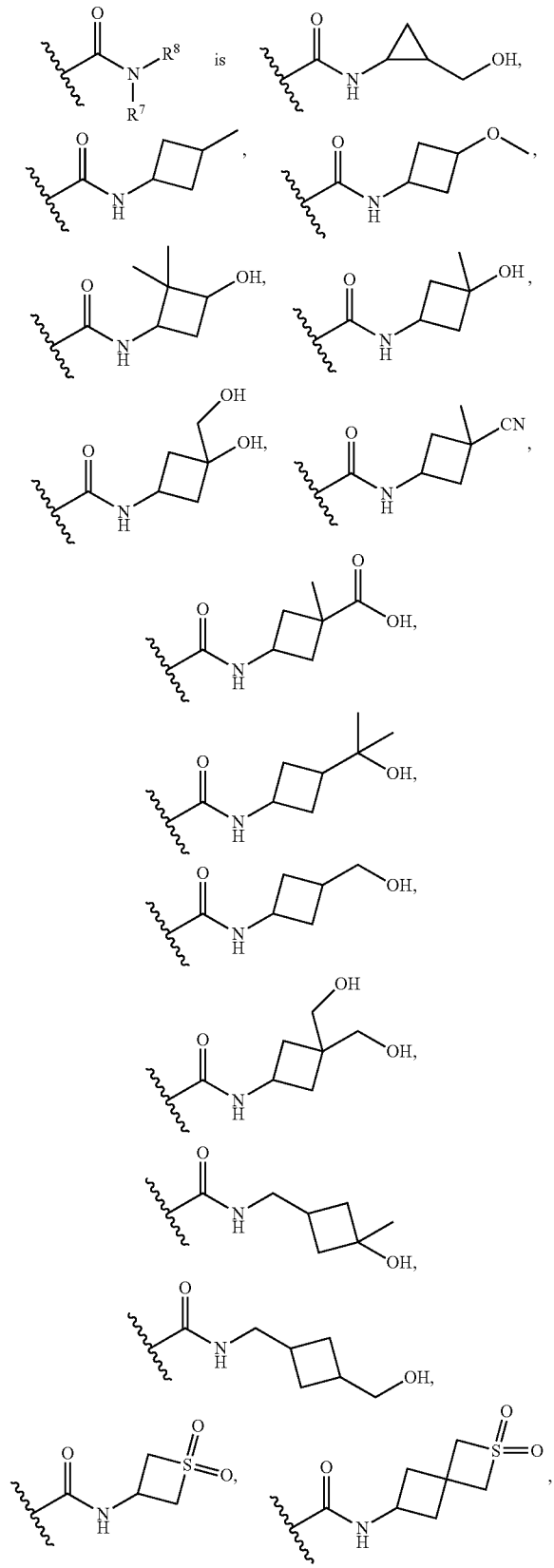

335
-continued
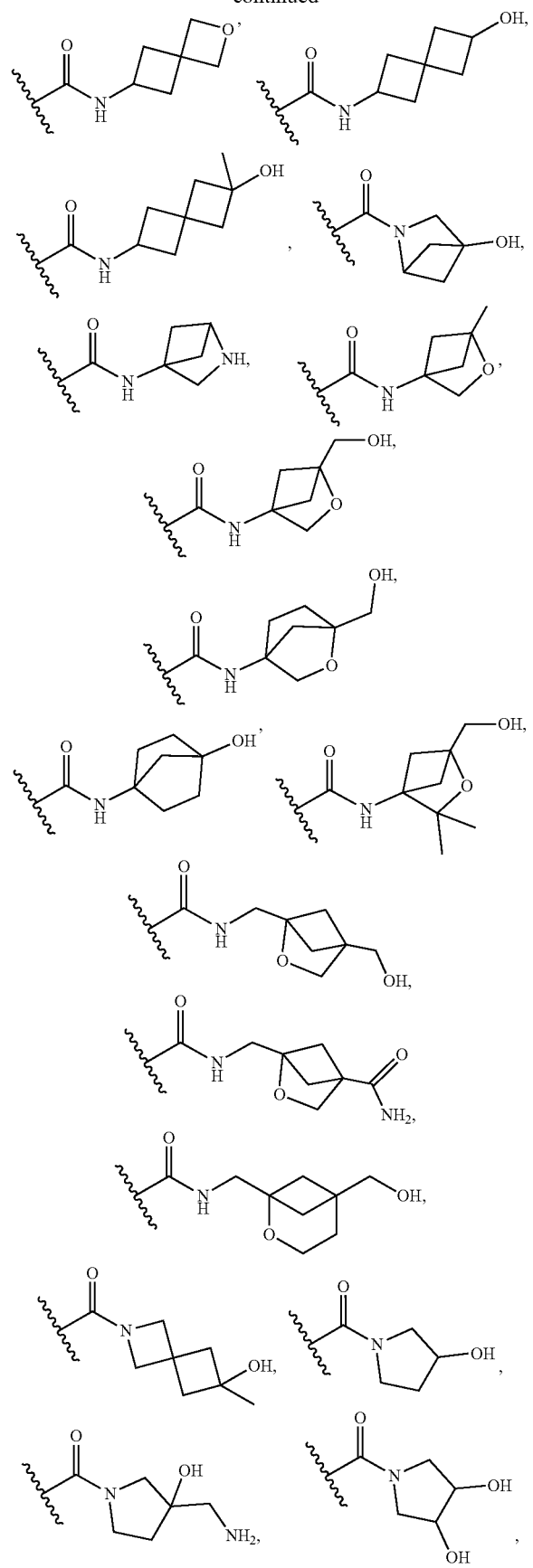
336
-continued
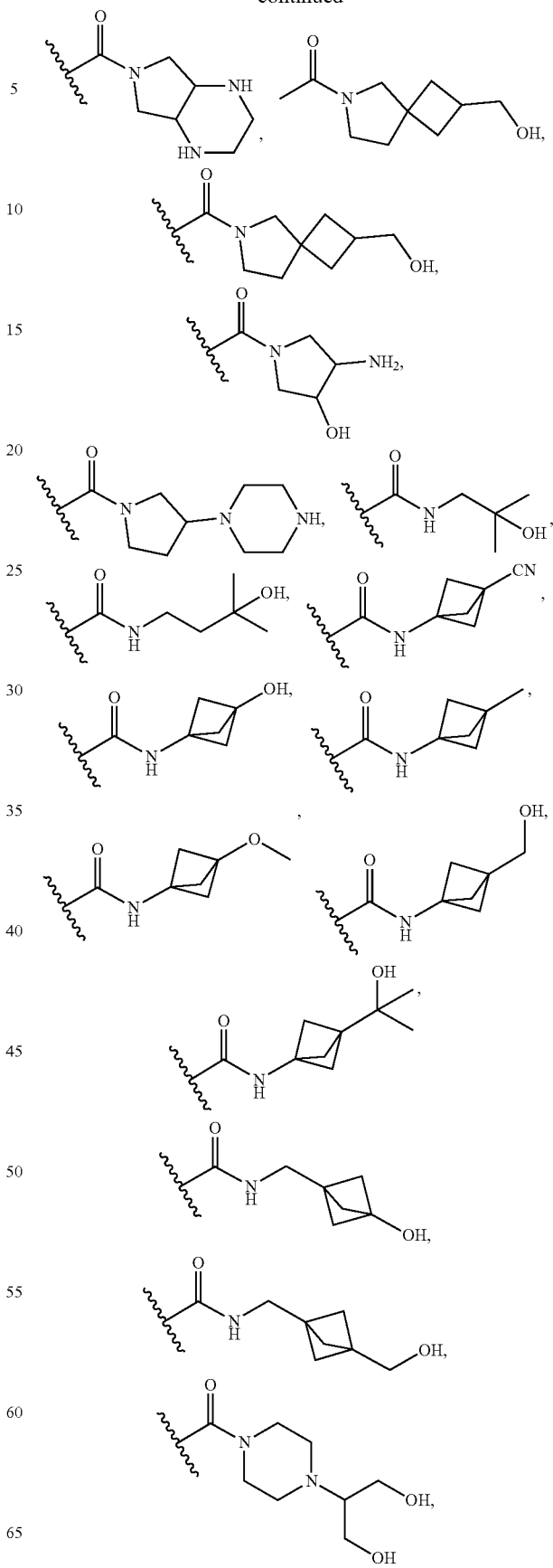

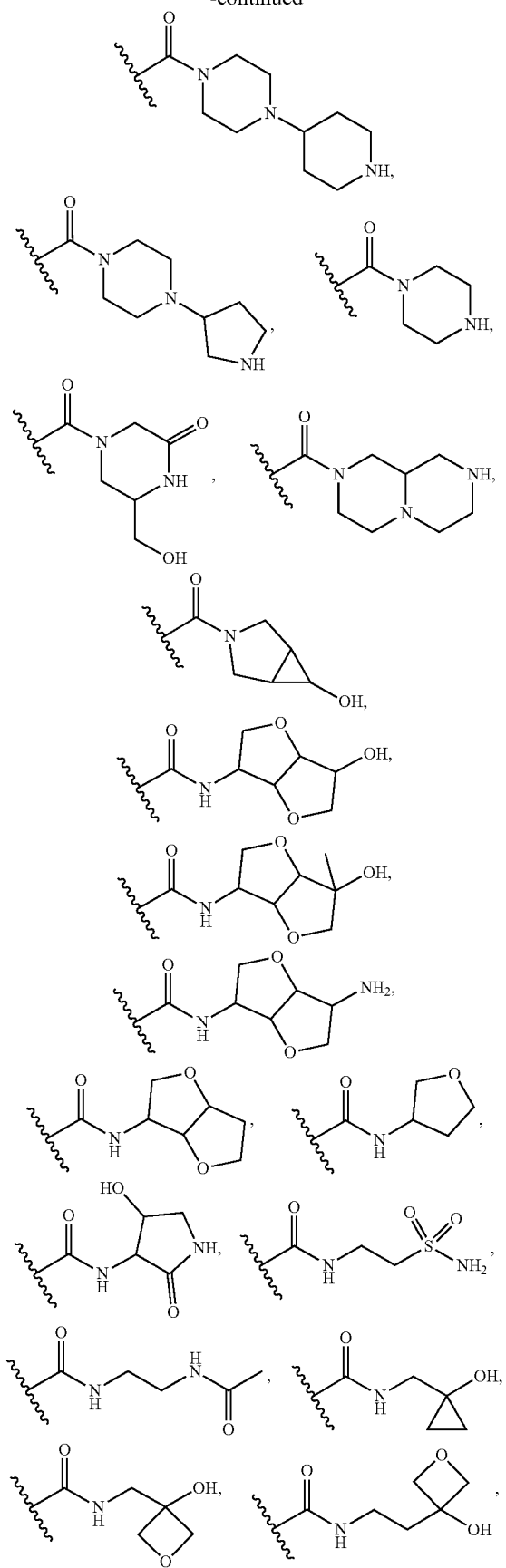
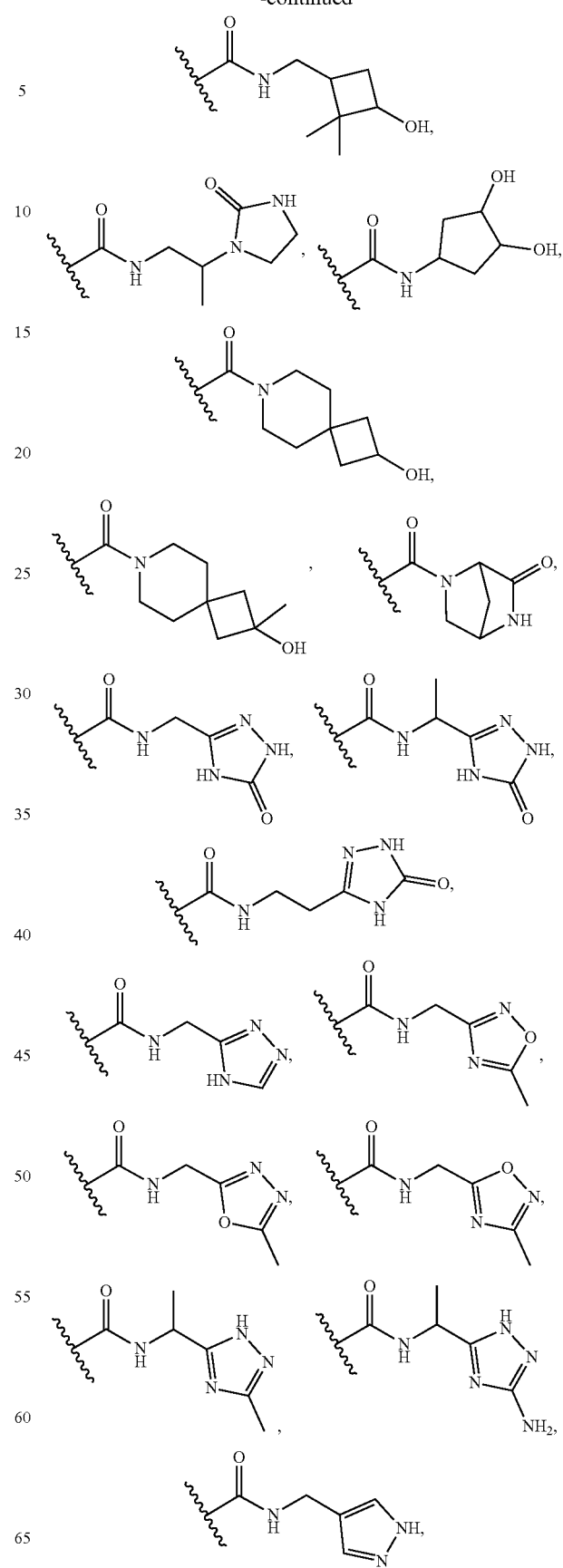

-continued
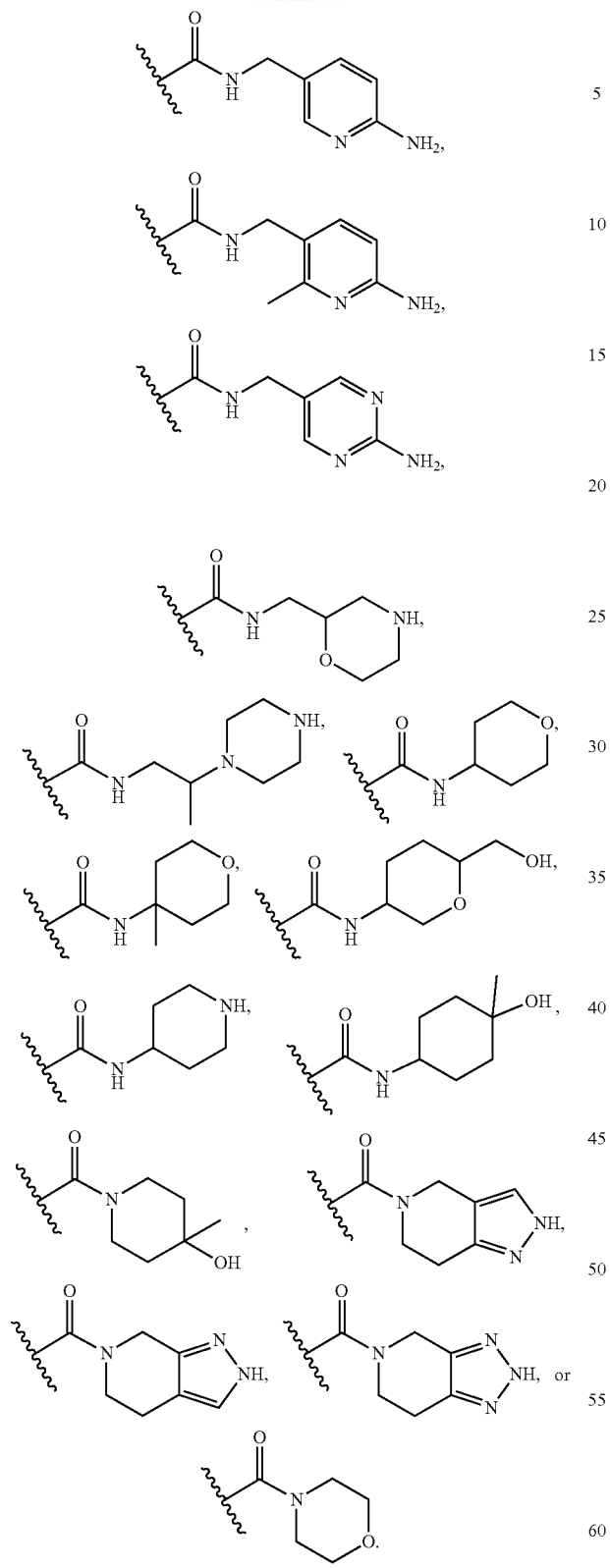
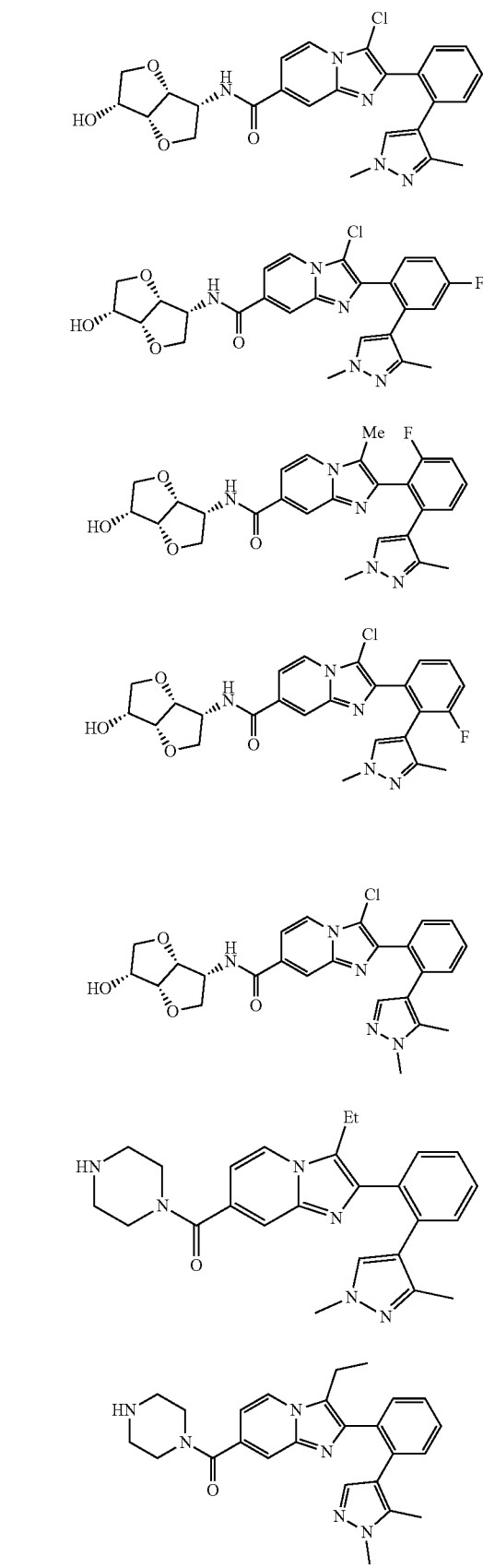
16. The compound of claim 1, or a pharmaceutically acceptable salt or solvate thereof, wherein the compound is a compound depicted in the table below, or a pharmaceutically acceptable salt or solvate thereof:

341
-continued
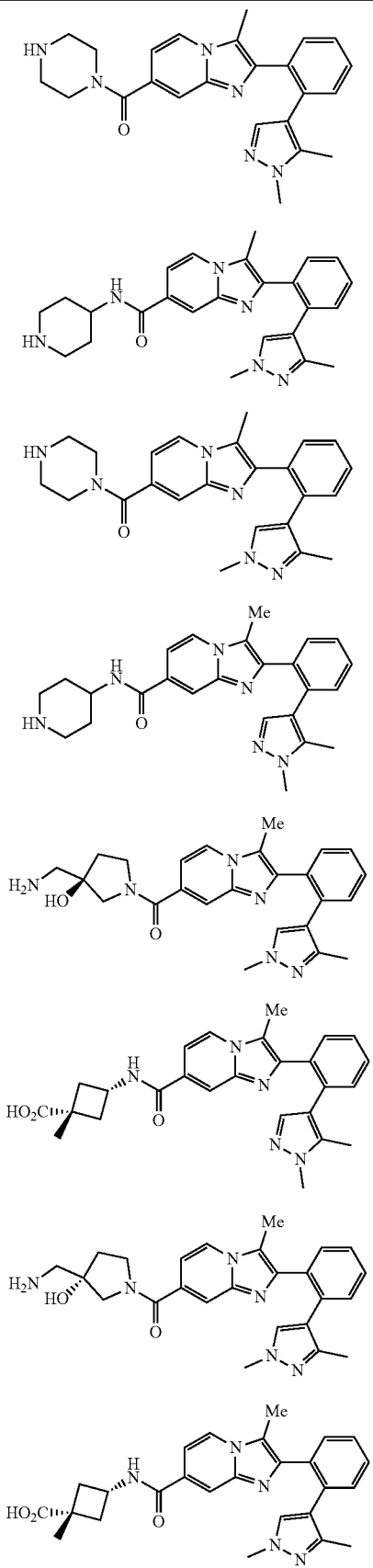
342
-continued
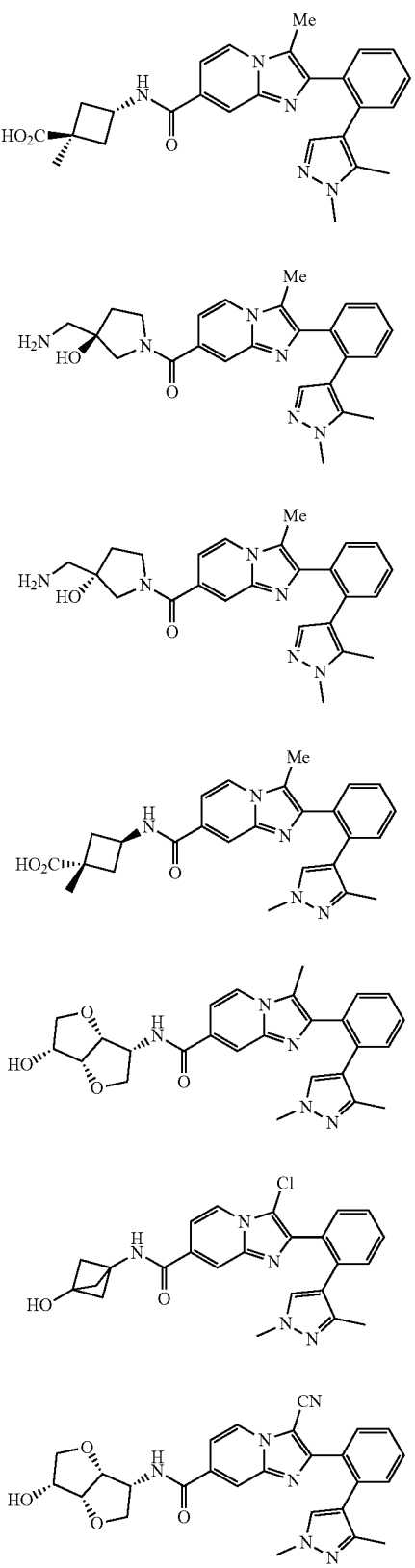

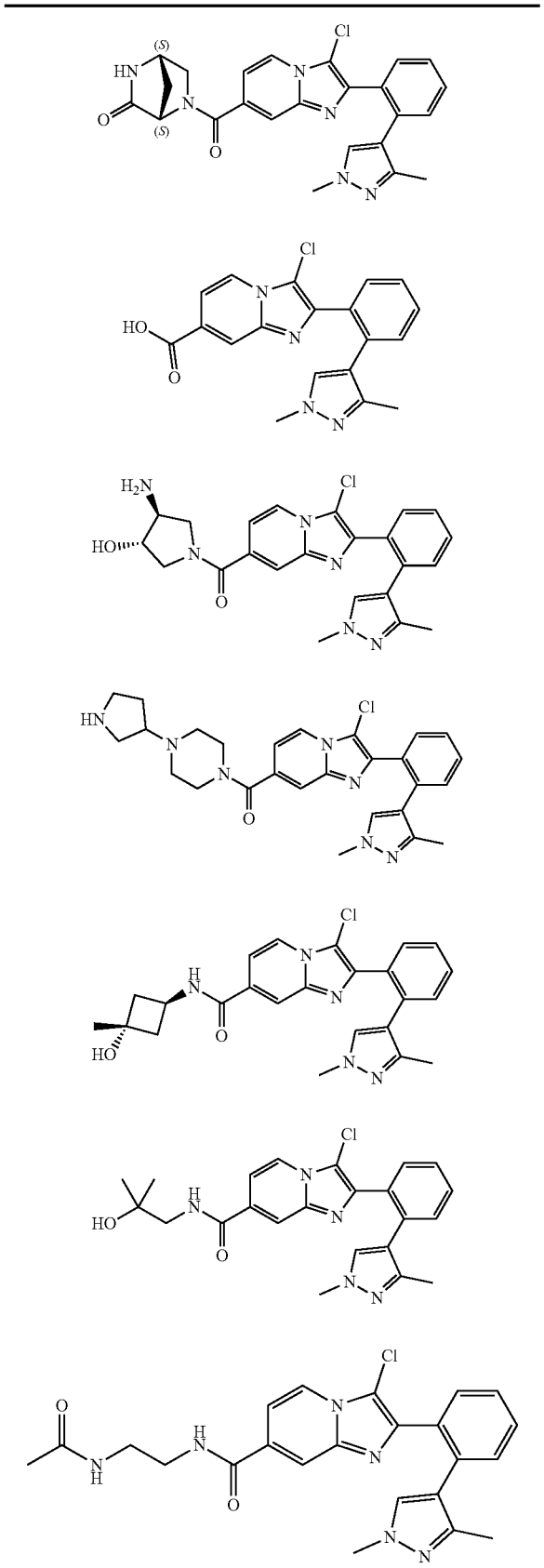
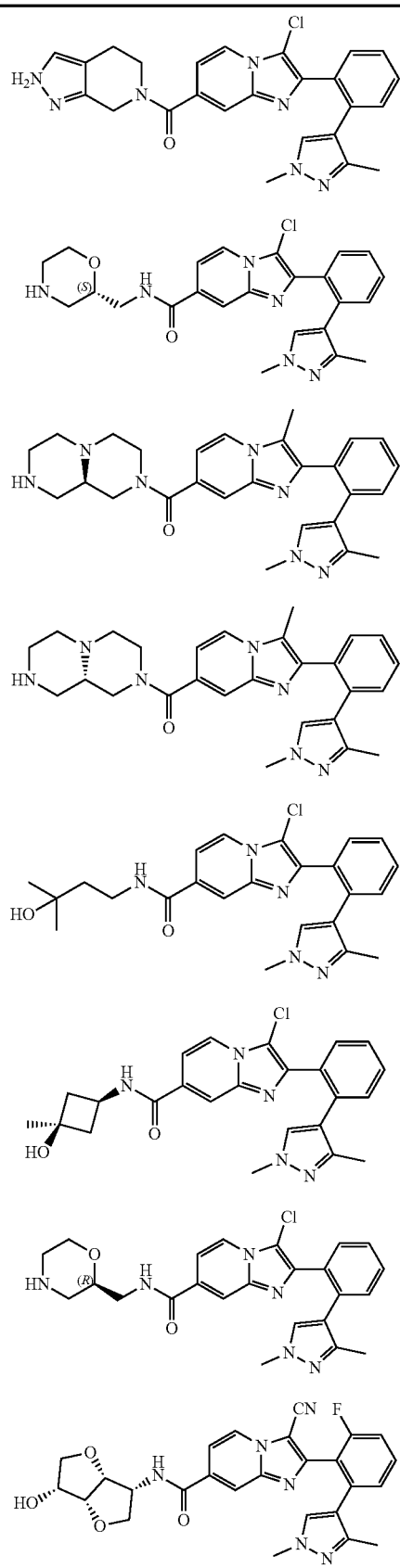

-continued
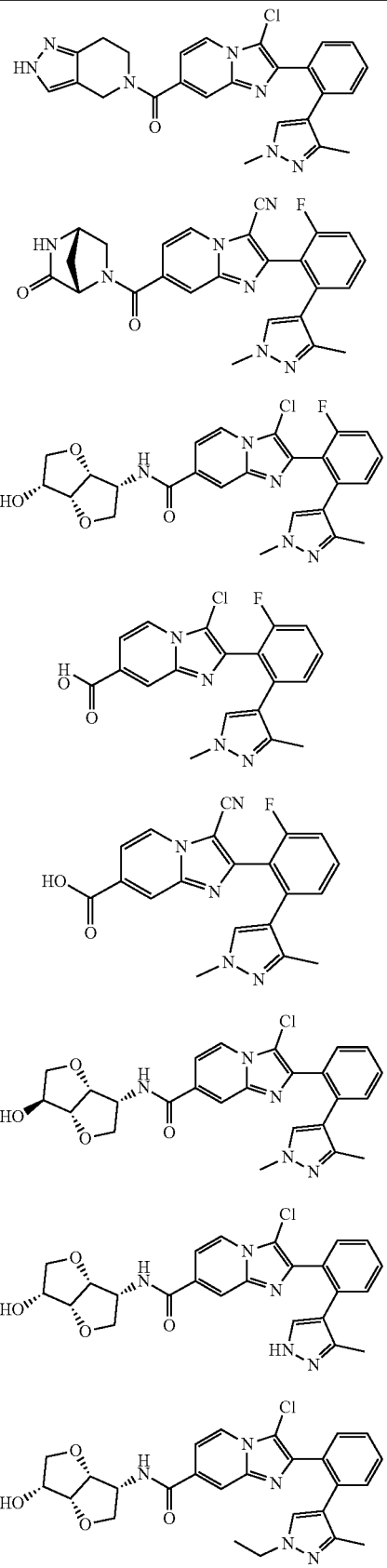
-continued
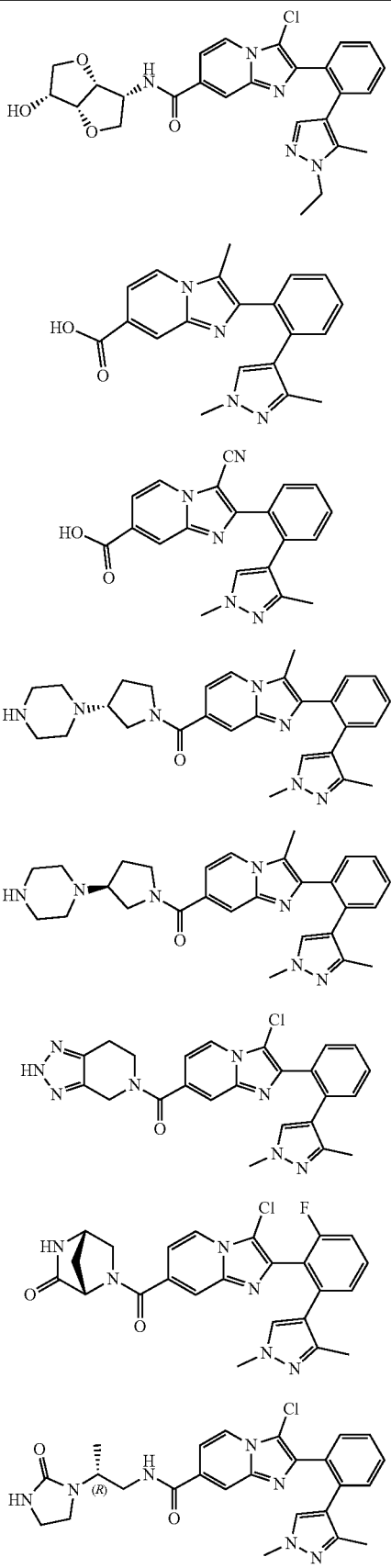

| 347 -continued | 348 -continued |
|---|---|
| 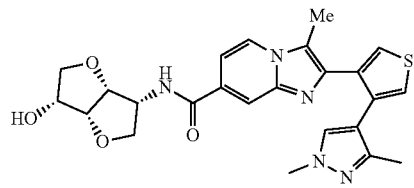 [SMILES: Cc1nn(C)cc1-c1cscc1-c1nc2cc(C(=O)N[C@@H]3CO[C@H]4[C@@H]3OC[C@H]4O)ccn2c1C] | 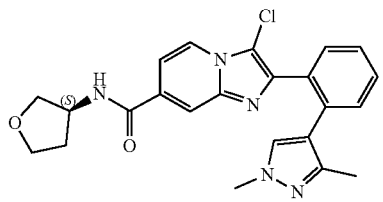 |
|  |  |
| 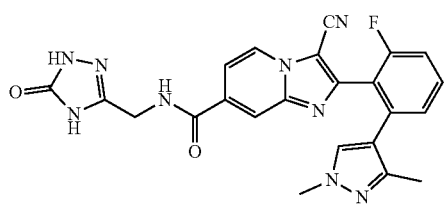 [SMILES: Cc1nn(C)cc1-c1cccc(F)c1-c1nc2cc(C(=O)NCc3n[nH]c(=O)[nH]3)ccn2c1C#N] | 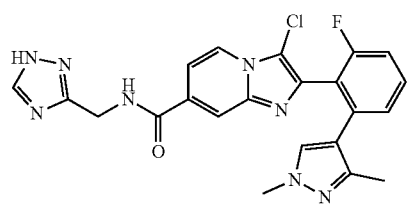 [SMILES: Cc1nn(C)cc1-c1cccc(F)c1-c1nc2cc(C(=O)NCc3nc[nH]n3)ccn2c1Cl] |
|  |  |
| 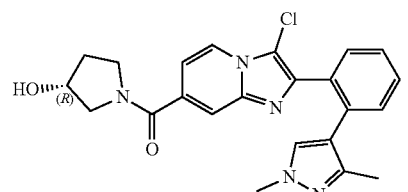 | 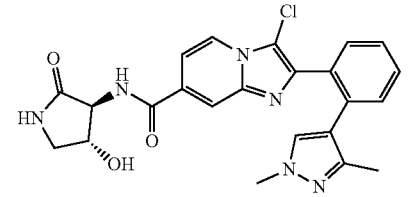 [SMILES: Cc1nn(C)cc1-c1ccccc1-c1nc2cc(C(=O)N[C@@H]3C(=O)NC[C@H]3O)ccn2c1Cl] |
| 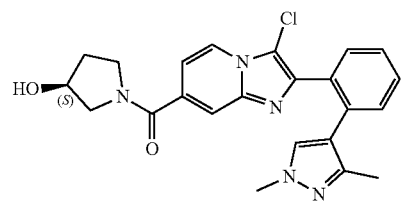 | 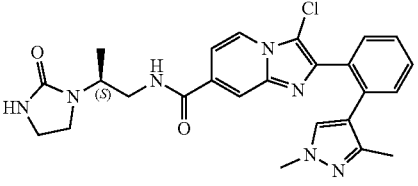 |
|  | 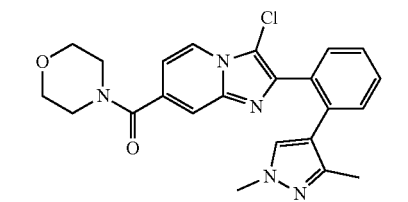 [SMILES: Cc1nn(C)cc1-c1ccccc1-c1nc2cc(C(=O)N3CCOCC3)ccn2c1Cl] |

349
-continued
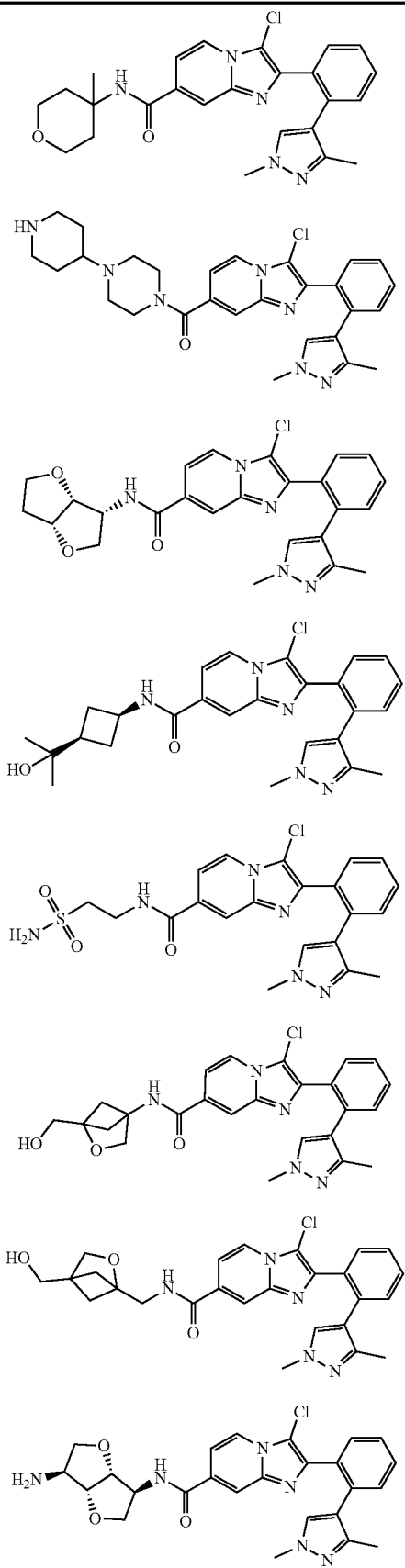
350
-continued
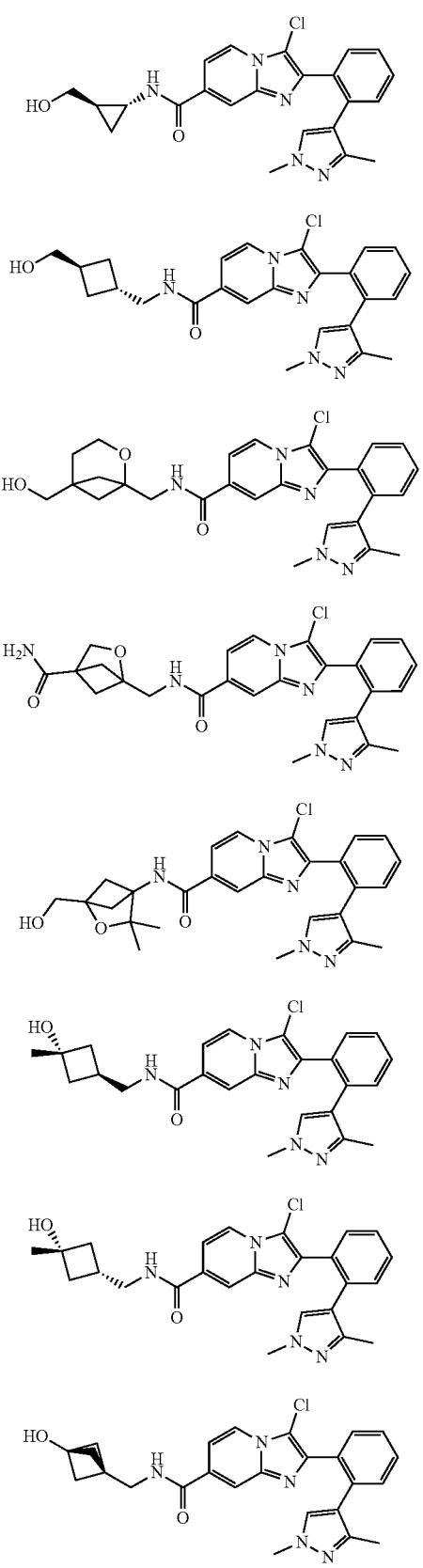

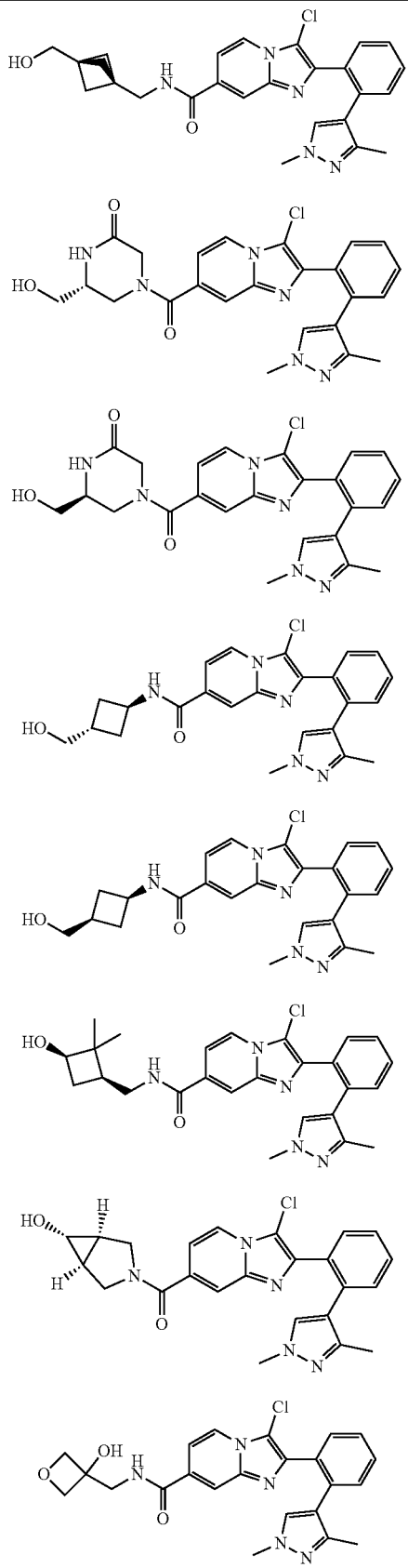
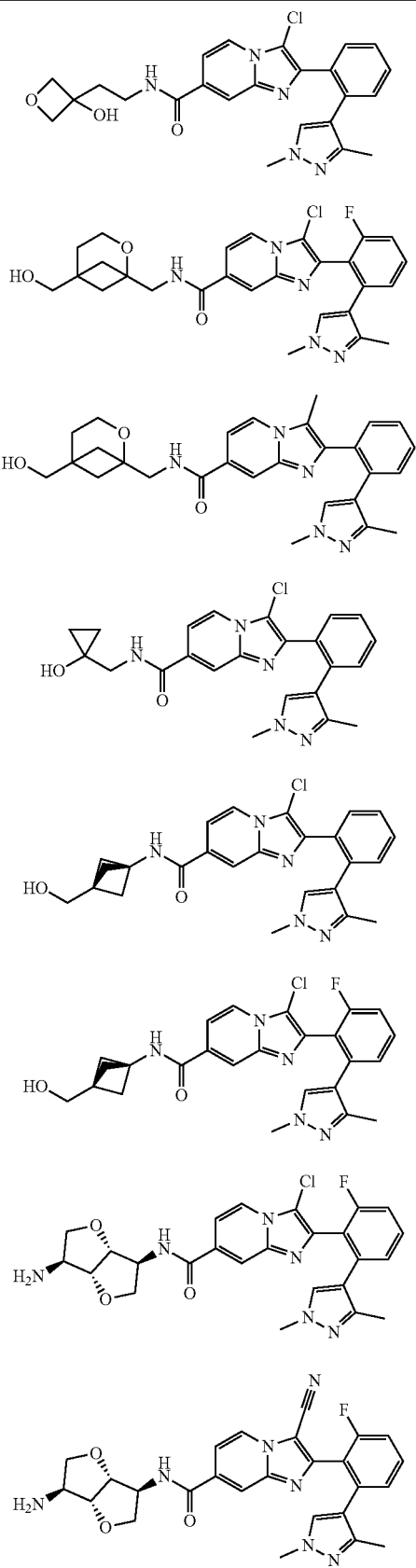

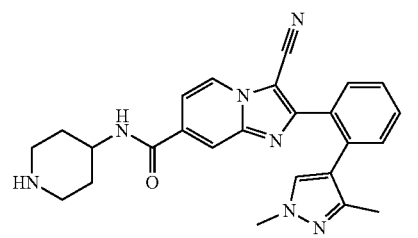 [SMILES: Cc1nn(C)cc1-c1ccccc1-c1nc2cc(C(=O)NC3CCNCC3)ccn2c1C#N]
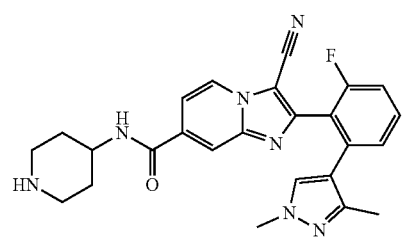 [SMILES: Cc1nn(C)cc1-c1cccc(F)c1-c1nc2cc(C(=O)NC3CCNCC3)ccn2c1C#N]
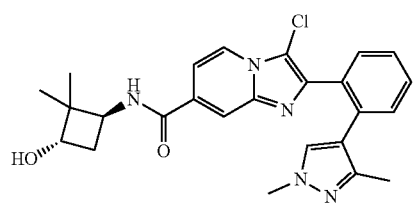 [SMILES: Cc1nn(C)cc1-c1ccccc1-c1nc2cc(C(=O)N[C@H]3C[C@H](O)C3(C)C)ccn2c1Cl]
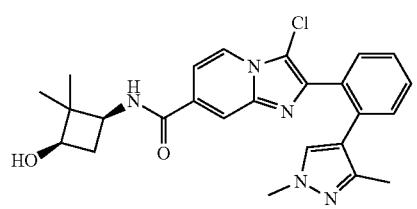 [SMILES: Cc1nn(C)cc1-c1ccccc1-c1nc2cc(C(=O)N[C@H]3C[C@@H](O)C3(C)C)ccn2c1Cl]
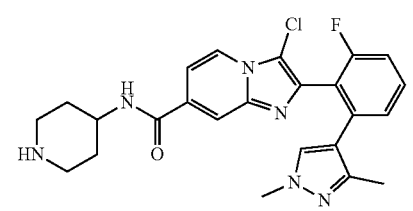 [SMILES: Cc1nn(C)cc1-c1cccc(F)c1-c1nc2cc(C(=O)NC3CCNCC3)ccn2c1Cl]
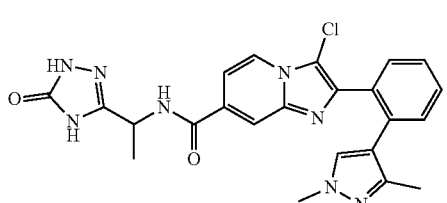
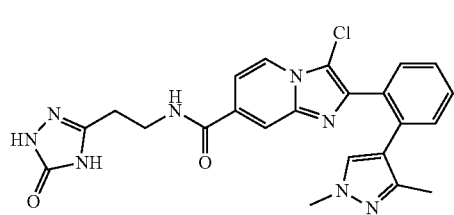 [SMILES: Cc1nn(C)cc1-c1ccccc1-c1nc2cc(C(=O)NCCc3n[nH]c(=O)[nH]3)ccn2c1Cl]
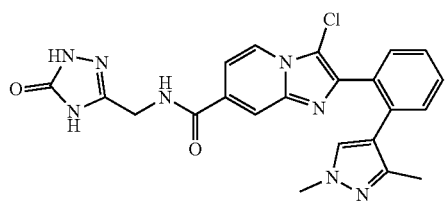 [SMILES: Cc1nn(C)cc1-c1ccccc1-c1nc2cc(C(=O)NCc3n[nH]c(=O)[nH]3)ccn2c1Cl]
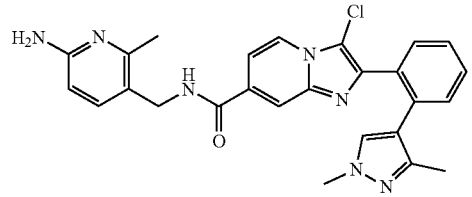 [SMILES: Cc1nc(N)ccc1CNC(=O)c1ccn2c(Cl)c(-c3ccccc3-c3cn(C)nc3C)nc2c1]
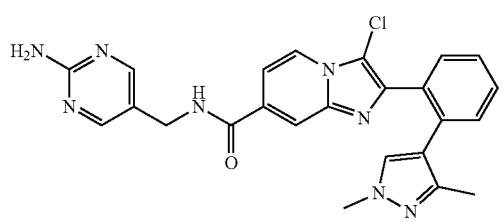 [SMILES: Cc1nn(C)cc1-c1ccccc1-c1nc2cc(C(=O)NCc3cnc(N)nc3)ccn2c1Cl]
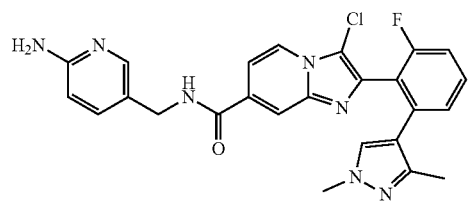 [SMILES: Cc1nn(C)cc1-c1cccc(F)c1-c1nc2cc(C(=O)NCc3ccc(N)nc3)ccn2c1Cl]
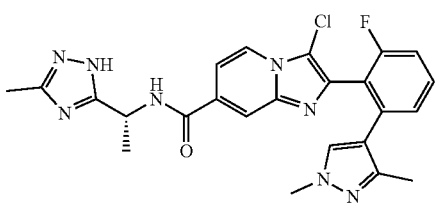
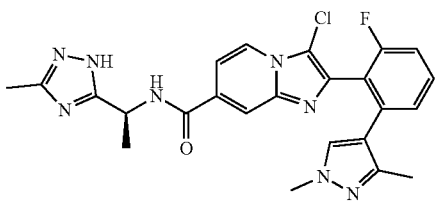 [SMILES: Cc1n[nH]c([C@H](C)NC(=O)c2ccn3c(Cl)c(-c4c(F)cccc4-c4cn(C)nc4C)nc3c2)n1]
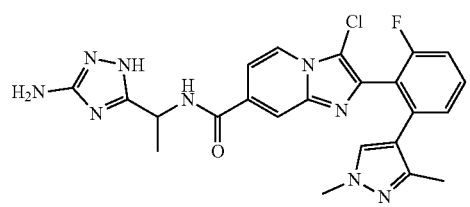 [SMILES: Cc1nn(C)cc1-c1cccc(F)c1-c1nc2cc(C(=O)NC(C)c3nc(N)n[nH]3)ccn2c1Cl]

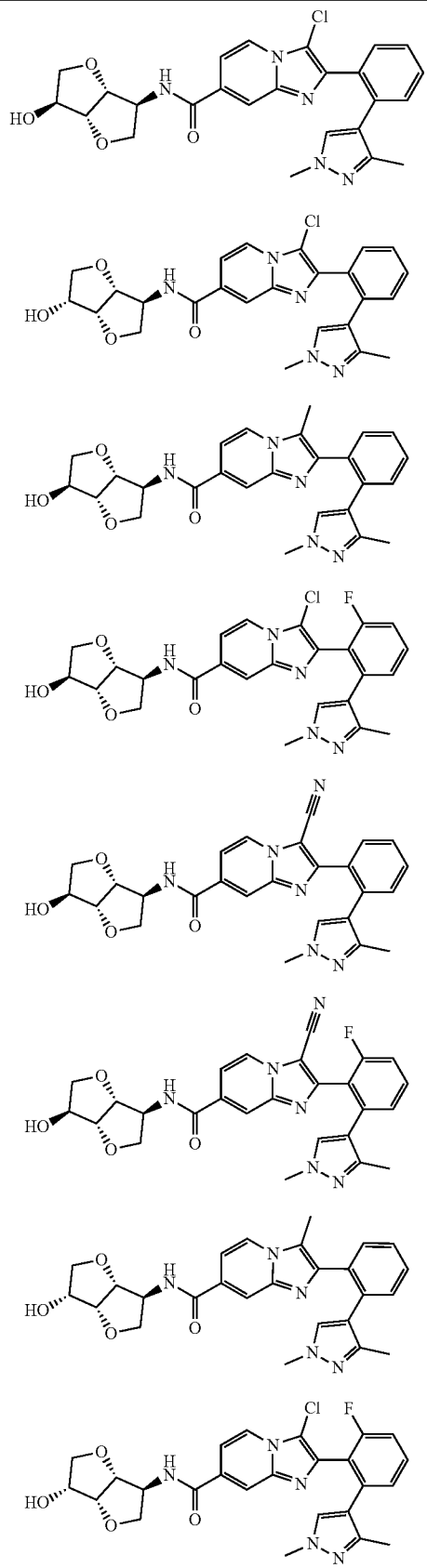
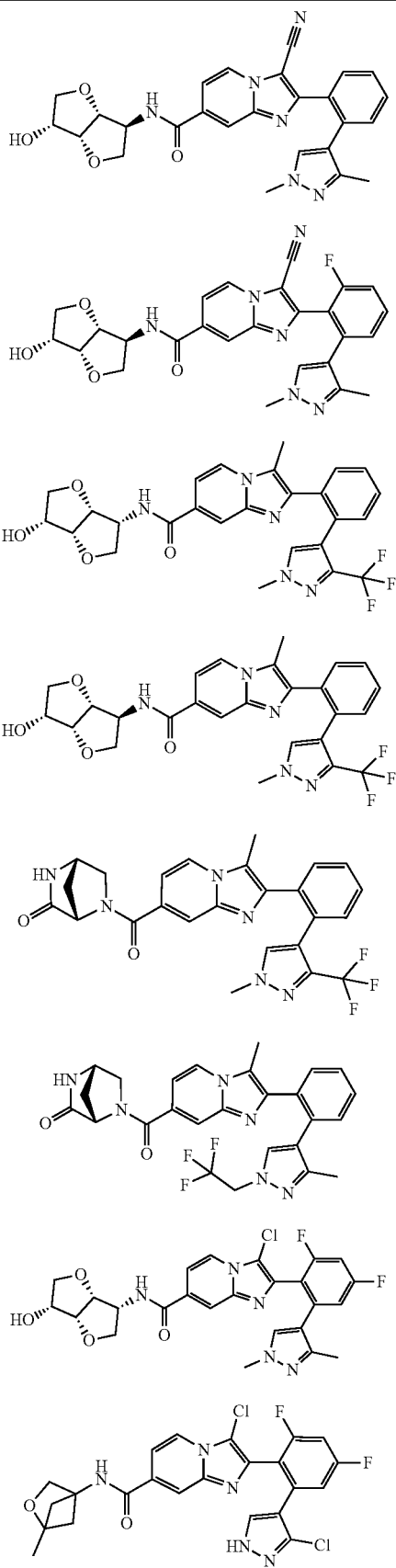

357
-continued
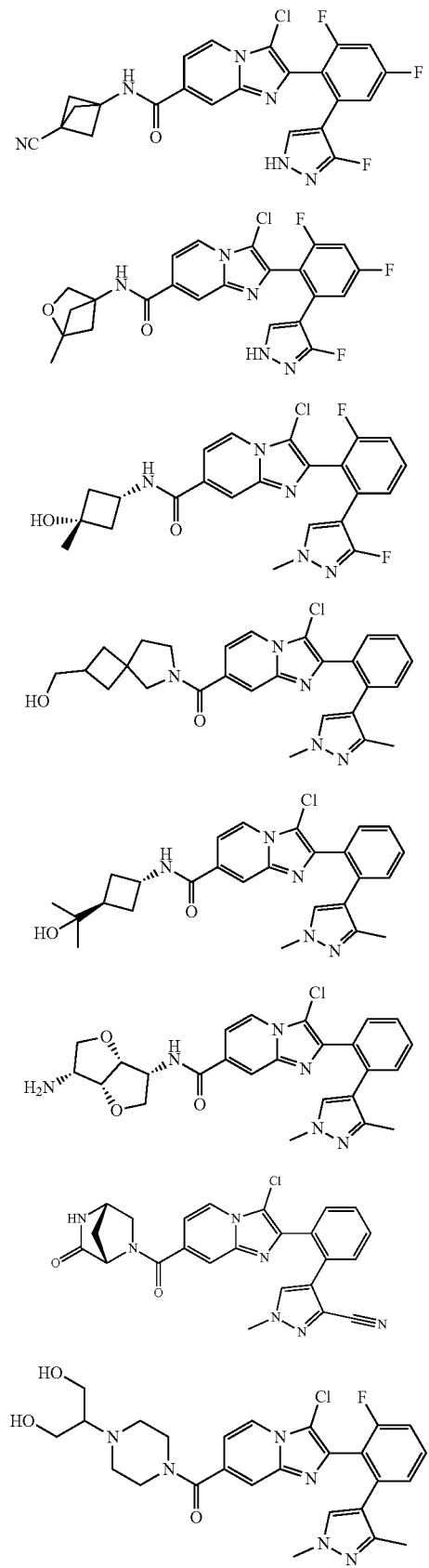
358
-continued
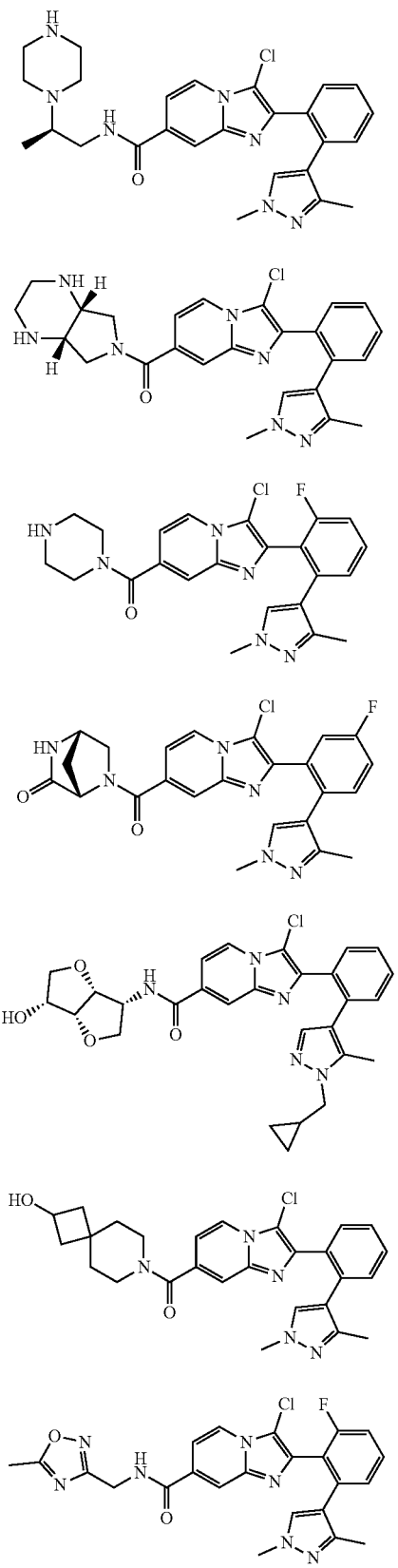

-continued
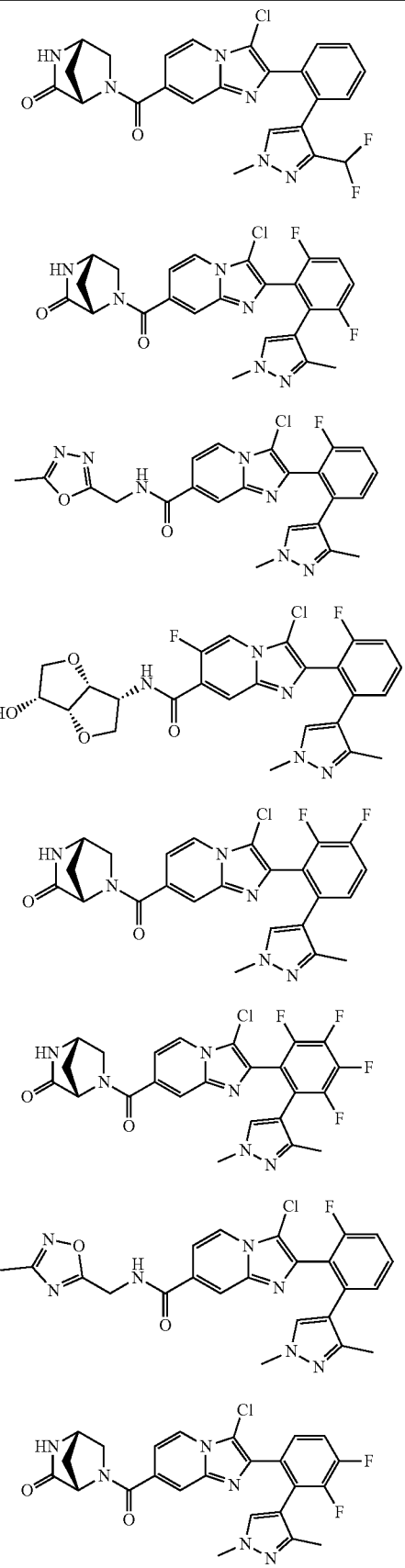
-continued
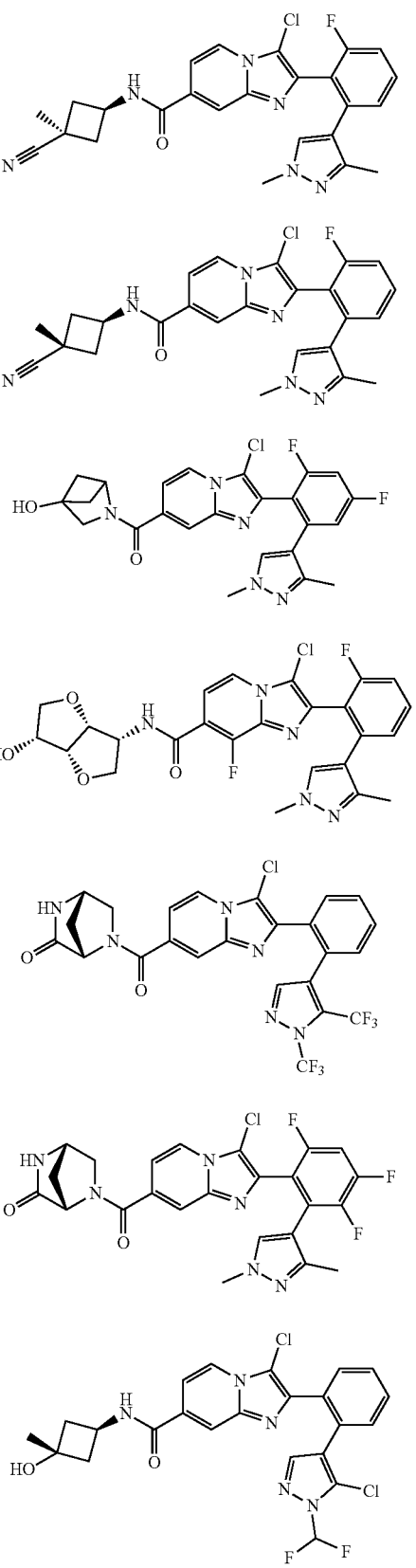

| 361 -continued | 362 -continued |
|---|---|
| 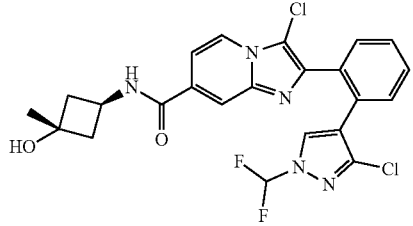 [SMILES: C[C@]1(O)C[C@H](NC(=O)c2ccn3c(Cl)c(-c4ccccc4-c4cn(C(F)F)nc4Cl)nc3c2)C1] | 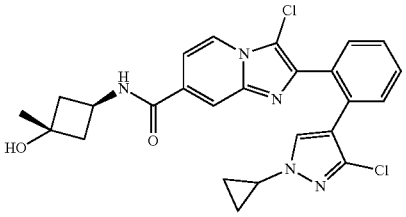 |
| 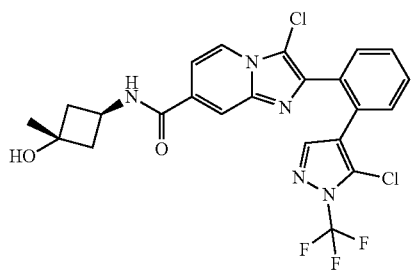 [SMILES: C[C@]1(O)C[C@H](NC(=O)c2ccn3c(Cl)c(-c4ccccc4-c4cnn(C(F)(F)F)c4Cl)nc3c2)C1] | 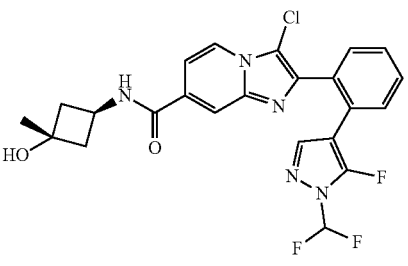 |
| 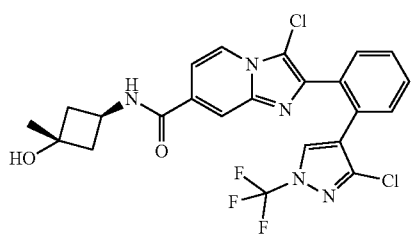 [SMILES: C[C@]1(O)C[C@H](NC(=O)c2ccn3c(Cl)c(-c4ccccc4-c4cn(C(F)(F)F)nc4Cl)nc3c2)C1] | 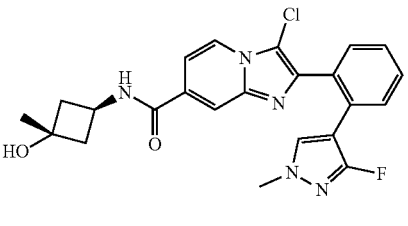 |
| 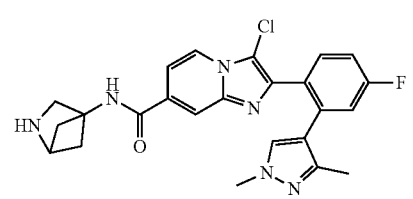 [SMILES: Cc1nn(C)cc1-c1cc(F)ccc1-c1nc2cc(C(=O)NC34CNC(C3)C4)ccn2c1Cl] | 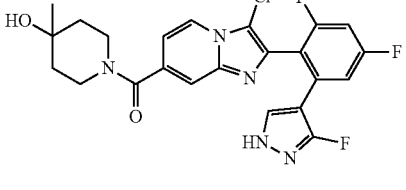 |
| 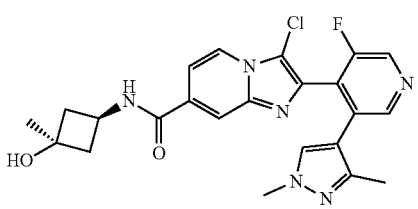 [SMILES: Cc1nn(C)cc1-c1cncc(F)c1-c1nc2cc(C(=O)N[C@H]3C[C@@](C)(O)C3)ccn2c1Cl] | 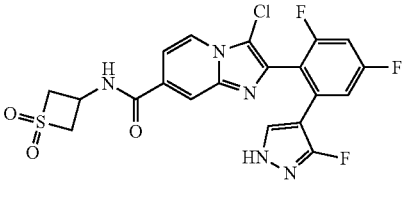 |
| 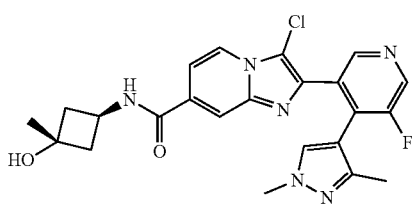 [SMILES: Cc1nn(C)cc1-c1c(F)cncc1-c1nc2cc(C(=O)N[C@H]3C[C@](C)(O)C3)ccn2c1Cl] | 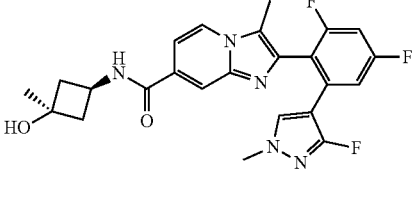 |
| 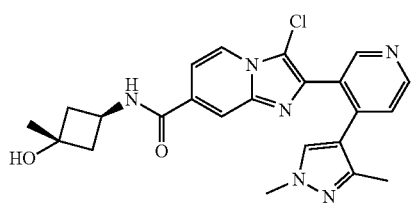 [SMILES: Cc1nn(C)cc1-c1ccncc1-c1nc2cc(C(=O)N[C@H]3C[C@](C)(O)C3)ccn2c1Cl] | 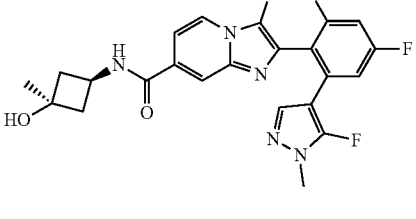 |

363
-continued
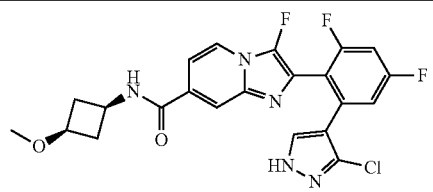
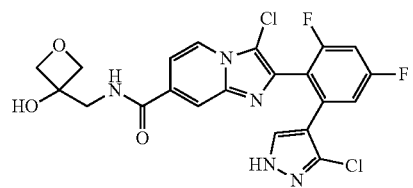 [SMILES: O=C(NCC1(O)COC1)c1ccn2c(Cl)c(-c3c(F)cc(F)cc3-c3c[nH]nc3Cl)nc2c1]
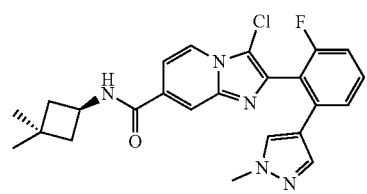
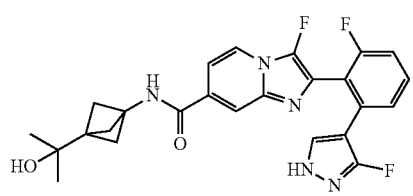 [SMILES: CC(C)(O)C12CC(NC(=O)c3ccn4c(F)c(-c5c(F)cccc5-c5c[nH]nc5F)nc4c3)(C1)C2]
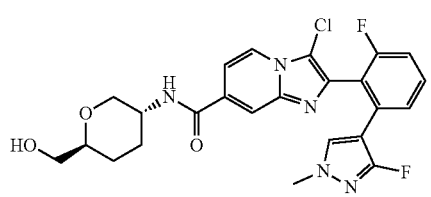 [SMILES: Cn1cc(-c2cccc(F)c2-c2nc3cc(C(=O)N[C@@H]4CC[C@@H](CO)OC4)ccn3c2Cl)c(F)n1]
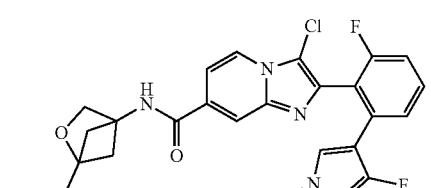
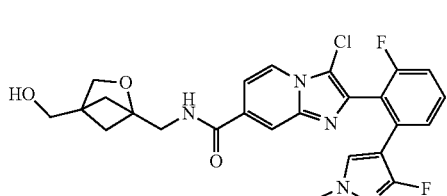
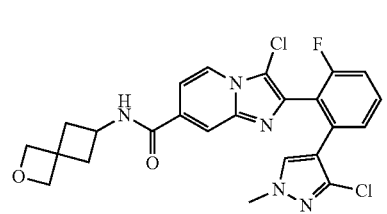 [SMILES: Cn1cc(-c2cccc(F)c2-c2nc3cc(C(=O)NC4CC5(COC5)C4)ccn3c2Cl)c(Cl)n1]
364
-continued
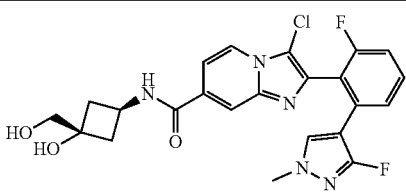
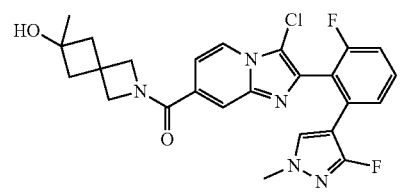 [SMILES: Cn1cc(-c2cccc(F)c2-c2nc3cc(C(=O)N4CC5(C4)CC(C)(O)C5)ccn3c2Cl)c(F)n1]
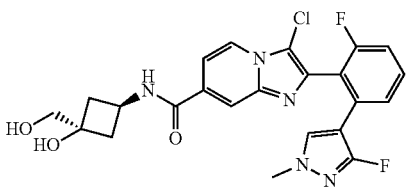 [SMILES: Cn1cc(-c2cccc(F)c2-c2nc3cc(C(=O)N[C@H]4C[C@](O)(CO)C4)ccn3c2Cl)c(F)n1]
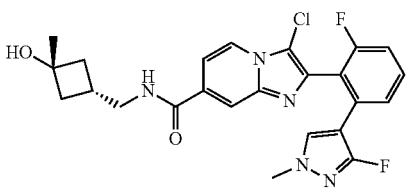 [SMILES: Cn1cc(-c2cccc(F)c2-c2nc3cc(C(=O)NC[C@H]4C[C@@](C)(O)C4)ccn3c2Cl)c(F)n1]
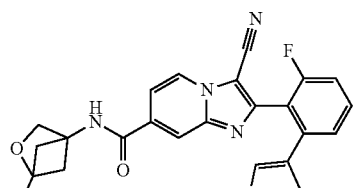
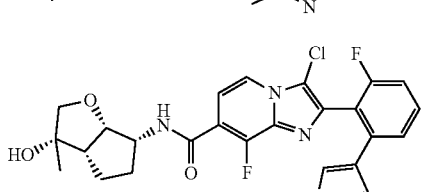
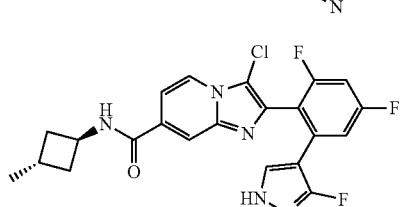
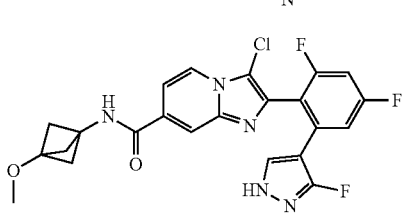

365
-continued
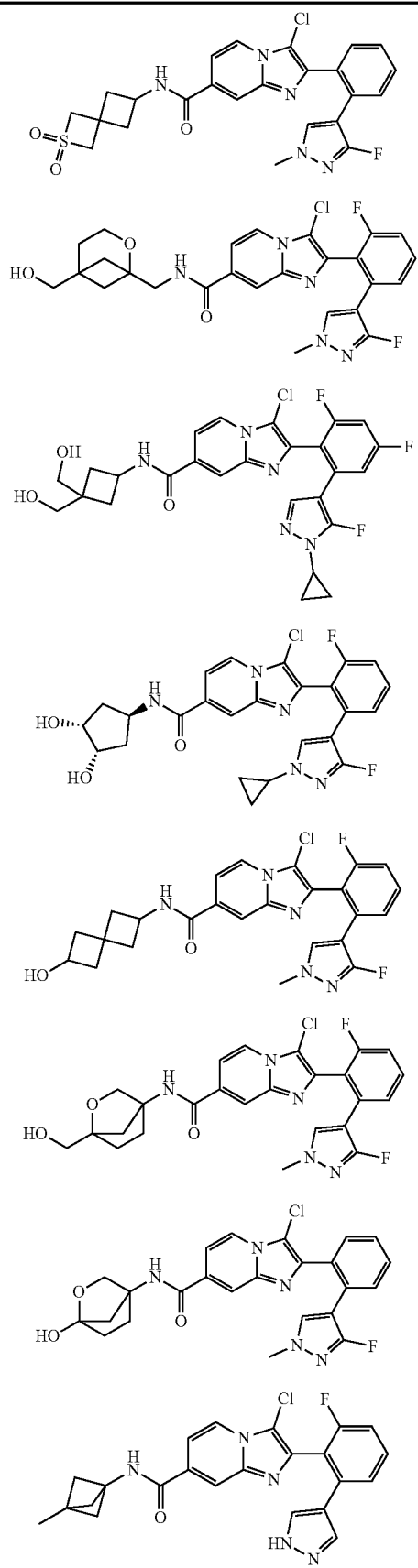
366
-continued
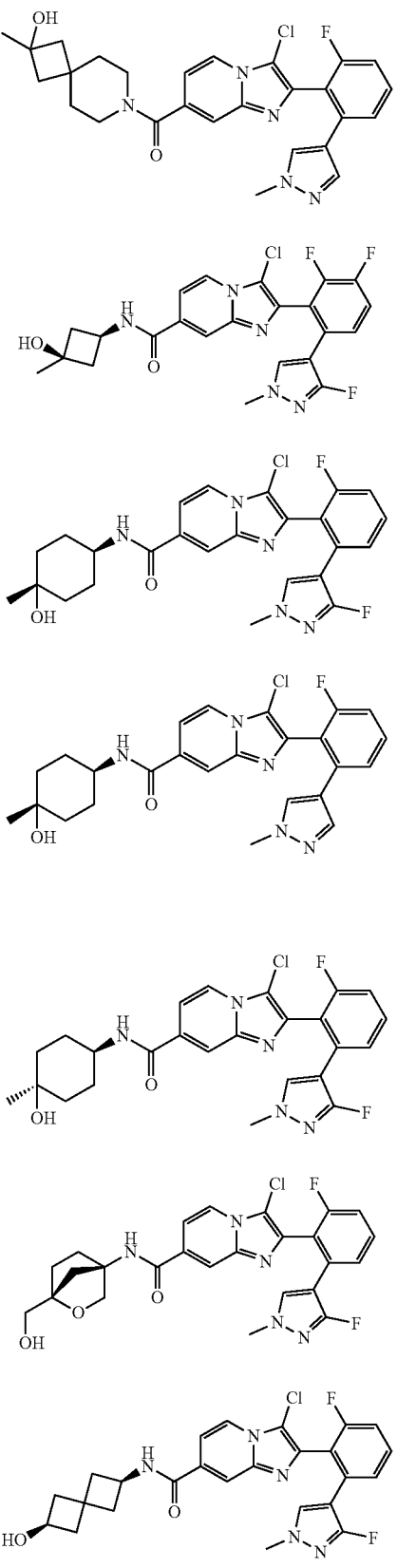

367
-continued
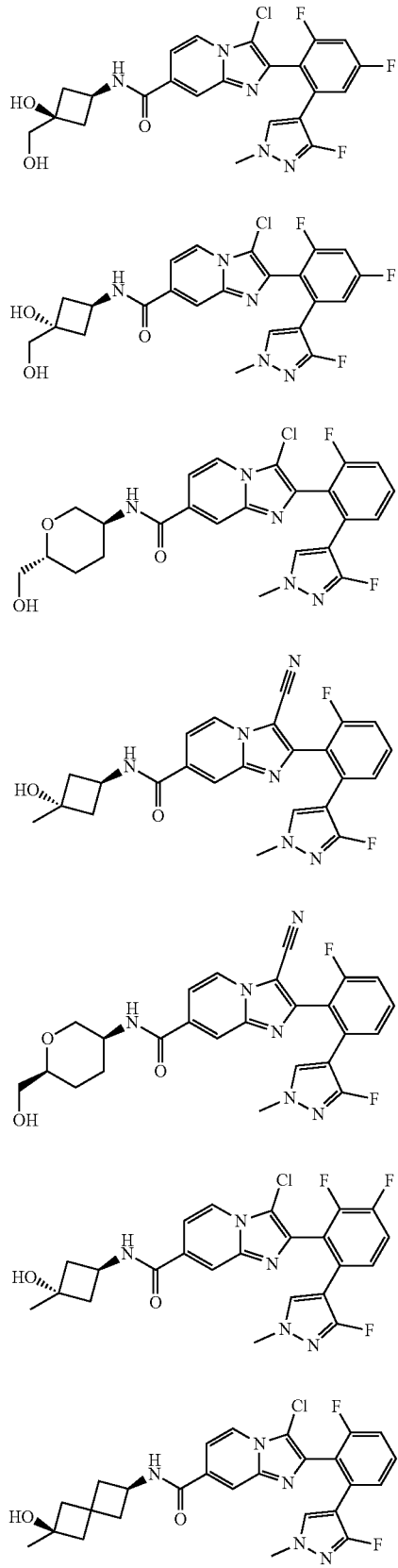
368
-continued
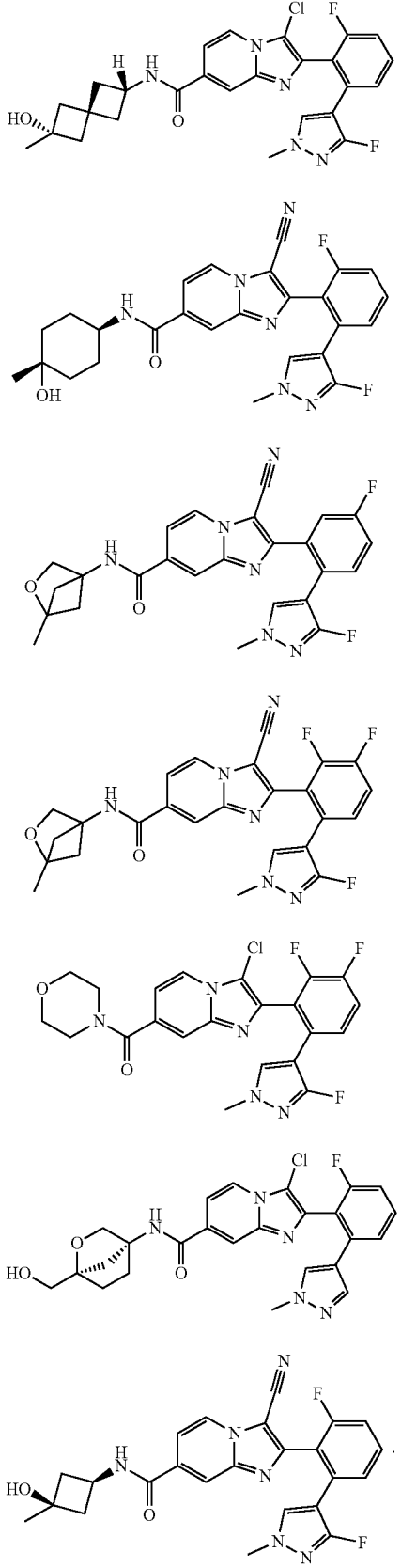

17. A pharmaceutical composition comprising a compound of claim 1, or a pharmaceutically acceptable salt or solvate thereof, and at least one pharmaceutically acceptable excipient.

18. A method for the treatment of a disease or disorder in a subject in need thereof, comprising administering to the subject a therapeutically effective amount of a compound of claim 1, or a pharmaceutically acceptable salt or solvate thereof; wherein the disease or disorder is selected from the group consisting of: migraine, medication overuse headache, cluster headache, general headache, trigeminal neuralgia, orofacial pain, and combinations thereof.

19. The method of claim 18, wherein the disease or disorder is migraine.

20. The method of claim 18, further comprising administration of a therapeutically effective amount of an additional therapeutic agent; wherein the additional therapeutic agent is selected from: beta blockers; antidepressants; anticonvulsants; phenothiazine anti-emetics; non-phenothiazine anti-emetics; non-steroidal anti-inflammatory drugs (NSAIDS); acetaminophen; caffeine; ergots; ditans; triptans; calcitonin gene-related peptide (CGRP) receptor antagonists; CGRP antibodies; and combinations thereof.

* * * * *

UNITED STATES PATENT AND TRADEMARK OFFICE
CERTIFICATE OF CORRECTION

| | | |
|---|---|---|
| PATENT NO. | : 12,281,114 B2 | Page 1 of 4 |
| APPLICATION NO. | : 18/800581 | |
| DATED | : April 22, 2025 | |
| INVENTOR(S) | : Shuwen He et al. | |

It is certified that error appears in the above-identified patent and that said Letters Patent is hereby corrected as shown below:

In the Specification

In Table 1, Compound 511, Column 271 should read:

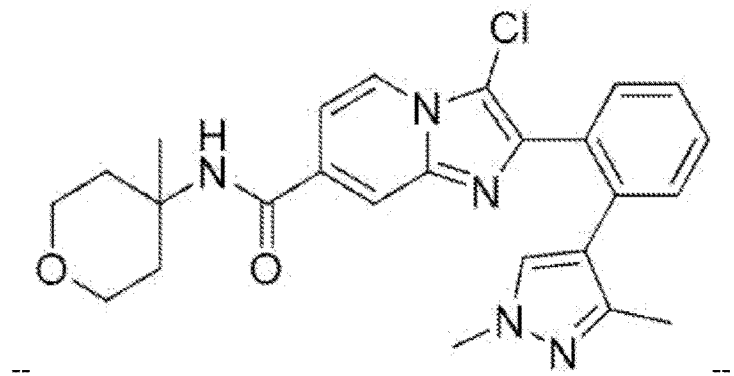

In Table 1, Compound 665, Column 283 should read:

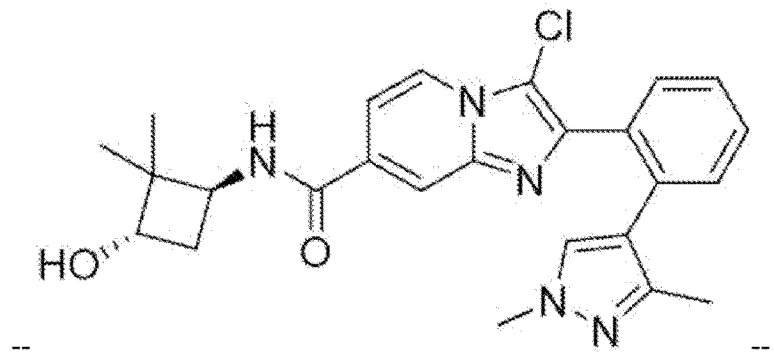

Signed and Sealed this
Twenty-ninth Day of July, 2025

Coke Morgan Stewart
*Acting Director of the United States Patent and Trademark Office*

CERTIFICATE OF CORRECTION (continued)
U.S. Pat. No. 12,281,114 B2

In Table 1, Compound 929, Column 321 should read:

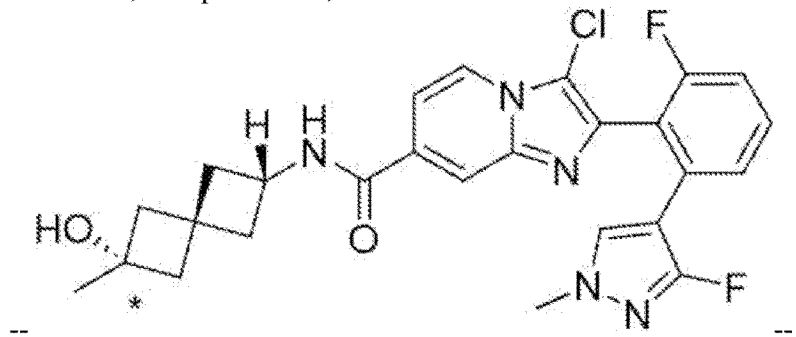

--                                                              --

In the Claims

In Claim 15, Column 336, Line 5 should read:

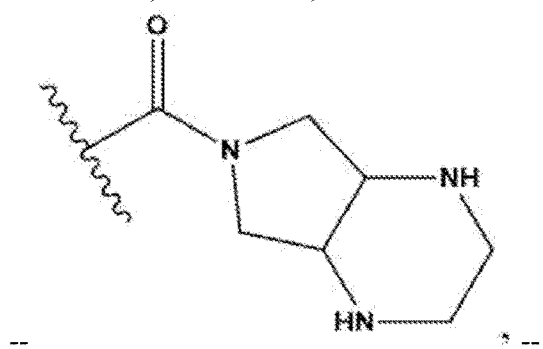

--                                                              --

In Claim 16, Column 344, Line 5 should read:

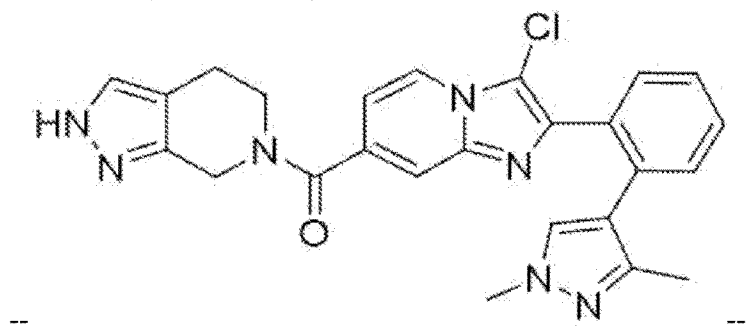

--                                                              --

In Claim 16, Column 345, Line 30 should read:

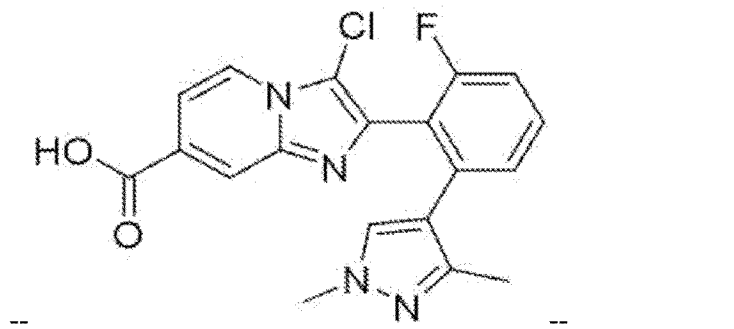

--                                                              --

CERTIFICATE OF CORRECTION (continued)
U.S. Pat. No. 12,281,114 B2

Page 3 of 4

In Claim 16, Column 353, Line 40 the following should be added:

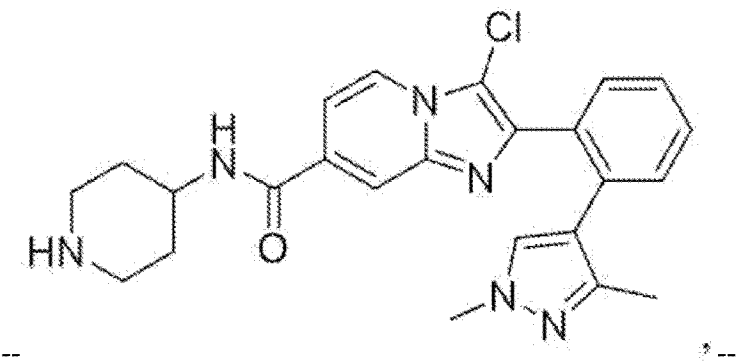

--                                                                      --

In Claim 16, Column 362, Lines 25-30 should read:

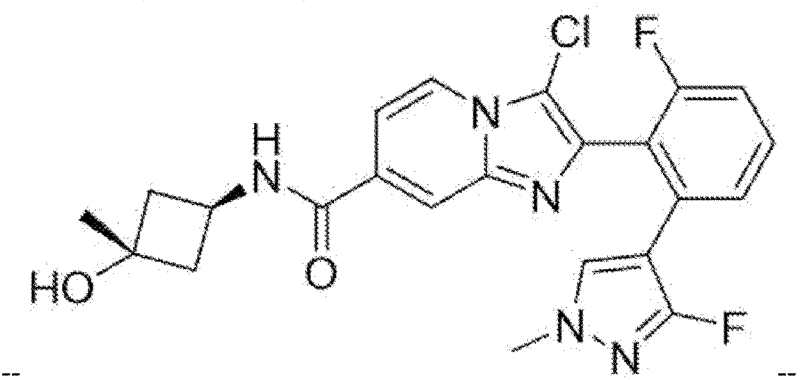

--                                                                      --

In Claim 16, Column 363, Lines 10-15 should read:

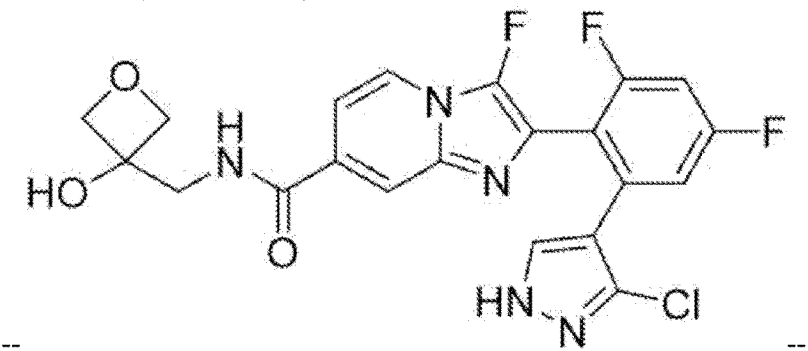

--                                                                      --

CERTIFICATE OF CORRECTION (continued)
U.S. Pat. No. 12,281,114 B2

In Claim 16, Column 363, Lines 20-25 should read:

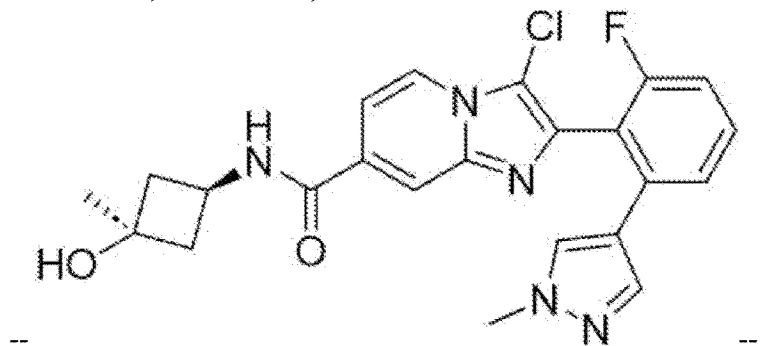

--                                                              --

In Claim 16, Column 363, Lines 60-65 should read:

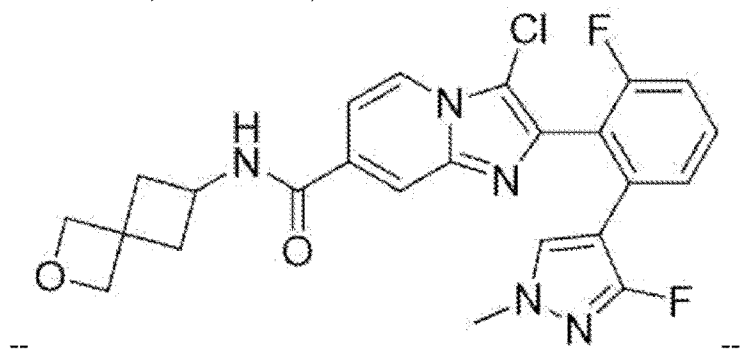

--                                                              --

In Claim 16, Column 365, Line 55 should read:

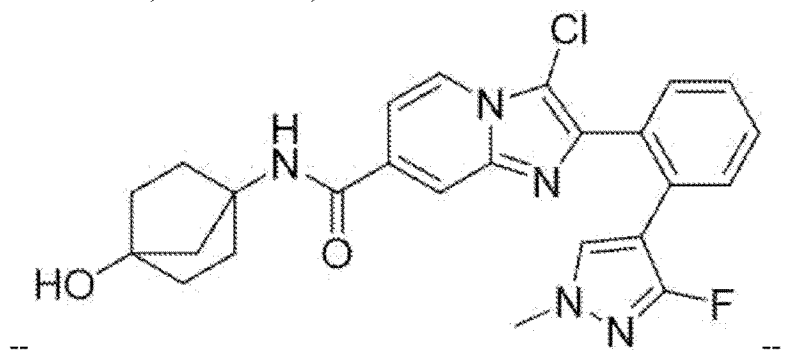

--                                                              --